US012612368B2

(12) United States Patent
Bhurruth-Alcor et al.

(10) Patent No.: US 12,612,368 B2
(45) Date of Patent: Apr. 28, 2026

(54) CANCER TREATMENTS TARGETING CANCER STEM CELLS

(71) Applicant: Remedy Plan, Inc., Gaithersburg, MD (US)

(72) Inventors: Yushma Bhurruth-Alcor, Ashburn, VA (US); Gregory Thomas Crimmins, Washington, DC (US); Dennise Alexandra De Jesús Diaz, Washington, DC (US); Caroline Mae Robb, Gaithersburg, MD (US)

(73) Assignee: Remedy Plan, Inc., Gaithersburg, MD (US)

( * ) Notice: Subject to any disclaimer, the term of this patent is extended or adjusted under 35 U.S.C. 154(b) by 1017 days.

(21) Appl. No.: 17/774,583

(22) PCT Filed: Nov. 6, 2020

(86) PCT No.: PCT/US2020/059329

§ 371 (c)(1),
(2) Date: May 5, 2022

(87) PCT Pub. No.: WO2021/092322

PCT Pub. Date: May 14, 2021

(65) Prior Publication Data

US 2023/0023124 A1 Jan. 26, 2023

Related U.S. Application Data

(60) Provisional application No. 62/931,531, filed on Nov. 6, 2019.

(51) Int. Cl.

| | |
|---|---|
| ***C07D 213/82*** | (2006.01) |
| ***A61K 45/06*** | (2006.01) |
| ***C07D 405/14*** | (2006.01) |
| ***C07D 417/12*** | (2006.01) |
| ***C07D 471/04*** | (2006.01) |

(52) U.S. Cl.

CPC ............ *C07D 213/82* (2013.01); *A61K 45/06* (2013.01); *C07D 405/14* (2013.01); *C07D 417/12* (2013.01); *C07D 471/04* (2013.01)

(58) Field of Classification Search

None

See application file for complete search history.

(56) References Cited

U.S. PATENT DOCUMENTS

| | | | |
|---|---|---|---|
| 4,278,681 | A | 7/1981 | Haskell et al. |
| 4,315,014 | A | 2/1982 | Mich et al. |
| 4,315,858 | A | 2/1982 | Doub et al. |
| 8,461,342 | B2 | 6/2013 | Siesel |
| 8,524,767 | B2 | 9/2013 | Miller et al. |

(Continued)

FOREIGN PATENT DOCUMENTS

| | | | |
|---|---|---|---|
| CN | 108314677 | B | 6/2020 |
| EP | 0015771 | A1 | 9/1980 |

(Continued)

OTHER PUBLICATIONS

Extended European Search Report, mailed Oct. 19, 2021, in connection with Application No. 19796696.3.

(Continued)

*Primary Examiner* — Brian J Davis

(74) *Attorney, Agent, or Firm* — Wolf, Greenfield & Sacks, P.C.

(57) ABSTRACT

Disclosed are compounds, methods, compositions, uses, and kits that allow for treating cancer. In some embodiments, the compounds are used to treat diseases or disorders. The compounds may treat cancer by targeting cancer stem cells. In some embodiments, the cancer is colorectal cancer, gastric cancer, gastrointestinal stromal tumor, ovarian cancer, lung cancer, breast cancer, pancreatic cancer, prostate cancer, testicular cancer, lymphoma, liver cancer, endometrial cancer, leukemia, or multiple myeloma. Disclosed are compounds, methods, compositions, uses, and kits that may be used in regenerative medicine. The compounds utilized in the disclosure are of Formula (0) and (I).

(0)

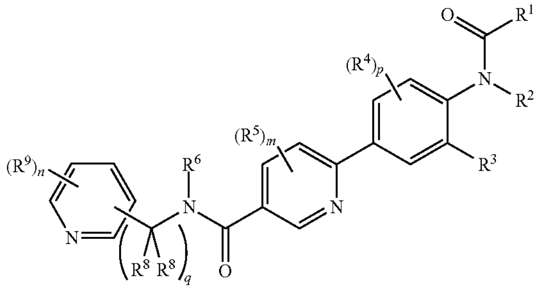

(I)

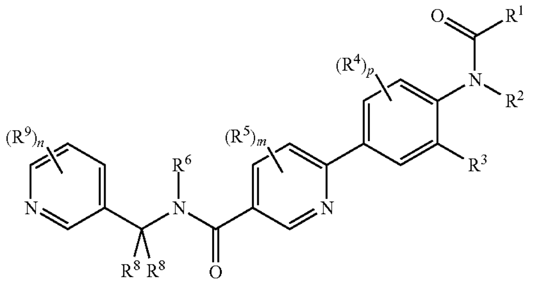

21 Claims, No Drawings

(56) References Cited

U.S. PATENT DOCUMENTS

| | | | |
|---|---|---|---|
| 2009/0131640 | A1 | 5/2009 | Berkelman |
| 2009/0233934 | A1 | 9/2009 | Oda et al. |
| 2010/0222319 | A1 | 9/2010 | Bernhart et al. |
| 2015/0231142 | A1 | 8/2015 | Van Goor et al. |
| 2018/0370909 | A1 | 12/2018 | Buchwald |
| 2022/0324842 | A1 | 10/2022 | Crimmins et al. |
| 2024/0376074 | A1 | 11/2024 | Bhurruth-Alcor et al. |

FOREIGN PATENT DOCUMENTS

| | | | |
|---|---|---|---|
| EP | 0015773 | A2 | 9/1980 |
| EP | 0706795 | A2 | 4/1996 |
| EP | 2589292 | A1 | 5/2013 |
| EP | 3431472 | B1 | 5/2023 |
| FR | 2904827 | B1 | 9/2008 |
| FR | 2921657 | A1 | 4/2009 |
| GB | 2273930 | A | 7/1994 |
| JP | S56-115784 | A | 9/1981 |
| JP | H02-127429 | A | 5/1990 |
| JP | H02-127512 | A | 5/1990 |
| JP | H10-152462 | A | 6/1998 |
| JP | H11-302173 | A | 11/1999 |
| JP | 2000-256194 | A | 9/2000 |
| JP | 2008-510726 | A | 4/2008 |
| JP | 2013-530199 | A | 7/2013 |
| JP | 2014-518223 | A | 7/2014 |
| JP | 5799117 | B2 | 10/2015 |
| JP | 2017-516774 | A | 6/2017 |
| JP | 2019-512503 | A | 5/2019 |
| KR | 102210267 | B1 | 2/2021 |
| WO | WO 97/48397 | A1 | 12/1997 |
| WO | WO 97/48696 | A1 | 12/1997 |
| WO | WO 2001/011965 | A1 | 2/2001 |
| WO | WO 02/060875 | A1 | 8/2002 |
| WO | WO 2003/003008 | A1 | 1/2003 |
| WO | WO 2003/003009 | A1 | 1/2003 |
| WO | WO 2003/055477 | A1 | 7/2003 |
| WO | WO 2003/059913 | A1 | 7/2003 |
| WO | WO 03/080054 | A1 | 10/2003 |
| WO | WO 2004/058234 | A2 | 7/2004 |
| WO | WO 2005/012299 | A1 | 2/2005 |
| WO | WO 2006/023844 | A2 | 3/2006 |
| WO | WO 2006/028958 | A2 | 3/2006 |
| WO | WO 2006/067445 | A2 | 6/2006 |
| WO | WO 2006/067446 | A1 | 6/2006 |
| WO | WO 2006/075160 | A1 | 7/2006 |
| WO | WO 2006/077387 | A2 | 7/2006 |
| WO | WO 2006/130403 | A1 | 12/2006 |
| WO | WO 2007/009715 | A1 | 1/2007 |
| WO | WO 2007/024922 | A1 | 3/2007 |
| WO | WO 2007/062028 | A2 | 5/2007 |
| WO | WO 2007/072999 | A1 | 6/2007 |
| WO | WO 2007/076055 | A2 | 7/2007 |
| WO | WO 2007/125331 | A2 | 11/2007 |
| WO | WO 2008/016643 | A2 | 2/2008 |
| WO | WO 2008/024963 | A1 | 2/2008 |
| WO | WO 2008/025857 | A2 | 3/2008 |
| WO | WO 2009/053694 | A1 | 4/2009 |
| WO | WO 2009/076142 | A2 | 6/2009 |
| WO | WO 2009/109610 | A1 | 9/2009 |
| WO | WO 2009/126863 | A2 | 10/2009 |
| WO | WO 2010/056549 | A1 | 5/2010 |
| WO | WO 2012/006475 | A1 | 1/2012 |
| WO | WO 2012/014994 | A1 | 2/2012 |
| WO | WO 2012/024179 | A1 | 2/2012 |
| WO | WO 2012/031197 | A1 | 3/2012 |
| WO | WO 2012/043891 | A1 | 4/2012 |
| WO | WO 2012/054110 | A2 | 4/2012 |
| WO | WO 2012/143415 | A1 | 10/2012 |
| WO | WO 2012/156919 | A1 | 11/2012 |
| WO | WO 2012/158784 | A2 | 11/2012 |
| WO | WO 2013/028445 | A1 | 2/2013 |
| WO | WO 2013/064460 | A1 | 5/2013 |
| WO | WO 2013/083991 | A1 | 6/2013 |
| WO | WO 2014/008214 | A1 | 1/2014 |
| WO | WO 2014/081299 | A1 | 5/2014 |
| WO | WO 2014/081300 | A1 | 5/2014 |
| WO | WO 2014/081301 | A1 | 5/2014 |
| WO | WO 2014/081303 | A1 | 5/2014 |
| WO | WO 2014/145642 | A2 | 9/2014 |
| WO | WO 2014/145873 | A2 | 9/2014 |
| WO | WO 2014/203217 | A1 | 12/2014 |
| WO | WO 2015/040424 | A1 | 3/2015 |
| WO | WO 2015/078949 | A1 | 6/2015 |
| WO | WO 2015/117053 | A1 | 8/2015 |
| WO | WO 2015/127137 | A1 | 8/2015 |
| WO | WO 2015/154820 | A1 | 10/2015 |
| WO | WO 2017/009650 | A1 | 1/2017 |
| WO | WO 2017/141036 | A1 | 8/2017 |
| WO | WO 2017/150209 | A1 | 9/2017 |
| WO | WO 2018/017589 | A1 | 1/2018 |
| WO | WO 2018/075842 | A1 | 4/2018 |
| WO | WO 2018/101424 | A1 | 6/2018 |
| WO | WO 2018/133795 | A1 | 7/2018 |
| WO | WO 2018/190352 | A1 | 10/2018 |
| WO | WO 2018/194885 | A1 | 10/2018 |
| WO | WO 2018/216640 | A1 | 11/2018 |
| WO | WO 2019/148125 | A1 | 8/2019 |
| WO | WO 2019/213570 | A1 | 11/2019 |
| WO | WO 2020/054712 | A1 | 3/2020 |
| WO | WO 2021/092322 | A1 | 5/2021 |
| WO | WO 2022/050286 | A1 | 3/2022 |

OTHER PUBLICATIONS

International Search Report and Written Opinion, mailed Aug. 19, 2019, in connection with Application No. PCT/US2019/030664.

International Preliminary Report on Patentability, mailed Nov. 19, 2020, in connection with Application No. PCT/US2019/030664.

International Search Report and Written Opinion, mailed Feb. 11, 2021, in connection with Application No. PCT/US2020/059329.

International Preliminary Report on Patentability, mailed May 19, 2022, in connection with Application No. PCT/US2020/059329.

International Search Report and Written Opinion, mailed Aug. 1, 2022, in connection with Application No. PCT/US2022/029259.

Asciutti et al., Diverse mechanisms of Wnt activation and effects of pathway inhibition on proliferation of human gastric carcinoma cells. Oncogene. Feb. 24, 2011;30(8):956-66. doi: 10.1038/onc.2010.475. Epub Nov. 1, 2010.

Audrito et al., NAMPT and NAPRT: Two Metabolic Enzymes With Key Roles in Inflammation. Front Oncol. Mar. 19, 2020;10:358. doi: 10.3389/fonc.2020.00358.

Benito-Martin et al., Endogenous NAMPT dampens chemokine expression and apoptotic responses in stressed tubular cells. Biochim Biophys Acta. Feb. 2014;1842(2):293-303. doi: 10.1016/j.bbadis.2013.11.022. Epub Nov. 25, 2013.

Ben-Porath et al., An embryonic stem cell-like gene expression signature in poorly differentiated aggressive human tumors. Nat Genet. May 2008;40(5):499-507. doi: 10.1038/ng.127.

Bermudez et al., Leukocyte Overexpression of Intracellular NAMPT Attenuates Atherosclerosis by Regulating PPARγ-Dependent Monocyte Differentiation and Function. Arterioscler Thromb Vasc Biol. Jun. 2017;37(6):1157-1167. doi: 10.1161/ATVBAHA.116.308187. Epub Apr. 13, 2017.

Bonnet et al., Human acute myeloid leukemia is organized as a hierarchy that originates from a primitive hematopoietic cell. Nat Med. Jul. 1997;3(7):730-7. doi: 10.1038/nm0797-730.

Busso et al., Pharmacological inhibition of nicotinamide phosphoribosyltransferase/visfatin enzymatic activity identifies a new inflammatory pathway linked to NAD. PLoS One. May 21, 2008;3(5):e2267. doi: 10.1371/journal.pone.0002267.

Cancer Genome Atlas Research Network, Comprehensive molecular characterization of gastric adenocarcinoma. Nature. Sep. 11, 2014;513(7517):202-9. doi: 10.1038/nature13480. Epub Jul. 23, 2014.

Chen et al., A restricted cell population propagates glioblastoma growth after chemotherapy. Nature. Aug. 23, 2012;488(7412):522-6. doi: 10.1038/nature11287.

(56) References Cited

OTHER PUBLICATIONS

Chen et al., Endogenous Nampt upregulation is associated with diabetic nephropathy inflammatory-fibrosis through the NF-κB p65 and Sirt1 pathway; NMN alleviates diabetic nephropathy inflammatory-fibrosis by inhibiting endogenous Nampt. Exp Ther Med. Nov. 2017;14(5):4181-4193. doi: 10.3892/etm.2017.5098. Epub Sep. 1, 2017.
Chen et al., NAMPT inhibitor protects ischemic neuronal injury in rat brain via anti-neuroinflammation. Neuroscience. Jul. 25, 2017;356:193-206. doi: 10.1016/j.neuroscience.2017.05.022. Epub May 19, 2017.
Colombo et al., Neutralization of extracellular NAMPT (nicotinamide phosphoribosyltransferase) ameliorates experimental murine colitis. J Mol Med (Berl). Apr. 2020;98(4):595-612. doi: 10.1007/s00109-020-01892-0. Epub Apr. 27, 2020.
Esposito et al., The NAMPT inhibitor FK866 reverts the damage in spinal cord injury. J Neuroinflammation. Apr. 10, 2012;9:66. doi: 10.1186/1742-2094-9-66.
Galli et al., Recent Advances in NAMPT Inhibitors: A Novel Immunotherapie Strategy. Front Pharmacol. May 12, 2020;11:656. doi: 10.3389/fphar.2020.00656. 20 pages.
Gerner et al., NAD metabolism fuels human and mouse intestinal inflammation. Gut. Oct. 2018;67(10):1813-1823. doi: 10.1136/gutjnl-2017-314241. Epub Sep. 6, 2017.
Gerner et al., Targeting NAD immunometabolism limits severe graft-versus-host disease and has potent antileukemic activity. Leukemia. Jul. 2020;34(7):1885-1897. doi: 10.1038/s41375-020-0709-0. Epub Jan. 23, 2020.
Guinney et al., The consensus molecular subtypes of colorectal cancer. Nat Med. Nov. 2015;21(11):1350-6. doi: 10.1038/nm.3967. Epub Oct. 12, 2015.
Hadjimichael et al., Common stemness regulators of embryonic and cancer stem cells. World J Stem Cells. Oct. 26, 2015;7(9):1150-84. doi: 10.4252/wjsc.v7.i9.1150.
Kim et al., NAMPT Is an Essential Regulator of RA-Mediated Periodontal Inflammation. J Dent Res. Jun. 2017;96(6):703-711. doi: 10.1177/0022034517690389. Epub Feb. 6, 2017.
Laranjeira et al., Therapeutic target discovery and drug development in cancer stem cells for leukemia and lymphoma: from bench to the clinic. Expert Opin Drug Discov. Nov. 2016;11(11):1071-1080. doi: 10.1080/17460441.2016.1236785. Epub Sep. 25, 2016.
Le et al., Inhibition of lactate dehydrogenase A induces oxidative stress and inhibits tumor progression. Proc Natl Acad Sci U S A. Feb. 2, 2010;107(5):2037-42. doi: 10.1073/pnas.0914433107. Epub Jan. 19, 2010.
Li et al., Epigenetic regulation of NfatC1 transcription and osteoclastogenesis by nicotinamide phosphoribosyl transferase in the pathogenesis of arthritis. Cell Death Discov. Feb. 6, 2019;5:62. doi: 10.1038/s41420-018-0134-6.
Moreno-Vinasco et al., Nicotinamide phosphoribosyltransferase inhibitor is a novel therapeutic candidate in murine models of inflammatory lung injury. Am J Respir Cell Mol Biol. Aug. 2014;51(2):223-8. doi: 10.1165/rcmb.2012-0519OC.
Moschen et al., A key role for Pre-B cell colony-enhancing factor in experimental hepatitis. Hepatology. Aug. 2011;54(2):675-86. doi: 10.1002/hep.24416. Epub Jun. 26, 2011.
Moschen et al., Visfatin, an adipocytokine with proinflammatory and immunomodulating properties. J Immunol. Feb. 1, 2007;178(3):1748-58. doi: 10.4049/jimmunol.178.3.1748.
O'Brien et al., A human colon cancer cell capable of initiating tumour growth in immunodeficient mice. Nature. Jan. 4, 2007;445(7123):106-10. doi: 10.1038/nature05372. Epub Nov. 19, 2006.
Romacho et al., Extracellular PBEF/NAMPT/visfatin activates pro-inflammatory signalling in human vascular smooth muscle cells through nicotinamide phosphoribosyltransferase activity. Diabetologia. Nov. 2009;52(11):2455-2463. doi: 10.1007/s00125-009-1509-2. Epub Aug. 29, 2009.
Roulsten et al., New strategies to maximize therapeutic opportunities for NAMPT inhibitors in oncology. Mol Cell Oncol. Jun. 10, 2015;3(1):e1052180. doi: 10.1080/23723556.2015.1052180.
Saunders et al., A DLL3-targeted antibody-drug conjugate eradicates high-grade pulmonary neuroendocrine tumor-initiating cells in vivo. Sci Transl Med. Aug. 26, 2015;7(302):302ra136. doi: 10.1126/scitranslmed.aac9459.
Seyfried et al., On the origin of cancer metastasis. Crit Rev Oncog. 2013;18(1-2):43-73. doi: 10.1615/critrevoncog.v18.i1-2.40.
Stromsdorfer et al., NAMPT-Mediated NAD(+) Biosynthesis in Adipocytes Regulates Adipose Tissue Function and Multi-organ Insulin Sensitivity in Mice. Cell Rep. Aug. 16, 2016;16(7):1851-60. doi: 10.1016/j.celrep.2016.07.027. Epub Aug. 4, 2016.
Taniguchi et al., Cancer stem cells in human gastrointestinal cancer. Cancer Sci. Nov. 2016;107(11):1556-1562. doi: 10.1111/cas.13069.
Travelli et al., Nicotinamide Phosphoribosyltransferase Acts as a Metabolic Gate for Mobilization of Myeloid-Derived Suppressor Cells. Cancer Res. Apr. 15, 2019;79(8):1938-1951. doi: 10.1158/0008-5472.CAN-18-1544. Epub Feb. 18, 2019.
Vallejo et al., Visfatin impairs endothelium-dependent relaxation in rat and human mesenteric microvessels through nicotinamide phosphoribosyltransferase activity. PLoS One. 2011;6(11):e27299. doi: 10.1371/journal.pone.0027299. Epub Nov. 3, 2011.
Wu et al., Targeting of nicotinamide phosphoribosyltransferase enzymatic activity ameliorates lung damage induced by ischemia/reperfusion in rats. Respir Res. Apr. 24, 2017;18(1):71. doi: 10.1186/s12931-017-0557-2.
Yerxa et al., New Visions in Ophthalmic Drug Development. Drug Discovery World. Dec. 14, 2002. 18 pages. Retrieved from <https://www.ddw-online.com/new-visions-in-ophthalmic-drug-development-1091-200212/>.
Zhang et al., Visfatin is regulated by interleukin-6 and affected by the PPAR-γ pathway in BeWo cells. Mol Med Rep. Jan. 2019;19(1):400-406. doi: 10.3892/mmr.2018.9671. Epub Nov. 20, 2018.
Zheng et al., FK866 attenuates sepsis-induced acute lung injury through c-jun-N-terminal kinase (JNK)-dependent autophagy. Life Sci. Jun. 1, 2020;250:117551. doi: 10.1016/j.lfs.2020.117551. Epub Mar. 13, 2020.
Evans et al., Suppression of leukocyte infiltration and cartilage degradation by selective inhibition of pre-B cell colony-enhancing factor/visfatin/nicotinamide phosphoribosyltransferase: Apo866-mediated therapy in human fibroblasts and murine collagen-induced arthritis. Arthritis Rheum. Jul. 2011;63(7):1866-77. doi: 10.1002/art.30338.
Wang et al., Nicotinamide phosphoribosyltransferase protects against ischemic stroke through SIRT1-dependent adenosine monophosphate-activated kinase pathway. Ann Neurol. Feb. 2011;69(2):360-74. doi: 10.1002/ana.22236. Epub Jan. 19, 2011.
Canadian Office Action, mailed Nov. 14, 2024, in connection with Application No. 3,135,740.
International Preliminary Report on Patentability, mailed Nov. 23, 2023, in connection with Application No. PCT/US2022/029259.
[No Author Listed], Benzamide, 3-(1-acetyl-1,2,3,4-tetrahydro-6-quinolinyl)-N-(3-Isoxazolylmethyl)-N-methyl-. CAS Registry File RN 2109509-83-1. STN Entry Date Aug. 7, 2017. 1 page.
[No Author Listed], Benzamide, 4-(1-acetyl-2,3-dihydro-1H-indol-5-yl)-N-(1-phenylethyl)-. CAS Registry File RN 1359334-09-0. STN Entry Date Mar. 2, 2012. 1 page.
[No Author Listed], Benzamide, 4-(1-acetyl-2,3-dihydro-1H-indol-5-yl)-N-(2-furanylmethyl)-. CAS Registry File RN 1358036-86-8. STN Entry Date Feb. 28, 2012. 1 page.
[No Author Listed], Benzamide, 4-(1-acetyl-2,3-dihydro-1H-indol-5-yl)-N-(2-thienylmethyl)-. CAS Registry File RN 1358948-71-6. STN Entry Date Mar. 1, 2012. 1 page.
[No Author Listed], Benzamide, 4-(1-acetyl-2,3-dihydro-1H-indol-5-yl)-N-[(1,3,5-trimethyl-1H-pyrazol-4-yl)methyl]-. CAS Registry File RN 1189708-01-7. STN Entry Date Oct. 23, 2009. 1 page.
[No Author Listed], Benzamide, 4-(1-acetyl-2,3-dihydro-1H-indol-5-yl)-N-[(5-methyl-2-furanyl)methyl]-. CAS Registry File RN 1358617-91-0. STN Entry Date Feb. 29, 2012. 1 page.
[No Author Listed], Benzamide, 4-[2,3-dihydro-1-(1-oxopropyl)-1H-indol-5-yl]-N-(2- thienylmethyl)-. CAS Registry File RN 1358617-23-8. STN Entry Date Feb. 29, 2012. 1 page.

(56) References Cited

OTHER PUBLICATIONS

[No Author Listed], Benzamide, 4-[2,3-dihydro-1-(1-oxopropyl)-1H-indol-5-yl]-N-[(1,3,5-trimethyl-1H-pyrazol-4-yl)methyl]-. CAS Registry File RN 1189881-08-0. STN Entry Date Oct. 25, 2009. 1 page.

[No Author Listed], Benzamide, 4-[2,3-dihydro-1-(1-oxopropyl)-1H-indol-5-yl]-N-[(5-methyl-2-furanyl)methyl]-. CAS Registry File RN 1358562-49-8. STN Entry Date Feb. 29, 2012. 1 page.

[No Author Listed], CAS Registry File RN 1359381-51-3. STN Entry Date Mar. 2, 2012.

[No Author Listed], CAS Registry File RN 1359381-43-3. STN Entry Date Mar. 2, 2012.

[No Author Listed], CAS Registry File RN 1359381-05-7. STN Entry Date Mar. 2, 2012.

[No Author Listed], CAS Registry File RN 1359369-01-9. STN Entry Date Mar. 2, 2012.

[No Author Listed], CAS Registry File RN 1359351-05-5. STN Entry Date Mar. 2, 2012.

[No Author Listed], CAS Registry File RN 1359202-70-2. STN Entry Date Mar. 1, 2012.

[No Author Listed], CAS Registry File RN 1358948-48-7. STN Entry Date Mar. 1, 2012.

[No Author Listed], CAS Registry File RN 1358948-13-6. STN Entry Date Mar. 1, 2012.

[No Author Listed], CAS Registry File RN 1358942-68-3. STN Entry Date Mar. 1, 2012.

[No Author Listed], CAS Registry File RN 1358931-36-8. STN Entry Date Mar. 1, 2012.

[No Author Listed], CAS Registry File RN 1358814-41-1. STN Entry Date Feb. 29, 2012.

[No Author Listed], CAS Registry File RN 1358814-23-9. STN Entry Date Feb. 29, 2012.

[No Author Listed], CAS Registry File RN 1358807-11-0. STN Entry Date Feb. 29, 2012.

[No Author Listed], CAS Registry File RN 1358668-90-2. STN Entry Date Feb. 29, 2012.

[No Author Listed], CAS Registry File RN 1358618-13-9. STN Entry Date Feb. 29, 2012.

[No Author Listed], CAS Registry File RN 1358617-31-8. STN Entry Date Feb. 29, 2012.

[No Author Listed], CAS Registry File RN 1358617-00-1. STN Entry Date Feb. 29, 2012.

[No Author Listed], CAS Registry File RN 1358481-23-8. STN Entry Date Feb. 29, 2012.

[No Author Listed], CAS Registry File RN 1358481-15-8. STN Entry Date Feb. 29, 2012.

[No Author Listed], CAS Registry File RN 1358480-80-4. STN Entry Date Feb. 29, 2012.

[No Author Listed], CAS Registry File RN 1358384-20-9. STN Entry Date Feb. 29, 2012.

[No Author Listed], CAS Registry File RN 1358384-07-2. STN Entry Date Feb. 29, 2012.

[No Author Listed], CAS Registry File RN 1358383-89-7. STN Entry Date Feb. 29, 2012.

[No Author Listed], CAS Registry File RN 1358383-49-9. STN Entry Date Feb. 29, 2012.

[No Author Listed], CAS Registry File RN 1358368-86-1. STN Entry Date Feb. 29, 2012.

[No Author Listed], CAS Registry File RN 1358302-05-2. STN Entry Date Feb. 29, 2012.

[No Author Listed], CAS Registry File RN 1358036-89-1. STN Entry Date Feb. 28, 2012.

[No Author Listed], CAS Registry File RN 1358036-74-4. STN Entry Date Feb. 28, 2012.

[No Author Listed], CAS Registry File RN 1358017-42-1. STN Entry Date Feb. 28, 2012.

[No Author Listed], CAS Registry File RN 1357757-07-3. STN Entry Date Feb. 28, 2012.

[No Author Listed], CAS Registry File RN 1357756-25-2. STN Entry Date Feb. 28, 2012.

Brucoli et al., Efficient solid-phase synthesis of a library of distamycin analogs containing novel biaryl motifs on SynPhase Lanterns. J Comb Chem. Jul.-Aug. 2009;11(4):576-86. doi: 10.1021/cc900009r.

Golub et al., Molecular classification of cancer: class discovery and class prediction by gene expression monitoring. Science. Oct. 15, 1999;286(5439):531-7. doi: 10.1126/science.286.5439.531.

Honma et al., Antiallergic agents. 2. N-(1H-tetrazol-5-yl)-6-phenyl-2-pyridinecarboxamides. J Med Chem. Oct. 1983;26(10):1499-504. doi: 10.1021/jm00364a026.

Singh et al., Small Molecule Inhibitor of NRF2 Selectively Intervenes Therapeutic Resistance in KEAP1-Deficient NSCLC Tumors. ACS Chem Biol. Nov. 18, 2016;11(11):3214-3225. doi: 10.1021/acschembio.6b00651. Epub Oct. 17, 2016.

CANCER TREATMENTS TARGETING CANCER STEM CELLS

RELATED APPLICATIONS

This application is a national stage filing under 35 U.S.C. § 371 of International PCT Application PCT/US2020/059329, filed Nov. 6, 2020, which claims priority under 35 U.S.C. § 119 (e) to U.S. Provisional Application, U.S. Ser. No. 62/931,531, filed Nov. 6, 2019, each of which is incorporated herein by reference.

BACKGROUND OF THE INVENTION

Cancer is ubiquitous and despite medical advances, remains among the leading cause of death worldwide. In 2017, an estimated 1.7 million new cases of cancer were diagnosed and 600,000 people died from the disease.[1] Cancer is the second leading cause of death globally and nearly 1 in 6 deaths is due to cancer. The number of new cases is expected to rise by about 70% over the next 2 decades. The economic impact of cancer is significant and is increasing. The total annual economic cost of cancer in 2010 was estimated at approximately 1.16 trillion US dollars.[2]

Cancer is a generic term for a large group of diseases that can affect any part of the body. Other terms used are malignant tumors and neoplasms. Cancer arises from the transformation of normal cells into tumor cells in multistage process that generally progresses from a pre-cancerous lesion to a malignant tumor. One defining feature of cancer is the rapid creation of abnormal cells that grow beyond their usual boundaries, and which can then invade adjoining parts of the body and spread to other organs, the latter process referred to as metastasizing. Metastases are a major cause of death from cancer. The most common cause of cancer death are cancers of lung, liver, colorectal, stomach, and breast.

While there has been some progress in treating subsets of cancer types, the average cancer death rate is still extremely high, with little overall improvement in the ongoing cancer crisis. Nearly all modern cancer treatments, including chemotherapy, targeted therapy, and immunotherapy, focus on de-bulking tumors without targeting the most dangerous cells in the tumor: cancer stem cells. Cancer stem cells are responsible for the spread of cancer cells throughout the body, the growth of tumors, cancer's resistance to chemotherapy, and the recurrence of tumors after treatment or surgical removal.[3,4] Because current treatments do not target the cancer stem cell population, they frequently lead to the rise of resistant tumors and continued cancer spread.

SUMMARY OF THE INVENTION

The discovery of cancer stem cells provides an opportunity to merge the fields of oncology and stem cell biology.[5,6] By targeting what makes cancer so dangerous—the embryonic stem cell or adult stem cell properties of cancer stem cells that form the basis for cancer growth, spread, and resistance—the development of effective and non-toxic therapies can be achieved via a strategy called cancer containment therapy. Therapies that can both diminish tumor bulk and disrupt cancer stem cells will change cancer treatment.[7]

Described herein are compounds that force differentiation of cancer stem cells, inhibiting the signaling pathways required for metastasis, which are the same pathways used by stem cells during differentiation and development.[8,9] These properties can be safely targeted because they only occur in stem cells and not healthy adult tissue.

Described herein are compounds that modulate nicotinamide phosphoribosyltransferase (NAMPT), the production of nicotinamide mononucleotide (NMN), the production of nicotinamide adenine dinucleotide (NAD), NAMPT signaling, a NAMPT pathway, and/or cellular metabolism.

These compounds will be more effective than traditional cancer treatments in decreasing tumor growth, prolonging life, and/or preventing metastasis and recurrence. And because the reactivation of embryonic properties is a property shared by many kinds of tumors, cancer containment therapy is expected to be effective on many different types of cancer, including leukemia and cancer of the colon, stomach, prostate, testicles, and breast.

Compounds, methods, compositions, uses, and kits that allow for treating proliferative diseases, benign neoplasms, and cancer are disclosed herein.

In one aspect, the disclosure provides compounds of Formula (0):

(0)

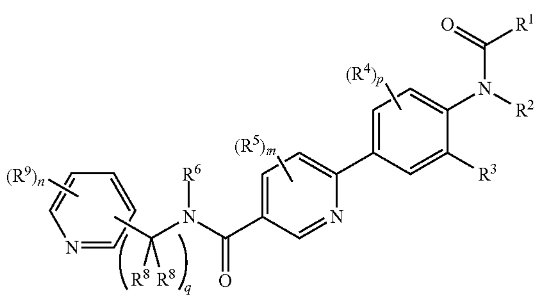

or a pharmaceutically acceptable salt, solvate, hydrate, polymorph, co-crystal, tautomer, stereoisomer, isotopically labeled derivative, or prodrug thereof, wherein the variables recited in Formula (0) are as described herein. In certain aspects, a compound of Formula (0) is of Formula (0a), (0b), or (0c):

(0a)

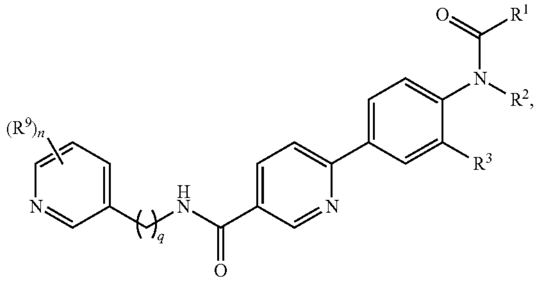

-continued (0b)

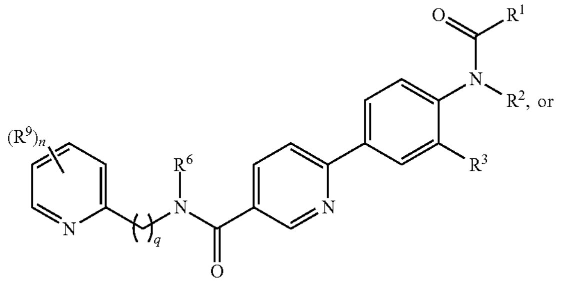

or (0c)

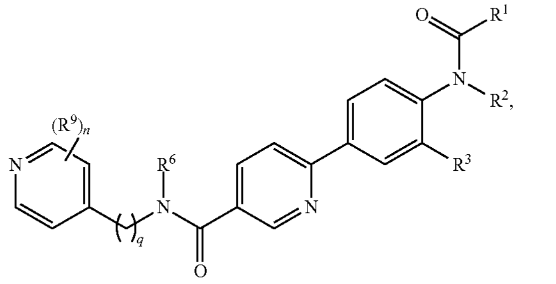

or a pharmaceutically acceptable salt, solvate, hydrate, polymorph, co-crystal, tautomer, stereoisomer, isotopically labeled derivative, or prodrug thereof, wherein the variables are as described herein.

In one aspect, the disclosure provides compounds of Formula (I):

(I)

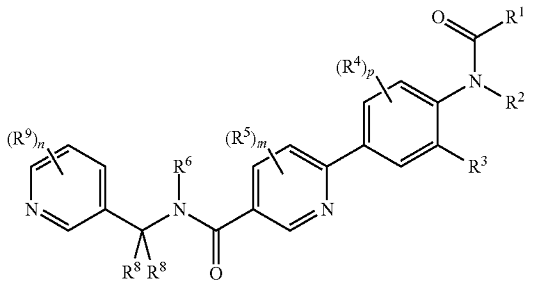

or a pharmaceutically acceptable salt, solvate, hydrate, polymorph, co-crystal, tautomer, stereoisomer, isotopically labeled derivative, or prodrug thereof, wherein the variables recited in Formula (I) are as described herein. In certain aspects, a compound of Formula (I) is of Formula (Ia):

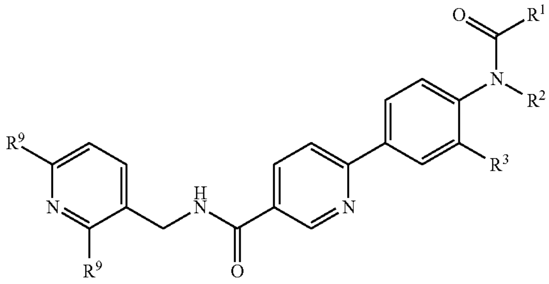

or a pharmaceutically acceptable salt, solvate, hydrate, polymorph, co-crystal, tautomer, stereoisomer, isotopically labeled derivative, or prodrug thereof, wherein the variables recited in Formula (Ia) are as described herein. In certain aspects, a compound of Formula (I) is of the formula:

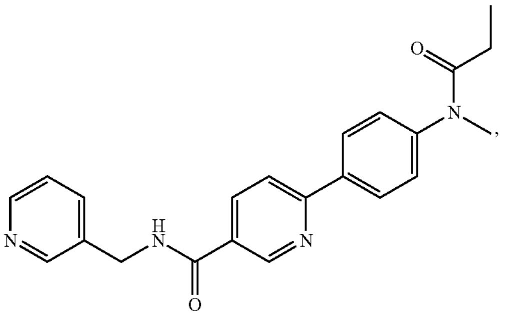

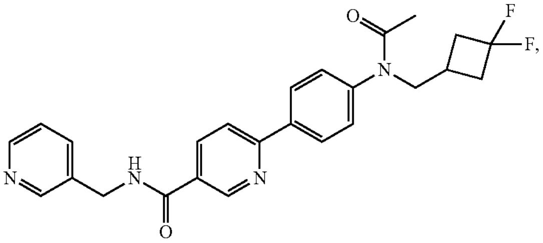

or

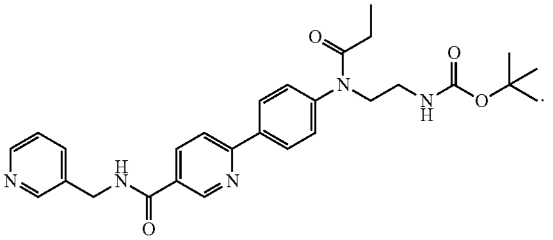

In another aspect, the present disclosure provides methods for treating cancer comprising administering to a subject a therapeutically effective amount of a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof, wherein the variables recited in Formula (0) or (I) are as described herein.

In certain embodiments, the cancer comprises cancer stem cells. In certain embodiments, the cancer involves or is associated with cancer stem cells. In certain embodiments, the cancer is colorectal cancer, gastric cancer, gastrointestinal stromal tumor, ovarian cancer, lung cancer, breast cancer, pancreatic cancer, testicular cancer, prostate cancer, liver cancer, or endometrial cancer. In certain embodiments, the cancer is leukemia (e.g., acute myeloid leukemia). In certain embodiments, the cancer is lymphoma. In certain embodiments, the cancer is multiple myeloma. In certain embodiments, the subject is in need of regenerative medicine or therapy.

In yet another aspect, the present disclosure provides methods and uses comprising contacting a cell with an effective amount of a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods and uses comprising killing a cell with an effective amount of a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods and uses comprising contacting a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof, with a cell, tissue, or biological sample to inhibit tumor growth, regenerate or differentiate one or more cells, prevent metastasis, kill cancer cells, reduce embryonic properties or adult stem cell properties of one or more cells, reduce cell viability, and/or prevent cell proliferation.

In certain aspects, the present disclosure provides methods of inhibiting NAMPT in a subject comprising administering to the subject a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of treating a disease or disorder in a subject by inhibiting NAMPT in a subject comprising administering to the subject a therapeutically effective amount of a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of inhibiting production of nicotinamide adenine dinucleotide in a subject, the method comprising administering to the subject a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of treating a disease or disorder in a subject by inhibiting the production of nicotinamide adenine dinucleotide in the subject, the method comprising administering to the subject a therapeutically effective amount of compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of inhibiting production of nicotinamide mononucleotide in a subject, the method comprising administering to the subject a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of treating a disease or disorder in a subject by inhibiting the production of nicotinamide mononucleotide in the subject, the method comprising administering to the subject a therapeutically effective amount of compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of reducing inflammatory cell infiltration in a subject, the method comprising administering to the subject a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of treating a disease or disorder in a subject by reducing inflammatory cell infiltration in the subject, the method comprising administering to the subject a therapeutically effective amount of compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of reducing cell proliferation in a subject, the method comprising administering to the subject a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of treating a disease or disorder in a subject by reducing cell proliferation in the subject, the method comprising administering to the subject a therapeutically effective amount of compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of reducing cellular metabolic activity or state in a subject, the method comprising administering to the subject a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of treating a disease or disorder in a subject by reducing cellular metabolic activity or state in the subject, the method comprising administering to the subject a therapeutically effective amount of a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof In certain aspects, the present disclosure provides methods of decreasing inflammatory activity in a subject, the method comprising administering to the subject a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of treating a disease or disorder in a subject by decreasing inflammatory activity in the subject, the method comprising administering to the subject a therapeutically effective amount of a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof In certain aspects, the present disclosure provides methods of decreasing NAMPT signaling in a subject, the method comprising administering to the subject a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of treating a disease or disorder in a subject by decreasing NAMPT signaling in the subject, the method comprising administering to the subject a therapeutically effective amount of a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of inhibiting a NAMPT pathway in a subject, the method comprising administering to the subject a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of treating a disease or disorder in a subject by inhibiting a NAMPT pathway in the subject, the method comprising administering to the subject a therapeutically effective amount of a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of inhibiting a NAMPT pathway in a cell, tissue, or biological sample, the method comprising contacting the cell, tissue, or biological sample with a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of decreasing NAMPT signaling in a cell, tissue, or biological sample, the method comprising contacting the cell, tissue, or biological sample with a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of decreasing inflammatory activity in a cell, tissue, or biological sample, the method comprising contacting the cell, tissue, or biological sample with a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of reducing cellular metabolic activity or state in a cell, tissue, or biological sample, the method comprising contacting the cell, tissue, or biological sample with a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of reducing cell proliferation in a cell, tissue, or biological sample, the method comprising contacting the cell, tissue, or biological sample with a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of reducing inflammatory cell infiltration in a cell, tissue, or biological sample, the method comprising contacting the cell, tissue, or biological sample with a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of inhibiting production of nicotinamide adenine dinucleotide in a cell, tissue, or biological sample, the method comprising contacting the cell, tissue, or biological sample with a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of inhibiting production of nicotinamide mononucleotide in a cell, tissue, or biological sample, the method comprising contacting the cell, tissue, or biological sample with a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In certain aspects, the present disclosure provides methods of inhibiting NAMPT in a cell, tissue, or biological sample, the method comprising contacting the cell, tissue, or biological sample with a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In some embodiments, the contacting is in vitro or ex vivo.

In certain aspects, the present disclosure provides methods of treating a disease or disorder in a subject comprising administering to the subject a therapeutically effective amount of a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof.

In some aspects, the present disclosure provides compositions comprising a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof; and optionally a pharmaceutically acceptable excipient. In certain embodiments, the composition is a pharmaceutical composition. In certain embodiments, the composition further comprises an additional pharmaceutical agent.

In certain aspects, the present disclosure provides methods of treating a disease or disorder in a subject in need thereof comprising administering to the subject a therapeutically effective amount of a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof, or composition disclosed herein, and an additional pharmaceutical agent. In some embodiments, the additional pharmaceutical agent is administered, before, concurrently with, or after the compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof, or composition disclosed herein.

In further aspects, the present disclosure provides kits comprising a compound disclosed herein (e.g., a compound of Formula (0) or (I)), or a pharmaceutically acceptable salt, solvate, hydrate, polymorph, co-crystal, tautomer, stereoisomer, isotopically labeled derivative, or prodrug thereof; or a composition as described herein; and instructions for using the compound, pharmaceutically acceptable salt, solvate, hydrate, polymorph, co-crystal, tautomer, stereoisomer, isotopically labeled derivative, prodrug, or pharmaceutical composition.

The details of certain embodiments of the invention are set forth in the Detailed Description of Certain Embodiments, as described below. Other features, objects, and advantages of the invention will be apparent from the Definitions, Examples, and Claims.

Definitions

For convenience, certain terms employed herein, in the specification, examples and appended claims are collected herein.

Unless otherwise required by context, singular terms shall include pluralities, and plural terms shall include the singular.

The language "in some embodiments" and the language "in certain embodiments" are used interchangeably.

The following definitions are more general terms used throughout the present application:

The singular terms "a," "an," and "the" include plural references unless the context clearly indicates otherwise. Similarly, the word "or" is intended to include "and" unless the context clearly indicates otherwise.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2% or 1% of a given value or range of values.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Michael B. Smith, *March's Advanced* Organic Chemistry, 7$^{th}$ Edition, John Wiley & Sons, Inc., New York, 2013; Richard C. Larock, Comprehensive Organic Transformations, John Wiley & Sons, Inc., New York, 2018; and Carruthers, Some Modern Methods of Organic Synthesis, 3$^{rd}$ Edition, Cambridge University Press, Cambridge, 1987.

Compounds described herein can include one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H. Tables of Resolving Agents and Optical Resolutions p. 268 (E. L. Eliel, Ed., Univ. of Notre Dame Press, Notre Dame, IN 1972). The disclosure additionally encompasses compounds as individual isomers substantially free of other isomers, and alternatively, as mixtures of various isomers.

In a formula, ∿∿ is a single bond where the stereochemistry of the moieties immediately attached thereto is not specified, - - - is absent or a single bond, and $\overset{\text{- - -}}{\text{———}}$ or $\overset{\text{———}}{\text{- - -}}$ is a single or double bond.

Unless otherwise provided, a formula depicted herein includes compounds that do not include isotopically enriched atoms and also compounds that include isotopically enriched atoms. Compounds that include isotopically enriched atoms may be useful as, for example, analytical tools, and/or probes in biological assays.

The term "aliphatic" includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups (e.g., halo, such as fluorine). As will be appreciated by one of ordinary skill in the art, "aliphatic" is intended herein to include alkyl, alkenyl, alkynyl, cycloalkyl, cycloalkenyl, and cycloalkynyl moieties.

When a range of values ("range") is listed, it is intended to encompass each value and sub-range within the range. A range is inclusive of the values at the two ends of the range unless otherwise provided. For example, "an integer between 1 and 4" refers to 1, 2, 3, and 4. For example "$C_{1-6}$ alkyl" is intended to encompass, $C_1$, $C_2$, $C_3$, $C_4$, $C_5$, $C_6$, $C_{1-6}$, $C_{1-6}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-s}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$), n-dodecyl ($C_{12}$) and the like. Unless otherwise specified, each instance of an alkyl group is independently optionally substituted, e.g., unsubstituted (an "unsubstituted alkyl") or substituted (a "substituted alkyl") with one or more substituents (e.g., halogen, such as F). In certain embodiments, the alkyl group is unsubstituted $C_{1-12}$ alkyl (e.g., —$CH_3$(Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted N-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)). The attachment point of alkyl may be a single bond (e.g., as in —$CH_3$), double bond (e.g., as in =$CH_2$), or triple bond (e.g., as in ≡CH). The moieties=$CH_2$ and ≡CH are also alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms and one or more (e.g., two, three, or four, as valency permits) carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$,

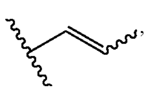, or 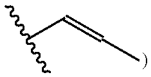)

may be in the (E)- or (Z)-configuration.

"Alkynyl" refers to a radical of a straight-chain or branched hydrocarbon group having from 2 to 20 carbon atoms and one or more (e.g., two, three, or four, as valency permits) carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 13 ring carbon atoms ("$C_{3-13}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_5$), cyclooctenyl ($C_5$), bicyclo[2.2.1]heptanyl ($C_7$), bicyclo[2.2.2]octanyl ($C_5$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or Spiro ring system such as a bicyclic system ("bicyclic carbocyclyl"). Carbocyclyl can be saturated, and saturated carbocyclyl is referred to as "cycloalkyl." In some embodiments, carbocyclyl is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{3-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_5$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. Carbocyclyl can be partially unsaturated. Carbocyclyl may include zero, one, or more (e.g., two, three, or four, as valency permits) C═C double bonds in all the rings of the carbocyclic ring system that are not aromatic or heteroaromatic. Carbocyclyl including one or more (e.g., two or three, as valency permits) C═C double bonds in the carbocyclic ring is referred to as "cycloalkenyl." Carbocyclyl including one or more (e.g., two or three, as valency permits) C═C triple bonds in the carbocyclic ring is referred to as "cycloalkynyl." Carbocyclyl includes aryl. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl. In certain embodiments, the carbocyclyl is substituted or unsubstituted, 3- to 7-membered, and monocyclic. In certain embodiments, the carbocyclyl is substituted or unsubstituted, 5- to 13-membered, and bicyclic.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl (C) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_5$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. In certain embodiments, the carbocyclyl includes 0, 1, or 2 C═C double bonds in the carbocyclic ring system, as valency permits.

"Carbocyclylalkyl", "X- to X-membered carbocyclyl-$C_{x-x}$ alkyl", or "X- to X-membered carbocyclyl-$C_{x-x}$-alkyl", wherein each instance of X is an integer, is a subset of "alkyl" and refers to an alkyl group substituted by a carbocyclyl group, wherein the point of attachment is on the alkyl moiety. For example, a 3- to 13-membered carbocyclyl-$C_{1-12}$-alkyl group refers to a $C_{1-12}$ alkyl group (e.g., methyl, ethyl propyl, isopropyl, butyl, isobutyl, sec-butyl, tert-butyl) substituted by a 3- to 13-membered carbocyclyl group (e.g., cyclopropyl, cyclobutyl, cyclopropyl, cyclopentyl, cyclohexyl).

"Heterocyclyl" or "heterocyclic" refers to a radical of a 3- to 13-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"). A heterocyclyl group can be saturated or can be partially unsaturated. Heterocyclyl may include zero, one, or more (e.g., two, three, or four, as valency permits) double bonds in all the rings of the heterocyclic ring system that are not aromatic or heteroaromatic. Partially unsaturated heterocyclyl groups includes heteroaryl. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl. In certain embodiments, the heterocyclyl is substituted or unsubstituted, 3- to 7-membered, and monocyclic. In certain embodiments, the heterocyclyl is substituted or unsubstituted, 5- to 13-membered, and bicyclic. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include aziridinyl, oxiranyl, or thiiranyl. Exemplary 4-membered heterocyclyl groups containing one heteroatom include azetidinyl, oxetanyl and thietanyl. Exemplary 5-membered heterocyclyl groups containing one heteroatom include tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include dioxolanyl, oxasulfuranyl, disulfuranyl, and oxazolidin-2-one. Exemplary 5-membered heterocyclyl groups containing three heteroatoms include triazolinyl, oxadiazolinyl, and thiadiazolinyl. Exemplary 6-membered heterocyclyl groups containing one heteroatom include piperidinyl, tetrahydropyranyl, dihydropyridinyl, and thianyl. Exemplary 6-membered heterocyclyl groups containing two heteroatoms include piperazinyl, morpholinyl, dithianyl, and dioxanyl. Exemplary 6-membered heterocyclyl groups containing two heteroatoms include triazinanyl. Exemplary 7-membered heterocyclyl groups containing one heteroatom include azepanyl, oxepanyl and thiepanyl. Exemplary 8-membered heterocyclyl groups containing one heteroatom include azocanyl, oxecanyl, and thiocanyl. Exemplary 5-membered heterocyclyl groups fused to a $C_6$ aryl ring (also referred to herein as a 5,6-bicyclic heterocyclic ring) include indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

"Heterocyclylalkyl", "X- to X-membered heterocyclyl-$C_{x-x}$ alkyl", or "X- to X-membered heterocyclyl-$C_{x-x}$-alkyl", wherein each instance of X is an integer, is a subset of "alkyl" and refers to an alkyl group substituted by a heterocyclyl group, wherein the point of attachment is on the alkyl moiety. For example, a 3- to 13-membered heterocyclyl-$C_{1-12}$-alkyl group refers to a $C_{1-12}$ alkyl group (e.g., methyl, ethyl propyl, isopropyl, butyl, isobutyl, sec-butyl, tert-butyl) substituted by a 3- to 13-membered heterocyclyl group (e.g., oxiranyl, oxetanyl, oxadiazolinyl, piperidinyl, tetrahydropyranyl, piperazinyl, morpholinyl).

"Aryl" refers to a radical of a monocyclic or polycyclic (e.g., bicyclic or tricyclic) 4n+2 aromatic ring system (e.g., having 6, 10, or 14 electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of "alkyl" and refers to an alkyl group substituted by an aryl group, wherein the point of attachment is on the alkyl moiety.

"Heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

"Heteroaralkyl" is a subset of "alkyl" and refers to an alkyl group substituted by a heteroaryl group, wherein the point of attachment is on the alkyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include pyrrolyl, furanyl and thiophenyl. Exemplary 5-membered heteroaryl groups containing two heteroatoms include imidazolyl, pyrazolyl, oxazolyl, isoxazolyl, thiazolyl, and isothiazolyl. Exemplary 5-membered heteroaryl groups containing three heteroatoms include triazolyl, oxadiazolyl, and thiadiazolyl. Exemplary 5-membered heteroaryl groups containing four heteroatoms include tetrazolyl. Exemplary 6-membered heteroaryl groups containing one heteroatom include pyridinyl. Exemplary 6-membered heteroaryl groups containing two heteroatoms include pyridazinyl, pyrimidinyl, and pyrazinyl. Exemplary 6-membered heteroaryl groups containing three or four heteroatoms include triazinyl and tetrazinyl, respectively. Exemplary 7-membered heteroaryl groups containing one heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, aliphatic, alkyl, alkenyl, alkynyl, carbocyclyl, heteroalkyl, heteroalkenyl, heteroalkynyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, heteroalkyl, "substituted" or "unsubstituted" heteroalkenyl, "substituted" or "unsubstituted" heteroalkynyl, "substituted" or "unsubstituted", "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. Unless otherwise provided, a substituent on a polycyclic ring may be on any substitutable position of any one of the monocyclic rings of the polycyclic ring. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, $S(=O)R^{aa}$—$OS(=O)R^{aa}$, —$Si(R^{aa})_3$—$OSi(R^{aa})_3$—$C(=S)N(R^{bb})_2$, —$C(=O)SR^{aa}$, —$C(=S)SR^{aa}$, —SC(=S)SR—, —SC(=O)SR—, —$OC(=O)SR^{aa}$, $SC(=O)OR^{aa}$, —$SC(=O)R^{aa}$ $P(=O)(R^{aa})_2$, —$P(=O)(OR^{cc})_2$, —$OP(=O)(R^{aa})_2$, —$OP(=O)(OR^{cc})_2$, —$P(=O)(N(R^{b})_2)_2$, —$OP(=O)(N(R^{bb})_2)_2$, —$NR^{bb}P(=O)(R^{aa})_2$, —$NR^{bb}P(=O)(OR^{cc})_2$, —$NR^{bb}P(=O)(N(R^{bb})_2)_2$, —$P(R^{cc})_2$, —$P(OR^{cc})_2$, —$P(R^{cc})_3{}^+X^-$, —$P(OR^{cc})_3{}^+X^-$, —$P(R^{cc})_4$, —$P(OR^{cc})_4$, —$OP(R^{cc})_2$, —$OP(R^{cc})_3{}^+X^-$, —$OP(OR^{cc})_2$, —$OP(OR^{cc})_3{}^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion; or two geminal hydrogens on a carbon atom are replaced with the group =O, =S, =NN($R^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NRfff CO$_2$R$^{ee}$, —NRffffC(=O)N(R$^{ff}$)$_2$, —C(=NRffff)OR$^{ee}$, —OC(=NRffff)R$^{ee}$, —OC(=NRffff)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal Rddd substituents can be joined to form =O or =S; wherein X$^-$ is a counterion;

each instance of R$^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$alkynyl, $C_{3-10}$ carbocyclyl, 3-10 membered heterocyclyl, $C_6$ to aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3$$^+$X$^-$, —NH($C_{1-6}$ alkyl)$_2$$_+$X$^-$, —NH$_2$($C_{1-6}$ alkyl)$^+$X$^-$, —NH$_3$$^+$X$^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the carbon atom substituents are independently halogen, substituted (e.g., substituted with one or more halogen) or unsubstituted $C_{1-6}$ alkyl, —OR$^{aa}$, SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, oco$_2$R$^{aa}$, —OC(=O)N(R$^{bb}$)$_2$, —NR$^{bb}$C(=O)R$^{aa}$, —NR$^{b}$CO$_2$R$^{aa}$, or —NR$^{bb}$C(=O)N(R$^{bb}$)$_2$. In certain embodiments, the carbon atom substituents are independently halogen, substituted (e.g., substituted with one or more halogen) or unsubstituted $C_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$, wherein R$^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group.

In certain embodiments, the carbon atom substituents are independently halogen, substituted (e.g., substituted with one or more halogen) or unsubstituted $C_{1-6}$ alkyl, —$OR^{aa}$, —$SR^{aa}$, —$N(R^{bb})_2$, —CN, —SCN, or —$NO_2$. In certain embodiments, the carbon atom substituents are independently halogen, substituted (e.g., substituted with one or more halogen moieties) or unsubstituted $C_{1-6}$ alkyl, —$OR^{aa}$, —$SR^{aa}$, —$N(R^{bb})_2$, —CN, —SCN, or —$NO_2$, wherein $R^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_{32}$—, $HPO_4^2$—, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(OR^{cc})_2$, —P(═O)$(R^{aa})_2$, —P(═O)$(N(R^{cc})_2)_2$, $C_1$ 0 alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the nitrogen atom substituents are independently substituted (e.g., substituted with one or more halogen) or unsubstituted $C_{1-6}$ alkyl, —C(═O)$R^{aa}$, —$CO_2R^{aa}$, —C(═O)$N(R^{bb})_2$, or a nitrogen protecting group. In certain embodiments, the nitrogen atom substituents are independently substituted (e.g., substituted with one or more halogen) or unsubstituted $C_{1-6}$ alkyl, —C(═O)$R^{aa}$, —$CO_2R^{aa}$, —C(═O)$N(R^{bb})_2$, or a nitrogen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the nitrogen atom substituents are independently substituted (e.g., substituted with one or more halogen) or unsubstituted $C_{1-6}$ alkyl or a nitrogen protecting group.

In certain embodiments, the substituent present on a nitrogen atom is a nitrogen protecting group (also referred to as an amino protecting group). Nitrogen protecting groups include —OH, —$OR^{aa}$, —$N(R^{cc})_2$, —C(═O)$R^{aa}$, —C(═O)$N(R^{cc})_2$, —$CO_2R^{aa}$, $SO_2R^{aa}$, —C(═$NR^{cc}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in Protecting Groups in Organic Synthesis, T. W. Greene and P. G. M. Wuts, 3rd edition, John Wiley & Sons, 1999, incorporated herein by reference.

Amide nitrogen protecting groups (e.g., —C(═O)$R^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(═O)$OR^{aa}$) include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., $—S(=O)_2R^{aa}$) include p-toluenesulfonamide (Ts), benzenesulfonamide, 2,3,6, -trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylaminoN'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In some embodiments, two instances of a nitrogen protecting group together with the nitrogen atoms to which the nitrogen protecting groups are attached are N,N'-isopropylidenediamine.

In certain embodiments, a nitrogen protecting group is Bn, Boc, Cbz, Fmoc, trifluoroacetyl, triphenylmethyl, acetyl, or Ts.

In certain embodiments, the oxygen atom substituents are independently substituted (e.g., substituted with one or more halogen) or unsubstituted $C_{1-6}$ alkyl, $—C(=O)R^{aa}$, $—CO_2R^{aa}$, $—C(=O)N(R^{bb})_2$, or an oxygen protecting group. In certain embodiments, the oxygen atom substituents are independently substituted (e.g., substituted with one or more halogen) or unsubstituted $C_{1-6}$ alkyl, $—C(=O)R^{aa}$, $—CO_2R^{aa}$, $—C(=O)N(R^{bb})_2$, or an oxygen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include $—R^{aa}$, $—N(R^{bb})_2$, $—C(=O)SR—$, $—C(=O)R^{aa}$, $CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2—P(R^{cc})_3{}^+X^-$, $—P(OR^{cc})_2$, $—P(OR^{cc})_3{}^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the sulfur atom substituents are independently substituted (e.g., substituted with one or more halogen) or unsubstituted $C_{1-6}$ alkyl, —C(═O)$R^{aa}$, —$CO_2R^{aa}$, —C(═O)N$(R^{bb})_2$, or a sulfur protecting group. In certain embodiments, the sulfur atom substituents are independently substituted (e.g., substituted with one or more halogen) or unsubstituted $C_{1-6}$ alkyl, —C(═O)$R^{aa}$, —$CO_2R^{aa}$, —C(═O)N$(R^{bb})_2$, or a sulfur protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the sulfur atom substituents are independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). In some embodiments, each sulfur protecting group is selected from the group consisting of —$R^{aa}$, —N$(R^{bb})_2$, —C(═O)S$R^{aa}$, —C(═O)$R^{aa}$, —$CO_2R^{aa}$, —C(═O)N$(R^{bb})_2$, —C(═N$R^{bb}$)$R^{aa}$, —C(═N$R^{bb}$)O$R^{aa}$, —C(═N$R^{bb}$)N$(R^{bb})_2$, —S(═O)$R^{aa}$, —$SO_2R^{aa}$, —Si$(R^{aa})_3$, —P$(R^{cc})_2$, —P$(R^{cc})_3^+X^-$, —P$(OR^{cc})_2$, —P$(OR^{cc})_3^+X^-$, —P(═O)$(R^{aa})_2$, —P(═O)$(OR^{cc})_2$, and —P(═O)(N$(R^{bb}$ 2$)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

Additional exemplary substituents include hydrogen, halogen, $C_{1-6}$ alkyl (e.g., methyl, ethyl, propyl, isopropyl, butyl, tert-butyl, sec-butyl), $C_{1-6}$ alkoxy, partially or fully halogenated $C_{1-6}$ alkyl (e.g., —$CF_3$, —$CHF_2$, —$CH_2F$), —CN, —$NO_2$, —O$R^{aa}$ (e.g., —OMe, —OEt), —S$R^a$, —N$(R^a)_2$ (e.g., —$NH_2$, —$NMe_2$), —N$R^a$(C═O)O$R^a$ (e.g., —NH(C═O)OMe, —NH(C═O)OEt, —NH(C═O)O$^t$Bu), COO$R^{aa}$ (e.g., —COOH, —COOMe, —COOEt), and —CO$R^{aa}$. Further examples include aryl and heteroaryl.

Additional exemplary substituents include hydrogen, halogen, $C_{1-6}$ alkyl (e.g., methyl, ethyl, propyl, isopropyl, butyl, tert-butyl, sec-butyl), $C_{1-6}$ alkoxy, partially or fully halogenated $C_{1-6}$ alkyl (e.g., —$CF_3$, —$CHF_2$, —$CH_2F$), —CN, —$NO_2$, —O$R^{aa}$ (e.g., —OMe, —OEt), —S$R^{aa}$, —N$(R^{aa})_2$ (e.g., —$NH_2$, —$NMe_2$), —N$R^{aa}$(C═O)O$R^{aa}$ (e.g., —NH(C═O)OMe, —NH(C═O)OEt, —NH(C═O)O$^t$Bu), —COO$R^{aa}$ (e.g., —COOH, —COOMe, —COOEt), and —CO$R^{aa}$. Further examples include aryl and heteroaryl.

The "molecular weight" of —R, wherein —R is any monovalent moiety, is calculated by subtracting the atomic weight of a hydrogen atom from the molecular weight of the molecule R—H. The "molecular weight" of -L-, wherein -L- is any divalent moiety, is calculated by subtracting the combined atomic weight of two hydrogen atoms from the molecular weight of the molecule H-L-H.

In certain embodiments, the molecular weight of a substituent is lower than 200, lower than 150, lower than 100, lower than 50, or lower than 25 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, and/or iodine atoms. In certain embodiments, a substituent consists of carbon, hydrogen, and/or fluorine atoms. In certain embodiments, a substituent does not comprise one or more, two or more, or three or more hydrogen bond donors. In certain embodiments, a substituent does not comprise one or more, two or more, or three or more hydrogen bond acceptors.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety.

The term "hydroxyl" or "hydroxy" refers to the group —OH.

The term "thiol" or "thio" refers to the group —SH.

The term "amine" or "amino" refers to the group —NH— or $—NH_2$.

The term "acyl" refers to a group having the general formula $—C(=O)R^{X1}$, $—C(=O)OR^{X1}$, $—C(=O)—O—C(=O)R^{X1}$, $—C(=O)SR^{X1}$, $—C(=O)N(R^{X1})_2$, $—C(=S)R^{X1}$, $—C(=S)N(R^{X1})_2$, and $—C(=S)S(R^{X1})$, $—C(=NR^{X1})R^{X1}$, $—C(=NR^{X1})OR^{X1}$, $—C(=NR^{X1})SR^{X1}$, and $—C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids ($—CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this disclosure include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, and p-xylene.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "crystalline" or "crystalline form" refers to a solid form substantially exhibiting three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks.

The term "amorphous" or "amorphous form" refers to a form of a solid ("solid form"), the form substantially lacking three-dimensional order. In certain embodiments, an amorphous form of a solid is a solid form that is substantially not crystalline. In certain embodiments, the X-ray powder diffraction (XRPD) pattern of an amorphous form includes a wide scattering band with a peak at 2θ of, e.g., between 20 and 70°, inclusive, using CuKα radiation. In certain embodiments, the XRPD pattern of an amorphous form further includes one or more peaks attributed to crystalline structures. In certain embodiments, the maximum intensity of any one of the one or more peaks attributed to crystalline structures observed at a 2θ of between 20 and 70°, inclusive, is not more than 300-fold, not more than 100-fold, not more than 30-fold, not more than 10-fold, or not more than 3-fold of the maximum intensity of the wide scattering band. In certain embodiments, the XRPD pattern of an amorphous form includes no peaks attributed to crystalline structures.

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure comprising at least two different components (e.g., compound of Formula (0) or (I) and an acid), wherein each of the components is independently an atom, ion, or molecule. In certain embodiments, none of the components is a solvent. In certain embodiments, at least one of the components is a solvent. A co-crystal of compound of Formula (0) or (I) and an acid is different from a salt formed from a compound of Formula (0) or (I) and the acid. In the salt, a compound disclosed herein is complexed with the acid in a way that proton transfer (e.g., a complete proton transfer) from the acid to a compound disclosed herein easily occurs at room temperature. In the co-crystal, however, a compound disclosed herein is complexed with the acid in a way that proton transfer from the acid to a compound disclosed herein does not easily occur at room temperature. In certain embodiments, in the co-crystal, there is no proton transfer from the acid to a compound disclosed herein. In certain embodiments, in the co-crystal, there is partial proton transfer from the acid to a compound disclosed herein. Co-crystals may be useful to improve the properties (e.g., solubility, stability, and ease of formulation) of a compound of Formula (0) or (I).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". A "rotational isomer or rotamer" is an isomer arising from restricted rotation about one single bond. The compounds disclosed herein include all rotational isomers of the isomer depicted. The compounds disclosed herein include all rotational isomers including, but not limited to the rotational isomer depicted. In some embodiments, a compound disclosed herein includes all rotational isomers. In certain embodiments, the disclosure provides compounds, or rotational isomers thereof. Isomers that differ in the arrangement of their atoms in space are termed "stereoisomers". In certain embodiments, if a phenyl group contains two substituents that are each bonded to adjacent carbons then the compound may be designated the ortho isomer. In certain embodiments, if a phenyl group contains two substituents that are each bonded to carbons separated by one ring carbon then the compound may be designated the meta isomer. In certain embodiments, if a phenyl group contains two substituents that are each bonded to carbons separated by two ring carbon then the compound may be designated the para isomer.

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein, the term "agent" means a molecule, group of molecules, complex or substance administered to an organism for diagnostic, therapeutic, preventative medical, or veterinary purposes. In certain embodiments, the agent is a pharmaceutical agent (e.g., a therapeutic agent, a diagnostic agent, or a prophylactic agent). In certain embodiments, the compositions disclosed herein comprise an agent(s), e.g., a first therapeutic agent (e.g., at least one (including, e.g., at least two, at least three). In some embodiments, the compositions can further comprise a second therapeutic agent, a targeting moiety, a diagnostic moiety as described herein.

As used herein, the term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

An agent (e.g., a therapeutic agent) can include a wide variety of different compounds, including chemical compounds and mixtures of chemical compounds (e.g., small organic or inorganic molecules) such as drug compounds (e.g., compounds approved for human or veterinary use by the U.S. Food and Drug Administration as provided in the Code of Federal Regulations (CFR)); targeting agents; isotopically labeled chemical compounds; agents useful in bioprocessing; carbohydrates; saccharines; monosaccharides; oligosaccharides; polysaccharides; biological macromolecules (e.g., peptides, proteins, and peptide analogs and derivatives); peptidomimetics; antibodies and antigen binding fragments thereof; nucleic acids (e.g., DNA or RNA); nucleotides; nucleosides; oligonucleotides; antisense oligonucleotides; polynucleotides; nucleic acid analogs and derivatives; nucleoproteins; mucoproteins; lipoproteins; synthetic polypeptides or proteins; small molecules linked to proteins; glycoproteins; steroids; lipids; hormones; vitamins; vaccines; immunological agents; an extract made from biological materials, such as bacteria, plants, fungi, or animal cells; animal tissues; naturally occurring or synthetic compositions; and any combinations thereof.

In some embodiments, the agent is in the form of a prodrug. The term "prodrug" refers to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound, or to form an amide prepared by the acid, or acid anhydride, or mixed anhydrides moieties of the prodrug moiety with a substituted or unsubstituted amine of the pharmaceutically active compound. Simple aliphatic or aromatic esters, amides, and anhydrides derived from acidic groups may comprise prodrugs. In some embodiments, the composition described herein incorporates one therapeutic agent or prodrug thereof. In some embodiments, the compositions described herein incorporates more than one therapeutic agents or prodrugs.

In some embodiments, the agent (e.g., a therapeutic agent) is a small molecule. As used herein, the term "small molecule" can refer to compounds that are "natural product-like." However, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary agents (e.g., a therapeutic agents) in the compositions include, but are not limited to, those found in *Harrison's Principles of Internal Medicine,* 13th Edition, Eds. T. R. Harrison et al. McGraw-Hill N.Y., NY; *Physicians' Desk Reference,* 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Gilman's The Pharmacological Basis of Therapeutics; and current edition of The Merck Index, the complete contents of all of which are incorporated herein by reference.

In some embodiments, exemplary therapeutic agents in the compositions include, but are not limited to, one or more of the agents listed in Paragraph [0148] of U.S. Pat. No. 9,381,253, incorporated by reference herein.

In other embodiments, exemplary therapeutic agents in the compositions include, but are not limited to, one or more of the therapeutic agents listed in International Publication Number WO 2013/169739, published Nov. 14, 2013, including the anti-hypertensive and/or a collagen modifying agents ("AHCM") disclosed, e.g., in Paragraphs 40-49, 283, 286-295; the microenvironment modulators disclosed, e.g., in Paragraphs 113-121, of WO 2013/169739, incorporated herein by reference. In some embodiments, the composition comprising the AHCM and/or the microenvironment modulator causes one or more of: reduces solid stress (e.g., growth-induced solid stress in tumors); decreases tumor fibrosis; reduces interstitial hypertension or interstitial fluid pressure (IFP); increases interstitial tumor transport; increases tumor or vessel perfusion; increases vascular diameters and/or enlarges compressed or collapsed blood vessels; reduces or depletes one or more of: cancer cells, or stromal cells (e.g., tumor associated fibroblasts or immune cells); decreases the level or production of extracellular matrix components, such as fibers (e.g., collagen, procollagen), and/or polysaccharides (e.g., glycosaminoglycans such as hyaluronan or hyaluronic acid); decreases the level or production of collagen or procollagen; decreases the level or production of hyaluronic acid; increases tumor oxygenation; decreases tumor hypoxia; decreases tumor acidosis; enables immune cell infiltration; decreases immunosuppression; increases antitumor immunity; decreases the production of cancer stem cells (also referred to herein as tumor-initiating cells); or enhances the efficacy (e.g., penetration or diffusion), of the therapy, e.g., the cancer therapy (e.g., radiation, photodynamic therapy, chemotherapeutics and immunotherapies) in a tumor or tumor vasculature, in the subject.

Agents, e.g., therapeutic agents, include the categories and specific examples disclosed herein. It is not intended that the category be limited by the specific examples. Those of ordinary skill in the art will recognize also numerous other compounds that fall within the categories, and that are useful according to the present disclosure.

Examples of therapeutic agents include, but are not limited to, antimicrobial agents, analgesics, anti-inflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anti-cancer properties, or a combination thereof. Other suitable therapeutic agents include contraceptives and vitamins as well as micro- and macronutrients. Still other examples include antiinfectives, such as antibiotics and antiviral agents; analgesics and analgesic combinations; anorexics; anthelmintics; antiarthritics; antiasthmatic agents; anticonvulsants; antidepressants; antidiuretic agents; antidiarrheals; antihistamines; antiinflammatory agents; antimigraine preparations; antinauseants; antinicotnauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; anti-hypertensives; diuretics; vasodilators including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird. The non-human animal may be a male or female at any stage of development. The non-human animal may be a transgenic animal or genetically engineered animal.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a medical history of symptoms). Treatment may also be continued after symptoms have resolved, for example, to delay and/or prevent recurrence of the disease or disorder.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The term "NAMPT" or "nicotinamide phosphoribosyltransferase" refers to a key enzyme in nicotinamide adenine dinucleotide (NAD) biosynthesis from the natural precursor nicotinamide. NAMPT catalyzes the phosphoribosylation of nicotinamide and is the rate-limiting enzyme in one of two pathways that salvage NAD. NAMPT specifically makes nicotinamide mononucleotide (NMN) as the product of the NAMPT enzymatic reaction. NAMPT is found both extracellular and intracellular. Thus, in some embodiments, NAMPT is intracellular NAMPT. In certain embodiments, NAMPT is extracellular NAMPT. NAMPT can be found in intracellular compartments and can be found in both nuclei and cytosol. NAMPT is expressed throughout the body including, but not limited to in the heart, brain, placenta, lungs, liver, skeletal muscle, kidney, and pancreas. NAMPT may also be referred to as pre-B-cell-colony-enhancing factor (PBEF) and visfatin. The protein is also known as NAmPRTase. NAMPT can lead to changes in downstream signal molecules such as sirtuins, PARPs, and NADases.[15] NAMPT plays a role in a variety of diseases and disorders see, for example: (i) WO 97/48696 for involvement of NAMPT in the treatment of cancer, (ii) WO 97/48397 for involvement of NAMPT in immunosuppression, (iii) WO 2003/80054 for involvement of NAMPT for the treatment of diseases involving angiogenesis, (iv) WO 2008/025857 for involvement of NAMPT for the treatment of rheumatoid arthritis and septic shock, and (v) WO 2009/109610 for involvement of NAMPT for the prophylaxis and treatment of ischemia.

The term "modulate," "modulating," "modulation," or "modulator" refer to the ability of a compound to reduce/increase, slow/speed up, halt/initiate, inhibit/stimulate, or prevent/cause activity of a particular biological target (e.g., NAMPT) in a cell relative to vehicle.

As used herein the term "activate", "activator", "stimulate", or "stimulator" in the context of enzymes, for example, in the context of NAMPT, refers to an increase in the activity of the enzyme. In some embodiments, the term refers to an increase of the level of enzyme activity, e.g., NAMPT activity, to a level that is statistically significantly higher than an initial level, which may, for example, be a baseline level of enzyme activity. In some embodiments, the term refers to an increase of the level of enzyme activity, e.g., NAMPT activity, to a level that is greater than 5%, greater than 10%, greater than 20%, greater than 30%, greater than 40%, greater than 50%, greater than 60%, greater than 70%, greater than 80%, greater than 85%, greater than 90%, greater than 95%, greater than 96%, greater than 97%, greater than 98%, greater than 99%, greater than 99.1%, greater than 99.5%, greater than 99.9%, greater than 99.99%, or greater than 99.999% of an initial level, which may, for example, be a baseline level of enzyme activity.

The term "inhibition," "inhibiting," "inhibit," or "inhibitor" refer to the ability of a compound to reduce, slow, halt or prevent activity of a particular biological target (e.g., NAMPT) in a cell relative to vehicle.

As used herein the term "inhibit" or "inhibition" in the context of enzymes, for example, in the context of NAMPT, refers to a reduction in the activity of the enzyme. In some embodiments, the term refers to a reduction of the level of enzyme activity, e.g., NAMPT activity, to a level that is statistically significantly lower than an initial level, which may, for example, be a baseline level of enzyme activity. In some embodiments, the term refers to a reduction of the level of enzyme activity, e.g., NAMPT activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

The terms "condition," "disease," and "disorder" are used interchangeably.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, and autoimmune diseases.

The terms "inflammatory disease" and "inflammatory condition" are used interchangeably herein, and refer to a disease or condition caused by, resulting from, or resulting in inflammation. Inflammatory diseases and conditions include those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

Additional exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, Type II diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds disclosed herein may also be useful in treating inflammation associated with cancer An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

In certain embodiments, the inflammatory disorder and/or the immune disorder is a gastrointestinal disorder. In some embodiments, the gastrointestinal disorder is selected from gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)). In certain embodiments, the gastrointestinal disorder is inflammatory bowel disease (IBD).

In certain embodiments, the inflammatory condition and/or immune disorder is a skin condition. In some embodiments, the skin condition is pruritus (itch), psoriasis, eczema, burns or dermatitis. In certain embodiments, the skin condition is psoriasis. In certain embodiments, the skin condition is pruritis.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrom's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

Cancer cells may exhibit properties that are similar to the properties of embryonic stem cells and/or adult stem cells. As used herein, cancer stem cells (CSCs) are cancer cells that have one or more embryonic features/properties or adult stem cell features/properties. CSCs are generally considered to be problematic cancer cells due to the ability to metastasize and form tumors at other sites in the body. As used herein, "embryonic features", "embryonic properties", or the like, refers to gene and/or miRNA expression and/or similar biological properties as an embryonic cell. Non-differentiated, cancer cells with embryonic properties have the ability to metastasize, are resistant to chemotherapies and radiation therapy, and have the ability to re-grow a tumor after most of the tumor has been removed or diminished after surgery and/or additional cancer therapeutic treatment. As used herein, "adult stem cell features", "adult stem cell properties", or the like, refers to gene and/or miRNA expression and/or similar biological properties as an adult stem cell. Cancer cells with adult stem properties may have the ability to metastasize, divide, differentiate, exhibit plasticity, exhibit a high rate of cell turnover, may be resistant to chemotherapies and radiation therapy, and may have the ability to re-grow a tumor after most of the tumor has been removed or diminished after surgery and/or additional cancer therapeutic treatment.

In some embodiments, the cancer stem cells are characterized by expression of genes and/or miRNAs associated with the embryonic state. In some embodiments, the cancer stem cells express one or more (e.g., 1, 2, 3, 4, 5, 6, or more) genes or miRNAs associated with the embryonic state.

In some embodiments, the cancer stem cells are characterized by one or more embryonic features. Examples of embryonic features include, without limitation, cellular self-renewal properties, hyperproliferative activity, multipotency, pluripotency, expression of embryonic markers, lack of differentiation markers, resistance to chemotherapy, motility, and the ability to give rise to different lineages of cells.

In some embodiments, the cancer stem cells are characterized by expression of genes and/or miRNAs associated with the adult stem cell state. In some embodiments, the cancer stem cells express one or more (e.g., 1, 2, 3, 4, 5, 6, or more) genes or miRNAs associated with the adult stem cell state.

In some embodiments, the cancer stem cells are characterized by one or more adult stem cell features. Examples of adult stem cell features include, without limitation, one or many of the following features (depending on cell type): cellular self-renewal properties, proliferative and/or hyperproliferative activity, multipotency, plasticity, pluripotency, resistance to chemotherapy, and the ability to give rise to different lineages of cells (transdifferentiation).

As used herein, the term "regenerative medicine" or "regenerative therapy" refers to promoting the regenerative capacity of a cell, tissue, and/or organ. Regenerative medicine encompasses cellular and/or tissue engineering to replace, engineer, or regenerate cells, tissues, and/or organs and/or restoring or improving one or more biological function of a cell, tissue, and/or organ that is dysfunctional or impaired; as well as tissue engineering and organ regeneration. As used herein, "regenerative capacity" refers to conversion of a cell, such as a stem cell, into dividing progenitor cell and differentiated tissue-specific cell. Regenerative capacity may additionally or alternatively refer to the ability of a cell, tissue, and/or organ to replicate, proliferate, regain function, and/or regenerate.

An "effective amount" of a composition described herein refers to an amount sufficient to elicit the desired biological response. An effective amount of a composition described herein may vary depending on such factors as the desired biological endpoint, the pharmacokinetics of the composition, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a composition or pharmaceutical composition described herein in a single dose. In certain embodiments, an effective amount is the combined amounts of a composition or pharmaceutical composition described herein in multiple doses.

A "therapeutically effective amount" of a composition described herein is an amount sufficient to provide a therapeutic benefit in the treatment of a condition or to delay or minimize one or more symptoms associated with the condition. A therapeutically effective amount of a composition means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "gene" refers to a nucleic acid fragment that provides a template that can be used for producing a gene product. In certain embodiments, the nucleic acid fragment includes regulatory sequences preceding and following the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "nucleic acid" or "nucleic acid sequence", "nucleic acid molecule", "nucleic acid fragment" or "polynucleotide" are used interchangeably. A polynucleotide molecule is a biopolymer composed of nucleotide monomers covalently bonded in a chain. DNA (deoxyribonucleic acid) and RNA (ribonucleic acid) are examples of polynucleotides with distinct biological function. DNA consists of two chains of polynucleotides, with each chain in the form of a helical spiral. RNA is more often found in nature as a single-strand folded onto itself. Exemplary types of RNA include double-stranded RNA (dsRNA), small interfering RNA (siRNA), short hairpin (shRNA), microRNA (miRNA), messenger RNA (mRNA), antisense RNA, transfer RNA (tRNA), small nuclear RNA (snRNA), and ribosomal RNA (rRNA).

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The phrases "compound of the disclosure", "compound as disclosed herein" and the like refer to any compound disclosed herein, such as in the specification and claims, including compounds of (i) Formula (0), (ii) Formula (I), (iii) all subgenera, and (iv) all compound species, including compounds as provided in the Additional Compounds section and in the Examples section including Tables E1, E2, and E3, or a pharmaceutically acceptable salt, solvate, hydrate, polymorph, co-crystal, tautomer, stereoisomer, isotopically labeled derivative, or prodrug thereof. Provisoed compounds are not included in phrases "compound of the disclosure", "compound as disclosed herein" and the like.

The disclosure is not intended to be limited in any manner by the above exemplary listing of substituents. Additional terms may be defined in other sections of this disclosure.

DETAILED DESCRIPTION OF CERTAIN EMBODIMENTS

Before the disclosed systems, compounds, compositions, methods, uses, and kits are described in more detail, it should be understood that the aspects described herein are not limited to specific embodiments, methods, systems, apparati, or configurations, and as such can, of course, vary. It is also to be understood that the terminology used herein is for the purpose of describing particular aspects only and, unless specifically defined herein, is not intended to be limiting.

The compounds of the disclosure, and compositions and kits thereof, are useful for cancer treatment and the treatment of proliferative diseases or used for regenerative medicine. The compounds may differentiate embryonic-like cancer stem cells, kill differentiated cancer stem cells, disrupt their proliferation, and/or inhibit their ability to form new tumors. The compounds may inhibit tumor growth, regenerate or differentiate one or more cells, prevent metastasis, kill cancer cells, reduce embryonic properties or adult stem cell properties of one or more cells, reduce cell viability, and/or prevent cell proliferation. Embryonic-like properties, including embryonic gene expression patterns, are re-activated across a variety of different types of cancers. Additionally, the compounds may differentiate adult-like cancer stem cells, kill differentiated adult cancer stem cells, disrupt their proliferation, and/or inhibit their ability to form new tumors. Adult stem cells are also associated with a variety of different types of cancers. In certain embodiments, the cancer is colorectal cancer, gastric cancer, gastrointestinal stromal tumor, ovarian cancer, lung cancer, breast cancer, pancreatic cancer, prostate cancer, testicular cancer, lymphoma, leukemia, or liver cancer. For example, embryonic-like properties have been found in cancer stem cells from solid tumors, such as colorectal cancer, gastric cancer, ovarian cancer, lung cancer, breast cancer, pancreatic cancer, and prostate cancer.[10] Embryonic-like properties have been also found in cancer stem cells from hematopoietic cancers, such as leukemia and lymphoma.[14]

Without wishing to be bound by a particular theory, the compounds and compositions disclosed herein are believed to modulate (e.g., inhibit) nicotinamide phosphoribosyltransferase (NAMPT), which is also referred to as Visfatin and Pre-B-Cell Colony-Enhancing Factor 1 (PBEF). NAMPT is an enzyme that catalyzes the first step in the biosynthesis of nicotinamide adenine dinucleotide (NAD) from nicotinamide.[15] Nicotinamide adenine dinucleotide is an essential cofactor for cellular metabolism. Nicotinamide mononucleotide (NMN) is the product of the NAMPT enzymatic reaction. NAMPT has been indicated in a wide variety of diseases and disorders, thus, modulation (i.e., inhibition) of NAMPT can treat a broad range of indications.[15,16,17] Further, NAMPT is also involved in signaling, displaying activity as an adipocytokine[18] and immunomodulatory cytokine[19]. Increased levels of NAMPT have been described in (i) metabolic/inflammatory conditions including obesity, type 2 diabetes, metabolic syndromes, atherogenic inflammatory diseases, and cardio-cerebro-vascular disorders, (ii) non-metabolic chronic inflammatory diseases including osteoarthritis and acute lung injury, (iii) infections like sepsis or intrauterine infection, and (iv) autoimmune inflammatory diseases including psoriasis, rheumatoid arthritis, Crohn's disease, and ulcerative colitis.[15] Accordingly, the compounds of the disclosure, and compositions and kits thereof, are useful for treating or preventing a wide variety of diseases and disorders.

Compounds

In certain aspects, the present disclosure provides compounds of Formula (0) or (I). Additional compounds are also provided herein.

In certain embodiments, a compound of the disclosure is a compound (e.g. a compound of Formula (0) or (I), or compound as described in the Additional Compounds section below), or a pharmaceutically acceptable salt, solvate, hydrate, polymorph, co-crystal, tautomer, stereoisomer, isotopically labeled derivative, or prodrug thereof. In certain embodiments, a compound of the disclosure is a compound (e.g., a compound of Formula (0) or (I), or compound as described in the Additional Compounds section below), or a pharmaceutically acceptable salt, tautomer, or stereoisomer thereof. In certain embodiments, a compound of the disclosure is a compound (e.g., a compound of Formula (0) or (I), or compound as described in the Additional Compounds section below), or a pharmaceutically acceptable salt thereof.

The compounds of the present disclosure may have a high aqueous solubility. Compared to certain similar known compounds, the compounds of the present disclosure may have a higher (e.g., at least 10%, at least 20%, at least 50%, at least 100%, at least 200%, at least 500%, or at least 1,000% higher) aqueous solubility.

The compounds of the present disclosure may have a high microsomal stability. Compared to certain similar known compounds, the compounds of the present disclosure may have a higher (e.g., at least 10%, at least 20%, at least 50%, at least 100%, at least 200%, at least 500%, or at least 1,000% higher) microsomal stability.

The compounds of the present disclosure may treat cancer. Compared to certain similar known compounds, the compounds of the present disclosure may be better at treating cancer (e.g., at least 10%, at least 20%, at least 50%, at least 100%, at least 200%, at least 500%, or at least 1,000% better), which may be evidenced by a decrease in cancer symptoms and/or tumor size.

Compounds of Formula (0) and (I)

In certain embodiments, provided herein is a compound of Formula (0):

(0)

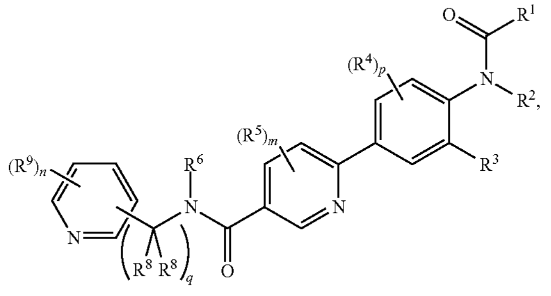

or a pharmaceutically acceptable salt, solvate, hydrate, polymorph, co-crystal, tautomer, stereoisomer, isotopically labeled derivative, or prodrug thereof, wherein:

$R^1$ is substituted or unsubstituted, $C_{1-12}$ alkyl or substituted or unsubstituted, $C_{1-12}$ heteroalkyl;

$R^2$ is hydrogen, substituted or unsubstituted, $C_{1-12}$ alkyl, substituted or unsubstituted, $C_{1-12}$ heteroalkyl, substituted or unsubstituted, 3- to 13-membered heterocyclyl-$C_{1-12}$-alkyl, substituted or unsubstituted, 3- to 13-membered carbocyclyl-$C_{1-12}$-alkyl, or a nitrogen protecting group;

when $R^2$ is unsubstituted methyl, $R^1$ is not unsubstituted ethyl;

$R^3$ is hydrogen, halogen, substituted or unsubstituted, $C_{1-6}$ alkyl, —$OR^a$, —$COOR^a$, —$COR^a$, —$N(R^a)_2$, —CN, or —(C═O)$N(R^a)_2$;

each instance of Ra is independently hydrogen, substituted or unsubstituted, $C_{1-6}$ alkyl, an oxygen protecting group when attached to an oxygen atom, or a nitrogen protecting group when attached to a nitrogen atom;

each instance of $R^4$ is independently hydrogen, halogen, substituted or unsubstituted, $C_{1-6}$ alkyl, —$OR^a$, —$COOR^a$, —$COR^a$, —$N(R^a)_2$, —CN, or —(C═O)N $(R^a)_2$;

each instance of $R^5$ is independently hydrogen, halogen, substituted or unsubstituted, $C_{1-6}$ alkyl, —$OR^a$, —$COOR^a$, —$COR^a$, —$N(R^a)_2$, —CN, or —(C═O)N $(R^a)_2$;

$R^6$ is hydrogen, substituted or unsubstituted, $C_{1-6}$ alkyl, or a nitrogen protecting group;

each instance of $R^8$ is independently hydrogen, halogen, or substituted or unsubstituted, $C_{1-6}$ alkyl;

each instance of $R^9$ is independently hydrogen, halogen, substituted or unsubstituted, $C_{1-6}$ alkyl, —$OR^a$, —$COOR^a$, —$COR^a$, —$N(R^a)_2$, —CN, or —(C═O)N $(R^a)_2$, or two instances of $R^9$ are joined to form a 3- to 13 membered heterocyclyl, 3- to 13 membered heterocyclyl, 6- to 12 membered aryl ring, or 5- to 14 membered heteroaryl ring;

n is an integer from 0 to 4, inclusive;

m is an integer from 0 to 3, inclusive;

p is an integer from 0 to 3, inclusive; and q is an integer selected from 0 and 1.

In certain embodiments, a compound of Formula (0) is of Formula (0a):

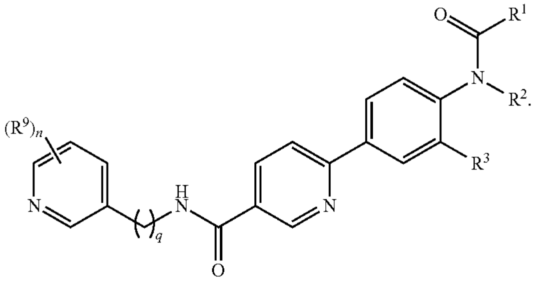

In certain embodiments, a compound of Formula (0) is of Formula (0b):

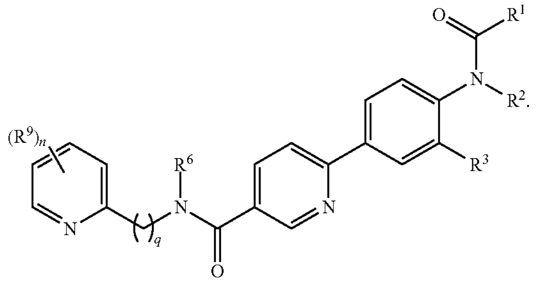

In certain embodiments, a compound of Formula (0) is of Formula (0c):

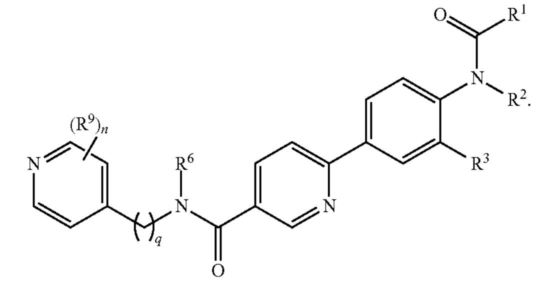

In certain embodiments, provided herein is a compound of Formula (I):

(I)

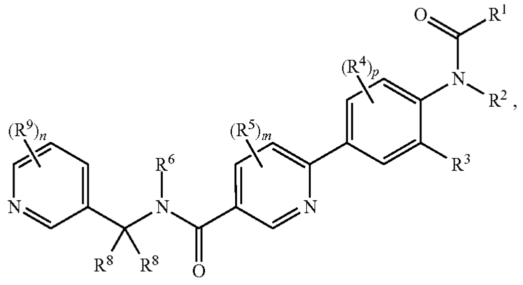

or a pharmaceutically acceptable salt, solvate, hydrate, polymorph, co-crystal, tautomer, stereoisomer, isotopically labeled derivative, or prodrug thereof, wherein:

$R^1$ is substituted or unsubstituted, $C_{1-12}$ alkyl or substituted or unsubstituted, $C_{1-12}$ heteroalkyl;

$R^2$ is hydrogen, substituted or unsubstituted, $C_{1-12}$ alkyl, substituted or unsubstituted, $C_{1-12}$ heteroalkyl, substituted or unsubstituted, 3- to 13-membered heterocyclyl-$C_{1-12}$-alkyl, substituted or unsubstituted, 3- to 13-membered carbocyclyl-$C_{1-12}$-alkyl, or a nitrogen protecting group;

when $R^2$ is unsubstituted methyl, $R^1$ is not unsubstituted ethyl;

$R^3$ is hydrogen, halogen, substituted or unsubstituted, $C_{1-6}$ alkyl, —$OR^a$, —$COOR^a$, —$COR^a$, —$N(R^a)_2$, —CN, or —(C═O)$N(R^a)_2$;

each instance of Ra is independently hydrogen, substituted or unsubstituted, $C_{1-6}$ alkyl, an oxygen protecting group when attached to an oxygen atom, or a nitrogen protecting group when attached to a nitrogen atom;

each instance of $R^4$ is independently hydrogen, halogen, substituted or unsubstituted, $C_{1-6}$ alkyl, —$OR^a$, —$COOR^a$, —$COR^a$, —$N(R^a)_2$, —CN, or —(C═O)N$(R^a)_2$;

each instance of $R^5$ is independently hydrogen, halogen, substituted or unsubstituted, $C_{1-6}$ alkyl, —$OR^a$, —$COOR^a$, —$COR^a$, —$N(R^a)_2$, —CN, or —(C═O)N$(R^a)_2$;

$R^6$ is hydrogen, substituted or unsubstituted, $C_{1-6}$ alkyl, or a nitrogen protecting group;

each instance of $R^1$ is independently hydrogen, halogen, or substituted or unsubstituted, $C_{1-6}$ alkyl;

each instance of $R^9$ is independently hydrogen, halogen, substituted or unsubstituted, $C_{1-6}$ alkyl, —$OR^a$, —$COOR^a$, —$COR^a$, —$N(R^a)_2$, —CN, or —(C═O)N$(R^a)_2$;

n is an integer from 0 to 4, inclusive;

m is an integer from 0 to 3, inclusive; and p is an integer from 0 to 3, inclusive.

In certain embodiments, a compound of Formula (I) is of Formula (Iz):

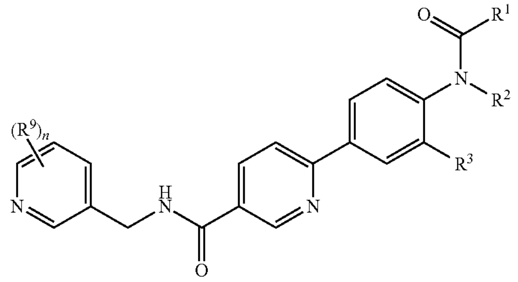

In certain embodiments, a compound of Formula (I) is of Formula (Ia):

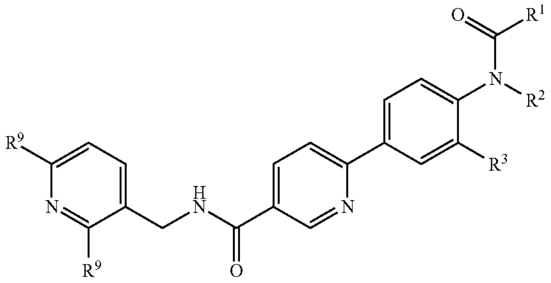

In certain embodiments, a compound of Formula (I) is of Formula (Ib):

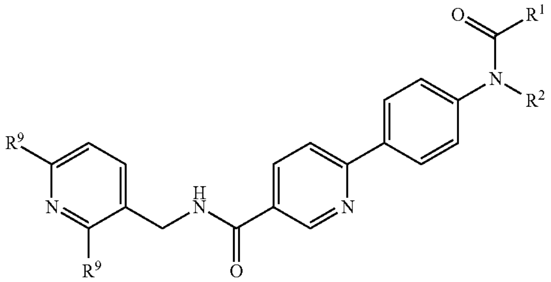

In certain embodiments, a compound of Formula (I) is of Formula (Ic):

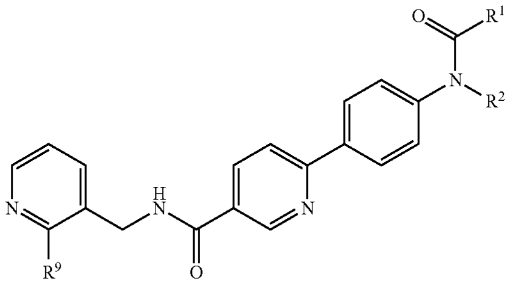

In certain embodiments, $R^1$ is substituted or unsubstituted, $C_1$ 12 alkyl. In certain embodiments, $R^1$ is substituted $C_{1-12}$ alkyl. In certain embodiments, $R^1$ is unsubstituted $C_1$ 12 alkyl. In certain embodiments, $R^1$ is substituted or unsubstituted, $C_{1-6}$ alkyl. In certain embodiments, $R^1$ is unsubstituted $C_{1-6}$ alkyl. In certain embodiments, $R^1$ is unsubstituted $C_1$ alkyl. In certain embodiments, $R^1$ is unsubstituted $C_2$ alkyl. In certain embodiments, $R^1$ is unsubstituted $C_3$ alkyl. In certain embodiments, $R^1$ is unsubstituted $C_4$ alkyl. In certain embodiments, $R^1$ is unsubstituted $C_5$ alkyl. In certain embodiments, $R^1$ is unsubstituted $C_6$ alkyl. In certain embodiments, $R^1$ is substituted $C_{1-6}$ alkyl. In certain embodiments, $R^1$ is substituted $C_1$ alkyl. In certain embodiments, $R^1$ is substituted $C_2$ alkyl. In certain embodiments, $R^1$ is substituted $C_3$ alkyl. In certain embodiments, $R^1$ is substituted $C_4$ alkyl. In certain embodiments, $R^1$ is substituted $C_5$ alkyl. In certain embodiments, $R^1$ is substituted $C_6$ alkyl. In certain embodiments, $R^1$ is fluorinated $C_{1-6}$ alkyl (e.g., —$CF_3$, —$CHF_2$, —$CH_2F$). In certain embodiments, $R^1$ is methyl. In certain embodiments, $R^1$ is ethyl. In some embodiments, $R^1$ is propyl. In certain embodiments, $R^1$ is substituted or unsubstituted, $C_{1-12}$ heteroalkyl. In certain embodiments, $R^1$ is unsubstituted $C_1$12 heteroalkyl. In certain embodiments, $R^1$ is substituted $C_1$12 heteroalkyl. In certain embodiments, $R^1$ is substituted or unsubstituted, $C_{1-6}$ heteroalkyl. In certain embodiments, $R^1$ is unsubstituted $C_{1-6}$ heteroalkyl. In certain embodiments, $R^1$ is unsubstituted $C_1$ heteroalkyl. In certain embodiments, $R^1$ is unsubstituted $C_2$ heteroalkyl. In certain embodiments, $R^1$ is unsubstituted $C_3$ heteroalkyl. In certain embodiments, $R^1$ is unsubstituted $C_4$ heteroalkyl. In certain embodiments, $R^1$ is unsubstituted $C_5$ heteroalkyl. In certain embodiments, $R^1$ is unsubstituted $C_6$ heteroalkyl. In certain embodiments, $R^1$ is substituted $C_{1-6}$ heteroalkyl. In certain embodiments, $R^1$ is substituted $C_1$ heteroalkyl. In certain embodiments, $R^1$ is substituted $C_2$ heteroalkyl. In certain embodiments, $R^1$ is substituted $C_3$ heteroalkyl. In certain embodiments, $R^1$ is substituted $C_4$ heteroalkyl. In certain embodiments, $R^1$ is substituted $C_5$ heteroalkyl. In certain embodiments, $R^1$ is substituted $C_6$ heteroalkyl. In some embodiments, $R^1$ is methoxy, ethoxy, or propoxy. In certain embodiments, $R^1$ is substituted with halo, —CN, —$NRa_2$, —$Co_2R^{aa}$, —C(═O)$R^{aa}$, OC(═O)$R^{aa}$, $OCO_2R^{aa}$, —C(═O)N$(R^{bb})_2$, —OC(═O)N$(R^{bb})_2$, —$NR^{bb}$C(═O)$R^{aa}$, —$NR^{bb}Co_2R^{aa}$, or —$NR^{bb}$C(═O)N$(R^{bb})_2$. In certain embodiments, $R^1$ is substituted with —$CO_2R^{aa}$, —OC(═O)$R^{aa}$, $OCO_2R^{aa}$, —C(═O)N$(R^{bb})_2$, —OC(═O)N$(R^{bb})_2$, —$NR^{bb}$C(═O)$R^{aa}$, —$NR^{bb}CO_2R^{aa}$, or —$NR^{bb}$C(═O)N$(R^{bb})_2$.

In some embodiments, $R^{bb}$ is hydrogen, methyl, ethyl, propyl, isopropyl, butyl, tertbutyl, or pentyl.

In certain embodiments, the substituent on the $R^1$ group is —CN, —F, —Cl, —N($R^a$)(C=O)O$R^a$, or —COO$R^a$. In certain embodiments, the substituent on the $R^1$ group is —CN, —F, —$C_1$, —N$Ra_2$, —N($R^a$)(C=O)O$R^a$, —COO$R^a$, or —(C=O)$R^a$. In certain embodiments, the substituent on the $R^1$ group is —CN, —F, —Cl, —$NH_2$, —NHC(=O)OEt, —NHC(=O)OMe, —NHC(=O)$O^t$Bu, or —C(=O)$CH_3$.

In certain embodiments, $R^2$ is hydrogen. In certain embodiments, $R^2$ is not hydrogen. In certain embodiments, $R^2$ is substituted or unsubstituted, $C_{1-12}$ alkyl. In certain embodiments, $R^2$ is unsubstituted $C_{1-12}$ alkyl. In certain embodiments, $R^2$ is substituted $C_{1-12}$ alkyl. In certain embodiments, $R^2$ is Me. In certain embodiments, $R^2$ is Et, Pr, or Bu. In certain embodiments, $R^2$ is a nitrogen protecting group.

In certain embodiments, $R^2$ is substituted or unsubstituted, $C_{1-12}$ alkyl. In certain embodiments, $R^2$ is unsubstituted $C_{1-12}$ alkyl. In certain embodiments, $R^2$ is substituted $C_{1-12}$ alkyl. In certain embodiments, $R^2$ is substituted or unsubstituted, $C_{1-6}$ alkyl. In certain embodiments, $R^2$ is unsubstituted $C_{1-6}$ alkyl. In certain embodiments, $R^2$ is unsubstituted $C_1$ alkyl. In certain embodiments, $R^2$ is unsubstituted $C_2$ alkyl. In certain embodiments, $R^2$ is unsubstituted $C_3$ alkyl. In certain embodiments, $R^2$ is unsubstituted $C_4$ alkyl. In certain embodiments, $R^2$ is unsubstituted $C_5$ alkyl. In certain embodiments, $R^2$ is unsubstituted $C_6$ alkyl. In certain embodiments, $R^2$ is substituted $C_{1-6}$ alkyl. In certain embodiments, $R^2$ is substituted $C_1$ alkyl. In certain embodiments, $R^2$ is substituted $C_2$ alkyl. In certain embodiments, $R^2$ is substituted $C_3$ alkyl. In certain embodiments, $R^2$ is substituted $C_4$ alkyl. In certain embodiments, $R^2$ is substituted $C_5$ alkyl. In certain embodiments, $R^2$ is substituted $C_6$ alkyl. In certain embodiments, $R^2$ is halogenated $C_{1-12}$ alkyl. In certain embodiments, $R^2$ is substituted $C_6$ alkyl. In certain embodiments, $R^2$ is fluorinated $C_{1-6}$ alkyl (e.g., —$CF_3$, —$CHF_2$, —$CH_2F$). In certain embodiments, $R^2$ is methyl. In certain embodiments, $R^2$ is ethyl. In some embodiments, $R^2$ is propyl. In certain embodiments, $R^2$ is substituted or unsubstituted, $C_{1-12}$ heteroalkyl. In certain embodiments, $R^2$ is substituted $C_{1-12}$ heteroalkyl. In certain embodiments, $R^2$ is unsubstituted $C_{1-12}$ heteroalkyl. In certain embodiments, $R^2$ is substituted or unsubstituted, $C_{1-6}$ heteroalkyl. In certain embodiments, $R^2$ is unsubstituted $C_{1-6}$ heteroalkyl. In certain embodiments, $R^2$ is unsubstituted $C_1$ heteroalkyl. In certain embodiments, $R^2$ is unsubstituted $C_2$ heteroalkyl. In certain embodiments, $R^2$ is unsubstituted $C_3$ heteroalkyl. In certain embodiments, $R^2$ is unsubstituted $C_4$ heteroalkyl. In certain embodiments, $R^2$ is unsubstituted $C_5$ heteroalkyl. In certain embodiments, $R^2$ is unsubstituted $C_6$ heteroalkyl. In certain embodiments, $R^2$ is substituted $C_{1-6}$ heteroalkyl. In certain embodiments, $R^2$ is substituted $C_1$ heteroalkyl. In certain embodiments, $R^2$ is substituted $C_2$ heteroalkyl. In certain embodiments, $R^2$ is substituted $C_3$ heteroalkyl. In certain embodiments, $R^2$ is substituted $C_4$ heteroalkyl. In certain embodiments, $R^2$ is substituted $C_5$ heteroalkyl. In certain embodiments, $R^2$ is substituted $C_6$ heteroalkyl. In some embodiments, $R^2$ is methoxy, ethoxy, or propoxy.

In certain embodiments, $R^2$ is substituted or unsubstituted, 3- to 13-membered heterocyclyl-$C_{1-12}$ alkyl. In certain embodiments, $R^2$ is unsubstituted 3- to 13-membered heterocyclyl-$C_{1-12}$ alkyl. In certain embodiments, $R^2$ is substituted 3- to 13-membered heterocyclyl-$C_{1-12}$ alkyl. In certain embodiments, $R^2$ is substituted or unsubstituted, 3- to 13-membered heterocyclyl-$C_{1-6}$ alkyl. In certain embodiments, $R^2$ is unsubstituted 3- to 6-membered heterocyclyl-$C_{1-6}$ alkyl. In certain embodiments, $R^2$ is unsubstituted 3- to 6-membered heterocyclyl-$C_1$ alkyl. In certain embodiments, $R^2$ is unsubstituted 3- to 6-membered heterocyclyl-$C_2$ alkyl. In certain embodiments, $R^2$ is unsubstituted 3- to 6-membered heterocyclyl-$C_3$ alkyl. In certain embodiments, $R^2$ is unsubstituted 3- to 6-membered heterocyclyl-$C_4$ alkyl. In certain embodiments, $R^2$ is unsubstituted 3- to 6-membered heterocyclyl-$C_5$ alkyl. In certain embodiments, $R^2$ is unsubstituted 3- to 6-membered heterocyclyl-$C_6$ alkyl. In certain embodiments, $R^2$ is substituted 3- to 6-membered heterocyclyl-$C_{1-6}$ alkyl. In certain embodiments, $R^2$ is substituted 3- to 6-membered heterocyclyl-$C_1$ alkyl. In certain embodiments, $R^2$ is substituted $C_2$ alkyl. In certain embodiments, $R^2$ is substituted 3- to 6-membered heterocyclyl-$C_3$ alkyl. In certain embodiments, $R^2$ is substituted 3- to 6-membered heterocyclyl-$C_4$ alkyl. In certain embodiments, $R^2$ is substituted 3- to 6-membered heterocyclyl-$C_5$ alkyl. In certain embodiments, $R^2$ is substituted 3- to 6-membered heterocyclyl-$C_6$ alkyl. In certain embodiments, $R^2$ is halogenated 3- to 6-membered heterocyclyl-$C_{1-12}$ alkyl. In certain embodiments, $R^2$ is substituted 3- to 6-membered heterocyclyl-$C_6$ alkyl.

In certain embodiments, $R^2$ is substituted or unsubstituted, 3- to 13-membered carbocyclyl-$C_{1-12}$ alkyl. In certain embodiments, $R^2$ is unsubstituted 3- to 13-membered carbocyclyl-$C_{1-12}$ alkyl. In certain embodiments, $R^2$ is substituted 3- to 13-membered carbocyclyl-$C_{1-12}$ alkyl. In certain embodiments, $R^2$ is substituted or unsubstituted, 3- to 13-membered carbocyclyl-$C_{1-6}$ alkyl. In certain embodiments, $R^2$ is unsubstituted 3- to 6-membered carbocyclyl-$C_{1-6}$ alkyl. In certain embodiments, $R^2$ is unsubstituted 3- to 6-membered carbocyclyl-$C_1$ alkyl. In certain embodiments, $R^2$ is unsubstituted 3- to 6-membered carbocyclyl-$C_2$ alkyl. In certain embodiments, $R^2$ is unsubstituted 3- to 6-membered carbocyclyl-$C_3$ alkyl. In certain embodiments, $R^2$ is unsubstituted 3- to 6-membered carbocyclyl-$C_4$ alkyl. In certain embodiments, $R^2$ is unsubstituted 3- to 6-membered carbocyclyl-$C_5$ alkyl. In certain embodiments, $R^2$ is unsubstituted 3- to 6-membered carbocyclyl-$C_6$ alkyl. In certain embodiments, $R^2$ is substituted 3- to 6-membered carbocyclyl-$C_{1-6}$ alkyl. In certain embodiments, $R^2$ is substituted 3- to 6-membered carbocyclyl-$C_1$ alkyl. In certain embodiments, $R^2$ is substituted $C_2$ alkyl. In certain embodiments, $R^2$ is substituted 3- to 6-membered carbocyclyl-$C_3$ alkyl. In certain embodiments, $R^2$ is substituted 3- to 6-membered carbocyclyl-$C_4$ alkyl. In certain embodiments, $R^2$ is substituted 3- to 6-membered carbocyclyl-$C_5$ alkyl. In certain embodiments, $R^2$ is substituted 3- to 6-membered carbocyclyl-$C_6$ alkyl. In certain embodiments, $R^2$ is halogenated 3- to 6-membered carbocyclyl-$C_1$ 12 alkyl. In certain embodiments, $R^2$ is substituted 3- to 6-membered carbocyclyl-$C_6$ alkyl.

In certain embodiments, $R^2$ is substituted $C_6$ heteroalkyl. In some embodiments, $R^2$ is methoxy, ethoxy, or propoxy.

In certain embodiments, $R^2$ is substituted with halo, —CN, —$NR^a_2$, —$CO_2R^{aa}$, C(=O)$R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, or —$NR^{bb}$C(=O)N($R^{bb}$)$_2$. In certain embodiments, $R^2$ is substituted with —$CO_2R^{aa}$, OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, or —$NR^{bb}$C(=O)N($R^{bb}$)$_2$.

In some embodiments, $R^{bb}$ is hydrogen, methyl, ethyl, propyl, isopropyl, butyl, tertbutyl, or pentyl.

In certain embodiments, the substituent on the $R^2$ group is —CN, —F, —Cl, —N($R^a$)(C=O)O$R^a$, or COO$R^a$.

In certain embodiments, the substituent on the $R^2$ group is —CN, —F, —Cl, —$N(R^a)(C{=}O)OR^a$, or —$COOR^a$. In certain embodiments, the substituent on the $R^2$ group is —CN, —F, —Cl, —$NR^a_2$, —$N(R^a)(C{=}O)OR^a$, —$COOR^a$, or —$(C{=}O)R^a$. In certain embodiments, the substituent on the $R^1$ group is —CN, —F, —Cl, —$NH_2$, —NHC(=O)OEt, —NHC(=O)OMe, —NHC(=O)$O^t$Bu, or —C(=O)$CH_3$.

In certain embodiments, when $R^2$ is unsubstituted methyl, $R^1$ is not unsubstituted ethyl. In some embodiments, when $R^2$ is methyl, $R^1$ is not ethyl.

In certain embodiments, when $R^2$ is unsubstituted methyl, $R^1$ is not unsubstituted n-propyl. In some embodiments, when $R^2$ is methyl, $R^1$ is not n-propyl.

In certain embodiments, when $R^2$ is unsubstituted methyl, $R^1$ is not unsubstituted ethoxy. In some embodiments, when $R^2$ is methyl, $R^1$ is not ethoxy.

In certain embodiments, $R^1$ is substituted or unsubstituted methyl, substituted or unsubstituted ethyl, methoxy, or ethoxy; and $R^2$ is substituted or unsubstituted methyl, substituted or unsubstituted ethyl, substituted or unsubstituted propyl, substituted or unsubstituted isopropyl, substituted or unsubstituted butyl, substituted or unsubstituted sec-butyl, substituted or unsubstituted 3- to 6-membered carbocyclyl-$C_1$ alkyl, substituted or unsubstituted 3- to 6-membered carbocyclyl-$C_2$ alkyl, substituted or unsubstituted 3- to 6-membered heterocyclyl-$C_1$ alkyl, or substituted or unsubstituted 3- to 6-membered heterocyclyl-$C_2$ alkyl.

In certain embodiments, $R^2$ is substituted $C_{1-6}$ alkyl. In some embodiments, $R^2$ is haloalkyl. In certain embodiments, $R^2$ is difluoroethyl. In some embodiments, $R^2$ is 2,2-difluoroethyl.

In some embodiments, $R^2$ is substituted or unsubstituted 3- to 6-membered carbocyclyl-$C_{1-6}$ alkyl. In some embodiments, $R^2$ is substituted or unsubstituted 3- to 6-membered carbocyclyl-$C_1$ alkyl. In some embodiments, $R^2$ is cyclopropylmethyl.

In some embodiments, $R^3$ is hydrogen, halogen, substituted or unsubstituted, $C_{1-6}$ alkyl, —$OR^a$, —$COOR^a$, —$COR^a$, —$N(R^a)_2$, —CN, or —$(C{=}O)N(R^a)_2$. In some embodiments, $R^3$ is hydrogen, chloro, bromo, iodo, substituted or unsubstituted, $C_{1-6}$ alkyl, —$OR^a$, —$COOR^a$, —$COR^a$, —$N(R^a)_2$, —CN, or —$(C{=}O)N(R^a)_2$. In some embodiments, $R^3$ is hydrogen, substituted or unsubstituted, $C_{1-6}$ alkyl, —$OR^a$, —$COOR^a$, —$COR^a$, —$N(R^a)_2$, —CN, or —$(C{=}O)N(R^a)_2$.

In some embodiments, $R^3$ is hydrogen. In certain embodiments, $R^3$ is halogen. In certain embodiments, $R^3$ is chloro, bromo, or iodo. In certain embodiments, $R^3$ is chloro. In certain embodiments, $R^3$ is fluoro. In certain embodiments, $R^3$ is —CN. In certain embodiments, $R^3$ is substituted or unsubstituted, $C_{1-6}$ alkyl (e.g., unsubstituted $C_{1-6}$ alkyl). In certain embodiments, $R^3$ is methyl. In certain embodiments, $R^3$ is ethyl. In some embodiments, $R^3$ is propyl or butyl. In certain embodiments, $R^3$ is fluorinated $C_{1-6}$ alkyl (e.g., fluorinated methyl, e.g., —$CF_3$). In certain embodiments, $R^3$ is —$OR^a$. In certain embodiments, $R^3$ is —OH. In certain embodiments, $R^3$ is —O(substituted or unsubstituted, $C_{1-6}$ alkyl) (e.g., —OMe). In certain embodiments, $R^3$ is —$COOR^a$. In certain embodiments, $R^3$ is —$COOR^a$, where Ra is hydrogen or substituted or unsubstituted, $C_{1-6}$ alkyl (e.g., —COOMe, —COOEt, —$COO(CH_2)_2CH_3$, —$COO(CH_2)_3CH_3$, or —$COOC(CH_3)_3$. In certain embodiments, $R^3$ is —$COR^a$. In certain embodiments, $R^3$ is —$COR^a$ where Ra is hydrogen or substituted or unsubstituted, $C_{1-6}$ alkyl (e.g., —COMe, —COEt, —$CO(CH_2)_2CH_3$, —$CO(CH_2)_3CH_3$, or —$COC(CH_3)_3$). In certain embodiments, $R^3$ is —$N(R^a)_2$. In certain embodiments, $R^3$ is —$NH_2$. In certain embodiments, $R^3$ is —$NHR^a$ (e.g., —NH(substituted or unsubstituted, $C_{1-6}$ alkyl), e.g., —NHMe). In certain embodiments, $R^3$ is —N(substituted or unsubstituted, $C_{1-6}$ alkyl)$_2$, e.g., —$N(Me)_2$). In certain embodiments, $R^3$ is —$C({=}O)N(R^a)_2$. In certain embodiments, $R^3$ is —$C({=}O)NH_2$. In certain embodiments, $R^3$ is —$C({=}O)NHR^a$ (e.g., —C(=O)NH (substituted or unsubstituted, $C_{1-6}$ alkyl), e.g., —C(=O) NHMe). In certain embodiments, $R^3$ is —C(=O)N(substituted or unsubstituted, $C_{1-6}$ alkyl)$_2$, e.g., —C(=O)N(Me)$_2$). In some embodiments, $R^3$ is halo or —$COOR^a$. In some embodiments, $R^3$ is chloro or —COOMe.

In certain embodiments, each instance of Ra is independently hydrogen, substituted or unsubstituted, $C_{1-6}$ alkyl, an oxygen protecting group when attached to an oxygen atom, or a nitrogen protecting group when attached to a nitrogen atom. In certain embodiments, each instance of Ra is hydrogen. In certain embodiments, no instance of Ra is hydrogen. In certain embodiments, at least one instance of Ra is substituted or unsubstituted, $C_{1-6}$ alkyl (e.g., unsubstituted $C_{1-6}$ alkyl). In certain embodiments, at least one instance of Ra is Me. In certain embodiments, at least one instance of Ra is Et, Pr, or Bu. In certain embodiments, at least one instance of Ra is fluorinated $C_{1-6}$ alkyl (e.g., fluorinated methyl, e.g., —$CF_3$).

In some embodiments, $R^4$ is hydrogen, halogen, substituted or unsubstituted, $C_{1-6}$ alkyl, —$OR^a$, —$COOR^a$, —$COR^a$, —$N(R^a)_2$, —CN, or —$(C{=}O)N(R^a)_2$. In some embodiments, $R^4$ is hydrogen. In certain embodiments, $R^4$ is halogen. In certain embodiments, $R^4$ is chloro. In certain embodiments, $R^4$ is fluoro. In certain embodiments, $R^4$ is —CN. In certain embodiments, $R^4$ is substituted or unsubstituted, $C_{1-6}$ alkyl (e.g., unsubstituted $C_{1-6}$ alkyl). In certain embodiments, $R^4$ is methyl. In certain embodiments, $R^4$ is ethyl. In some embodiments, $R^4$ is propyl or butyl. In certain embodiments, $R^4$ is fluorinated $C_{1-6}$ alkyl (e.g., fluorinated methyl, e.g., —$CF_3$). In certain embodiments, $R^4$ is —$OR^a$. In certain embodiments, $R^4$ is —OH. In certain embodiments, $R^4$ is —O(substituted or unsubstituted, $C_{1-6}$ alkyl) (e.g., —OMe). In certain embodiments, $R^4$ is —$COOR^a$. In certain embodiments, $R^4$ is —$COOR^a$ where Ra is hydrogen or substituted or unsubstituted, $C_{1-6}$ alkyl. In certain embodiments, $R^4$ is —$COR^a$. In certain embodiments, $R^4$ is —$COR^a$ where Ra is hydrogen or substituted or unsubstituted, $C_{1-6}$ alkyl. In certain embodiments, $R^4$ is —$N(R^a)_2$. In certain embodiments, $R^4$ is —$NH_2$. In certain embodiments, $R^4$ is —$NHR^a$ (e.g., —NH(substituted or unsubstituted, $C_{1-6}$ alkyl)). In certain embodiments, $R^4$ is —N(substituted or unsubstituted, $C_{1-6}$ alkyl)$_2$, e.g., —$N(Me)_2$). In certain embodiments, $R^4$ is —$C({=}O)N(R^a)_2$. In certain embodiments, $R^4$ is —$C({=}O)N(R^a)_2$, where Ra is hydrogen or substituted or unsubstituted, $C_{1-6}$ alkyl.

In certain embodiments, p is 0. In some embodiments, p is 1. In certain embodiments, p is 2. In some embodiments, p is 3.

In certain embodiments, the phenyl ring which bears $R^3$ and optionally, bears $R^4$ is represented

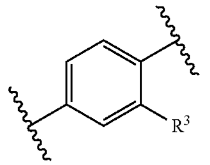

.

In some embodiments, the phenyl ring which bears $R^3$ and optionally, bears $R^4$ is represented by:

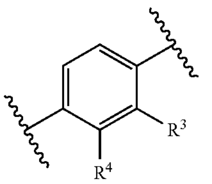
,
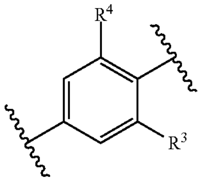
, or
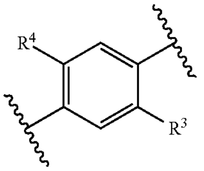
.

In certain embodiments, the phenyl ring which bears $R^3$ and optionally, bears $R^4$ is represented by:

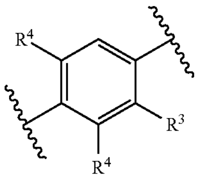
, or
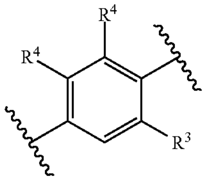
.

In certain embodiments, the phenyl ring which bears $R^3$ and optionally, bears $R^4$ is represented by:

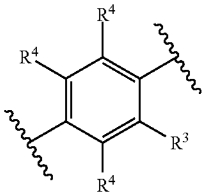
.

In certain embodiments, each instance of $R^5$ is independently hydrogen, halogen, substituted or unsubstituted, $C_{1-6}$ alkyl, —$OR^a$, —$N(Ra)_2$, or —CN. In certain embodiments, each instance of $R^5$ is independently —$COOR^a$, —$COR^a$, or —(C═O)$N(Ra)_2$. In certain embodiments, at least one instance of $R^5$ is hydrogen. In certain embodiments, each instance of $R^5$ is hydrogen. In certain embodiments, at least one instance of $R^5$ is not hydrogen. In certain embodiments, no instance of $R^5$ is hydrogen. In certain embodiments, at least one instance of $R^5$ is halogen. In certain embodiments, at least one instance of $R^5$ is F. In certain embodiments, at least one instance of $R^5$ is Cl. In certain embodiments, at least one instance of $R^5$ is substituted or unsubstituted, $C_{1-6}$ alkyl (e.g., unsubstituted $C_{1-6}$ alkyl). In certain embodiments, at least one instance of $R^5$ is Me. In certain embodiments, at least one instance of $R^5$ is Et, Pr, or Bu. In certain embodiments, at least one instance of $R^5$ is fluorinated $C_{1-6}$ alkyl (e.g., fluorinated methyl, e.g., —$CF_3$). In certain embodiments, at least one instance of $R^5$ is —$OR^a$. In certain embodiments, at least one instance of $R^5$ is —OH. In certain embodiments, at least one instance of $R^5$ is —O(substituted or unsubstituted, $C_{1-6}$ alkyl) (e.g., —OMe). In certain embodiments, at least one instance of $R^5$ is —$N(Ra)_2$. In certain embodiments, at least one instance of $R^5$ is —$NH_2$. In certain embodiments, at least one instance of $R^5$ is —$NHR^a$ (e.g., —NH(substituted or unsubstituted, $C_{1-6}$ alkyl), e.g., —NHMe). In certain embodiments, at least one instance of $R^5$ is —N(substituted or unsubstituted, $C_{1-6}$ alkyl$)_2$, e.g., —$N(Me)_2$. In certain embodiments, at least one instance of $R^5$ is —CN. In certain embodiments, at least one instance of $R^5$ is halogen, substituted or unsubstituted, $C_{1-6}$ alkyl, or —$OR^a$.

In certain embodiments, m is 0. In some embodiments, m is 1. In certain embodiments, m is 2. In some embodiments, m is 3.

In some embodiments, m is 0, and p is 0. In some embodiments, m is 0, and p is 1. In some embodiments, m is 0, p is 0, and n is 0. In some embodiments, m is 0, p is 0, and n is 1. In some embodiments, m is 0, p is 1, and n is 1.

In certain embodiments, the central pyridinyl ring, which optionally bears $R^5$, is represented by:

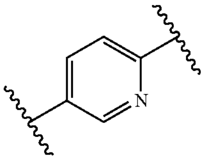
.

In certain embodiments, the central pyridinyl ring, which optionally bears $R^5$, is represented by:

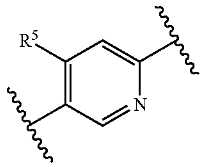
,
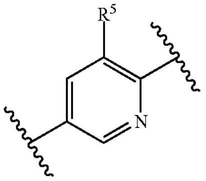
, or
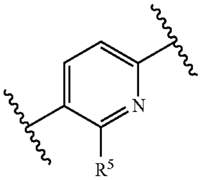
.

In certain embodiments, the central pyridinyl ring, which optionally bears $R^5$, is represented by:

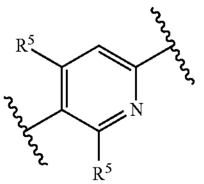
,
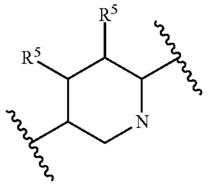
, or
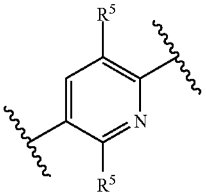
.

In certain embodiments, the central pyridinyl ring, which optionally bears $R^5$, is represented by:

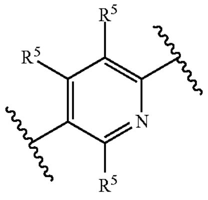

.

In certain embodiments, $R^6$ is hydrogen, substituted or unsubstituted, $C_{1-6}$ alkyl, or a nitrogen protecting group. In certain embodiments, $R^6$ is hydrogen. In certain embodiments, $R^6$ is substituted or unsubstituted, $C_{1-6}$ alkyl. In some embodiments, $R^6$ is substituted or unsubstituted methyl. In certain embodiments, $R^6$ is substituted or unsubstituted ethyl. In some embodiments, $R^6$ is nitrogen protecting group selected from tosyl, tert-butyloxycarbonyl, acetyl, or benzoyl.

In certain embodiments, each instance of $R^1$ is independently hydrogen, halogen, or substituted or unsubstituted, $C_{1-6}$ alkyl. In certain embodiments, each instance of $R^1$ is hydrogen. In certain embodiments, one instance of $R^1$ is hydrogen. In certain embodiments, at least one instance of $R^1$ is halogen. In certain embodiments, at least one instance of $R^1$ is substituted or unsubstituted, $C_{1-6}$ alkyl.

In certain embodiments, at least one instance of $R^1$ is unsubstituted $C_{1-6}$ alkyl (e.g., methyl, ethyl, propyl). In certain embodiments, at least one instance of $R^1$ is $C_{1-6}$ alkyl substituted with at least one instance of halogen (e.g., F).

In certain embodiments, q is 0. In some embodiments, q is 1.

In some embodiments, q is 0 and n is 0, 1, or 2. In some embodiments, q is 1 and n is 0, 1, or 2.

In some embodiments, each instance of $R^9$ is independently hydrogen, halogen, substituted or unsubstituted, $C_{1-6}$ alkyl, —$OR^a$, —$COOR^a$, —$COR^a$, —$N(R^a)_2$, —CN, or —(C═O)$N(R^a)_2$, or two instances of $R^9$ are joined to form a 3- to 13 membered heterocyclyl, 3- to 13 membered heterocyclyl, 6- to 12 membered aryl ring, or 5- to 14 membered heteroaryl ring. In certain embodiments, each instance of $R^9$ is independently hydrogen, halogen, substituted or unsubstituted, $C_{1-6}$ alkyl, —$OR^a$, —$COOR^a$, —$COR^a$, —$N(R^a)_2$, —CN, or —(C═O)$N(R^a)_2$. Each instance of $R^9$ is independently hydrogen, halogen, substituted or unsubstituted, $C_{1-6}$ alkyl, —$OR^a$, or —$N(R^a)_2$. In certain embodiments, at least one instance of $R^9$ is hydrogen. In certain embodiments, each instance of $R^9$ is hydrogen. In certain embodiments, at least one instance of $R^9$ is not hydrogen. In certain embodiments, no instance of $R^9$ is hydrogen. In certain embodiments, at least one instance of $R^9$ is halogen. In certain embodiments, at least one instance of $R^9$ is F. In certain embodiments, at least one instance of $R^9$ is Cl. In certain embodiments, at least one instance of $R^9$ is substituted or unsubstituted, $C_{1-6}$ alkyl (e.g., unsubstituted $C_{1-6}$ alkyl). In certain embodiments, at least one instance of $R^9$ is Me. In certain embodiments, at least one instance of $R^9$ is Et. In certain embodiments, at least one instance of $R^9$ is Pr or Bu. In certain embodiments, at least one instance of $R^9$ is fluorinated $C_{1-6}$ alkyl (e.g., fluorinated methyl, e.g., —$CF_3$). In certain embodiments, at least one instance of $R^9$ is —$OR^a$. In certain embodiments, at least one instance of $R^9$ is —OH. In certain embodiments, at least one instance of $R^9$ is —O(substituted or unsubstituted, $C_{1-6}$ alkyl). In certain embodiments, at least one instance of $R^9$ is —OMe. In certain embodiments, at least one instance of $R^9$ is —$N(R^a)_2$. In certain embodiments, at least one instance of $R^9$ is —$NH_2$. In certain embodiments, at least one instance of $R^9$ is —$NHR^a$ (e.g., —NH(substituted or unsubstituted, $C_{1-6}$ alkyl), e.g., —NHMe). In certain embodiments, at least one instance of $R^9$ is —$NHR^a$, wherein Ra is a substituted $C_{1-6}$ alkyl. In certain embodiments, at least one instance of $R^9$ is —$NHR^a$, wherein Ra is a $C_{1-6}$ alkyl substituted with —$NH_2$, —NHMe, or —$NMe_2$. In certain embodiments, at least one instance of $R^9$ is —$NHR^a$, wherein Ra is an unsubstituted $C_{1-6}$ alkyl. In certain embodiments, at least one instance of $R^9$ is —N(substituted or unsubstituted, $C_{1-6}$ alkyl)$_2$. In certain embodiments, at least one instance of $R^9$ is —$N(Me)_2$. In certain embodiments, at least one instance of $R^9$ is —CN. In certain embodiments, at least one instance of $R^9$ is halogen, substituted or unsubstituted, $C_{1-6}$ alkyl, or —$OR^a$. In certain embodiments, more than one instance of $R^9$ is $C_{1-6}$ alkyl (e.g., two instances of $R^9$ are methyl). In certain embodiments, more than one instance of $R^9$ is halogen (e.g., two instances of $R^9$ are fluoro). In some embodiments, one instance of $R^9$ is $C_{1-6}$ alkyl, and a second instance of $R^9$ is halogen. In some embodiments, one instance of $R^9$ is methyl, and a second instance of $R^9$ is fluoro.

In certain embodiments, n is 0. In some embodiments, n is 1. In certain embodiments, n is 2. In some embodiments, n is 3. In certain embodiments, n is 4.

In certain embodiments, the terminal pyridinyl ring, which optionally bears $R^9$, is represented by:

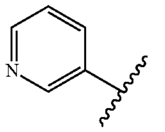

.

In certain embodiments, the terminal pyridinyl ring, which optionally bears $R^9$, is represented by:

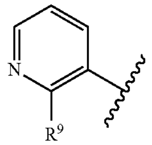

,

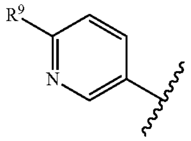

,

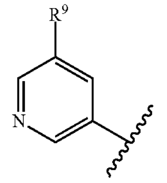

, or

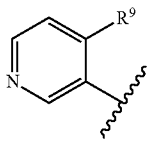

.

In some embodiments, the terminal pyridinyl ring, which optionally bears $R^9$, is represented by:

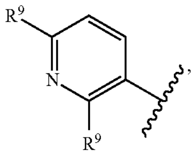

,

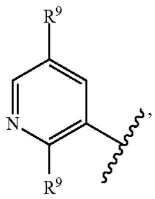

,

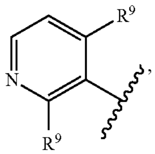

,

-continued

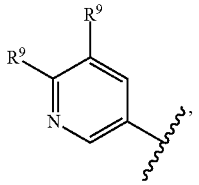

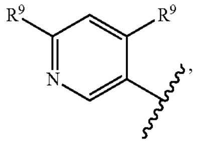

or

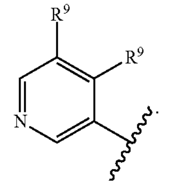

In certain embodiments, the terminal pyridinyl ring, which optionally bears $R^9$, is represented by:

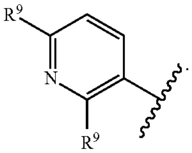

In some embodiments, the terminal pyridinyl ring, which optionally bears $R^9$, is represented by:

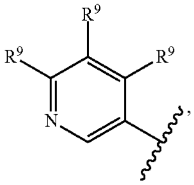

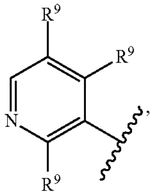

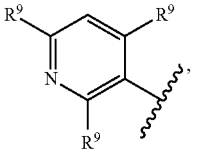

or

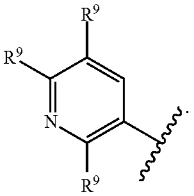

In certain embodiments, the terminal pyridinyl ring, which optionally bears $R^9$, is represented by:

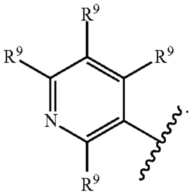

In certain embodiments, the terminal pyridinyl ring, which optionally bears $R^9$, is represented by:

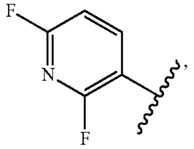

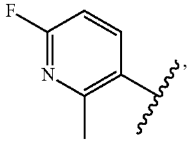

or

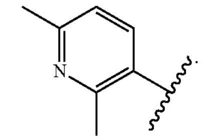

In certain embodiments, the terminal pyridinyl ring, which optionally bears $R^9$, is represented by:

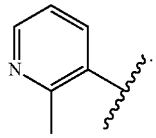 [SMILES: *c1cccnc1C]

In certain embodiments, the terminal pyridinyl ring, which optionally bears $R^9$, is represented by:

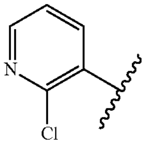

or

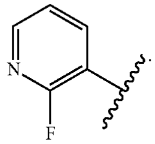

In certain embodiments, the terminal pyridinyl ring, which optionally bears $R^9$, is represented by

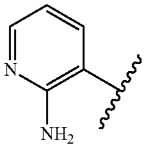

or

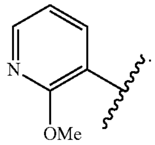

In certain embodiments, the terminal pyridinyl ring, which optionally bears $R^9$, is represented by:

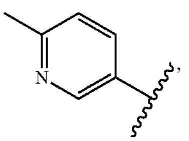

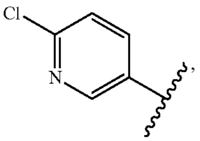

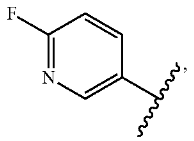

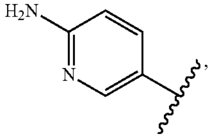

or

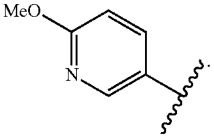

In some embodiments, two instances of $R^9$ are joined to form a 3- to 13 membered heterocyclyl, 3- to 13 membered heterocyclyl, 6- to 12 membered aryl ring, or 5- to 14 membered heteroaryl ring. In certain embodiments, two instances of $R^9$ are joined to form a 5-membered heteroaryl ring. In certain embodiments, two instances of $R^9$ are joined to form a 5-membered heterocyclyl ring. In some embodiments, two instances of $R^9$ are joined to form pyrrolyl, imidazolyl, pyrazolyl, furanyl, oxazolyl, isooxazolyl, thiophenyl, thiazolyl, isothiazolyl, triazolyl, pyrrolinyl, pyrazolinyl, or imidazolinyl. In certain embodiments, two instances of $R^9$ are joined to form a 5-membered heteroaryl or heterocyclyl ring, and when viewed together with the pyridinyl ring to which the $R^9$ groups are attached, the group is represented by:

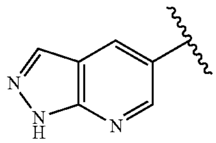,
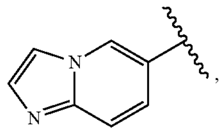,
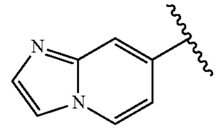,
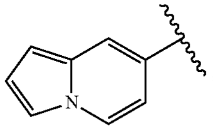,
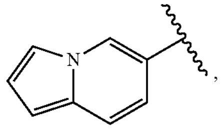,
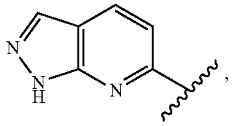,
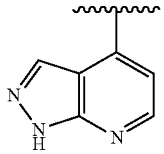,
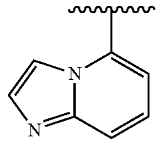,
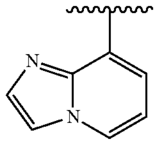,
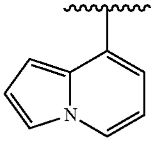, or
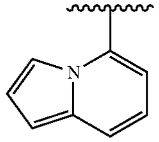.

In certain embodiments, $R^3$ is halo or —COOR$^a$, $R^2$ is $C_{1-6}$ haloalkyl or 3- to 6-membered carbocyclyl-$C_{1-6}$ alkyl, and $R^1$ is substituted or unsubstituted $C_{1-6}$ alkyl. In certain embodiments, $R^3$ is halo or —COOR$^a$, $R^2$ is $C_{1-6}$ haloalkyl or 3- to 6-membered carbocyclyl-$C_{1-6}$ alkyl, and $R^1$ is substituted or unsubstituted methyl.

In some embodiments, a compound of Formula (I) is of the Formula (Iz), wherein each $R^9$ is independently selected from methyl, fluoro, chloro, methoxy, and amino, and $R^3$ is methyl, fluoro, or chloro. In certain embodiments, each $R^9$ is independently selected from methyl, fluoro, chloro, methoxy, and amino, and $R^3$ is methyl. In some embodiments, each $R^9$ is independently selected from methyl, fluoro, and chloro, and $R^3$ is methyl. In certain embodiments, each $R^9$ is methyl, and $R^3$ is methyl. In some embodiments, each $R^9$ is methyl. In certain embodiments, $R^3$ is methyl.

In some embodiments, a compound of Formula (I) is of the formula:

(Ia)

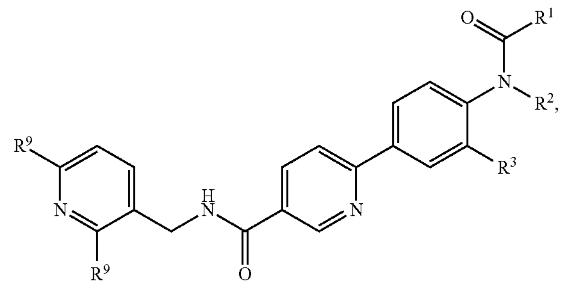

(Ib)

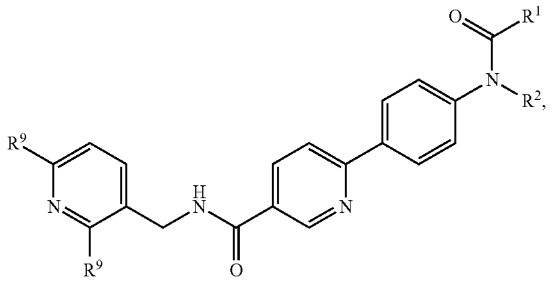, or (Ic)

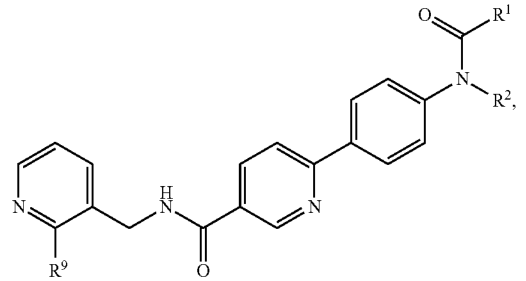

wherein each $R^9$ is independently selected from methyl, fluoro, chloro, methoxy, and amino; and $R^3$ is methyl, fluoro, or chloro. In certain embodiments, each $R^9$ is independently selected from methyl, fluoro, chloro, methoxy, and amino; and $R^3$ is methyl. In some embodiments, each $R^9$ is independently selected from methyl, fluoro, and chloro; and $R^3$ is methyl. In certain embodiments, each $R^9$ is methyl; and $R^3$ is methyl. In some embodiments, each $R^9$ is methyl. In certain embodiments, $R^3$ is methyl.

In some embodiments, a compound of Formula (I) is of the Formula (Iz), wherein each $R^9$ is independently selected from methyl, fluoro, chloro, methoxy, and amino, and $R^3$ is methyl, fluoro, or chloro. In certain embodiments, each $R^9$ is independently selected from methyl, fluoro, chloro, methoxy, and amino, and $R^3$ is chloro. In some embodiments, each $R^9$ is independently selected from methyl, fluoro, and chloro, and $R^3$ is chloro. In certain embodiments, each $R^9$ is methyl, and $R^3$ is chloro. In some embodiments, each $R^9$ is methyl. In certain embodiments, $R^3$ is chloro.

In some embodiments, a compound of Formula (I) is of the formula:

(Ia)

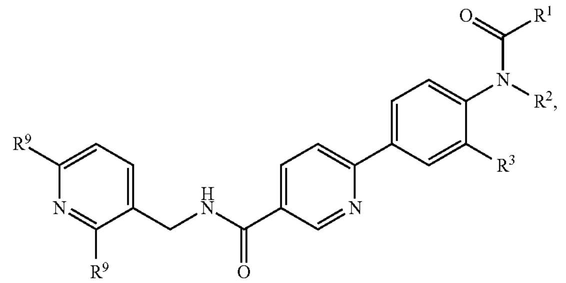

(Ib)

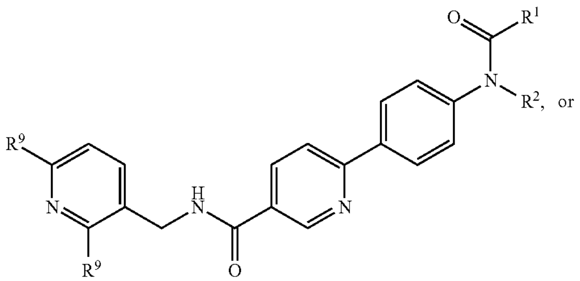

(Ic)

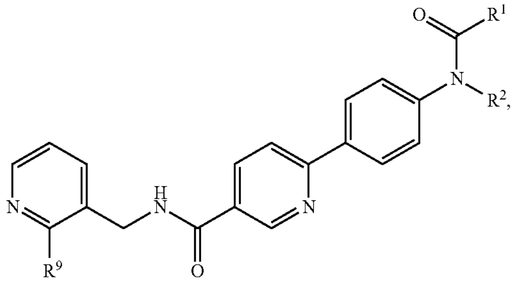

wherein each $R^9$ is independently selected from methyl, fluoro, chloro, methoxy, and amino; and $R^3$ is methyl, fluoro, or chloro. In certain embodiments, each $R^9$ is independently selected from methyl, fluoro, chloro, methoxy, and amino; and $R^3$ is chloro. In some embodiments, each $R^9$ is independently selected from methyl, fluoro, and chloro; and $R^3$ is chloro. In certain embodiments, each $R^9$ is methyl; and $R^3$ is chloro. In some embodiments, each $R^9$ is methyl. In certain embodiments, $R^3$ is chloro.

In some embodiments, a compound of Formula (0) is of the formula (0a), (0b), or (0c), wherein each $R^9$ is independently selected from methyl, fluoro, chloro, methoxy, and amino, or two instances of $R^9$ are joined to form a ring, and $R^3$ is methyl, fluoro, or chloro. In certain embodiments, each $R^9$ is independently selected from methyl, fluoro, chloro, methoxy, and amino, and $R^3$ is methyl. In some embodiments, each $R^9$ is independently selected from methyl, fluoro, and chloro, and $R^3$ is methyl. In certain embodiments, each $R^9$ is methyl, and $R^3$ is methyl. In some embodiments, each $R^9$ is methyl. In certain embodiments, $R^3$ is methyl.

In some embodiments, a compound of Formula (0) is of the formula (0a), (0b), or (0c), wherein each $R^9$ is independently selected from methyl, fluoro, chloro, methoxy, and amino, or two instances of $R^9$ are joined to form a ring, and $R^3$ is methyl, fluoro, or chloro. In certain embodiments, each $R^9$ is independently selected from methyl, fluoro, chloro, methoxy, and amino, and $R^3$ is chloro. In some embodiments, each $R^9$ is independently selected from methyl, fluoro, and chloro, and $R^3$ is chloro. In certain embodiments, each $R^9$ is methyl, and $R^3$ is chloro. In some embodiments, each $R^9$ is methyl. In certain embodiments, $R^3$ is chloro.

In certain embodiments, q is 1 in a compound of Formula (0). In certain embodiments, q is 1 in a compound of Formula (0a). In certain embodiments, q is 1 in a compound of Formula (0b). In certain embodiments, q is 1 in a compound of Formula (0c). In some embodiments, q is 1 and $R^3$ is methyl, chloro or —$COOR^a$ in a compound of Formula (0), (0a), (0b), or (0c).

In certain embodiments, q is 0 in a compound of Formula (0). In certain embodiments, q is 0 in a compound of Formula (0a). In certain embodiments, q is 0 in a compound of Formula (0b). In certain embodiments, q is 0 in a compound of Formula (0c). In some embodiments, q is 0 and $R^3$ is methyl, chloro or —$COOR^a$ in a compound of Formula (0), (0a), (0b), or (0c).

In certain embodiments, a compound of Formula (0) or (I) is of the formula:

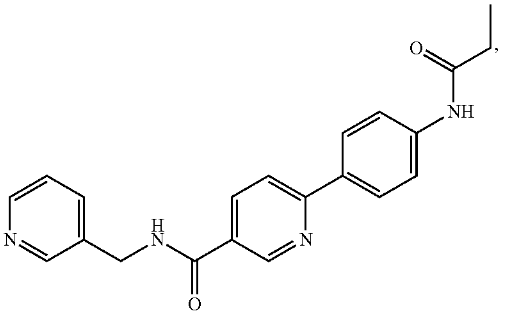

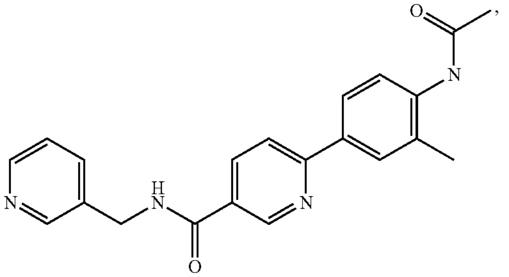

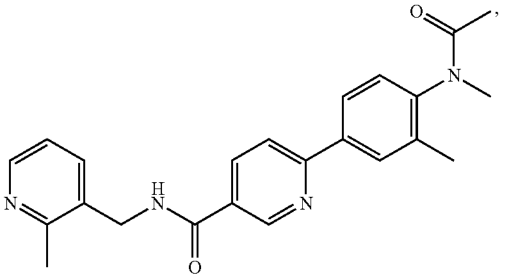

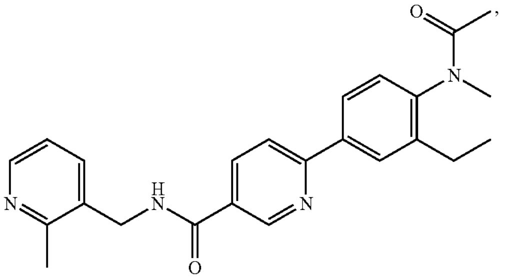

-continued
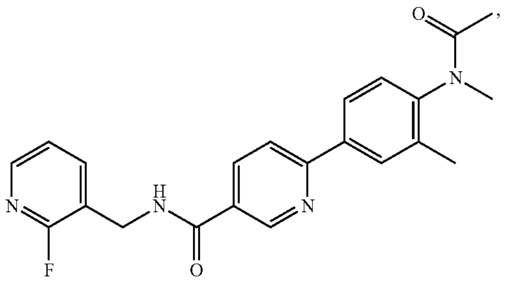
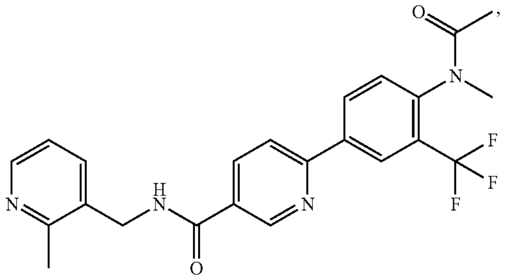
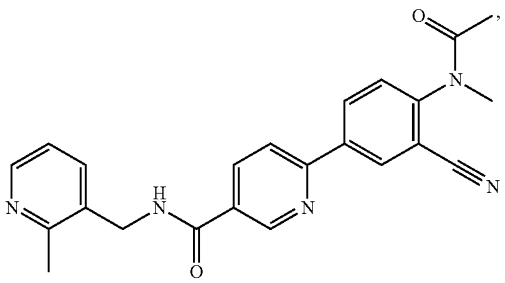
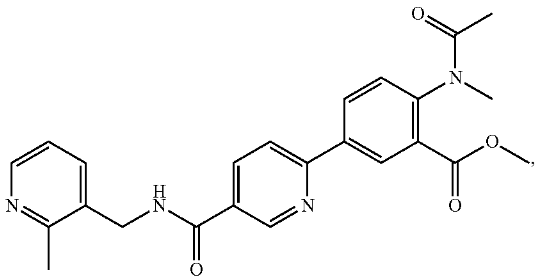
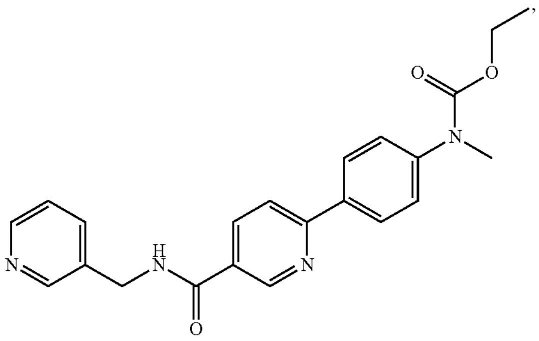
-continued
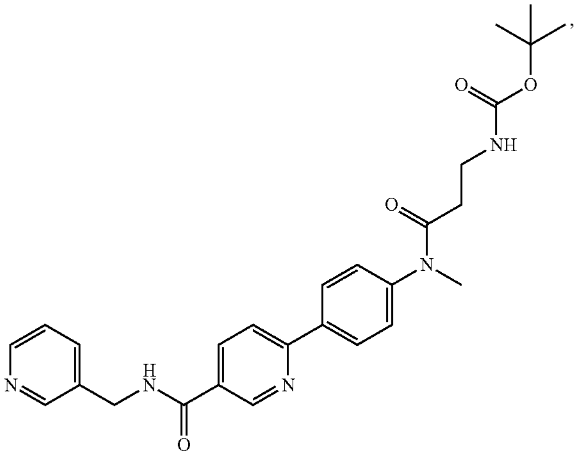
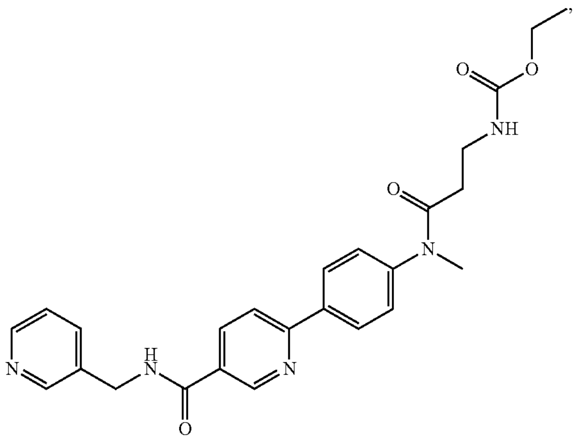
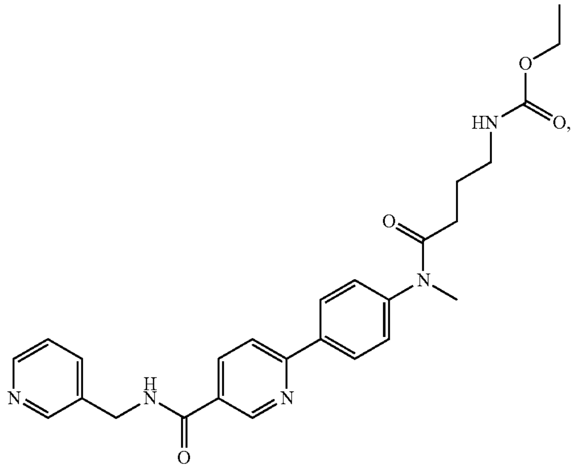
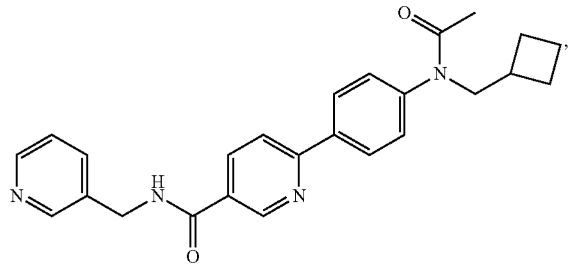

-continued
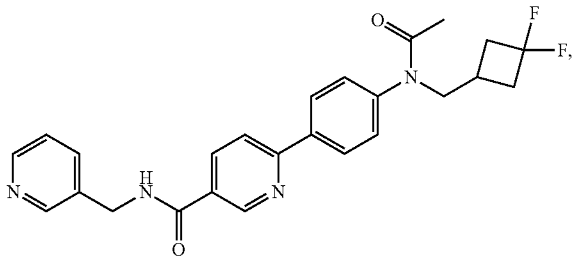
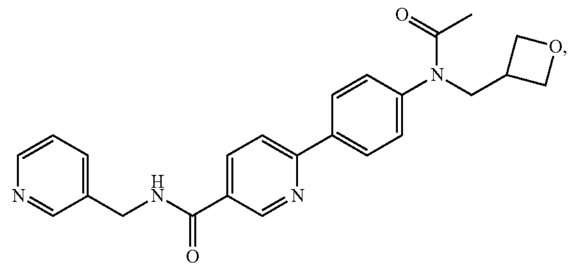
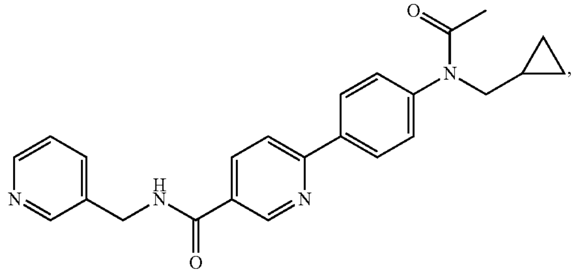
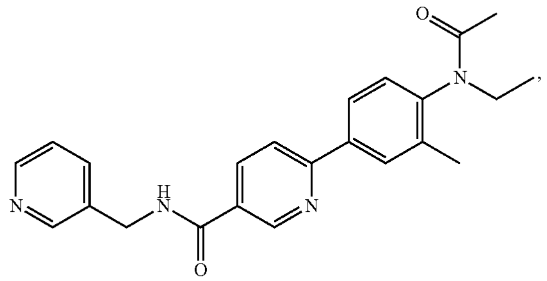
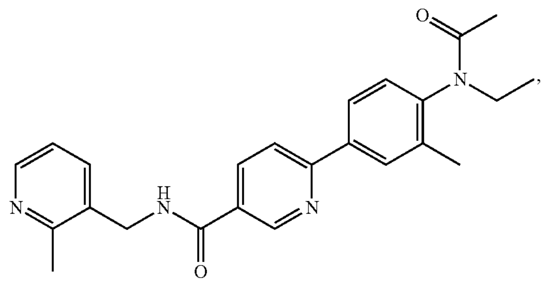
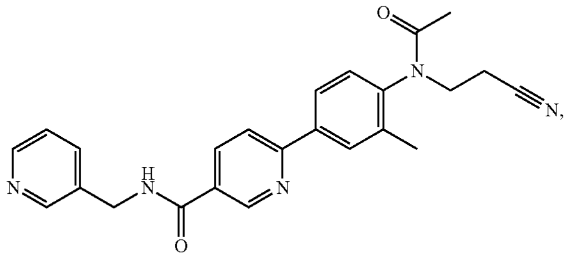
-continued
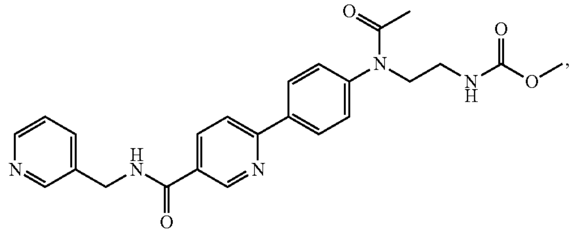
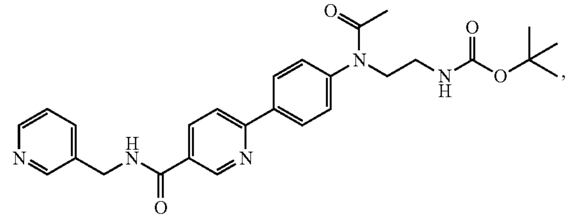
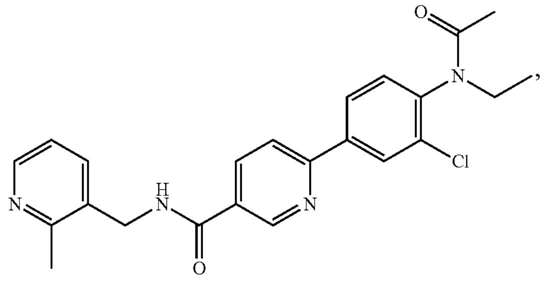
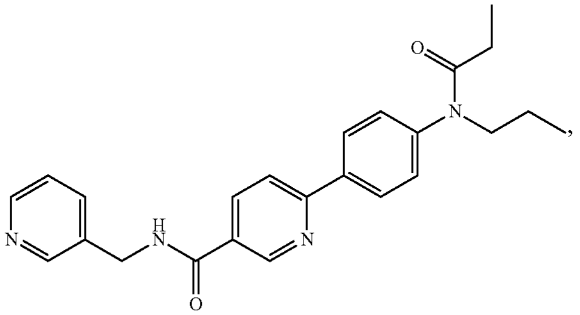
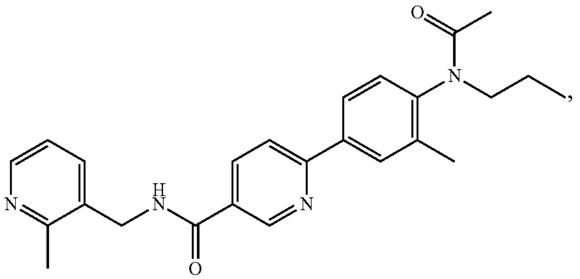
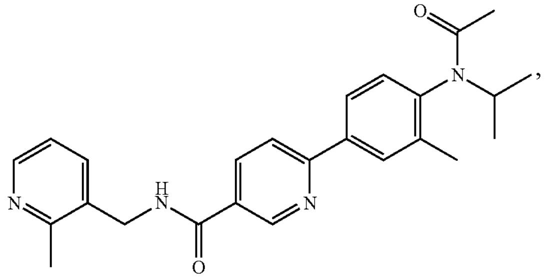

-continued
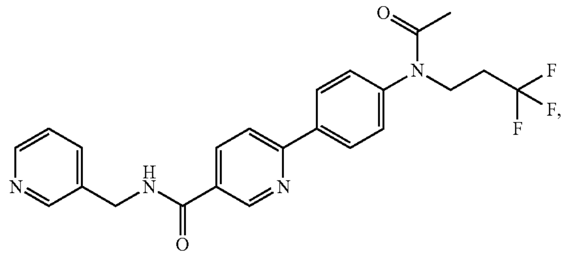
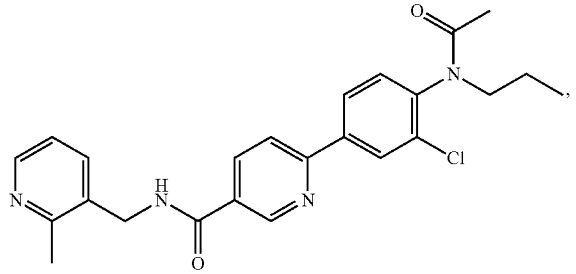
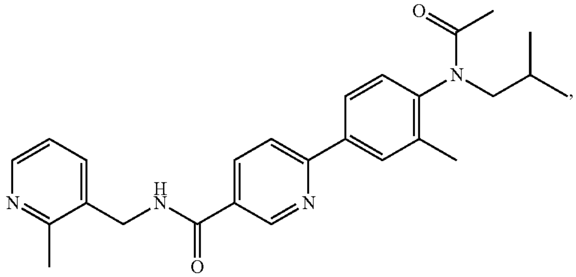
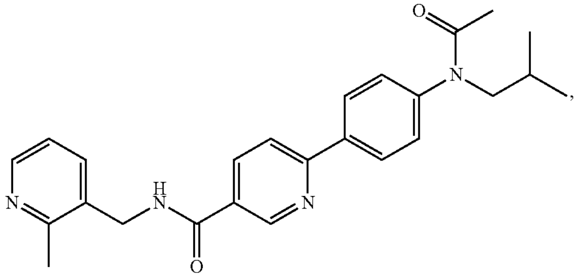
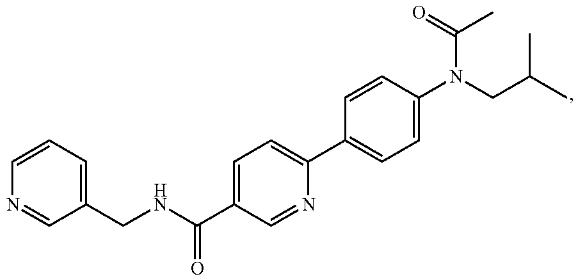
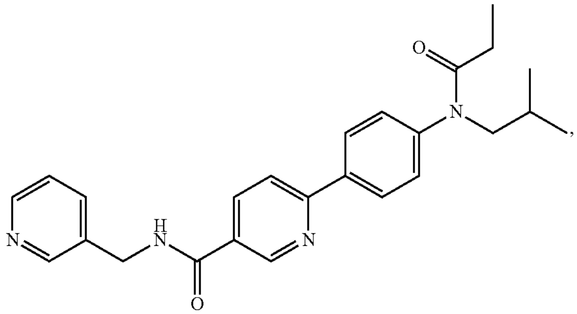
-continued
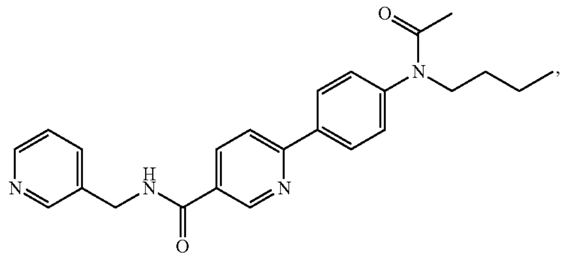
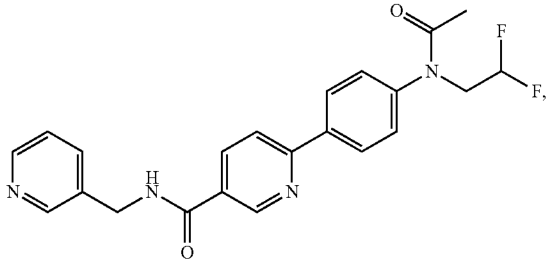
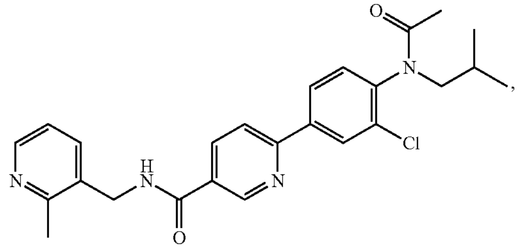
and
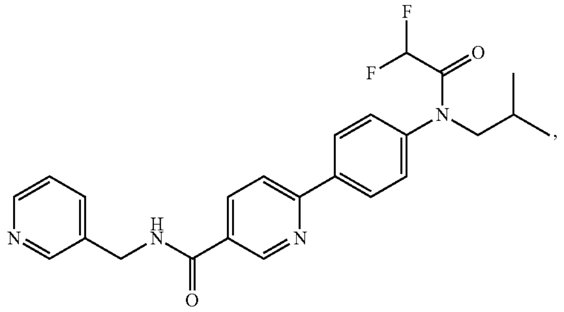
or a pharmaceutically acceptable salt, hydrate, polymorph, co-crystal, tautomer, stereoisomer, isotopically labeled derivative, or prodrug thereof.
In some embodiments, a compound of Formula (0) or (I) is a compound of the formula:
I-389
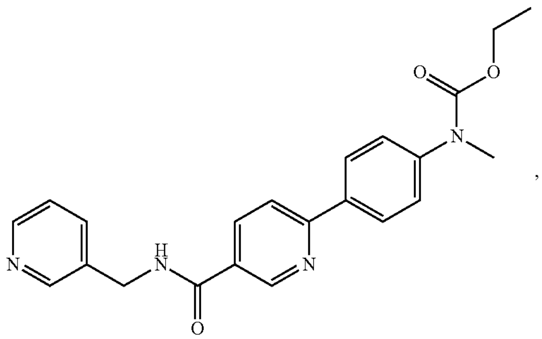

-continued
I-403
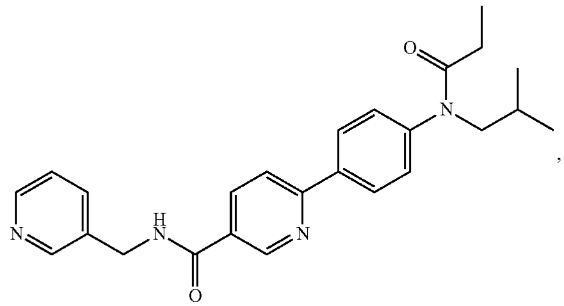
,
I-404
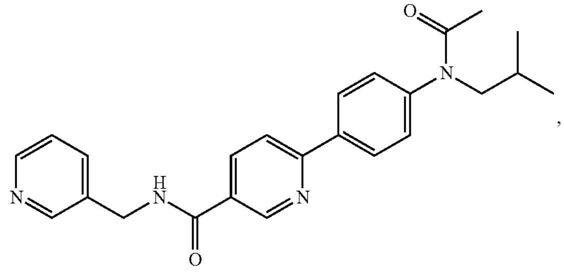
,
I-410
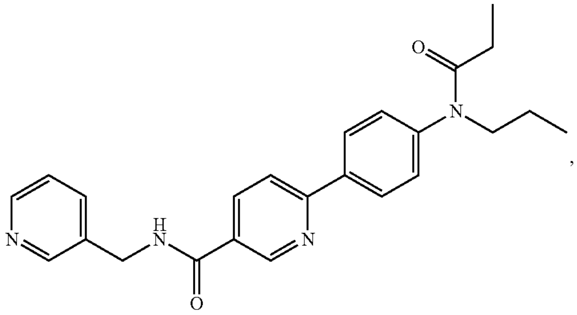
,
I-411
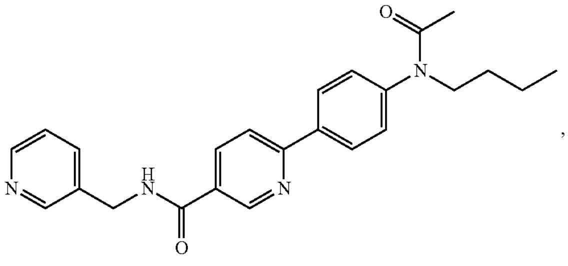
,
I-412
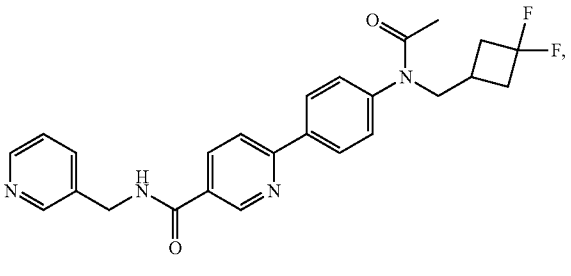
,
-continued
I-421
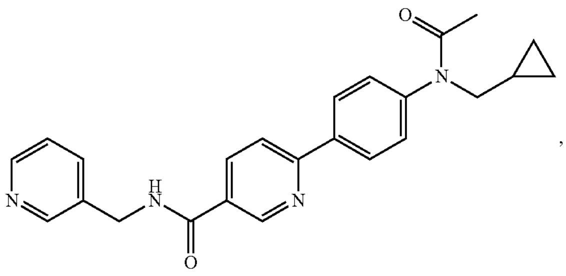
,
I-425
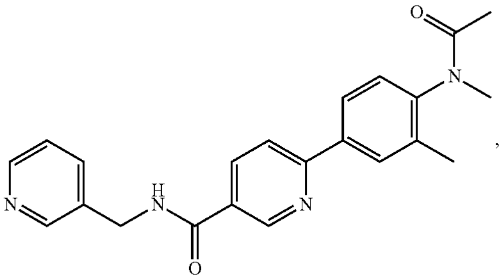
,
I-428
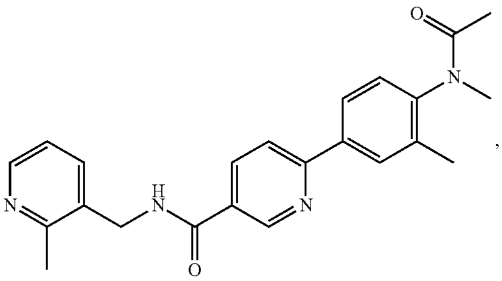
,
I-429
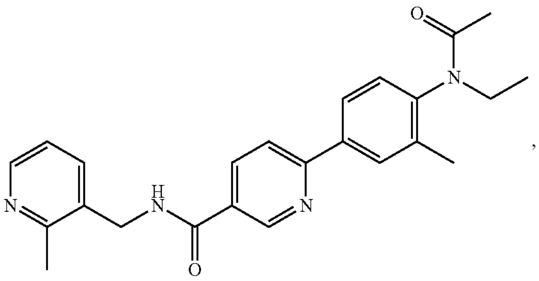
,
I-430
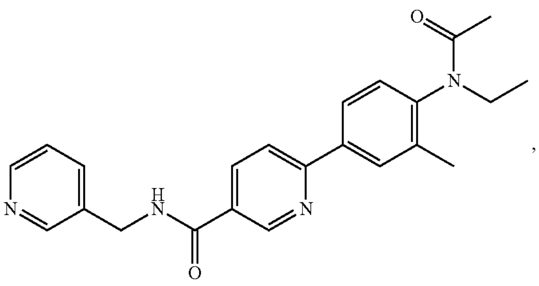
, -continued
I-436
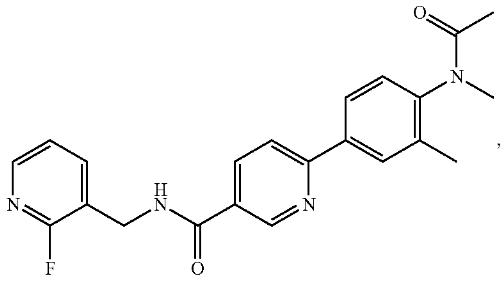
,
I-444
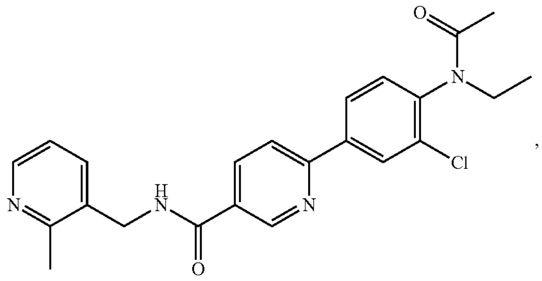
,
I-445
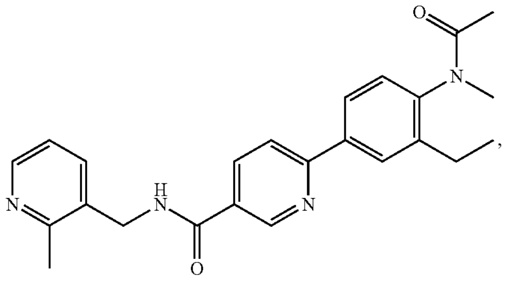
,
I-446
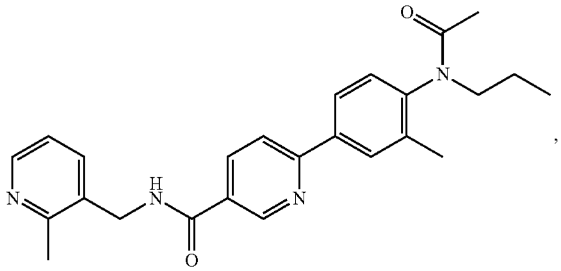
,
I-447
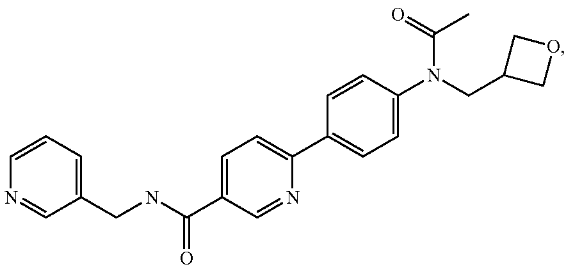
,
-continued
I-448
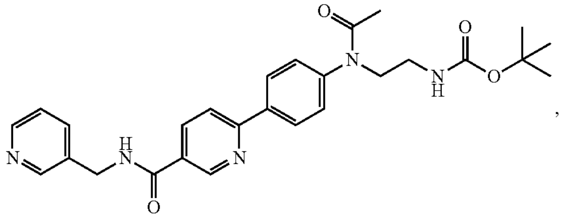
,
I-449
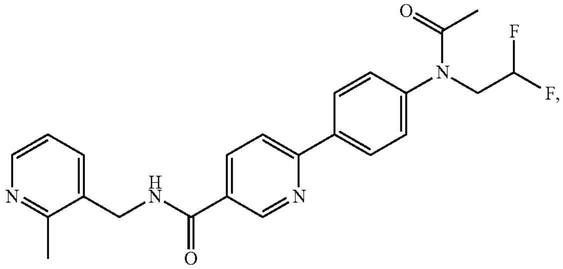
,
I-453
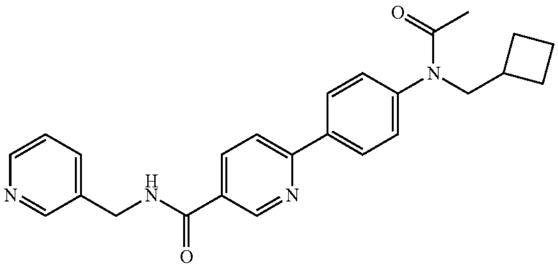
,
I-454
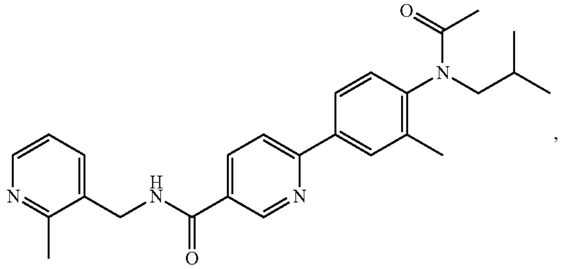
,
I-455
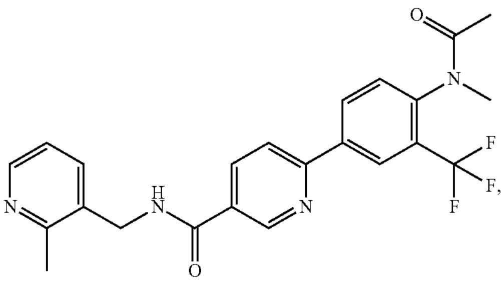
, -continued
I-456
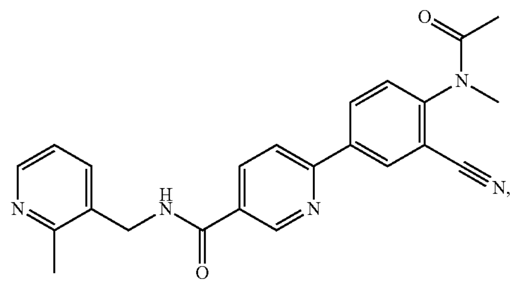
I-457
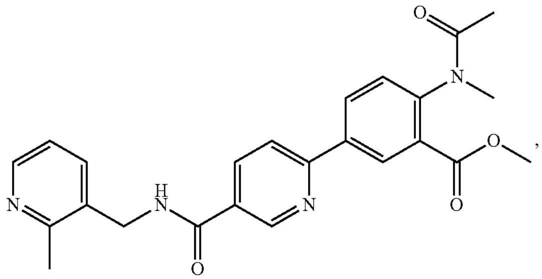
,
I-458
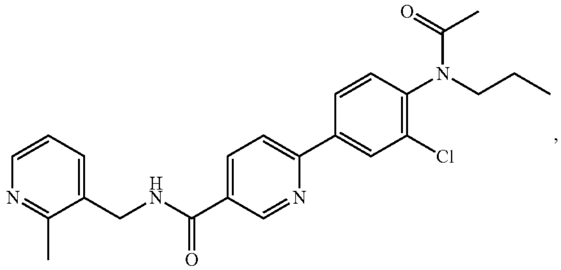
,
I-459
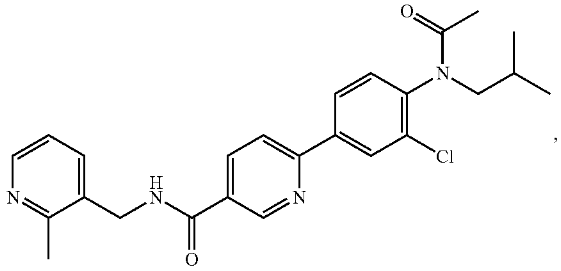
,
I-466
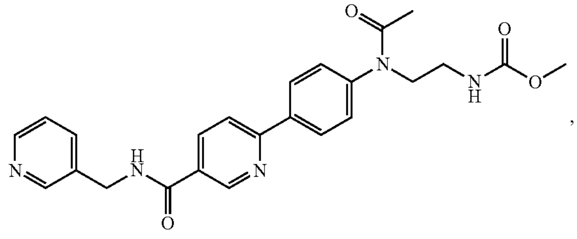
,
-continued
I-467
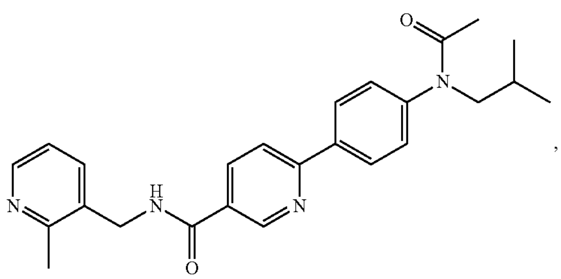
,
I-468
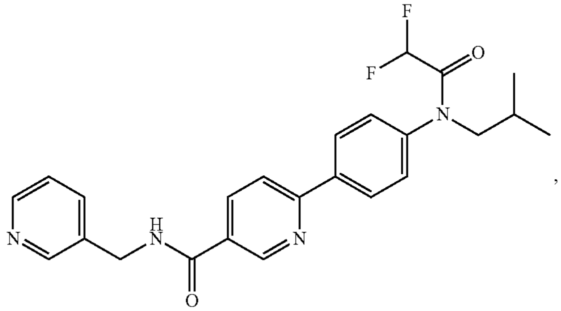
,
I-482
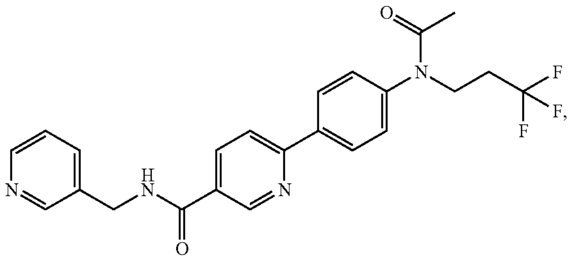
I-483
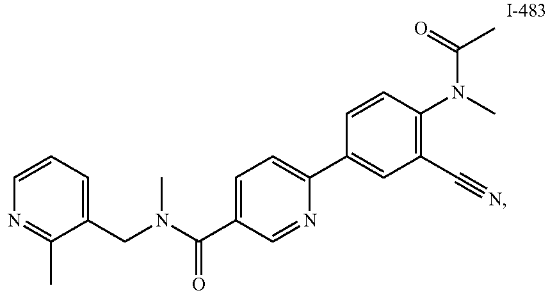
I-484
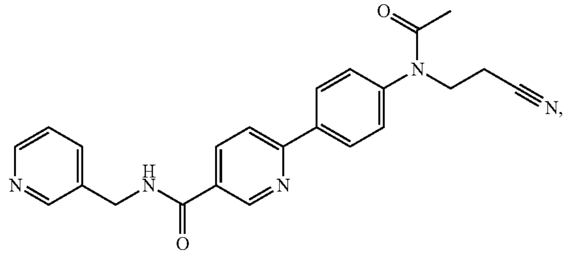

-continued
I-485
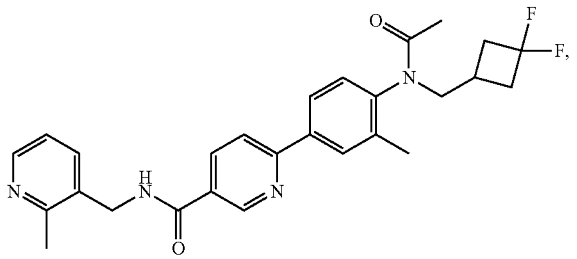
I-486
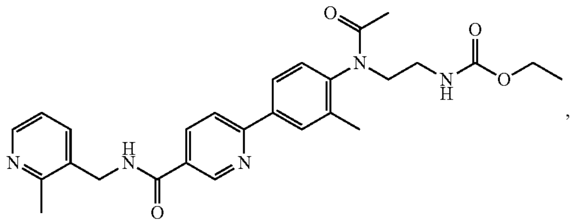
,
I-487
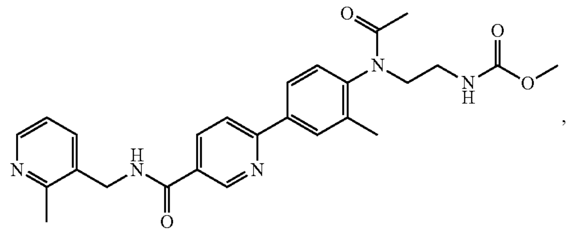
,
I-488
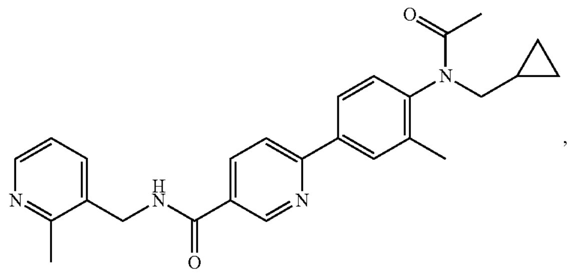
,
I-489
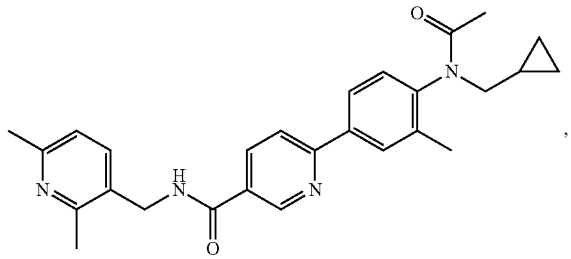
,
-continued
I-491
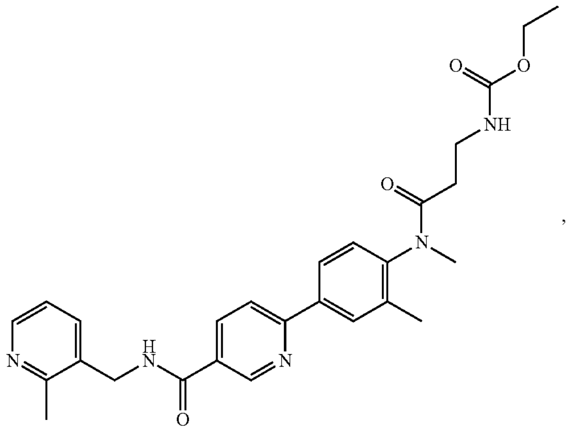
,
I-492
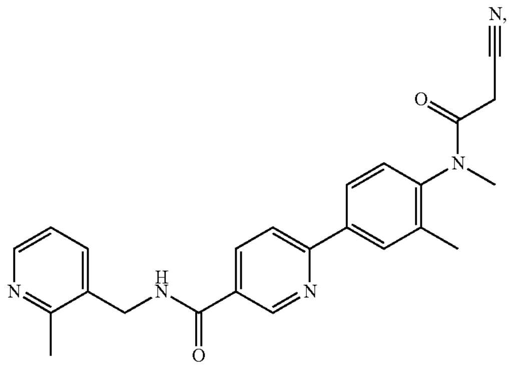
I-495
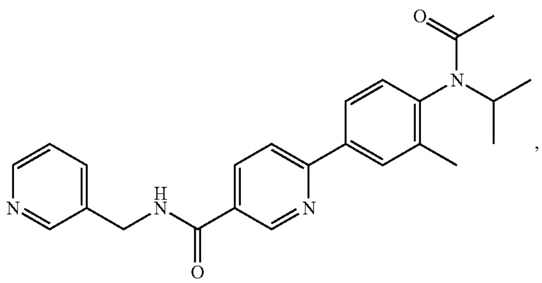
,
I-497
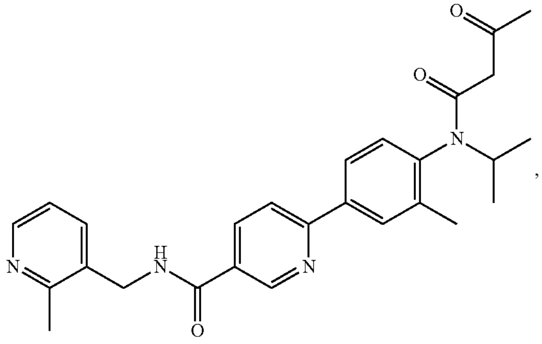
, -continued
I-499
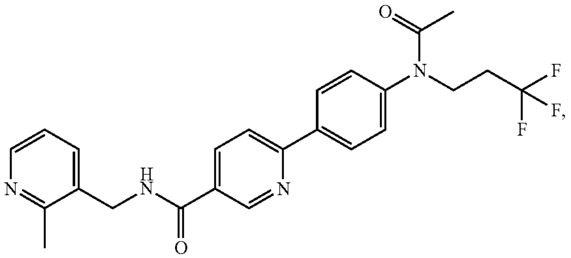
I-500
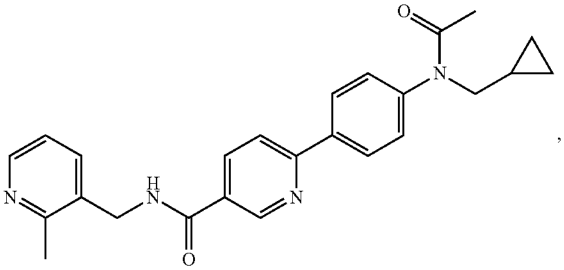
,
I-501
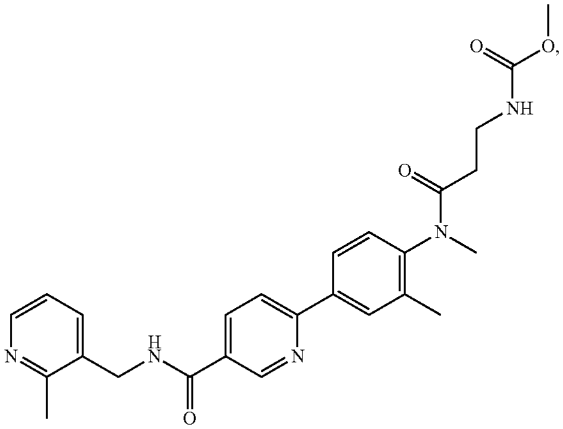
I-502
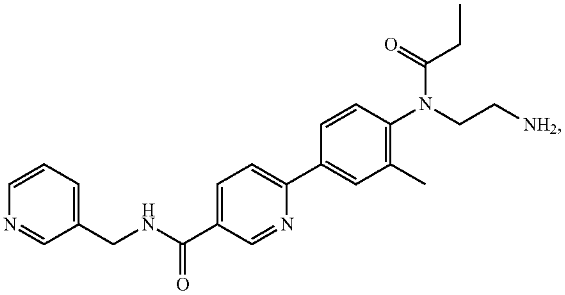
I-503
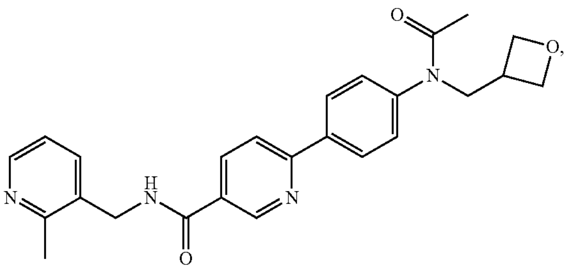
-continued
I-510
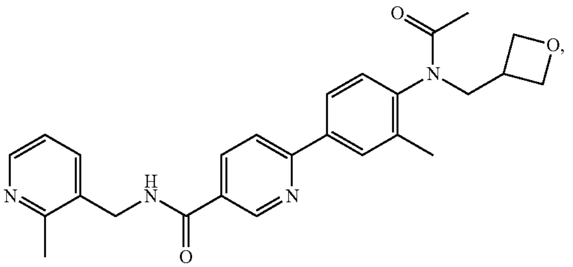
I-512
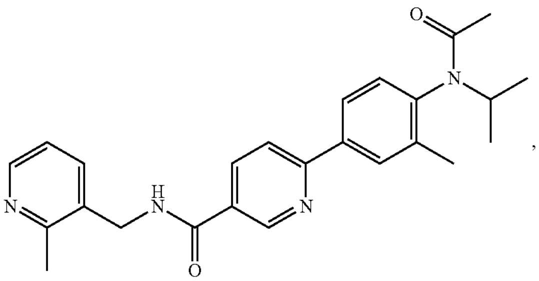
,
I-517
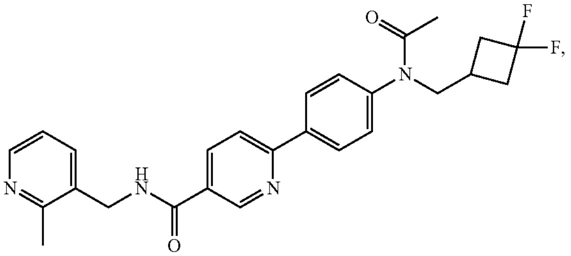
I-593
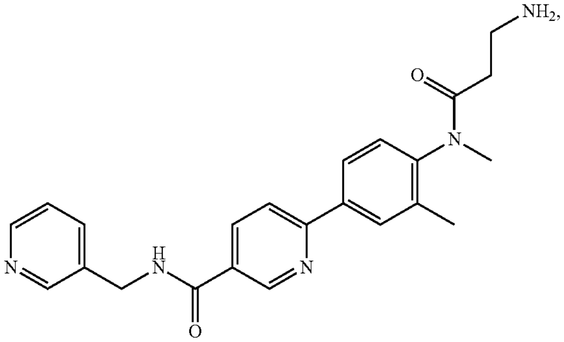
I-594
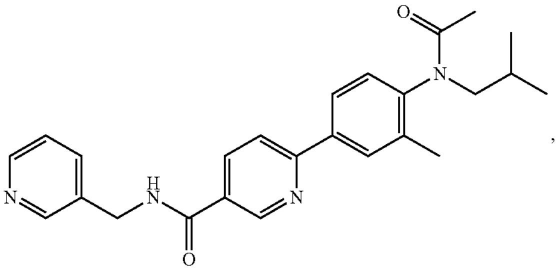
, -continued
I-595
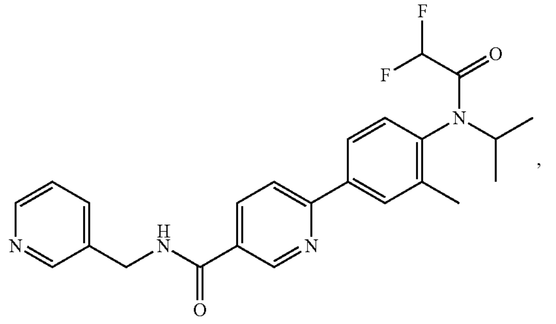
I-596
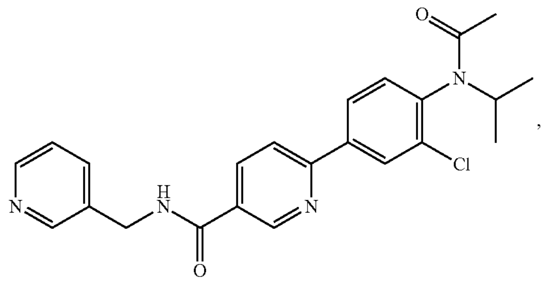
I-599
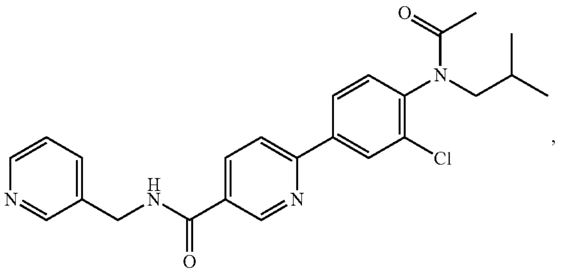
I-600
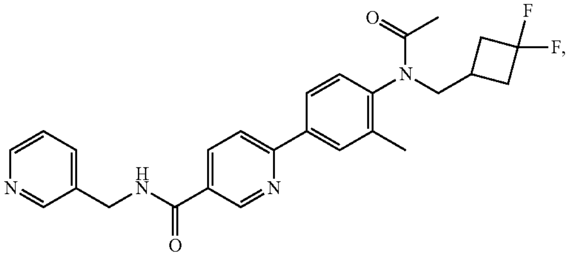
I-601
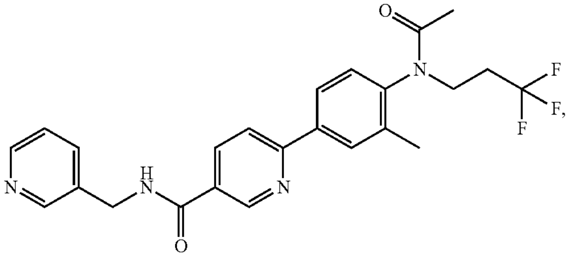
-continued
I-602
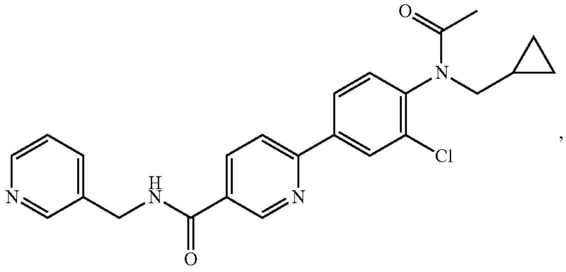
I-603
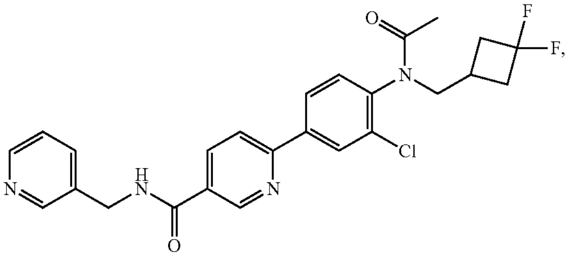
I-604
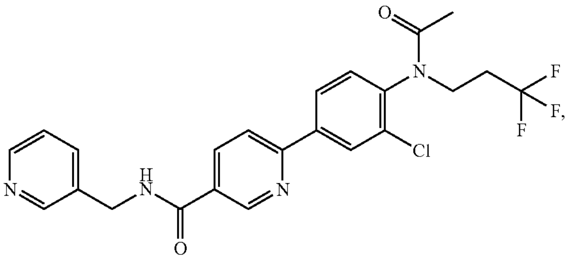
I-605
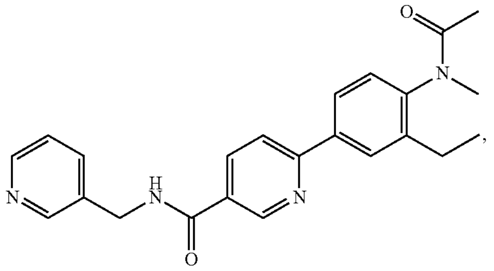
I-606
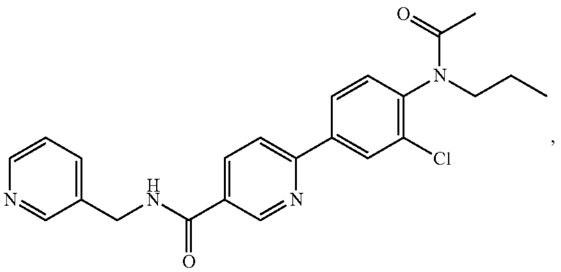

-continued
I-608
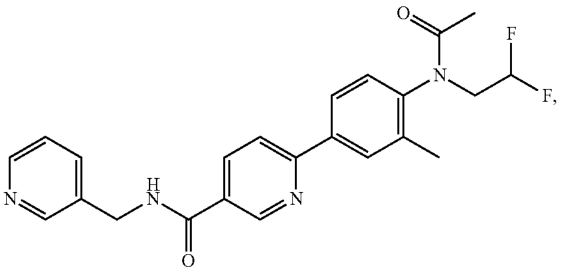
I-609
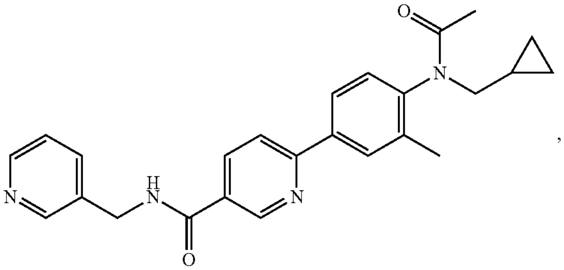
,
I-610
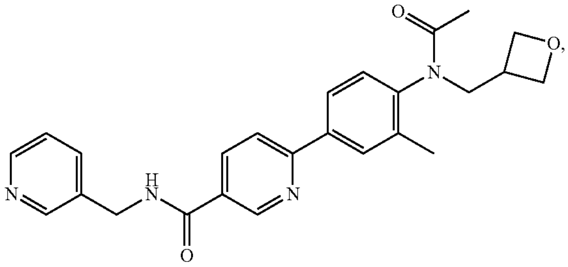
I-611
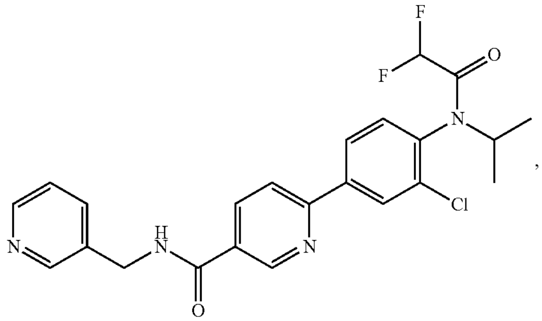
,
I-619
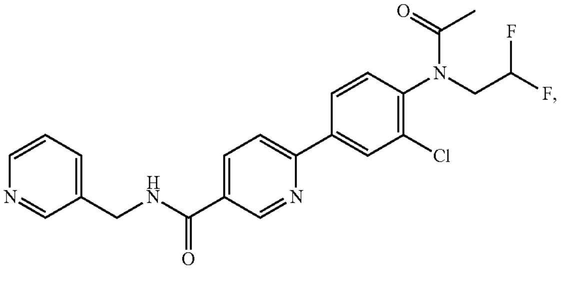
-continued
I-620
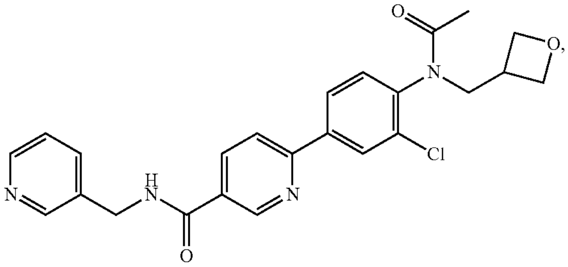
I-626
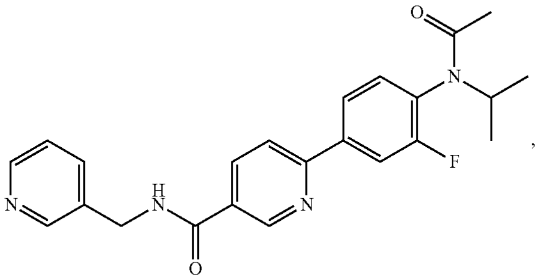
,
I-629
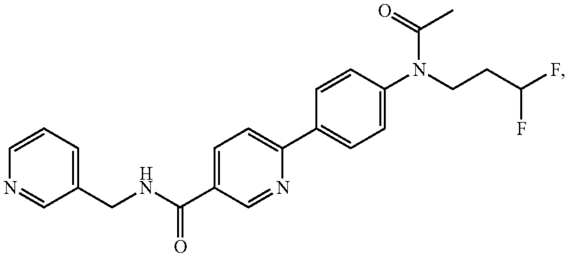
I-631
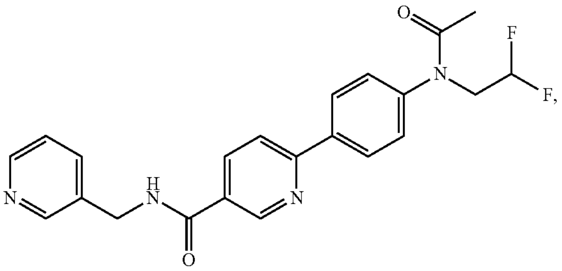
I-639
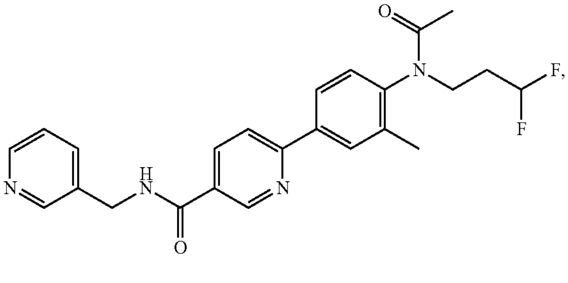

-continued
I-652
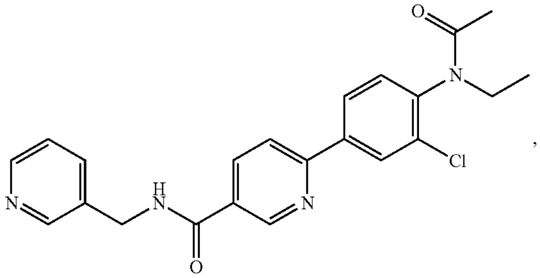
,
I-658
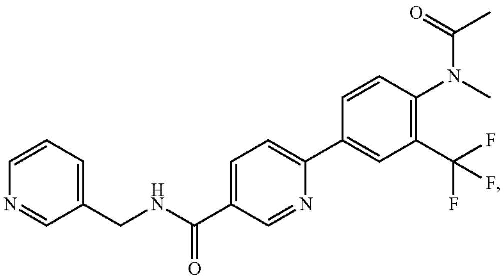
I-662
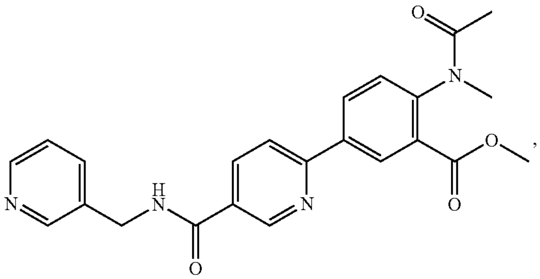
,
I-663
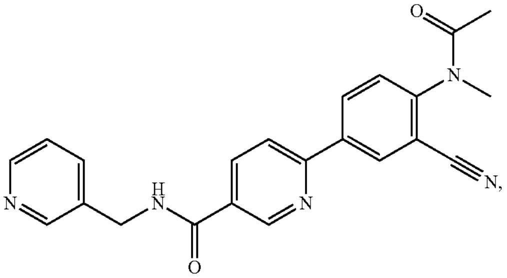
I-674
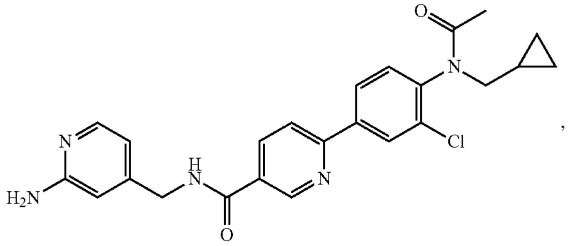
,
-continued
I-676
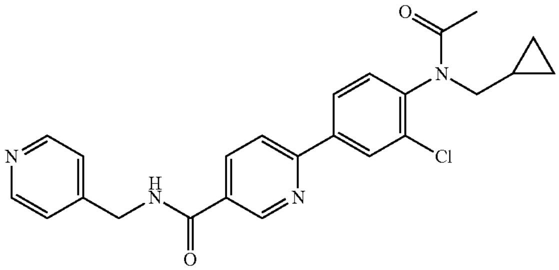
,
I-677
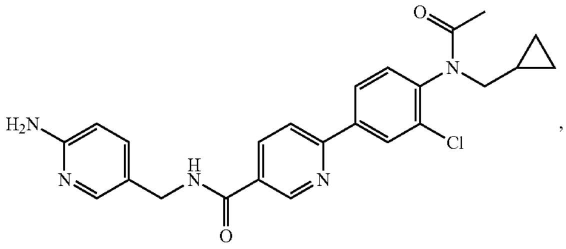
,
I-679
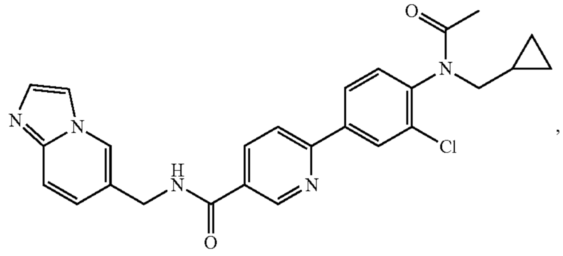
,
I-681
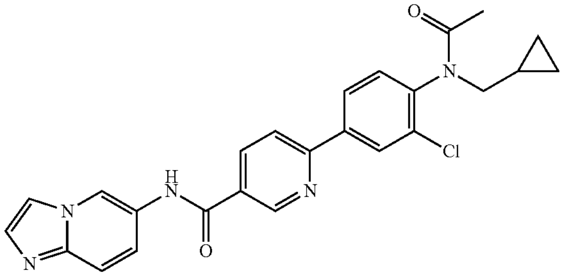
,
I-683
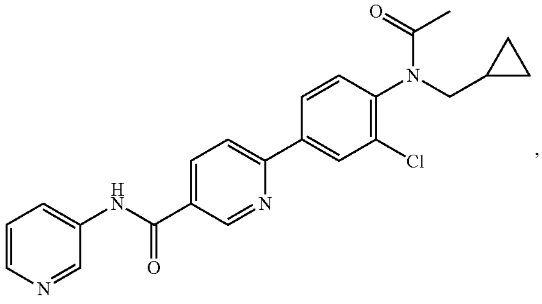
, -continued
I-684
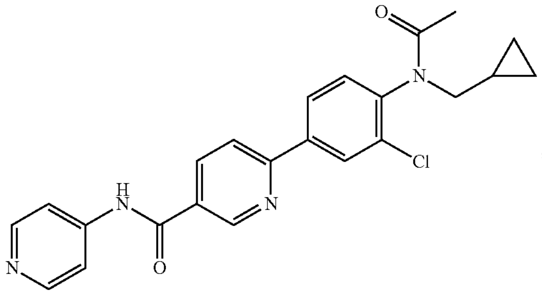
,
I-685
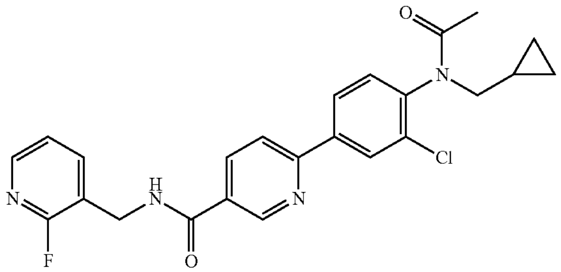
,
I-687
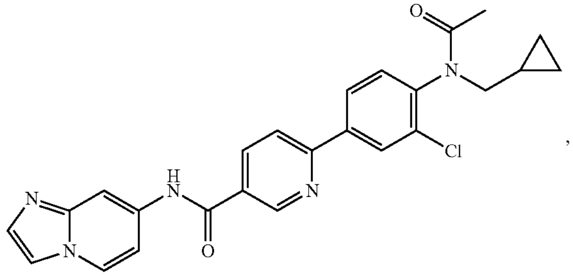
,
I-689
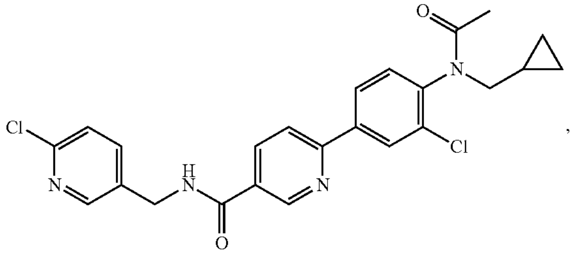
,
I-690
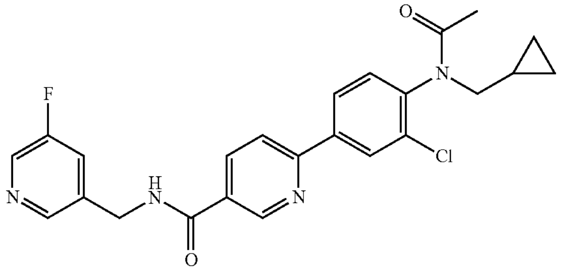
,
-continued
I-693
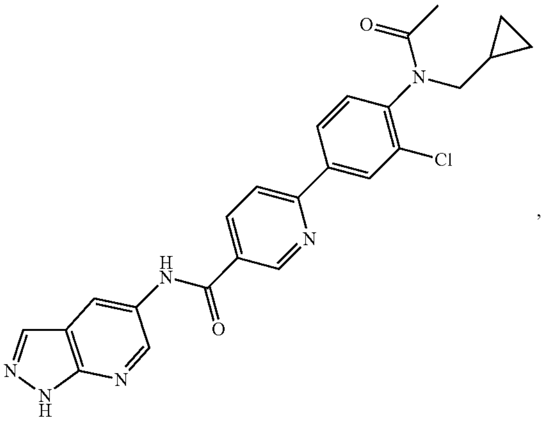
,
I-T2135
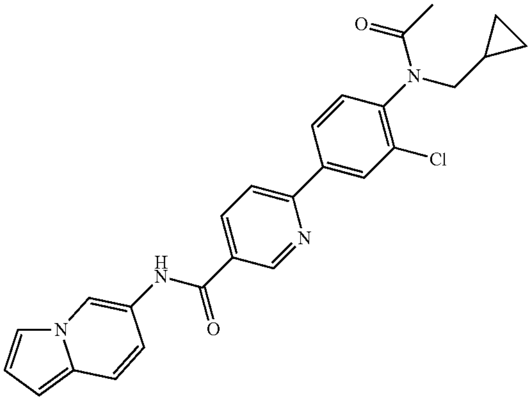
,
I-T2136
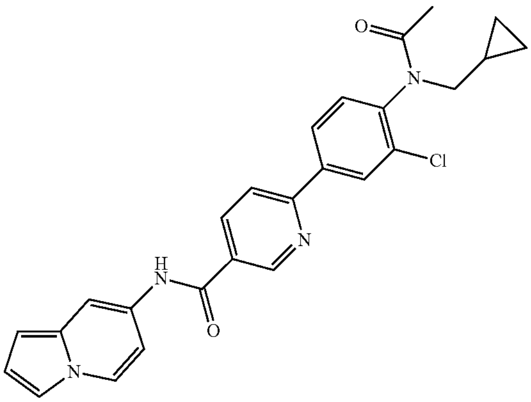
, -continued
I-T2157
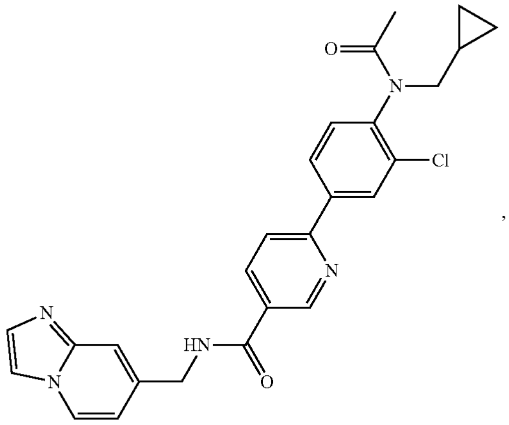
,
I-T2158
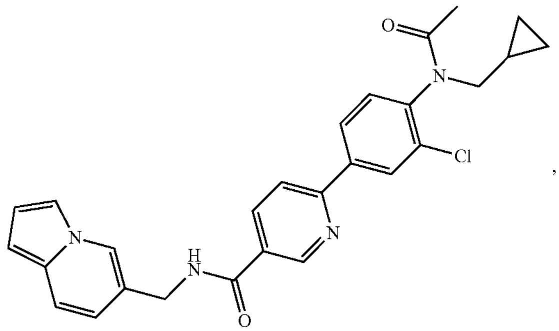
,
I-T2159
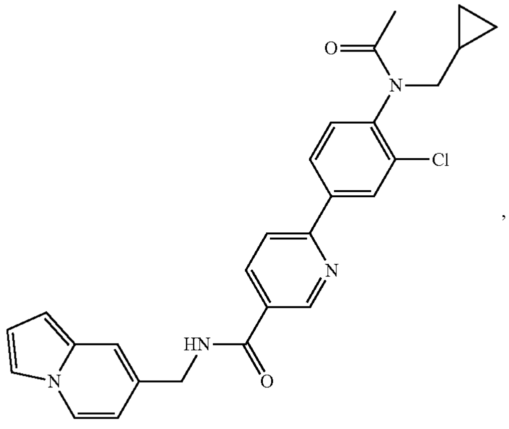
,
-continued
I-T2160
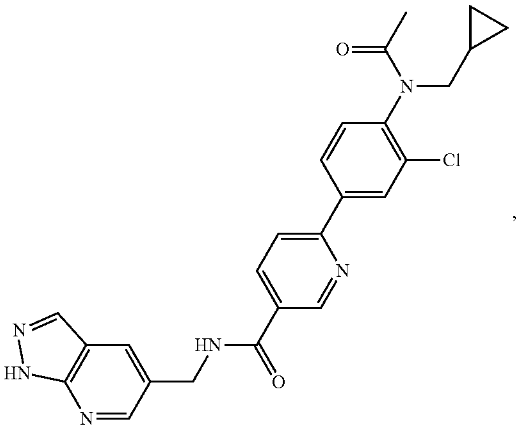
,
I-696
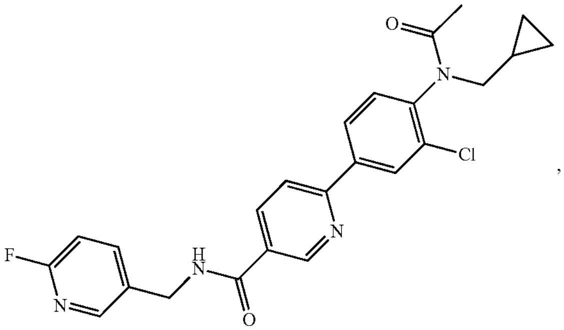
,
I-T2162
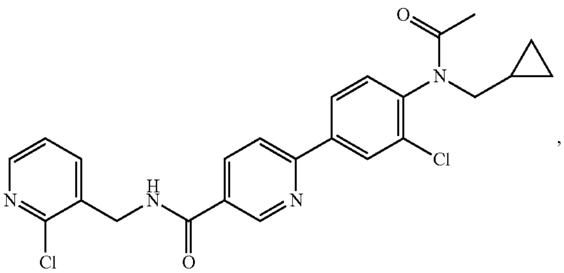
,
I-T2163
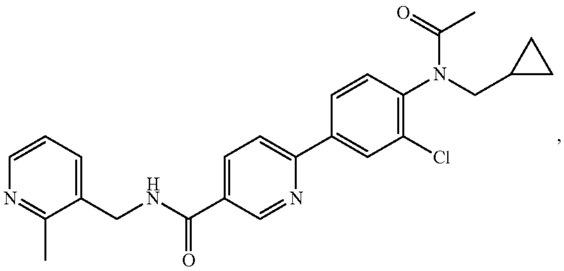
, -continued
I-697
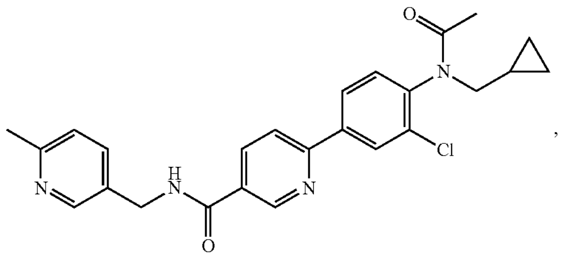
,
I-T2165
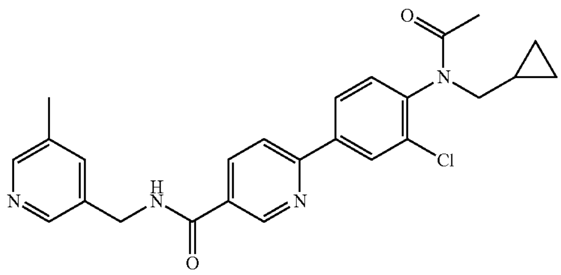
,
I-T2166
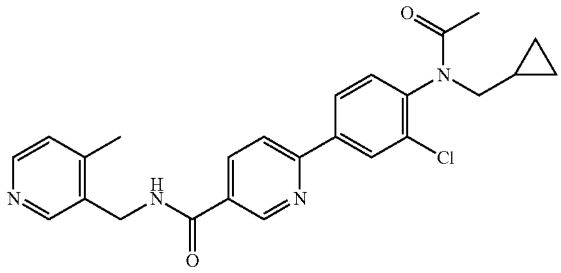
,
I-T2167
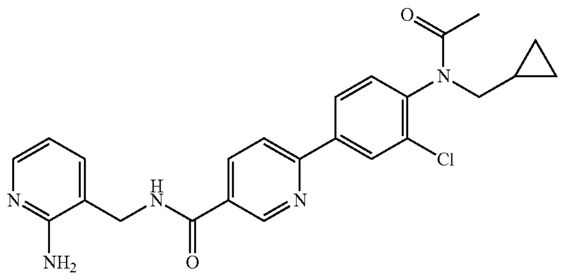
,
I-T2168
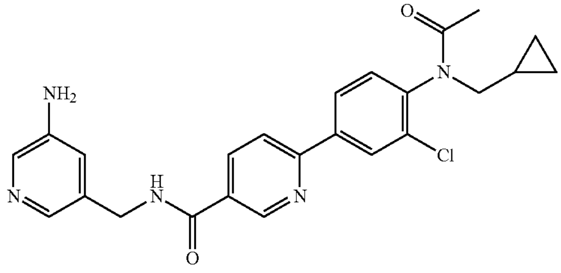
,
-continued
I-T2169
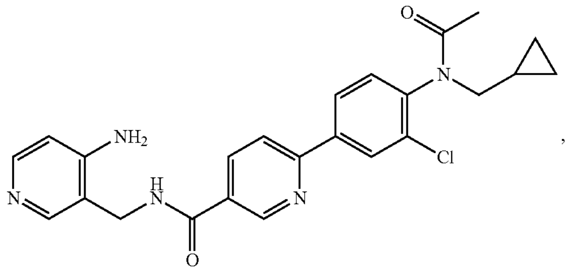
,
I-T2170
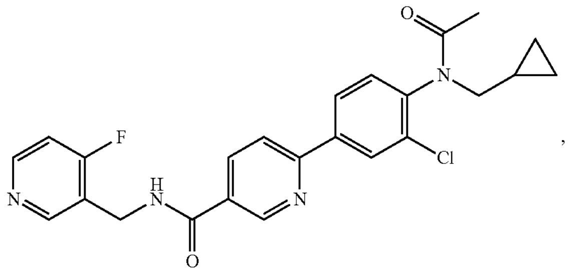
,
I-T2171
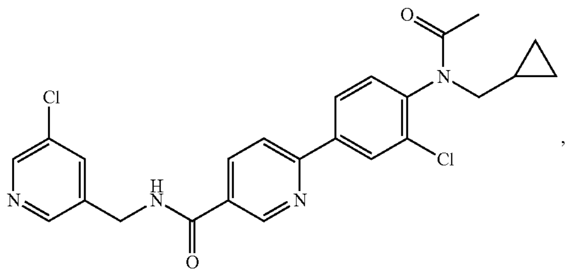
,
I-T2172
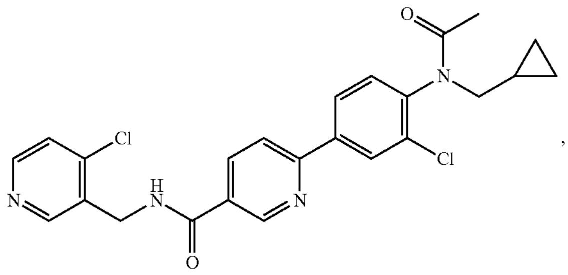
,
I-T2173
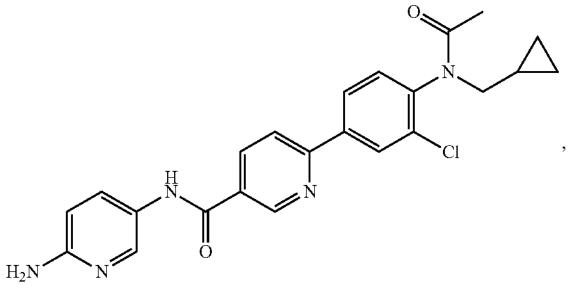
, -continued
I-698
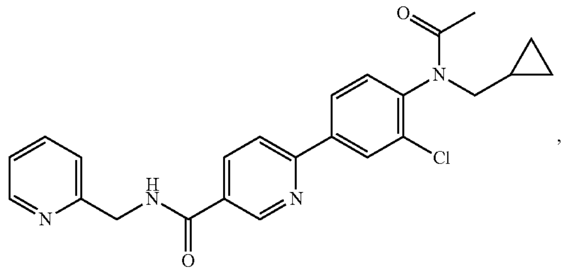
,
I-T2230
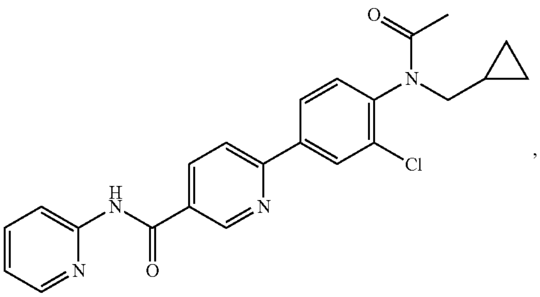
,
I-T2233
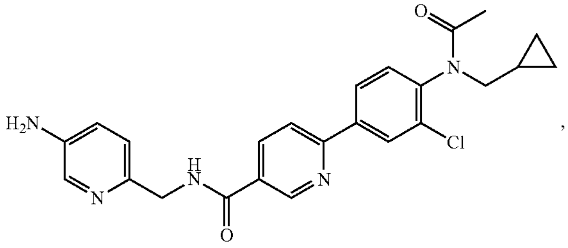
,
I-T2234
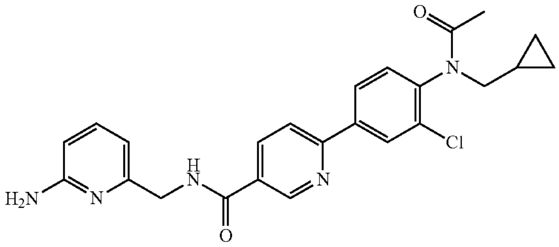
,
I-T2174
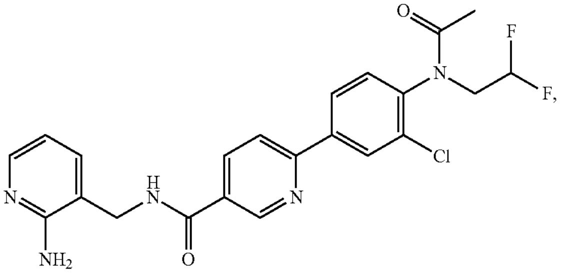
-continued
I-T2106
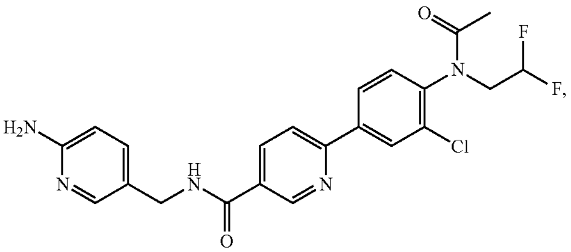
I-T2175
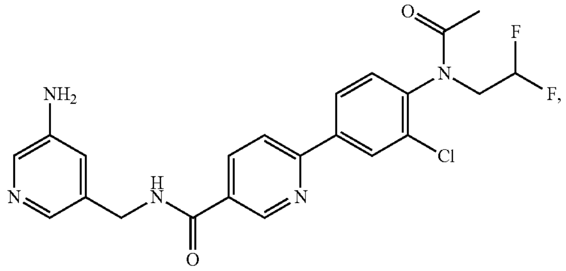
I-T2176
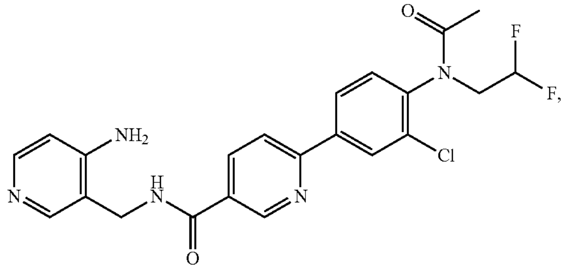
I-T2177
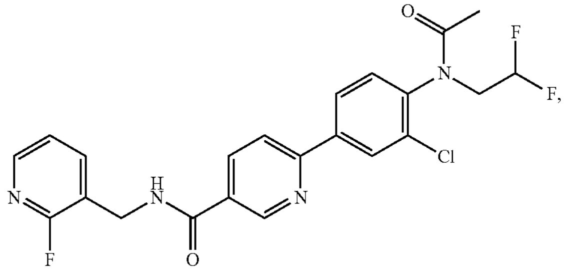
I-T2178
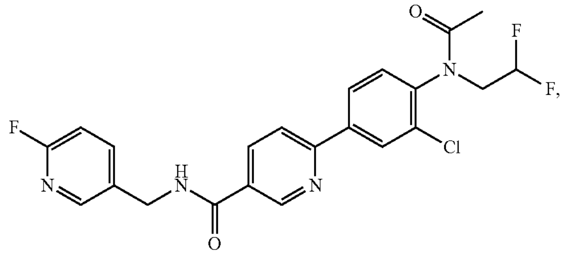

-continued
I-T2179
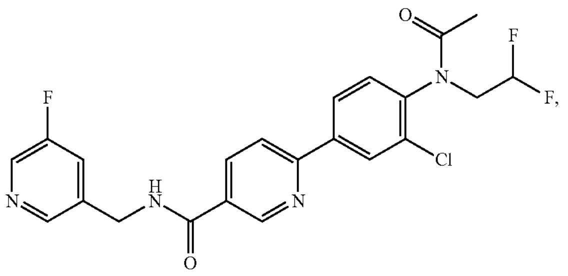
I-T2180
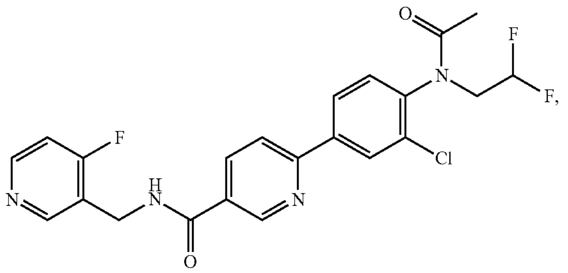
I-T2181
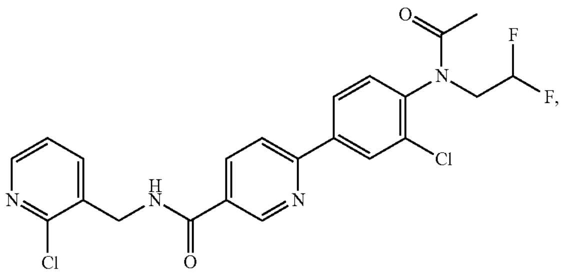
I-T2182
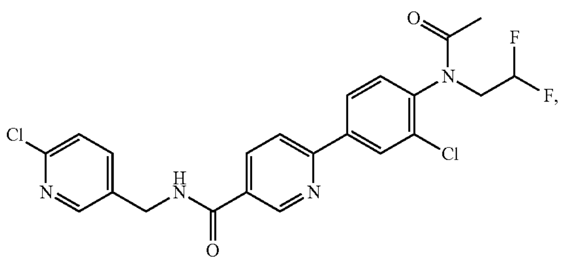
I-T2183
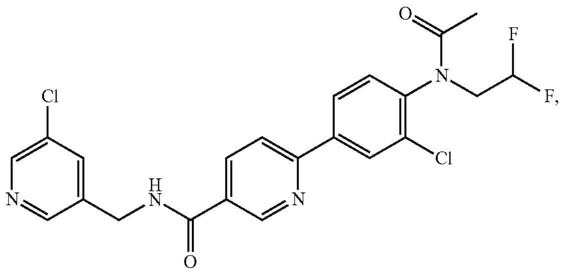
-continued
I-T2184
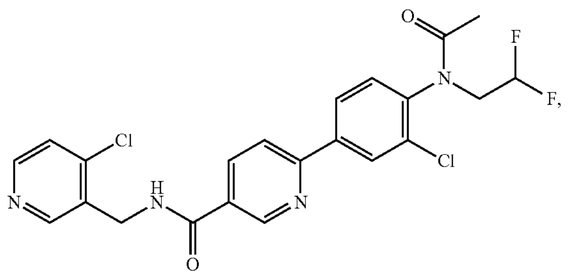
I-T2185
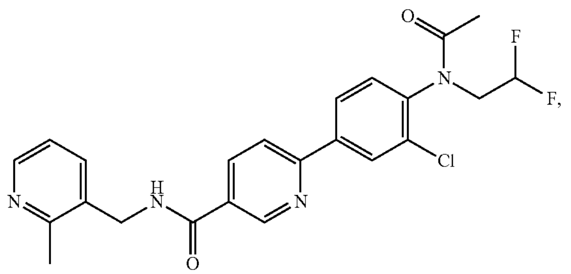
I-T2186
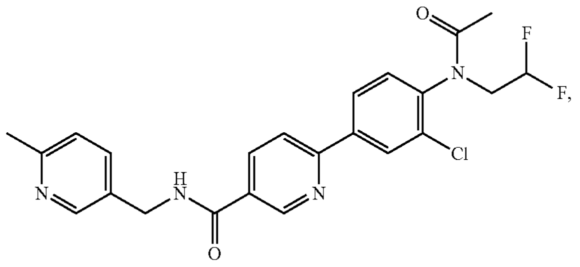
I-T2187
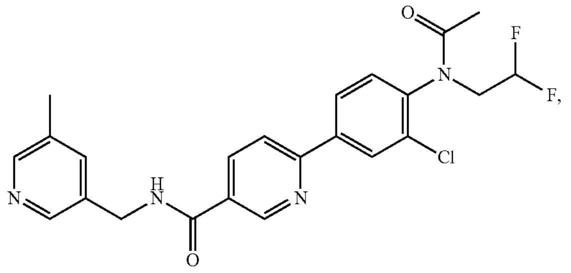
I-T2188
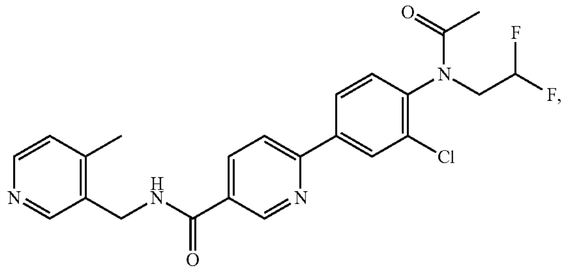

-continued
I-T2101
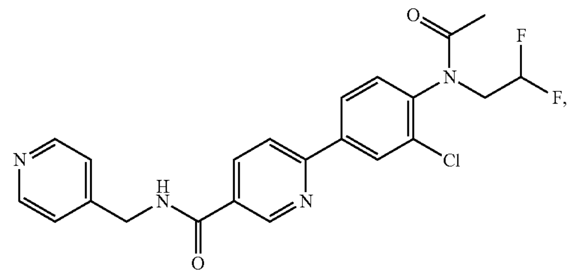
I-T2102
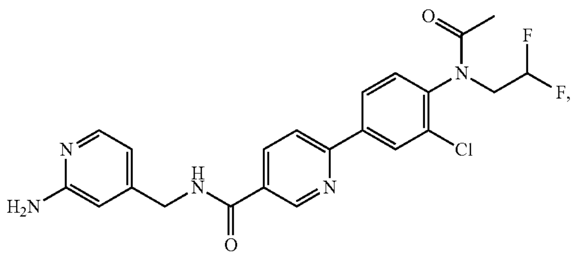
I-T2189
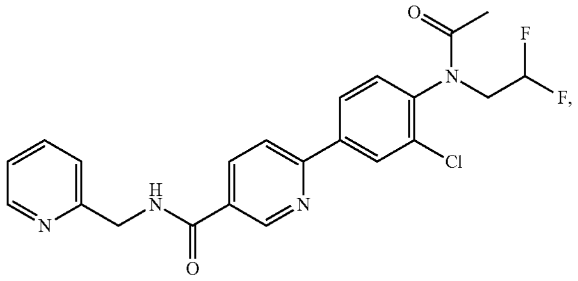
I-T2190
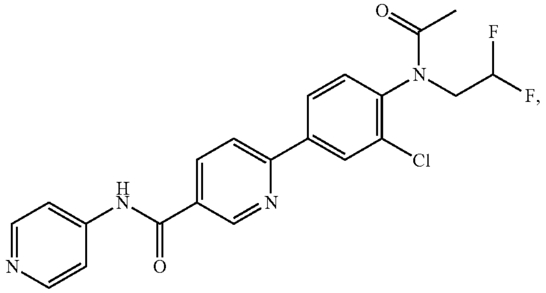
-continued
I-T2191
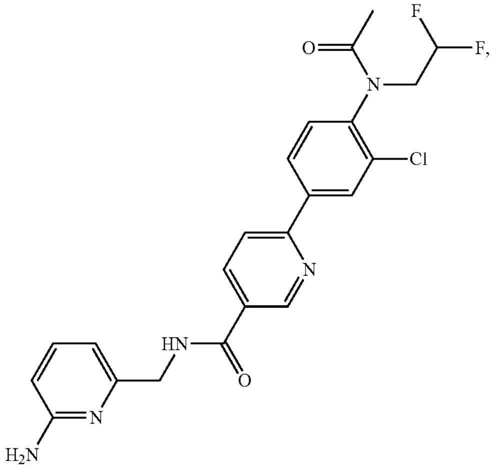
I-T2109
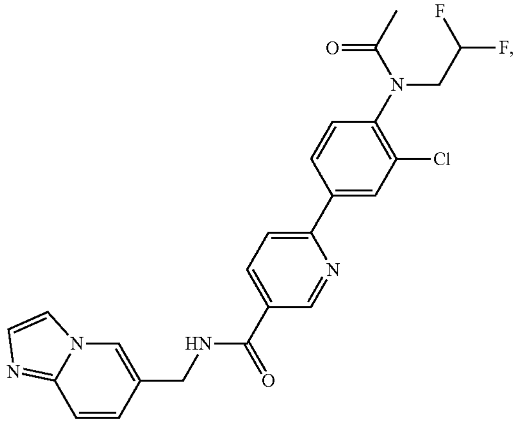
I-T2192
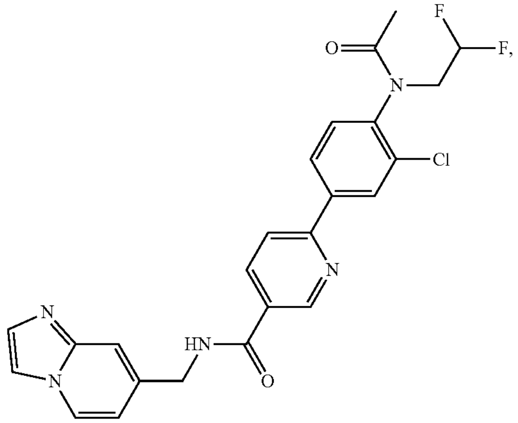

-continued
I-T2193
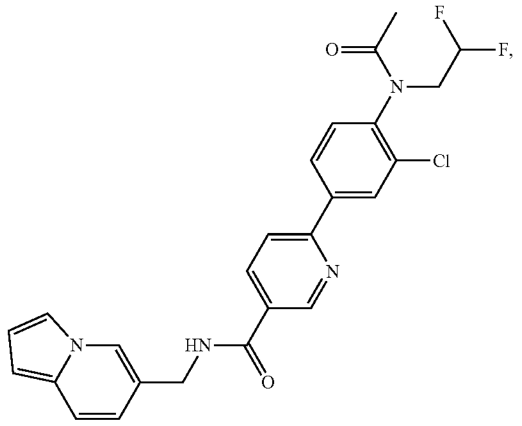
I-T2194
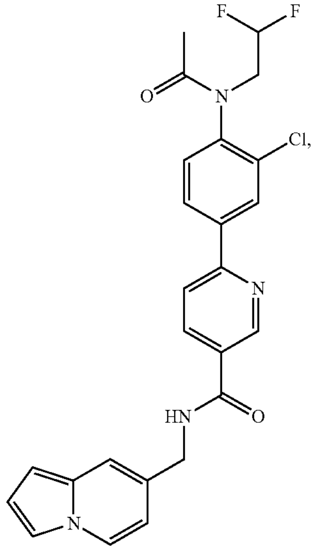
I-T2195
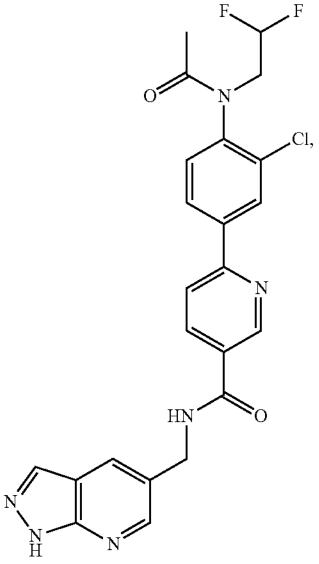
-continued
I-T2196
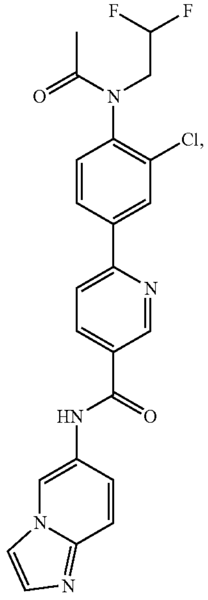
I-T2197
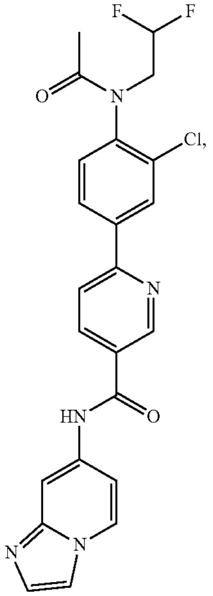

I-T2198
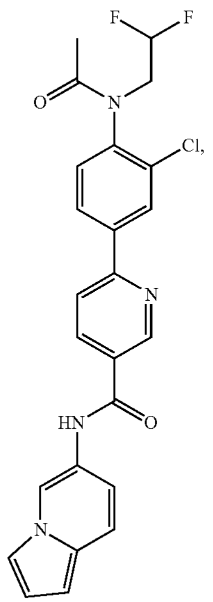
I-T2199
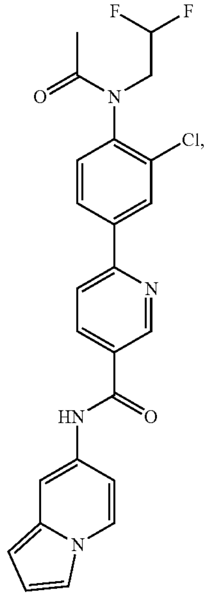
I-T2200
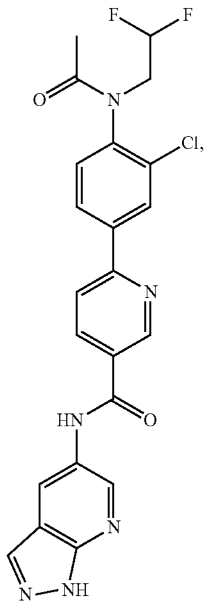
I-T2231
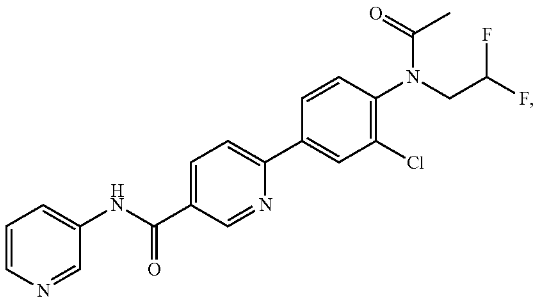
I-T2231
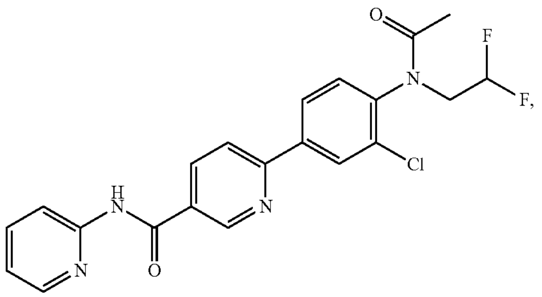
I-T2235
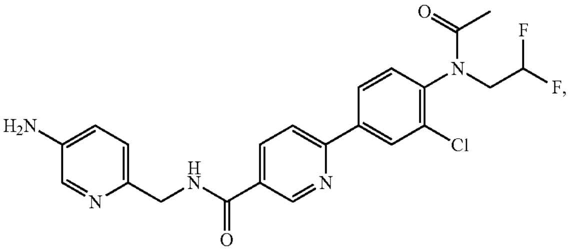

-continued
I-T2236
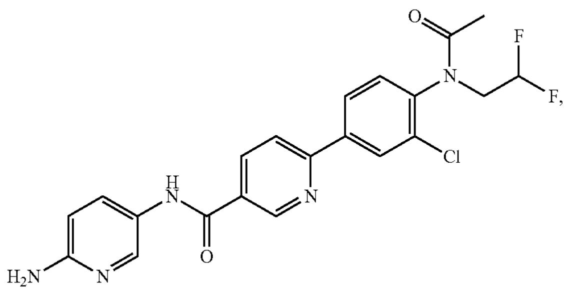
I-T2120
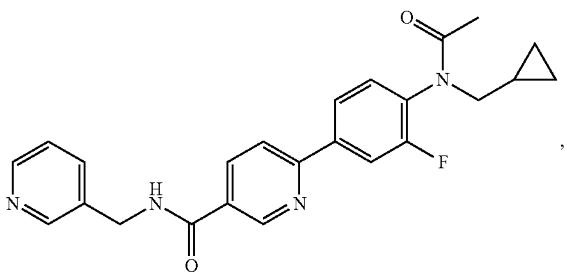
,
I-T2211
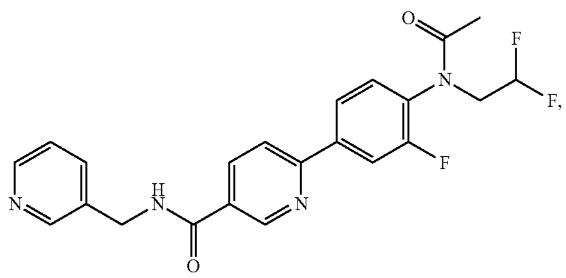
I-T2206
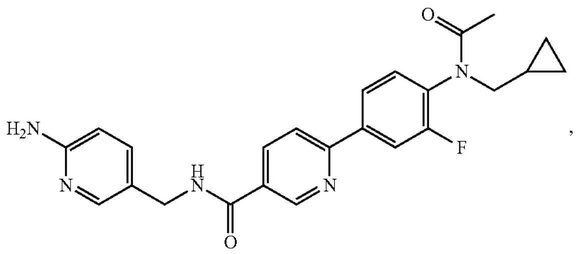
,
I-T2107
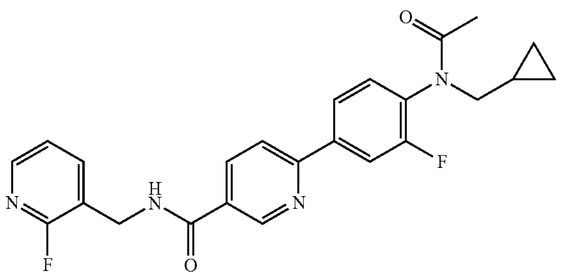
,
-continued
I-T2208
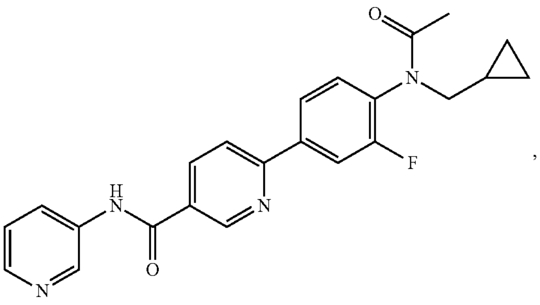
,
I-T2209
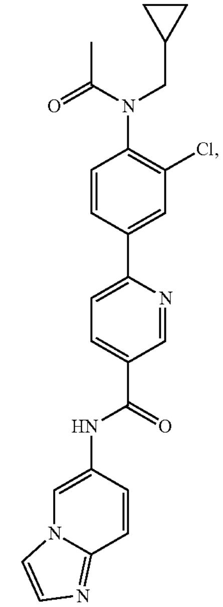
I-T2210
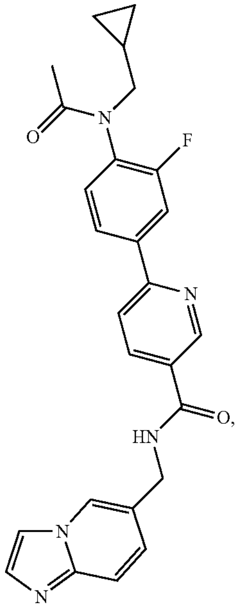

-continued
I-T2212
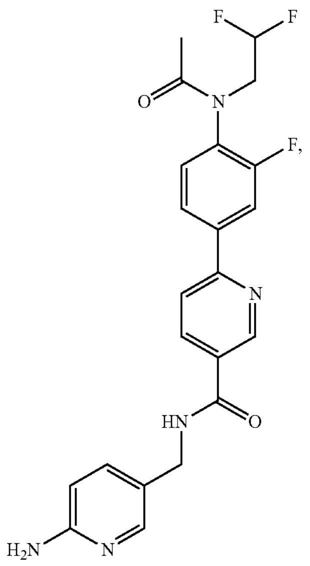
I-T2213
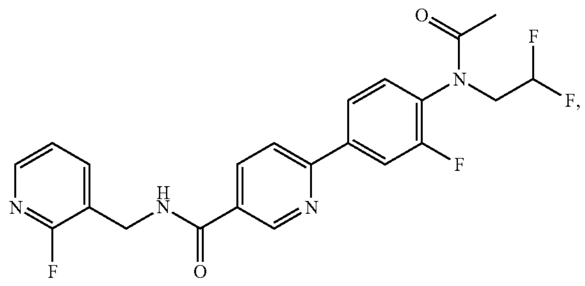
I-T2214
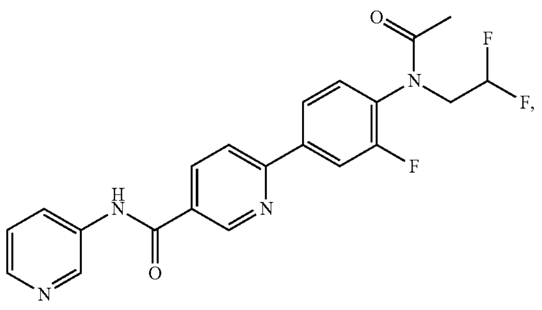
-continued
I-T2215
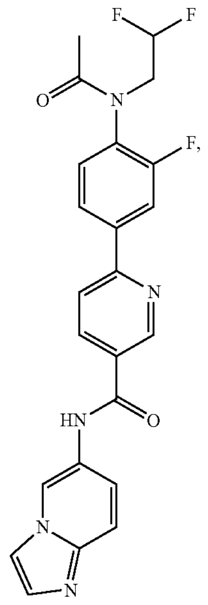
I-T2216
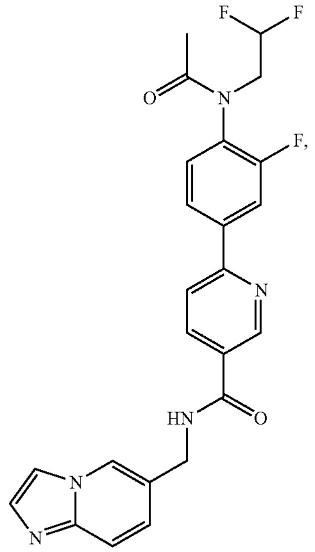

I-T2237
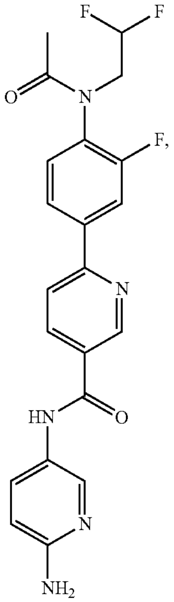
I-T2217
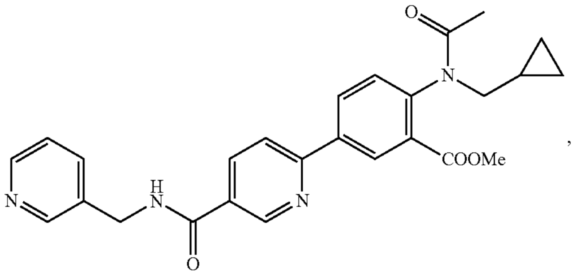
,
I-T2218
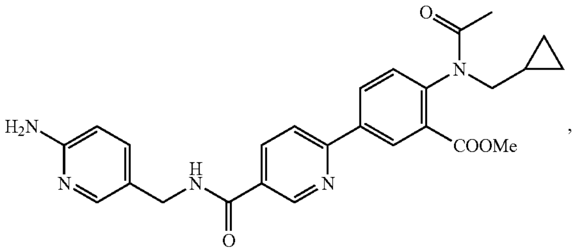
,
I-T2219
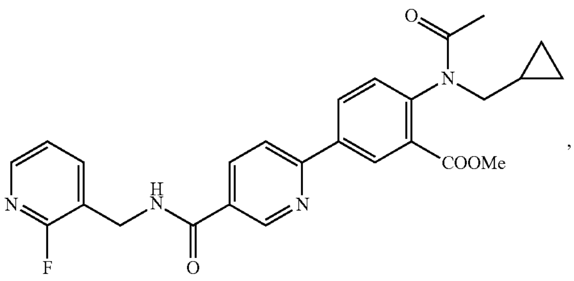
,
I-T220
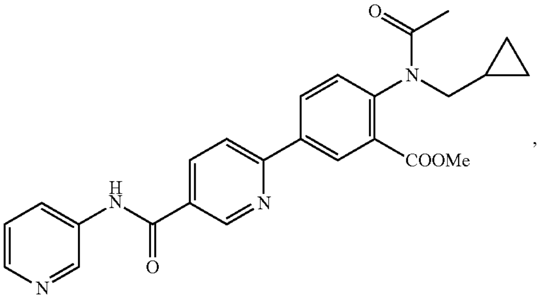
,
I-T2221
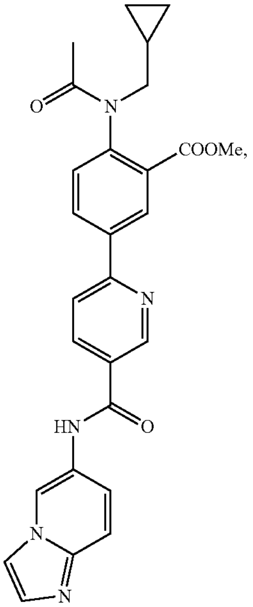
I-T2222
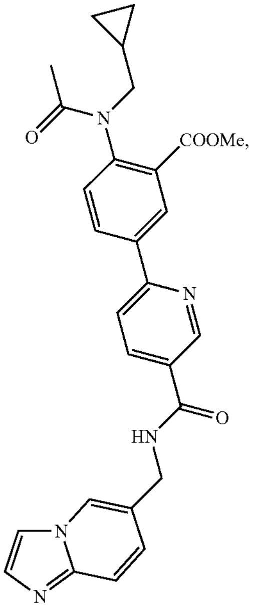

-continued
I-T2223
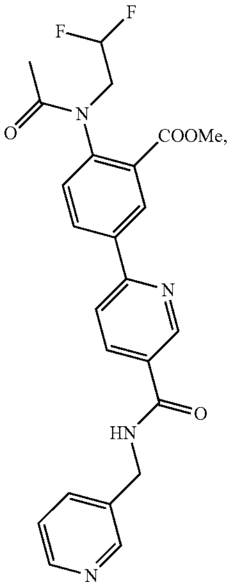
I-T2224
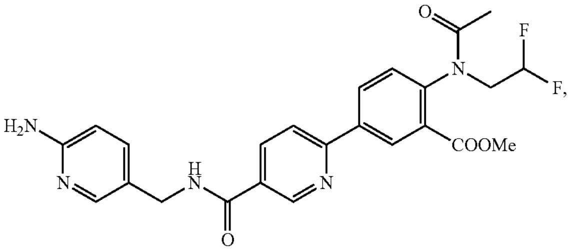
I-T2225
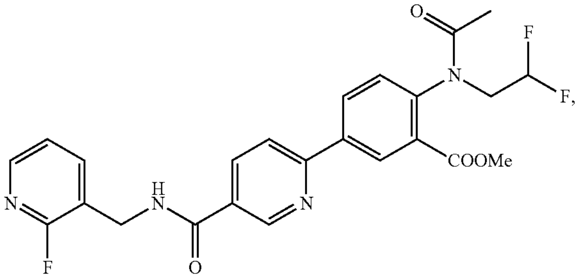
I-T2226
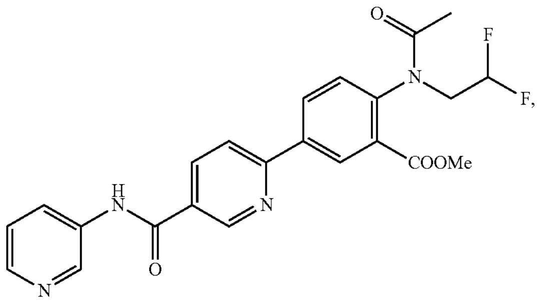
-continued
I-T2227
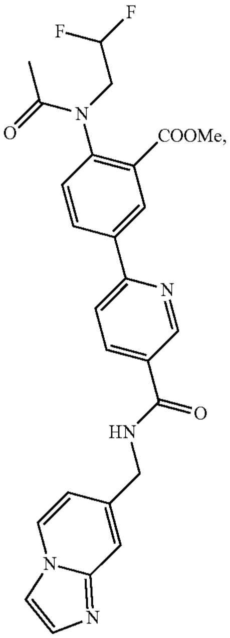
I-T2228
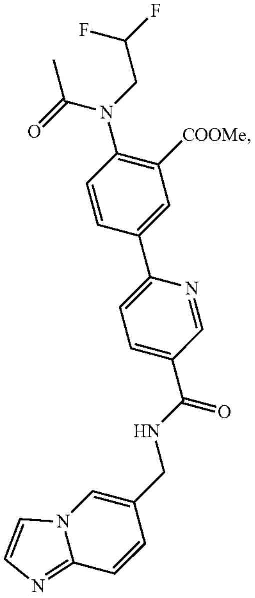

-continued
I-T2238
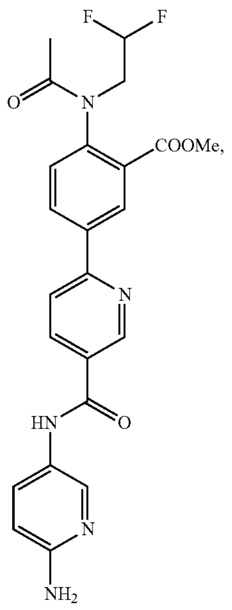
I-T2239
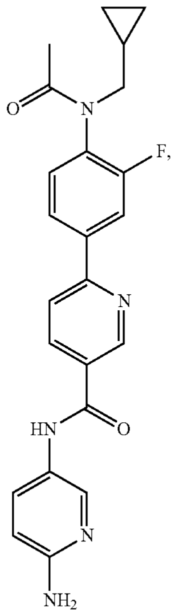
-continued
I-T2240
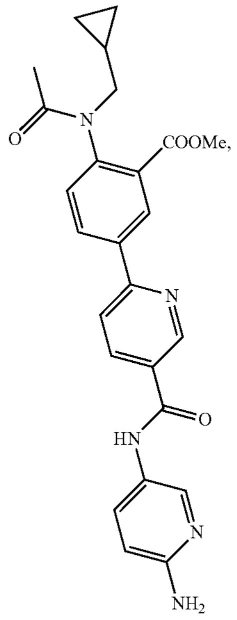
I-T2241
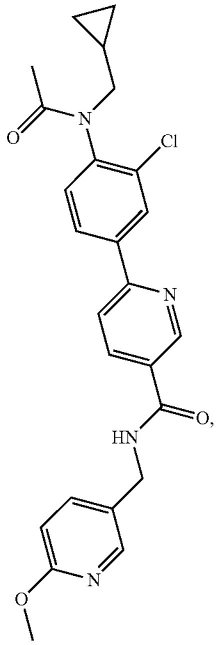

-continued
I-T2242
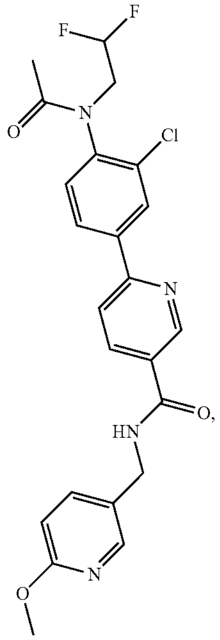
I-T2243
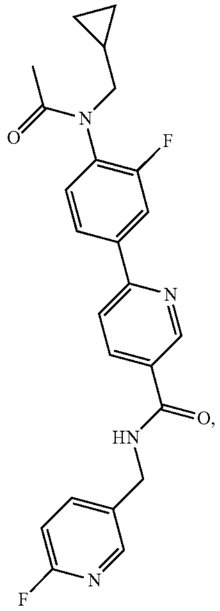
-continued
I-T2244
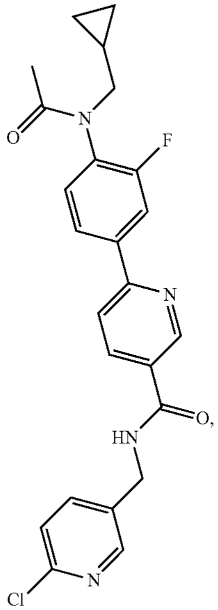
I-T2245
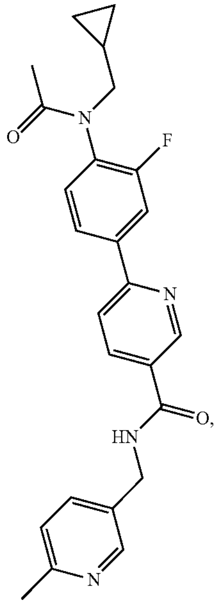

-continued
I-T2246
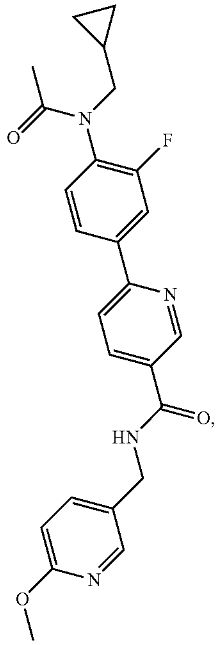
I-T2247
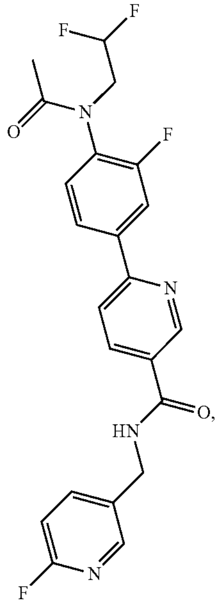
-continued
I-T2248
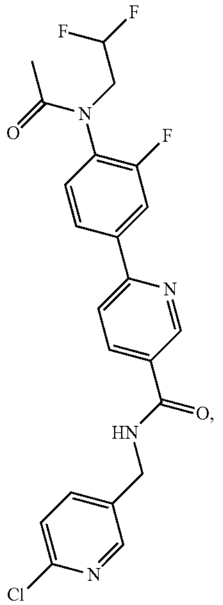
I-T2249
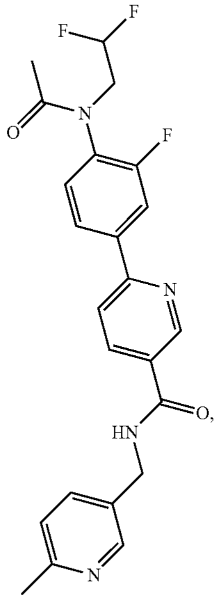

-continued
I-T2250
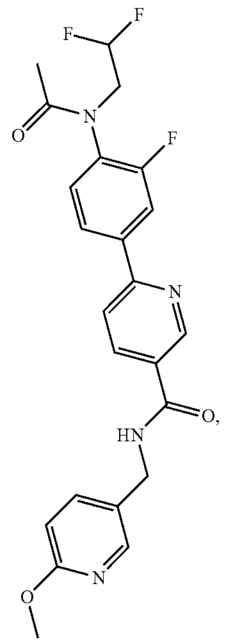
I-T2251
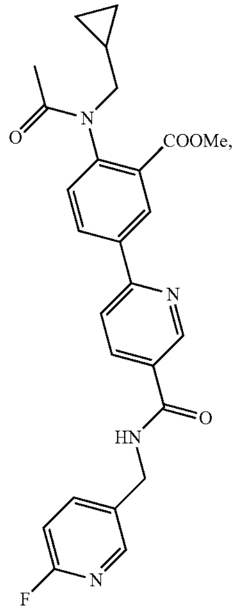
-continued
I-T2252
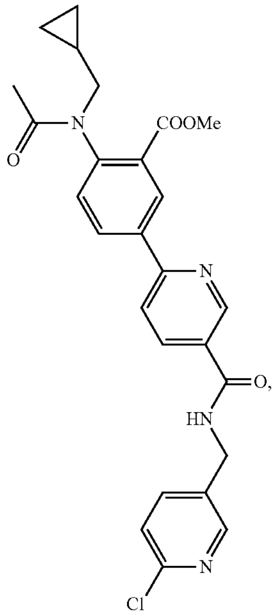
I-T2253
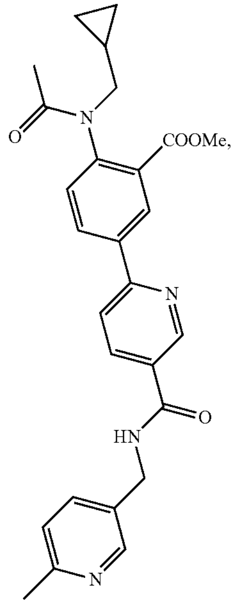

-continued
I-T2254
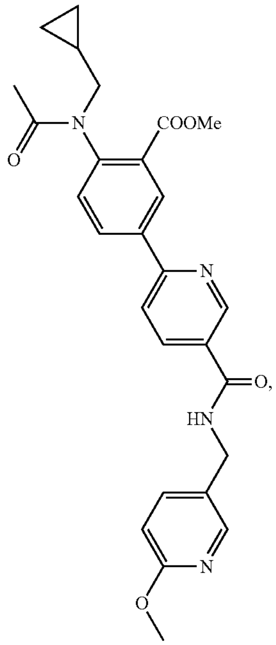
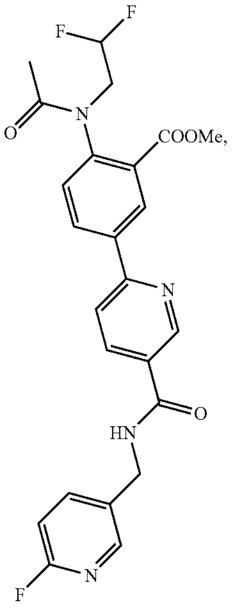
I-T2255
-continued
I-T2256
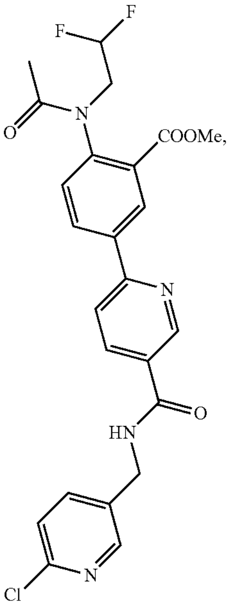
I-T2257
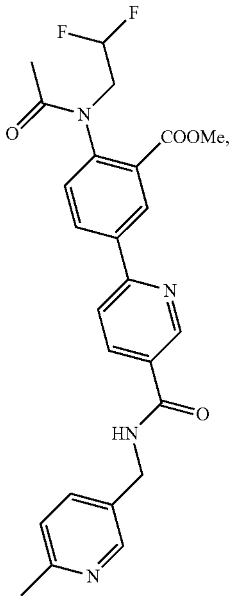
or -continued

I-T2258

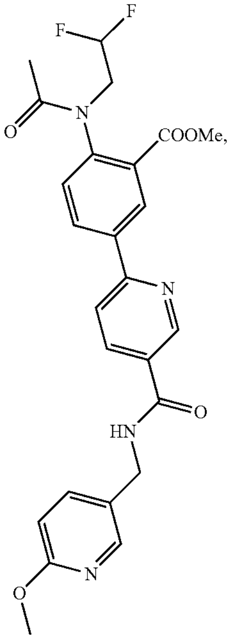

or a pharmaceutically acceptable salt, hydrate, polymorph, co-crystal, tautomer, stereoisomer, isotopically labeled derivative, or prodrug thereof.

In certain embodiments, the compound is selected from the group consisting of: I-466, I-467, I-468, I-482, I-483, I-484, I-485, I-486, I-487, I-488, I-489, I-491, I-492, I-495, I-497, I-499, I-500, I-501, I-502, I-503, I-510, I-512, I-517, I-593, I-594, I-595, I-596, I-599, I-600, I-601, I-602, I-603, I-604, I-605, I-606, I-608, I-609, I-610, I-611, I-619, I-620, I-626, I-629, I-631, I-639, I-652, I-658, I-662, I-663, I-677, I-685, I-689, I-690, I-T2106, I-T2107, I-T2120, I-T2161, I-T2162, I-T2163, I-T2164, I-T2165, I-T2166, I-T2167, I-T2168, I-T2169, I-T2170, I-T2171, I-T2172, I-T2174, I-T2175, I-T2176, I-T2177, I-T2178, I-T2179, I-T2180, I-T2181, I-T2182, I-T2183, I-T2184, I-T2185, I-T2186, I-T2187, I-T2188, I-T2206, I-T2211, I-T2212, I-T2213, I-T2217, I-T2218, I-T2219, I-T2223, I-T2224, I-T2225, I-T2241, I-T2242, I-T2243, I-T2244, I-T2245, I-T2246, I-T2247, I-T2248, I-T2249, I-T2250, I-T2251, I-T2252, I-T2253, I-T2254, I-T2255, I-T2256, I-T2257, and I-T2258, or a pharmaceutically acceptable salt, hydrate, polymorph, co-crystal, tautomer, stereoisomer, isotopically labeled derivative, or prodrug thereof.

In certain embodiments, the compound is selected from the group consisting of: 1-674, I-676, 1-679, I-681, I-683, I-684, I-687, I-T2101, I-T2102, I-T2109, I-T2135, I-T2136, I-T2139, I-T2157, I-T2158, I-T2159, I-T2160, I-T2173, I-T2189, I-T2190, I-T2191, I-T2192, I-T2193, I-T2194, I-T2195, I-T2196, I-T2197, I-T2198, I-T2199, I-T2200, I-T2208, I-T2209, I-T2210, I-T2214, I-T2215, I-T2216, I-T2220, I-T2221, I-T2222, I-T2226, I-T2227, I-T2228, I-T2229, I-T2230, I-T2231, I-T2232, I-T2233, I-T2234, I-T2235, I-T2236, I-T2237, I-T2238, I-T2239, and I-T2240, or a pharmaceutically acceptable salt, hydrate, polymorph, co-crystal, tautomer, stereoisomer, isotopically labeled derivative, or prodrug thereof.

In certain embodiments, the compound is selected from the group consisting of: I-403, I-404, I-412, I-453, I-468, I-495, I-594, I-595, I-596, I-599, I-600, I-601, I-602, I-603, I-604, I-606, I-609, I-610, I-611, I-619, I-620, I-626, I-652, I-662, I-677, I-679, I-681, I-683, I-685, I-689, I-690, I-696, and 1-697, or a pharmaceutically acceptable salt, hydrate, polymorph, co-crystal, tautomer, stereoisomer, isotopically labeled derivative, or prodrug thereof.

In certain embodiments, the compound is selected from the group consisting of:

I-403

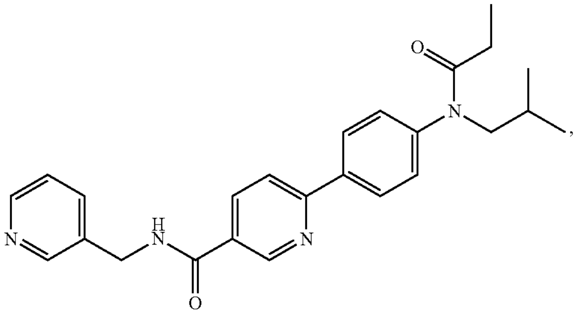

I-404

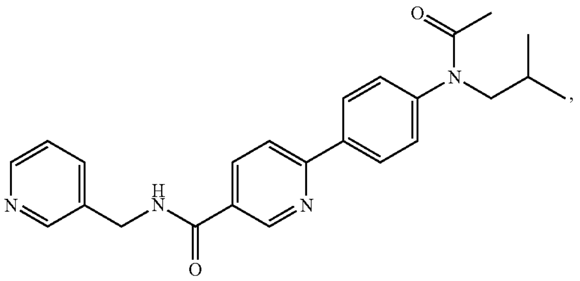

I-412

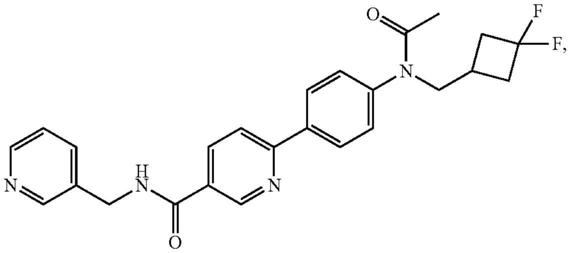

I-453

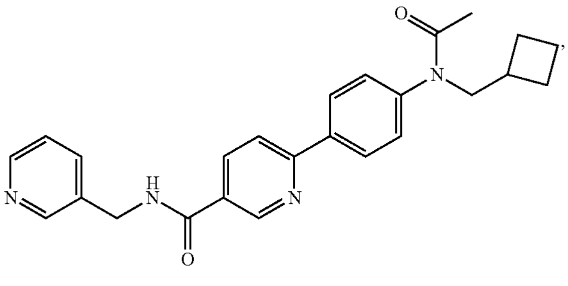

-continued
I-468
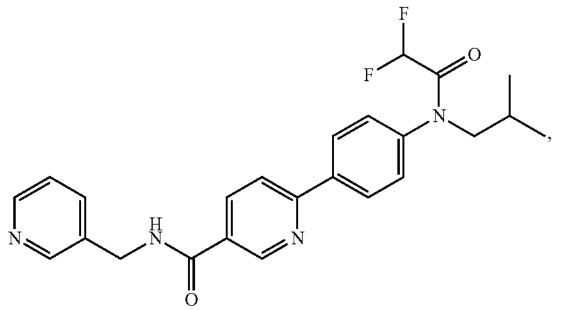
I-495
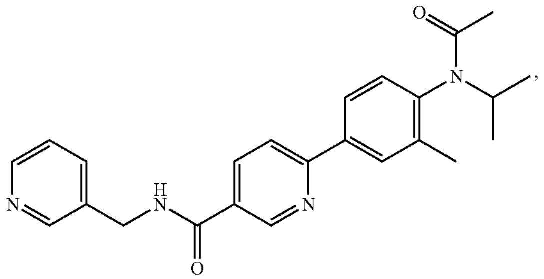
I-594
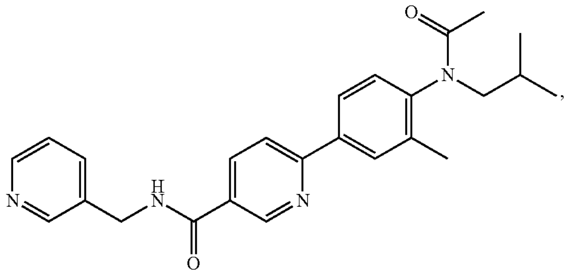
I-595
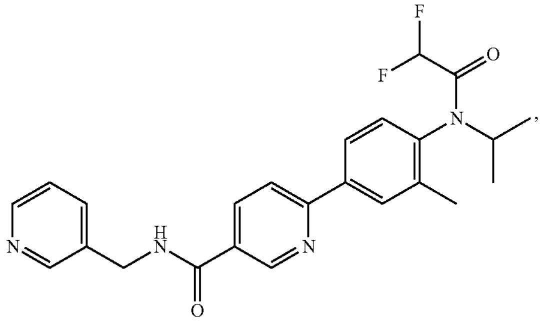
I-596
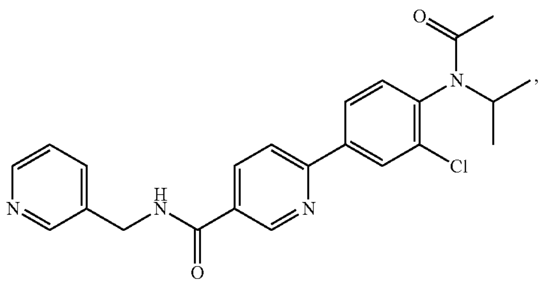
-continued
I-599
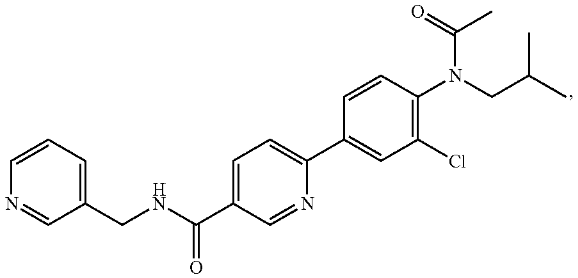
I-600
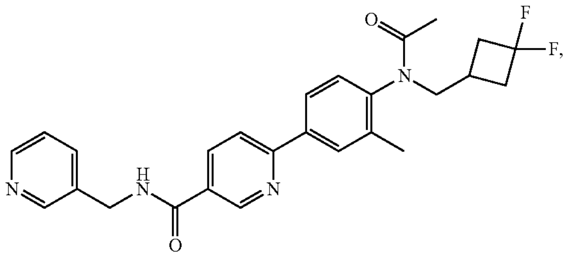
I-601
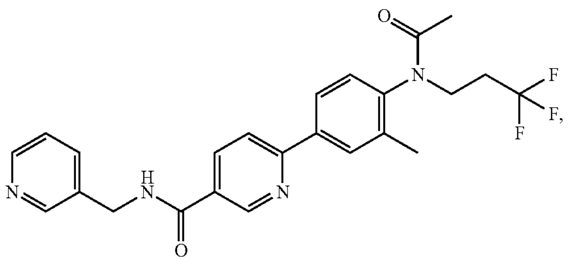
I-602
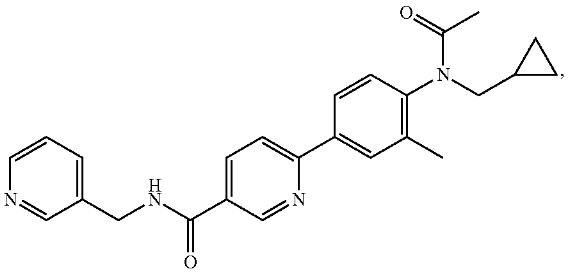
I-603
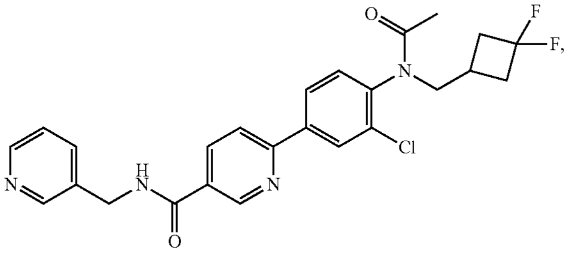

-continued
I-604
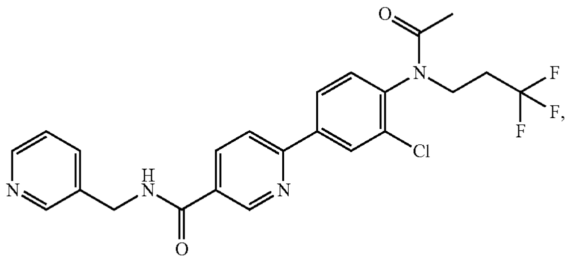
I-606
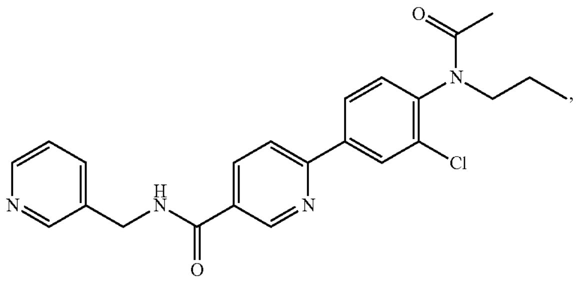
I-609
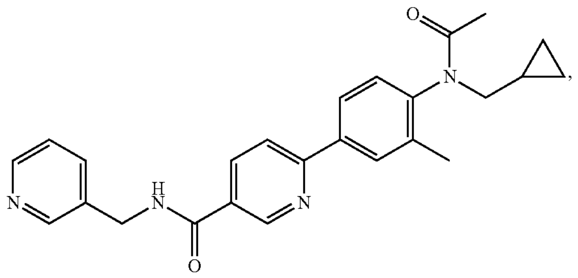
I-610
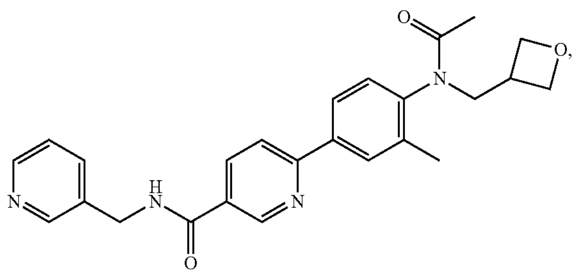
I-611
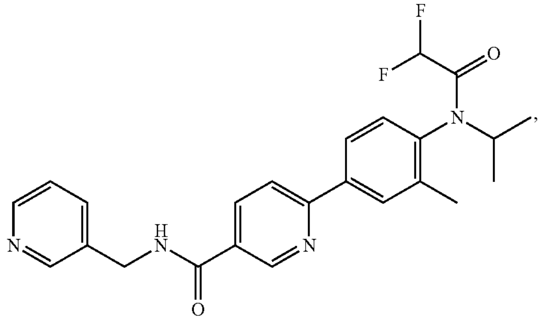
-continued
I-619
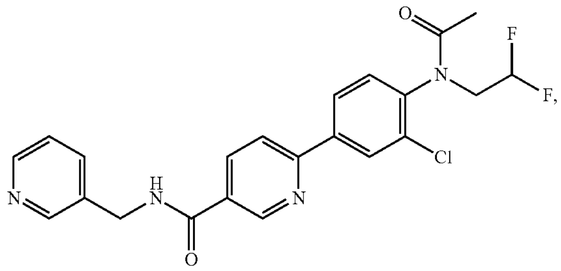
I-620
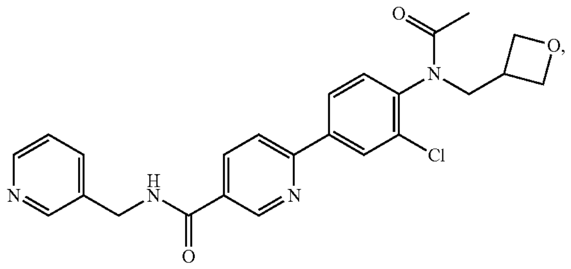
I-626
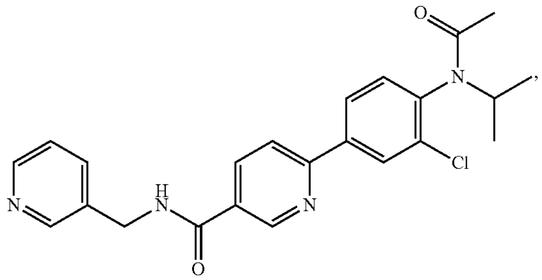
I-652
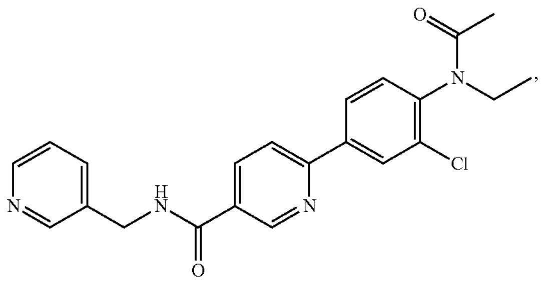
I-662
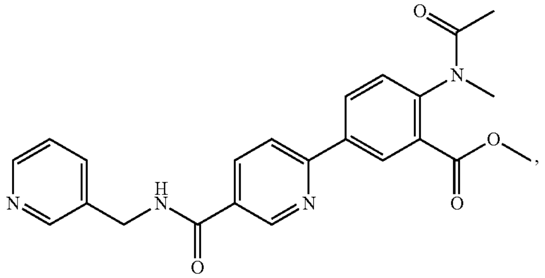

-continued
I-677
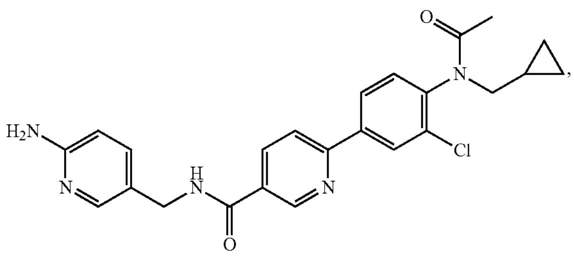,
I-679
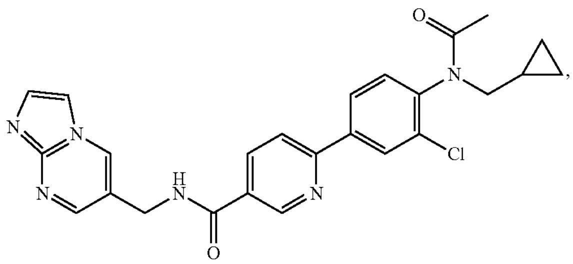,
I-681
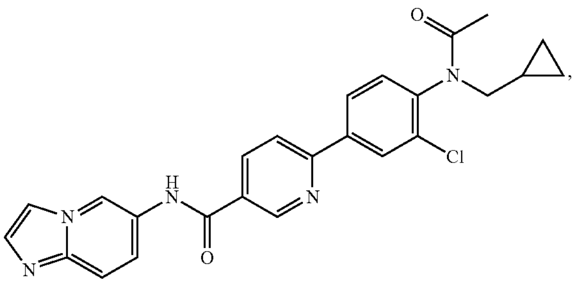,
I-683
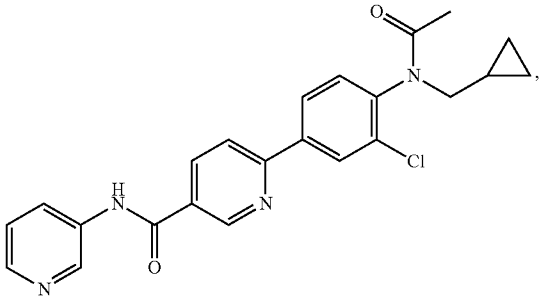,
I-685
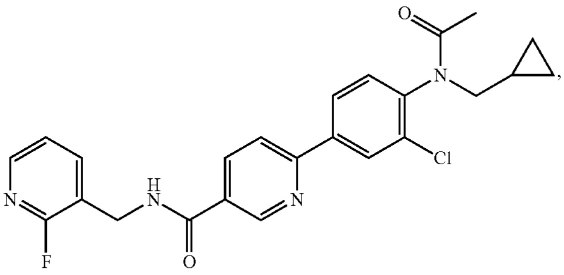,
-continued
I-689
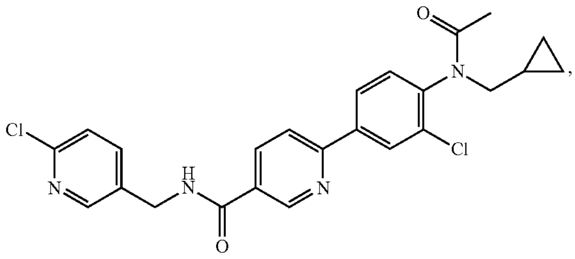,
I-690
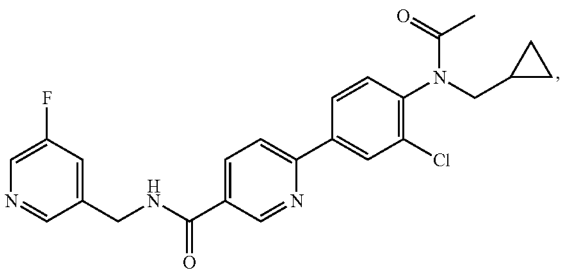,
I-696
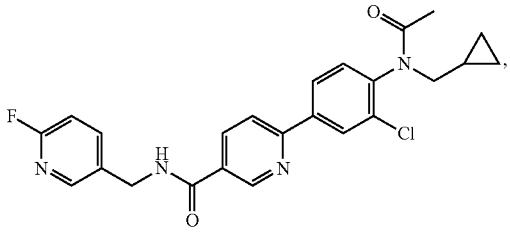, and
I-697
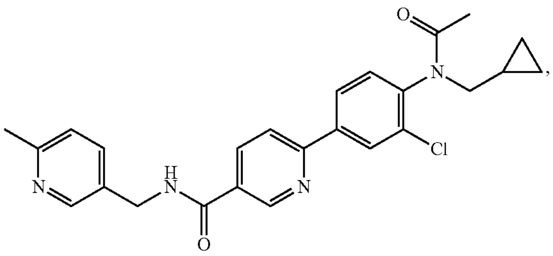,
or a pharmaceutically acceptable salt, hydrate, polymorph, co-crystal, tautomer, stereoisomer, isotopically labeled derivative, or prodrug thereof.
In certain aspects a compound of Formula (0) or (I) is not of the formula:
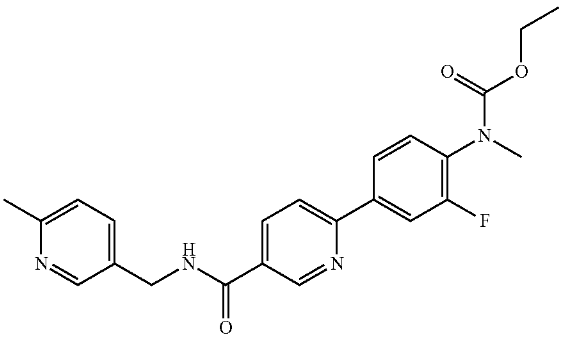, -continued
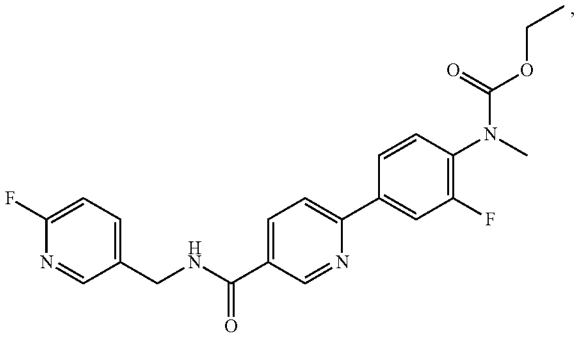
,
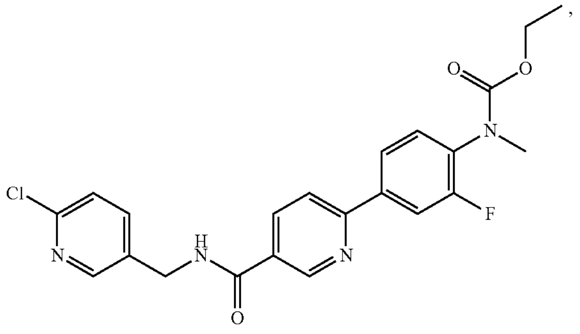
,
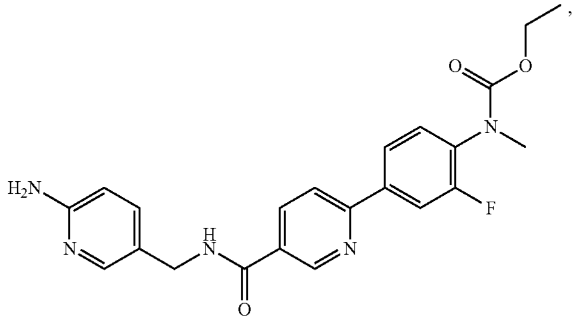
,
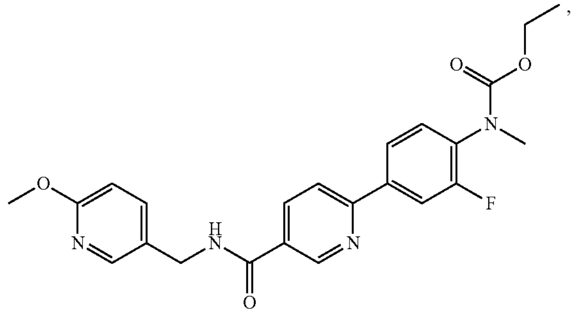
,
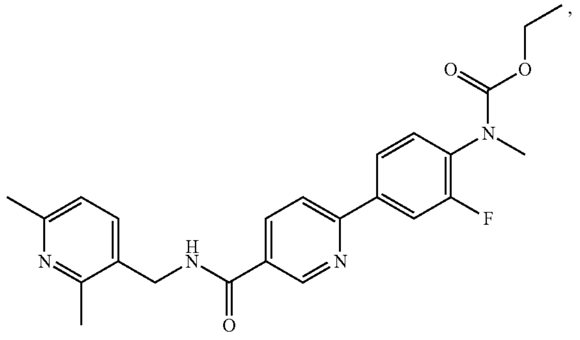
,
-continued
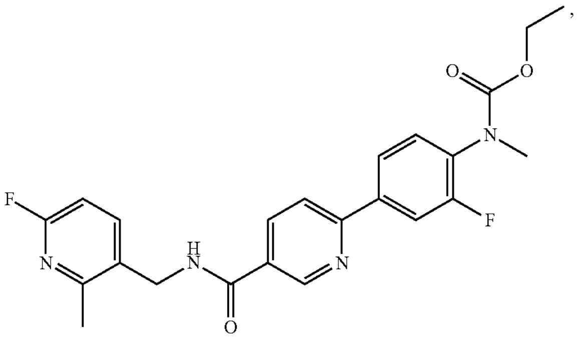
,
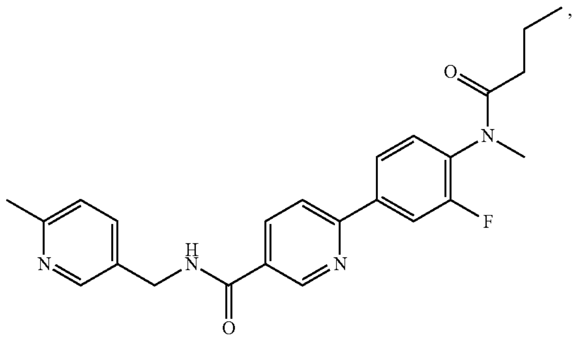
,
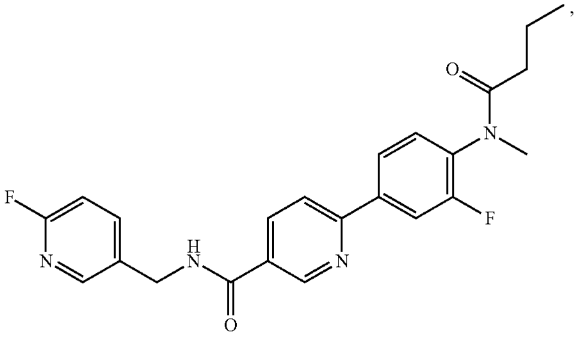
,
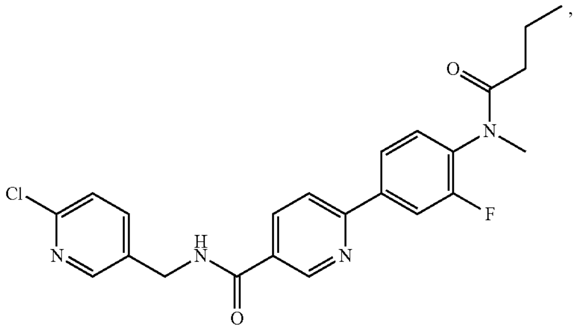
,
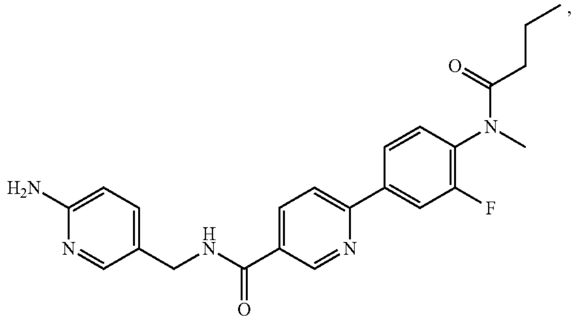
, -continued
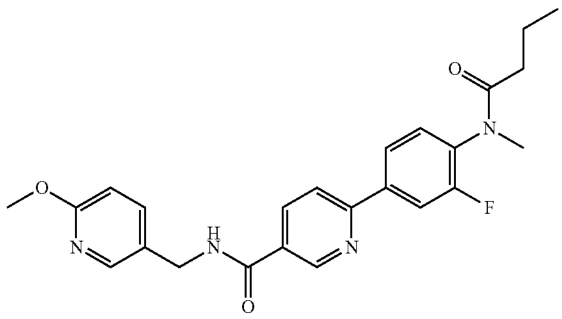
,
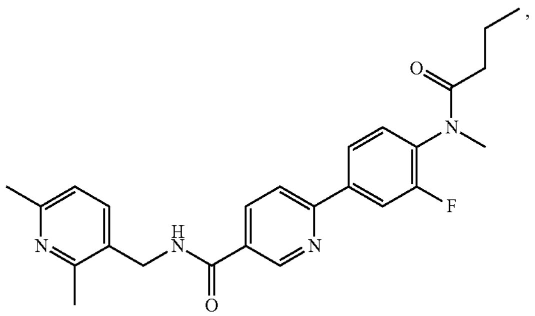
, or
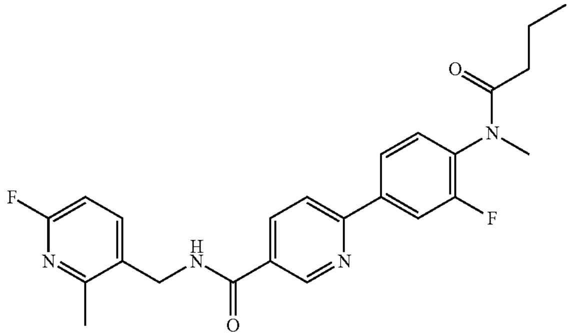
.
In certain embodiments, a compound of Formula (0) or (I) is not a compound disclosed in: International PCT Application No. PCT/US2019/030664, filed May 3, 2019, which is incorporated herein by reference. In certain aspects a compound of Formula (0) or (I) is not of the formula:
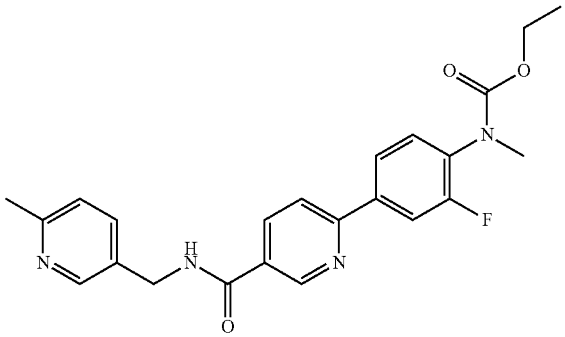
,
-continued
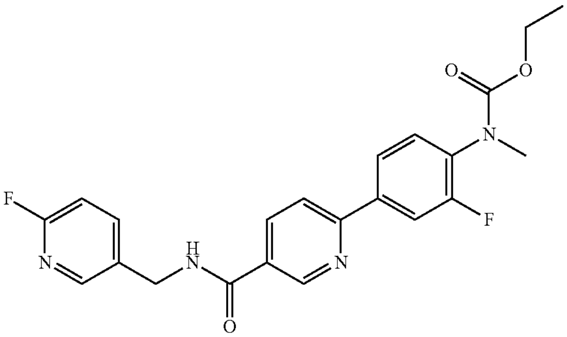
,
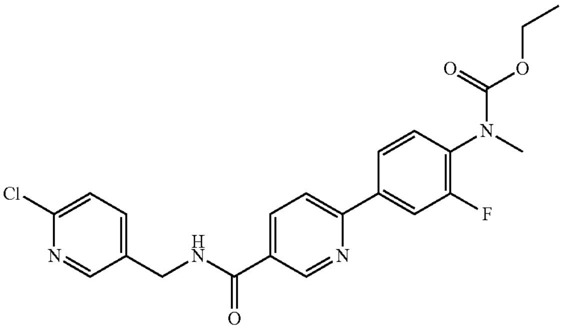
,
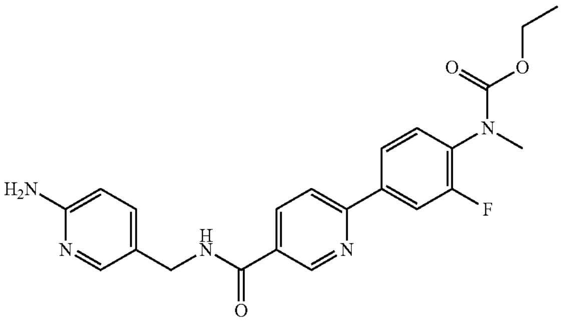
,
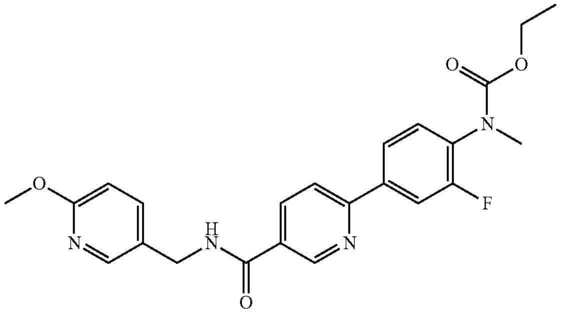
,
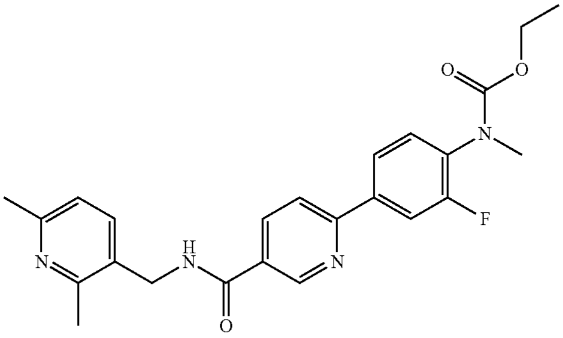
, -continued
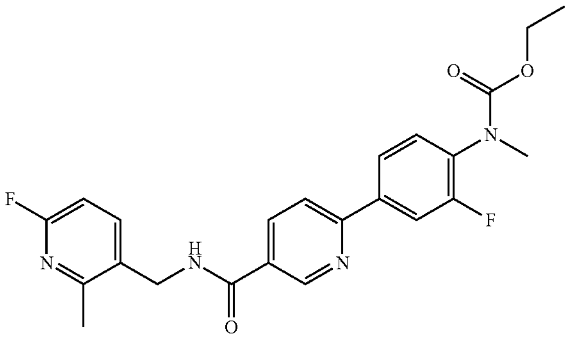
,
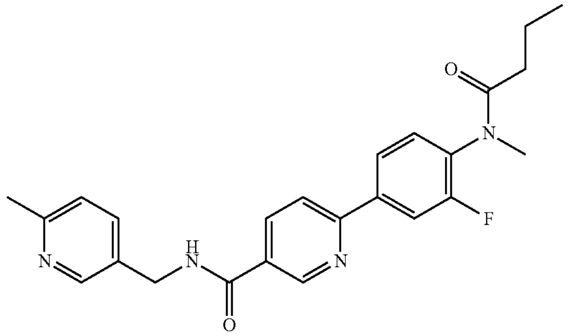
,
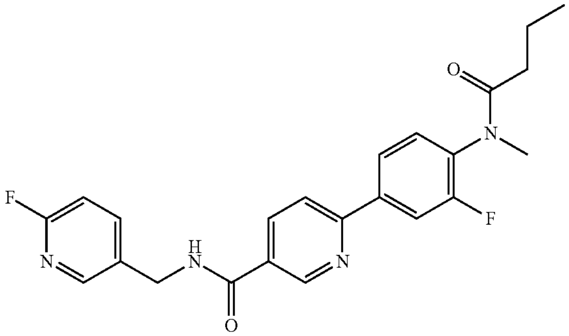
,
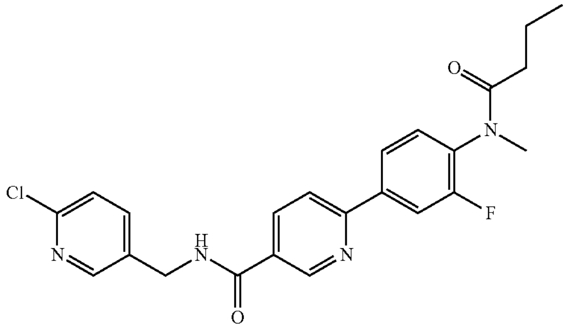
,
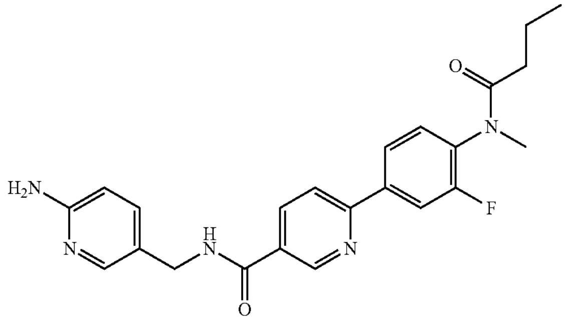
,
-continued
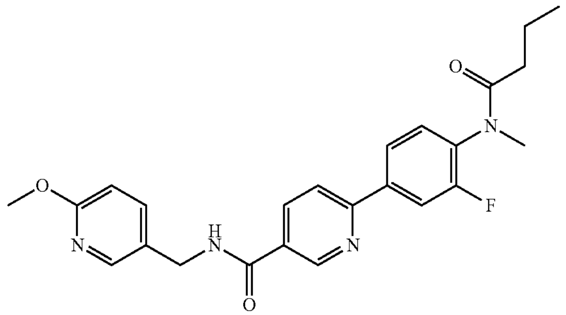
,
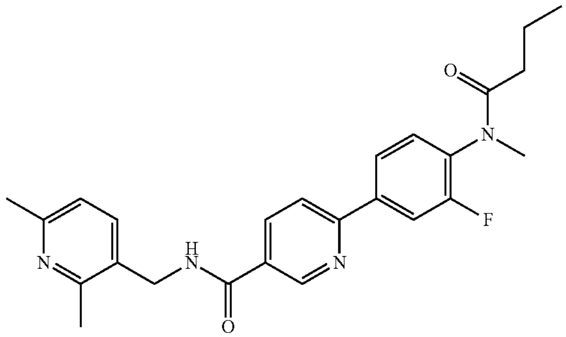
,
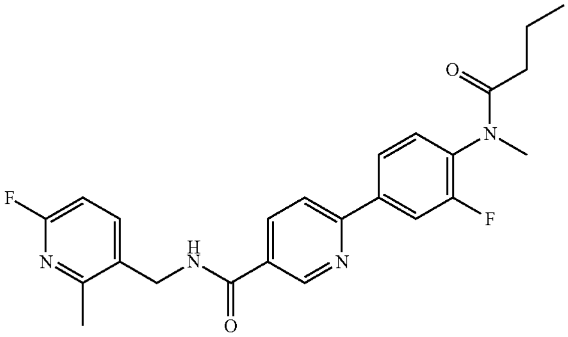
,
or International PCT Application No. PCT/US2019/030664, filed May 3, 2019, which is incorporated herein by reference.
Additional Compounds
Also provided herein are compounds selected from the group consisting of:
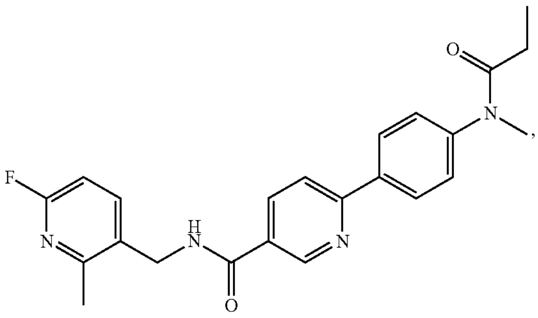
, -continued
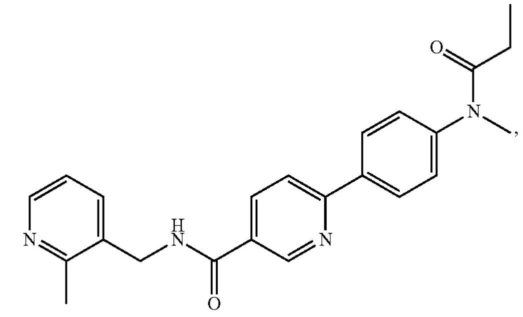
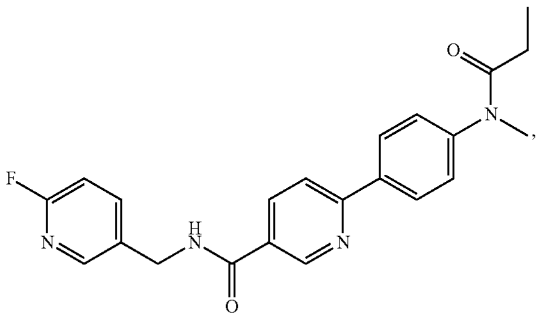
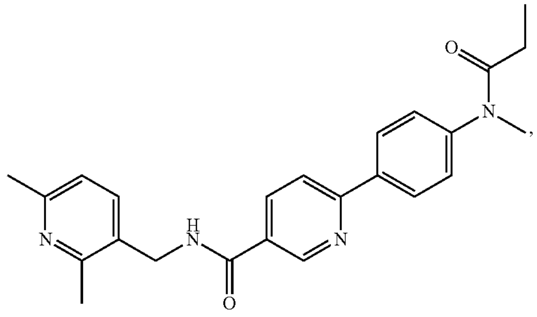
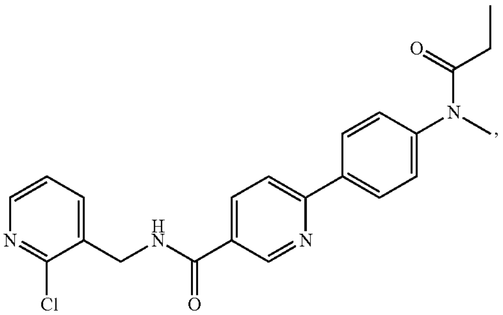
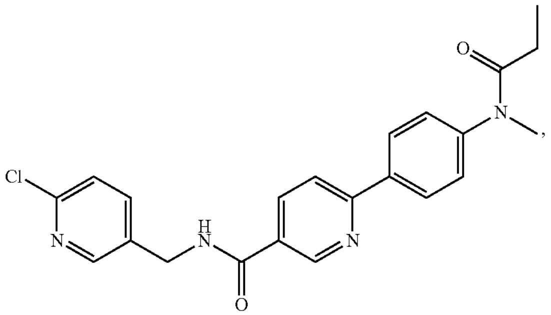
-continued
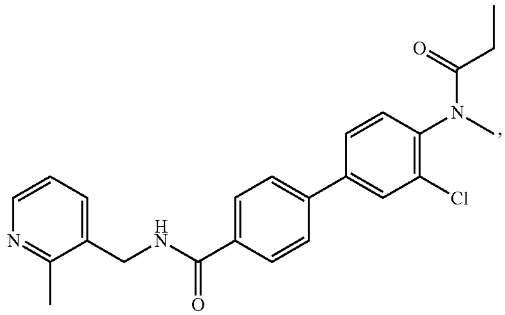
and
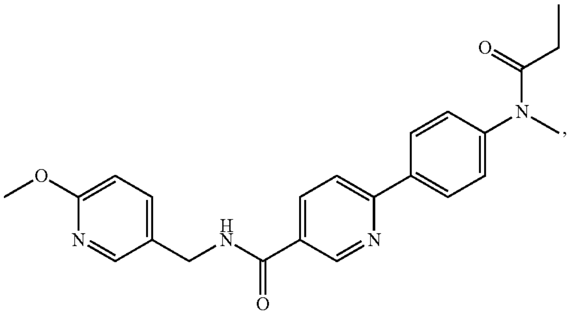
a pharmaceutically acceptable salt, hydrate, polymorph, co-crystal, tautomer, stereoisomer, isotopically labeled derivative, or prodrug thereof.
Also provided herein are compounds selected from the group consisting of:
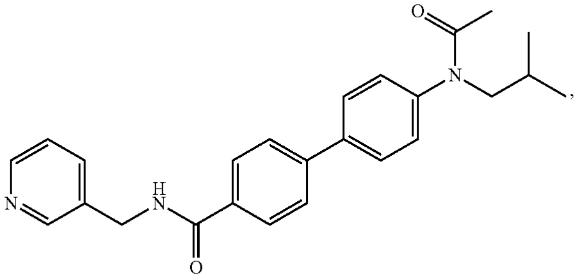
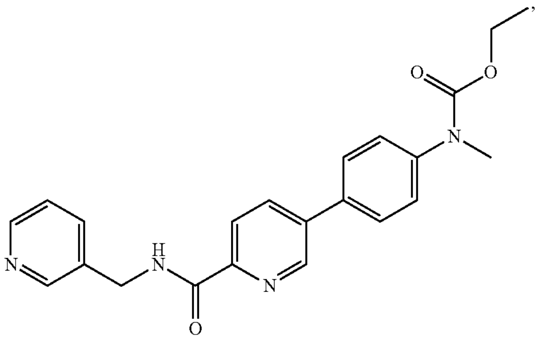

-continued
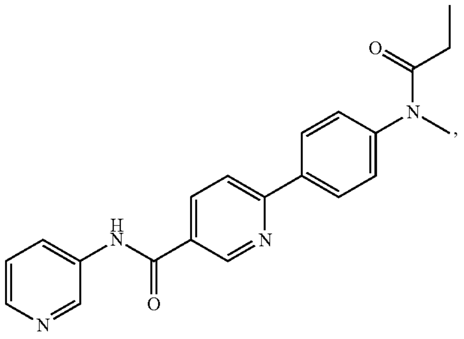
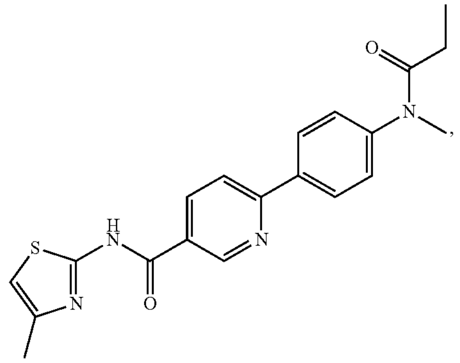
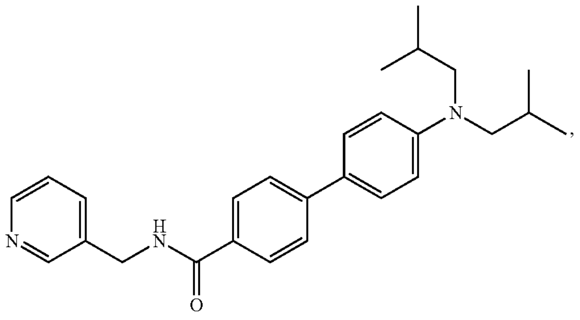
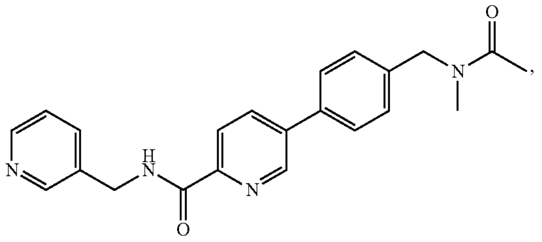
, and
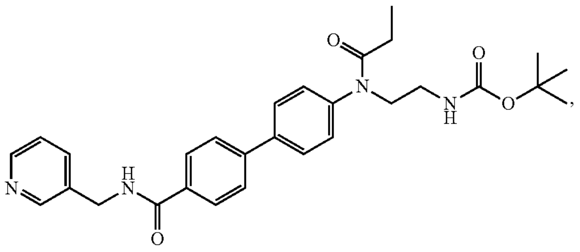
or a pharmaceutically acceptable salt, solvate, hydrate, polymorph, co-crystal, tautomer, stereoisomer, isotopically labeled derivative, or prodrug thereof.
Also provided herein are compounds selected from the group consisting of:
I-450
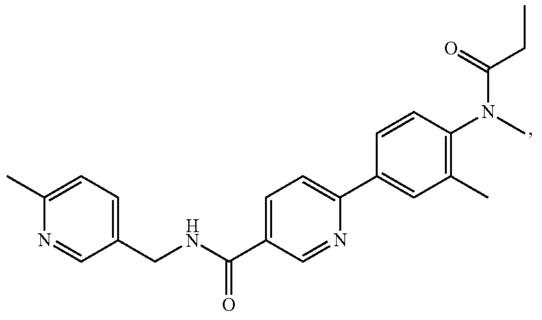
I-451
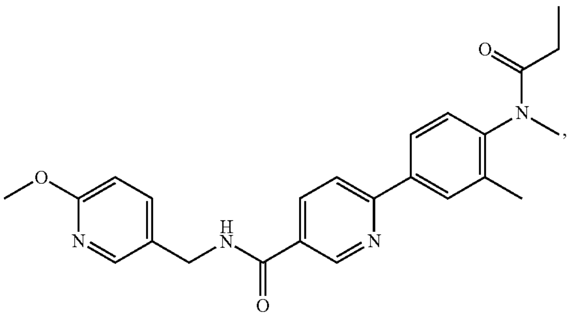
I-452
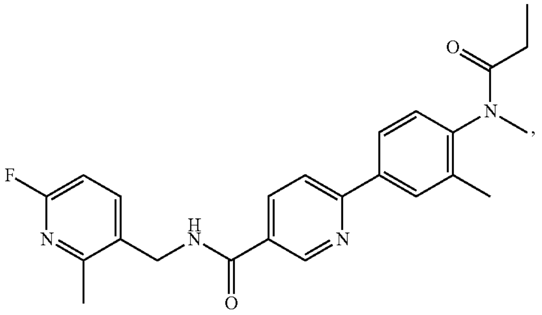
I-496
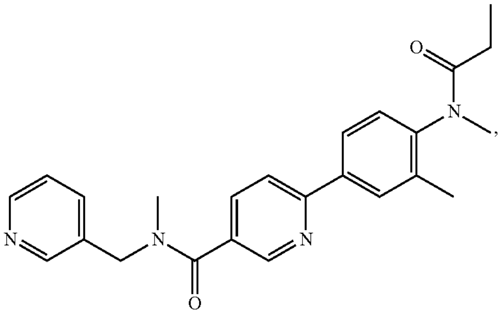

-continued

I-511

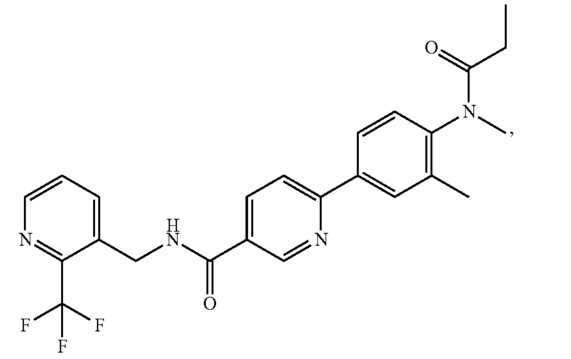

I-331

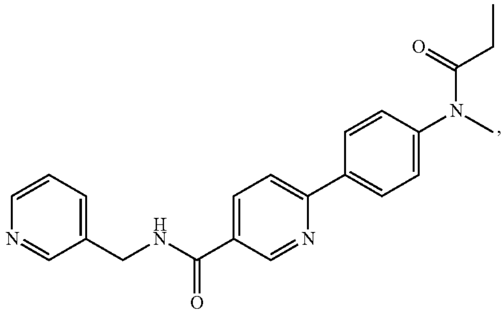

, and

I-527

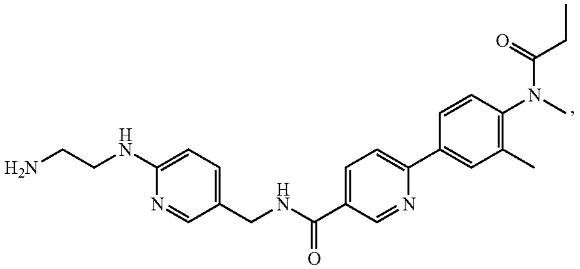

or a pharmaceutically acceptable salt, solvate, hydrate, polymorph, co-crystal, tautomer, stereoisomer, isotopically labeled derivative, or prodrug thereof.

In some embodiments, the compound is selected from the group consisting of: I-481, I-597, I-624, I-630, and I-675, or a pharmaceutically acceptable salt, solvate, hydrate, polymorph, co-crystal, tautomer, stereoisomer, isotopically labeled derivative, or prodrug thereof.

In certain embodiments, the compound selected from the group consisting of: 1-331, I-496, 1-511, I-450, and 1-527, or a pharmaceutically acceptable salt, solvate, hydrate, polymorph, co-crystal, tautomer, stereoisomer, isotopically labeled derivative, or prodrug thereof.

In certain embodiments, the compound selected from the group consisting of: I-331, I-402, I-597, I-624, and I-630, or a pharmaceutically acceptable salt, hydrate, polymorph, co-crystal, tautomer, stereoisomer, isotopically labeled derivative, or prodrug thereof.

Also provided herein are compounds selected from the group consisting of:

I-460

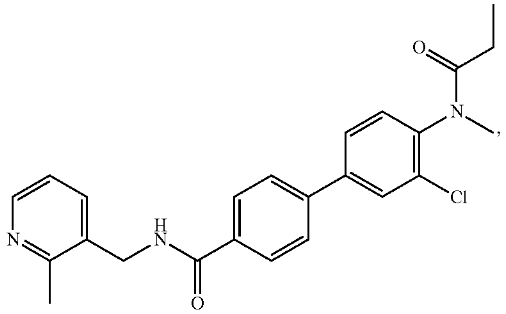

I-481

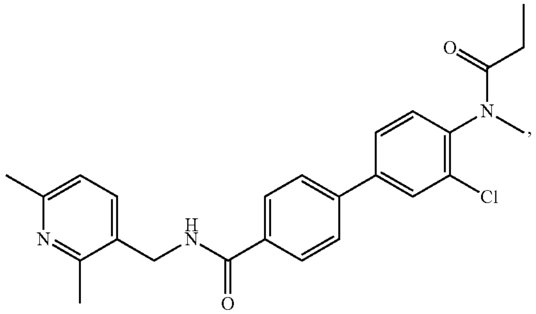

I-597

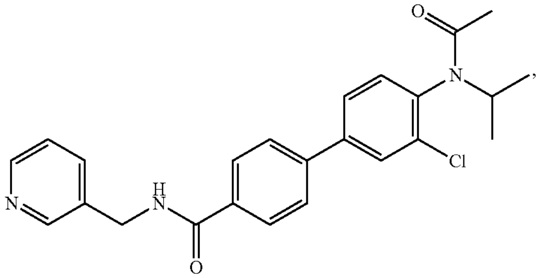

I-624

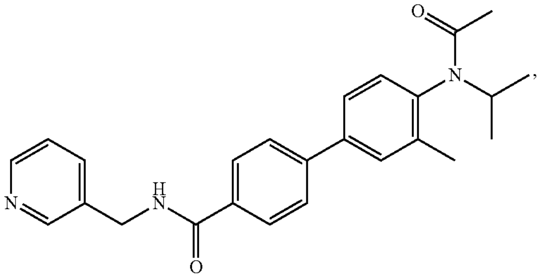

I-630

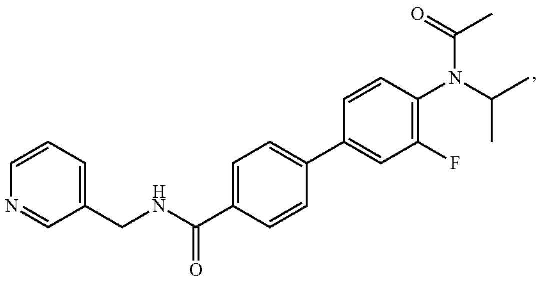

, and

-continued

I-675

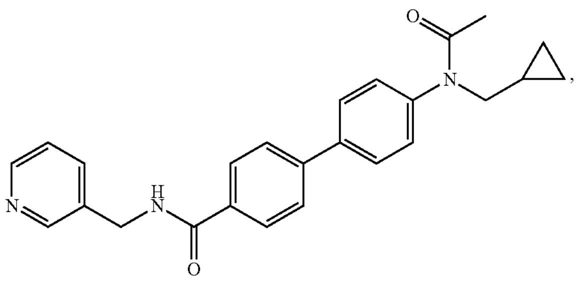

or a pharmaceutically acceptable salt, solvate, hydrate, polymorph, co-crystal, tautomer, stereoisomer, isotopically labeled derivative, or prodrug thereof.

Compositions and Kits

The present disclosure provides compositions (e.g., pharmaceutical compositions) comprising a compound of the disclosure (e.g., a compound of Formula (0) or (I), any compound described herein, or any compound appearing within the section, entitled "Additional Compounds"), and an excipient (e.g., pharmaceutically acceptable excipient). In certain embodiments, the composition is a pharmaceutical composition. In certain embodiments, the excipient is a pharmaceutically acceptable excipient.

The present disclosure also provides compositions further comprising an additional pharmaceutical agent.

Compositions described herein can be prepared by any method known in the art. In general, such preparatory methods include bringing a compound of the disclosure described herein into association with an excipient and may include one or more agents or accessory ingredients, and then, if necessary and/or desirable, shaping, and/or packaging the product into a desired single- or multi-dose unit. In certain embodiments, the agent is a pharmaceutical agent.

In certain embodiments, the compound of the disclosure is in the form of a pharmaceutically acceptable salt, solvate, hydrate, polymorph, co-crystal, tautomer, stereoisomer, isotopically labeled derivative, or prodrug.

Compositions can be prepared, packaged, and/or sold in bulk, as a single unit dose, and/or as a plurality of single unit doses. A "unit dose" is a discrete amount of the composition comprising a predetermined amount of the agent. The amount of the agent is generally equal to the dosage of the agent which would be administered to a subject and/or a convenient fraction of such a dosage, such as one-half or one-third of such a dosage.

Relative amounts of the compound of the disclosure, excipient, agent, and/or any additional ingredients in a composition described herein will vary, depending upon the identity, size, and/or condition of the subject treated and further depending upon the route by which the composition is to be administered. The composition may comprise between 0.1% and 100% (w/w) agent.

Excipients and accessory ingredients used in the manufacture of provided compositions include inert diluents, dispersing and/or granulating agents, surface active agents and/or emulsifiers, disintegrating agents, binding agents, preservatives, buffering agents, lubricating agents, and/or oils.

Excipients and accessory ingredients, such as cocoa butter, PEGylated lipids, phospholipids, suppository waxes, coloring agents, coating agents, sweetening, flavoring, and perfuming agents, may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

In certain embodiments, the compositions further comprise an agent, and are useful for delivering said agent (e.g., to a subject, tissue, biological sample, or cell). In certain embodiments, the compositions are pharmaceutical compositions which are useful for treating a disease in a subject in need thereof. In certain embodiments, the disease is cancer. In certain embodiments, the cancer is colorectal cancer (e.g., colon cancer or rectal cancer). In certain embodiments, the cancer is gastric cancer. In certain embodiments, the cancer is gastrointestinal stromal tumor. In certain embodiments, the cancer is ovarian cancer (e.g., ovarian adenocarcinoma). In certain embodiments, the cancer is lung cancer (e.g., small cell lung cancer). In certain embodiments, the cancer is non-small cell lung cancer. In certain embodiments, the cancer is breast cancer. In certain embodiments, the cancer is pancreatic cancer (e.g., pancreatic carcinoma or pancreatic adenocarcinoma). In certain embodiments, the cancer is prostate cancer (e.g., prostate adenocarcinoma). In certain embodiments, the cancer is testicular cancer. In certain embodiments, the cancer is liver cancer. In certain embodiments, the cancer is endometrial cancer (e.g., uterine cancer). In certain embodiments, the cancer is lymphoma, such as non-Hodgkin's lymphoma (e.g., B-cell non-Hodgkin's lymphoma). In certain embodiments, the cancer is B-cell lymphoma (e.g., Burkitt's B-cell lymphoma, large B-cell lymphoma). In certain embodiments, the cancer is T-cell lymphoma. In certain embodiments, the cancer is Burkitt's lymphoma (e.g., Burkitt's B-cell lymphoma). In certain embodiments, the cancer is large cell immunoblastic lymphoma. In certain embodiments, the cancer is leukemia. In certain embodiments, the cancer is acute lymphocytic leukemia (ALL), acute myelogenous leukemia (AML) (also known as acute myeloid leukemia, acute myeloblastic leukemia, acute granulocytic leukemia, acute myelocytic leukemia, and acute nonlymphocytic leukemia), chronic lymphocytic leukemia (CLL), or chronic myelogenous leukemia (CML) (also known as chronic myeloid leukemia). In certain embodiments, the cancer is AML. In some embodiments, the cancer is a subtype of AML selected from undifferentiated acute myeloblastic leukemia (M0), acute myeloblastic leukemia with minimal maturation (M1), acute myeloblastic leukemia with maturation (M2), acute promyelocytic leukemia (APL) (M3), acute myelomonocytic leukemia (M4), acute myelomonocytic leukemia with eosinophilia (M4 eos), acute monocytic leukemia (M5), acute erythroid leukemia (M6), and acute megakaryoblastic leukemia (M7). In certain embodiments, the cancer is acute monocytic leukemia or acute lymphocytic leukemia (e.g., B-cell acute lymphocytic leukemia). In certain embodiments, the cancer is acute lymphoblastic leukemia (e.g., B-cell acute lymphoblastic leukemia or T-cell acute lymphoblastic leukemia). In certain embodiments, the cancer is multiple myeloma (e.g., B-cell myeloma).

A composition, as described herein, can be administered in combination with one or more additional agents. In certain embodiments, the agents are organic molecules. In certain embodiments, the agents are inorganic molecules. In certain embodiments, the agents are targeting agents. In certain embodiments, the agents are isotopically labeled chemical compounds. In certain embodiments, the agents are agents useful in bioprocessing. In certain embodiments, the agents are pharmaceutical agents (e.g., therapeutically and/or prophylactically active agents). Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, polynucleotides, lipids, hormones, vitamins, vaccines, immunological agents, and cells.

In certain embodiments, the compound of the disclosure described herein is provided in an effective amount in the composition. In certain embodiments, the effective amount is a therapeutically effective amount. In certain embodiments, the effective amount is an amount effective for treating cancer in a subject in need thereof. In certain embodiments, the effective amount is an amount effective for inhibiting the signaling pathway required for metastasis in a subject or cell.

In certain embodiments, the effective amount is an amount effective for inhibiting the activity of NAMPT by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of NAMPT by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of NAMPT by a range between a percentage described in this paragraph and another percentage described in this paragraph, inclusive.

In certain embodiments, the effective amount is an amount effective for increasing the activity of NAMPT by at least 5%, at least 10%, at least 20%, at least 30%, at least 40%, at least 50%, at least 60%, at least 70%, at least 80%, at least 85%, at least 90%, at least 95%, at least 96%, at least 97%, at least 98%, at least 99%, at least 99.1%, at least 99.5%, at least 99.9%, at least 99.99%, or at least 99.999% of an initial level, which may, for example, be a baseline level of enzyme activity. In certain embodiments, the effective amount is an amount effective for increasing the activity of NAMPT by not more than 10%, not more than 20%, not more than 30%, not more than 40%, not more than 50%, not more than 60%, not more than 70%, not more than 80%, not more than 90%, not more than 95%, not more than 98%, or not more than 99.9%. In certain embodiments, the effective amount is an amount effective for increasing the activity of NAMPT by a range between a percentage described in this paragraph and another percentage described in this paragraph, inclusive.

In certain embodiments, the effective amount is an amount effective for inhibiting the signaling of NAMPT by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the signaling of NAMPT by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the signaling of NAMPT by a range between a percentage described in this paragraph and another percentage described in this paragraph, inclusive.

In certain embodiments, the effective amount is an amount effective for increasing the signaling of NAMPT by at least 5%, at least 10%, at least 20%, at least 30%, at least 40%, at least 50%, at least 60%, at least 70%, at least 80%, at least 85%, at least 90%, at least 95%, at least 96%, at least 97%, at least 98%, at least 99%, at least 99.1%, at least 99.5%, at least 99.9%, at least 99.99%, or at least 99.999% of an initial level, which may, for example, be a baseline level of enzyme activity.

In certain embodiments, the effective amount is an amount effective for increasing the signaling of NAMPT by not more than 10%, not more than 20%, not more than 30%, not more than 40%, not more than 50%, not more than 60%, not more than 70%, not more than 80%, not more than 90%, not more than 95%, not more than 98%, or not more than 99.9%. In certain embodiments, the effective amount is an amount effective for increasing the signaling of NAMPT by a range between a percentage described in this paragraph and another percentage described in this paragraph, inclusive.

In certain embodiments, the cell is in vitro. In certain embodiments, the cell is ex vivo. In certain embodiments, the cell is in vivo.

Compositions may be formulated into liquid dosage forms for oral and parenteral administration include pharmaceutically acceptable emulsions, microemulsions, solutions, suspensions, syrups and elixirs. In addition to the agents, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compositions described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the disclosure, it is often desirable to slow the absorption of the compound from subcutaneous or intramuscular injection. This can be accomplished by the use of a liquid suspension of crystalline or amorphous material with poor water solubility. The rate of absorption of the compound then depends upon its rate of dissolution, which, in turn, may depend upon crystal size and crystalline form. Alternatively, delayed absorption of a parenterally administered drug form may be accomplished by dissolving or suspending the compound in an oil vehicle.

Compositions for rectal or vaginal administration are typically suppositories which can be prepared by mixing the compositions described herein with suitable non-irritating excipients or carriers such as cocoa butter, polyethylene glycol, or a suppository wax which are solid at ambient temperature but liquid at body temperature and therefore melt in the rectum or vaginal cavity and release the compound of the disclosure.

Compositions may be formulated into solid dosage forms for oral administration include capsules, tablets, pills, powders, and granules. In such solid dosage forms, the compound of the disclosure is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the compound of the disclosure only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The compound of the disclosure can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the compound of the disclosure can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the compound of the disclosure only, or preferentially, in a certain part of the intestinal tract, optionally, in a delayed manner. Examples of encapsulating agents which can be used include polymeric substances and waxes.

Dosage forms for topical and/or transdermal administration of a composition described herein may include ointments, pastes, creams, lotions, gels, powders, solutions, sprays, inhalants, and/or patches. Generally, the compound of the disclosure is admixed under sterile conditions with a pharmaceutically acceptable carrier or excipient and/or any needed preservatives and/or buffers as can be required.

Suitable devices for use in delivering intradermal compositions described herein include short needle devices. Intradermal compositions can be administered by devices which limit the effective penetration length of a needle into the skin. Alternatively, or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the polymer in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 100% (w/w) compound of the disclosure, although the concentration of the compound of the disclosure can be as high as the solubility limit of the compound of the disclosure in the solvent. Formulations for topical administration may further comprise one or more of the additional ingredients described herein.

A composition described herein can be prepared, packaged, and/or sold in a formulation suitable for pulmonary administration via the buccal cavity. Such a formulation may comprise dry particles which comprise the compound of the disclosure. Such compositions are conveniently in the form of dry powders for administration using a device comprising a dry powder reservoir to which a stream of propellant can be directed to disperse the powder and/or using a self-propelling solvent/powder dispensing container such as a device comprising the agent dissolved and/or suspended in a low-boiling propellant in a sealed container. Dry powder compositions may include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the compound of the disclosure may constitute 0.1 to 100% (w/w) of the composition. The propellant may further comprise additional ingredients such as a liquid non-ionic and/or solid anionic surfactant and/or a solid diluent.

Compositions described herein formulated for pulmonary delivery may provide the compound of the disclosure in the form of droplets of a solution and/or suspension. Such formulations can be prepared, packaged, and/or sold as aqueous and/or dilute alcoholic solutions and/or suspensions, optionally sterile, comprising the compound of the disclosure, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate.

Formulations described herein as being useful for pulmonary delivery are useful for intranasal delivery of a pharmaceutical composition described herein. Another formulation suitable for intranasal administration is a coarse powder comprising the compound of the disclosure. Such a formulation is administered by rapid inhalation through the nasal passage from a container of the powder held close to the nares.

Formulations for nasal administration may, for example, comprise from about as little as 0.1% (w/w) to as much as 100% (w/w) of the compound of the disclosure, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) agent, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the compound of the disclosure.

A composition described herein can be prepared, packaged, and/or sold in a formulation for ophthalmic administration. Such formulations may, for example, be in the form of eye drops including, for example, a 0.1-100% (w/w) solution and/or suspension of the compound of the disclosure in an aqueous or oily liquid carrier or excipient. Such drops may further comprise buffering agents, salts, and/or one or more other of the additional ingredients described herein. Other ophthalmically-administrable formulations which are useful include those which comprise the compound of the disclosure in microcrystalline form and/or in a liposomal preparation. Ear drops and/or eye drops are also contemplated as being within the scope of this disclosure.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Compositions provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the cancer being treated and the severity of the cancer; the activity of the specific compound of the disclosure employed; the specific composition employed; the age, body weight, general health, sex, and diet of the subject; the time of administration, route of administration, and rate of excretion of the specific compound of the disclosure employed; the duration of the treatment; drugs used in combination or coincidental with the specific compound of the disclosure employed; and like factors well known in the medical arts.

The compositions provided herein can be administered by any route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically, contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the compound of the disclosure (e.g., its stability in the environment of the gastrointestinal tract), and/or the condition of the subject (e.g., whether the subject is able to tolerate oral administration). In certain embodiments, the composition described herein is suitable for topical administration to the eye of a subject.

In some embodiments, administration of any of the compositions described herein occurs at least one hour prior to treatment with another cancer therapy.

The compositions can be administered in combination with additional agents that improve their activity (e.g., potency and/or efficacy) in treating a disease or disorder (e.g., cancer) in a subject in need thereof and/or in inhibiting the signaling pathway in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a composition described herein, including a compound of the disclosure described herein, and an agent show a synergistic effect that is absent in a composition including one of the compounds of the disclosure or the agent, but not both.

The composition can be administered concurrently with, prior to, or subsequent to one or more additional agents, which are different from the composition and may be useful as, e.g., combination therapies. Each additional pharmaceutical agent may be administered at a dose and/or on a time schedule determined for that pharmaceutical agent. The additional pharmaceutical agents may also be administered together with each other and/or with the compound of the disclosure or composition described herein in a single dose or administered separately in different doses. The particular combination to employ in a regimen will take into account compatibility of the compound of the disclosure described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is a chemotherapeutic agent. In certain embodiments, the additional pharmaceutical agent is a differentiation agent (e.g., retinoids, all-trans retinoic acid (ATRA), vitamin D, peroxisome proliferator activated receptor gamma (PPAR gamma) inhibitors). In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compound of the disclosures described herein or pharmaceutical compositions can be administered in combination with an anti-cancer therapy including surgery, radiation therapy, transplantation (e.g., stem cell transplantation, bone marrow transplantation), immunotherapy, and chemotherapy. In some embodiments, the subject is administered concurrently with, prior to, or subsequent to one or more additional agents, such as one or more additional cancer therapies. In some embodiments, the one or more additional cancer therapy includes an immunotherapy. In general, immunotherapy, also called biologic therapy, is a type of cancer treatment that boosts a subject's natural defenses to treat cancer. In certain embodiments, the immunotherapy utilizes compounds biologically produced by the subject. In certain embodiments, the immunotherapy utilizes compounds not biologically produced by the subject. In certain embodiments, the immunotherapy utilizes cells from the subject. In certain embodiments, the immunotherapy utilizes cells not from the subject. In certain embodiments, the immunotherapy utilizes compounds biologically produced by an organism that is not the subject. In certain embodiments, the immunotherapy utilizes cells biologically produced by an organism that is not the subject. In certain embodiments, the immunotherapy includes at least one chemical modification to compounds or cells from the subject. In certain embodiments, the immunotherapy includes at least one chemical modification to compounds or cells not from the subject.

In some embodiments, the additional pharmaceutical agent is selected from the group consisting of nicotinic acid, ibrutinib, idelalisib, lenalidomide, a BCL-2 inhibitor, venetoclax, FLT3 inhibitor, IDH 1/2 inhibitor, glasdegib, azacytidine, cyclophosphamide, decitabine, enasidenib, erastin, gilterinib, idasanutlin, ivosidenib, ixazomib, midostaurin, navitoclax, onvasertib, cyclosporin A, PARP inhibitor, pacritinib, phorbol 12-myristate 13-acetate (PMA), ruxolitinib, S055746, selinexor (KPT-330), trametinib, tretinoin, etoposide, P7C3, napabucasin, olaparib, AraC, daunorubicin, 1-methyl-3-nitro-1-nitrosoguanidinium (MNNG), melphalan, verapamil, etoposide, cisplatin, anti-PD1, tumor necrosis factor-related apoptosis-inducing ligand (TRAIL), EX527, sirtinol, cambinol, vorinostat, valproic acid, butyrate, JPH203, L-asparaginase, bortezomib, rituximab, PGP-4008, β-lapachone, β-methylene adenosine 5'-diphosphate (APCP), gemcitabine, Lu-DOTATATE, fluorouracil (5-FU), pemetrexed, onvansertib, cedazuridine, galinpepimut-S, cedazuridine/decitabine, cytarabine/daunorubicin, uproleselan, gedatolisib, devimistat, glasdegib, idasanutlin, ganetespib, tipifarnib, midostaurin, pevonedistat, ivosidenib, crenolanib, quizartinib, pracinostat, guadecitabine, DFP 10917, vosaroxin, rexlemestrocel-L-mesoblast, treosulfan, sapacitabine, enasidenib, volasertib, and temozolomide.

In some embodiments, the BCL-2 inhibitor is veneteoclax, navitoclax, oblimersen, APG 2575, BCL201, BGB-11417, LP-108, or S65487.

In some embodiments, the additional pharmaceutical agent is a Toll like Receptor 4 ($TLR_4$) inhibitor. In some embodiments, the Toll like Receptor 4 inhibitor is TAK-242, E5564, OM-174, GSK1795091, GLA-SE, NI-0101, AV-411, ASO4, amitriptyline, cyclobenzaprine, ketotifen, imipramine, mianserin, ibudilast, pinocembrin, resatorvid, naloxone, naltrexone, LPS-RS, propentofylline, tapentadol, palmitoylethanolamide, In some embodiments, the additional pharmaceutical agent is a sirtuin inhibitor. In some embodiments the sirtuin inhibitor is nicotinamide, a nicotinamide derivative, benzamide, 3'-phenethyloxy-2-anilino benzamide analogues, AK7, 1,4-dihydropyridine, cambinol, EX-527, AGK2,3'-(3-fluoro-phenethyloxy)-2-anilinobenzamide, SirReal2, UBCS0137, ELT-11c, or thioacyllysine-containing compounds.

In some embodiments, the additional pharmaceutical agent is selected ibrutinib or idelalisib.

In some embodiments, the additional pharmaceutical agent is lenalidomide.

In some embodiments, the additional pharmaceutical agent is selected from the group consisting of venetoclax, FLT3 inhibitor, IDH 1/2 inhibitor, glasdegib, azacytidine, cyclophosphamide, decitabine, enasidenib, erastin, gilterinib, idasanutlin, ivosidenib, ixazomib, midostaurin, navitoclax, onvasertib, pacritinib, PMA, ruxolitinib, S055746, selinexor (KPT-330), trametinib, tretinoin, etoposide, and napabucasin.

In some embodiments, the additional pharmaceutical agent is P7C3.

In some embodiments, the FLT3 inhibitor is selected from the group consisting of sorafenib, sunitinib, lestaurtinib, tandutinib, ponatinib, midostaurin, gilteritinib, quizartinib, crenolanib, cabozantinib, ibrutinib, and KW-2449. In some embodiments, the FLT3 inhibitor is sorafenib, sunitinib, ponatinib, cabozantinib, ibrutinib, midostaurin, or gilteritinib. In some embodiments, the FLT3 inhibitor is midostaurin or gilteritinib.

In some embodiments, the IDH 1/2 inhibitor is selected from the group consisting of ivosidenib and enasidenib.

In some embodiments, the PARP inhibitor is selected from the group consisting of olaparib, rucaparib, niraparib, talazoparib, veliparib, pamiparib, CEP 9722, CEP-8983, E7016, iniparib, and 3-aminobenzamide. In some embodiments, the PARP inhibitor is selected from the group consisting of olaparib, rucaparib, niraparib, and talazoparib. In some embodiments, the PARP inhibitor is selected from the group consisting of veliparib, pamiparib, CEP 9722, CEP-8983, E7016, iniparib, and 3-aminobenzamide.

In certain embodiments, the additional pharmaceutical agent is an HDAC inhibitor.

In certain embodiments, the additional pharmaceutical agent is nicotinic acid.

In some embodiments, the additional pharmaceutical agent is afatinib, afatinib dimaleate, alectinib, atezolizumab, bevacizumab, brigatinib, capmatinib, capmatinib hydrochloride, carboplatin, carboplatin-taxol, ceritinib, crizotinib, dabrafenib, dabrafenib mesylate, dacomitinib, docetaxel, doxorubicin, doxorubicin hydrochloride, durvalumab, entrectinib, erlotinib, erlotinib hydrochloride, everolimus, etoposide phosphate, etoposide, gefitinib, gemcitabine, gemcitabine hydrochloride, gemcitabine-cisplatin, ipilimumab, lorlatinib, lurbinectedin, methotrexate, methotrexate sodium, necitumumab, nivolumab, osimertinib mesylate, osimertinib, paclitaxel, paclitaxel albumin-stabilized nanoparticle formulation, pembrolizumab, pralsetinib, pemetrexed, pemetrexed disodium, ramucirumab, selpercatinib, topotecan, topotecan hydrochloride, trametinib, vinorelbine, or vinorelbine tartrate.

In some embodiments, the additional pharmaceutical agent is selected from the group consisting of topoisomerase II inhibitors (e.g., etoposide, doxorubicin), topoisomerase I inhibitors (e.g., irinotecan, CPT-11, camptostar, topotecan), tubulin interacting agents (e.g., paclitaxel, docetaxel, epothilones), thymidilate synthase inhibitors (e.g., 5-fluorouracil or 5-FU), alkylating agents (e.g., temozolomide, cyclophosphamide), farnesyl protein transferase inhibitors (e.g., Lonafarnib, L778,123, BMS 214662), signal transduction inhibitors (e.g., gefitinib), antibodies to EGFR (e.g., cetuximab), cytarabine, aromatase inhibitors (e.g., exemestance, anastrozole, letrozole).

In some embodiments, the additional pharmaceutical agent is cytarabine.

In some embodiments, the additional pharmaceutical agent is an aromatase inhibitor. In some embodiments, the aromatase inhibitor is aminoglutethimide, testolactone, anastrozole, letrozole, exemestane, vorozole, formestane, fadrozole, 1,4,6-androstatrien-3,17-dione, or 4-androstene-3,6,17-trione.

In certain embodiments, the additional pharmaceutical agent is an anti-cancer or anti-neoplastic agent. In some embodiments, the additional pharmaceutical agent is cytarabine, doxorubicin, cyclophosphamide, FX-11, uracil mustard, chlormethine, hexamethylmelamine, zevalin, trisenox, xeloda, aminoglutethimide, 6-thioguanine, pentostatine, mithramycin, ifosfamide, pipobroman, triethylenemelamine, methyltestosterone, amsacrine, mitotane, levamisole, triamcinolone, testosterone, fluoxymesterone, dromostanolone propionate, triethylenethiophosphoramine, streptozocin, 6-mercaptopurine, deoxycoformycin, mitomycin-C, 17a-ethinylestradiol, diethylstilbestrol, testolactone, megestrolacetate, methylprednisolone, chlorotrianisene, hydroxyprogesterone, medroxyprogesteroneacetate, toremifene, navelbene, anastrazole, letrazole, reloxafme, droloxafme, porfimer, thiotepa, altretamine, lerozole, fulvestrant, exemestane, 5-HT3 receptor inhibitor (e.g., dolansetron, granisetron, ondansetron) or dexamethasone.

In some embodiments, the additional pharmaceutical agent is cytarabine, doxorubicin, cyclophosphamide, FX-11, uracil mustard, chlormethine, hexamethylmelamine, zevalin, trisenox, xeloda, aminoglutethimide, 6-thioguanine, pentostatine, mithramycin, ifosfamide, pipobroman, triethylenemelamine, methyltestosterone, amsacrine, mitotane, levamisole, triamcinolone, testosterone, fluoxymesterone, dromostanolone propionate, triethylenethiophosphoramine, streptozocin, 6-mercaptopurine, deoxycoformycin, mitomycin-C, 17a-ethinylestradiol, diethylstilbestrol, testolactone, megestrolacetate, methylprednisolone, chlorotrianisene, hydroxyprogesterone, medroxyprogesteroneacetate, toremifene, navelbene, anastrazole, letrazole, reloxafme, droloxafme, porfimer, thiotepa, altretamine, lerozole, fulvestrant, exemestane, or dexamethasone, with a 5-HT3 receptor inhibitor (e.g., dolansetron, granisetron, ondansetron).

In some embodiments, the additional pharmaceutical agent is cytarabine, doxorubicin, cyclophosphamide, FX-11, uracil mustard, chlormethine, hexamethylmelamine, zevalin, trisenox, xeloda, aminoglutethimide, 6-thioguanine, pentostatine, mithramycin, ifosfamide, pipobroman, triethylenemelamine, methyltestosterone, amsacrine, mitotane, levamisole, triamcinolone, testosterone, fluoxymesterone, dromostanolone propionate, triethylenethiophosphoramine, streptozocin, 6-mercaptopurine, deoxycoformycin, mitomycin-C, 17a-ethinylestradiol, diethylstilbestrol, testolactone, megestrolacetate, methylprednisolone, chlorotrianisene, hydroxyprogesterone, medroxyprogesteroneacetate, toremifene, navelbene, anastrazole, letrazole, reloxafme, droloxafme, porfimer, thiotepa, altretamine, lerozole, fulvestrant, exemestane, or a 5-HT3 receptor inhibitor (e.g., dolansetron, granisetron, ondansetron), with dexamethasone.

In some embodiments, the additional pharmaceutical agent is cytarabine. In some embodiments, the additional pharmaceutical agent is doxorubicin. In some embodiments, the additional pharmaceutical agent is cyclophosphamide. In some embodiments, the additional pharmaceutical agent is FX-11. In certain embodiments, the additional pharmaceutical agent is uracil mustard. In some embodiments, the additional pharmaceutical agent is chlormethine. In some embodiments, the additional pharmaceutical agent is hexamethylmelamine. In some embodiments, the additional pharmaceutical agent is zevalin. In some embodiments, the additional pharmaceutical agent is trisenox. In some embodiments, the additional pharmaceutical agent is xeloda. In some embodiments, the additional pharmaceutical agent is aminoglutethimide. In some embodiments, the additional pharmaceutical agent is 6-thioguanine. In some embodiments, the additional pharmaceutical agent is pentostatine. In some embodiments, the additional pharmaceutical agent is mithramycin. In some embodiments, the additional pharmaceutical agent is ifosfamide. In some embodiments, the additional pharmaceutical agent is pipobroman. In some embodiments, the additional pharmaceutical agent is triethylenemelamine. In some embodiments, the additional pharmaceutical agent is methyltestosterone. In some embodiments, the additional pharmaceutical agent is amsacrine. In some embodiments, the additional pharmaceutical agent is mitotane. In some embodiments, the additional pharmaceutical agent is levamisole. In some embodiments, the additional pharmaceutical agent is triamcinolone. In some embodiments, the additional pharmaceutical agent is testosterone. In some embodiments, the additional pharmaceutical agent is fluoxymesterone. In some embodiments, the additional pharmaceutical agent is dromostanolone propionate. In some embodiments, the additional pharmaceutical agent is triethylenethiophosphoramine. In some embodiments, the additional pharmaceutical agent is streptozocin. In some embodiments, the additional pharmaceutical agent is 6-mercaptopurine. In some embodiments, the additional pharmaceutical agent is deoxycoformycin. In some embodiments, the additional pharmaceutical agent is mitomycin-C. In some embodiments, the additional pharmaceutical agent is 17a-ethinylestradiol. In some embodiments, the additional pharmaceutical agent is diethylstilbestrol. In some embodiments, the additional pharmaceutical agent is testolactone. In some embodiments, the additional pharmaceutical agent is megestrolacetate. In some embodiments, the additional pharmaceutical agent is methylprednisolone. In some embodiments, the additional pharmaceutical agent is chlorotrianisene. In some embodiments, the additional pharmaceutical agent is hydroxyprogesterone. In some embodiments, the additional pharmaceutical agent is medroxyprogesteroneacetate. In some embodiments, the additional pharmaceutical agent is toremifene. In some embodiments, the additional pharmaceutical agent is navelbene. In some embodiments, the additional pharmaceutical agent is anastrazole. In some embodiments, the additional pharmaceutical agent is letrazole. In some embodiments, the additional pharmaceutical agent is reloxafme. In some embodiments, the additional pharmaceutical agent is droloxafme. In some embodiments, the additional pharmaceutical agent is porfimer. In some embodiments, the additional pharmaceutical agent is thiotepa. In some embodiments, the additional pharmaceutical agent is altretamine. In some embodiments, the additional pharmaceutical agent is lerozole. In some embodiments, the additional pharmaceutical agent is fulvestrant. In some embodiments, the additional pharmaceutical agent is exemestane. In some embodiments, the additional pharmaceutical agent is a 5-HT3 receptor inhibitor. In some embodiments, the additional pharmaceutical agent is dolansetron. In some embodiments, the additional pharmaceutical agent is granisetron. In some embodiments, the additional pharmaceutical agent is ondansetron. In some embodiments, the additional pharmaceutical agent is dexamethasone.

In some embodiments, the additional pharmaceutical agent is for treating small cell lung cancer. In some embodiments, the additional pharmaceutical agent is everolimus, atezolizumab, doxorubicin, doxorubicin hydrochloride, durvalumab, etoposide phosphate, etoposide, topotecan, topotecan hydrochloride, pembrolizumab, lurbinectedin, methotrexate, methotrexate sodium, or nivolumab.

In some embodiments, the additional pharmaceutical agent is ibrutinib. In some embodiments, the additional pharmaceutical agent is idelalisib. In some embodiments, the additional pharmaceutical agent is lenalidomide. In some embodiments, the additional pharmaceutical agent is venetoclax. In some embodiments, the additional pharmaceutical agent is FLT3 inhibitor. In some embodiments, the additional pharmaceutical agent is IDH 1/2 inhibitor. In some embodiments, the additional pharmaceutical agent is glasdegib. In some embodiments, the additional pharmaceutical agent is azacytidine. In some embodiments, the additional pharmaceutical agent is cyclophosphamide. In some embodiments, the additional pharmaceutical agent is decitabine. In some embodiments, the additional pharmaceutical agent is enasidenib. In some embodiments, the additional pharmaceutical agent is erastin. In some embodiments, the additional pharmaceutical agent is gilterinib. In some embodiments, the additional pharmaceutical agent is idasanutlin. In some embodiments, the additional pharmaceutical agent is ivosidenib. In some embodiments, the additional pharmaceutical agent is ixazomib. In some embodiments, the additional pharmaceutical agent is midostaurin. In some embodiments, the additional pharmaceutical agent is navitoclax. In some embodiments, the additional pharmaceutical agent is onvasertib. In some embodiments, the additional pharmaceutical agent is cyclosporin A. In some embodiments, the additional pharmaceutical agent is pacritinib. In some embodiments, the additional pharmaceutical agent is phorbol 12-myristate 13-acetate (PMA). In some embodiments, the additional pharmaceutical agent is ruxolitinib. In some embodiments, the additional pharmaceutical agent is S055746. In some embodiments, the additional pharmaceutical agent is selinexor (KPT-330). In some embodiments, the additional pharmaceutical agent is trametinib. In some embodiments, the additional pharmaceutical agent is tretinoin. In some embodiments, the additional pharmaceutical agent is etoposide. In some embodiments, the additional pharmaceutical agent is $P7C_3$. In some embodiments, the additional pharmaceutical agent is napabucasin. In some embodiments, the additional pharmaceutical agent is olaparib. In some embodiments, the additional pharmaceutical agent is AraC. In some embodiments, the additional pharmaceutical agent is daunorubicin. In some embodiments, the additional pharmaceutical agent is 1-methyl-3-nitro-1-nitrosoguanidinium (MNNG). In some embodiments, the additional pharmaceutical agent is melphalan. In some embodiments, the additional pharmaceutical agent is verapamil. In some embodiments, the additional pharmaceutical agent is etoposide. In some embodiments, the additional pharmaceutical agent is cisplatin. In some embodiments, the additional pharmaceutical agent is anti-PD1. In some embodiments, the additional pharmaceutical agent is tumor necrosis factor-related apoptosis-inducing ligand (TRAIL). In some embodiments, the additional pharmaceutical agent is EX527. In some embodiments, the additional pharmaceutical agent is sirtinol. In some embodiments, the additional pharmaceutical agent is cambinol. In some embodiments, the additional pharmaceutical agent is vorinostat. In some embodiments, the additional pharmaceutical agent is valproic acid. In some embodiments, the additional pharmaceutical agent is butyrate. In some embodiments, the additional pharmaceutical agent is JPH203. In some embodiments, the additional pharmaceutical agent is L-asparaginase. In some embodiments, the additional pharmaceutical agent is bortezomib. In some embodiments, the additional pharmaceutical agent is rituximab. In some embodiments, the additional pharmaceutical agent is cyclosporin-A. In some embodiments, the additional pharmaceutical agent is PGP-4008. In some embodiments, the additional pharmaceutical agent is (3-lapachone. In some embodiments, the additional pharmaceutical agent is β-methylene adenosine 5'-diphosphate (APCP). In some embodiments, the additional pharmaceutical agent is gemcitabine. In some embodiments, the additional pharmaceutical agent is Lu-DOTATATE. In some embodiments, the additional pharmaceutical agent is fluorouracil (5-FU). In some embodiments, the additional pharmaceutical agent is pemetrexed. In some embodiments, the additional pharmaceutical agent is temozolomide. In some embodiments, the additional pharmaceutical agent is onvansertib. In some embodiments, the additional pharmaceutical agent is cedazuridine. In some embodiments, the additional pharmaceutical agent is galinpepimut-S. In some embodiments, the additional pharmaceutical agent is cedazuridine/decitabine. In some embodiments, the additional pharmaceutical agent is cytarabine/daunorubicin. In some embodiments, the additional pharmaceutical agent is uproleselan. In some embodiments, the additional pharmaceutical agent is gedatolisib. In some embodiments, the additional pharmaceutical agent is devimistat. In some embodiments, the additional pharmaceutical agent is glasdegib. In some embodiments, the additional pharmaceutical agent is idasanutlin. In some embodiments, the additional pharmaceutical agent is ganetespib. In some embodiments, the additional pharmaceutical agent is tipifarnib. In some embodiments, the additional pharmaceutical agent is midostaurin. In some embodiments, the additional pharmaceutical agent is pevonedistat. In some embodiments, the additional pharmaceutical agent is ivosidenib. In some embodiments, the additional pharmaceutical agent is crenolanib. In some embodiments, the additional pharmaceutical agent is quizartinib. In some embodiments, the additional pharmaceutical agent is pracinostat. In some embodiments, the additional pharmaceutical agent is guadecitabine. In some embodiments, the additional pharmaceutical agent is DFP 10917. In some embodiments, the additional pharmaceutical agent is vosaroxin. In some embodiments, the additional pharmaceutical agent is rexlemestrocel-L-mesoblast. In some embodiments, the additional pharmaceutical agent is treosulfan. In some embodiments, the additional pharmaceutical agent is sapacitabine. In some embodiments, the additional pharmaceutical agent is enasidenib. In some embodiments, the additional pharmaceutical agent is volasertib.

In some embodiments, the immunotherapy may involve one of more of the following steps: preventing or inhibiting the growth of cancer cells; preventing cancer from spreading to other parts of the body; and improving the ability and activity of the immune system to kill cancer cells. Non-limiting examples of immunotherapies include: monoclonal antibodies, checkpoint inhibitors, non-specific immunotherapies, oncolytic virus therapy, T cell therapies, and cancer vaccines.

In certain embodiments, the immunotherapy utilizes monoclonal antibodies. In some embodiments, the monoclonal antibodies target (bind to) and/or block an abnormal protein on a cancer cell.

In certain embodiments, the immunotherapy includes immunotherapeutic strategies for leukemia. In some embodiments, the immunotherapy includes vaccination with leukemia-associated antigens. In certain embodiments, the immunotherapy includes adoptive transfer of allogeneic natural killer cells.

In certain embodiments, the immunotherapy utilizes checkpoint inhibitors. In certain embodiments, the immune checkpoint inhibitors are monoclonal antibodies. Immune checkpoints are regulators of immune activation by maintaining immune homeostasis and preventing autoimmunity. In cancer cells, immune checkpoint mechanisms are often activated to suppress the nascent anti-cancer immune response. In some embodiments, the checkpoint inhibitor is an inhibitor of PD-1 (programmed cell death protein 1). In some embodiments, the checkpoint inhibitor is an inhibitor of PD-L1 (programmed death-ligand 1). In some embodiments, the checkpoint inhibitor is an inhibitor of CTLA-4 (cytotoxic T-lymphocyte-associated protein 4). Examples of immune checkpoint inhibitors include, without limitation, Ipilimumab (Yervoy), Nivolumab (Opdivo), Pembrolizumab (Keytruda), Atezolizumab (Tecentriq), Avelumab (Bavencio), and Durvalumab (Imfinzi).

In certain embodiments, the immunotherapy is non-specific immunotherapy (e.g., interferons or interleukins). In certain embodiments, the immunotherapy is an oncolytic virus therapy.

In certain embodiments, the immunotherapy is a T cell therapy. In some embodiments, the T cell therapy is chimeric antigen receptor (CAR) T cell therapy.

In certain embodiments, the immunotherapy is an anti-cancer vaccine.

Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunomodulatory agents (e.g., IL-1, 2, 4, 6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab)). Exemplary chemotherapeutic agents include, but are not limited to, anti-estrogens (e.g. tamoxifen, raloxifene, and megestrol), LHRH agonists (e.g. goserelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), *vinca* alkaloids (e.g. vincristine, vinblastine, vindesine, and vinorelbine), taxoids (e.g. paclitaxel or a paclitaxel equivalent) docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), paclitaxel albumin-stabilized nanoparticle formulation, and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonuclotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g. 1-methyl-4-phenylpyridinium ion), cell cycle inhibitors (e.g., staurosporine), actinomycin (e.g. actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK$^{T}$M), SGX523, PF-04217903, PF−02341066, PF−299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Novartis), XL765 (Sanofi Aventis), PF−4691502 (Pfizer), GDC0980 (Genetech), SF1126 (Semafoe), and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In some embodiments, the compound or composition is substantially soluble in water (e.g., hydrophilic). In some embodiments, the compound or composition is substantially insoluble in water (e.g., hydrophobic). In some embodiments, the compound or composition is substantially insoluble in water and greater than about 10,000 parts water are required to dissolve 1 part compound of the disclosure.

In some embodiments, the percentage of the composition that comprises a compound of the disclosure is between about 1 and about 100% (e.g., about 1%, about 2%, about 3%, about 4%, about 5%, about 10%, about 15%, about 20%, about 30%, about 40%, about 50%, about 60%, about 70%, about 80%, about 90%, or about 100%). In some embodiments, the percentage of the composition that comprise a compound of the disclosure is less than about 50%, e.g., less than about 40%, less than about 35%, less than about 30%, less than about 25%, less than about 20%, less than about 15%, or less than about 10%. In some embodiments, the percentage of the composition that comprise a compound of the disclosure is between about 5% and about 50%, about 5% and about 40%, about 5% and about 30%, about 5% and about 25%, or about 5% and about 20%. In some embodiments, the percentage of the composition that comprise a compound of the disclosure is between about 5% and 90%. In some embodiments, the percentage of the composition that comprise a compound of the disclosure is between about 5% and about 75%. In some embodiments, the composition that comprise a compound of the disclosure is between about 5% and about 50%. In some embodiments, the percentage of the composition that comprise a compound of the disclosure is between about 10% and about 25%.

In some embodiments, the total amount of the compound of the disclosure present in the composition is greater than about 1% (e.g., about 1%, about 2%, about 3%, about 4%, about 5%, about 6%, about 7%, about 8%, about 9%, about 10%, about 12%, about 15%, about 20%, about 25%, about 30%, or more) of the total size or weight of the composition. In some embodiments, the total amount of the compound of the disclosure present in the composition is greater than about 10% (e.g., about 12%, about 15%, about 20%, about 25%, about 30%, or more) of the total size or weight of the composition.

In some embodiments, the compound of the disclosure is incorporated into a composition at a dose that is less than the dose or amount of said compound in free form to have a desired effect (e.g., a desired therapeutic effect). In certain embodiments, the composition increases the amount of the compound of the disclosure delivered to a tissue or cell in need thereof and reduces the amount of the compound of the disclosure exposed to a non-target tissue or cell, as compared to the free compound.

In another aspect, provided are kits comprising a compound of the disclosure; or a pharmaceutical composition as described herein; and instructions for using the compound of the disclosure or pharmaceutical composition of the disclosure.

In some embodiments, the kits further comprise an additional pharmaceutical agent as described herein. In certain embodiments, the kits further comprise instructions regarding the order of use of the compound of the disclosure or composition of the disclosure and the additional pharmaceutical agent. In some embodiments, the instructions provide that a compound of the disclosure or composition of the disclosure is administered before the additional pharmaceutical agent. In some embodiments, the instructions provide that a compound of the disclosure or composition of the disclosure is administered concurrently with the additional pharmaceutical agent. In some embodiments, the instructions provide that a compound of the disclosure or composition of the disclosure is administered after the additional pharmaceutical agent.

In certain embodiments, the instructions of the kit may also include information as required by a regulatory agency such as the U.S. Food and Drug Administration (FDA). In certain embodiments, the information included in the kits is prescribing information. In certain embodiments, the kits and instructions provide for delivering a compound of the disclosure. In certain embodiments, the kits and instructions provide for delivering a composition. In certain embodiments, the kits and instructions provide for treating cancer in a subject in need thereof. In certain embodiments, the kits and instructions provide for inhibiting the signaling pathway in a subject or cell.

Methods of Treatment and Prevention and Uses

Also provided herein are methods and uses for treating or preventing any disease as described herein using a compound or composition as described herein.

In some embodiments, the present disclosure provides methods for treating cancer comprising administering to a subject a therapeutically effective amount of a compound of Formula (0) or (I), or a pharmaceutically acceptable salt, solvate, hydrate, polymorph, co-crystal, tautomer, stereoisomer, isotopically labeled derivative, or prodrug thereof, wherein the variables recited in Formula (0) or (I) are as described herein.

In certain embodiments, the cancer comprises cancer stem cells. In certain embodiments, the cancer involves or is associated with cancer stem cells. In certain embodiments, the cancer is colorectal cancer, gastric cancer, gastrointestinal stromal tumor, ovarian cancer, lung cancer, breast cancer, pancreatic cancer, testicular cancer, prostate cancer, liver cancer, or endometrial cancer. In certain embodiments, the cancer is leukemia (e.g., acute myeloid leukemia). In certain embodiments, the cancer is lymphoma. In certain embodiments, the cancer is multiple myeloma. In certain embodiments, the subject is in need of regenerative medicine or therapy.

In yet another aspect, the present disclosure provides methods and uses comprising contacting a cell with an effective amount of a compound of Formula (0) or (I), or a pharmaceutically acceptable salt, solvate, hydrate, polymorph, co-crystal, tautomer, stereoisomer, isotopically labeled derivative, or prodrug thereof.

In certain aspects, the present disclosure provides methods and uses comprising killing a cell with an effective amount of a compound of Formula (0) or (I), or a pharmaceutically acceptable salt, solvate, hydrate, polymorph, co-crystal, tautomer, stereoisomer, isotopically labeled derivative, or prodrug thereof.

In certain aspects, the present disclosure provides methods and uses comprising contacting a compound of Formula (0) or (I), or a pharmaceutically acceptable salt, solvate, hydrate, polymorph, co-crystal, tautomer, stereoisomer, isotopically labeled derivative, or prodrug thereof, with a cell, tissue, or biological sample to inhibit tumor growth, regenerate or differentiate one or more cells, prevent metastasis, kill cancer cells, reduce embryonic properties or adult stem cell properties of one or more cells, reduce cell viability, and/or prevent cell proliferation.

In certain embodiments, the present disclosure provides methods of modulating NAMPT in a subject comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by modulating NAMPT in a subject comprising administering to the subject a therapeutically effective amount of a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of inhibiting NAMPT in a subject comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by inhibiting NAMPT in a subject comprising administering to the subject a therapeutically effective amount of a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of modulating inflammatory activity in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by modulating inflammatory activity in the subject, the method comprising administering to the subject a therapeutically effective amount of a compound disclosed herein, or a pharmaceutically acceptable salt, solvate, hydrate, polymorph, co-crystal, tautomer, stereoisomer, isotopically labeled derivative, or prodrug thereof In certain embodiments, the present disclosure provides methods of decreasing inflammatory activity in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by decreasing inflammatory activity in the subject, the method comprising administering to the subject a therapeutically effective amount of a compound disclosed herein, or a pharmaceutically acceptable salt, solvate, hydrate, polymorph, co-crystal, tautomer, stereoisomer, isotopically labeled derivative, or prodrug thereof In certain embodiments, the present disclosure provides methods of modulating cellular metabolism in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by modulating cellular metabolism in the subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of decreasing cellular metabolism in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by decreasing cellular metabolism in the subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of modulating cellular metabolic activity or state in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by modulating cellular metabolic activity or state in the subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of reducing cellular metabolic activity or state in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by reducing cellular metabolic activity or state in the subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of reducing cell proliferation in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by reducing cell proliferation in the subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of reducing inflammatory cell infiltration in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by reducing inflammatory cell infiltration in the subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of modulating production of nicotinamide adenine dinucleotide in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by modulating the production of nicotinamide adenine dinucleotide in the subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of inhibiting production of nicotinamide adenine dinucleotide in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by inhibiting the production of nicotinamide adenine dinucleotide in the subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of modulating production of nicotinamide mononucleotide in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by modulating the production of nicotinamide mononucleotide in the subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of inhibiting production of nicotinamide mononucleotide in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by inhibiting the production of nicotinamide mononucleotide in the subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of modulating a NAMPT pathway in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of inhibiting a NAMPT pathway in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by modulating a NAMPT pathway in the subject, the method comprising administering to the subject a therapeutically effective amount of a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by inhibiting a NAMPT pathway in the subject, the method comprising administering to the subject a therapeutically effective amount of a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of modulating NAMPT signaling in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by modulating NAMPT signaling in the subject, the method comprising administering to the subject a therapeutically effective amount of a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of decreasing NAMPT signaling in a subject, the method comprising administering to the subject a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject by decreasing NAMPT signaling in the subject, the method comprising administering to the subject a therapeutically effective amount of a compound disclosed herein, or a pharmaceutically acceptable salt, solvate, hydrate, polymorph, co-crystal, tautomer, stereoisomer, isotopically labeled derivative, or prodrug thereof.

In certain embodiments, the present disclosure provides methods of treating a disease or disorder in a subject comprising administering to the subject a therapeutically effective amount of a compound disclosed herein, or a pharmaceutically acceptable salt, solvate, hydrate, polymorph, co-crystal, tautomer, stereoisomer, isotopically labeled derivative, or prodrug thereof, or composition disclosed herein. In some embodiments, the disease or disorder is associated with changes in NAMPT, NMN, NAD, cellular metabolism, and/or NAMPT signaling. In some embodiments, the disease or disorder is mediated by NAMPT, NMN, NAD, cellular metabolism, and/or NAMPT signaling.

In some embodiments, the disclosure provides methods and uses for treating or preventing a disease or disorder described herein in a subject in need thereof comprising administering to the subject a therapeutically effective amount of a compound of Formula (0) or (I), or a pharmaceutically acceptable salt, solvate, hydrate, polymorph, co-crystal, tautomer, stereoisomer, isotopically labeled derivative, or prodrug thereof. In some embodiments, the disclosure provides methods and uses for treating or preventing a disease or disorder described herein in a subject in need thereof comprising administering to the subject a therapeutically effective amount of composition comprising a compound of Formula (0) or (I), or a pharmaceutically acceptable salt, solvate, hydrate, polymorph, co-crystal, tautomer, stereoisomer, isotopically labeled derivative, or prodrug thereof. In some embodiments, the disclosure provides methods and uses for treating or preventing a disease or disorder described herein in a subject in need thereof comprising administering to the subject a therapeutically effective amount of compound as described in the Additional Compounds section, or a pharmaceutically acceptable salt, solvate, hydrate, polymorph, co-crystal, tautomer, stereoisomer, isotopically labeled derivative, or prodrug thereof. In some embodiments, the disclosure provides methods and uses for treating or preventing a disease or disorder described herein in a subject in need thereof comprising administering to the subject a therapeutically effective amount of composition comprising a compound as described in the Additional Compounds section, or a pharmaceutically acceptable salt, solvate, hydrate, polymorph, co-crystal, tautomer, stereoisomer, isotopically labeled derivative, or prodrug thereof. In some embodiments, the disclosure provides methods and uses for treating or preventing a disease or disorder described herein in a subject in need thereof comprising administering to the subject a therapeutically effective amount of a compound of Table E1 or Table E2, or a pharmaceutically acceptable salt, solvate, hydrate, polymorph, co-crystal, tautomer, stereoisomer, isotopically labeled derivative, or prodrug thereof. In some embodiments, the disclosure provides methods and uses for treating or preventing a disease or disorder described herein in a subject in need thereof comprising administering to the subject a therapeutically effective amount of composition comprising a compound of Table E1 or Table E2, or a pharmaceutically acceptable salt, solvate, hydrate, polymorph, co-crystal, tautomer, stereoisomer, isotopically labeled derivative, or prodrug thereof. In some embodiments, the disease or disorder is associated with changes in NAMPT, NMN, NAD, cellular metabolism, and/or NAMPT signaling. In some embodiments, the disease or disorder is mediated by NAMPT, NMN, NAD, cellular metabolism, and/or NAMPT signaling.

In some embodiments, the disease or disorder is associated with changes in by NAMPT, NMN, NAD, cellular metabolism, and/or NAMPT signaling, wherein the disease or disorder is cancer, heart failure, dilated cardiomyopathy, pain, inflammation, acute respiratory distress syndrome, ventilator-induced lung injury, graft-versus-host disease (GCDH), arthritis, rheumatoid arthritis, acute lung injury, pneumonia, pneumonitis, severe acute respiratory distress syndrome, colitis, inflammatory bowel disease (IBD), diabetes, obesity, axon degeneration, a tissue repair disorder, asthma, chronic obstructive pulmonary disease (COPD), osteoarthritis, osteoporosis, fibrotic diseases, dermatosis, psoriasis, atopic dermatitis, ultra-violet induced skin damage, an autoimmune disease, Alzheimer's disease, stroke, atherosclerosis, restenosis, glomerulonephritis, cachexia, inflammation associated with infection, vascular inflammation, an atherothrombotic disease, Acquired Immune Deficiency Syndrome (AIDS), adult respiratory distress syndrome, ataxia telangiectasia, atherogenic inflammatory disease, a cardiovascular disorder, a cerebrovascular disorder, acute coronary syndrome, polycystic ovary syndrome, preeclampsia, sepsis, septic shock, an intrauterine infection, Crohn's disease (CD), ulcerative colitis (UC), a neurodegenerative disorder, COVID-19, pulmonary inflammation, a coronavirus infection, and a tumor.

In some embodiments, the disease or disorder is mediated by NAMPT, NMN, NAD, cellular metabolism, and/or NAMPT signaling, wherein the disease or disorder is cancer, heart failure, dilated cardiomyopathy, pain, inflammation, acute respiratory distress syndrome, ventilator-induced lung injury, graft-versus-host disease (GCDH), arthritis, rheumatoid arthritis, acute lung injury, pneumonia, pneumonitis, severe acute respiratory distress syndrome, colitis, inflammatory bowel disease (IBD), diabetes, obesity, axon degeneration, a tissue repair disorder, asthma, chronic obstructive pulmonary disease (COPD), osteoarthritis, osteoporosis, fibrotic diseases, dermatosis, psoriasis, atopic dermatitis, ultra-violet induced skin damage, an autoimmune disease, Alzheimer's disease, stroke, atherosclerosis, restenosis, glomerulonephritis, cachexia, inflammation associated with infection, vascular inflammation, an atherothrombotic disease, Acquired Immune Deficiency Syndrome (AIDS), adult respiratory distress syndrome, ataxia telangiectasia, atherogenic inflammatory disease, a cardiovascular disorder, a cerebrovascular disorder, acute coronary syndrome, polycystic ovary syndrome, preeclampsia, sepsis, septic shock, an intrauterine infection, Crohn's disease (CD), ulcerative colitis (UC), a neurodegenerative disorder, COVID-19, pulmonary inflammation, a coronavirus infection, and a tumor.

In some embodiments, the disease or disorder is cancer, heart failure, dilated cardiomyopathy, pain, inflammation, acute respiratory distress syndrome, ventilator-induced lung injury, graft-versus-host disease (GCDH), arthritis, rheumatoid arthritis, acute lung injury, pneumonia, pneumonitis, severe acute respiratory distress syndrome, colitis, inflammatory bowel disease (IBD), diabetes, obesity, axon degeneration, a tissue repair disorder, asthma, chronic obstructive pulmonary disease (COPD), osteoarthritis, osteoporosis, fibrotic diseases, dermatosis, psoriasis, atopic dermatitis, ultra-violet induced skin damage, an autoimmune disease, Alzheimer's disease, stroke, atherosclerosis, restenosis, glomerulonephritis, cachexia, inflammation associated with infection, vascular inflammation, an atherothrombotic disease, Acquired Immune Deficiency Syndrome (AIDS), adult respiratory distress syndrome, ataxia telangiectasia, atherogenic inflammatory disease, a cardiovascular disorder, a cerebrovascular disorder, acute coronary syndrome, polycystic ovary syndrome, preeclampsia, sepsis, septic shock, an intrauterine infection, Crohn's disease (CD), ulcerative colitis (UC), a neurodegenerative disorder, COVID-19, pulmonary inflammation, a coronavirus infection, and a tumor.

In some embodiments, the disease or disorder is selected from heart failure, dilated cardiomyopathy, pain, graft-versus-host disease (GCDH), diabetes, obesity, axon degeneration, tissue repair disorders, asthma, osteoporosis, fibrotic diseases, dermatosis, psoriasis, atopic dermatitis, ultra-violet induced skin damage, Alzheimer's disease, stroke, atherosclerosis, restenosis, glomerulonephritis, cachexia, Acquired Immune Deficiency Syndrome (AIDS), adult respiratory distress syndrome, ataxia telangiectasia, cardiovascular disorder, cerebrovascular disorder, acute coronary syndrome, polycystic ovary syndrome, preeclampsia, sepsis, septic shock, intrauterine infection, neurodegenerative disorder, and a tumor.

In some embodiments, the disease or disorder is selected from diabetes, rheumatoid arthritis, inflammatory bowel disease, acute respiratory distress syndrome, and ventilator-induced lung injury.

In some embodiments, the disease or disorder is cancer. In some embodiments, the disease or disorder is heart failure. In some embodiments, the disease or disorder is dilated cardiomyopathy. In some embodiments, the disease or disorder is pain. In certain embodiments, the disease or disorder is acute respiratory distress syndrome. In some embodiments, the disease or disorder is ventilator-induced lung injury. In some embodiments, the disease or disorder is inflammation. In some embodiments, the disease or disorder is graft-versus-host disease (GCDH). In some embodiments, the disease or disorder is arthritis. In some embodiments, the disease or disorder is acute lung injury. In some embodiments, the disease or disorder is colitis. In some embodiments, the disease or disorder is inflammatory bowel disease (IBD). In some embodiments, the disease or disorder is diabetes. In some embodiments, the disease or disorder is obesity. In some embodiments, the disease or disorder is axon degeneration. In some embodiments, the disease or disorder is a tissue repair disorder. In some embodiments, the disease or disorder is asthma. In some embodiments, the disease or disorder is chronic obstructive pulmonary disease (COPD). In some embodiments, the disease or disorder is osteoarthritis. In some embodiments, the disease or disorder is osteoporosis. In some embodiments, the disease or disorder is fibrotic diseases. In some embodiments, the disease or disorder is dermatosis. In some embodiments, the disease or disorder is psoriasis. In some embodiments, the disease or disorder is atopic dermatitis. In some embodiments, the disease or disorder is ultra-violet induced skin damage. In some embodiments, the disease or disorder is an autoimmune disease. In some embodiments, the disease or disorder is Alzheimer's disease. In some embodiments, the disease or disorder is stroke. In some embodiments, the disease or disorder is atherosclerosis. In some embodiments, the disease or disorder is restenosis. In some embodiments, the disease or disorder is glomerulonephritis. In some embodiments, the disease or disorder is cachexia. In some embodiments, the disease or disorder is inflammation associated with infection. In some embodiments, the disease or disorder is vascular inflammation. In some embodiments, the disease or disorder is an atherothrombotic disease. In some embodiments, the disease or disorder is Acquired Immune Deficiency Syndrome (AIDS). In some embodiments, the disease or disorder is adult respiratory distress syndrome. In some embodiments, the disease or disorder is ataxia telangiectasia. In some embodiments, the disease or disorder is atherogenic inflammatory disease. In some embodiments, the disease or disorder is a cardiovascular disorder. In some embodiments, the disease or disorder is a cerebrovascular disorder. In some embodiments, the disease or disorder is acute coronary syndrome. In some embodiments, the disease or disorder is polycystic ovary syndrome. In some embodiments, the disease or disorder is preeclampsia. In some embodiments, the disease or disorder is sepsis. In some embodiments, the disease or disorder is septic shock. In some embodiments, the disease or disorder is an intrauterine infection. In some embodiments, the disease or disorder is Crohn's disease (CD). In some embodiments, the disease or disorder is ulcerative colitis (UC). In some embodiments, the disease or disorder is a neurodegenerative disorder. In some embodiments, the disease or disorder is a tumor. In some embodiments, the disease or disorder is COVID-19. In some embodiments, the disease or disorder is pulmonary inflammation. In some embodiments, the disease or disorder is a coronavirus infection. In certain embodiments, the disease or disorder is pneumonia. In some embodiments, the disease or disorder is pneumonitis. In some embodiments, the disease or disorder is severe acute respiratory distress syndrome.

In some embodiments, the autoimmune disease is systemic lupus erythematosus, multiple sclerosis, ankylosing spondylitis, tissue and organ rejection, glomerulonephritis, Goodpasture's syndrome, necrotizing vasculitis, lymphadenitis, peri-arteritis nodosa, rheumatoid arthritis, psoriatic arthritis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy. In some embodiments, the autoimmune disease is systemic lupus erythematosus, multiple sclerosis, ankylosing spondylitis, or tissue and organ rejection.

In some embodiments, the graft-versus host disease is acute graft-versus-host disease or chronic graft-versus-host disease.

In some embodiments, the arthritis is osteoarthritis, rheumatoid arthritis, psoriatic arthritis, juvenile arthritis, fibromyalgia, gout, lupus, ankylosing spondylitis, reactive arthritis, septic arthritis, thumb arthritis, knee arthritis, infectious arthritis, degenerative arthritis, Reiter's arthritis, crystalline arthritis or inflammatory arthritis. In some embodiments, the arthritis is osteoarthritis, rheumatoid arthritis, or psoriatic arthritis. In some embodiments, the arthritis is osteoarthritis or rheumatoid arthritis.

In some embodiments, the neurodegenerative disorder is Alzheimer's disease, Parkinson's disease, amyotrophic lateral sclerosis, tauopathies (including frontotemporal dementia), Huntington's disease, multiple sclerosis, Friedreich's ataxia, Lewy body disease, or spinal muscular atrophy.

In some embodiments, the intrauterine infection is chorioamnionitis.

In some embodiments, the diabetes is type 2 diabetes.

In some embodiments, the cerebrovascular disorder is stroke, carotid stenosis, vertebral stenosis and intracranial stenosis, aneurysms, or vascular malformations. In some embodiments, the cerebrovascular disorder is stroke.

In some embodiments, the cardiovascular disorder is acute coronary syndrome, heart failure, dilated cardiomyopathy, or cardiomyopathy.

In certain embodiments, the tumor is a solid tumor. In some embodiments, the tumor is a colorectal tumor, ovarian tumor, breast tumor, gastric tumor, prostate tumor, thyroid tumor, pancreatic tumor, melanoma, gliomas, sarcoma, endometrial tumor, carcinoma tumor, or hematological malignancy.

Some aspects of the invention relate to methods, uses, compositions, and kits for administration to a subject in need thereof. In some embodiments, the subject is a subject having, suspected of having, or at risk of developing a disease or disorder (e.g., proliferative disease, cancer). As used herein, "subject," "individual," and "patient" may be used interchangeably. In some embodiments, the subject is a mammalian subject, including but not limited to a dog, cat, horse, cow, pig, sheep, goat, chicken, rodent, or primate. In some embodiments, the subject is a human subject, such as a patient. The human subject may be a pediatric or adult subject.

As used herein "treating" includes amelioration, cure, prevent it from becoming worse, slow the rate of progression, to prevent the disorder from re-occurring (i.e., to prevent a relapse), or to prevent or slow the rate of metastasis. An effective amount of a compound or composition refers to an amount of the compound or composition that results in a therapeutic effect. For example, in methods or uses for treating cancer in a subject, an effective amount of a chemotherapeutic agent is any amount that provides an anti-cancer effect, such as reduces or prevents proliferation of a cancer cell or is cytotoxic towards a cancer cell.

The methods and uses disclosed herein involve administering any of the compounds of the disclosure or compositions described herein in an effective amount to a subject. In certain embodiments the subject has a proliferative disease. In other embodiments, the subject is in need of regenerative medicine. In certain aspects, these uses and methods inhibit tumor growth, regenerate or differentiate one or more cells, prevent metastasis, kill cancer cells, reduce embryonic properties or adult stem cell properties of one or more cells, reduce cell viability, and/or prevent cell proliferation.

The methods and uses disclosed herein involve administering any of the compounds of the disclosure or compositions described herein in an effective amount to a subject having a proliferative disease. In some embodiments, the proliferative disease is cancer. In some embodiments, the proliferative disease is a benign neoplasm.

The methods and uses disclosed herein involve administering any of the compounds of the disclosure or compositions described herein in an effective amount to a subject in need of regenerative medicine or regenerative therapy. In some embodiments, the subject is in need of restoring or improving one or more biological function of a cell, tissue, and/or organ that is dysfunctional or impaired. In some embodiments, the subject is in need of tissue engineering and organ regeneration. In some embodiments, the compounds or compositions described herein regenerate or differentiate cells, tissues, and/or organs that may be damaged.

Methods and uses disclosed herein involve administering any of the compounds of the disclosure or compositions described herein in an effective amount to a subject having cancer or at risk of having cancer. In some embodiments, the cancer is characterized by the presence of cancer stem cells. In some embodiments, the cancer comprises, involves, or is associated with stem cells. In some embodiments, the subject has undergone or is currently undergoing a cancer therapy (e.g. chemotherapeutic, immunotherapeutic, surgery, radiation). Whether a subject is deemed "at risk" of having a disease or disorder, such as cancer, may be determined by a skilled practitioner.

In some embodiments, the disclosure provides methods and uses for treating cancer in a subject in need thereof comprising administering to the subject a therapeutically effective amount of a compound of Formula (0) or (I), or a pharmaceutically acceptable salt, solvate, hydrate, polymorph, co-crystal, tautomer, stereoisomer, isotopically labeled derivative, or prodrug thereof. In some embodiments, the disclosure provides methods and uses for treating cancer in a subject in need thereof comprising administering to the subject a therapeutically effective amount of composition comprising a compound of Formula (0) or (I), or a pharmaceutically acceptable salt, solvate, hydrate, polymorph, co-crystal, tautomer, stereoisomer, isotopically labeled derivative, or prodrug thereof. In some embodiments, the disclosure provides methods and uses for treating cancer in a subject in need thereof comprising administering to the subject a therapeutically effective amount of compound as described in the Additional Compounds section, or a pharmaceutically acceptable salt, solvate, hydrate, polymorph, co-crystal, tautomer, stereoisomer, isotopically labeled derivative, or prodrug thereof. In some embodiments, the disclosure provides methods and uses for treating cancer in a subject in need thereof comprising administering to the subject a therapeutically effective amount of composition comprising a compound as described in the Additional Compounds section, or a pharmaceutically acceptable salt, solvate, hydrate, polymorph, co-crystal, tautomer, stereoisomer, isotopically labeled derivative, or prodrug thereof. In some embodiments, the disclosure provides methods and uses for treating cancer in a subject in need thereof comprising administering to the subject a therapeutically effective amount of a compound of Table E1 or Table E2, or a pharmaceutically acceptable salt, solvate, hydrate, polymorph, co-crystal, tautomer, stereoisomer, isotopically labeled derivative, or prodrug thereof. In some embodiments, the disclosure provides methods and uses for treating cancer in a subject in need thereof comprising administering to the subject a therapeutically effective amount of composition comprising a compound of Table E1 or Table E2, or a pharmaceutically acceptable salt, solvate, hydrate, polymorph, co-crystal, tautomer, stereoisomer, isotopically labeled derivative, or prodrug thereof.

In certain embodiments, the cancer is colorectal cancer. Colorectal cancer is a cancer that starts in the colon or the rectum. These cancers may also be referred to as colon cancer or rectal cancer, depending on where the cancer begins. Colon cancer and rectal cancer are often grouped together due to several shared features. Most colorectal cancers start as a growth on the inner lining of the colon or rectum. The colorectal cancer (CRC) Subtyping Consortium has unified six independent molecular classification systems, based on gene expression data, into a single consensus system with four distinct groups, known as the Consensus Molecular Subtypes (CMS). The CMS were determined and correlated with epigenomic, transcriptomic, microenvironmental, genetic, prognostic and clinical characteristics. The CMS1 subtype is immunogenic and hypermutated. CMS2 tumors are activated by the WNT-β-catenin pathway and generally are associated with higher overall survival rates. CMS3 feature a metabolic cancer phenotype. CMS4 cancers are associated with the lowest survival rates and have a strong stromal gene signature. Molecular subtypes CMS2 and CMS4 exhibit the highest levels of embryonic signaling.[11]

In certain embodiments, the cancer is gastric cancer. Gastric cancer is a cancer that begins in the stomach. Stomach cancers tend to develop slowly over many years. Before a true cancer develops, pre-cancerous changes often occur in the inner lining (mucosa) of the stomach. These early changes rarely cause symptoms and therefore often go undetected. The types of stomach cancer include adenocarcinoma, lymphoma, gastrointestinal stromal tumor (GIST), carcinoid tumor, squamous cell carcinoma, small cell carcinoma, and leiomyosarcoma. The Cancer Genome Atlas (TCGA) project recently uncovered four molecular subtypes of gastric cancer: Epstein-Barr virus (EBV), microsatellite instability (MSI), genomically stable (GS), and chromosomal instability (CIN). The GS (genomically stable) and CIN (chromosomal instability) molecular subtypes exhibit the highest levels embryonic signaling, as measured by comprehensive analysis of gene expression patterns across gastric cancer subtypes.[12,13]

In some embodiments, the cancer is ovarian cancer. In certain embodiments, the cancer is lung cancer. In some embodiments, the cancer is breast cancer. In some embodiments, the cancer is pancreatic cancer. In certain embodiments, the cancer is prostate cancer. In some embodiments, the cancer is testicular cancer. In certain embodiments, the cancer is liver cancer. In some embodiments, the cancer is endometrial cancer.

In some embodiments, the cancer is lymphoma. In certain embodiments, the cancer is non-Hodgkin's lymphoma. In some embodiments, the cancer is Hodgkin's lymphoma. In some embodiments, the cancer is B-cell lymphoma (e.g., large B-cell lymphoma). In certain embodiments, the cancer is Burkitt's lymphoma (e.g., Burkitt's B-cell lymphoma). In some embodiments, the cancer is large cell immunoblastic lymphoma.

In certain embodiments, the cancer is leukemia. In certain embodiments, the cancer is acute lymphocytic leukemia (ALL), acute myelogenous leukemia (AML) (also known as acute myeloid leukemia, acute myeloblastic leukemia, acute granulocytic leukemia, acute myelocytic leukemia, and acute nonlymphocytic leukemia), chronic lymphocytic leukemia (CLL), or chronic myelogenous leukemia (CML) (also known as chronic myeloid leukemia). In certain embodiments, the cancer is AML. In some embodiments, the cancer is a subtype of AML selected from undifferentiated acute myeloblastic leukemia (M0), acute myeloblastic leukemia with minimal maturation (M1), acute myeloblastic leukemia with maturation (M2), acute promyelocytic leukemia (APL) (M3), acute myelomonocytic leukemia (M4), acute myelomonocytic leukemia with eosinophilia (M4 eos), acute monocytic leukemia (M5), acute erythroid leukemia (M6), and acute megakaryoblastic leukemia (M7). In some embodiments, the cancer is acute monocytic leukemia or acute lymphocytic leukemia (e.g., B-cell acute lymphocytic leukemia). In some embodiments, the cancer is acute lymphoblastic leukemia (e.g., B-cell acute lymphoblastic leukemia or T-cell acute lymphoblastic leukemia).

In some embodiments, the cancer is myeloma. In certain embodiments, plasmacytoma. In certain embodiments, the cancer is localized myeloma. In some embodiments, the cancer is extramedullary myeloma. In some embodiments, the cancer is multiple myeloma. In certain embodiments, the cancer is B-cell myeloma.

In some embodiments, the cancer is small cell lung cancer. In some embodiments, the cancer is small cell carcinoma (oat cell cancer). In some embodiments, the cancer is combined small cell carcinoma.

In some embodiments, the cancer is breast cancer. In some embodiments, the cancer is ductal carcinoma in situ (DCIS). In some embodiments, the cancer is invasive ductal carcinoma (IDC). In some embodiments, the cancer is tubular carcinoma of the breast. In some embodiments, the cancer is medullary carcinoma of the breast. In some embodiments, the cancer is mucinous Carcinoma of the breast. In some embodiments, the cancer is papillary carcinoma of the breast. In some embodiments, the cancer is cribriform carcinoma of the breast. In some embodiments, the cancer is invasive lobular carcinoma (ILC). In some embodiments, the cancer is inflammatory breast cancer. In some embodiments, the cancer is lobular carcinoma in situ (LCIS). In some embodiments, the cancer is male breast cancer. In some embodiments, the cancer is molecular subtypes of breast cancer. In some embodiments, the cancer is Paget's disease of the nipple. In some embodiments, the cancer is phyllodes tumors of the breast. In some embodiments, the cancer is metastatic breast cancer.

In certain embodiments, the cancer is colorectal cancer, gastric cancer, gastrointestinal stromal tumor, ovarian cancer, lung cancer, breast cancer, pancreatic cancer, testicular cancer, prostate cancer, liver cancer, or endometrial cancer. In certain embodiments, the cancer is leukemia (e.g., acute myeloid leukemia). In certain embodiments, the cancer is lymphoma. In certain embodiments, the cancer is multiple myeloma. In certain embodiments, the subject is in need of regenerative medicine or therapy. In some embodiments, the cancer is selected from breast, prostate, lung, colon, cervix, ovary, skin, CNS, bladder, pancreas, leukemia, lymphoma, and Hodgkin's disease.

In certain embodiments, the subject has been administered an additional therapy. In certain embodiments, the subject is further administered (co-administration) an additional therapy (e.g., before, concurrently with, and/or after the administration of a compound or composition described herein). The additional therapy is different from a compound or composition described herein. In certain embodiments, the additional therapy alone is ineffective, or less effective as compared with co-administration with (e.g., before, concurrently with, and/or after) a compound or composition described herein, in a method or use described herein.

In some embodiments, the additional therapy is radiation. In some embodiments, the radiation is fractionate radiation. In some embodiments, the additional therapy is surgery. In some embodiments, the additional therapy is an organ transplant. In some embodiments, the additional therapy is a kidney transplant. In some embodiments, the additional therapy is a bone marrow transplant. In certain embodiments, the additional therapy is a lung transplant. In some embodiments, the additional therapy is T cell replacement therapy.

In certain embodiments, the disclosure provides methods of treating a disease or disorder in a subject in need thereof comprising administering to the subject a therapeutically effective amount of a compound disclosed herein, or a pharmaceutically acceptable salt, solvate, hydrate, polymorph, co-crystal, tautomer, stereoisomer, isotopically labeled derivative, or prodrug thereof, or composition disclosed herein, and an additional pharmaceutical agent. In some embodiments, the additional pharmaceutical agent is administered, before, concurrently with, or after the compound disclosed herein, or a pharmaceutically acceptable salt, solvate, hydrate, polymorph, co-crystal, tautomer, stereoisomer, isotopically labeled derivative, or prodrug thereof, or composition disclosed herein.

In certain embodiments, the subject has been administered an additional pharmaceutical agent. In certain embodiments, the subject is further administered (co-administration) an additional pharmaceutical agent (e.g., before, concurrently with, and/or after the administration of a compound or composition described herein). The additional pharmaceutical agent is different from a compound or composition described herein. In certain embodiments, the additional therapy alone is ineffective, or less effective as compared with co-administration with (e.g., before, concurrently with, and/or after) a compound or composition described herein, in a method or use described herein.

The exact amount of a compound of the disclosure required to achieve an effective amount will vary from subject to subject, depending, for example, on species, age, and general condition of a subject, severity of the side effects or disorder, identity of the particular compound of the disclosure, mode of administration, and the like.

An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of an agent described herein.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks or longer. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

Any of the compounds or compositions described herein may be administered in a therapeutically effective amount. In some embodiments, the methods and uses involve administering a compound or composition comprising any of the compounds described herein to achieve a desired amount (e.g., a therapeutically effective amount) of the compound at a particular site in the subject. In some embodiments, the methods and uses involve administering a compound or composition comprising any of the compounds described herein to achieve a desired amount (e.g., a therapeutically effective amount) of the compound at the site of a tumor in the subject.

Dosage may be adjusted appropriately to achieve a desired local level of the compound.

"Dose" and "dosage" are used interchangeably herein. In some embodiments, the amount of the compound administered to a subject is about 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound of the disclosure described herein. In certain embodiments, a dose described herein includes independently between 1 mg and 3 mg, inclusive, of a compound of the disclosure described herein. In certain embodiments, a dose described herein includes independently between 3 mg and 10 mg, inclusive, of a compound of the disclosure described herein. In certain embodiments, a dose described herein includes independently between 10 mg and 30 mg, inclusive, of a compound of the disclosure described herein. In certain embodiments, a dose described herein includes independently between 30 mg and 100 mg, inclusive, of a compound of the disclosure described herein.

In some embodiments, the subject is administered an initial dose of any one of the compounds or compositions described herein, followed by one or more additional doses of any of the compounds or compositions described herein. In some embodiments, the initial dose may contain a different amount of any of the compounds described herein as compared to the one or more additional doses. In some embodiments, the initial dose is a higher dose (e.g., contains more of any one of the compounds described herein) as compared to the one or more additional doses.

Dose ranges as described herein provide guidance for the administration of provided compounds or compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

Efficacy in treating cancer, for example, can be measured by determining the growth, replication, proliferation, metastasis, and/or gene expression profile of one or more cancer cells. An effective amount, therefore, is an amount that is deemed by the clinician to be toxicologically tolerable, yet efficacious.

Without being bound to a particular theory, the compounds disclosed herein are thought to induce the differentiation of embryonic cells and/or cells exhibiting characteristics of embryonic cells and/or induce the differentiation of adult stem cells and/or cells exhibiting characteristics of adult stem cells. In some embodiments, the methods and uses disclosed herein involve administering any of the compounds or compositions described herein in an effective amount to a subject in need of regenerative medicine or regenerative therapy. In some embodiments, the subject is in need of restoring or improving one or more biological function of a cell, tissue, and/or organ that is dysfunctional or impaired. In some embodiments, the subject is in need of tissue engineering and organ regeneration. In some embodiments, the compounds or compositions described herein regenerate or differentiate cells, tissues, and/or organs that may be damaged. In some embodiments, the subject has experienced brain injury (e.g., injury or damage to the brain tissue or cells) and/or injury to the central nervous system (e.g., injury or damage to the tissue or cells of the central nervous system) and is in need of repair of said tissue or cells. In some embodiments, the subject has experienced heart injury (e.g., injury or damage to the heart tissue or cells) and is in need of repair of said tissue or cells.

In some embodiments, the administration of any of the compounds or compositions described herein is by oral administration, intravenous administration (e.g., systemic intravenous injection), parental administration, subcutaneous administration, intramuscular administration, mucosal administration, transdermal administration, intradermal administration, intravaginal administration, intraperitoneal administration, topical administration, nasal administration, buccal administration, sublingual administration; by intratracheal regional administration via blood and/or lymph supply, and/or direct administration to an affected site.

Additional Methods and Uses

The present disclosure also provides methods for contacting a cell with an effective amount of a compound of the disclosure (e.g., a compound of Formula (0) or (I), a compound as described in the Additional Compounds section, a compound of Tables E1, E2, or E3, or a compound as otherwise provided herein). The present disclosure also provides uses for contacting a cell with an effective amount of a compound of the disclosure. In certain aspects, these uses and methods inhibit tumor growth, regenerate or differentiate one or more cells, prevent metastasis, kill cancer cells, reduce embryonic properties or adult stem cell properties of one or more cells, reduce cell viability, and/or prevent cell proliferation.

The present disclosure also provides methods of modulating NAMPT in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of inhibiting NAMPT in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of modulating production of nicotinamide adenine dinucleotide in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of inhibiting production of nicotinamide adenine dinucleotide in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of modulating production of nicotinamide mononucleotide in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of inhibiting production of nicotinamide mononucleotide in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of reducing inflammatory cell infiltration in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of reducing cell proliferation in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of modulating cellular metabolic activity or state in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of reducing cellular metabolic activity or state in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of modulating cellular metabolism a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of reducing cellular metabolism in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of modulating inflammatory activity in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of decreasing inflammatory activity in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of modulating NAMPT signaling in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of decreasing NAMPT signaling in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of modulating a NAMPT pathway in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

The present disclosure also provides methods of inhibiting a NAMPT pathway in a cell, tissue, or biological sample, the method comprising contacting the cell, tissue, or biological sample with a compound disclosed herein, or a pharmaceutically acceptable salt, solvate, hydrate, polymorph, co-crystal, tautomer, stereoisomer, isotopically labeled derivative, or prodrug thereof, or composition disclosed herein.

In some embodiments, any of the compounds described herein are contacted with a cell in vivo, e.g. in an organism. In some embodiments, any of the compounds described herein are contacted with a cell in vitro, e.g., in cell culture. In some embodiments, any of the compounds described herein are contacted with a cell ex vivo, meaning the cell is removed from an organism prior to the contacting. As will be evident to one of skill in the art, the term cell may be used to refer to a single cell as well as a population of cells. In some embodiments, the populations cells are contacted with any of the compounds described herein to regenerate or differentiate one or more cells in the population of cells. In some embodiments, the populations cells are contacted with any of the compounds described herein for use in personalized medicine, for example for diagnostic and/or therapeutic purposes.

In general, any cells known in the art may be used in the methods and uses described herein. In some embodiments, the cell is of a cell line. In some embodiments, the cell is obtained from an organism, such as a subject. In some embodiments, the cell is a cancer cell (e.g., a cancer stem cell). In some embodiments, the cell is a stem cell. In some embodiments, the cell is an adult stem cell. In some embodiments, the cell is an embryonic stem cell. In some embodiments, the cell is an induced pluripotent stem cell. In some embodiments, the cell is a neural cell, such as a neural stem cell. In some embodiments, the cell is an adult stem cell, such as a stomach stem cell or intestinal stem cell.

In some embodiments, the methods and uses further comprise inhibiting the growth of cells. In certain embodiments, the methods and uses comprise contacting a cell with a compound or composition described herein to kill a cell, reduce cell viability, and/or prevent cell proliferation. In some embodiments, the methods and uses comprise contacting a cell with a compound or composition described herein to prevent metastasis or inhibit tumor growth. In certain embodiments, the methods and uses comprise contacting a cell with a compound or composition described herein to regenerate or differentiate one or more cells. In certain embodiments, the methods and uses comprise contacting a cell with a compound or composition described herein to reduce embryonic properties or adult stem cell properties of one or more cells. In other embodiments, the methods and uses comprise killing cells. In some embodiments, the methods and uses comprise reducing cell viability. In some embodiments, the methods and uses comprise preventing cell proliferation. In some embodiments, the cells are stem cells. In some embodiments, the cells are selected from the group consisting of a cancer stem cell, an embryonic stem cell, an induced pluripotent stem cell, a neural stem cell, a differentiated cancer cell, or an adult stem cell. In certain embodiments, the cells are cancer stem cells. In certain embodiments, the cells are embryonic stem cells. In certain embodiments, the cells are adult stem cells. In certain embodiments, the disclosure provides methods and uses of inhibiting the growth of cells and/or killing cells with an effective amount of a compound of the disclosure. In certain aspects, inhibiting the growth of cells and/or killing cells is useful in the treatment of proliferative diseases, including cancer.

In some embodiments, the methods and uses further comprise measuring or assessing the level of one or more embryonic properties of the cell. In some embodiments, the level of one or more embryonic properties of the cell is assessed following contacting the cell with any of the compounds or compositions described herein. In some embodiments, the level of one or more embryonic properties following contacting the cell with any of the compounds or compositions described herein is compared to the level of one or more embryonic properties in a reference sample or prior to contacting the cell with the compound or composition. In some embodiments, the contacting the cell with any of the compounds or compositions described herein reduces one or more embryonic properties of the cell. In some aspects, the methods and uses described herein may be used to determine whether a cell is susceptible to treatment with the compounds or compositions described herein. In some embodiments, if the level of one or more embryonic properties is reduced following contacting the cell with any of the compounds or compositions described herein, the cell is determined to be susceptible to treatment with the compound or composition. In some embodiments, if the level of one or more embryonic properties is reduced following contacting the cell with any of the compounds or compositions described herein, the compound or composition is determined to be a candidate for a disease or disorder associated with the cell.

In some embodiments, the methods and uses further comprise measuring or assessing the level of one or more adult stem cell properties of the cell. In some embodiments, the level of one or more adult stem cell properties of the cell is assessed following contacting the cell with any of the compounds or compositions described herein. In some embodiments, the level of one or more adult stem cell properties following contacting the cell with any of the compounds or compositions described herein is compared to the level of one or more adult stem cell properties in a reference sample or prior to contacting the cell with the compounds or composition. In some embodiments, the contacting the cell with any of the compounds or compositions described herein reduces one or more adult stem cell properties of the cell. In some aspects, the methods and uses described herein may be used to determine whether a cell is susceptible to treatment with the compounds or compositions described herein. In some embodiments, if the level of one or more adult stem cell properties is reduced following contacting the cell with any of the compounds or compositions described herein, the cell is determined to be susceptible to treatment with the compound or composition. In some embodiments, if the level of one or more adult stem cell properties is reduced following contacting the cell with any of the compounds or compositions described herein, the compound or composition is determined to be a candidate for a disease or disorder associated with the cell.

In some embodiments, the methods and uses described herein may be used for regenerative medicine. In some embodiments, a cell is contacted with any of the compounds or compositions described herein to promote differentiation and/or loss of one or more embryonic properties of the cell. In some embodiments, a cell is contacted with any of the compounds or compositions described herein to promote differentiation and/or loss of one or more adult stem cell properties of the cell. In some embodiments, a cell is contacted with any of the compounds or compositions described herein to promote regenerative capacity of the cell. In some embodiments, contacting the cell with any of the compounds or compositions described herein enhances the regenerative capacity of the cell. In some embodiments, contacting the cell with any of the compounds or compositions described herein regenerates a population of cells, such as a tissue or an organ. In some embodiments, the regenerated population of cells, such as a tissue or an organ may be administered or implanted into a subject. In some embodiments, the subject is the same subject from which a cell was obtained. In some embodiments, the subject is a different subject from which a cell was obtained (e.g., autotransplantation). In some embodiments, the subject is a different subject from which a cell was obtained but belongs to the same species (e.g., allotransplantation). In some embodiments, the subject is a different subject from which a cell was obtained and belongs to a different species (e.g., xenotransplantation).

EXAMPLES

In order that the present disclosure may be more fully understood, the following examples are set forth. The synthetic and biological examples described in this Application are offered to illustrate the compounds, pharmaceutical compositions, methods, and uses provided herein and are not to be construed in any way as limiting their scope.

The following abbreviations are used: acetonitrile (ACN); dichloromethane (DCM); ethyl acetate (EtOAc); hours (h); reaction mixture (RM); retention time ($R_t$); room temperature (RT).

Example 1. Synthesis and Characterization

The following compounds were prepared according to 4 different schemes shown below (Schemes 1, 2, 3, 4, 5, 6, 7, 8, 9, 10, and 11). Compounds I-402, I-403, I-404, I-406, I-410, I-411, I-412, I-417, I-421, I-429, I-430, I-444, I-446, I-447, I-448, I-449, I-453, I-454, I-458, I-459, I-460, I-503, I-510, I-517, I-610, I-619, I-620, and 1-652 were synthesized according to Scheme 1. Compounds I-319 and I-484 were synthesized according to Scheme 2. Compounds I-330 and I-389 were synthesized according to Scheme 3. Compounds I-353, I-354, I-355, I-390, I-392, I-393, I-394, I-395, 1-396, 1-397, I-425, I-428, I-436, I-445, I-455, I-456, I-457, 1-331, I-481, I-496, I-511, I-605, and I-658 were synthesized according to Scheme 4.

The different LC-MS and prep HPLC methods used are described below.

Method 1 (LC-MS): 2 min_low_3_97_BEH: LC/MS System: Acquity UPLC coupled with SQD mass spectrometer; Column: Acquity UPLC BEH C18 (50 mm×2.1 mm i.d., 1.7 m packing diameter); mobile phase A: 0.1% formic acid in water, mobile phase B: 0.1% formic acid in acetonitrile; gradient: 0.0 min 97% A, 3% B, flow rate 0.9 ml/min; 1.5 min 3% A, 97% B, flow rate 0.9 ml/min; 1.9 min 3% A, 97% B, flow rate 0.9 ml/min; 2.0 min 97% A, 3% B, flow rate 0.05 ml/min; column temperature: 40° C.; UV detection: from 210 nm to 350 nm; MS conditions: Ionisation Mode: alternate-scan Positive and Negative Electrospray (ES+/ES−); Scan Range: 100 to 1000 AMU.

Method 2 (LC-MS): 2 min_high_3_97_BEH: LC/MS System: Acquity UPLC coupled with SQD mass spectrometer; Column: Acquity UPLC BEH C18 (50 mm×2.1 mm i.d., 1.7 m packing diameter); mobile phase A: 10 mM aqueous solution of ammonium bicarbonate (adjusted to pH 10 with ammonia), mobile phase B: acetonitrile; gradient: 0.0 min 97% A, 3% B, flow rate 0.9 ml/min; 1.5 min 3% A, 97% B, flow rate 0.9 ml/min; 1.9 min 3% A, 97% B, flow rate 0.9 ml/min; 2.0 min 97% A, 3% B, flow rate 0.05 ml/min; column temperature: 40° C.; UV detection: from 210 nm to 350 nm; MS conditions: Ionisation Mode: alternate-scan Positive and Negative Electrospray (ES+/ES−); Scan Range: 100 to 1500 AMU.

Method 3 (LC-MS): 4 min_low_3_97_BEH: LC/MS System: Acquity UPLC coupled with SQD mass spectrometer; Column: Acquity UPLC BEH C18 (50 mm×2.1 mm i.d., 1.7 m packing diameter); mobile phase A: 0.1% formic acid in water, mobile phase B: 0.1% formic acid in acetonitrile; gradient: 0.0 min 97% A, 3% B, flow rate 0.9 ml/min; 3.2 min 97% A, 3% B, flow rate 0.9 ml/min; 3.9 min 3% A, 97% B, flow rate 0.9 ml/min; 4.0 min 97% A, 3% B, flow rate 0.05 ml/min; column temperature: 40° C.; UV detection: from 210 nm to 350 nm; MS conditions: Ionisation Mode: alternate-scan Positive and Negative Electrospray (ES+/ES−); Scan Range: 100 to 1500 AMU.

Method 4 (LC-MS): 4 min_high_3_97_BEH: LC/MS System: Acquity UPLC coupled with SQD mass spectrometer; Column: Acquity UPLC BEH C18 (50 mm×2.1 mm i.d., 1.7 m packing diameter); mobile phase A: 10 mM aqueous solution of ammonium bicarbonate (adjusted to pH 10 with ammonia), mobile phase B: acetonitrile; gradient: 0.0 min 95% A, 5% B, flow rate 0.5 ml/min; 3.0 min 95% A, 5% B, flow rate 0.5 ml/min; 17.50 min 5% A, 95% B, flow rate 0.5 ml/min; 19.00 min 5% A, 95% B, flow rate 0.5 ml/min; 19.50 min 95% A, 5% B, flow rate 0.5 ml/min; 20.00 min 95% A, 5% B, flow rate 0.5 ml/min; column temperature: 40° C.; UV detection: from 210 nm to 350 nm; MS conditions: Ionisation Mode: alternate-scan Positive and Negative Electrospray (ES+/ES−); Scan Range: 100 to 1500 AMU.

Method 5 (LC-MS): 12 min_low_3_97_BEH: LC/MS System: Acquity UPLC coupled with SQD mass spectrometer; Column: Acquity UPLC BEH C18 (50 mm×2.1 mm i.d., 1.7 m packing diameter); mobile phase A: 0.1% formic acid in water, mobile phase B: 0.1% formic acid in acetonitrile; gradient: 0.0 min 97% A, 3% B, flow rate 0.9 ml/min; 1.5 min 97% A, 3% B, flow rate 0.9 ml/min; 11.5 min 3% A, 97% B, flow rate 0.9 ml/min; 12.0 min 97% A, 3% B, flow rate 0.05 ml/min; column temperature: 40° C.; UV detection: from 210 nm to 350 nm; MS conditions: Ionisation Mode: alternate-scan Positive and Negative Electrospray (ES+/ES−); Scan Range: 100 to 1500 AMU.

Method 6 (LC-MS): 12 min_high_3_97_BEH: LC/MS System: Acquity UPLC coupled with SQD mass spectrometer; Column: Acquity UPLC BEH C18 (50 mm×2.1 mm i.d., 1.7 m packing diameter); mobile phase A: 10 mM aqueous solution of ammonium bicarbonate (adjusted to pH 10 with ammonia), mobile phase B: acetonitrile; gradient: 0.0 min 97% A, 3% B, flow rate 0.9 ml/min; 1.5 min 97% A, 3% B, flow rate 0.9 ml/min; 11.5 min 3% A, 97% B, flow rate 0.9 ml/min; 12.0 min 97% A, 3% B, flow rate 0.05 ml/min; column temperature: 40° C.; UV detection: from 210 nm to 350 nm; MS conditions: Ionisation Mode: alternate-scan Positive and Negative Electrospray (ES+/ES−); Scan Range: 100 to 1500 AMU.

Method 7 (LC-MS): (8_min_low_pH_3_97_BEH): LC/MS System: Acquity UPLC coupled with SQD mass spectrometer; Column: Acquity UPLC BEH C18 (100 mm×2.1 mm i.d., 1.7 m packing diameter); mobile phase A: Water+0.1% of Formic Acid, mobile phase B: Acetonitrile+0.1% of Formic Acid; gradient: 0.0 min 97% A, 3% B, flow rate 0.6 ml/min; 0.5 min 97% A, 3% B, flow rate 0.6 ml/min; 7.0 min 3% A, 97% B, flow rate 0.6 ml/min; 7.5 min 3% A, 97% B, flow rate 0.6 ml/min; 7.6 min 97% A, 3% B, flow rate 0.6 ml/min; 8.0 min 97% A, 3% B, flow rate 0.6 ml/min; column temperature: 40° C.; UV detection: from 210 nm to 400 nm; MS conditions: Ionisation Mode: Electrospray Positive and Negative (ES+/ES−); Scan Range: 100 to 1500 AMU.

Method 8 (LC-MS): (8_min_high_pH_3_97_BEH): LC/MS System: Acquity UPLC coupled with SQD mass spectrometer; Column: Acquity UPLC BEH C18 (100 mm×2.1 mm i.d., 1.7 m packing diameter); mobile phase A: Water+0.05% of Ammonia, mobile phase B: Acetonitrile+0.05% of Ammonia; gradient: 0.0 min 97% A, 3% B, flow rate 0.6 ml/min; 0.5 min 97% A, 3% B, flow rate 0.6 ml/min; 7.0 min 3% A, 97% B, flow rate 0.6 ml/min; 7.5 min 3% A, 97% B, flow rate 0.6 ml/min; 7.6 min 97% A, 3% B, flow rate 0.6 ml/min; 8.0 min 97% A, 3% B, flow rate 0.6 ml/min; column temperature: 40° C.; UV detection: from 210 nm to 400 nm; MS conditions: Ionisation Mode: Electrospray Positive and Negative (ES+/ES−); Scan Range: 100 to 1500 AMU.

LC-MS Method (preparative): Method 9 (prep-HPLC): C_high: LC/MS System: Waters Mass Directed Auto Purification System with QDa mass spectrometer; Column: XBridge C18 OBD (30×150 mm, 5 m) with XBridge C18 OBD Guard Cartridge (30×10 mm, 5 μm); mobile phase A: 10 mM aqueous solution of ammonium bicarbonate (adjusted to pH 10 with ammonia), mobile phase B: acetonitrile; gradient: 0.0 min 97% A, 3% B, flow rate 50 ml/min; 1.0 min 70% A, 30% B, flow rate 50 ml/min; 10.0 min 20% A, 80% B, flow rate 50 ml/min; 10.5 min 0% A, 100% B, flow rate 50 ml/min; 15.0 min 0% A, 100% B, flow rate 50 ml/min; column temperature: 40° C.; UV detection: from 210 nm to 350 nm; MS conditions: Ionisation Mode: alternate-scan Positive and Negative Electrospray (ES+/ES−); Scan Range: 50 to 1200 AMU.

LC-MS Method (preparative): Method 10 (prep-HPLC): C_low: LC/MS System: Waters Mass Directed Auto Purification System with QDa mass spectrometer; Column: XBridge C18 OBD (30×150 mm, 5 m) with XBridge C18 OBD Guard Cartridge (30×10 mm, 5 m); mobile phase A: 0.1% formic acid in water, mobile phase B: 0.1% formic acid in acetonitrile; gradient: 0.0 min 97% A, 3% B, flow rate 50 ml/min; 1.0 min 70% A, 30% B, flow rate 50 ml/min; 10.0 min 20% A, 80% B, flow rate 50 ml/min; 10.5 min 0% A, 100% B, flow rate 50 ml/min; 15.0 min 0% A, 100% B, flow rate 50 ml/min; column temperature: 40° C.; UV detection: from 210 nm to 350 nm; MS conditions: Ionisation Mode: alternate-scan Positive and Negative Electrospray (ES+/ES−); Scan Range: 50 to 1200 AMU.

LC-MS Method 11 (preparative): LC/MS System: Agilent 1260 Infinity II (LC/MSD); Column: XBridge C18 (30×150 mm, 5 m); mobile phase A: 0.1% ammonium hydroxide in water, mobile phase B: Acetonitrile; gradient: 0.0 min 60% A, 40% B, flow rate 50 mL/min; 0.8 min 60% A, 40% B, flow rate 50 mL/min; 5.0 min 35% A, 65% B, flow rate 50 mL/min; 5.01 min 0% A, 100% B, flow rate 50 mL/min; 5.90 min 0% A, 100% B, flow rate 50 mL/min; 5.95 min 60% A, 40% B; column temperature: 25° C.; UV detection: from 200 nm to 350 nm; MS conditions: Ionisation Mode: alternate-scan Positive and Negative Electrospray (ES+/ES−); Scan Range: 100 to 1000 AMU.

LC-MS Method 12 (preparative): LC/MS System: Agilent 1260 Infinity II (LC/MSD); Column: SunFire C18 (30×150 mm, 5 m); mobile phase A: 0.1% formic acid in water, mobile phase B: Acetonitrile; gradient: 0.0 min 75% A, 25% B, flow rate 50 mL/min; 0.8 min 75% A, 25% B, flow rate 50 mL/min; 5.0 min 50% A, 50% B, flow rate 50 mL/min; 5.01 min 0% A, 100% B, flow rate 50 mL/min; 5.90 min 0% A, 100% B, flow rate 50 mL/min; 5.95 min 75% A, 25% B; column temperature: 25° C.; UV detection: from 200 nm to 350 nm; MS conditions: Ionisation Mode: alternate-scan Positive and Negative Electrospray (ES+/ES−); Scan Range: 100 to 1000 AMU.

LC-MS Method 13 (analytical, 12 min_low_3_97_BEH): LC/MS System: Agilent 1290 Infinity II LC/SFC coupled with Agilent Technologies 6540 UHD Q-TOF Mass Spectrometer; Column: Acquity UPLC BEH C18 (50 mm×2.1 mm i.d., 1.7 m packing diameter); mobile phase A: 0.1% formic acid in water, mobile phase B: 0.1% formic acid in Acetonitrile; gradient: 0.0 min 97% A, 3% B, flow rate 0.5 mL/min; 9.5 min 3% A, 97% B, flow rate 0.5 mL/min; 10 min 0% A, 100% B, flow rate 0.5 mL/min; 11.95 min 0% A, 100% B, flow rate 0.5 mL/min; 12.0 min 97% A, 3% B; column temperature: 40° C.; UV detection: from 190 nm to 400 nm; MS conditions: Ionisation Mode: alternate-scan Positive and Negative Electrospray (ES+/ES−); Ion Source: ESI; Spray Voltage: 3500 V; Scan Range: 100 to 1700 AMU.

Synthesis according to Scheme 1.

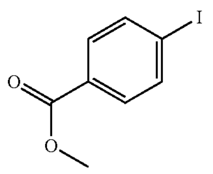

+

-continued

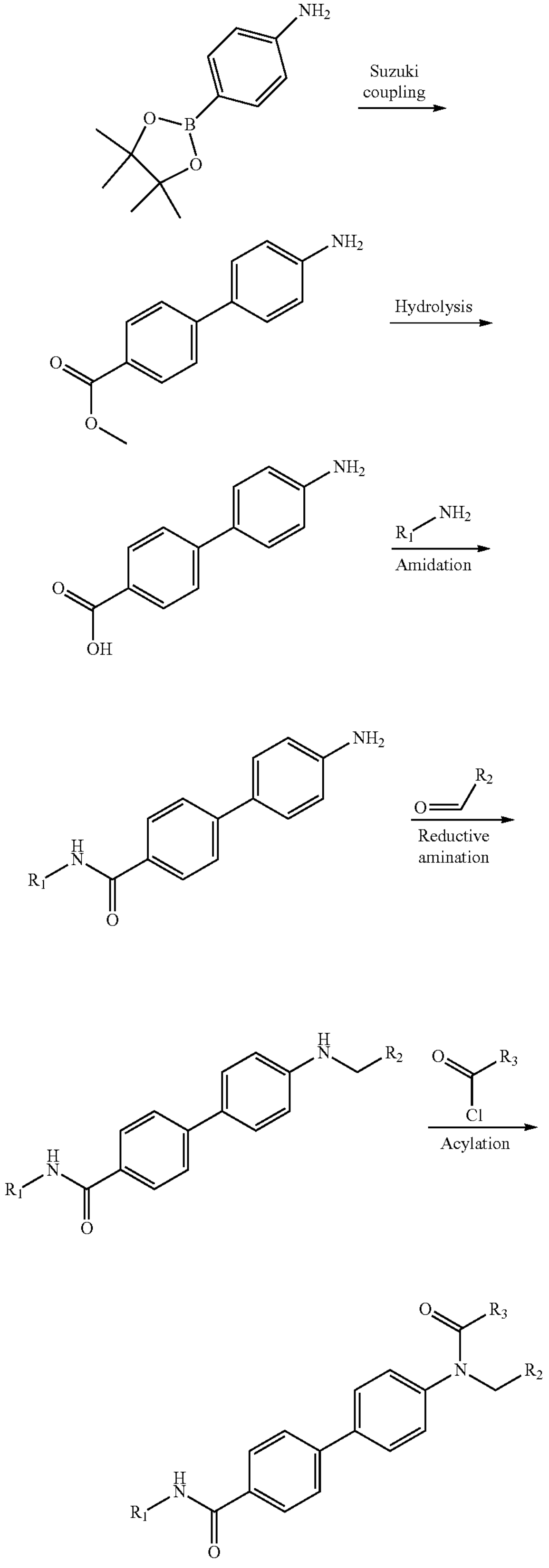

Step 1: Suzuki Coupling

Preparation of methyl 6-(4-aminophenyl)pyridine-3-carboxylate

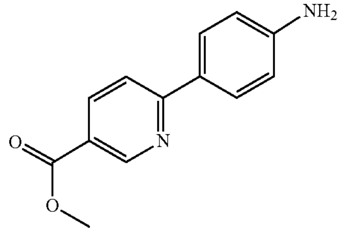 [SMILES: COC(=O)c1ccc(-c2ccc(N)cc2)nc1]

To a solution of 4-(4,4,5,5-tetramethyl-1,3,2-dioxaborolan-2-yl)aniline (10 g, 45.6 mmol) and methyl 6-bromopyridine-3-carboxylate (11.8 g, 54.8 mmol) in a mixture of 1,4 dioxane (500 mL) and water (50 mL), was added $K_3PO_4$ (29.1 g, 137 mmol). The reaction mixture was degassed with Argon for 5 min when Pd(dppf)$Cl_2$xDCM (1.86 g, 2.28 mmol) was added. The reaction mixture was heated to 70° C. and stirred overnight. After cooling to RT, water was added (15 ml). The aqueous layer was separated and the organic layer was concentrated in vacuo. The remaining residue was dissolved in EtOAC, and washed with a saturated solution of $NaHCO_3$, then brine. The organic layer was concentrated in vacuo and the remaining residue was triturated with acetonitrile to afford methyl 6-(4-aminophenyl) pyridine-3-carboxylate as a brown solid (6.5 g, 63%).

LC-MS (Method 2): $R_t$=0.95 min; m/z=227.44 $(M+H)^+$

Step 2: Hydrolysis

Preparation of 6-(4-aminophenyl)pyridine-3-carboxylic acid

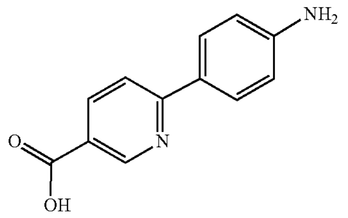 [SMILES: Nc1ccc(-c2ccc(C(=O)O)cn2)cc1]

To a solution of methyl 6-(4-aminophenyl)pyridine-3-carboxylate (1.5 g, 5.8 mmol) in a mixture of THF (50 mL) and water (10 mL), was added LiOH— $H_2O$ (1.3 g, 30 mmol). The reaction mixture was stirred at 40° C. overnight. THF was removed in vacuo. The aqueous layer was additionally diluted with water (500 ml) and acidified with 1N HCl to pH=2. The resulting precipitate was collected by filtration, washed with MeOH and dried in vacuo to afford 6-(4-aminophenyl)pyridine-3-carboxylic acid as a white solid (1.1 g, 86%).

LC-MS (Method 1): $R_t$=0.43 min; m/z=215.11 $(M+H)^+$

Step 3: Amidation

Preparation of 6-(4-aminophenyl)-N-(3-pyridylmethyl)pyridine-3-carboxamide

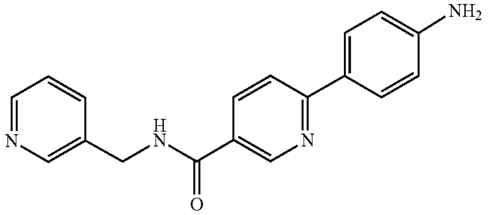 [SMILES: Nc1ccc(-c2ccc(C(=O)NCc3cccnc3)cn2)cc1]

To a solution of 6-(4-aminophenyl)pyridine-3-carboxylic acid (1.1 g, 4.9 mmol) in dry DMF (30 mL) was added DIPEA (1.7 mL, 9.7 mmol), HATU (2.2 g, 5.9 mmol) and 3-pyridylmethanamine (0.48 mL, 4.9 mmol). The reaction mixture was stirred at RT overnight.

Upon complete conversion, the reaction mixture was diluted with EtOAc and washed with sat. $NaHCO_3$, then 5% aq LiCl. The organic layer was separated, dried over $MgSO_4$ and evaporated to dryness to give an oily crude product that was additionally precipitated from DCM to afford 6-(4-aminophenyl)-N-(3-pyridylmethyl)pyridine-3-carboxamide (1.3 g, 69%).

LC-MS (Method 2): $R_t$=0.65 min; m/z=207.18 $(M+H)^+$

Step 4: Reductive Amination

Preparation of 6-[4-(isobutylamino)phenyl]-N-(3-pyridylmethyl)pyridine-3-carboxamide

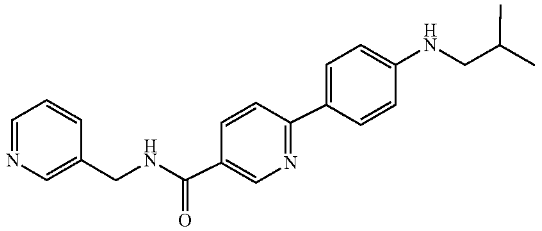 [SMILES: CC(C)CNc1ccc(-c2ccc(C(=O)NCc3cccnc3)cn2)cc1]

A solution of 6-(4-aminophenyl)-N-(3-pyridylmethyl) pyridine-3-carboxamide (200 g, 0.585 mmol), Isobutyraldehyde (58.7 μL, 0.643 mmol), tetramethylammonium triacetoxyborohydride (308 mg, 1.17 mmol) and acetic acid (a catalytic amount) in 1,2-dichloroethane (20 mL) was heated at reflux overnight. The resulted solution was cooled to RT and washed with a saturated solution of aqueous sodium bicarbonate, dried and concentrated in vacuo to afford crude 6-[4-(isobutylamino)phenyl]-N-(3-pyridylmethyl)pyridine-3-carboxamide (83 mg). It was used as such in the next step.

LC-MS (Method 2): $R_t$=1.03 min; m/z=361.32 $(M+H)^+$

Step 5: Acylation

Preparation of 6-[4-[isobutyl(propanoyl)amino]phenyl]-N-(3-pyridylmethyl)pyridine-3-carboxamide (I-403)

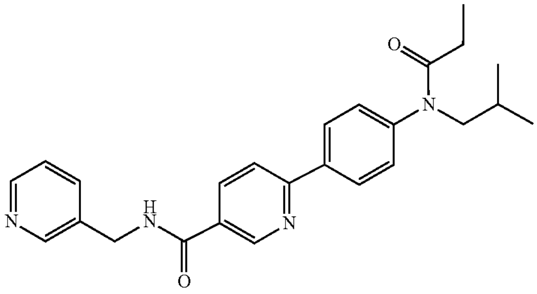 [SMILES: CCC(=O)N(CC(C)C)c1ccc(-c2ccc(C(=O)NCc3cccnc3)cn2)cc1]

To a solution of 6-[4-(isobutylamino)phenyl]-N-(3-pyridylmethyl)pyridine-3-carboxamide (40.0 mg, 0.04 mmol) in dry DCM (5 mL) at 0° C. (ice bath), was added triethylamine (24.8 μL, 0.16 mmol) followed by propionyl chloride (7.74 μL, 0.08 mmol). The resulting mixture was stirred at 0° C. for 5 min and then at RT overnight until complete conversion. The solvent was removed in vacuo. Purification of the resulting crude by prep HPLC (Method 9) afforded 6-[4-[isobutyl(propanoyl)amino]phenyl]-N-(3-pyridylmethyl)pyridine-3-carboxamide as a yellow paste (4.91 mg, 27%).

LC-MS (Method 8): $R_t$=3.85 min; m/z=417.27 $(M+H)^+$ $^1H$ NMR (500 MHz, DMSO-$d_6$): δ [ppm]=0.85 (d, J=6.71 Hz, 6H) 0.93 (t, J=7.35 Hz, 3H) 1.60-1.70 (m, 1H) 2.08 (br. s., 2H) 3.55 (d, J=7.63 Hz, 2H) 4.55 (d, J=5.80 Hz, 2H) 7.38 (dd, J=4.88, 7.63 Hz, 1H) 7.45 (d, J=8.54 Hz, 2H) 7.74-7.79 (m, 1H) 8.13 (d, J=8.55 Hz, 1H) 8.21 (d, J=8.54 Hz, 2H) 8.30-8.35 (m, 1H) 8.48 (dd, J=1.53, 4.58 Hz, 1H) 8.59 (d, J=1.83 Hz, 1H) 9.13 (d, J=1.83 Hz, 1H) 9.33 (t, J=5.94 Hz, 1H).

Compounds I-402, I-404, I-406, I-410, I-411, I-412, I-417, I-421, I-429, I-430, I-444, I-446, I-447, I-448, I-449, I-453, I-454, I-458, I-459, and I-460 were synthesized following Scheme 1 and the corresponding Steps 1 to 5.

Preparation of 4-[4-[acetyl(isobutyl)amino]phenyl]-N-(3-pyridylmethyl)benzamide (I-402)

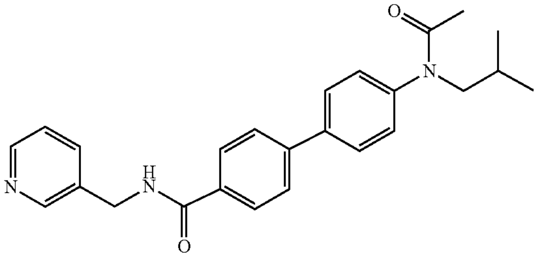

Purification by prep HPLC (Method 9) afforded 4-[4-[acetyl(isobutyl)amino]phenyl]-N-(3-pyridyl-methyl)benzamide as a yellow paste (15 mg, 23%).

LC-MS (Method 4): $R_t$=3.88 min; m/z=402.24 $(M+H)^+$ $^1H$ NMR (400 MHz, DMSO-$d_6$): δ [ppm] 0.84 (d, J=6.72 Hz, 6H) 1.63 (dt, J=13.63, 7.00 Hz, 1H) 1.80 (br. s., 3H) 3.53 (d, J=7.46 Hz, 2H) 4.51 (d, J=5.99 Hz, 2H) 7.35 (ddd, J=7.86, 4.80, 0.67 Hz, 1H) 7.42 (d, J=8.07 Hz, 2H) 7.73 (dt, J=7.89, 1.93 Hz, 1H) 7.77-7.85 (m, 4H) 7.94-8.03 (m, 2H) 8.45 (dd, J=4.77, 1.71 Hz, 1H) 8.56 (d, J=1.83 Hz, 1H) 9.17 (t, J=5.93 Hz, 1H).

Preparation of 6-[4-[isobutyl(propanoyl)amino]phenyl]-N-(3-pyridylmethyl)pyridine-3-carboxamide (I-404)

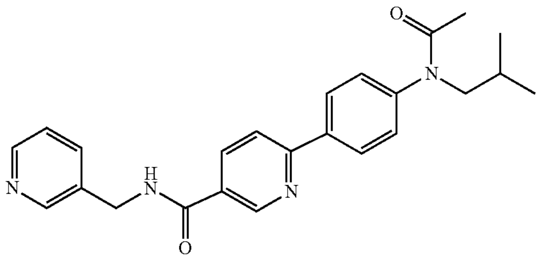 [SMILES: CC(=O)N(CC(C)C)c1ccc(-c2ccc(C(=O)NCc3cccnc3)cn2)cc1]

Purification by prep HPLC (Method 9) afforded 6-[4-[isobutyl(propanoyl)amino]phenyl]-N-(3-pyridylmethyl) pyridine-3-carboxamide as a yellow paste (2.61 mg, 17%)

LC-MS (Method 8): $R_t$=3.58 min; m/z=403.26 $(M+H)^+$ $^1$H NMR (500 MHz, DMSO-$d_6$): δ [ppm]=0.85 (d, J=6.71 Hz, 6H) 1.23 (s, 3H) 1.60-1.69 (m, 1H) 3.56 (d, J=7.32 Hz, 2H) 4.55 (d, J=5.80 Hz, 2H) 7.35-7.40 (m, 1H) 7.47 (d, J=8.24 Hz, 2H) 7.72-7.80 (m, 1H) 8.14 (d, J=8.24 Hz, 1H) 8.21 (d, J=8.55 Hz, 2H) 8.33 (dd, J=2.44, 8.24 Hz, 1H) 8.45-8.51 (m, 1H) 8.59 (d, J=1.83 Hz, 1H) 9.13 (d, J=1.83 Hz, 1H) 9.34 (t, J=8.89 Hz, 1H).

Preparation of 6-[4-[propanoyl(propyl)amino]phenyl]-N-(3-pyridylmethyl)pyridine-3-carboxamide (I-410)

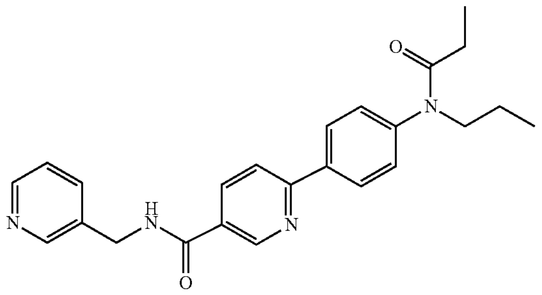 [SMILES: CCCN(C(=O)CC)c1ccc(-c2ccc(C(=O)NCc3cccnc3)cn2)cc1]

Purification by prep HPLC (Method 9) afforded 6-[4-[propanoyl(propyl)amino]phenyl]-N-(3-pyridylmethyl) pyridine-3-carboxamide as a yellow oil (2.2 mg, 7%).

LC-MS (Method 8): $R_t$=3.56 min; m/z=403.26 $(M+H)^+$ $^1$H NMR (500 MHz, DMSO-$d_6$): δ [ppm]=0.83 (t, J=7.48 Hz, 3H) 0.93 (t, J=7.32 Hz, 3H) 1.37-1.49 (m, 2H) 2.05 (br. s., 2H) 3.60-3.66 (m, 2H) 4.55 (d, J=5.80 Hz, 2H) 7.37 (dd, J=4.88, 7.63 Hz, 1H) 7.43 (d, J=8.24 Hz, 2H) 7.76 (d, J=7.93 Hz, 1H) 8.13 (d, J=8.24 Hz, 1H) 8.22 (d, J=8.24 Hz, 2H) 8.33 (dd, J=2.29, 8.39 Hz, 1H) 8.47 (dd, J=1.37, 4.73 Hz, 1H) 8.59 (d, J=1.83 Hz, 1H) 9.14 (d, J=1.83 Hz, 1H) 9.36 (t, J=5.95 Hz, 1H).

Preparation of 6-[4-[acetyl(butyl)amino]phenyl]-N-(3-pyridylmethyl)pyridine-3-carboxamide (I-411)

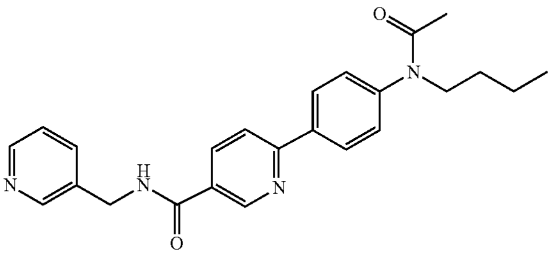 [SMILES: CCCCN(C(C)=O)c1ccc(-c2ccc(C(=O)NCc3cccnc3)cn2)cc1]

Purification by prep HPLC (Method 9) afforded 6-[4-[acetyl(butyl)amino]phenyl]-N-(3-pyridylmethyl)pyridine-3-carboxamide as a yellow oil (2.0 mg, 14%).

LC-MS (Method 8): $R_t$=3.59 min; m/z=403.26 $(M+H)^+$ $^1$H NMR (500 MHz, DMSO-$d_6$): δ [ppm]=0.84 (t, J=7.32 Hz, 3H) 1.20-1.31 (m, 2H) 1.34-1.45 (m, 2H) 1.80 (br. s., 3H) 3.67 (t, J=7.48 Hz, 2H) 4.55 (d, J=5.80 Hz, 2H) 7.37 (dd, J=4.88, 7.32 Hz, 1H) 7.44 (d, J=8.24 Hz, 2H) 7.72-7.81 (m, 1H) 8.14 (d, J=8.24 Hz, 1H) 8.22 (d, J=8.24 Hz, 2H) 8.33 (dd, J=2.29, 8.39 Hz, 1H) 8.47 (dd, J=1.53, 4.88 Hz, 1H) 8.59 (d, J=1.83 Hz, 1H) 9.14 (d, J=1.83 Hz, 1H) 9.36 (t, J=5.80 Hz, 1H).

Preparation of 6-[4-[acetyl-[(3,3-difluorocyclobutyl)methyl]amino]phenyl]-N-(3-pyridylmethyl)pyridine-3-carboxamide (I-412)

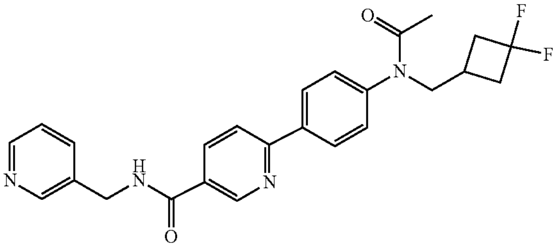 [SMILES: CC(=O)N(CC1CC(F)(F)C1)c1ccc(-c2ccc(C(=O)NCc3cccnc3)cn2)cc1]

Purification by prep HPLC (Method 9) afforded 6-[4-[acetyl-[(3,3-difluorocyclobutyl)methyl]amino]-phenyl]-N-(3-pyridylmethyl)pyridine-3-carboxamide as a white paste (1.4 mg, 3%)

LC-MS (Method 8): $R_t$=3.54 min; m/z=451.23 $(M+H)^+$ $^1$H NMR (500 MHz, DMSO-$d_6$): δ [ppm]=1.80 (br. s., 3H) 2.18-2.29 (m, 4H) 2.54-2.60 (m, 1H) 3.85 (d, J=6.71 Hz, 2H) 4.55 (d, J=5.80 Hz, 2H) 7.38 (dd, J=7.93, 4.88 Hz, 1H) 7.46 (d, J=8.24 Hz, 2H) 7.76 (d, J=7.93 Hz, 1H) 8.15 (d, J=8.24 Hz, 1H) 8.23 (d, J=8.55 Hz, 2H) 8.33 (dd, J=8.39, 2.29 Hz, 1H) 8.48 (dd, J=4.88, 1.53 Hz, 1H) 8.59 (d, J=1.83 Hz, 1H) 9.14 (d, J=2.14 Hz, 1H) 9.34 (t, J=5.80 Hz, 1H).

Preparation of 6-[4-[acetyl(cyclopropylmethyl) amino]phenyl]-N-(3-pyridylmethyl)pyridine-3-carboxamide (I-421)

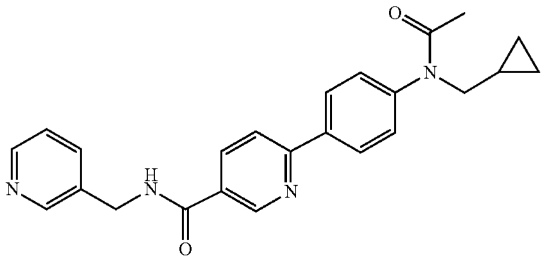 [SMILES: CC(=O)N(CC1CC1)c1ccc(-c2ccc(C(=O)NCc3cccnc3)cn2)cc1]

Purification by prep HPLC (Method 9) afforded 6-[4-[acetyl(cyclopropylmethyl)amino]phenyl]-N-(3-pyridylmethyl)pyridine-3-carboxamide as a yellow paste (2 mg, 4%).

LC-MS (Method 8): $R_t$=3.36 min; m/z=401.25 $(M+H)^+$ $^1$H-NMR (600 MHz, DMSO-dd$_6$): δ [ppm]=0.04-0.09 (m, 2H) 0.36-0.41 (m, 2H) 0.90 (br. s., 1H) 1.81 (br. s., 3H) 3.55 (d, J=7.15 Hz, 2H) 4.55 (d, J=5.69 Hz, 2H) 7.38 (dd, J=7.70, 4.58 Hz, 1H) 7.47 (d, J=7.89 Hz, 2H) 7.77 (d, J=7.52 Hz, 1H) 8.15 (d, J=8.62 Hz, 1H) 8.23 (d, J=8.07 Hz, 2H) 8.33 (dd, J=8.25, 2.38 Hz, 1H) 8.48 (d, J=3.30 Hz, 1H) 8.59 (s, 1H) 9.14 (d, J=1.83 Hz, 1H) 9.34 (t, J=5.78 Hz, 1H).

Preparation oftert-butyl N-[2-[N-propanoyl-4-[4-(3-pyridylmethylcarbamoyl)phenyl]anilino]ethyl]carbamate (I-417)

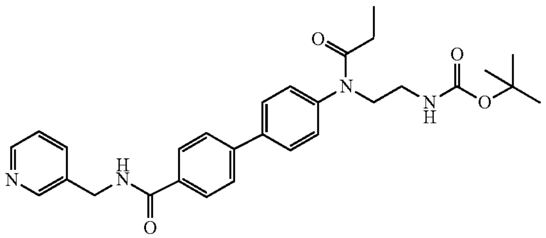 [SMILES: CCC(=O)N(CCNC(=O)OC(C)(C)C)c1ccc(-c2ccc(C(=O)NCc3cccnc3)cc2)cc1]

Purification by prep HPLC (Method 9) afforded tert-butyl N-[2-[N-propanoyl-4-[4-(3-pyridylmethylcarbamoyl)phenyl] anilino]ethyl]carbamate as a white solid (3 mg, 4%).

LC-MS (Method 8): $R_t$=3.99 min; m/z=503.42 $(M+H)^+$ $^1$H-NMR (600 MHz, DMSO-dd$_6$): δ [ppm]=0.93 (br. s., 3H) 1.32 (s, 9H) 2.02 (br. s., 2H) 3.08 (d, J=6.05 Hz, 2H) 3.67 (t, J=6.33 Hz, 2H) 4.53 (d, J=5.87 Hz, 2H) 6.87 (br. s., 1H) 7.37 (dd, J=7.70, 4.77 Hz, 1H) 7.45 (d, J=7.70 Hz, 2H) 7.75 (d, J=7.70 Hz, 1H) 7.82 (dd, J=12.93, 8.34 Hz, 4H) 8.00 (d, J=8.44 Hz, 2H) 8.42-8.50 (m, 1H) 8.58 (d, J=2.20 Hz, 1H), 9.10-9.21 (t, 1H).

Preparation of 6-[4-[acetyl(ethyl)amino]-3-methyl-phenyl]-N-[(2-methyl-3-pyridyl)methyl]pyridine-3-carboxamide (I-429)

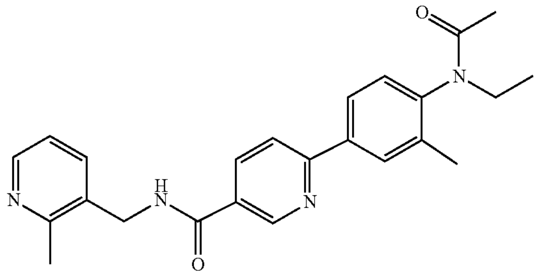 [SMILES: CCN(C(C)=O)c1ccc(-c2ccc(C(=O)NCc3cccnc3C)cn2)cc1C]

Purification by flash column chromatography over silica gel (10% MeOH in DCM) afforded 6-[4-[acetyl(ethyl) amino]-3-methyl-phenyl]-N-[(2-methyl-3-pyridyl)methyl] pyridine-3-carboxamide as a white amorphous solid (18 mg, 29%).

LC-MS (Method 8): $R_t$=3.28 min; m/z=403.16 $(M+H)^+$ $^1$H NMR (400 MHz, DMSO-dd$_6$): δ [ppm]=1.03 (t, J=7.18 Hz, 3H) 1.66 (s, 3H) 2.27 (s, 3H) 2.53 (s, 3H) 3.21 (m, 1H) 3.93 (m, 1H) 4.51 (d, J=5.58 Hz, 2H) 7.19 (dd, J=7.78, 5.03 Hz, 1H) 7.33 (d, J=8.09 Hz, 1H) 7.63 (dd, J=7.78, 1.80 Hz, 1H) 8.04 (dd, J=8.54, 2.29 Hz, 1H) 8.13 (dd, J=8.21, 0.94 Hz, 1H) 8.17 (d, J=2.19 Hz, 1H) 8.31-8.35 (m, 2H) 9.13 (dd, J=2.36, 0.93 Hz, 1H) 9.21 (t, J=5.58 Hz, 1H).

Preparation of 6-[4-[acetyl(ethyl)amino]-3-methyl-phenyl]-N-(3-pyridylmethyl)pyridine-3-carboxamide (I-430)

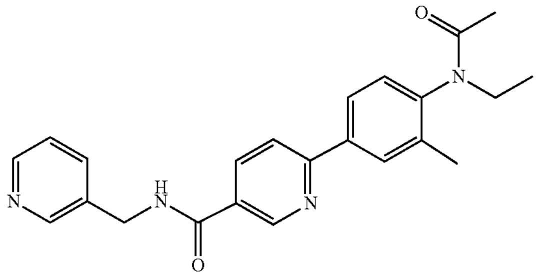 [SMILES: CCN(C(C)=O)c1ccc(-c2ccc(C(=O)NCc3cccnc3)cn2)cc1C]

Purification by flash column chromatography over silica gel (10% MeOH in DCM) afforded 6-[4-[acetyl(ethyl) amino]-3-methyl-phenyl]-N-(3-pyridylmethyl)pyridine-3-carboxamide as a white amorphous solid (15 mg, 25%).

LC-MS (Method 8): $R_t$=3.17 min; m/z=389.16 $(M+H)^+$ $^1$H NMR (400 MHz, DMSO-dd$_6$): δ [ppm]=1.03 (t, J=7.25 Hz, 3H) 1.66 (s, 3H) 2.27 (s, 3H) 3.21 (m, 1H) 3.93 (m, 1H) 4.54 (d, J=5.96 Hz, 2H) 7.33 (d, J=7.98 Hz, 1H) 7.37 (ddd, J=7.98, 4.92, 0.85 Hz, 1H) 7.75 (dd, J=7.85 Hz, 1H) 8.04 (dd, J=8.41, 2.38 Hz, 1H) 8.13 (dd, J=8.39, 0.85 Hz, 1H) 8.17 (d, J=81.94 Hz, 1H) 8.32 (dd, J=8.45, 2.38 Hz, 1H) 8.47 (dd, J=4.89, 1.60 Hz, 1H) 8.58 (d, J=2.31 Hz, 1H) 9.12 (dd, J=2.38, 0.85 Hz, 1H) 9.32 (t, J=5.96 Hz, 1H).

Preparation of 4-[4-(diisobutylamino)phenyl]-N-(3-pyridylmethyl)benzamide(I-406)

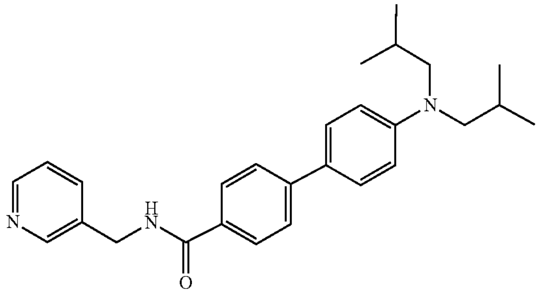 [SMILES: CC(C)CN(CC(C)C)c1ccc(-c2ccc(C(=O)NCc3cccnc3)cc2)cc1]

I-406 was isolated during the preparation of 4'-(N-isobutylpropionamido)-N-(pyridin-3-ylmethyl)-[1,1'-biphenyl]-4-carboxamide following Scheme 1. Purification by prep HPLC (Method 9) afforded 4-[4-(diisobutylamino) phenyl]-N-(3-pyridylmethyl)benzamide as a yellow paste (13 mg, 0.2%).

LC-MS (Method 8): $R_t$=6.00 min; m/z=416.37 $(M+H)^+$ $^1$H-NMR (300 MHz, DMSO–dd$_6$): δ [ppm] 0.87 (d, J=6.72 Hz, 12H) 2.01 (dt, J=13.48, 6.89 Hz, 2H) 3.20 (d, J=7.21 Hz, 4H) 4.49 (d, J=5.75 Hz, 2H) 6.73 (d, J=8.93 Hz, 2H) 7.35 (dd, J=7.95, 4.77 Hz, 1H) 7.53 (d, J=8.93 Hz, 2H) 7.62-7.76 (m, 3H) 7.89 (d, J=8.44 Hz, 2H) 8.45 (dd, J=4.77, 1.59 Hz, 1H) 8.55 (d, J=1.96 Hz, 1H) 9.05 (t, J=5.93 Hz, 1H).

Preparation of 6-[4-[acetyl(propyl)amino]-3-methyl-phenyl]-N-[(2-methyl-3-pyridyl)methyl]-pyridine-3-carboxamide (I-446)

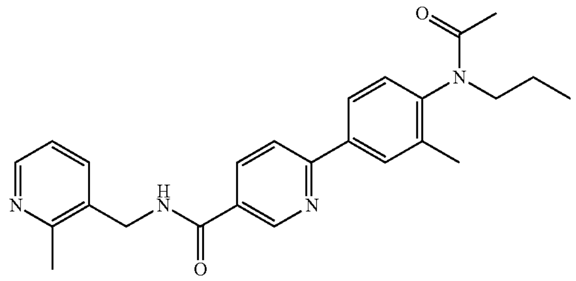 [SMILES: CCCN(C(C)=O)c1ccc(-c2ccc(C(=O)NCc3cccnc3C)cn2)cc1C]

Purification by prep HPLC (Method 9) afforded 6-[4-[acetyl(propyl)amino]-3-methyl-phenyl]-N-[(2-methyl-3-pyridyl)methyl]pyridine-3-carboxamide as an orange paste (2 mg, 4%).

LC-MS (Method 8): $R_t$=3.58 min; m/z=417.21 $(M+H)^+$ $^1$H-NMR (500 MHz, DMSO–dd$_6$): δ [ppm]=0.84 (t, J=7.40 Hz, 3H) 1.41-1.51 (m, 2H) 1.67 (s, 3H) 2.28 (s, 3H) 2.53 (s, 3H) 3.04-3.12 (m, 1H) 3.85-3.93 (m, 1H) 4.52 (d, J=5.43 Hz, 2H) 7.20 (dd, J=5.08, 7.90 Hz, 1H) 7.33 (d, J=8.30 Hz, 1H) 7.63 (d, J=7.28 Hz, 1H) 8.04 (d, J=7.28 Hz, 1H) 8.13 (d, J=8.00 Hz, 1H) 8.17 (s, 1H) 8.32-8.36 (m, 2H) 9.15 (d, J=1.63 Hz, 1H) 9.22 (t, J=5.46 Hz, 1H).

Preparation of 6-[4-[acetyl(isobutyl)amino]-3-methyl-phenyl]-N-[(2-methyl-3-pyridyl)methyl]pyridine-3-carboxamide (I-454)

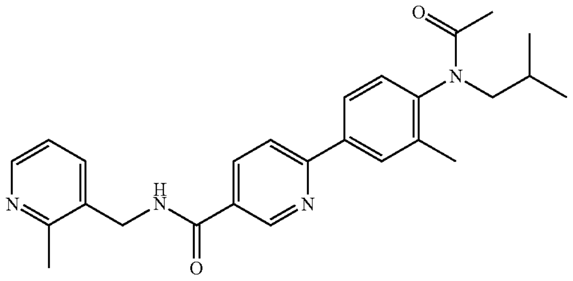 [SMILES: CC(=O)N(CC(C)C)c1ccc(-c2ccc(C(=O)NCc3cccnc3C)cn2)cc1C]

Purification by flash column chromatography over silica gel (10% MeOH in DCM) and additional trituration with diethyl ether afforded 6-[4-[acetyl(isobutyl)amino]-3-methyl-phenyl]-N-[(2-methyl-3-pyridyl)methyl]pyridine-3-carboxamide as a white solid (14 mg, 21%).

LC-MS (Method 8): $R_t$=3.85 min; m/z=431.16 $(M+H)^+$ $^1$H-NMR (300 MHz, DMSO–d$_6$): δ [ppm]=0.87 (dd, J=6.61, 16.81 Hz, 6H), 1.62-1.77 (m, 1H), 1.68 (s, 3H) 2.27 (s, 3H) 2.52 (s, 3H), 2.86 (dd, J=5.80, 13.20 Hz, 1H), 3.90 (dd, J=8.90, 13.20 Hz, 1H), 4.51 (d, J=5.81 Hz, 2H), 7.15-7.24 (m, 1H), 7.33 (d, J=8.17 Hz, 1H), 7.62 (dd, J=1.44, 7.88, 1H) 8.04 (dd, J=1.91, 8.10, 1H), 8.09-8.18 (m, 2H) 8.30-8.36 (m, 2H), 9.12 (d, J=1.90 Hz, 1H), 9.21 (t, J=5.28 Hz, 1H).

Preparation of 6-[4-[acetyl(cyclobutylmethyl)amino] phenyl]-N-(3-pyridylmethyl)pyridine-3-carboxamide (I-453)

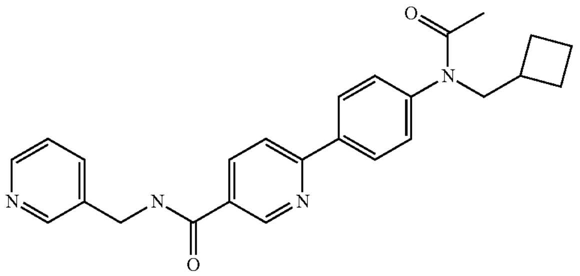

Purification by flash column chromatography over silica gel (10% MeOH in DCM) and additional trituration with diethyl ether afforded 6-[4-[acetyl(cyclobutylmethyl)amino] phenyl]-N-(3-pyridylmethyl)pyridine-3-carboxamide as a white solid (19 mg, 23%).

LC-MS (Method 8): $R_t$=3.72 min; m/z=415.13 $(M+H)^+$ $^1$H-NMR (300 MHz, DMSO–d$_6$): δ [ppm]=1.50-1.65 (m, 2H), 1.67-1.94 (m, 7H), 2.35 (q, J=7.78, 1H), 3.73 (d, J=7.42 Hz, 2H), 4.53 (d, J=5.81 Hz, 2H), 7.32-7.43 (m, 3H), 7.75 (dt, J=1.83, 7.85 Hz, 1H), 8.12 (d, J=8.37 Hz, 1H), 8.37 (d, J=8.37, 2H), 8.31 (dd, J=2.33, 8.37 Hz, 1H), 8.46 (dd, J=1.55, 4.77 Hz, 1H), 8.58 (d, J=1.65, 1H), 9.12 (d, J=2.03 Hz, 1H), 9.32 (t, J=5.72 Hz, 1H).

Preparation of 6-[4-[acetyl(oxetan-3-ylmethyl) amino]phenyl]-N-(3-pyridylmethyl)pyridine-3-carboxamide (I-447)

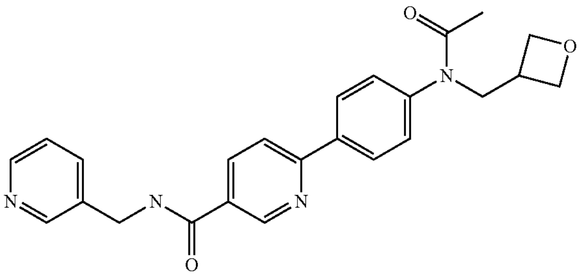

Purification by flash column chromatography over silica gel (10% MeOH in DCM) and additional trituration with diethyl ether afforded 6-[4-[acetyl(oxetan-3-ylmethyl) amino]phenyl]-N-(3-pyridylmethyl)pyridine-3-carboxamide as a white solid (6 mg, 14%).

LC-MS (Method 8): $R_t$=2.75 min; m/z=417.16 $(M+H)^+$ $^1$H-NMR (500 MHz, DMSO-$d_6$): δ [ppm]=1.78 (s, 3H), 3.07 (m, 1H), 4.01 (d, J=7.41 Hz, 2H), 4.18 (t, J=6.19 Hz, 1H), 4.48-4.57 (m, 2H), 7.37 (dd, J=7.82, 4.77 Hz, 1H), 7.42 (d, J=8.21 Hz, 2H), 7.76 (d, J=8.21, 1H), 8.15 (d, J=8.02 Hz, 1H), 8.22 (d, J=8.21 Hz, 2H), 8.33 (dd, J=8.34, 2.04 Hz, 1H), 8.47 (d, J=4.72, 1H), 8.59 (s, 1H), 9.14 (d, J=2.01 Hz, 1H), 9.33 (t, J=6.31 Hz, 1H).

Preparation of tert-butyl N-[2-[N-acetyl-4-[5-(3-pyridylmethylcarbamoyl)-2-pyridyl]anilino]ethyl] carbamate (I-448)

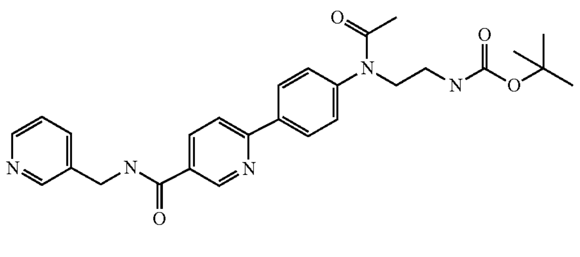

Purification by flash column chromatography over silica gel (10% MeOH in DCM) and additional trituration with diethyl ether afforded tert-butyl N-[2-[N-acetyl-4-[5-(3-pyridylmethyl carbamoyl)-2-pyridyl]anilino]ethyl]carbamate (6 mg, 13%).

LC-MS (Method 8): $R_t$=3.44 min; m/z=490.20 $(M+H)^+$ $^1$H-NMR (500 MHz, DMSO-$d_6$): δ [ppm]=1.31 (s, 9H), 1.78 (s, 3H), 3.07 (bs, 2H), 3.68 (bs, 2H), 4.54 (d, J=5.10 Hz, 2H), 6.87 (bs, 1H), 7.37 (m, 1H), 7.48 (d, J=6.85 Hz, 2H), 7.76 (d, J=7.19, 1H), 8.14 (d, J=7.92 Hz, 1H), 8.21 (d, J=7.39 Hz, 2H), 8.32 (d, J=7.74 Hz, 1H), 8.47 (d, J=3.69, 1H), 8.59 (s, 1H), 9.13 (s, 1H), 9.32 (t, J=5.10 Hz, 1H).

Preparation of 6-[4-[acetyl(ethyl)amino]-3-chloro-phenyl]-N-[(2-methyl-3-pyridyl)methyl]pyridine-3-carboxamide (I-444)

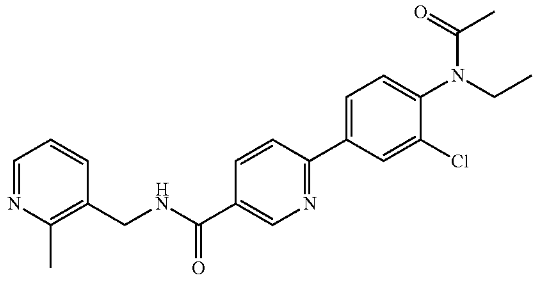 [SMILES: CCN(C(C)=O)c1ccc(-c2ccc(C(=O)NCc3cccnc3C)cn2)cc1Cl]

Purification by flash column chromatography over silica gel (10% MeOH in DCM) and additional trituration with acetone afforded 6-[4-[acetyl(ethyl)amino]-3-chloro-phenyl]-N-[(2-methyl-3-pyridyl)methyl]pyridine-3-carboxamide as a white solid (27 mg, 23%).

m.p.=96.3 &120.4° C. (mixture of polymorphs)

LC-MS (Method 8): $R_t$=3.51 min; m/z=423.14 $(M+H)^+$ $^1$H-NMR (500 MHz, DMSO-d6): δ [ppm]=1.04 (d, J=7.21 Hz, 3H), 1.72 (s, 3H), 2.54 (s, 3H), 3.39 (m, 1H), 3.88 (m, 1H), 4.52 (d, J=5.77 Hz, 2H), 7.21 (dd, J=7.46, 5.04 Hz, 1H), 7.62-7.64 (m, 2H), 8.22-8.26 (m, 2H), 8.32-8.39 (m, 2H), 8.41 (d, J=1.65 Hz, 1H), 9.16 (d, J=1.65 Hz, 1H), 9.25 (t, J=5.77 Hz, 1H).

Preparation of 6-[4-[acetyl(2,2-difluoroethyl)amino] phenyl]-N-[(2-methyl-3-pyridyl)methyl]pyridine-3-carboxamide (I-449)

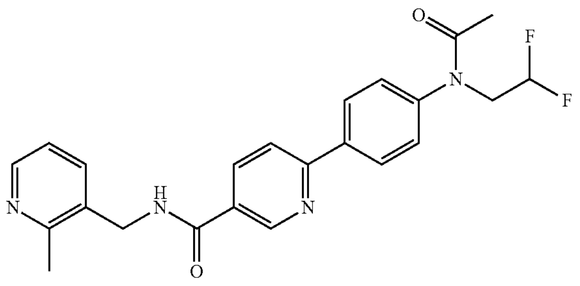

This compound was prepared following Scheme 1*. Purification by flash column chromatography over silica gel (10% MeOH in DCM) and additional trituration with acetone afforded 6-[4-[acetyl(ethyl)amino]-3-chloro-phenyl]-N-[(2-methyl-3-pyridyl)methyl]pyridine-3-carboxamide as a white solid (16 mg, 24%).

m.p.=155.5° C.

LC-MS (Method 8): $R_t$=3.32 min; m/z=425.14 $(M+H)^+$ $^1$H-NMR (500 MHz, DMSO-d6): δ [ppm]=1.86 (s, 3H), 2.53 (s, 3H), 4.07 (t, J=14.51 Hz, 2H), 4.51 (d, J=5.41 Hz, 2H), 6.18 (t, J=54.90 Hz, 1H), 7.20 (dd, J=7.31, 5.19 Hz, 1H), 7.50 (d, J=7.55 Hz, 2H), 7.64 (d, J=7.55 Hz, 1H), 8.15 (d, J=8.29 Hz, 1H), 8.24 (d, J=8.01 Hz, 2H), 8.32-8.37 (m, 2H) 9.15 (s, 1H), 9.22 (t, J=5.41 Hz, 1H).

*The reductive amination step described in Scheme 1 was replaced by the following procedure: A mixture of methyl 6-(4-aminophenyl)pyridine-3-carboxylate (100 mg, 0.438 mmol), 1-ethoxy-2,2-difluoro-ethanol (61.3 mg, 0.486 mmol) and molecular sieves (4A°, 50 mg) in toluene (10 mL) was heated at 80° C. for 2 hours. The reaction mixture was concentrated and re-dissolved in 1,2-dichloroethane (10.0 mL), then sodium triacetoxyborohydride (416 mg, 1.96 mmol) was added and the reaction mixture was stirred overnight at RT. It was then diluted with DCM and washed with sat. $NaHCO_3$. The organic layer was dried and concentrated to give a crude residue which was purified by column chromatography (60% EtOAc in cyclohexane) to afford methyl 6-[4-(2,2-difluoroethylamino)phenyl]pyridine-3-carboxylate as an off-white solid (45 mg, 35%).

LC-MS (Method 2): $R_t$=1.05 min, m/z=293.03 $(M+H)^+$

Preparation of 6-[4-[acetyl(propyl)amino]-3-chloro-phenyl]-N-[(2-methyl-3-pyridyl)methyl]pyridine-3-carboxamide (I-458)

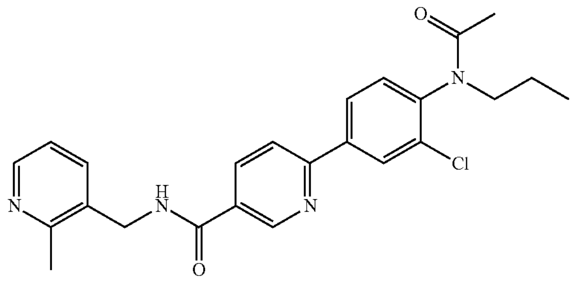 [SMILES: CCCN(C(C)=O)c1ccc(-c2ccc(C(=O)NCc3cccnc3C)cn2)cc1Cl]

Purification by flash column chromatography over silica gel (10% MeOH in DCM) afforded 6-[4-[acetyl(propyl)amino]-3-chloro-phenyl]-N-[(2-methyl-3-pyridyl)methyl]pyridine-3-carboxamide as a white foam (27 mg, 50%).

LC-MS (Method 8): $R_t$=3.84 min; m/z=437.16 $(M+H)^+$ $^1$H-NMR (300 MHz, DMSO-$d_6$): δ [ppm]=0.83 (t, J=7.30 Hz, 3H), 1.44 (sxt, J=7.30 Hz, 2H), 1.71 (s, 3H), 2.52 (s, 3H), 3.18-3.31 (m, 1H), 3.74-3.86 (m, 1H), 4.50 (d, J=5.65 Hz, 2H), 7.19 (dd, J=4.98, 7.82 Hz, 1H), 7.59-7.66 (m, 2H), 8.22 (dd, J=1.95, 8.25 Hz, 2H), 8.31-8.41 (m, 3H), 9.15 (d, J=1.93 Hz, 1H), 9.24 (t, J=5.80 Hz, 1H).

Preparation of 6-[4-[acetyl(isobutyl)amino]-3-chloro-phenyl]-N-[(2-methyl-3-pyridyl)methyl]pyridine-3-carboxamide (I-459)

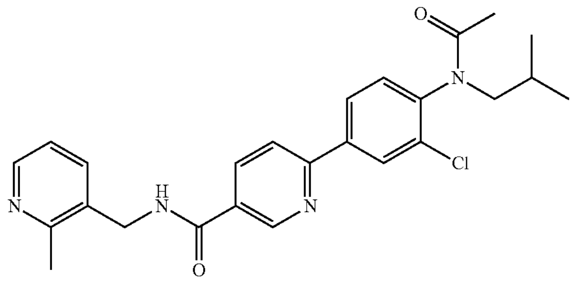 [SMILES: CC(=O)N(CC(C)C)c1ccc(-c2ccc(C(=O)NCc3cccnc3C)cn2)cc1Cl]

Purification by flash column chromatography over silica gel (10% MeOH in DCM) afforded 6-[4-[acetyl(isobutyl)amino]-3-chloro-phenyl]-N-[(2-methyl-3-pyridyl)methyl]pyridine-3-carboxamide as a white foam (26 mg, 49%).

LC-MS (Method 8): $R_t$=4.10 min; m/z=451.15 $(M+H)^+$ $^1$H-NMR (300 MHz, DMSO-$d_6$): δ [ppm]=0.87 (dd, J=6.82, 8.30 Hz, 6H), 1.61-1.74 (m, 1H), 1.73 (s, 3H), 2.52 (s, 3H), 3.00-3.09 (m, 1H), 3.75-3.86 (m, 1H), 4.50 (d, J=5.36 Hz, 2H), 7.19 (dd, J=4.86, 7.52 Hz, 1H), 7.62 (dd, J=2.13, 7.75 Hz, 2H), 8.21 (dd, J=2.03, 8.14 Hz, 2H), 8.31-8.41 (m, 3H), 9.14 (d, J=2.01 Hz, 1H), 9.24 (t, J=6.34 Hz, 1H).

Preparation of 4-[3-chloro-4-[methyl(propanoyl)amino]phenyl]-N-[(2-methyl-3-pyridyl)methyl]benzamide (I-460)

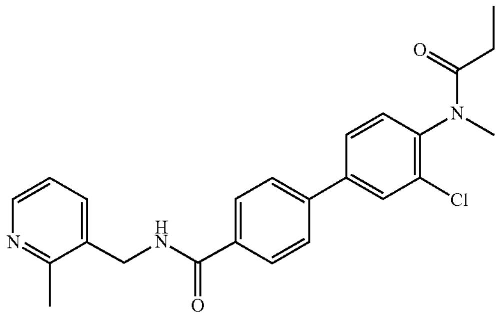 [SMILES: CCC(=O)N(C)c1ccc(-c2ccc(C(=O)NCc3cccnc3C)cc2)cc1Cl]

Trituration with MeOH/diethyl-ether afforded 4-[3-chloro-4-[methyl(propanoyl)amino]phenyl]-N-[(2-methyl-3-pyridyl)methyl]benzamide as a white solid (25 mg, 38%).

LC-MS (Method 2): $R_t$=0.94 min; m/z=422.15 $(M+H)^+$ $^1$H-NMR (400 MHz, DMSO-$d_6$): δ [ppm]=0.93 (t, J=7.36 Hz, 3H), 1.93 (bs, 2H), 2.52 (s, 3H), 3.09 (s, 3H), 4.49 (d, J=5.40 Hz, 2H), 7.17-7.21 (m, 1H), 7.59 (d, J=7.56 Hz, 1H), 7.63 (d, J=8.36 Hz, 1H), 7.82 (d, J=8.12 Hz, 1H), 7.87 (d, J=8.08 Hz, 1H), 7.98-8.03 (m, 3H), 8.32 (d, J=4.04 Hz, 1H), 9.08 (t, J=6.24 Hz, 1H).

6-[4-[Acetyl(oxetan-3-ylmethyl)amino]phenyl]-N-[(2-methyl-3-pyridyl)methyl]pyridine-3-carboxamide (I-503)

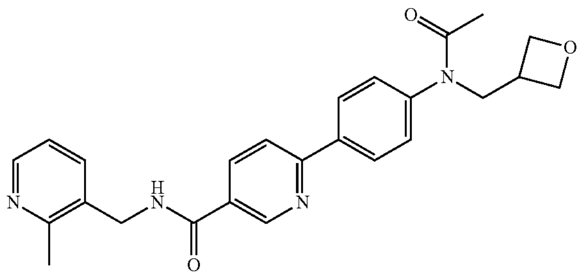 [SMILES: CC(=O)N(CC1COC1)c1ccc(-c2ccc(C(=O)NCc3cccnc3C)cn2)cc1]

Purification by flash column chromatography over silica gel (10% MeOH in EtOAc) afforded 6-[4-[acetyl(oxetan-3-ylmethyl)amino]phenyl]-N-[(2-methyl-3-pyridyl)methyl]pyridine-3-carboxamide as a white amorphous solid (24 mg, 35%).

LC-MS (Method 8): Rt=2.86 min; m/z=431.16 $(M+H)^+$.

$^1$H-NMR (500 MHz, DMSO-$d_6$): δ 1.79 (bs, 1H), 2.54 (s, 3H), 3.08 (m, 1H), 4.02 (d, J=7.33 Hz, 2H), 4.18 (t, J=6.51 Hz, 2H), 4.52 (m, 4H), 7.21 (dd, J=7.64, 4.87 Hz, 1H), 7.42 (d, J=8.09 Hz, 2H), 7.64 (d, J=7.79 Hz, 1H), 8.15 (d, J=8.78

Hz, 1H), 8.22 (d, J=7.87 Hz, 2H), 8.34 (d, J=7.40 Hz, 2H), 9.15 (d, J=1.75 Hz, 1H), 9.22 (t, J=5.64 Hz, 1H).

6-[4-[Acetyl(oxetan-3-ylmethyl)amino]-3-methyl-phenyl]-N-[(2-methyl-3-pyridyl)methyl]pyridine-3-carboxamide (I-510)

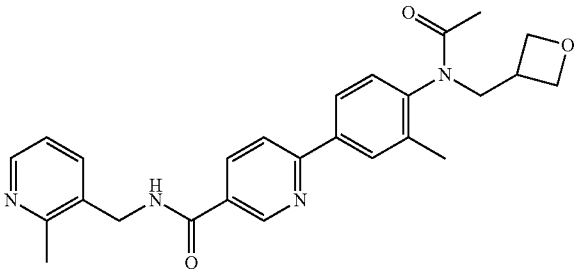 [SMILES: CC(=O)N(CC1COC1)c1ccc(-c2ccc(C(=O)NCc3cccnc3C)cn2)cc1C]

Purification by flash column chromatography over silica gel (10% MeOH in DCM) afforded 6-[4-[acetyl(oxetan-3-ylmethyl)amino]-3-methyl-phenyl]-N-[(2-methyl-3-pyridyl)methyl]pyridine-3-carboxamide as a white amorphous solid (38 mg, 34%).

LC-MS (Method 8): Rt=2.99 min; m/z=445.16 $(M+H)^+$.

$^1$H NMR (500 MHz, DMSO-$d_6$): δ 1.67 (s, 3H), 2.26 (s, 3H), 2.54 (s, 3H), 3.04-3.15 (m, 1H), 3.54-3.64 (m, 1H), 4.13 (t, J=6.1 Hz, 1H), 4.21-4.29 (m, 2H), 4.48-4.54 (m, 3H), 4.54-4.60 (m, 1H), 7.21 (dd, J=7.6, 4.9 Hz, 1H), 7.29 (d, J=8.2 Hz, 1H), 7.64 (d, J=7.7 Hz, 1H), 8.04 (d, J=8.1 Hz, 1H), 8.14 (d, J=8.3 Hz, 1H), 8.17 (s, 1H), 8.34 (d, J=5.9 Hz, 2H), 9.14 (s, 1H), 9.22 (t, J=5.5 Hz, 1H).

6-[4-[Acetyl-[(3,3-difluorocyclobutyl)methyl]amino]phenyl]-N-[(2-methyl-3-pyridyl)methyl]pyridine-3-carboxamide (I-517)

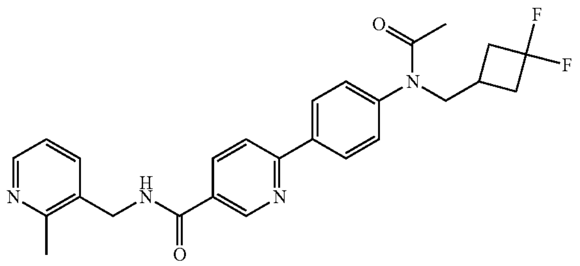 [SMILES: CC(=O)N(CC1CC(F)(F)C1)c1ccc(-c2ccc(C(=O)NCc3cccnc3C)cn2)cc1]

Purification by flash column chromatography over silica gel (10% MeOH in EtOAc) afforded 6-[4-[acetyl-[(3,3-difluorocyclobutyl)methyl]amino]phenyl]-N-[(2-methyl-3-pyridyl)methyl]pyridine-3-carboxamide as a white amorphous solid (55 mg, 24%).

LC-MS (Method 8): Rt=3.67 min; m/z=465.14 $(M+H)^+$.

$^1$H-NMR (300 MHz, DMSO-$d_6$): δ 1.79 (bs, 3H), 2.14-2.30 (m, 4H), 2.53 (s, 3H), 2.58 (m, 2H), 3.84 (d, J=6.71 Hz, 2H), 4.51 (d, J=5.53 Hz, 2H), 7.20 (dd, J=7.81, 4.79 Hz, 1H), 7.45 (d, J=8.64 Hz, 2H), 7.63 (d, J=7.81 Hz, 1H), 8.15 (d, J=8.31 Hz, 1H), 8.22 (d, J=8.58 Hz, 2H), 8.31-8.36 (m, 2H), 9.14 (d, J=2.06 Hz, 1H), 9.21 (t, J=5.53 Hz, 1H).

6-[4-[Acetyl(oxetan-3-ylmethyl)amino]-3-methyl-phenyl]-N-(3-pyridylmethyl)pyridine-3-carboxamide (I-610)

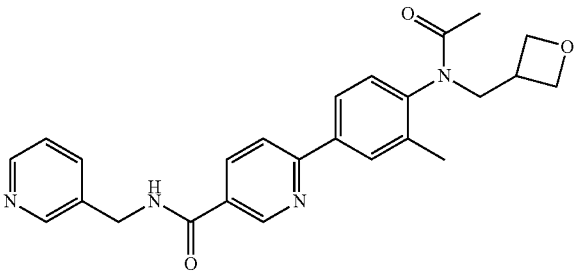 [SMILES: CC(=O)N(CC1COC1)c1ccc(-c2ccc(C(=O)NCc3cccnc3)cn2)cc1C]

Purification by flash column chromatography over silica gel (10% MeOH in DCM) afforded 6-[4-[acetyl(oxetan-3-ylmethyl)amino]-3-methyl-phenyl]-N-(3-pyridylmethyl)pyridine-3-carboxamide as a yellow amorphous solid (45 mg, 26%).

LC-MS (Method 8): Rt=2.88 min; m/z=431.24 $(M+H)^+$.

$^1$H-NMR (600 MHz, DMSO-$d_6$) δ 1.67 (s, 3H), 2.26 (s, 3H), 3.05-3.14 (m, 1H), 3.60 (dd, J=13.73, 7.63 Hz, 1H), 4.13 (t, J=6.10 Hz, 1H), 4.21-4.28 (m, 2H), 4.50-4.59 (m, 4H), 7.29 (d, J=8.24 Hz, 1H), 7.38 (dd, J=7.78, 4.73 Hz, 1H), 7.77 (d, J=7.90 Hz, 1H), 8.04 (d, J=7.93 Hz, 1H), 8.14 (d, J=8.54 Hz, 1H), 8.17 (s, 1H), 8.33 (dd, J=8.24, 2.14 Hz, 1H), 8.48 (d, J=4.88 Hz, 1H), 8.59 (s, 1H), 9.13 (d, J=1.83 Hz, 1H), 9.33 (t, J=5.95 Hz, 1H).

6-[4-[Acetyl(2,2-difluoroethyl)amino]-3-chloro-phenyl]-N-(3-pyridylmethyl)pyridine-3-carboxamide (I-619)

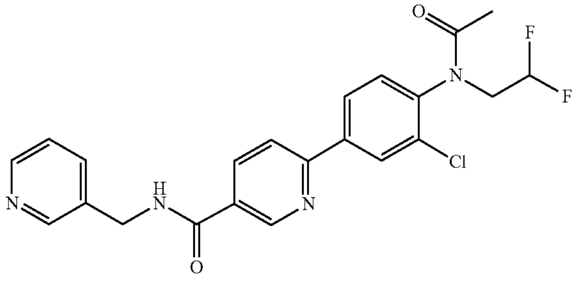 [SMILES: CC(=O)N(CC(F)F)c1ccc(-c2ccc(C(=O)NCc3cccnc3)cn2)cc1Cl]

Purification by flash column chromatography over silica gel (10% MeOH in DCM) afforded 6-[4-[acetyl(2,2-difluoroethyl)amino]-3-chloro-phenyl]-N-(3-pyridylmethyl)pyridine-3-carboxamide as a white amorphous solid (60 mg, 28%).

LC-MS (Method 8): Rt=3.61 min; m/z=445.14 $(M+H)^+$.

$^1$H-NMR (400 MHz, DMSO-$d_6$): δ 1.79 (s, 3H), 3.52-3.82 (m, 1H), 4.15-4.37 (m, 1H), 4.54 (d, J=5.75 Hz, 2H), 6.20 (t, J=55.99 Hz, 1H), 7.37 (ddd, J=7.86, 4.80, 0.92 Hz, 1H), 7.68 (d, J=8.31 Hz, 1H), 7.73-7.78 (m, 1H), 8.20-8.26 (m, 2H), 8.35 (dd, J=8.31, 2.32 Hz, 1H), 8.41 (d, J=2.08 Hz, 1H), 8.47 (dd, J=4.83, 1.65 Hz, 1H), 8.56-8.59 (m, 1H), 9.14 (dd, J=2.38, 0.79 Hz, 1H), 9.35 (t, J=5.81 Hz, 1H).

6-[4-[Acetyl(oxetan-3-ylmethyl)amino]-3-chloro-phenyl]-N-(3-pyridylmethyl)pyridine-3-carboxamide (I-620)

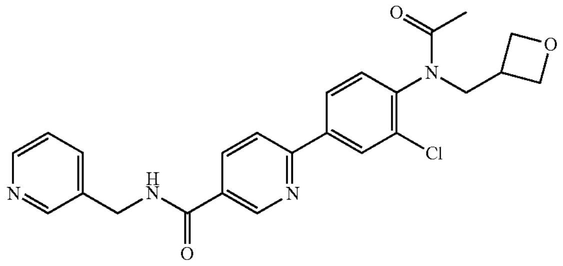 [SMILES: CC(=O)N(CC1COC1)c1ccc(-c2ccc(C(=O)NCc3cccnc3)cn2)cc1Cl]

Purification by flash column chromatography over silica gel (10% MeOH in DCM) afforded 6-[4-[acetyl(oxetan-3-ylmethyl)amino]-3-chloro-phenyl]-N-(3-pyridylmethyl) pyridine-3-carboxamide as a white amorphous solid (37 mg, 48%).

LC-MS (Method 8): Rt=3.08 min; m/z=451.17 $(M+H)^+$.

$^1$H-NMR (400 MHz, DMSO-$d_6$): δ 1.71 (s, 3H), 3.02-3.12 (m, 1H), 3.84 (dd, J=13.75, 7.64 Hz, 1H), 4.07 (dd, J=13.82, 7.46 Hz, 1H), 4.19 (dt, J=16.38, 6.11 Hz, 2H), 4.50-4.59 (m, 4H), 7.37 (ddd, J=7.83, 4.83, 0.67 Hz, 1H), 7.60 (d, J=8.31 Hz, 1H), 7.76 (dt, J=7.73, 2.00 Hz, 1H), 8.20-8.25 (m, 2H), 8.35 (dd, J=8.38, 2.38 Hz, 1H), 8.40 (d, J=2.08 Hz, 1H), 8.47 (dd, J=4.83, 1.65 Hz, 1H), 8.58 (d, J=1.59 Hz, 1H), 9.14 (dd, J=2.20, 0.73 Hz, 1H), 9.35 (t, J=5.69 Hz, 1H).

6-[4-[Acetyl(ethyl)amino]-3-chloro-phenyl]-N-(3-pyridylmethyl)pyridine-3-carboxamide (I-652)

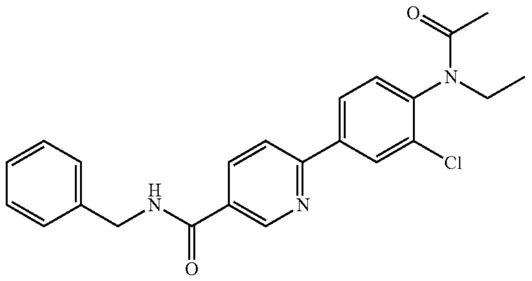 [SMILES: CCN(C(C)=O)c1ccc(-c2ccc(C(=O)NCc3ccccc3)cn2)cc1Cl]

Purification by flash column chromatography over silica gel (0-10% MeOH in EtOAc) afforded 6-[4-[acetyl(ethyl) amino]-3-chloro-phenyl]-N-(3-pyridylmethyl)pyridine-3-carboxamide (24 mg, 11%).

LC-MS (Method 8): Rt=3.37 min; m/z=409.55 $(M+H)^+$.

$^1$H NMR (300 MHz, DMSO-$d_6$): δ 1.03 (t, J=7.14 Hz, 3H), 1.71 (s, 3H), 3.34-3.43 (m, 1H), 3.87 (dd, J=13.76, 7.14 Hz, 1H), 4.54 (d, J=5.75 Hz, 2H), 7.37 (dd, J=7.93, 4.79 Hz, 1H), 7.63 (d, J=8.19 Hz, 1H), 7.76 (br d, J=8.01 Hz, 1H), 8.19-8.27 (m, 2H), 8.29-8.42 (m, 2H), 8.47 (d, J=4.88 Hz, 1H), 8.58 (d, J=1.92 Hz, 1H), 9.14 (d, J=2.09 Hz, 1H), 9.35 (t, J=5.49 Hz, 1H).

Synthesis according to Scheme 2.

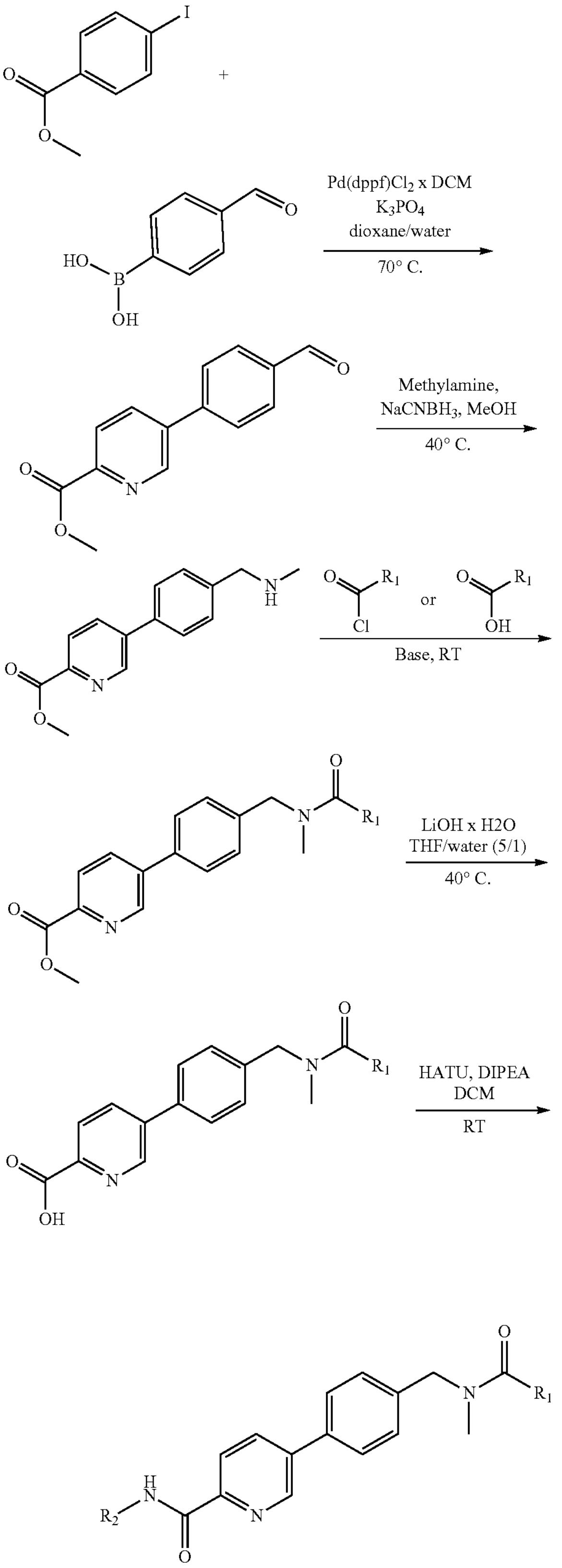

Preparation of methyl 5-(4-formylphenyl)pyridine-2-carboxylate

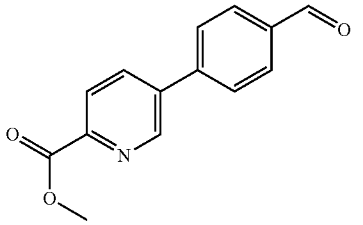 [SMILES: COC(=O)c1ccc(-c2ccc(C=O)cc2)cn1]

To a solution of methyl 5-iodopyridine-2-carboxylate (400 mg, 1.5 mmol) and (4-formylphenyl)boronic acid (200 mg, 1.3 mmol) in a mixture of dioxane (9.4 mL) and water (0.94 mL), was added $K_3PO_4$ (566 mg, 2.7 mmol). The reaction mixture was degassed with Argon for 5 min when Pd(dppf)$Cl_2$xDCM (54 mg, 0.067 mmol) was added. The reaction mixture was heated to 70° C. for 3 h. After cooling to RT, water was added (15 ml). The aqueous layer was separated, and the organic layer was concentrated in vacuo. The remaining residue was dissolved in EtOAC, and washed with a saturated solution of $NaHCO_3$, then brine. The organic layer was concentrated in vacuo and the remaining residue was triturated with acetonitrile to afford methyl 5-(4-formylphenyl)pyridine-2-carboxylate (200 mg, 62%).

LC-MS (Method 1): $R_t$=0.83 min; m/z=242.49 $(M+H)^+$

Preparation of methyl 5-[4-(methylaminomethyl)phenyl]pyridine-2-carboxylate

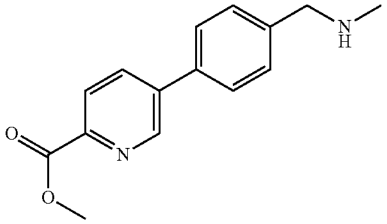 [SMILES: CNCc1ccc(-c2ccc(C(=O)OC)nc2)cc1]

To a solution of methyl 5-(4-formylphenyl)pyridine-2-carboxylate (200 mg, 0.829 mmol) in MeOH (10 mL) was added methylamine (33% in ethanol, 310 μL, 2.49 mmol), followed by molecular sieves 3A, acetic acid (47.5 μL, 0.829 mmol) and $NaBH_3CN$ (156 mg, 2.49 mmol). The reaction mixture was stirred at 40° C. overnight. The mixture was filtered through a pad of diatomaceous earth and washed with MeOH. The filtrate was concentrated under reduced pressure. The remaining residue was suspended in DCM (20 ml), washed with sat. $NaHCO_3$ (20 ml) then reduced in vacuo to afford methyl 5-[4-(methylaminomethyl)phenyl]pyridine-2-carboxylate (200 mg, 42%). The crude product was used as such in a next step.

LC-MS (Method 1): $R_t$=0.52 min; m/z=257.60 $(M+H)^+$

Preparation of methyl 5-[4-[[acetyl(methyl)amino]methyl]phenyl]pyridine-2-carboxylate

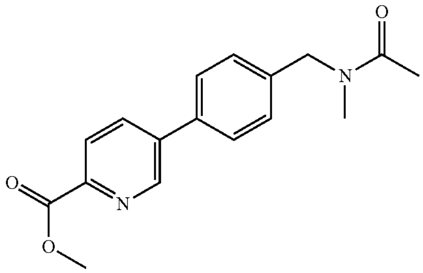 [SMILES: COC(=O)c1ccc(-c2ccc(CN(C)C(C)=O)cc2)cn1]

To a solution of methyl 5-[4-(methylaminomethyl)phenyl]pyridine-2-carboxylate (100 mg, 0.339 mmol) in dry dichlorometane (10 mL) at 0° C. (ice bath), was added triethylamine (0.095 mL, 0.679 mmol) followed by acetyl chloride (0.036 mL, 0.509 mmol). The resulting mixture was stirred at 0° C. for 5 min and then at RT for 1 h. The reaction mixture was quenched with sat. $NaHCO_3$. The layers were separated, and the organic layer was concentrated in vacuo. The remaining residue was purified by column chromatography (10% MeOH in DCM) and then triturated with acetonitrile to afford methyl 5-[4-[[acetyl(methyl)amino]methyl]phenyl]pyridine-2-carboxylate as a white solid (95 mg, 94%).

LC-MS (Method 1): $R_t$=0.77 min; m/z=299.57 $(M+H)^+$

Preparation of 5-[4-[[acetyl(methyl)amino]methyl]phenyl]pyridine-2-carboxylic acid

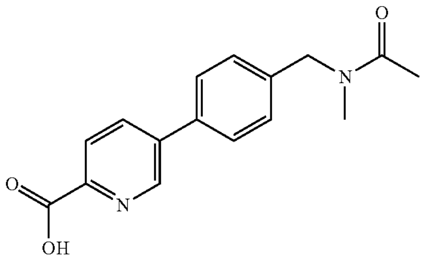 [SMILES: CC(=O)N(C)Cc1ccc(-c2ccc(C(=O)O)nc2)cc1]

To a solution of methyl 4-[5-[methyl(propanoyl)amino]-2-pyridyl]benzoate (50.0 mg, 0.168 mmol) in a mixture of tetrahydrofuran (2 mL) and water (0.7 mL), was added LiOH— $H_2O$ (6 LiOH (11.4 mg, 0.475 mmol). The reaction mixture was stirred at RT for 3 h. THF was removed in vacuo. The aqueous layer was diluted with water (1 mL) and then acidified with 1N HCl to pH=2. The product was extracted with EtOAc and the organic layer was concentrated in vacuo to afford 5-[4-[[acetyl(methyl)amino]-methyl]phenyl]pyridine-2-carboxylic acid (90 mg). The crude product was used as such in the next step.

LC-MS (Method 1): $R_t$=0.54 min; m/z=285.56 $(M+H)^+$

Preparation of 5-[4-[[acetyl(methyl)amino]methyl] phenyl]-N-(3-pyridylmethyl)pyridine-2-carboxamide (I-319)

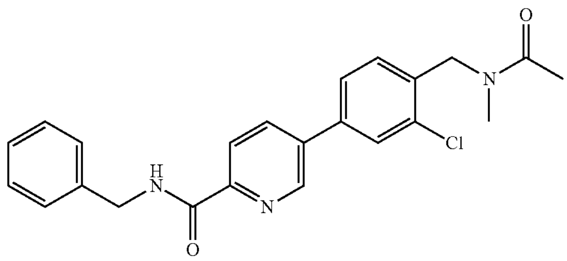 [SMILES: CC(=O)N(C)Cc1ccc(-c2ccc(C(=O)NCc3ccccc3)nc2)cc1Cl]

To a solution of 5-[4-[[acetyl(methyl)amino]methyl]phenyl]pyridine-2-carboxylic acid (49.0%, 90.0 mg, 0.155 mmol) in dry DCM (1.5 mL) was added DIPEA (55 μL, 0.31 mmol), HATU (30.2 mg, 0.186 mmol) and 3-pyridylmethanamine (24 μL, 0.160 mmol). The reaction mixture was stirred at RT for 3 h until complete conversion. The reaction mixture was washed with water (2×5 ml). The organic layer was concentrated in vacuo. Purification by flash column chromatography over silica gel (10% MeOH in DCM) and additional trituration with acetonitrile afforded 5-[4-[acetyl (methyl)amino]methyl]phenyl]-N-(3-pyridylmethyl)pyridine-2-carboxamide as a white solid (7 mg, 12%).

LC-MS (Method 6): $R_t$=2.82 min; m/z=375.62 $(M+H)^+$ $^1H$ NMR (500 MHz, DMSO-$d_6$, 80° C.): 6 [ppm]=2.08 (s, 3H), 2.95 (br. s., 3H), 4.57 (d, J=6.41 Hz, 2H), 4.57 (s, 2H) 7.33 (dd, J=8.26, 5.00 Hz, 1H), 7.38 (d, J=8.46 Hz, 2H), 7.76 (d, J=8.46 Hz, 3H), 8.12 (d, J=8.26 Hz, 1H), 8.24 (dd, J=8.36, 2.23 Hz, 1H), 8.45 (d, J=4.96 Hz, 1H), 8.59 (s, 1H), 8.92 (d, J=1.70 Hz, 1H), 9.13 (t, J=6.41 Hz, 1H).

Preparation of 6-[4-[acetyl(2-cyanoethyl)amino] phenyl]-N-(3-pyridylmethyl)pyridine-3-carboxamide (I-484)

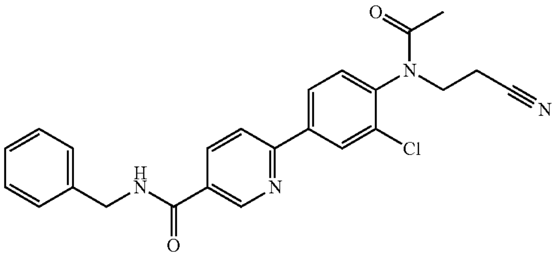 [SMILES: CC(=O)N(CCC#N)c1ccc(-c2ccc(C(=O)NCc3ccccc3)cn2)cc1Cl]

Starting from 6-[4-[acetyl(2-cyanoethyl)amino]phenyl] pyridine-3-carboxylic acid (77.0 mg, 0.22 mmol, 90%) and 3-(aminomethyl)pyridine (31.1 mg, 0.29 mmol), purification by flash column chromatography (silica gel, 10% MeOH in DCM) and trituration with diethyl ether afforded 6-[4-[acetyl(2-cyanoethyl)amino]phenyl]-N-(3-pyridylmethyl) pyridine-3-carboxamide as a white solid (26 mg, 28%).

LC-MS (Method 8): $R_t$=2.84 min; m/z=400.16 $(M+H)^+$.

$^1H$ NMR (400 MHz, DMSO-$d_6$): δ 1.83 (bs, 3H), 2.73 (t, J=6.58 Hz, 2H), 3.91 (t, J=6.58 Hz, 2H), 4.53 (d, J=5.88 Hz, 2H), 7.37 (ddd, J=7.80, 4.64, 0.89 Hz, 1H), 7.50 (d, J=8.34 Hz, 2H), 7.75 (dd, J=8.05, 2.26 Hz, 1H), 8.15 (d, J=8.35 Hz, 1H), 8.25 (d, J=8.56 Hz, 2H), 8.32 (dd, J=8.05, 2.26 Hz, 1H), 8.47 (dd, J=5.07, 1.80 Hz, 1H), 8.58 (d, J=2.37 Hz, 1H), 9.13 (dd, J=2.37, 0.82 Hz, 1H), 9.32 (t, J=5.88 Hz, 1H).

Note: The reductive amination (Step 2) was replaced by a Michael addition as follows:

Preparation of methyl 6-[4-(2-cyanoethylamino) phenyl]pyridine-3-carboxylate

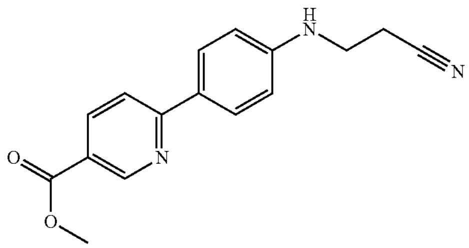 [SMILES: COC(=O)c1ccc(-c2ccc(NCCC#N)cc2)nc1]

A mixture of methyl 6-(4-aminophenyl)pyridine-3-carboxylate (200.0 mg, 0.88 mmol), but-3-enenitrile (2.18 ml, 26.30 mmol) and $AlCl_3$ (234 mg, 1.75 mmol) in acetonitrile (1.2 mL) was heated at 60° C. for 2 h. The RM was diluted with DCM and washed with aq. $NaHCO_3$. The organic layer was dried and concentrated in vacuo. Purification by flash column chromatography (silica gel, 0-60% EtOAc in cyclohexane) afforded methyl 6-[4-(2-cyanoethylamino)phenyl] pyridine-3-carboxylate (64 mg, 26%).

LC-MS (Method 2): $R_t$=0.93 min; m/z=282.14 $(M+H)^+$.

Synthesis According to Scheme 3

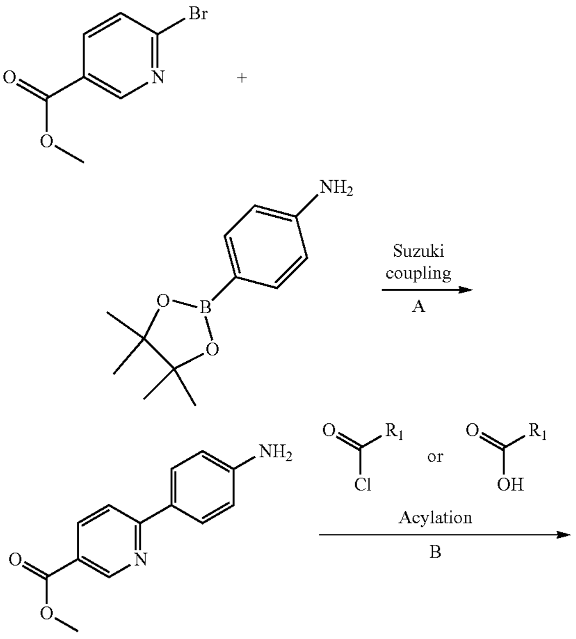

-continued

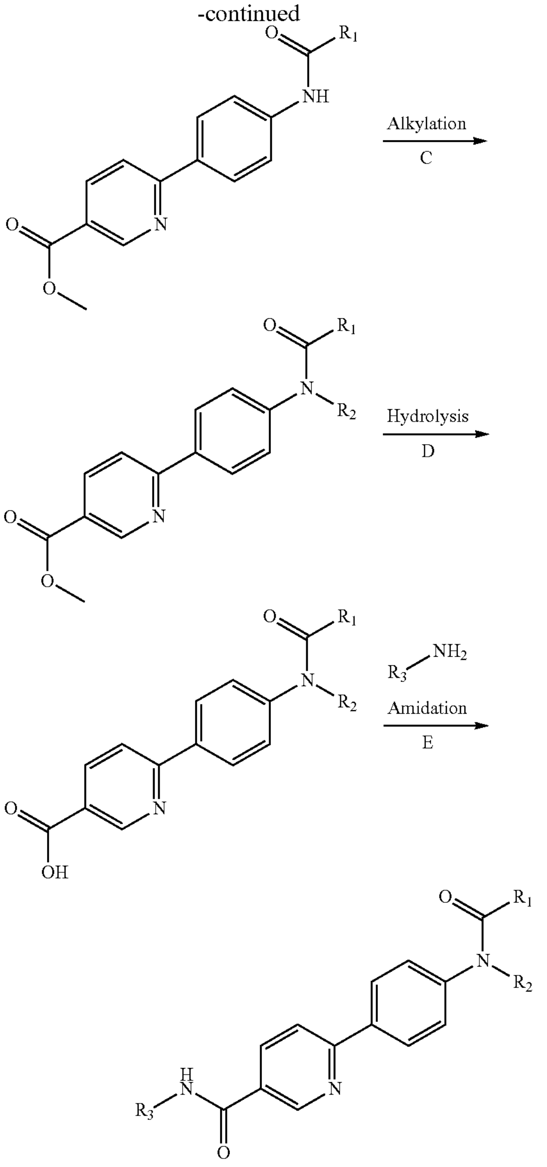

Step 1: Suzuki coupling

Preparation of methyl 5-(4-aninophenyl)pyridine-2-carboxylate

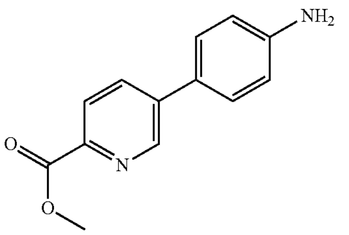 [SMILES: COC(=O)c1ccc(-c2ccc(N)cc2)cn1]

To a solution of methyl 5-iodopyridine-2-carboxylate (274 mg, 1.0 mmol) and 4-(4,4,5,5-tetramethyl-1,3,2-dioxaborolan-2-yl)aniline (200 mg, 0.91 mmol) in a mixture of 1,4-dioxane (7 mL) and water (0.7 mL), was added $K_3PO_4$ (581 mg, 2.7 mmol). The reaction mixture was degassed with argon for 5 min when $Pd(dppf)Cl_2xDCM$ (37 mg, 0.046 mmol) was added. The reaction mixture was heated to 80° C. and stirred overnight. After cooling to RT, the organic layer was concentrated in vacuo. The remaining residue was dissolved in EtOAC (50 mL) and washed with a saturated solution of $NaHCO_3$, then brine. The organic layer was concentrated in vacuo and triturated with acetonitrile to afford methyl 5-(4-aminophenyl)pyridine-2-carboxylate (171 mg, 82%).

LC-MS (Method 1): $R_t$=0.63 min; m/z=229.52 $(M+H)^+$

Step 2: Acylation

Preparation of methyl 5-[4-(ethoxycarbonylamino) phenyl]pyridine-2-carboxylate

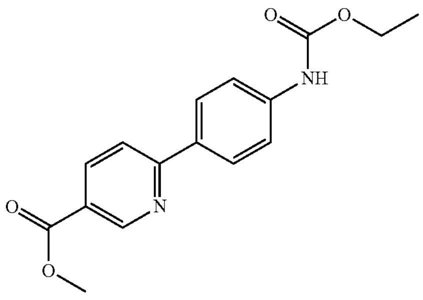 [SMILES: CCOC(=O)Nc1ccc(-c2ccc(C(=O)OC)cn2)cc1]

To a solution of methyl 5-(4-aminophenyl)pyridine-2-carboxylate (46.0 mg, 0.202 mmol) in dry dichlorometane (5 mL) at 0° C. (ice bath), was added triethylamine (56 μL, 0.40 mmol) followed by ethyl chloroformate (0.0231 mL, 0.242 mmol). The resulting mixture was stirred at 0° C. for 5 min and then at RT overnight until complete conversion of the starting material. The reaction mixture was washed with sat. $NaHCO_3$. The layers were separated, and the organic layer was concentrated in vacuo to afford crude methyl 5-[4-(ethoxycarbonylamino)phenyl]pyridine-2-carboxylate (60 mg). The crude product was used as such in a next step.

LC-MS (Method 1): $R_t$=0.92 min; m/z=301.53 $(M+H)^+$

Step 3: Alkylation

Preparation of 5-[4-[ethoxycarbonyl(methyl)amino] phenyl]pyridine-2-carboxylic acid

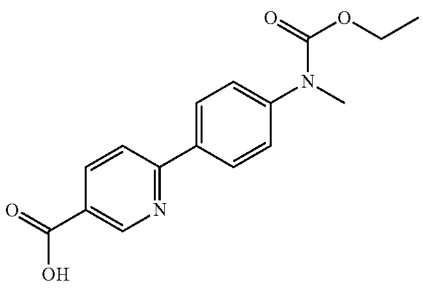 [SMILES: CCOC(=O)N(C)c1ccc(-c2ccc(C(=O)O)cn2)cc1]

To a solution of methyl 5-[4-(ethoxycarbonylamino)phenyl]pyridine-2-carboxylate (60.0 mg, 0.200 mmol) in dry DMF (2 mL), was added NaH (16 mg, 0.40 mmol). The RM was stirred at RT for 10 min. MeI (16 μL, 0.26 mmol) was then added and the reaction mixture was stirred at RT overnight. It was quenched with sat. $NH_4Cl$ (5 mL) and washed with EtOAc (2×10 ml). The aqueous layer was acidified to pH 4 and extracted with EtOAc. The combined organic layers were dried over $MgSO_4$ and evaporated in vacuo to afford crude 5-[4-[ethoxycarbonyl (methyl)amino] phenyl]pyridine-2-carboxylic acid (27 mg). It was used as such in the next step.

LC-MS (Method 1): $R_t$=0.74 min; m/z=301.59 $(M+H)^+$

Step 5: Amidation

Preparation of ethyl N-methyl-N-[4-[6-(3-pyridylmethylcarbamoyl)-3-pyridyl]phenyl]-carbamate (I-330)

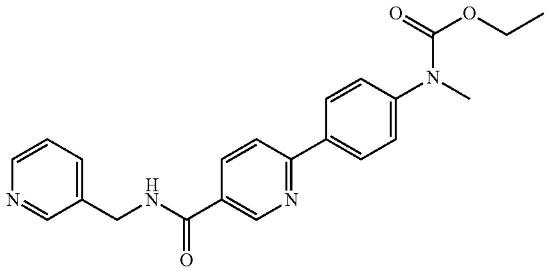 [SMILES: CCOC(=O)N(C)c1ccc(-c2ccc(C(=O)NCc3cccnc3)cn2)cc1]

To a solution of 5-[4-[ethoxycarbonyl(methyl)amino]phenyl]pyridine-2-carboxylic acid (27.0 mg, 0.0899 mmol) in dry dichlorometane (2 mL), were added DIPEA (32 μL, 0.18 mmol), HATU (18 mg, 0.11 mmol), and 3-pyridylmethanamine (11 μL, 0.11 mmol). The reaction mixture was stirred at RT for 3 h until complete conversion into the desired product. It was then diluted with dichlorometane and washed with water. The organic layer was concentrated in vacuo. Purification by flash column chromatography over silica gel (10% MeOH in DCM) and additional trituration with acetone and heptane afforded ethyl N-methyl-N-[4-[6-(3-pyridylmethylcarbamoyl)-3-pyridyl]phenyl]carbamate as a white solid (11 mg, 31%).

LC-MS (Method 6): $R_t$=3.76 min; m/z=391.68 $(M+H)^+$ $^1H$ NMR (500 MHz, DMSO-$d_6$): δ [ppm]=1.19 (t, J=7.02 Hz, 3H), 3.27 (s, 3H), 4.10 (q, J=7.02 Hz, 2H), 4.53 (d, J=6.42 Hz, 2H), 7.35 (dd, J=7.78, 4.70 Hz, 1H), 7.47 (d, J=8.39 Hz, 2H), 7.74 (d, J=8.18 Hz, 1H), 7.80 (d, J=8.39 Hz, 2H), 8.10 (d, J=8.28, 1H), 8.29 (dd, J=8.28, 2.42 Hz, 1H), 8.45 (dd, J=4.86, 1.44 Hz, 1H), 8.56 (d, J=1.82, 1H), 8.97 (d, J=2.20 Hz, 1H), 9.49 (t, J=6.42 Hz, 1H), Compound 1-389 was synthesized following Scheme 3 and the corresponding Steps 1 to 5.

Preparation of ethyl N-methyl-N-[4-[5-(3-pyridylmethylcarbamoyl)-2-pyridyl]phenyl]carbamate (I-389)

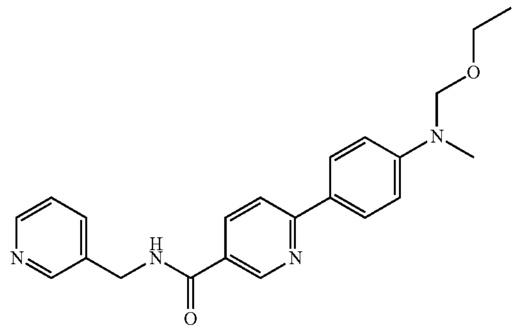 [SMILES: CCOCN(C)c1ccc(-c2ccc(C(=O)NCc3cccnc3)cn2)cc1]

Purification by prep HPLC (Method 9) afforded ethyl N-methyl-N-[4-[5-(3-pyridylmethyl-carbamoyl)-2-pyridyl] phenyl]carbamate as a white solid (44 mg, 28%).

m.p. 97.4° C.

LC-MS (Method 8): $R_t$=3.58 min; m/z=391.25 $(M+H)^+$ $^1H$ NMR (300 MHz, DMSO-$d_6$): δ [ppm]=1.18 (t, J=7.05 Hz, 3H), 3.27 (s, 3H), 4.10 (q, J=7.08 Hz, 2H), 4.53 (d, J=5.57 Hz, 2H), 7.36 (dd, J=7.84, 4.88 Hz, 1H), 7.45 (d, J=8.71 Hz, 2H), 7.75 (d, J=7.66 Hz, 1H), 8.06-8.18 (m, 3H), 8.30 (dd, J=8.45, 2.35 Hz, 1H), 8.46 (dd, J=4.70, 1.57 Hz, 1H), 8.58 (d, J=1.74 Hz, 1H), 9.10 (d, J=1.74 Hz, 1H), 9.29 (t, J=5.84 Hz, 1H).

Synthesis according to Scheme 4.

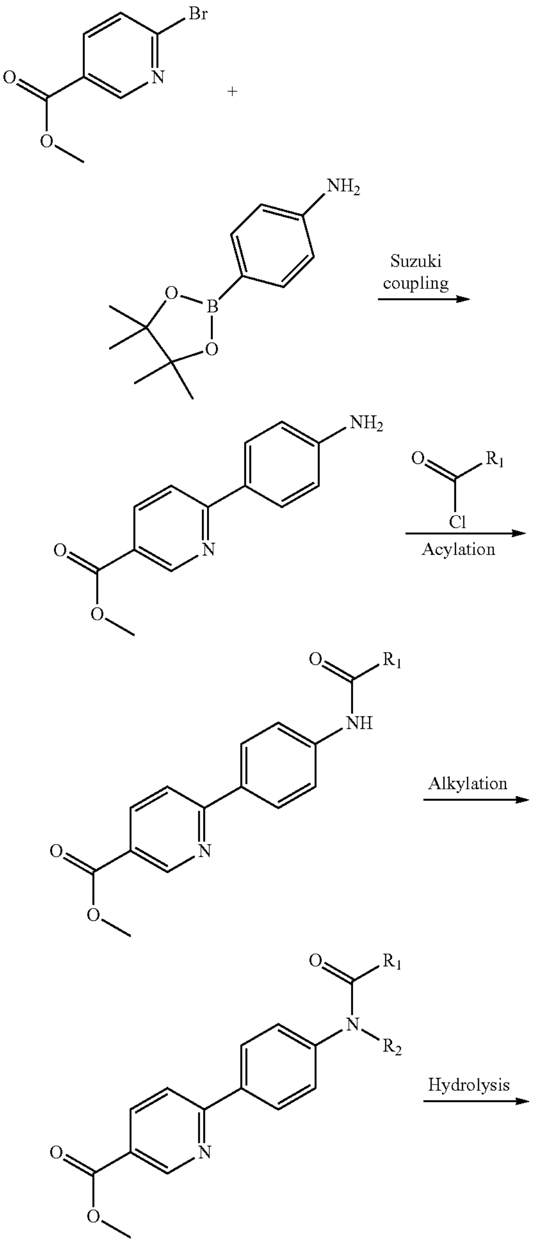

-continued

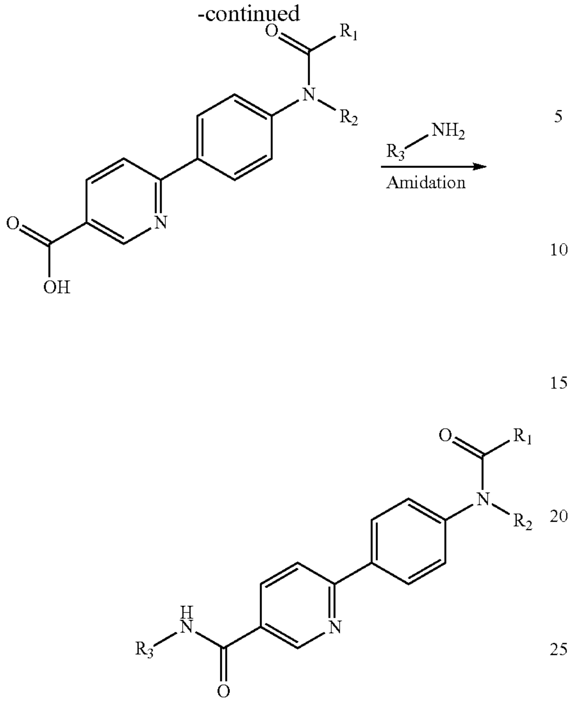

Step 1: Suzuki Coupling

Preparation of methyl 6-(4-aminophenyl)pyridine-3-carboxylate

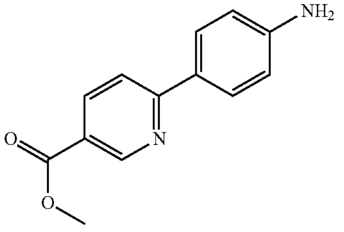 [SMILES: COC(=O)c1ccc(-c2ccc(N)cc2)nc1]

To a solution of 4-(4,4,5,5-tetramethyl-1,3,2-dioxaborolan-2-yl)aniline (10 g, 45.6 mmol) and methyl 6-bromopyridine-3-carboxylate (11.8 g, 54.8 mmol) in a mixture of 1,4-dioxane (500 mL) and water (50 mL), was added $K_3PO_4$ (29.1 g, 137 mmol). The reaction mixture was degassed with Argon for 5 min when Pd(dppf)$Cl_2$xDCM (1.86 g, 2.28 mmol) was added. The reaction mixture was heated to 70° C. and stirred overnight. After cooling to RT, the organic layer was concentrated in vacuo. The remaining residue was dissolved in EtOAC (50 mL) and washed with a saturated solution of $NaHCO_3$ and brine. The organic layer was concentrated in vacuo. The remaining residue was triturated with acetonitrile to afford methyl 6-(4-aminophenyl)pyridine-3-carboxylate as a brown solid (6.5 g, 62%).

LC-MS (Method 2): $R_t$=0.95 min; m/z=229.59 $(M+H)^+$

Step 2: Acylation

Preparation of methyl 6-[4-(propanoylamino)phenyl]pyridine-3-carboxylate

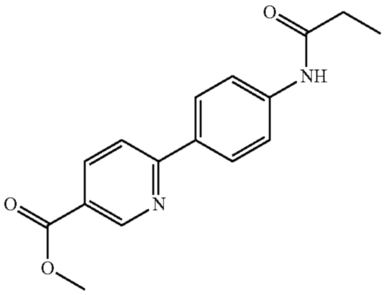 [SMILES: CCC(=O)Nc1ccc(-c2ccc(C(=O)OC)cn2)cc1]

To a solution of methyl 6-(4-aminophenyl)pyridine-3-carboxylate (6.5 g, 28 mmol) in dry dichloromethane (200 mL) at 0° C. (ice bath), was added triethylamine (7.9 mL, 57 mmol) followed by propionyl chloride (2.7 mL, 31 mmol). The resulting mixture was stirred at 0° C. for 5 min and then at RT for 4 h until complete conversion into the desired product. The reaction mixture was washed with 0.1 M HCl (2×300 mL). The solvent was removed in vacuo. The remaining residue was triturated with dichloromethane to afford methyl 6-[4-(propanoylamino)phenyl]pyridine-3-carboxylate as an orange solid (7.2 g, 81%).

LC-MS (Method 2): $R_t$=0.89 min; m/z=285.65 $(M+H)^+$

Step 3: Alkylation

Preparation of 6-[4-[methyl(propanoyl)amino]phenyl]pyridine-3-carboxylic acid

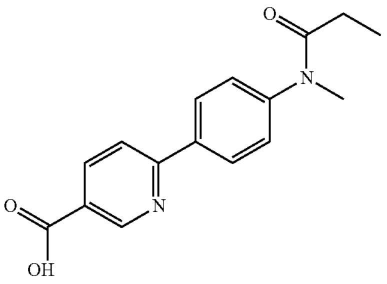 [SMILES: CCC(=O)N(C)c1ccc(-c2ccc(C(=O)O)cn2)cc1]

To a solution of methyl 6-[4-(propanoylamino)phenyl]pyridine-3-carboxylate (7.17 g, 25.2 mmol) in dry tetrahydrofuran (400 mL), was added NaH (2.52 g, 63 mmol). The RM was stirred at RT for 10 min. MeI (9.86 mL, 50.4 mmol) was then added and the reaction mixture was stirred at RT overnight. After removal of the solvent, water was added, and the solution was acidified with 1N HCl to pH=4. The resulting precipitate was collected by filtration, washed with acetonitrile and dried in vacuo to afford 6-[4-[methyl(propanoyl)amino]phenyl]pyridine-3-carboxylic acid as a yellow solid (5.3 g, 74%).

LC-MS (Method 1): $R_t$=0.40 min; m/z=285.64 $(M+H)^+$

Step 5: Amidation

Preparation of 6-[4-[methyl(propanoyl)amino]phenyl]-N-(3-pyridyl)pyridine-3-carboxamide (I-353)

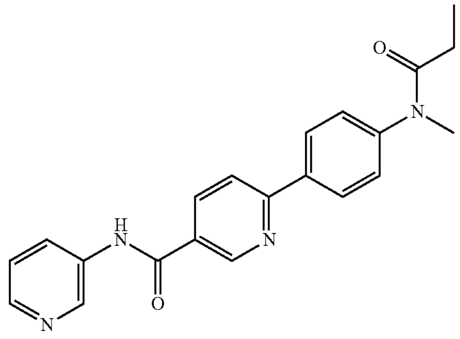 [SMILES: CCC(=O)N(C)c1ccc(-c2ccc(C(=O)Nc3cccnc3)cn2)cc1]

To a solution of 6-[4-[methyl(propanoyl)amino]phenyl]pyridine-3-carboxylic acid (80 mg, 0.27 mmol) in dry DMF (10 mL), were added DIPEA (94 μL, 0.54 mmol), HATU (94 μL, 0.54 mmol) and 3-aminopyridine (31 mg, 0.32 mmol). The reaction mixture was stirred at 40° C. for 6 h and quenched after complete conversion into the desired product. The reaction mixture diluted with EtOAc and washed with sat. $NaHCO_3$. The organic layer was concentrated in vacuo. Purification by flash column chromatography over silica gel (10% MeOH in DCM) and additional trituration with diethyl-ether afforded 6-[4-[methyl(propanoyl)amino]phenyl]-N-(3-pyridyl)pyridine-3-carboxamide as a white solid (11 mg, 11%).

m.p. 185.04° C.

LC-MS (Method 8): $R_t$=3.26 min; m/z=361.67 $(M+H)^+$ $^1$H NMR (600 MHz, DMSO-$d_6$): δ [ppm]=0.96 (t, J=7.34 Hz, 3H), 2.15 (br. s., 2H), 3.23 (s, 3H), 7.40-7.45 (m, 1H), 7.50 (d, J=8.62 Hz, 2H), 8.21 (d, J=8.44 Hz, 2H), 8.26 (d, J=8.62 Hz, 2H), 8.35 (dd, J=4.77, 1.47 Hz, 1H), 8.43 (dd, J=8.25, 2.38 Hz, 1H), 8.96 (d, J=2.57 Hz, 1H), 9.23 (dd, J=2.29, 0.83 Hz, 1H), 10.66 (s, 1H).

Compounds 1-354, 1-355, 1-390, 1-392, 1-393, 1-394, 1-395, 1-396, 1-397, I-425, I-428, I-436, I-445, I-455, I-456, I-457, 1-331, I-481, I-496, I-511, I-605, and 1-658 were synthesized following Scheme 4 and the corresponding Steps 1 to 5.

Preparation of 6-[4-[methyl(propanoyl)amino]phenyl]-N-(4-methylthiazol-2-yl)pyridine-3-carboxamide (I-355)

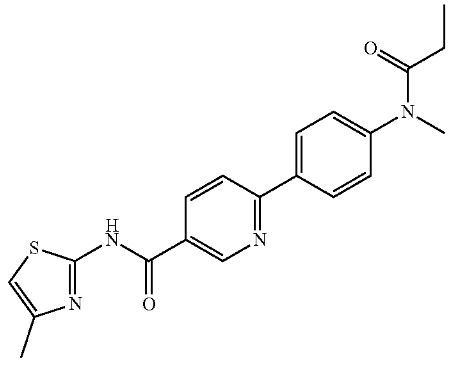 [SMILES: CCC(=O)N(C)c1ccc(-c2ccc(C(=O)Nc3nc(C)cs3)cn2)cc1]

Purification by prep HPLC (Method 9) afforded 6-[4-[methyl(propanoyl)amino]phenyl]-N-(4-methylthiazol-2-yl)pyridine-3-carboxamide as an orange solid (14.5 mg, 24%).

m.p. 176.4° C.

LC-MS (Method 8): $R_t$=2.62 min; m/z=381.64 $(M+H)^+$ $^1$H NMR (300 MHz, DMSO-$d_6$): δ [ppm] 0.94 (t, J=7.40 Hz, 3H), 2.15 (br. s., 2H), 2.31 (d, J=0.87 Hz, 3H), 3.21 (s, 3H), 6.81 (s, 1H), 7.47 (d, J=8.54 Hz, 2H), 8.10-8.30 (m, 3H), 8.50 (dd, J=8.36, 2.44 Hz, 1H), 9.28 (d, J=1.57 Hz, 1H), 12.83 (br. s., 1H).

Preparation of N-[(6-fluoro-2-methyl-3-pyridyl)methyl]-6-[4-[methyl(propanoyl)amino]phenyl]pyridine-3-carboxamide (I-390)

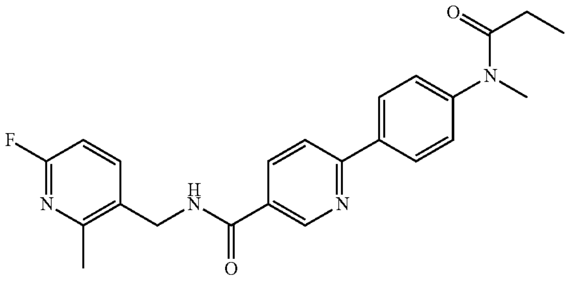 [SMILES: CCC(=O)N(C)c1ccc(-c2ccc(C(=O)NCc3ccc(F)nc3C)cn2)cc1]

Purification by flash column chromatography over silica gel (10% MeOH in DCM) and additional trituration with hexane afforded N-[(6-fluoro-2-methyl-3-pyridyl)methyl]-6-[4-[methyl(propanoyl)-amino]phenyl]pyridine-3-carboxamide as a white solid (32 mg, 74%).

LC-MS (Method 3): $R_t$=3.56 min; m/z=407.68 $(M+H)^+$ $^1$H NMR (300 MHz, DMSO-$d_6$): δ ppm 0.94 (t, J=7.40 Hz, 3H), 2.12 (br. s., 2H), 3.20 (s, 3H), 4.50 (d, J=5.40 Hz, 2H), 6.96 (dd, J=8.36, 2.79 Hz, 1H), 7.46 (d, J=8.54 Hz, 2H), 7.84 (t, J=8.36 Hz, 1H), 8.12 (d, J=8.19 Hz, 1H), 8.20 (d, J=8.71 Hz, 2H), 8.31 (dd, J=8.27, 2.00 Hz, 1H), 9.12 (d, J=1.92 Hz, 1H), 9.20 (t, J=5.40 Hz, 1H).

Preparation of 6-[4-[methyl(propanoyl)amino]phenyl]-N-[(2-methyl-3-pyridyl)methyl]pyridine-3-carboxamide (I-392)

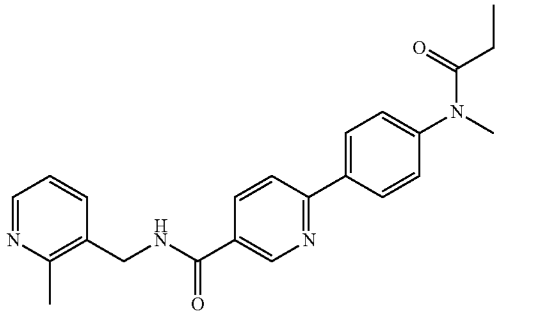 [SMILES: CCC(=O)N(C)c1ccc(-c2ccc(C(=O)NCc3cccnc3C)cn2)cc1]

Purification by prep HPLC (Method 9) afforded 6-[4-[methyl(propanoyl)amino]phenyl]-N-[(2-methyl-3-pyridyl)methyl]pyridine-3-carboxamide as a white solid (35 mg, 50%).

LC-MS (Method 4): $R_t$=1.28 min; m/z=389.72 $(M+H)^+$ $^1$H NMR (500 MHz, DMSO–$d_6$): δ [ppm]=0.94 (t, J=7.8 Hz, 3H), 2.05-2.21 (m, 2H), 2.53 (s, 3H), 3.21 (s, 3H), 4.51 (d, J=5.7 Hz, 2H), 7.20 (dd, J=5.1, 7.9 Hz, 1H), 7.46 (d, J=8.3 Hz, 2H), 7.63 (d, J=7.9 Hz, 1H), 8.13 (d, J=8.4 Hz, 1H), 8.21 (d, J=8.4 Hz, 2H), 8.31-8.36 (m, 2H), 9.14 (d, J=1.88 Hz, 1H), 9.21 (t, J=5.6 Hz, 1H).

Preparation of N-[(6-fluoro-3-pyridyl)methyl]-6-[4-[methyl(propanoyl)amino]phenyl]pyridine-3-carboxamide (I-393)

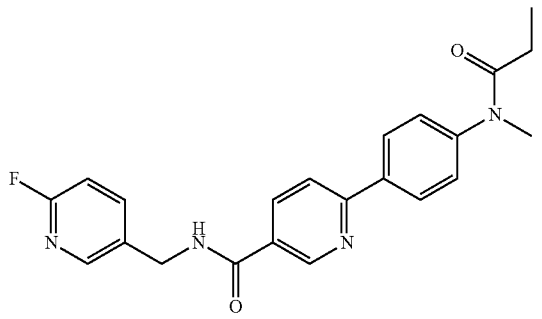 [SMILES: CCC(=O)N(C)c1ccc(-c2ccc(C(=O)NCc3ccc(F)nc3)cn2)cc1]

Purification by prep HPLC (Method 9) afforded N-[(6-fluoro-3-pyridyl)methyl]-6-[4-[methyl(propanoyl)amino]phenyl]pyridine-3-carboxamide as a white solid (27 mg, 23%).

LC-MS (Method 8): $R_t$=3.44 min; m/z=393.73 $(M+H)^+$ $^1$H NMR (300 MHz, DMSO–$d_6$): δ [ppm]=0.93 (t, J=7.4 Hz, 3H), 2.03-2.21 (m, 2H), 3.20 (s, 3H), 4.53 (d, J=6.1 Hz, 2H), 7.16 (dd, J=2.8, 8.4 Hz, 1H), 7.45 (d, J=8.8 Hz, 2H), 7.96 (dt, J=2.5, 8.2 Hz, 1H), 8.12 (d, J=8.3 Hz, 1H), 8.20 (d, J=8.8 Hz, 2H), 8.21-8.24 (m, 1H), 8.30 (dd, J=2.4, 8.3 Hz, 1H), 9.11 (d, J=2.07 Hz, 1H), 9.30 (t, J=5.5 Hz, 1H).

Preparation of N-[(2,6-dimethyl-3-pyridyl)methyl]-6-[4-[methyl(propanoyl)amino]phenyl]pyridine-3-carboxamide (I-394)

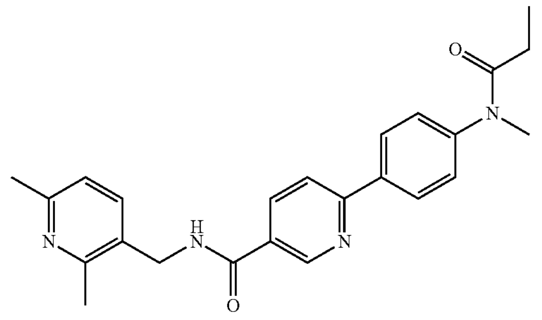 [SMILES: CCC(=O)N(C)c1ccc(-c2ccc(C(=O)NCc3ccc(C)nc3C)cn2)cc1]

Purification by prep HPLC (Method 9) afforded N-[(2,6-dimethyl-3-pyridyl)methyl]-6-[4-[methyl(propanoyl)amino]phenyl]pyridine-3-carboxamide as a white solid (29 mg, 30%).

LC-MS (Method 8): $R_t$=2.51 min; m/z=403.76 $(M+H)^+$ $^1$H NMR (300 MHz, DMSO–$d_6$): δ [ppm]=0.94 (t, J=7.5 Hz, 3H), 2.04-2.21 (m, 2H), 2.39 (s, 3H), 3.20 (s, 3H), 4.46 (d, J=5.4 Hz, 2H), 7.09 (d, J=7.7 Hz, 1H), 7.45 (d, J=8.6 Hz, 2H), 7.51 (d, J=7.7 Hz, 1H), 8.11 (d, J=8.7 Hz, 1H), 8.20 (d, J=8.4 Hz, 2H), 8.31 (dd, J=2.2, 8.4 Hz, 1H), 9.11 (d, J=2.2 Hz, 1H), 9.14 (t, J=5.5 Hz, 1H).

Preparation of N-[(2-chloro-3-pyridyl)methyl]-6-[4-[methyl(propanoyl)amino]phenyl]pyridine-3-carboxamide (I-395)

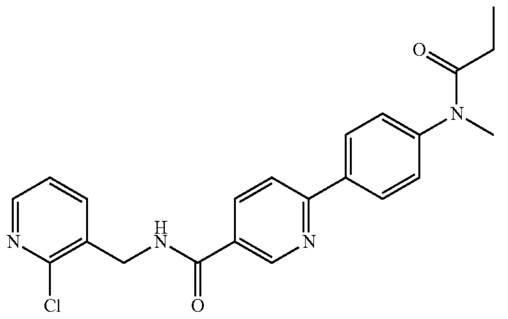 [SMILES: CCC(=O)N(C)c1ccc(-c2ccc(C(=O)NCc3cccnc3Cl)cn2)cc1]

Purification by prep HPLC (Method 9) afforded N-[(2-chloro-3-pyridyl)methyl]-6-[4-[methyl(propanoyl)amino]phenyl]pyridine-3-carboxamide as a white solid (30 mg, 50%).

LC-MS (Method 6): $R_t$=3.44 min; m/z=409.14 $(M+H)^+$ $^1$H NMR (300 MHz, DMSO–$d_6$): δ [ppm] 0.94 (t, J=7.4 Hz, 3H), 2.13 (bs, 2H), 3.21 (s, 3H), 4.56 (d, J=5.5 Hz, 2H), 7.44-7.40 (m, 1H), 7.47 (d, J=8.6 Hz, 2H), 7.85 (dd, J=7.6, 1.8 Hz, 1H), 8.14 (d, J=8.4 Hz, 1H), 8.21 (d, J=8.5 Hz, 2H), 8.38-8.30 (m, 2H), 9.15 (d, J=1.6 Hz, 1H), 9.33 (t, J=5.6 Hz, 1H).

Preparation of N-[(6-chloro-3-pyridyl)methyl]-6-[4-[methyl(propanoyl)amino]phenyl]pyridine-3-carboxamide (I-396)

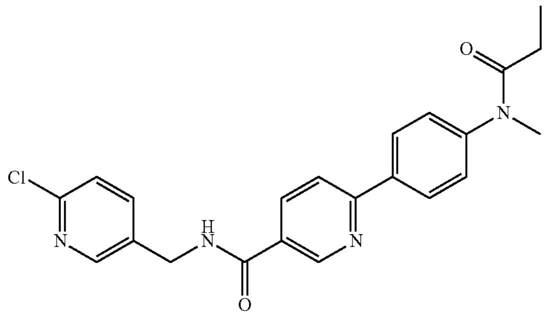 [SMILES: CCC(=O)N(C)c1ccc(-c2ccc(C(=O)NCc3ccc(Cl)nc3)cn2)cc1]

Purification by prep HPLC (Method 9) afforded N-[(6-chloro-3-pyridyl)methyl]-6-[4-[methyl(propanoyl)amino]phenyl]pyridine-3-carboxamide as a white solid (45 mg, 79%).

LC-MS (Method 6): $R_t$=1.28 min; m/z=389.72 $(M+H)^+$ $^1$H NMR (300 MHz, DMSO–$d_6$): δ [ppm] 0.95 (t, J=7.4 Hz, 3H), 2.15 (bs, 2H), 3.21 (s, 3H), 4.54 (d, J=5.7 Hz, 2H), 7.47 (d, J=8.6 Hz, 2H), 7.50 (d, J=8.2 Hz, 1H), 7.84 (dd, J=8.2, 2.5 Hz, 1H), 8.14 (d, J=8.4 Hz, 1H), 8.21 (d, J=8.6 Hz, 2H), 8.31 (dd, J=8.4, 2.3 Hz, 1H), 8.42 (d, J=2.4 Hz, 1H), 9.12 (d, J=1.7 Hz, 1H), 9.33 (t, J=5.8 Hz, 1H).

Preparation of N-[(6-methoxy-3-pyridyl)methyl]-6-[4-[methyl(propanoyl)amino]phenyl]pyridine-3-carboxamide (I-397)

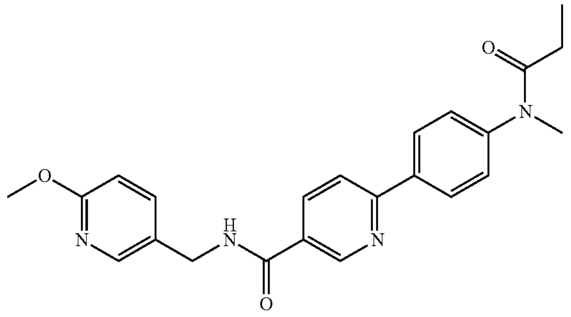 [SMILES: CCC(=O)N(C)c1ccc(-c2ccc(C(=O)NCc3ccc(OC)nc3)cn2)cc1]

Purification by prep HPLC (Method 9) afforded N-[(6-methoxy-3-pyridyl)methyl]-6-[4-[methyl(propanoyl)amino]phenyl]pyridine-3-carboxamide as a white solid (38 mg, 67%).

LC-MS (Method 6): $R_t$=3.40 min; m/z=405.22 $(M+H)^+$ $^1$H NMR (300 MHz, DMSO-$d_6$): δ [ppm] 0.94 (t, J=7.5 Hz, 3H), 2.14 (bs, 2H), 3.21 (s, 3H), 3.83 (s, 3H), 4.45 (d, J=5.6 Hz, 2H), 6.80 (d, J=8.4 Hz, 1H), 7.46 (d, J=8.6 Hz, 2H), 7.70 (dd, J=8.6, 2.4 Hz, 1H), 8.12 (d, J=8.4 Hz, 1H), 8.16 (d, J=2.4 Hz, 1H), 8.21 (d, J=8.6 Hz, 2H), 8.30 (dd, J=8.4, 2.4 Hz, 1H), 9.11 (d, J=2.0 Hz, 1H), 9.24 (t, J=5.9 Hz, 1H).

Preparation of 6-[4-(propanoylamino)phenyl]-N-(3-pyridylmethyl)pyridine-3-carboxamide (I-354)

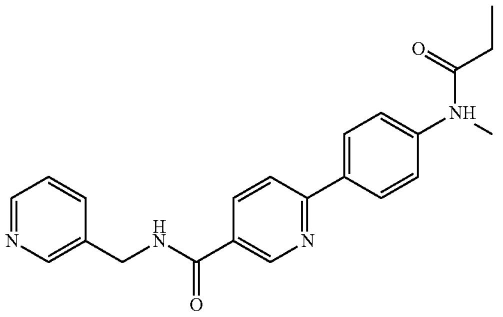 [SMILES: CCC(=O)N(C)c1ccc(-c2ccc(C(=O)NCc3cccnc3)cn2)cc1]

Purification by prep HPLC (Method 9) afforded 6-[4-(propanoylamino)phenyl]-N-(3-pyridylmethyl)pyridine-3-carboxamide as white solid (4 mg, 7%).

LC-MS (Method 8): $R_t$=2.95 min; m/z=361.67 $(M+H)^+$ $^1$H-NMR (300 MHz, DMSO-$d_6$): δ [ppm]=1.09 (t, J=7.58 Hz, 3H), 2.35 (q, J=7.61 Hz, 2H), 4.53 (d, J=5.57 Hz, 2H), 7.36 (dd, J=7.75, 4.79 Hz, 1H), 7.73 (d, J=8.71 Hz, 3H), 8.02 (d, J=8.01 Hz, 1H), 8.10 (d, J=8.71 Hz, 2H), 8.26 (dd, J=8.36, 2.26 Hz, 1H), 8.43-8.50 (m, 1H), 8.57 (d, J=1.57 Hz, 1H), 9.07 (d, J=1.57 Hz, 1H), 9.28 (t, J=5.75 Hz, 1H), 10.07 (s, 1H).

Preparation of 6-[4-[acetyl(methyl)amino]-3-methyl-phenyl]-N-(3-pyridylmethyl)pyridine-3-carboxamide (I-425)

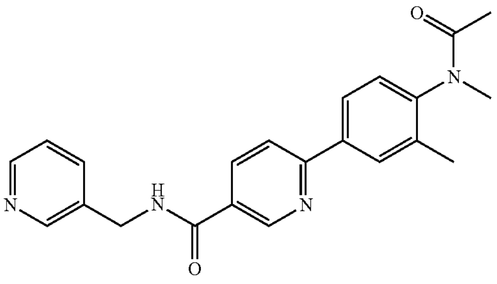 [SMILES: CC(=O)N(C)c1ccc(-c2ccc(C(=O)NCc3cccnc3)cn2)cc1C]

Purification by flash column chromatography over silica gel (10% MeOH in DCM) afforded 6-[4-[acetyl(methyl)amino]-3-methyl-phenyl]-N-(3-pyridylmethyl)pyridine-3-carboxamide as an orange paste (14 mg, 24%).

LC-MS (Method 4): $R_t$=1.17 min; m/z=375.40 $(M+H)^+$ $^1$H NMR (500 MHz, DMSO-d6): δ [ppm]=1.69 (s, 3H) 2.28 (s, 3H), 3.09 (s, 3H), 4.55 (d, J=5.81 Hz, 2H), 7.35-7.42 (m, 2H), 7.77 (d, J=8.26, 1H), 8.05 (d, J=8.99, 1H), 8.11-8.18 (m, 2H), 8.32 (dd, J=2.11, 8.45 Hz, 1H), 8.48 (d, J=4.53 Hz, 1H), 8.59 (br.s.,1H), 9.13 (d, J=2.00 Hz, 1H), 9.33 (t, J=5.80 Hz, 1H).

Preparation of 6-[4-[acetyl(methyl)amino]-3-methyl-phenyl]-N-[(2-methyl-3-pyridyl)methyl]pyridine-3-carboxamide (I-428)

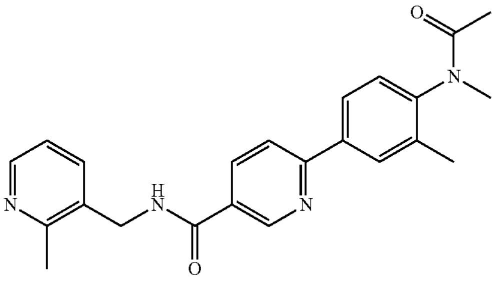 [SMILES: CC(=O)N(C)c1ccc(-c2ccc(C(=O)NCc3cccnc3C)cn2)cc1C]

Purification by flash column chromatography over silica gel (10% MeOH in DCM) afforded 6-[4-[acetyl(methyl)amino]-3-methyl-phenyl]-N-[(2-methyl-3-pyridyl)methyl]pyridine-3-carboxamide as a white solid (18 mg, 31%).

LC-MS (Method 6): $R_t$=3.04 min; m/z=389.16 $(M+H)^+$ $^1$H-NMR (500 MHz, DMSO-$d_6$): δ [ppm]=1.69 (s, 3H), 2.28 (s, 3H), 2.54 (s, 3H), 3.09 (s, 3H), 4.52 (d, J=5.6 Hz, 2H), 7.21 (dd, J=7.6, 4.9 Hz, 1H), 7.40 (d, J=8.2 Hz, 1H), 7.64 (d, J=7.6 Hz, 1H), 8.06 (dd, J=8.2, 1.6 Hz, 1H), 8.14 (d, J=8.3 Hz, 1H), 8.17 (d, J=1.2 Hz, 1H), 8.39-8.29 (m, 2H), 9.14 (d, J=1.6 Hz, 1H), 9.22 (t, J=5.6 Hz, 1H).

Preparation of 6-[4-[acetyl(methyl)amino]-3-methyl-phenyl]-N-[(2-fluoro-3-pyridyl)methyl]pyridine-3-carboxamide (I-436)

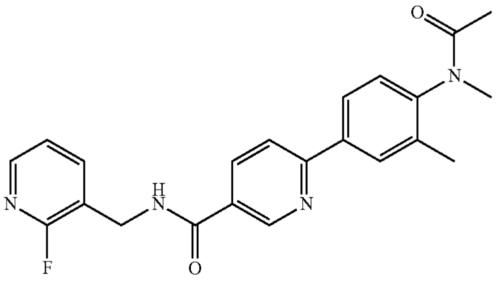 [SMILES: CC(=O)N(C)c1ccc(-c2ccc(C(=O)NCc3cccnc3F)cn2)cc1C]

Purification by flash column chromatography over silica gel (10% MeOH in DCM) afforded 6-[4-[acetyl(methyl)amino]-3-methyl-phenyl]-N-[(2-fluoro-3-pyridyl)methyl]pyridine-3-carboxamide as a white solid (25 mg, 22%).

LC-MS (Method 6): $R_t$=3.21 min; m/z=393.13 $(M+H)^+$ $^1$H-NMR (500 MHz, DMSO-$d_6$): δ [ppm]=1.69 (s, 3H), 2.28 (s, 3H), 3.09 (s, 3H), 4.54 (d, J=5.5 Hz, 2H), 7.35 (t, J=5.3 Hz, 1H), 7.40 (d, J=8.2 Hz, 1H), 7.95 (t, J=8.6 Hz, 1H), 8.06 (d, J=8.2 Hz, 1H), 8.20-8.12 (m, 3H), 8.33 (dd, J=8.3, 2.1 Hz, 1H), 9.13 (d, J=1.7 Hz, 1H), 9.33 (t, J=5.6 Hz, 1H).

Preparation of 6-[4-[acetyl(methyl)amino]-3-ethyl-phenyl]-N-[(2-methyl-3-pyridyl)methyl]pyridine-3-carboxamide (I-445)

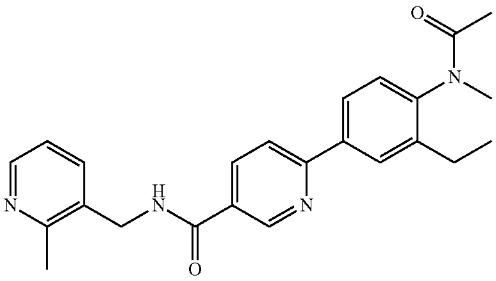 [SMILES: CCc1cc(-c2ccc(C(=O)NCc3cccnc3C)cn2)ccc1N(C)C(C)=O]

Purification by flash column chromatography over silica gel (10% MeOH in DCM) and additional trituration with diethyl ether afforded 6-[4-[acetyl(methyl)amino]-3-ethyl-phenyl]-N-[(2-methyl-3-pyridyl)methyl]pyridine-3-carboxamide as a white solid (62 mg, 62%).

LC-MS (Method 8): $R_t$=3.27 min; m/z=403.16 $(M+H)^+$ $^1$H-NMR (500 MHz, DMSO-$d_6$): δ [ppm]=1.25 (t, J=7.5 Hz, 3H), 1.70 (s, 3H), 2.54 (s, 3H), 2.60 (q, J=7.5 Hz, 2H), 3.10 (s, 3H), 4.52 (d, J=5.5 Hz, 2H), 7.21 (dd, J=7.5, 5.5 Hz, 1H), 7.39 (d, J=8.5 Hz, 1H), 7.64 (d, J=7.5 Hz, 1H), 8.05 (dd, J=8.0, 2.0 Hz, 1H), 8.16 (d, J=8.0 Hz, 1H), 8.18 (d, J=2.0 Hz, 1H), 8.34 (dd, J=8.5, 2.5 Hz, 2H), 9.15 (d, J=2.0 Hz, 1H), 9.22 (t, J=5.5 Hz, 1H).

Preparation of 6-[4-[acetyl(methyl)amino]-3-(trifluoromethyl)phenyl]-N-[(2-methyl-3-pyridyl)methyl]pyridine-3-carboxamide (I-455)

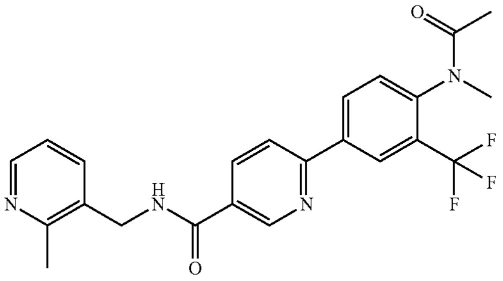 [SMILES: CC(=O)N(C)c1ccc(-c2ccc(C(=O)NCc3cccnc3C)cn2)cc1C(F)(F)F]

Purification by flash column chromatography over silica gel (10% MeOH in DCM) afforded 6-[4-[acetyl(methyl)amino]-3-(trifluoromethyl)phenyl]-N-[(2-methyl-3-pyridyl)methyl]pyridine-3-carboxamide as a white solid (18 mg, 22%).

LC-MS (Method 8): $R_t$=3.48 min; m/z=443.07 $(M+H)^+$ $^1$H-NMR (400 MHz, DMSO-$d_6$, mixture of rotamers at 25° C.): 6 [ppm]=1.68 and 2.18 (s, 3H), 2.53 (s, 3H) 3.10 and 3.27 (s, 3H), 4.52 (d, J=5.84 Hz, 2H), 7.63 (dd, J=7.70, 1.67 Hz, 1H), 7.57 and 7.77 (d, J=8.38 Hz, 1H), 8.25 and 8.30 (dd, J=8.29, 0.80 Hz, 1H), 8.33 (dd, J=4.77, 1.55 Hz, 1H), 8.37 (d, J=2.22 Hz, 1H), 8.36 and 8.40 (d, J=2.02 Hz, 1H), 8.48 and 8.55 (dd, J=8.29, 1.96 Hz, 1H), 8.49 and 8.59 (d, J=2.02 Hz, 1H), 9.16 and 9.18 (dd, J=2.02, 0.80 Hz, 1H), 9.26 (t, J=5.84 Hz, 1H).

Preparation of 6-[4-[acetyl(methyl)amino]-3-cyano-phenyl]-N-[(2-methyl-3-pyridyl)methyl]pyridine-3-carboxamide (I-456)

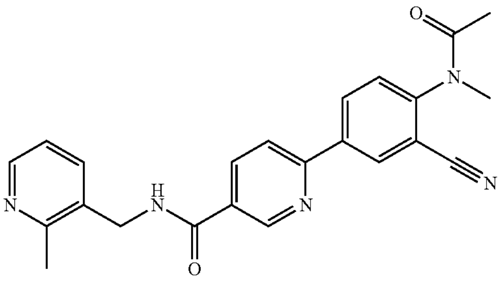 [SMILES: CC(=O)N(C)c1ccc(-c2ccc(C(=O)NCc3cccnc3C)cn2)cc1C#N]

Purification by flash column chromatography over silica gel (10% MeOH in DCM) afforded 6-[4-[acetyl(methyl)amino]-3-cyano-phenyl]-N-[(2-methyl-3-pyridyl)methyl]pyridine-3-carboxamide as a white solid (10 mg, 15%).

LC-MS (Method 2): $R_t$=0.73 min; m/z=400.10 $(M+H)^+$ $^1$H-NMR (500 MHz, DMSO-$d_6$): δ [ppm]=2.82 (s, 3H), 2.54 (s, 3H), 3.21 (s, 3H), 4.52 (d, J=5 Hz, 2H), 7.19-7.22 (m, 1H), 7.63 (d, J=6.0 Hz, 1H), 7.81 (d, J=8.0 Hz, 1H), 8.28 (d, J=8.0 Hz, 1H), 8.33-8.35 (m, 1H), 8.40 (d, J=7.5 Hz, 1H), 8.79 (d, J=8.5 Hz, 1H), 8.73 (s, 1H), 9.17 (s, 1H), 9.26 (t, J=4.5 Hz, 1H).

Preparation of methyl 2-[acetyl(methyl)amino]-5-[5-[(2-methyl-3-pyridyl)methylcarbamoyl]-2-pyridyl]benzoate (I-457)

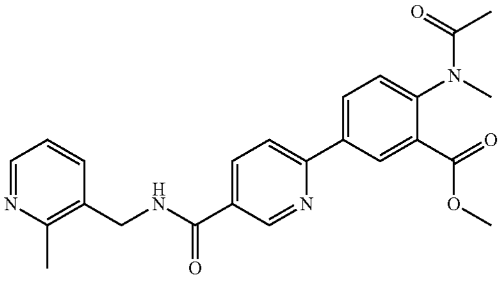 [SMILES: COC(=O)c1cc(-c2ccc(C(=O)NCc3cccnc3C)cn2)ccc1N(C)C(C)=O]

Purification by flash column chromatography over silica gel (10% MeOH in DCM) afforded methyl 2-[acetyl(methyl)amino]-5-[5-[(2-methyl-3-pyridyl)methylcarbamoyl]-2-pyridyl]-benzoate as a white solid (2 mg, 3%).

LC-MS (Method 2): $R_t$=0.74 min; m/z=433.12 $(M+H)^+$ $^1$H-NMR (500 MHz, DMSO-$d_6$): δ [ppm]=1.65 (s, 3H), 2.54 (s, 3H), 3.08 (s, 3H), 3.87 (s, 3H), 4.52 (d, J=5.0, 2H), 7.21 (t, J=6.0 Hz, 1H), 7.62-7.65 (m, 2H), 8.22 (d, J=8.5 Hz, 1H), 8.34 (d, J=5.0 Hz, 1H), 8.38 (d, J=8.5 Hz, 1H), 8.45 (d, J=8.0 Hz, 1H), 8.71 (s, 1H), 9.17 (s, 1H), 9.26 (t, J=5.5 Hz, 1H).

6-[4-[Methyl(propanoyl)amino]phenyl]-N-(3-pyridylmethyl)pyridine-3-carboxamide (I-331)

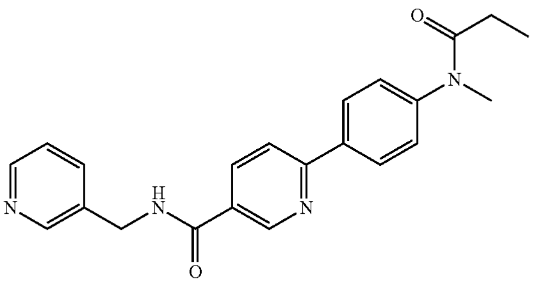 [SMILES: CCC(=O)N(C)c1ccc(-c2ccc(C(=O)NCc3cccnc3)cn2)cc1]

Purification by flash column chromatography afforded 6-[4-[methyl(propanoyl)amino]phenyl]-N-(3-pyridylmethyl)pyridine-3-carboxamide (50 mg) as a colourless solid. m.p.=115.7° C.

LC-MS (Method 2): $R_t$=0.75 min; m/z=375.64 $(M+H)^+$.

$^1$H NMR (500 MHz, DMSO-$d_6$): δ 0.95 (t, J=7.3 Hz, 3H), 2.13 (br. s., 2H), 3.21 (s, 3H), 4.55 (d, J=5.8 Hz, 2H), 7.40 (dd, J=7.6, 4.9 Hz, 1H), 7.47 (d, J=8.2 Hz, 2H), 7.80 (d, J=7.6 Hz, 1H), 8.14 (d, J=8.2 Hz, 1H), 8.21 (d, J=8.2 Hz, 2H), 8.32 (dd, J=8.2, 1.8 Hz, 1H), 8.49 (d, J=4.9 Hz, 1H), 8.60 (s, 1H), 9.13 (s, 1H), 9.28-9.38 (m, 1H).

4-[3—Chloro-4-[methyl(propanoyl)amino]phenyl]-N-[(2,6-dimethyl-3-pyridyl)methyl]benzamide (I-481)

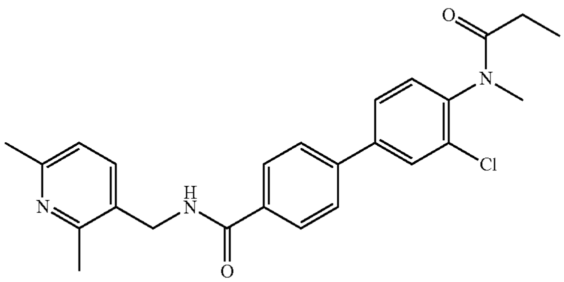 [SMILES: CCC(=O)N(C)c1ccc(-c2ccc(C(=O)NCc3ccc(C)nc3C)cc2)cc1Cl]

Purification by flash column chromatography (silica gel, 10% MeOH in DCM) afforded 4-[3-chloro-4-[methyl(propanoyl)amino]phenyl]-N-[(2,6-dimethyl-3-pyridyl)methyl] benzamide as a white amorphous solid (465 mg, 69%).

LC-MS (Method 8): $R_t$=4.05 min; m/z=436.20 $(M+H)^+$.

$^1$H-NMR (400 MHz, DMSO-$d_6$): δ 0.93 (t, J=7.83 Hz, 3H), 1.86 (m, 1H), 1.99 (m, 1H), 2.38 (s, 3H), 3.09 (s, 3H), 4.44 (d, J=5.71 Hz, 2H), 7.03 (d, J=7.81 Hz, 1H), 7.48 (d, J=7.81 Hz, 1H), 7.63 (d, J=8.22 Hz, 1H), 7.81 (dd, J=8.24, 2.18 Hz, 1H), 7.86 (d, J=8.50 Hz, 2H), 7.97-8.02 (m, 3H), 9.04 (t, J=5.71 Hz, 1H).

N-methyl-6-[3-methyl-4-[methyl(propanoyl)amino]phenyl]-N-(3-pyridylmethyl)pyridine-3-carboxamide (I-496)

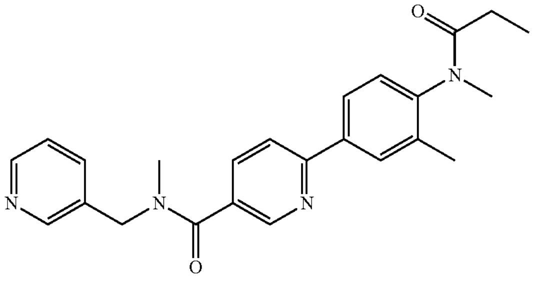 [SMILES: CCC(=O)N(C)c1ccc(-c2ccc(C(=O)N(C)Cc3cccnc3)cn2)cc1C]

Purification by flash column chromatography (silica gel, 5% MeOH in DCM) afforded N-methyl-6-[3-methyl-4-[methyl(propanoyl)amino]phenyl]-N-(3-pyridylmethyl) pyridine-3-carboxamide as a white amorphous solid (25 mg, 30%).

LC-MS (Method 8): $R_t$=3.31 min; m/z=403.20 $(M+H)^+$.

$^1$H-NMR (300 MHz, DMSO-$d_6$): δ 0.90 (t, J=7.90 Hz, 3H), 1.73-2.02 (m, 2H), 2.24 (s, 3H), 2.95 (s, 3H), 3.08 (s, 3H), 4.72 (s, 2H), 7.31-7.45 (m, 2H), 7.62-7.84 (m, 1H), 7.88-8.15 (m, 4H), 8.51 (d, J=4.60 Hz, 1H), 8.48 (d, J=4.53 Hz, 1H), 8.60 (br.s.,0.5H), 8.79 (br.s.,0.5H).

6-[3-Methyl-4-[methyl(propanoyl)amino]phenyl]-N-[[2-(trifluoromethyl)-3-pyridyl]methyl]pyridine-3-carboxamide (I-511)

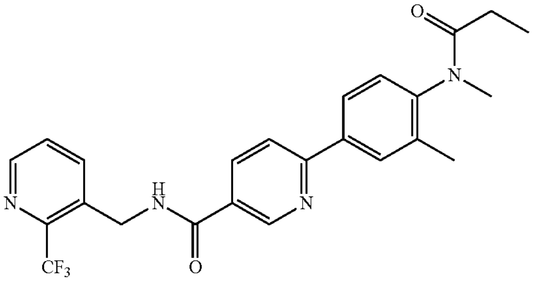 [SMILES: CCC(=O)N(C)c1ccc(-c2ccc(C(=O)NCc3cccnc3C(F)(F)F)cn2)cc1C]

Purification by flash column chromatography (silica gel, 10% MeOH in DCM) afforded 6-[3-methyl-4-[methyl(propanoyl)amino]phenyl]-N-[[2-(trifluoromethyl)-3-pyridyl]methyl]pyridine-3-carboxamide as a white amorphous solid (41.1 mg, 39%).

LC-MS (Method 8): $R_t$=3.96 min; m/z=457.11 $(M+H)^+$.

$^1$H NMR (500 MHz, DMSO-$d_6$): δ 0.92 (t, J=7.4 Hz, 3H), 1.84 (q, J=7.4 Hz, 1H), 1.98 (q, J=7.5 Hz, 1H), 2.27 (s, 3H), 3.10 (s, 3H), 4.72 (d, J=5.1 Hz, 2H), 7.39 (d, J=8.2 Hz, 1H), 7.73 (dd, J=7.9, 4.7 Hz, 1H), 8.06 (d, J=8.1 Hz, 2H), 8.14-8.19 (m, 2H), 8.35 (dd, J=8.4, 2.2 Hz, 1H), 8.65 (d, J=4.4 Hz, 1H), 9.16 (d, J=1.8 Hz, 1H), 9.39 (t, J=5.7 Hz, 1H).

6-[4-[Acetyl(methyl)amino]-3-ethyl-phenyl]-N-(3-pyridylmethyl)pyridine-3-carboxamide (I-605)

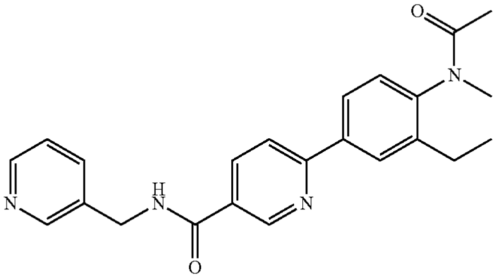 [SMILES: CCc1cc(-c2ccc(C(=O)NCc3cccnc3)cn2)ccc1N(C)C(C)=O]

Purification by flash column chromatography (silica gel, 10% MeOH in DCM) afforded 6-[4-[acetyl(methyl)amino]-3-ethyl-phenyl]-N-(3-pyridylmethyl)pyridine-3-carboxamide as a white amorphous solid (25 mg, 19%).

LC-MS (Method 8): $R_t$=3.17 min; m/z=389.22 $(M+H)^+$.

$^1$H NMR (500 MHz, DMSO-$d_6$) δ 1.25 (t, J=7.48 Hz, 3H), 1.69 (s, 3H), 2.60 (q, J=7.63 Hz, 2H), 3.10 (s, 3H), 4.55 (d, J=5.80 Hz, 2H), 7.37-7.41 (m, 2H), 7.78 (d, J=7.63 Hz, 1H), 8.06 (dd, J=8.24, 2.14 Hz, 1H), 8.16 (d, J=8.24 Hz, 1H), 8.18 (d, J=2.14 Hz, 1H), 8.33 (dd, J=8.39, 2.29 Hz, 1H), 8.49 (dd, J=4.73, 1.37 Hz, 1H), 8.60 (s, 1H), 9.14 (d, J=1.83 Hz, 1H), 9.33 (t, J=5.80 Hz, 1H).

6-[4-[Acetyl(methyl)amino]-3-(trifluoromethyl)phenyl]-N-(3-pyridylmethyl)pyridine-3-carboxamide (I-658)

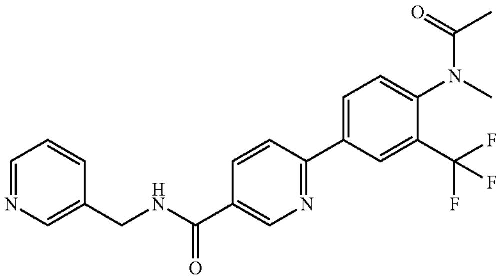 [SMILES: CC(=O)N(C)c1ccc(-c2ccc(C(=O)NCc3cccnc3)cn2)cc1C(F)(F)F]

Purification by flash column chromatography (silica gel, 0-10% MeOH in EtOAc) afforded 6-[4-[acetyl(methyl)amino]-3-(trifluoromethyl)phenyl]-N-(3-pyridylmethyl)pyridine-3-carboxamide as a white amorphous solid (21 mg, 35%).

LC-MS (Method 8): $R_t$=3.33 min; m/z=429.52 $(M+H)^+$.

$^1$H NMR (300 MHz, DMSO-$d_6$): δ 1.68 (s, 3H), 3.10 (s, 3H), 4.55 (m, 2H), 7.37 (m, 1H), 7.77 (m, 2H), 8.20-8.4 (m, 2H), 8.47 (m, 1H), 8.5-8.67 (m, 3H), 9.17 (m, 1H), 9.37 (m, 1H).

Synthesis according to Scheme 5.

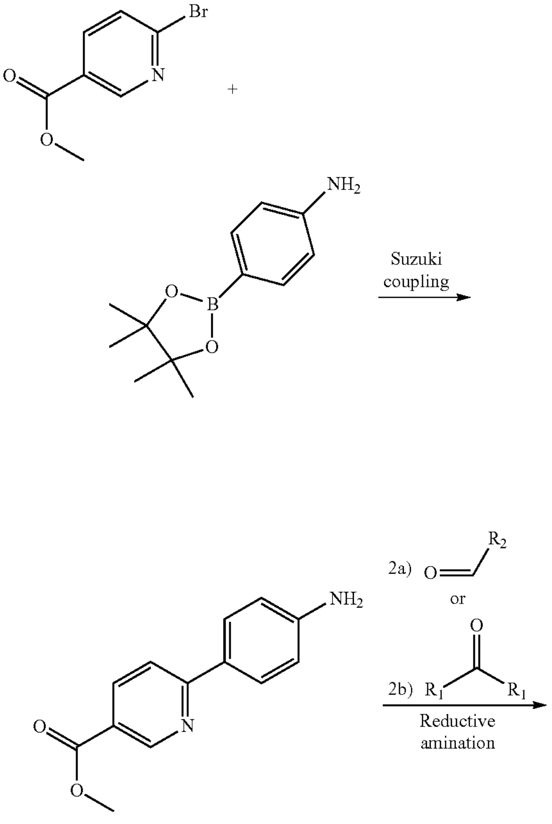

-continued

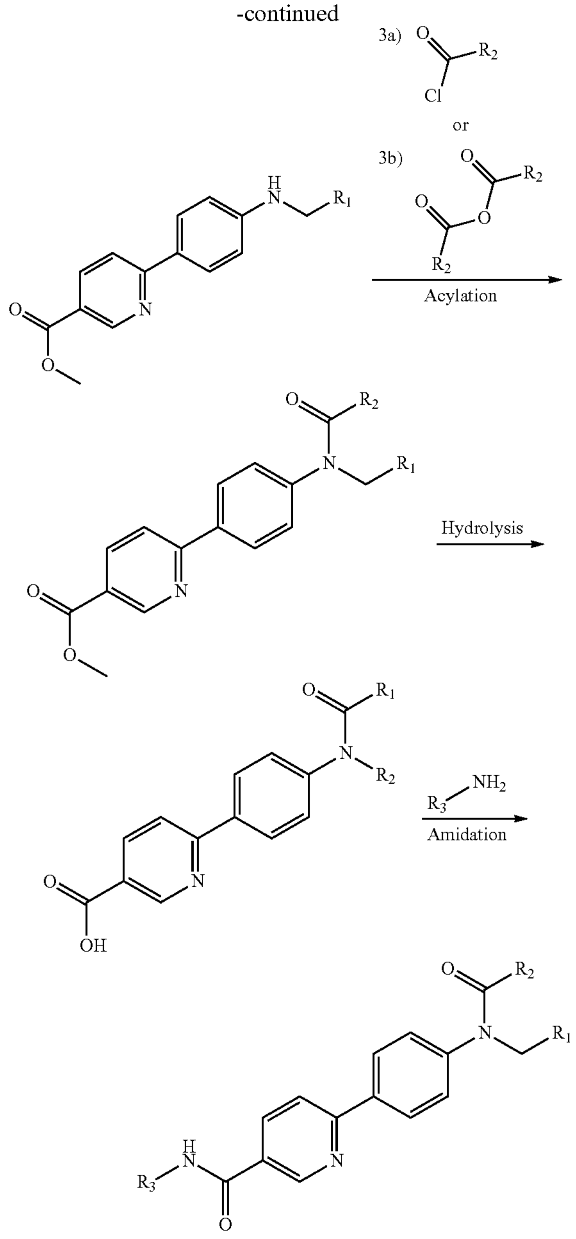

Scheme 5 with procedures 2a/3a

Step 1: Suzuki coupling (per Scheme 1—Step 1)

Methyl 6-(4-aminophenyl)pyridine-3-carboxylate

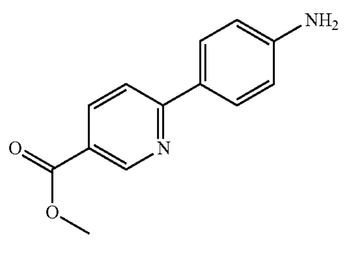 [SMILES: COC(=O)c1ccc(-c2ccc(N)cc2)nc1]

Starting from 4-(4,4,5,5-tetramethyl-1,3,2-dioxaborolan-2-yl)aniline (10 g, 45.6 mmol) and methyl 6-bromopyridine-3-carboxylate (11.8 g, 54.8 mmol), trituration with ACN afforded methyl 6-(4-aminophenyl)pyridine-3-carboxylate as a brown solid (6.5 g, 63%). LC-MS (Method 2): $R_t$=0.95 min; m/z=227.44 $(M+H)^+$.

Step 2: Reductive amination (per Scheme 1—Step 4)

Methyl 6-[4-(isobutylamino)phenyl]pyridine-3-carboxylate

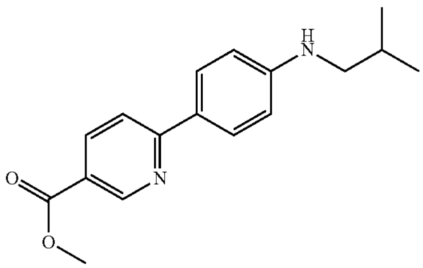 [SMILES: COC(=O)c1ccc(-c2ccc(NCC(C)C)cc2)nc1]

Starting from 6-(4-aminophenyl)pyridine-3-carboxylate (400 mg, 1.51 mmol) and isobutyraldehyde (179 μL, 1.96 mmol), purification by flash column chromatography (silica gel, 0-60% EtOAc in cyclohexane) afforded methyl 6-[4-(isobutylamino)phenyl]pyridine-3-carboxylate (350 mg, 61%).

LC-MS (Method 2): $R_t$=1.29 min; m/z=285.10 $(M+H)^+$.

Step 3a: Acylation (per Scheme 1—Step 5)

Methyl 6-[4-[acetyl(isobutyl)amino]phenyl]pyridine-3-carboxylate

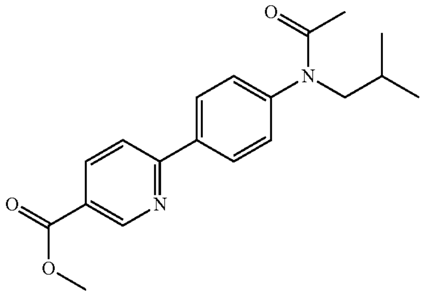 [SMILES: COC(=O)c1ccc(-c2ccc(N(CC(C)C)C(C)=O)cc2)nc1]

Acylation starting from methyl 6-[4-(isobutylamino)phenyl]pyridine-3-carboxylate (100 mg, 0.35 mmol) and acetyl chloride (75 μL, 1.1 mmol) afforded methyl 6-[4-[acetyl(isobutyl)amino]phenyl]pyridine-3-carboxylate (115 mg) which was used as such in the next step.

LC-MS (Method 2): $R_t$=1.11 min; m/z=327.08 $(M+H)^+$.

Step 4: Hydrolysis (per Scheme 1—Step 2)

6-[4-[acetyl(isobutyl)amino]phenyl]pyridine-3-carboxylic acid

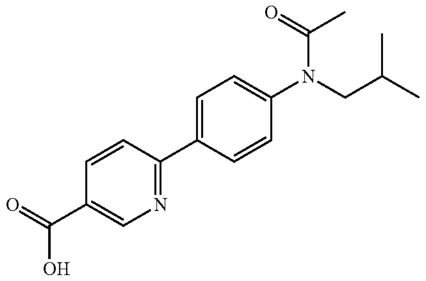 [SMILES: CC(=O)N(CC(C)C)c1ccc(-c2ccc(C(=O)O)cn2)cc1]

Hydrolysis afforded 6-[4-[acetyl(isobutyl)amino]phenyl]pyridine-3-carboxylic acid (110 mg) which was used as such in the next step.

LC-MS (Method 2): $R_t$=0.49 min; m/z=313.09 (M+H)$^+$.

Step 5: Amidation (per Scheme 2—Step 5)

6-[4-[Acetyl(isobutyl)amino]phenyl]-N-[(2-methyl-3-pyridyl)methyl]pyridine-3-carboxamide (I-467)

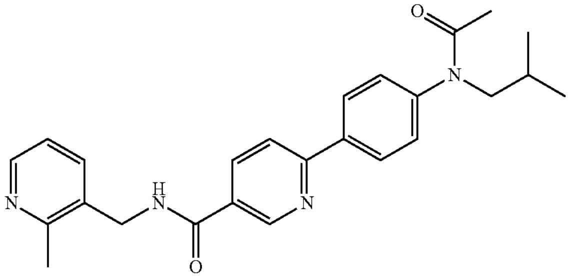 [SMILES: CC(=O)N(CC(C)C)c1ccc(-c2ccc(C(=O)NCc3cccnc3C)cn2)cc1]

Starting from 6-[4-[acetyl(isobutyl)amino]phenyl]pyridine-3-carboxylic acid (110 mg, 0.282 mmol) and 3-pyridylmethanamine-2-methyl (0.0434 mL, 0.366 mmol), purification by flash column chromatography (silica gel, 10% MeOH in DCM) afforded 6-[4-[acetyl(isobutyl)amino]phenyl]-N-[(2-methyl-3-pyridyl)methyl]pyridine-3-carboxamide (42 mg, 35%) as a white amorphous solid.

LC-MS (Method 8): $R_t$=3.68 min; m/z=417.16 (M+H)$^+$.

$^1$H-NMR (400 MHz, DMSO-$d_6$): δ 0.84 (d, J=6.64 Hz, 6H), 1.63 (m, 1H), 1.81 (bs, 3H), 2.53 (s, 3H), 3.55 (d, J=7.61 Hz, 2H), 4.51 (d, J=5.64 Hz, 2H), 7.18 (dd, J=7.57, 4.78 Hz, 1H), 7.46 (d, J=8.34 Hz, 2H), 7.63 (dd, J=7.58, 1.48 Hz, 1H), 8.13 (d, J=8.60 Hz, 1H), 8.20 (d, J=8.60 Hz, 2H), 8.31-8.34 (m, 2H), 9.13 (dd, J=2.25, 0.79 Hz, 1H), 9.21 (t, J=5.64 Hz, 1H).

6-[4-[Acetyl(3,3,3-trifluoropropyl)amino]phenyl]-N-(3-pyridylmethyl)pyridine-3-carboxamide (I-482)

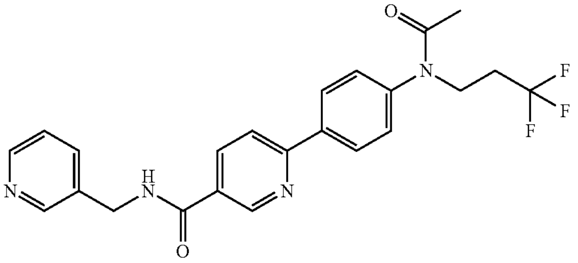 [SMILES: CC(=O)N(CCC(F)(F)F)c1ccc(-c2ccc(C(=O)NCc3cccnc3)cn2)cc1]

Purification by flash column chromatography (silica gel, 10% MeOH in DCM) and coevaporation from diethylether afforded 6-[4-[acetyl(3,3,3-trifluoropropyl)amino]phenyl]-N-(3-pyridylmethyl)pyridine-3-carboxamide as a yellowish amorphous solid (55.4 mg, 49%).

LC-MS (Method 8): $R_t$=3.42 min; m/z=443.19 (M+H)$^+$.

$^1$H NMR (400 MHz, DMSO-$d_6$): δ 1.82 (s, 3H), 2.52 (bs, 2H), 3.91 (t, J=7.2 Hz, 2H), 4.55 (d, J=5.8 Hz, 2H), 7.38 (ddd, J=7.8, 4.8, 0.9 Hz, 1H), 7.51 (d, J=8.4 Hz, 2H), 7.77 (ddd, J=7.8, 2.3, 1.7 Hz, 1H), 8.16 (d, J=8.4 Hz, 1H), 8.25 (d, J=8.6 Hz, 2H), 8.34 (dd, J=8.4, 2.3 Hz, 1H), 8.48 (dd, J=4.8, 1.7 Hz, 1H), 8.59 (dd, J=2.3, 0.7 Hz, 1H), 9.14 (dd, J=2.3, 0.8 Hz, 1H), 9.33 (t, J=5.9 Hz, 1H).

6-[4-[Acetyl-[(3,3-difluorocyclobutyl)methyl]amino]-3-methyl-phenyl]-N-[(2-methyl-3-pyridyl)methyl]pyridine-3-carboxamide (I-485)

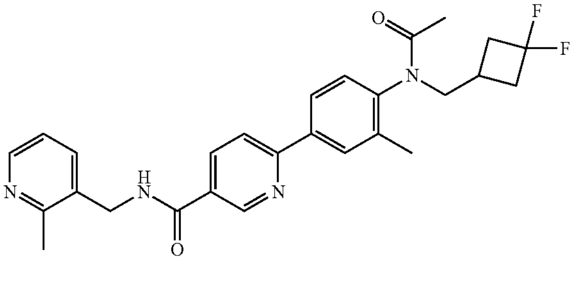 [SMILES: CC(=O)N(CC1CC(F)(F)C1)c1ccc(-c2ccc(C(=O)NCc3cccnc3C)cn2)cc1C]

Purification by flash column chromatography (silica gel, 10% MeOH in DCM) and coevaporation from diethylether afforded 6-[4-[acetyl-[(3,3-difluorocyclobutyl)methyl]amino]-3-methyl-phenyl]-N-[(2-methyl-3-pyridyl)methyl]pyridine-3-carboxamide as a yellowish amorphous solid (9.3 mg, 38%).

LC-MS (Method 8): $R_t$=3.81 min; m/z=479.19 (M+H)$^+$.

$^1$H NMR (500 MHz, DMSO-$d_6$): δ 1.69 (s, 3H), 2.16-2.34 (m, 3H), 2.27 (s, 3H), 2.54 (s, 3H), 2.56-2.70 (m, 2H), 3.35-3.39 (m, 1H), 4.09-4.14 (m, 1H), 4.52 (d, J=5.6 Hz, 2H), 7.18-7.23 (m, 1H), 7.35 (d, J=8.2 Hz, 1H), 7.64 (d, J=7.7 Hz, 1H), 8.05 (d, J=7.9 Hz, 1H), 8.14 (d, J=8.4 Hz, 1H), 8.18 (s, 1H), 8.31-8.36 (m, 2H), 9.14 (d, J=2.1 Hz, 1H), 9.22 (t, J=5.8 Hz, 1H).

6-[4-[Acetyl(cyclopropylmethyl)amino]-3-methyl-phenyl]-N-[(2-methyl-3-pyridyl)methyl]pyridine-3-carboxamide (I-488)

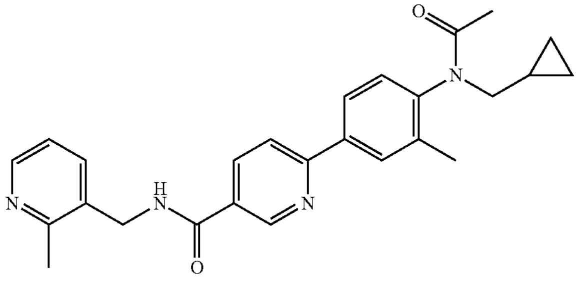 [SMILES: CC(=O)N(CC1CC1)c1ccc(-c2ccc(C(=O)NCc3cccnc3C)cn2)cc1C]

Purification by flash column chromatography (silica gel, 10% MeOH in DCM) and additionally by prep HPLC (Method 9) afforded 6-[4-[acetyl(cyclopropylmethyl)amino]-3-methyl-phenyl]-N-[(2-methyl-3-pyridyl)methyl]pyridine-3-carboxamide as a white amorphous solid (4 mg, 3%).

LC-MS (Method 8): $R_t$=3.53 min; m/z=429.34 $(M+H)^+$.

$^1$H NMR (500 MHz, DMSO-$d_6$): δ 0.02-0.09 (m, 2H), 0.35-0.43 (m, 2H), 0.87-0.94 (m, 1H), 1.68 (s, 3H), 2.31 (s, 3H), 2.54 (s, 3H), 3.16-3.22 (m, 2H), 3.67-3.74 (m, 2H), 4.52 (d, J=4.8 Hz, 2H), 7.18-7.23 (m, 1H), 7.40 (d, J=7.8 Hz, 1H), 7.64 (d, J=7.4 Hz, 1H), 8.06 (d, J=7.7 Hz, 1H), 8.14 (d, J=8.2 Hz, 1H), 8.17 (s, 1H), 8.31-8.36 (m, 2H), 9.14 (s, 1H), 9.20-9.27 (m, 1H).

6-[4-[Acetyl(cyclopropylmethyl)amino]-3-methyl-phenyl]-N-[(2,6-dimethyl-3-pyridyl)methyl]pyridine-3-carboxamide (I-489)

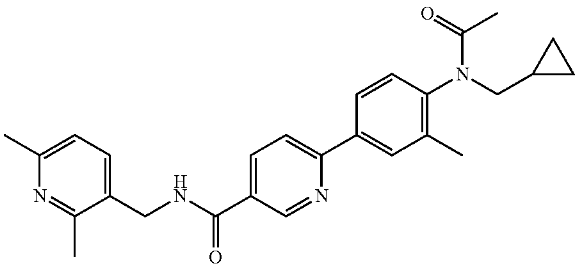 [SMILES: CC(=O)N(CC1CC1)c1ccc(-c2ccc(C(=O)NCc3ccc(C)nc3C)cn2)cc1C]

Purification by flash column chromatography (silica gel, 10% MeOH in EtOAc) and additionally by prep HPLC (Method 9) afforded 6-[4-[acetyl(cyclopropylmethyl)amino]-3-methyl-phenyl]-N-[(2,6-dimethyl-3-pyridyl)methyl]pyridine-3-carboxamide as a white amorphous solid (4 mg, 3%).

LC-MS (Method 8): $R_t$=3.83 min; m/z=443.29 $(M+H)^+$.

$^1$H NMR (500 MHz, DMSO-$d_6$): δ 0.01-0.09 (m, 2H), 0.35-0.43 (m, 2H), 0.87-0.95 (m, 1H), 1.69 (s, 3H), 2.31 (s, 3H), 2.39 (s, 3H), 2.50 (signal under DMSO, 3H), 3.16-3.22 (m, 2H), 3.67-3.74 (m, 2H), 4.47 (d, J=5.6 Hz, 2H), 7.05 (d, J=7.9 Hz, 1H), 7.40 (d, J=8.2 Hz, 1H), 7.51 (d, J=7.7 Hz, 1H), 8.06 (d, J=8.4 Hz, 1H), 8.13 (d, J=8.2 Hz, 1H), 8.16 (s, 1H), 8.33 (dd, J=8.4 Hz, J=2.2 Hz, 1H), 9.12 (d, J=1.6 Hz, 1H), 9.17 (t, J=5.3 Hz, 1H).

6-[4-[Acetyl(3,3,3-trifluoropropyl)amino]phenyl]-N-[(2-methyl-3-pyridyl)methyl]pyridine-3-carboxamide (I-499)

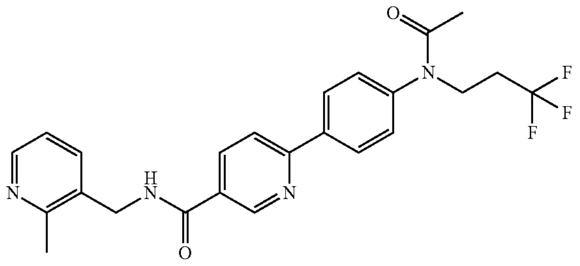 [SMILES: CC(=O)N(CCC(F)(F)F)c1ccc(-c2ccc(C(=O)NCc3cccnc3C)cn2)cc1]

Purification by flash column chromatography (silica gel, 10% MeOH in DCM) and coevaporation from diethylether afforded 6-[4-[acetyl(3,3,3-trifluoropropyl)amino]phenyl]-N-[(2-methyl-3-pyridyl)methyl]pyridine-3-carboxamide as a white amorphous solid (20 mg, 34%).

LC-MS (Method 8): $R_t$=3.64 min; m/z=457.11 $(M+H)^+$.

$^1$H NMR (500 MHz, DMSO-$d_6$): δ 1.82 (s, 3H), 2.50 (signal under DMSO, 2H), 2.54 (s, 3H), 3.91 (t, J=7.3 Hz, 2H), 4.52 (d, J=5.6 Hz, 2H), 7.21 (dd, J=7.7, 4.8 Hz, 1H), 7.51 (d, J=8.0 Hz, 2H), 7.64 (d, J=7.7 Hz, 1H), 8.16 (d, J=8.4 Hz, 1H), 8.25 (d, J=8.4 Hz, 2H), 8.31-8.37 (m, 2H), 9.15 (d, J=2.2 Hz, 1H), 9.22 (t, J=5.6 Hz, 1H).

6-[4-[Acetyl(cyclopropylmethyl)amino]phenyl]-N-[(2-methyl-3-pyridyl)methyl]pyridine-3-carboxamide (I-500)

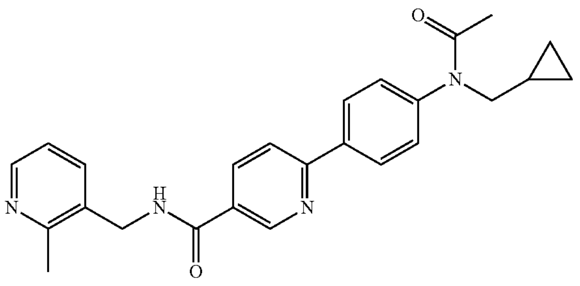 [SMILES: CC(=O)N(CC1CC1)c1ccc(-c2ccc(C(=O)NCc3cccnc3C)cn2)cc1]

Purification by flash column chromatography (silica gel, 10% MeOH in EtOAc) and additionally by prep HPLC (Method 9) afforded 6-[4-[acetyl(cyclopropylmethyl)amino]phenyl]-N-[(2-methyl-3-pyridyl)methyl]pyridine-3-carboxamide as a white amorphous solid (12 mg, 10%).

LC-MS (Method 4): $R_t$=1.45 min; m/z=415.15 $(M+H)^+$.

$^1$H-NMR (300 MHz, DMSO-$d_6$): δ 0.05 (m, 2H), 0.37 (m, 2H), 0.88 (m, 1H), 1.80 (bs, 3H), 2.53 (s, 3H), 3.54 (d, J=7.01 Hz, 2H), 4.52 (d, J=5.62 Hz, 2H), 7.20 (dd, J=7.89, 4.91 Hz, 1H), 7.46 (d, J=8.64 Hz, 2H), 7.63 (dd, J=7.36, 1.49 Hz, 1H), 8.14 (d, J=8.11 Hz, 1H), 8.22 (d, J=8.45 Hz, 2H), 8.33 (m, 2H), 9.13 (d, J=2.15 Hz, 1H), 9.22 (t, J=5.62 Hz, 1H).

6-[4-[Acetyl(isobutyl)amino]-3-methyl-phenyl]-N-(3-pyridylmethyl)pyridine-3-carboxamide (I-594)

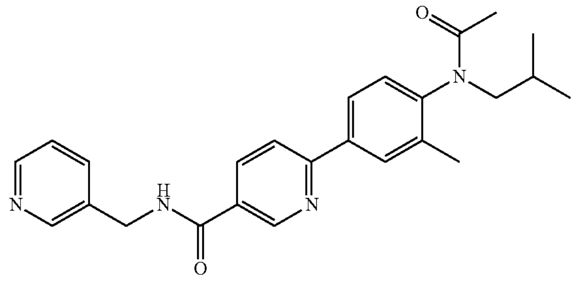 [SMILES: CC(=O)N(CC(C)C)c1ccc(-c2ccc(C(=O)NCc3cccnc3)cn2)cc1C]

Purification by flash column chromatography (silica gel, 10% MeOH in DCM) and trituration from diethylether afforded 6-[4-[acetyl(isobutyl)amino]-3-methyl-phenyl]-N-(3-pyridylmethyl)pyridine-3-carboxamide as a white amorphous solid (35 mg, 42%).

LC-MS (Method 2): $R_t$=0.90 min; m/z=417.23 $(M+H)^+$.

$^1$H NMR (300 MHz, DMSO-$d_6$): δ 0.85 (d, J=6.79 Hz, 3H), 0.90 (d, J=6.79 Hz, 3H), 1.68 (s, 3H), 1.69-1.76 (m, 1H), 2.27 (s, 3H), 2.86 (dd, J=13.33, 6.01 Hz, 1H), 3.90 (dd, J=13.41, 8.71 Hz, 1H), 4.54 (d, J=5.75 Hz, 2H), 7.31-7.39 (m, 2H), 7.73-7.78 (m, 1H), 8.01-8.08 (m, 1H), 8.09-8.18 (m, 2H), 8.32 (dd, J=8.27, 2.35 Hz, 1H), 8.47 (dd, J=4.70, 1.74 Hz, 1H), 8.58 (d, J=1.74 Hz, 1H), 9.12 (d, J=1.74 Hz, 1H), 9.32 (t, J=5.75 Hz, 1H).

6-[4-[Acetyl(isobutyl)amino]-3-chloro-phenyl]-N-(3-pyridylmethyl)pyridine-3-carboxamide (I-599)

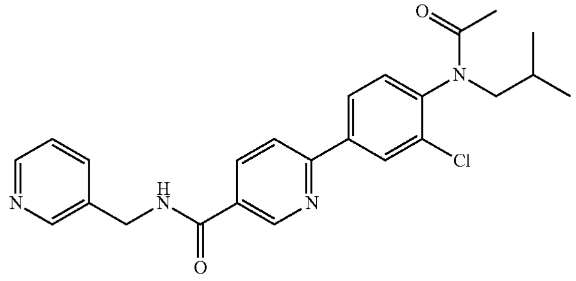

Purification by flash column chromatography (silica gel, 10% MeOH in DCM) afforded 6-[4-[acetyl(isobutyl)amino]-3-chloro-phenyl]-N-(3-pyridylmethyl)pyridine-3-carboxamide as a white amorphous solid (43 mg, 47%).

LC-MS (Method 8): $R_t$=4.01 min; m/z=437.13 $(M+H)^+$.

$^1$H NMR (300 MHz, DMSO-$d_6$): δ 0.88 (dd, J=8.19, 6.79 Hz, 6H), 1.67 (m, 1H), 1.73 (s, 3H), 3.03 (m, 1H), 3.81 (m, 1H), 4.54 (d, J=5.70 Hz, 2H), 7.37 (m, 1H), 7.63 (d, J=8.36 Hz, 1H), 7.75 (m, 1H), 8.19-8.25 (m, 2H), 8.35 (dd, J=8.36, 2.26 Hz, 1H), 8.40 (d, J=2.09 Hz, 1H), 8.47 (dd, J=4.88, 1.57 Hz, 1H), 8.58 (s, 1H), 9.14 (d, J=2.09 Hz, 1H), 9.35 (t, J=5.70 Hz, 1H).

6-[4-[Acetyl(3,3,3-trifluoropropyl)amino]-3-methyl-phenyl]-N-(3-pyridylmethyl)pyridine-3-carboxamide (I-601)

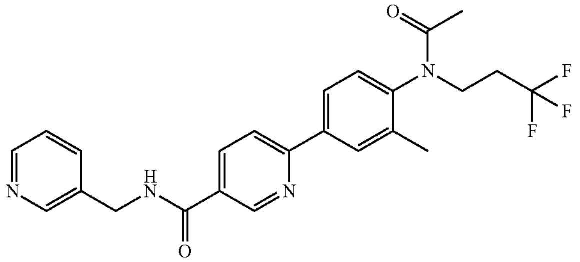 [SMILES: CC(=O)N(CCC(F)(F)F)c1ccc(-c2ccc(C(=O)NCc3cccnc3)cn2)cc1C]

Purification by flash column chromatography (silica gel, 10% MeOH in DCM) and coevaporation from diethylether afforded 6-[4-[acetyl(3,3,3-trifluoropropyl)amino]-3-methyl-phenyl]-N-(3-pyridylmethyl)pyridine-3-carboxamide as a white amorphous solid (24 mg, 30%).

LC-MS (Method 8): $R_t$=3.70 min; m/z=457.31 $(M+H)^+$.

$^1$H NMR (500 MHz, DMSO-$d_6$): δ 1.70 (s, 3H), 2.29 (s, 3H), 2.52-2.65 (m, 2H), 3.25-3.30 (m, 1H), 4.18-4.25 (m, 1H), 4.55 (d, J=5.80 Hz, 2H), 7.38 (dd, J=7.63, 4.88 Hz, 1H), 7.43 (d, J=8.24 Hz, 1H), 7.77 (d, J=7.93 Hz, 1H), 8.07 (dd, J=8.39, 1.68 Hz, 1H), 8.15 (d, J=8.24 Hz, 1H), 8.20 (s, 1H), 8.33 (dd, J=8.39, 2.29 Hz, 1H), 8.48 (dd, J=4.88, 1.22 Hz, 1H), 8.59 (s, 1H), 9.13 (d, J=1.53 Hz, 1H), 9.33 (t, J=5.95 Hz, 1H).

6-[4-[Acetyl(cyclopropylmethyl)amino]-3-chloro-phenyl]-N-(3-pyridylmethyl)pyridine-3-carboxamide (I-602)

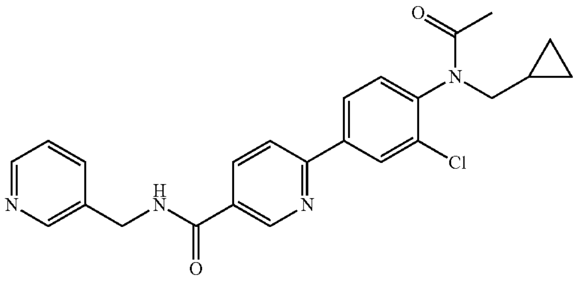 [SMILES: CC(=O)N(CC1CC1)c1ccc(-c2ccc(C(=O)NCc3cccnc3)cn2)cc1Cl]

Purification by flash column chromatography (silica gel, 10% MeOH in DCM) afforded 6-[4-[acetyl(cyclopropylmethyl)amino]-3-chloro-phenyl]-N-(3-pyridylmethyl)pyridine-3-carboxamide as a white amorphous solid (67 mg, 66%).

LC-MS (Method 8): $R_t$=3.77 min; m/z=435.22 $(M+H)^+$.

$^1$H NMR (300 MHz, DMSO-$d_6$): δ 0.01-0.08 (m, 2H), 0.30-0.43 (m, 2H), 0.81-0.96 (m, 1H), 1.73 (s, 3H), 3.22 (dd, J=13.93, 7.32 Hz, 1H), 3.73 (dd, J=13.93, 6.97 Hz, 1H), 4.54 (d, J=5.75 Hz, 2H), 7.37 (dd, J=7.75, 4.79 Hz, 1H), 7.66 (d, J=8.19 Hz, 1H), 7.76 (dt, J=7.88, 1.81 Hz, 1H), 8.19-8.26 (m, 2H), 8.32-8.38 (m, 1H), 8.40 (d, J=1.92 Hz, 1H), 8.47 (dd, J=4.70, 1.57 Hz, 1H), 8.58 (d, J=1.92 Hz, 1H), 9.14 (d, J=1.92 Hz, 1H), 9.35 (t, J=4.54 Hz, 1H).

6-[4-[Acetyl-[(3,3-difluorocyclobutyl)methyl]amino]-3-chloro-phenyl]-N-(3-pyridylmethyl)pyridine-3-carboxamide (I-603)

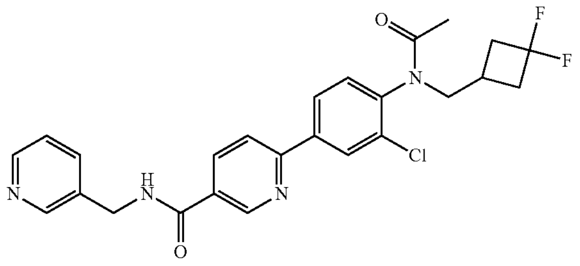 [SMILES: CC(=O)N(CC1CC(F)(F)C1)c1ccc(-c2ccc(C(=O)NCc3cccnc3)cn2)cc1Cl]

Purification by flash column chromatography (silica gel, 10% MeOH in DCM) afforded 6-[4-[acetyl-[(3,3-difluoro-cyclobutyl)methyl]amino]-3-chloro-phenyl]-N-(3-pyridyl-methyl)pyridine-3-carboxamide as a white amorphous solid (25 mg, 64%).

LC-MS (Method 8): $R_t$=3.95 min; m/z=485.16 $(M+H)^+$.

$^1$H NMR (500 MHz, DMSO-$d_6$): δ 1.74 (s, 3H), 2.21-2.34 (m, 3H) 2.55-2.67 (m, 2H), 3.58 (dd, J=14.04, 6.71 Hz, 1H), 3.98 (dd, J=14.04, 6.71 Hz, 1H), 4.55 (d, J=5.80 Hz, 2H), 7.38 (dd, J=7.63, 4.88 Hz, 1H), 7.65 (d, J=8.24 Hz, 1H), 7.77 (br d, J=7.93 Hz, 1H), 8.22-8.26 (m, 2H), 8.35 (br d, J=2.14 Hz, 1H), 8.42 (d, J=2.14 Hz, 1H), 8.46-8.49 (m, 1H), 8.59 (s, 1H), 9.15 (d, J=1.83 Hz, 1H), 9.36 (t, J=5.80 Hz, 1H).

6-[4-[Acetyl(3,3,3-trifluoropropyl)amino]-3-chloro-phenyl]-N-(3-pyridylmethyl)pyridine-3-carboxamide (I-604)

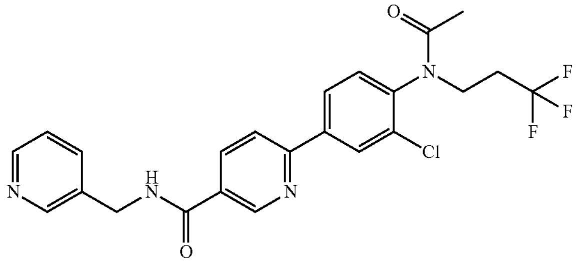 [SMILES: CC(=O)N(CCC(F)(F)F)c1ccc(-c2ccc(C(=O)NCc3cccnc3)cn2)cc1Cl]

Purification by flash column chromatography (silica gel, 10% MeOH in DCM) afforded 6-[4-[acetyl(3,3,3-trifluoro-propyl)amino]-3-chloro-phenyl]-N-(3-pyridylmethyl)pyridine-3-carboxamide as a white amorphous solid (37 mg, 66%).

LC-MS (Method 8): $R_t$=3.95 min; m/z=477.14 $(M+H)^+$.

$^1$H NMR (500 MHz, DMSO-$d_6$): δ 1.75 (s, 3H), 2.53-2.60 (m, 2H), 3.47 (dt, J=14.27, 7.36 Hz, 1H), 4.11-4.18 (m, 1H), 4.55 (d, J=5.80 Hz, 2H), 7.38 (dd, J=7.63, 4.88 Hz, 1H), 7.71 (d, J=8.24 Hz, 1H), 7.77 (br d, J=7.63 Hz, 1H), 8.23-8.28 (m, 2H), 8.36 (dd, J=8.24, 2.14 Hz, 1H), 8.44 (d, J=1.83 Hz, 1H), 8.48 (d, J=3.97 Hz, 1H), 8.59 (s, 1H), 9.16 (d, J=1.53 Hz, 1H), 9.36 (t, J=5.80 Hz, 1H).

6-[4-[Acetyl(2,2-difluoroethyl)amino]-3-methyl-phenyl]-N-(3-pyridylmethyl)pyridine-3-carboxamide (I-608)*

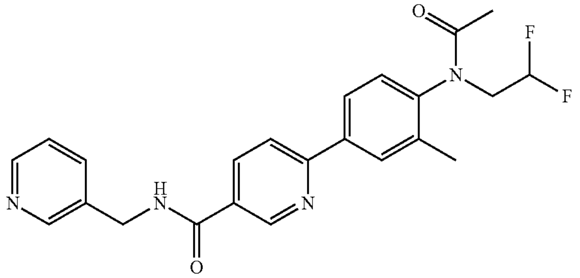 [SMILES: CC(=O)N(CC(F)F)c1ccc(-c2ccc(C(=O)NCc3cccnc3)cn2)cc1C]

Purification by flash column chromatography (silica gel, 10% MeOH in DCM) afforded 6-[4-[acetyl(2,2-difluoro-ethyl)amino]-3-methyl-phenyl]-N-(3-pyridylmethyl)pyridine-3-carboxamide as a white amorphous solid (26 mg, 67%).

LC-MS (Method 8): $R_t$=3.38 min; m/z=425.09 $(M+H)^+$.

$^1$H NMR (500 MHz, DMSO-$d_6$): δ 1.75 (s, 3H), 2.29 (s, 3H), 3.64-3.74 (m, 1H), 4.18-4.31 (m, 1H), 4.55 (d, J=5.49 Hz, 2H), 6.23 (t, J=55.00 Hz, 1H), 7.38 (dd, J=7.78, 4.73 Hz, 1H), 7.41 (d, J=8.24 Hz, 1H), 7.76 (d, J=7.60 Hz, 1H), 8.06 (dd, J=8.09, 1.98 Hz, 1H), 8.14 (d, J=8.55 Hz, 1H), 8.17 (s, 1H), 8.33 (dd, J=8.24, 2.44 Hz, 1H), 8.47 (d, J=4.81 Hz, 1H), 8.59 (s, 1H), 9.13 (d, J=2.14 Hz, 1H), 9.33 (t, J=5.80 Hz, 1H).

* The reductive amination step was replaced by the same procedure as described for I-449 above. Starting from methyl 6-(4-amino-3-methyl-phenyl)pyridine-3-carboxylate (250 mg, 1.01 mmol) and 1-ethoxy-2,2-difluoro-ethanol (140 mg, 1.11 mmol), purification by flash column chromatography (silica gel, 60% EtOAc in cyclohexane) afforded methyl 6-[4-(2,2-difluoroethylamino)-3-methyl-phenyl]pyridine-3-carboxylate as a yellow paste (100 mg, 27%). LC-MS (Method 2): Rt=1.12 min, m/z=307.12 $(M+H)^+$.

6-[4-[Acetyl(cyclopropylmethyl)amino]-3-chloro-phenyl]-N-[(2-amino-4-pyridyl)methyl]pyridine-3-carboxamide (I-674)

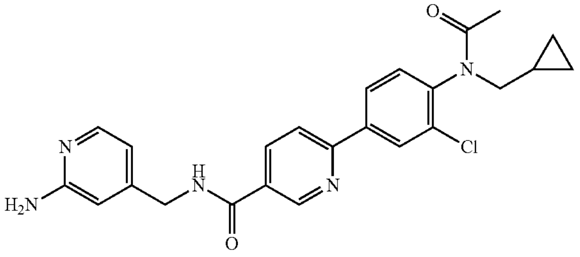 [SMILES: CC(=O)N(CC1CC1)c1ccc(-c2ccc(C(=O)NCc3ccnc(N)c3)cn2)cc1Cl]

Purification by prep HPLC (Method 11) afforded 6-[4-[acetyl(cyclopropylmethyl)amino]-3-chloro-phenyl]-N-[(2-amino-4-pyridyl)methyl]pyridine-3-carboxamide as a white amorphous solid (5.6 mg, 8%).

LC-MS (Method 7): $R_t$=2.87 min; m/z=450.59 $(M+H)^+$.

$^1$H NMR (300 MHz, DMSO-$d_6$): δ 0.01-0.08 (m, 2H), 0.33-0.40 (m, 2H), 0.82-0.94 (m, 1H), 1.73 (s, 3H), 3.18-3.27 (m, 1H), 3.69-3.78 (m, 1H), 4.37 (d, J=5.86 Hz, 2H), 5.86 (s, 2H), 6.36 (s, 1H), 6.43 (d, J=5.29 Hz, 1H), 7.66 (d, J=8.29 Hz, 1H), 7.81 (d, J=5.29 Hz, 1H), 8.20-8.27 (m, 2H), 8.36 (dd, J=8.37, 2.28 Hz, 1H), 8.40 (d, J=2.03 Hz, 1H), 9.16 (d, J=1.93 Hz, 1H), 9.27 (t, J=5.79 Hz, 1H).

6-[4-[Acetyl(cyclopropylmethyl)amino]-3-chloro-phenyl]-N-(4-pyridylmethyl)pyridine-3-carboxamide (I-676)

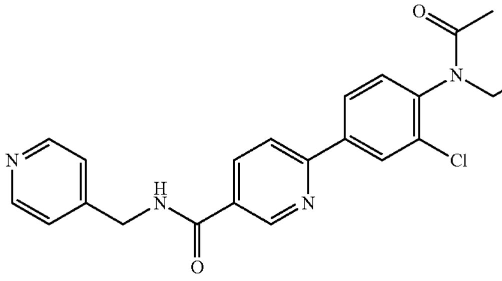

Purification by flash column chromatography (silica gel, 10% MeOH in DCM) afforded 6-[4-[acetyl(cyclopropylmethyl)amino]-3-chloro-phenyl]-N-(4-pyridylmethyl)pyridine-3-carboxamide as a white solid (26 mg, 40%).

LC-MS (Method 8): $R_t$=3.72 min; m/z=435.05 $(M+H)^+$.

$^1$H NMR (300 MHz, DMSO-$d_6$): δ 0.01-0.08 (m, 2H), 0.37 (m, 2H), 0.83-0.94 (m, 1H), 1.74 (s, 3H), 3.20-3.27 (m, 1H), 3.74 (m, 1H), 4.55 (br d, J=5.49 Hz, 2H), 7.35 (br d, J=4.27 Hz, 2H), 7.67 (br d, J=8.24 Hz, 1H), 8.20-8.28 (m, 2H), 8.35-8.44 (m, 2H), 8.52 (br d, J=4.58 Hz, 2H), 9.18 (br s, 1H), 9.40 (br t, J=5.34 Hz, 1H).

6-[4-[Acetyl(cyclopropylmethyl)amino]-3-chloro-phenyl]-N-[(6-amino-3-pyridyl)methyl]pyridine-3-carboxamide (I-677)

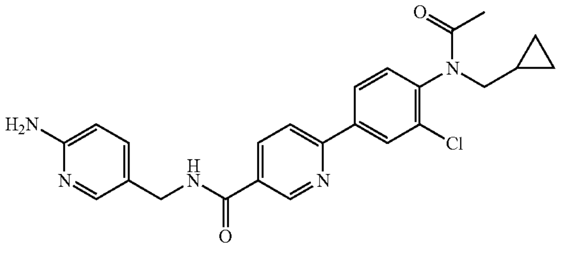 [SMILES: CC(=O)N(CC1CC1)c1ccc(-c2ccc(C(=O)NCc3ccc(N)nc3)cn2)cc1Cl]

Purification by flash column chromatography (silica gel, 10% MeOH in DCM) afforded 6-[4-[acetyl(cyclopropylmethyl)amino]-3-chloro-phenyl]-N-(4-pyridylmethyl)pyridine-3-carboxamide as a white amorphous solid (17 mg, 25%).

LC-MS (Method 8): $R_t$=3.61 min; m/z=450.01 $(M+H)^+$.

$^1$H NMR (300 MHz, DMSO-$d_6$): δ 0.01-0.05 (m, 2H), 0.32-0.39 (m, 2H), 0.80-0.94 (m, 1H), 1.72 (s, 3H), 3.17-3.26 (m, 1H), 3.68-3.77 (m, 1H), 4.30 (d, J=5.64 Hz, 2H), 5.82 (bs, 2H), 6.40 (d, J=8.52 Hz, 1H), 7.36 (dd, J=8.42, 2.32 Hz, 1H), 7.65 (d, J=8.32 Hz, 1H), 7.89 (d, J=2.13 Hz, 1H), 8.19-8.24 (m, 2H), 8.32 (dd, J=8.42, 2.32 Hz, 1H), 8.39 (d, J=2.03 Hz, 1H), 9.11 (d, J=2.08 Hz, 1H), 9.12 (t, J=5.74 Hz, 1H).

6-[4-[Acetyl(cyclopropylmethyl)amino]-3-chloro-phenyl]-N-(imidazo[1,2-a]pyridin-6-ylmethyl)pyridine-3-carboxamide (I-679)

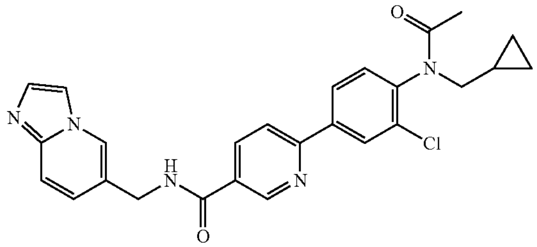 [SMILES: CC(=O)N(CC1CC1)c1ccc(-c2ccc(C(=O)NCc3ccc4nccn4c3)cn2)cc1Cl]

Purification by flash column chromatography (silica gel, 10% MeOH in DCM) afforded 6-[4-[acetyl(cyclopropylmethyl)amino]-3-chloro-phenyl]-N-(imidazo[1,2-a]pyridin-6-ylmethyl)pyridine-3-carboxamide as a light brown amorphous solid (14 mg, 19%).

LC-MS (Method 8): $R_t$=3.73 min; m/z=474.02 $(M+H)^+$.

$^1$H NMR (300 MHz, DMSO-$d_6$): δ 0.01-0.07 (m, 2H), 0.32-0.41 (m, 2H), 0.80-0.94 (m, 1H), 1.73 (s, 3H), 3.18-3.26 (m, 1H), 3.68-3.77 (m, 1H), 4.52 (d, J=5.68 Hz, 2H), 7.25 (dd, J=9.24, 1.70 Hz, 1H), 7.52-7.57 (m, 2H), 7.66 (d, J=8.27 Hz, 1H), 7.94-7.96 (m, 1H), 8.20-8.26 (m, 2H), 8.36 (dd, J=8.34, 2.22 Hz, 1H), 8.40 (d, J=1.94 Hz, 1H), 8.50-8.52 (m, 1H), 9.16 (d, J=2.10 Hz, 1H), 9.32 (t, J=5.63 Hz, 1H).

6-[4-[Acetyl(cyclopropylmethyl)amino]-3-chloro-phenyl]-N-imidazo[1,2-a]pyridin-6-yl-pyridine-3-carboxamide (I-681)

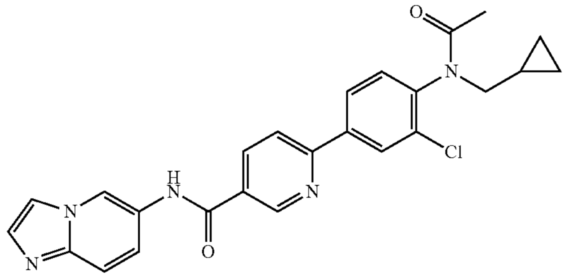 [SMILES: CC(=O)N(CC1CC1)c1ccc(-c2ccc(C(=O)Nc3ccc4nccn4c3)cn2)cc1Cl]

Purification by flash column chromatography (silica gel, 10% MeOH in DCM) afforded 6-[4-[acetyl(cyclopropylmethyl)amino]-3-chloro-phenyl]-N-imidazol[1,2-a]pyridin-6-yl-pyridine-3-carboxamide as a light yellow solid (16 mg, 24%).

LC-MS (Method 8): $R_t$=3.94 min; m/z=460.02 $(M+H)^+$.

$^1$H NMR (300 MHz, DMSO-$d_6$): δ 0.02-0.10 (m, 2H), 0.36-0.45 (m, 2H), 0.86-0.99 (m, 1H), 1.77 (s, 3H), 3.23-3.30 (m, 1H), 3.71-3.78 (m, 1H), 7.45 (dd, J=9.75, 1.92 Hz, 1H), 7.58 (d, J=1.22 Hz, 1H), 7.63 (d, J=9.75 Hz, 1H), 7.72 (d, J=8.36 Hz, 1H), 8.09 (s, 1H), 8.30 (dd, J=8.27, 2.00 Hz, 1H), 8.34 (d, J=8.54 Hz, 1H), 8.45-8.51 (m, 2H), 9.27 (d, J=1.57 Hz, 1H), 9.37-9.40 (m, 1H), 10.63 (s, 1H).

6-[4-[Acetyl(cyclopropylmethyl)amino]-3-chloro-phenyl]-N-(3-pyridyl)pyridine-3-carboxamide (I-683)

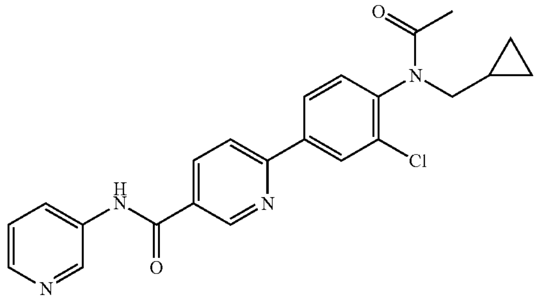 [SMILES: CC(=O)N(CC1CC1)c1ccc(-c2ccc(C(=O)Nc3cccnc3)cn2)cc1Cl]

Purification by flash column chromatography (silica gel, 10% MeOH in DCM) afforded 6-[4-[acetyl(cyclopropylmethyl)amino]-3-chloro-phenyl]-N-(3-pyridyl)pyridine-3-carboxamide as a light brown solid (28 mg, 45%).

LC-MS (Method 8): $R_t$=3.97 min; m/z=421.15 $(M+H)^+$.

$^1$H NMR (300 MHz, DMSO-$d_6$): δ 0.02-0.11 (m, 2H), 0.35-0.45 (m, 2H), 0.86-0.99 (m, 1H), 1.77 (s, 3H), 3.21-3.30 (m, 1H), 3.71-3.78 (m, 1H), 7.47 (dd, J=8.36, 4.70 Hz, 1H), 7.72 (d, J=8.36 Hz, 1H), 8.22-8.40 (m, 4H), 8.45-8.51 (m, 2H), 8.98 (d, J=2.26 Hz, 1H), 9.26 (d, J=1.74 Hz, 1H), 10.73 (s, 1H).

6-[4-[Acetyl(cyclopropylmethyl)amino]-3-chloro-phenyl]-N-(4-pyridyl)pyridine-3-carboxamide (I-684)

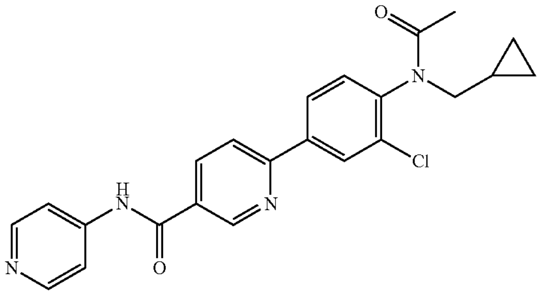 [SMILES: CC(=O)N(CC1CC1)c1ccc(-c2ccc(C(=O)Nc3ccncc3)cn2)cc1Cl]

Purification by flash column chromatography (silica gel, 10% MeOH in DCM) afforded 6-[4-[acetyl(cyclopropylmethyl)amino]-3-chloro-phenyl]-N-(4-pyridyl)pyridine-3-carboxamide as a white solid (29 mg, 47%).

LC-MS (Method 8): $R_t$=4.00 min; m/z=421.01 $(M+H)^+$.

$^1$H NMR (300 MHz, DMSO-$d_6$): δ 0.02-0.10 (m, 2H), 0.36-0.43 (m, 2H), 0.84-0.98 (m, 1H), 1.74 (s, 3H), 3.22-3.31 (m, 1H), 3.73-3.81 (m, 1H), 7.72 (d, J=8.36 Hz, 1H), 7.79-7.83 (m, 2H), 8.30 (dd, J=8.27, 2.00 Hz, 1H), 8.34 (d, J=8.36 Hz, 1H), 8.45-8.50 (m, 2H), 8.51-8.56 (m, 2H), 9.24 (d, J=2.26, Hz, 1H), 10.85 (s, 1H).

6-[4-[Acetyl(cyclopropylmethyl)amino]-3-chloro-phenyl]-N-[(2-fluoro-3-pyridyl)methyl]pyridine-3-carboxamide (I-685)

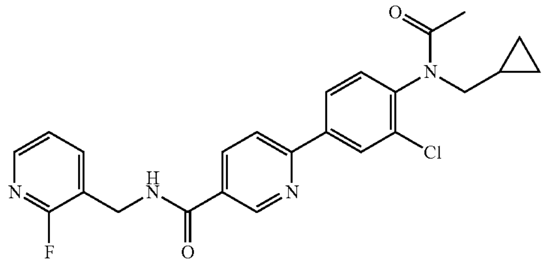 [SMILES: CC(=O)N(CC1CC1)c1ccc(-c2ccc(C(=O)NCc3cccnc3F)cn2)cc1Cl]

Purification by flash column chromatography (silica gel, 10% MeOH in DCM) afforded 6-[4-[acetyl(cyclopropylmethyl)amino]-3-chloro-phenyl]-N-[(2-fluoro-3-pyridyl)methyl]pyridine-3-carboxamide as a white solid (17 mg, 26%).

LC-MS (Method 8): $R_t$=4.07 min; m/z=452.97 $(M+H)^+$.

$^1$H NMR (300 MHz, DMSO-$d_6$): δ 0.02-0.07 (m, 2H), 0.35-0.43 (m, 2H), 0.88-0.97 (m, 1H), 1.76 (s, 3H), 3.21-3.31 (m, 2H), 3.70-3.77 (m, 2H), 4.56 (d, J=5.75 Hz, 2H), 7.32-7.37 (m, 1H), 7.66 (d, J=8.36 Hz, 1H), 7.94-8.00 (m, 1H), 8.12-8.16 (m, 1H), 8.20-8.26 (m, 2H), 8.35 (dd, J=8.40, 2.29 Hz, 1H), 8.40 (d, J=2.09 Hz, 1H), 9.14 (d, J=2.08 Hz, 1H), 9.34 (t, J=5.39 Hz, 1H).

6-[4-[2-aminoethyl(propanoyl)amino]-3-methyl-phenyl]-N-(3-pyridylmethyl)pyridine-3-carboxamide (I-502)

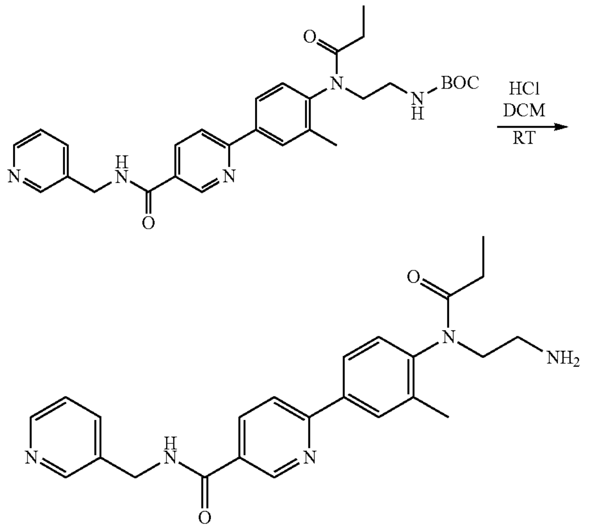 [SMILES: CCC(=O)N(CCNC(=O)OC(C)(C)C)c1ccc(-c2ccc(C(=O)NCc3cccnc3)cn2)cc1C ; "RT" ; CCC(=O)N(CCN)c1ccc(-c2ccc(C(=O)NCc3cccnc3)cn2)cc1C]

Tert-butyl N-[2-[2-methyl-N-propanoyl-4-[5-(3-pyridylmethylcarbamoyl)-2-pyridyl]anilino]ethyl]carbamate was prepared following Scheme 5 procedures 2a/3a. Per Scheme 8—Step 2, starting from tert-butyl N-[2-[2-methyl-N-propanoyl-4-[5-(3-pyridylmethylcarbamoyl)-2-pyridyl]anilino]ethyl]carbamate (125 mg, 0.23 mmol), 6-[4-[2-aminoethyl(propanoyl)amino]-3-methyl-phenyl]-N-(3-pyridylmethyl)pyridine-3-carboxamide was obtained as a yellow solid (72 mg, 70%).

LC-MS (Method 8): $R_t$=2.91 min, m/z=418.13 $(M+H)^+$.

$^1$H NMR (500 MHz, DMSO-$d_6$): δ 0.91 (t, J=7.4 Hz, 3H), 1.76-1.87 (m, 1H), 1.93-2.03 (m, 1H), 2.26 (s, 3H), 2.68 (t, J=7.1 Hz, 2H), 3.05-3.15 (m, 1H), 3.31-3.41 (bs, under water signal, 2H), 3.95-4.09 (m, 1H), 4.55 (d, J=5.8 Hz, 2H), 7.37 (dd, J=7.8, 5.1 Hz, 1H), 7.40 (d, J=8.2 Hz, 1H), 7.77 (d, J=7.9 Hz, 1H), 8.04 (dd, J=8.2, 1.9 Hz, 1H), 8.13 (d, J=8.3 Hz, 1H), 8.17 (d, J=1.8 Hz, 1H), 8.33 (dd, J=8.3, 2.3 Hz, 1H), 8.48 (dd, J=4.8, 1.5 Hz, 1H), 8.59 (d, J=1.8 Hz, 1H), 9.13 (d, J=1.9 Hz, 1H), 9.35 (t, J=5.9 Hz, 1H).

Ethyl N-[2-[N-acetyl-2-methyl-4-[5-[(2-methyl-3-pyridyl)methylcarbamoyl]-2-pyridyl]anilino]ethyl] carbamate (I-486)

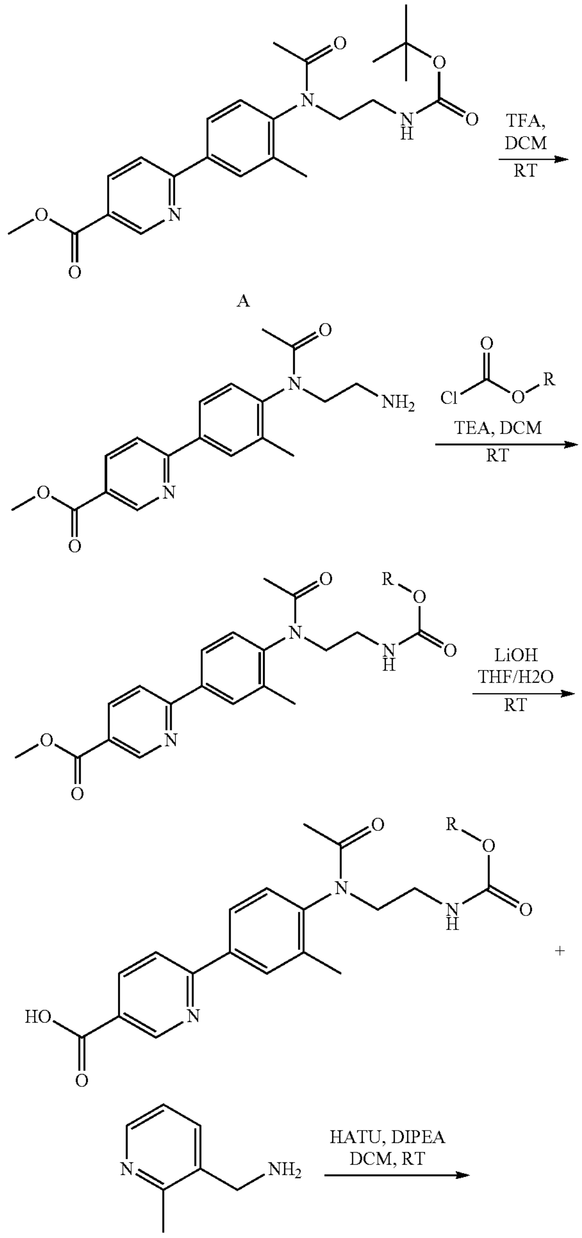

-continued

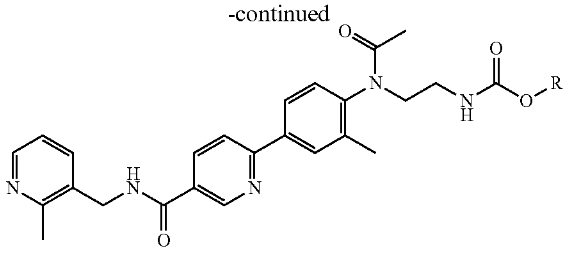

R = Me, Et

Intermediate A was prepared following Scheme 5 using tert-butyl N-(2-oxoethyl)carbamate in step 2a and propionyl chloride in step 3a.

Methyl 6-[4-[acetyl(2-aminoethyl)amino]-3-methyl-phenyl]pyridine-3-carboxylate

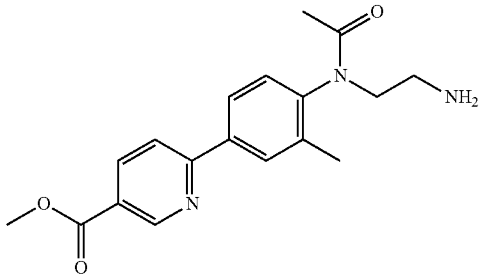 [SMILES: COC(=O)c1ccc(-c2ccc(N(CCN)C(C)=O)c(C)c2)nc1]

To a solution of methyl 6-[4-[acetyl-[2-(tert-butoxycarbonylamino)ethyl]amino]-3-methyl-phenyl]pyridine-3-carboxylate (647 mg, 1.5 mmol) in DCM (20 ml), was added TFA (2.2 mL, 29 mmol) and the reaction mixture was stirred at RT for 2 h. The RM was concentrated, redissolved in DCM and washed with sat. $NaHCO_3$(aq). The organic layer was dried over $Na_2SO_4$ and concentrated to afford methyl 6-[4-[acetyl(2-aminoethyl)amino]-3-methyl-phenyl]pyridine-3-carboxylate as a yellow oil (345 mg) which was used as such in the next step.

LC-MS (Method 2): $R_t$=0.8 min; m/z=328.15 $(M+H)^+$.

$^1$H NMR (300 MHz, DMSO-$d_6$): δ 1.66 (s, 3H), 2.27 (s, 3H), 2.63 (t, J=7.1 Hz, 2H), 3.03-3.14 (m, 1H), 3.9 (s, 3H), 3.92-4.05 (m, 1H), 7.4 (d, J=8.11 Hz, 1H), 8.05 (dd, J=7.95, 1.95 Hz, 1H), 8.13 (m, 2H), 8.36 (dd, J=8.44, 2.27 Hz, 1H), 9.13-9.17 (m, 1H).

Methyl 6-[4-[acetyl-[2-(ethoxycarbonylamino)ethyl] amino]-3-methyl-phenyl]pyridine-3-carboxylate

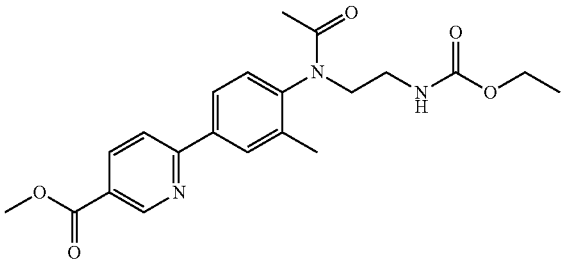 [SMILES: CCOC(=O)NCCN(C(C)=O)c1ccc(-c2ccc(C(=O)OC)cn2)cc1C]

Per Scheme 3—Step 2, starting from methyl 6-[4-[acetyl (2-aminoethyl)amino]-3-methyl-phenyl]pyridine-3-carboxylate (173 mg, 0.50 mmol) and ethyl chloroformate (48 μL, 0.54 mmol), methyl 6-[4-[acetyl-[2-(ethoxycarbonylamino)ethyl]amino]-3-methyl-phenyl]pyridine-3-carboxylate was obtained as a yellow solid (183 mg).

LC-MS (Method 2): $R_t$=0.95 min; m/z=400.19 $(M+H)^+$.

$^1$H NMR (300 MHz, DMSO-$d_6$): δ 1.09 (t, J=7.03 Hz, 3H), 1.66 (s, 3H), 2.25 (s, 3H), 3.02-3.15 (m, 2H), 3.15-3.24 (m, 1H), 3.86-3.96 (m, 5H), 3.97-4.1 (m, 1H), 7.15 (t, J=4.85 Hz, 1H), 7.45 (d, J=8.12 Hz, 1H), 8.05 (dd, J=8.23, 2.0 Hz, 1H), 8.15-8.21 (m, 2H), 8.36 (dd, J=8.33, 2.32 Hz, 1H), 9.16 (d, J=2.11, 1H).

6-[4-[Acetyl-[2-(ethoxycarbonylamino)ethyl] amino]-3-methyl-phenyl]pyridine-3-carboxylic acid

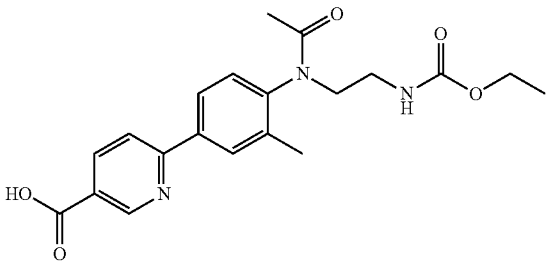 [SMILES: CCOC(=O)NCCN(C(C)=O)c1ccc(-c2ccc(C(=O)O)cn2)cc1C]

Hydrolysis per Scheme 1—Step 2 afforded 6-[4-[acetyl-[2-(ethoxycarbonylamino)ethyl]amino]-3-methyl-phenyl] pyridine-3-carboxylic acid (151 mg) as a yellow solid which was used as such in the next step.

LC-MS (Method 2): $R_t$=0.42 min; m/z=386.15 $(M+H)^+$.

$^1$H NMR (400 MHz, DMSO-$d_6$): δ 1.09 (t, J=7.03 Hz, 3H), 1.67 (s, 3H), 2.25 (s, 3H), 3.03-3.15 (m, 2H), 3.15-3.23 (m, 1H), 3.91 (q, J=7.09 Hz, 2H), 3.95-4.07 (m, 1H), 7.14 (t, J=5.57 Hz, 1H), 7.44 (d, J=8.2 Hz, 1H), 8.04 (dd, J=8.28, 2.15 Hz, 1H), 8.14 (dd, J=8.36, 0.7 Hz, 1H), 8.17 (d, J=1.59 Hz, 1H), 8.33 (dd, J=8.36, 2.29 Hz, 1H), 9.13 (dd, J=2.13, 0.7 Hz, 1H).

Ethyl N-[2-[N-acetyl-2-methyl-4-[5-[(2-methyl-3-pyridyl)methylcarbamoyl]-2-pyridyl]anilino]ethyl] carbamate (I-486)

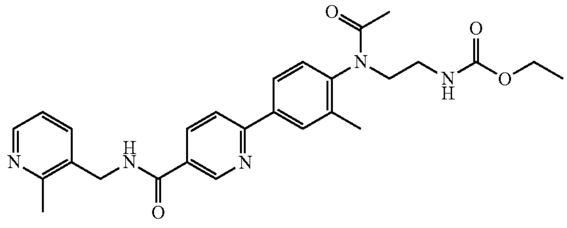 [SMILES: CCOC(=O)NCCN(C(C)=O)c1ccc(-c2ccc(C(=O)NCc3cccnc3C)cn2)cc1C]

Scheme 2—Step 5 was followed. Purification by flash column chromatography (silica gel, 0-10% MeOH in DCM) and coevaporation from diethyl ether afforded N-[2-[N-acetyl-2-methyl-4-[5-[(2-methyl-3-pyridyl)methylcarbamoyl]-2-pyridyl]anilino]ethyl]carbamate as a white amorphous solid (22 mg, 53.9%).

LC-MS (Method 8): $R_t$=3.25 min, m/z=490.2 $(M+H)^+$.

$^1$H NMR (400 MHz, DMSO-$d_6$, 80° C.): δ 1.12 (t, J=6.8 Hz, 3H), 1.69 (s, 3H), 2.28 (s, 3H), 2.55 (s, 3H), 3.19 (bs, 3H), 3.96 (q, J=6.9 Hz, 2H), 4.03 (bs, 1H), 4.53 (d, J=5.9 Hz, 2H), 6.74 (s, 1H), 7.18 (dd, J=7.5, 5.0 Hz, 1H), 7.40 (d, J=7.3 Hz, 1H), 7.65 (d, J=7.2 Hz, 1H), 8.01 (d, J=7.8 Hz, 1H), 8.06 (d, J=8.3 Hz, 1H), 8.12 (s, 1H), 8.31 (d, J=8.1 Hz, 1H), 8.34 (d, J=4.5 Hz, 1H), 8.94 (s, 1H), 9.13 (s, 1H).

Methyl N-[2-[N-acetyl-2-methyl-4-[5-[(2-methyl-3-pyridyl)methylcarbamoyl]-2-pyridyl]anilino]ethyl] carbamate (I-487)

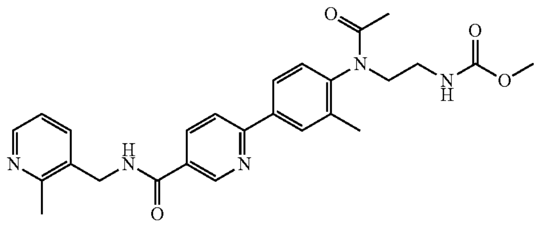 [SMILES: COC(=O)NCCN(C(C)=O)c1ccc(-c2ccc(C(=O)NCc3cccnc3C)cn2)cc1C]

Compound I-487 was prepared similiarly to I-486. Purification by flash column chromatography (silica gel, 0-10% MeOH in DCM) and coevaporation from diethyl ether afforded methyl N-[2-[N-acetyl-2-methyl-4-[5-[(2-methyl-3-pyridyl)methylcarbamoyl]-2-pyridyl]anilino]ethyl]carbamate as a white amorphous solid (18 mg, 34%).

LC-MS (Method 8): $R_t$=3.05 min, m/z=476.25 $(M+H)^+$.

$^1$H NMR (500 MHz, DMSO-$d_6$): δ 1.70 (s, 3H), 2.28 (s, 3H), 2.56 (s, 3H), 3.20 (bs, 3H), 3.52 (s, 3H), 4.04 (bs, 1H), 4.54 (d, J=5.3 Hz, 2H), 6.79 (bs, 1H), 7.19 (dd, J=7.5, 4.8 Hz, 1H), 7.40 (d, J=7.7 Hz, 1H), 7.66 (d, J=7.6 Hz, 1H), 8.02 (d, J=7.8 Hz, 1H), 8.06 (d, J=8.2 Hz, 1H), 8.13 (s, 1H), 8.32 (dd, J=8.3, 2.1 Hz, 1H), 8.35 (d, J=4.7 Hz, 1H), 8.94 (s, 1H), 9.13 (s, 1H).

6-[4-[Acetyl(cyclopropylmethyl)amino]-3-chloro-phenyl]-N-imidazo[1,2-a]pyridin-7-yl-pyridine-3-carboxamide (I-687)

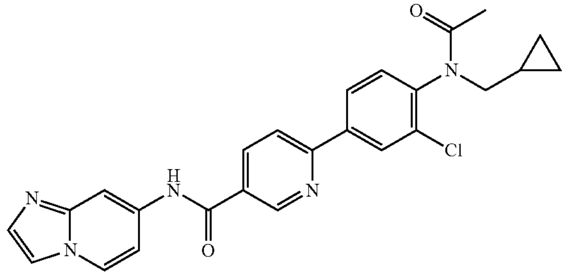 [SMILES: CC(=O)N(CC1CC1)c1ccc(-c2ccc(C(=O)Nc3ccn4ccnc4c3)cn2)cc1Cl]

Purification by prep HPLC (Method 11) afforded 6-[4-[acetyl(cyclopropylmethyl)amino]-3-chloro-phenyl]-N-imidazo[1,2-a]pyridin-7-yl-pyridine-3-carboxamide as a white foam (20 mg, 29%). LC-MS (Method 13): $R_t$=4.61 min; m/z=460.13 $(M+H)^+$. $^1$H-NMR (300 MHz, DMSO-$d_6$): δ 0.01-0.09 (m, 2H), 0.32-0.42 (m, 2H), 0.83-0.97 (m, 1H), 1.74 (s, 3H), 3.18-3.28 (m, 1H), 3.69-3.79 (m, 1H), 7.24 (dd, J=7.50, 2.09 Hz, 1H), 7.50 (d, J=1.12 Hz, 1H), 7.68 (d, J=8.21 Hz, 1H), 7.85-7.87 (m, 1H), 8.14-8.17 (m, 1H), 8.24-8.34 (m, 2H), 8.43-8.48 (m, 2H), 8.51 (d, J=7.40 Hz, 1H), 9.23 (d, J=2.13 Hz, 1H), 10.70 (bs, 1H).

6-[4-[Acetyl(cyclopropylmethyl)amino]-3-chloro-phenyl]-N-[(6-chloro-3-pyridyl)methyl]pyridine-3-carboxamide (I-689)

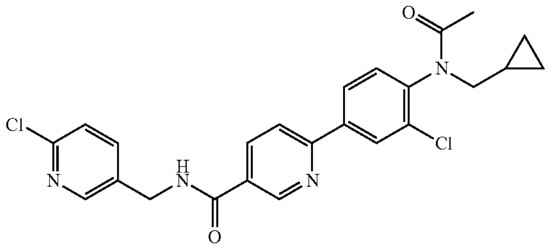 [SMILES: CC(=O)N(CC1CC1)c1ccc(-c2ccc(C(=O)NCc3ccc(Cl)nc3)cn2)cc1Cl]

Purification by flash column chromatography (silica gel, 10% MeOH in DCM) afforded 6-[4-[acetyl(cyclopropylmethyl)amino]-3-chloro-phenyl]-N-[(6-chloro-3-pyridyl)methyl]pyridine-3-carboxamide as a white solid (20 mg, 36%). LC-MS (Method 8): $R_t$=4.28 min; m/z=468.93 $(M+H)^+$. $^1$H-NMR (300 MHz, DMSO-$d_6$): δ 0.02-0.08 (m, 2H), 0.34-0.44 (m, 2H), 0.81-0.94 (m, 1H), 1.73 (s, 3H), 3.21-3.30 (m, 1H), 3.69-3.76 (m, 1H), 4.53 (d, J=5.75 Hz, 2H), 7.46-7.53 (m, 1H), 7.66 (d, J=8.36 Hz, 1H), 7.83 (dd, J=8.27, 2.53 Hz, 1H), 8.20-8.26 (m, 2H), 8.31-8.36 (m, 1H), 8.39-8.43 (m, 2H), 9.13 (d, J=1.74 Hz, 1H), 9.36 (t, J=5.75 Hz, 1H).

6-[4-[Acetyl(cyclopropylmethyl)amino]-3-chloro-phenyl]-N-[(5-fluoro-3-pyridyl)methyl]pyridine-3-carboxamide (I-690)

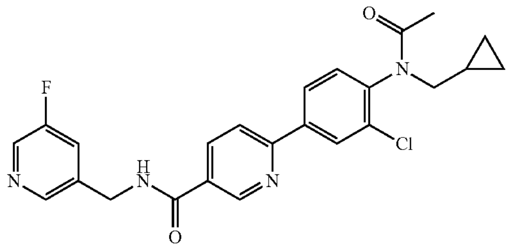 [SMILES: CC(=O)N(CC1CC1)c1ccc(-c2ccc(C(=O)NCc3cncc(F)c3)cn2)cc1Cl]

Purification by flash column chromatography (silica gel, 10% MeOH in DCM) afforded 6-[4-[acetyl(cyclopropylmethyl)amino]-3-chloro-phenyl]-N-[(5-fluoro-3-pyridyl)methyl]pyridine-3-carboxamide as a white solid (12 mg, 22%). LC-MS (Method 8): $R_t$=3.99 min; m/z=453.02 $(M+H)^+$. $^1$H-NMR (300 MHz, DMSO-$d_6$): δ 0.04-0.11 (m, 2H), 0.34-0.44 (m, 2H), 0.81-1.01 (m, 1H), 1.76 (s, 3H), 3.20-3.31 (m, 1H), 3.70-3.77 (m, 1H), 4.61 (d, J=5.75 Hz, 2H), 7.67-7.75 (m, 2H), 8.20-8.26 (m, 2H), 8.33-8.37 (m, 1H), 8.40 (d, J=1.89 Hz, 1H), 8.45-8.50 (m, 2H), 9.14 (d, J=1.57 Hz, 1H), 9.36 (t, J=5.69 Hz, 1H).

6-[4-[Acetyl(cyclopropylmethyl)amino]-3-chloro-phenyl]-N-(1H-pyrazolo[3,4-b]pyridin-5-yl)pyridine-3-carboxamide (I-693)

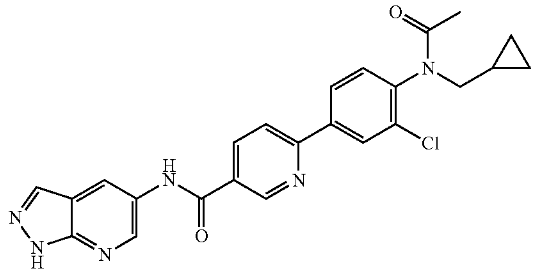 [SMILES: CC(=O)N(CC1CC1)c1ccc(-c2ccc(C(=O)Nc3cnc4[nH]ncc4c3)cn2)cc1Cl]

Purification by prep HPLC (Method 11) afforded 6-[4-[acetyl(cyclopropylmethyl)amino]-3-chloro-phenyl]-N-(1H-pyrazolo[3,4-b]pyridin-5-yl)pyridine-3-carboxamide as white foam (6 mg, 8%). LC-MS (Method 7): $R_t$=3.84 min; m/z=461.00 $(M+H)^+$. $^1$H-NMR (300 MHz, DMSO-$d_6$): δ 0.01-0.08 (m, 2H), 0.33-0.42 (m, 2H), 0.83-0.95 (m, 1H), 1.74 (s, 3H), 3.17-3.28 (m, 1H), 3.70-3.79 (m, 1H), 7.68 (d, J=8.32 Hz, 1H), 8.14 (s, 1H), 8.24-8.32 (m, 2H), 8.44 (d, J=2.10 Hz, 1H), 8.48 (dd, J=8.28, 2.25 Hz, 1H), 8.64 (d, J=2.41 Hz, 1H), 8.74 (d, J=2.41 Hz, 1H), 9.26 (d, J=2.06 Hz, 1H).

6-[4-[Acetyl(cyclopropylmethyl)amino]-3-chloro-phenyl]-N-[(6-fluoro-3-pyridyl)methyl]pyridine-3-carboxamide (I-696)

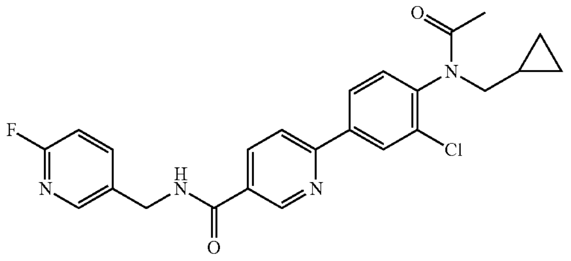 [SMILES: CC(=O)N(CC1CC1)c1ccc(-c2ccc(C(=O)NCc3ccc(F)nc3)cn2)cc1Cl]

Purification by prep HPLC (Method 11) afforded 6-[4-[acetyl(cyclopropylmethyl)amino]-3-chloro-phenyl]-N-[(6-fluoro-3-pyridyl)methyl]pyridine-3-carboxamide as a white foam (13 mg, 24%). LC-MS (Method 7): $R_t$=4.16 min; m/z=453.02 $(M+H)^+$. $^1$H-NMR (500 MHz, DMSO-$d_6$): δ 0.01-0.07 (m, 2H), 0.34-0.41 (m, 2H), 0.85-0.93 (m, 1H), 1.74 (s, 3H), 3.20-3.26 (m, 1H), 3.71-3.77 (m, 1H), 4.54 (d, J=6.07 Hz, 2H), 7.17 (dd, J=8.46, 2.71 Hz, 1H), 7.67 (d, J=8.24 Hz, 1H), 7.97 (td, J=8.19, 2.36 Hz, 1H), 8.22-8.26 (m, 3H), 8.34 (dd, J=8.33, 2.22 Hz, 1H), 8.40 (d, J=1.82 Hz, 1H), 9.14 (d, J=1.96 Hz, 1H), 9.36 (t, J=5.79 Hz, 1H).

6-[4-[Acetyl(cyclopropylmethyl)amino]-3-chloro-phenyl]-N-[(6-methyl-3-pyridyl)methyl]pyridine-3-carboxamide (I-697)

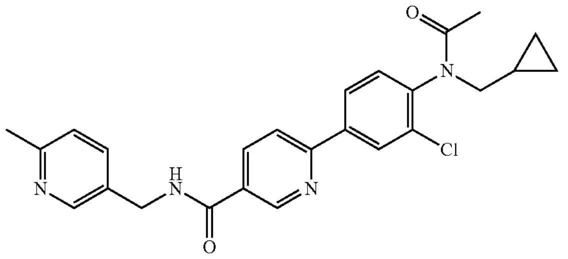 [SMILES: CC(=O)N(CC1CC1)c1ccc(-c2ccc(C(=O)NCc3ccc(C)nc3)cn2)cc1Cl]

Purification by preparative HPLC (Method 11) afforded 6-[4-[acetyl(cyclopropylmethyl)amino]-3-chloro-phenyl]-N-[(6-methyl-3-pyridyl)methyl]pyridine-3-carboxamide as a white foam (21 mg, 40%). LC-MS (Method 7): $R_t$=2.94 min; m/z=449.05 $(M+H)^+$. $^1$H-NMR (500 MHz, DMSO-$d_6$): δ 0.01-0.07 (m, 2H), 0.34-0.41 (m, 2H), 0.86-0.93 (m, 1H), 1.74 (s, 3H), 2.44 (s, 3H), 3.20-3.26 (m, 1H), 3.71-3.77 (m, 1H), 4.49 (d, J=5.79 Hz, 2H), 7.22 (d, J=8.65 Hz, 1H), 7.64 (dd, J=8.07, 2.34 Hz, 1H), 7.67 (d, J=8.42 Hz, 1H), 8.23 (bd, J=3.60 Hz, 2H), 8.34 (dd, J=8.20, 2.12 Hz, 1H), 8.40 (d, J=1.99 Hz, 1H), 8.44 (bd, J=1.99 Hz, 1H), 9.14 (d, J=2.05 Hz, 1H), 9.32 (t, J=5.72 Hz, 1H).

6-[4-[Acetyl(cyclopropylmethyl)amino]-3-chloro-phenyl]-N-(2-pyridylmethyl)pyridine-3-carboxamide (I-698)

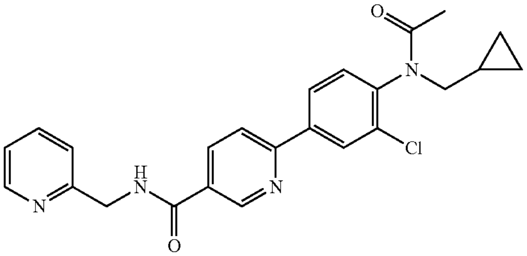 [SMILES: CC(=O)N(CC1CC1)c1ccc(-c2ccc(C(=O)NCc3ccccn3)cn2)cc1Cl]

Purification by preparative HPLC (Method 11) afforded 6-[4-[acetyl(cyclopropyl methyl)amino]-3-chloro-phenyl]-N-(2-pyridylmethyl)pyridine-3-carboxamide as a white foam (28 mg, 56%). LC-MS (Method 7): $R_t$=3.25 min; m/z=435.10 $(M+H)^+$. $^1$H-NMR (500 MHz, DMSO-$d_6$): δ 0.01-0.08 (m, 2H), 0.32-0.42 (m, 2H), 0.83-0.94 (m, 1H), 1.74 (s, 3H), 3.18-3.27 (m, 1H), 3.669-3.78 (m, 1H), 4.61 (d, J=5.79 Hz, 2H), 7.24-7.30 (m, 1H), 7.37 (d, J=8.04 Hz, 1H), 7.66 (d, J=8.32 Hz, 1H), 7.76 (td, J=7.68, 1.80 Hz, 1H), 8.20-8.27 (m, 2H), 8.35-8.42 (m, 2H), 8.49-8.53 (m, 1H) 9.17 (d, J=2.53 Hz, 1H), 9.39 (t, J=5.79 Hz, 1H).

4-[4-[Acetyl(cyclopropylmethyl)amino]phenyl]-N-(3-pyridylmethyl)benzamide (I-675)

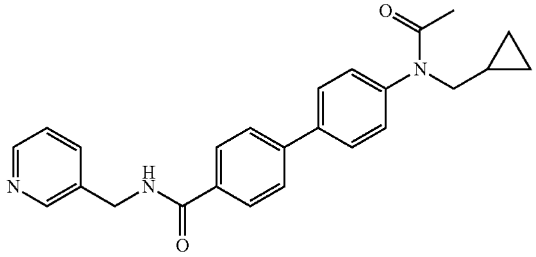 [SMILES: CC(=O)N(CC1CC1)c1ccc(-c2ccc(C(=O)NCc3cccnc3)cc2)cc1]

Purification by flash column chromatography (silica gel, 10% MeOH in DCM) afforded 4-[4-[acetyl(cyclopropylmethyl)amino]phenyl]-N-(3-pyridylmethyl)benzamide as a white solid (29 mg, 25%).

LC-MS (Method 8): $R_t$=3.71 min; m/z=400.47 $(M+H)^+$. $^1$H-NMR (300 MHz, DMSO-$d_6$): δ 0.02-0.11 (m, 2H), 0.33-0.42 (m, 2H), 0.82-0.95 (m, 1H), 1.78 (br s, 3H), 3.52 (d, J=6.97 Hz, 2H), 4.51 (d, J=5.8 Hz, 2H), 7.32-7.39 (m, 1H), 7.40-7.49 (m, 2H), 7.73 (dt, J=8.06, 1.81 Hz, 1H), 7.82 (m, 4H), 7.94-8.03 (m, 2H), 8.46 (dd, J=4.79, 1.65 Hz, 1H), 8.56 (d, J=1.74 Hz, 1H), 9.16 (t, J=5.82 Hz, 1H).

Scheme 5 with Procedures 2a/3b

Step 1: Suzuki coupling (per Scheme 1—Step 1)

Methyl 6-(4-amino-3-methyl-phenyl)pyridine-3-carboxylate

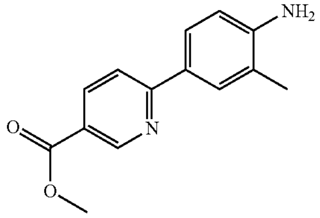 [SMILES: COC(=O)c1ccc(-c2ccc(N)c(C)c2)nc1]

Step 1 was carried out using 2-methyl-4-(4,4,5,5-tetramethyl-1,3,2-dioxaborolan-2-yl)aniline (3.56 g, 15.3 mmol) and methyl 6-bromopyridine-3-carboxylate (3.00 g, 13.9 mmol). The remaining residue was triturated with ACN to afford methyl 6-(4-amino-3-methyl-phenyl)pyridine-3-carboxylate as a green solid (1.69 g, 43%).

LC-MS (Method 2): $R_t$=0.93 min; m/z=243.09 $(M+H)^+$.

Step 2a: Reductive amination (per Scheme 1—Step 4)

Methyl 6-[4-(cyclopropylmethylamino)-3-methyl-phenyl]pyridine-3-carboxylate

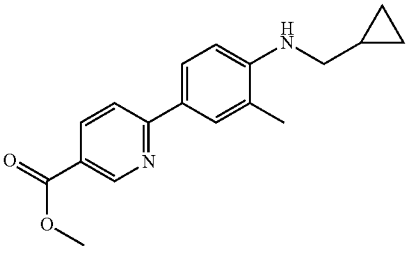 [SMILES: COC(=O)c1ccc(-c2ccc(NCC3CC3)c(C)c2)nc1]

Step 2, starting from methyl 6-(4-amino-3-methyl-phenyl)pyridine-3-carboxylate (250 mg, 0.83 mmol) and cyclopropanecarbaldehyde (69.3 μL, 0.91 mmol) afforded methyl 6-[4-(cyclopropylmethylamino)-3-methyl-phenyl]pyridine-3-carboxylate (330 mg, 93%) which was used as such in the next step.

LC-MS (Method 2): $R_t$=1.29 min; m/z=297.23 $(M+H)^+$.

Step 3b: Acylation

Methyl 6-[4-[acetyl(cyclopropylmethyl)amino]-3-methyl-phenyl]pyridine-3-carboxylate

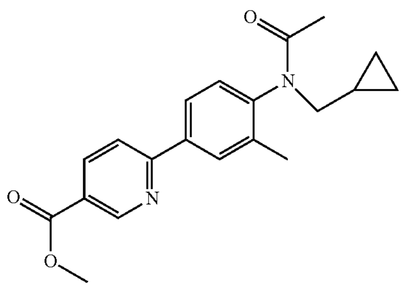 [SMILES: COC(=O)c1ccc(-c2ccc(N(CC3CC3)C(C)=O)c(C)c2)nc1]

To stirred solution of methyl 6-[4-(cyclopropylmethylamino)-3-methyl-phenyl]pyridine-3-carboxylate (330 mg, 0.78 mmol) in dry DCM (7 mL), were added acetic anhydride (0.074 mL, 0.78 mmol) and 4-dimethylaminopyridine (48 mg, 0.39 mmol). The RM was stirred at RT overnight. It was diluted with DCM, washed with sat. $NaHCO_3$, dried and concentrated in vacuo to afford the crude product. Purification by flash column chromatography (silica gel, 0-20% MeOH in DCM) afforded methyl 6-[4-[acetyl(cyclopropylmethyl)amino]-3-methyl-phenyl]pyridine-3-carboxylate (290 mg, 82%).

LC-MS (Method 2): $R_t$=1.10 min; m/z=339.16 $(M+H)^+$.

Step 4: Hydrolysis (Per Scheme 1—Step 2)

6-[4-[Acetyl(cyclopropylmethyl)amino]-3-methyl-phenyl]pyridine-3-carboxylic acid

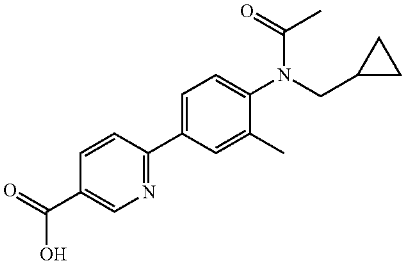 [SMILES: CC(=O)N(CC1CC1)c1ccc(-c2ccc(C(=O)O)cn2)cc1C]

Hydrolysis of methyl 6-[4-[acetyl(cyclopropylmethyl)amino]-3-methyl-phenyl]pyridine-3-carboxylate (290 mg, 0.64 mmol) afforded crude 6-[4-[acetyl(cyclopropylmethyl)amino]-3-methyl-phenyl]pyridine-3-carboxylic acid (250 mg) which was used as such in the next step.

LC-MS (Method 2): $R_t$=0.47 min; m/z=325.04 $(M+H)^+$.

Step 5: Amidation (per Scheme 2—Step 5)

6-[4-[Acetyl(cyclopropylmethyl)amino]-3-methyl-phenyl]-N-(3-pyridylmethyl)pyridine-3-carboxamide (I-609)

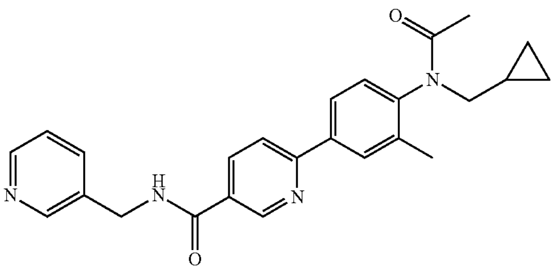 [SMILES: CC(=O)N(CC1CC1)c1ccc(-c2ccc(C(=O)NCc3cccnc3)cn2)cc1C]

Starting from 6-[4-[acetyl(cyclopropylmethyl)amino]-3-methyl-phenyl]pyridine-3-carboxylic acid (100 mg, 0.284 mmol) and 3-pyridylmethanamine (0.035 mL, 0.37 mmol), purification by flash column chromatography (silica gel, 10% MeOH in DCM) afforded 6-[4-[acetyl(cyclopropylmethyl)amino]-3-methyl-phenyl]-N-(3-pyridylmethyl)pyridine-3-carboxamide (44 mg, 37%) as a white amorphous solid.

LC-MS (Method 8): $R_t$=3.55 min; m/z=415.19 $(M+H)^+$.

$^1$H NMR (500 MHz, DMSO-$d_6$): δ 0.01-0.12 (m, 2H), 0.36-0.43 (m, 2H), 0.84-0.98 (m, 1H), 1.69 (s, 3H), 2.31 (s, 3H), 3.17-3.22 (m, 1H), 3.68-3.74 (m, 1H), 4.55 (d, J=5.80 Hz, 2H), 7.36-7.41 (m, 2H), 7.77 (d, J=7.90 Hz, 1H), 8.06 (dd, J=8.24, 1.83 Hz, 1H), 8.14 (d, J=8.24 Hz, 1H), 8.17 (d, J=1.53 Hz, 1H), 8.33 (dd, J=8.39, 2.29 Hz, 1H), 8.48 (dd, J=4.73, 1.37 Hz, 1H), 8.59 (s, 1H), 9.13 (d, J=1.83 Hz, 1H), 9.33 (t, J=5.80 Hz, 1H).

6-[4-[(2,2-Difluoroacetyl)-isobutyl-amino]phenyl]-N-(3-pyridylmethyl)pyridine-3-carboxamide (I-468)#

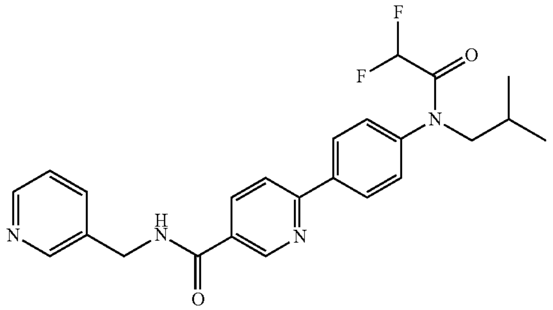 [SMILES: CC(C)CN(C(=O)C(F)F)c1ccc(-c2ccc(C(=O)NCc3cccnc3)cn2)cc1]

Purification by flash column chromatography (silica gel, 10% MeOH in DCM) and trituration from diethyl ether afforded 6-[4-[(2,2-difluoroacetyl)-isobutyl-amino]phenyl]-N-(3-pyridylmethyl)pyridine-3-carboxamide as a yellowish solid (26 mg, 21%).

LC-MS (Method 8): $R_t$=4.01 min; m/z=439.14 $(M+H)^+$.

$^1$H-NMR (500 MHz, DMSO-$d_6$): δ 0.87 (d, J=6.70 Hz, 6H), 1.70 (m, 1H) 3.61 (d, J=7.49 Hz, 2H), 4.54 (d, J=5.82 Hz, 2H), 6.18 (t, J=52.9 Hz, 1H), 7.38 (dd, J=7.73, 4.78 Hz, 1H), 7.55 (d, J=8.30 Hz, 2H), 7.77 (d, J=7.73 Hz, 1H), 8.17 (d, J=8.27 Hz, 1H), 8.26 (d, J=8.30 Hz, 2H), 8.34 (dd,

J=8.11, 1.75 Hz, 1H)8.48 (d, J=4.78 Hz, 1H) 8.59 (s, 1H), 9.14 (s, 1H), 9.33 (t, J=5.82 Hz, 1H).

#The acylation reaction was performed after the last step because the N-acyl substituent was cleaved during hydrolysis of the methyl ester.

6-[4-[Acetyl-[(3,3-difluorocyclobutyl)methyl]amino]-3-methyl-phenyl]-N-(3-pyridylmethyl)pyridine-3-carboxamide (I-600)

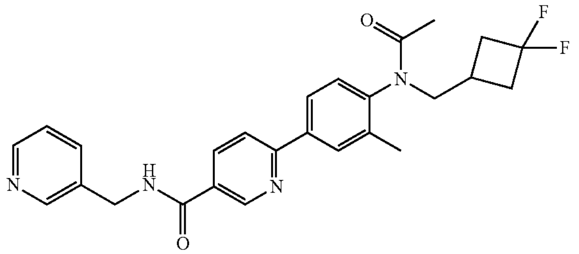 [SMILES: CC(=O)N(CC1CC(F)(F)C1)c1ccc(-c2ccc(C(=O)NCc3cccnc3)cn2)cc1C]

Purification by flash column chromatography (silica gel, 20% MeOH in DCM) afforded 6-[4-[acetyl-[(3,3-difluorocyclobutyl)methyl]amino]-3-methyl-phenyl]-N-(3-pyridylmethyl)pyridine-3-carboxamide as a white amorphous solid (40 mg, 47%).

LC-MS (Method 8): $R_t$=3.72 min; m/z=465.23 $(M+H)^+$.

$^1$H NMR (400 MHz, $CDCl_3$): δ 1.78 (s, 3H), 2.14-2.24 (m, 1H), 2.30 (s, 3H), 2.31-2.42 (m, 2H), 2.47-2.67 (m, 2H), 3.32-3.41 (m, 1H), 4.16-4.24 (m, 1H), 4.71 (d, J=5.40 Hz, 2H), 6.53 (t, J=5.40 Hz, 1H), 7.15 (d, J=8.31 Hz, 1H), 7.26-7.33 (m, 1H), 7.68-7.77 (m, 1H, 7.79-7.83 (m, 1H), 7.87 (dd, J=8.01, 2.02 Hz, 1H), 8.00 (d, J=1.47 Hz, 1H), 8.21 (dd, J=8.38, 2.38 Hz, 1H), 8.56 (dd, J=4.83, 1.90 Hz, 1H), 8.64 (d, J=1.96 Hz, 1H), 9.05 (d, J=1.71 Hz, 1H).

6-[4-[Acetyl(propyl)amino]-3-chloro-phenyl]-N-(3-pyridylmethyl)pyridine-3-carboxamide (I-606)

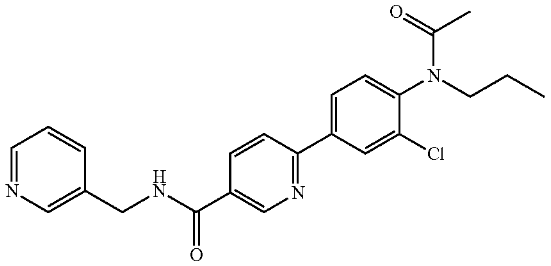 [SMILES: CCCN(C(C)=O)c1ccc(-c2ccc(C(=O)NCc3cccnc3)cn2)cc1Cl]

Purification by flash column chromatography (silica gel, 20% MeOH in DCM) afforded 6-[4-[acetyl(propyl)amino]-3-chloro-phenyl]-N-(3-pyridylmethyl)pyridine-3-carboxamide as a white amorphous solid (65 mg, 50%).

LC-MS (Method 8): $R_t$=3.72 min; m/z=423.16 $(M+H)^+$.

$^1$H NMR (500 MHz, 80° C., DMSO-$d_6$): δ 0.87 (t, J=7.1 Hz, 3H), 1.45-1.54 (m, 2H), 1.74 (s, 3H), 3.27-3.36 (m, 1H), 3.78-3.88 (m, 1H), 4.55 (d, J=5.8 Hz, 2H), 7.36 (dd, J=7.9, J=4.7, 1H), 7.58 (d, J=7.8, 1H) 7.77 (d, J=7.8, 1H) 8.13-8.21 (m, 2H), 8.32-8.37 (m, 2H), 8.47 (d, J=4.7, 1H), 8.60 (bs, 1H), 9.11 (t, J=5.6 Hz, 1H), 9.14 (bs, 1H).

Scheme 5 with procedures 2b.i/3a

Step 1: Suzuki coupling (per Scheme 1—Step 1)

Methyl 6-(4-amino-3-chloro-phenyl)pyridine-3-carboxylate

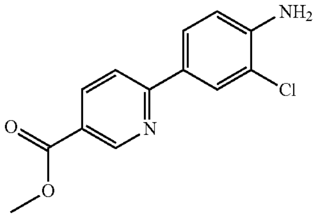 [SMILES: COC(=O)c1ccc(-c2ccc(N)c(Cl)c2)nc1]

Step 1 was followed starting from 2-chloro-4-(4,4,5,5-tetramethyl-1,3,2-dioxaborolan-2-yl)aniline (1.00 g, 3.94 mmol) and methyl 6-bromopyridine-3-carboxylate (0.852 g, 3.94 mmol). The remaining residue was triturated with ACN to afford methyl 6-(4-amino-3-chloro-phenyl)pyridine-3-carboxylate as a brownish solid (0.75 g, 66%).

LC-MS (Method 2): $R_t$=1.02 min; m/z=263.03 $(M+H)^+$.

Step 2b.i: Reductive Amination

Methyl 6-[3-chloro-4-(isopropylamino)phenyl]pyridine-3-carboxylate

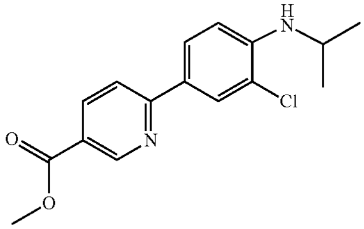 [SMILES: COC(=O)c1ccc(-c2ccc(NC(C)C)c(Cl)c2)nc1]

To a solution of methyl 6-(4-amino-3-chloro-phenyl)pyridine-3-carboxylate (290 mg, 1.10 mmol) in acetic acid (3 mL), were added $Na_2SO_4$ (157 mg, 1.10 mmol) and acetone (0.491 mL, 6.62 mmol). The RM was stirred at 50° C. for 30 min followed by addition of tetramethylammonium triacetoxyborohydride (702 mg, 3.31 mmol) at RT. Stirring was continued at 50° C. for 2 h. The RM was poured into cold aq. $NaHCO_3$ solution which was extracted with EtOAc. The organic layers were combined, dried and concentrated in vacuo. Purification by flash column chromatography (silica gel, 50% EtOAc in cycloxehane) afforded methyl 6-[3-chloro-4-(isopropylamino)phenyl]pyridine-3-carboxylate (79 mg, 23%) as a white amorphous solid.

LC-MS (Method 2): $R_t$=1.41 min; m/z=305.05 $(M+H)^+$.

Step 3a: Acylation (Per Scheme 1—Step 5)

Methyl 6-[4-[acetyl(isopropyl)amino]-3-chloro-phenyl]pyridine-3-carboxylate

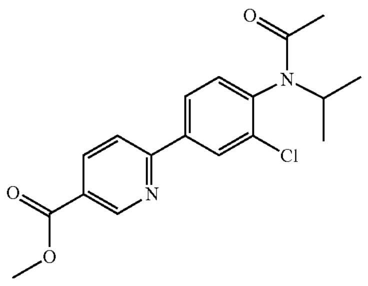 [SMILES: COC(=O)c1ccc(-c2ccc(N(C(C)=O)C(C)C)c(Cl)c2)nc1]

Acylation starting from methyl 6-[3-chloro-4-(isopropylamino)phenyl]pyridine-3-carboxylate (79 mg, 0.26 mmol) afforded crude methyl 6-[4-[acetyl(isopropyl)amino]-3-chloro-phenyl]pyridine-3-carboxylate (90 mg) which was used as such in the next step.

LC-MS (Method 2): $R_t$=1.16 min; m/z=347.00 $(M+H)^+$.

Step 4: Hydrolysis (per Scheme 1—Step 2)

6-[4-[Acetyl(isopropyl)amino]-3-chloro-phenyl]pyridine-3-carboxylic acid

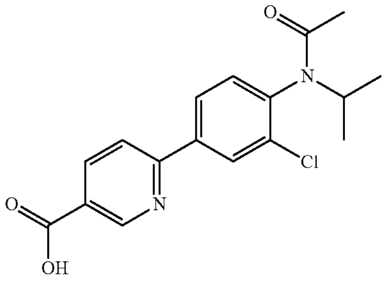 [SMILES: CC(=O)N(c1ccc(-c2ccc(C(=O)O)cn2)cc1Cl)C(C)C]

Hydrolysis of methyl 4-[4-[acetyl(isopropyl)amino]-3-chloro-phenyl]benzoate (90.0 mg, 0.26 mmol) afforded 6-[4-[acetyl(isopropyl)amino]-3-chloro-phenyl]pyridine-3-carboxylic acid (87 mg) which was used as such in the next step.

LC-MS (Method 2): $R_t$=0.49 min; m/z=333.06 $(M+H)^+$.

Step 5: Amidation (per Scheme 2—Step 5)

6-[4-[Acetyl(isopropyl)amino]-3-chloro-phenyl]-N-(3-pyridylmethyl)pyridine-3-carboxamide (I-596)

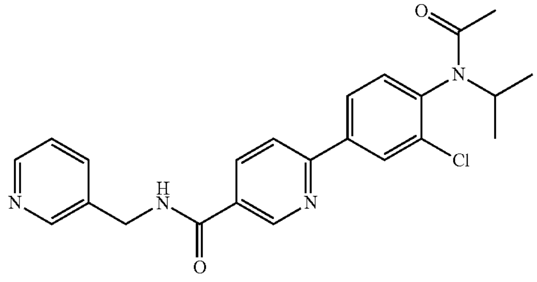

Starting from 6-[4-[acetyl(isopropyl)amino]-3-chloro-phenyl]pyridine-3-carboxylic acid (87 mg, 0.26 mmol) and 3-pyridylmethanamine (0.038 g, 0.35 mmol), 6-[4-[acetyl(isopropyl)amino]-3-chloro-phenyl]-N-(3-pyridylmethyl)pyridine-3-carboxamide (40 mg, 36%) was obtained as a white amorphous solid.

LC-MS (Method 8): $R_t$=3.64 min; m/z=423.16 $(M+H)^+$.

$^1$H NMR (300 MHz, DMSO-$d_6$): δ 0.94 (d, J=6.97 Hz, 3H), 1.18 (d, J=6.79 Hz, 3H), 1.67 (s, 3H), 4.54 (d, J=5.70 Hz, 2H), 4.67-4.80 (m, 1H), 7.36 (dd, J=7.60, 4.73 Hz, 1H), 7.56 (d, J=8.19 Hz, 1H), 7.76 (dt, J=7.93, 1.87 Hz, 1H), 8.19-8.27 (m, 2H), 8.35 (dd, J=8.36, 2.26 Hz, 1H), 8.41 (d, J=2.06 Hz, 1H), 8.47 (dd, J=4.79, 1.48 Hz, 1H), 8.58 (d, J=1.74 Hz, 1H), 9.15 (d, J=1.74 Hz, 1H), 9.36 (t, J=5.66 Hz, 1H).

Scheme 5 with procedures 2b.i/3b

6-[3-chloro-4-[(2,2-difluoroacetyl)-isopropyl-amino]phenyl]-N-(3-pyridylmethyl)pyridine-3-carboxamide (I-611)

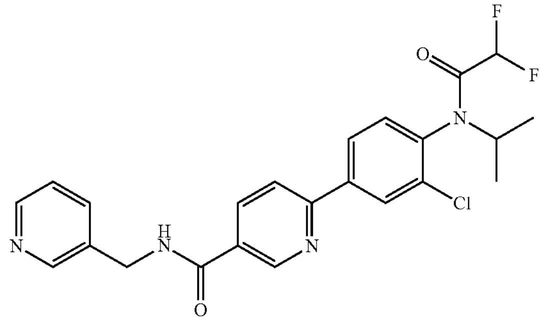 [SMILES: CC(C)N(C(=O)C(F)F)c1ccc(-c2ccc(C(=O)NCc3cccnc3)cn2)cc1Cl]

Purification by flash column chromatography (silica gel, 10% MeOH in DCM) afforded 6-[3-chloro-4-[(2,2-difluoroacetyl)-isopropyl-amino]phenyl]-N-(3-pyridylmethyl)pyridine-3-carboxamide as a white amorphous solid (27 mg, 43%).

LC-MS (Method 8): $R_t$=4.10 min; m/z=459.15 $(M+H)^+$.

$^1$H NMR (500 MHz, DMSO-$d_6$): δ 1.05 (d, J=6.71 Hz, 3H), 1.26 (d, J=6.71 Hz, 3H), 4.55 (d, J=5.80 Hz, 2H), 4.59-4.67 (m, 1H), 5.96 (t, J=52.50 Hz, 1H), 7.38 (dd, J=7.78, 5.04 Hz, 1H), 7.67 (d, J=8.24 Hz, 1H), 7.77 (d, J=7.93 Hz, 1H), 8.24-8.29 (m, 2H), 8.37 (dd, J=8.24, 2.14 Hz, 1H), 8.45 (d, J=2.14 Hz, 1H), 8.48 (dd, J=4.73, 1.37 Hz, 1H), 8.59 (d, J=1.53 Hz, 1H), 9.16 (d, J=1.53 Hz, 1H), 9.37 (t, J=5.80 Hz, 1H)

4-[4-[Acetyl(isopropyl)amino]-3-methyl-phenyl]-N-(3-pyridylmethyl)benzamide (I-624)

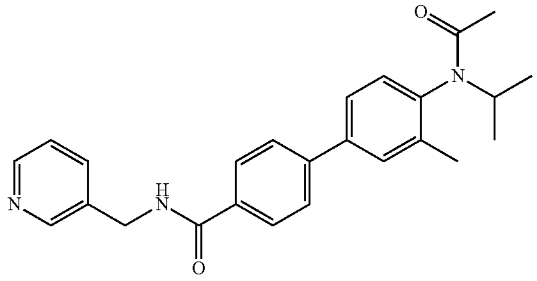 [SMILES: CC(=O)N(c1ccc(-c2ccc(C(=O)NCc3cccnc3)cc2)cc1C)C(C)C]

Purification by flash column chromatography (silica gel, 10% MeOH in DCM) afforded 4-[4-[acetyl(isopropyl) amino]-3-methyl-phenyl]-N-(3-pyridylmethyl)benzamide as a white amorphous solid (85 mg, 46%).

LC-MS (Method 8): $R_t$=3.75 min; m/z=402.50 $(M+H)^+$.

$^1H$ NMR (300 MHz, DMSO-$d_6$): δ 0.90 (d, J=6.79 Hz, 3H), 1.17 (d, J=6.62 Hz, 3H), 1.61 (s, 3H), 2.26 (s, 3H), 4.51 (d, J=5.92 Hz, 2H), 4.62-4.72 (m, 1H), 7.24 (d, J=8.01 Hz, 1H), 7.36 (dd, J=7.84, 4.70 Hz, 1H), 7.64 (dd, J=8.19, 2.26 Hz, 1H), 7.71-7.80 (m, 2H), 7.83 (d, J=8.36 Hz, 2H), 7.98 (d, J=8.36 Hz, 2H), 8.46 (dd, J=4.70, 1.39 Hz, 1H), 8.56 (d, J=1.92 Hz, 1H), 9.16 (t, J=5.92 Hz, 1H).

6-[4-[Acetyl(isopropyl)amino]-3-fluoro-phenyl]-N-(3-pyridylmethyl)pyridine-3-carboxamide (I-626)

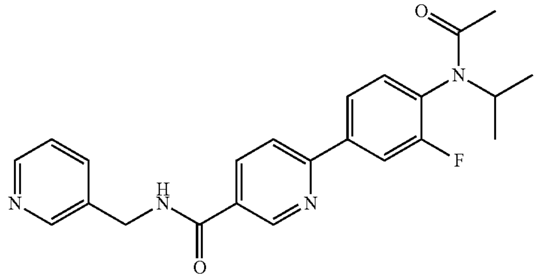

Purification by flash column chromatography (silica gel, 10% MeOH in DCM) and coevaporation from diethyl ether afforded 6-[4-[acetyl(isopropyl)amino]-3-fluoro-phenyl]-N-(3-pyridylmethyl)pyridine-3-carboxamide as a white amorphous solid (54 mg, 53%).

LC-MS (Method 8): Rt=3.46 min; m/z=407.50 $(M+H)^+$.

$^1H$ NMR (500 MHz, DMSO-$d_6$): δ 0.95 (d, J=5.50 Hz, 3H), 1.09 (d, J=6.40 Hz, 3H), 1.70 (s, 3H), 4.55 (d, J=5.20 Hz, 2H), 4.79-4.87 (m, 1H), 7.38 (dd, J=7.60, 4.60 Hz, 1H), 7.51 (t, J=8.10 Hz, 1H), 7.77 (d, J=7.60 Hz, 1H), 8.12 (d, J=7.90 Hz, 1H), 8.17 (d, J=10.70 Hz, 1H), 8.23 (d, J=8.20 Hz, 1H), 8.36 (d, J=6.70 Hz, 1H), 8.48 (d, J=3.10 Hz, 1H), 8.59 (s, 1H), 9.15 (s, 1H), 9.36 (br s, 1H).

4-[4-[Acetyl(isopropyl)amino]-3-fluoro-phenyl]-N-(3-pyridylmethyl)benzamide (I-630)

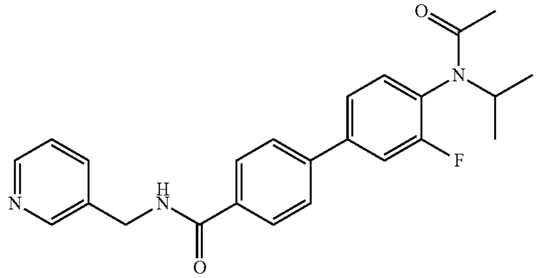 [SMILES: CC(=O)N(c1ccc(-c2ccc(C(=O)NCc3cccnc3)cc2)cc1F)C(C)C]

Purification by flash column chromatography (silica gel, 10% MeOH in DCM) afforded 4-[4-[acetyl(isopropyl) amino]-3-fluoro-phenyl]-N-(3-pyridylmethyl)benzamide as a white amorphous solid (50 mg, 38%).

LC-MS (Method 4): Rt=1.59 min; m/z=406.24 $(M+H)^+$.

$^1H$ NMR (300 MHz, DMSO-$d_6$): δ 0.93 (d, J=6.94 Hz, 3H), 1.07 (d, J=6.77 Hz, 3H), 1.68 (s, 3H), 4.51 (d, J=6.09 Hz, 2H), 4.75-4.86 (m, 1H), 7.19 (dd, J=7.70 Hz, H=4.68 Hz, 1H), 7.45 (t, J=8.13 Hz, 1H), 7.65-7.76 (m, 2H), 7.83 (dd, J=11.35, J=1.80, 1H), 7.89 (d, J=7.87 Hz, 2H), 7.99 (d, J=8.47, 2H), 8.46 (dd, J=4.52, J=1.45, 1H), 8.56 (d, J=1.90 Hz, 1H), 9.18 (t, J=5.77 Hz, 1H).

Scheme 5 with procedures 2b.ii/3b

Step 1: Suzuki coupling (per Scheme 1—Step 1)

Methyl 6-(4-amino-3-methyl-phenyl)pyridine-3-carboxylate

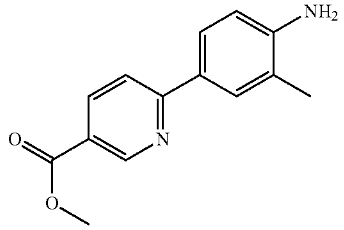 [SMILES: COC(=O)c1ccc(-c2ccc(N)c(C)c2)nc1]

Starting from 2-methyl-4-(4,4,5,5-tetramethyl-1,3,2-dioxaborolan-2-yl)aniline (2.01 g, 8.61 mmol) and methyl 6-bromopyridine-3-carboxylate (1.55 g, 7.17 mmol), purification by flash chromatography (silica gel, 0-100% EtOAc in cyclohexane) afforded methyl 6-(4-amino-3-methyl-phenyl)pyridine-3-carboxylate (1.03 g, 59%).

LC-MS (Method 2): $R_t$=0.92 min; m/z=243.10 $(M+H)^+$.

Step 2b.ii: Reductive amination

Methyl 6-[4-(isopropylamino)-3-methyl-phenyl] pyridine-3-carboxylate

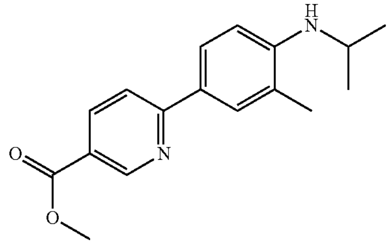 [SMILES: COC(=O)c1ccc(-c2ccc(NC(C)C)c(C)c2)nc1]

To a solution of methyl 6-(4-amino-3-methyl-phenyl) pyridine-3-carboxylate (300 mg, 1.24 mmol) in MeOH (20.0 mL) and acetone (0.367 mL, 4.95 mmol), were added $SiEt_3H$ (0.791 mL, 4.95 mmol) and InCl3 (0.200 g, 0.904 mmol). The RM was stirred at RT overnight and the solvent removed under reduced pressure. The remaining residue was suspended in DCM, washed with sat. $NaHCO_3$ and brine. The organic layer was dried and concentrated in vacuo. Purified by flash column chromatography (silica gel, 10% MeOH in DCM) to afford 240 mg of methyl 6-[4-(isopropylamino)-3-methyl-phenyl]pyridine-3-carboxylate as a yellow solid.

LC-MS (Method 2): $R_t$=1.30 min; m/z=285.16 $(M+H)^+$.

Step 3b: Acylation

Methyl 6-[4-[acetyl(isopropyl)amino]-3-methyl-phenyl]pyridine-3-carboxylate

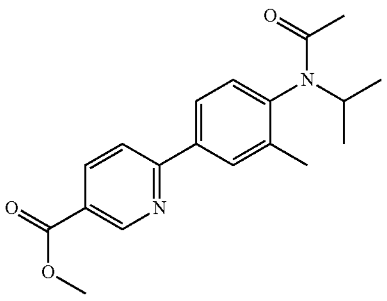 [SMILES: COC(=O)c1ccc(-c2ccc(N(C(C)=O)C(C)C)c(C)c2)nc1]

Acylation of methyl 6-[4-(isopropylamino)-3-methyl-phenyl]pyridine-3-carboxylate (130 mg, 0.46 mmol), afforded methyl 6-[4-[acetyl(isopropyl)amino]-3-methyl-phenyl]pyridine-3-carboxylate (120 mg) which was used as such in the next step.

LC-MS (Method 2): $R_t$=1.08 min; m/z=327.11 $(M+H)^+$.

Step 4: Hydrolysis (per Scheme 1—Step 2)

6-[4-[Acetyl(isopropyl)amino]-3-methyl-phenyl]pyridine-3-carboxylic acid

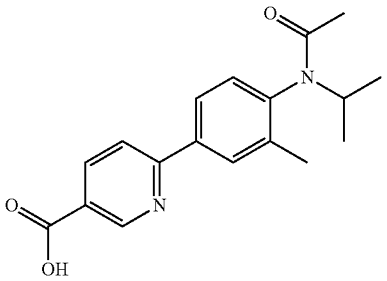 [SMILES: CC(=O)N(c1ccc(-c2ccc(C(=O)O)cn2)cc1C)C(C)C]

Hydrolysis of methyl 6-[4-[acetyl(isopropyl)amino]-3-methyl-phenyl]pyridine-3-carboxylate (120 mg, 0.37 mmol) afforded 6-[4-[acetyl(isopropyl)amino]-3-methyl-phenyl]pyridine-3-carboxylic acid (110 mg) which was used as such in the next step.

LC-MS (Method 2): $R_t$=0.44 min; m/z=313.08 $(M+H)^+$.

Step 5: Amidation (per Scheme 2—Step 5)

6-[4-[Acetyl(isopropyl)amino]-3-methyl-phenyl]-N-(3-pyridylmethyl)pyridine-3-carboxamide (I-495)

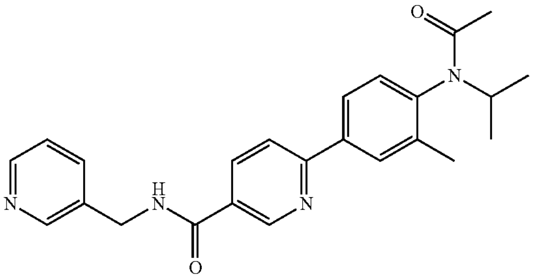 [SMILES: CC(=O)N(c1ccc(-c2ccc(C(=O)NCc3cccnc3)cn2)cc1C)C(C)C]

Starting from 6-[4-[acetyl(isopropyl)amino]-3-methyl-phenyl]pyridine-3-carboxylic acid (60.0 mg, 0.19 mmol) and 3-pyridylmethanamine (0.02 mL, 0.23 mmol), purification of the crude product by flash column chromatography (silica gel, 10% MeOH in DCM) afforded 6-[4-[acetyl(isopropyl)amino]-3-methyl-phenyl]-N-(3-pyridylmethyl)pyridine-3-carboxamide (15 mg, 19%) as a white amorphous solid.

LC-MS (Method 8): $R_t$=3.40 min; m/z=403.20 $(M+H)^+$.

$^1$H NMR (300 MHz, DMSO-$d_6$): δ 0.89 (d, J=6.76 Hz, 3H), 1.17 (d, J=6.65 Hz, 3H), 2.28 (s, 3H), 1.61 (s, 3H), 4.53 (d, J=5.70 Hz, 2H), 4.62-4.72 (m, 1H), 7.27 (d, J=8.39 Hz, 1H), 7.33-7.39 (m, 1H), 7.76 (dt, J=7.96, 1.93 Hz, 1H), 8.04 (dd, J=8.14, 1.93 Hz, 1H), 8.11-8.19 (m, 2H), 8.32 (dd, J=8.36, 2.26 Hz, 1H), 8.47 (dd, J=4.63, 1.48 Hz, 1H), 8.58 (d, J=1.74 Hz, 1H), 9.12 (d, J=2.13 Hz, 1H), 9.32 (t, J=5.89 Hz, 1H).

6-[4-[(2,2-Difluoroacetyl)-isopropyl-amino]-3-methyl-phenyl]-N-(3-pyridylmethyl)pyridine-3-carboxamide (I-595)

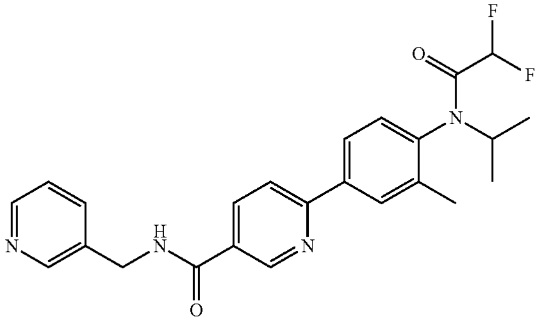 [SMILES: Cc1cc(-c2ccc(C(=O)NCc3cccnc3)cn2)ccc1N(C(=O)C(F)F)C(C)C]

Purification by flash column chromatography (silica gel, 10% MeOH/DCM) and coevaporation from diethylether afforded 6-[4-[(2,2-difluoroacetyl)-isopropyl-amino]-3-methyl-phenyl]-N-(3-pyridylmethyl)pyridine-3-carboxamide as a white amorphous solid (89 mg, 70%).

LC-MS (Method 8): $R_t$=3.84 min; m/z=439.31 $(M+H)^+$.

$^1$H NMR (400 MHz, DMSO-$d_6$): δ 1.00 (d, J=6.85 Hz, 3H), 1.24 (d, J=6.60 Hz, 3H), 2.29 (s, 3H), 4.50-4.58 (m, 3H), 5.84 (t, J=52.70 Hz, 1H), 7.37-7.41 (m, 2H), 7.78 (dt, J=7.86, 1.82 Hz, 1H), 8.07 (dd, J=8.31, 1.96 Hz, 1H), 8.16 (d, J=8.31 Hz, 1H), 8.20 (d, J=1.83 Hz, 1H), 8.34 (dd, J=8.31, 2.32 Hz, 1H), 8.48 (dd, J=4.83, 1.65 Hz, 1H), 8.59 (d, J=1.83 Hz, 1H), 9.13 (d, J=1.59 Hz, 1H), 9.34 (t, J=5.87 Hz, 1H).

4-[4-[Acetyl(isopropyl)amino]-3-chloro-phenyl]-N-(3-pyridylmethyl)benzamide (I-597)

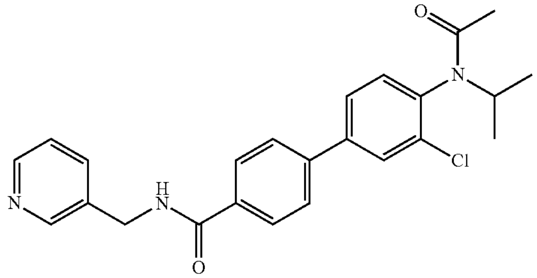

Purification by flash column chromatography (silica gel, 10% MeOH/DCM) afforded 4-[4-[acetyl(isopropyl)amino]-3-chloro-phenyl]-N-(3-pyridylmethyl)benzamide as a white amorphous solid (27 mg, 59%).

LC-MS (Method 8): $R_t$=3.90 min; m/z=422.15 $(M+H)^+$.

$^1H$ NMR (300 MHz, DMSO-$d_6$): δ 0.94 (d, J=6.79 Hz, 3H), 1.17 (d, J=6.62 Hz, 3H), 1.67 (s, 3H), 4.51 (d, J=5.92 Hz, 2H), 4.72 (m, 1H), 7.35 (dd, J=7.82, 4.74 Hz, 1H), 7.51 (d, J=8.36 Hz, 1H), 7.73 (dt, J=7.79, 1.85 Hz, 1H), 7.83 (dd, J=8.27, 2.18 Hz, 1H), 7.86-7.94 (m, 2H), 7.95-8.03 (m, 2H), 8.05 (d, J=2.09 Hz, 1H), 8.46 (m, 1H), 8.56 (d, J=1.57 Hz, 1H), 9.19 (t, J=5.92 Hz, 1H).

6-(4-(N-isopropyl-3-oxobutanamido)-3-methylphenyl)-N-((2-methylpyridin-3-yl)methyl)nicotinamide (I-497)

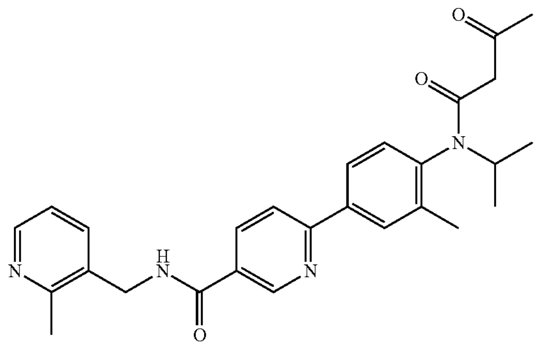 [SMILES: CC(=O)CC(=O)N(c1ccc(-c2ccc(C(=O)NCc3cccnc3C)cn2)cc1C)C(C)C]

Purification by prep. HPLC (Method 9) afforded 6-(4-(N-isopropyl-3-oxobutanamido)-3-methylphenyl)-N-((2-methylpyridin-3-yl)methyl)nicotinamide as a paste (2.5 mg, 3.8%). LC-MS (Method 4): $R_t$=1.06 min, m/z=459.29 $(M+H)^+$. $^1H$ NMR (300 MHz, $CDCl_3$): δ 0.97 (d, J=6.41 Hz, 3H), 1.28 (d, J=6.41 Hz, 3H), 1.50-1.69 (bs, 3H), 1.73 and 2.08 (s, 3H), 2.28 and 2.32 (s, 3H), 2.62 (s, 3H), 3.09 (s, 1H), 4.69 (d, J=5.61 Hz, 2H), 4.80-4.92 (m, 1H), 6.42 (t, J=5.7 Hz, 1H), 7.09-7.21 (m, 2H), 7.61 (d, J=7.64 Hz, 1H), 7.78-7.88 (m, 2H), 7.96-8.03 (m, 1H), 8.21 (dd, J=8.46, 2.15 Hz, 1H), 8.45 (d, J=4.8 Hz, 1H), 9.04-9.07 (m, 1H).

Scheme 5 with procedures 2b.ii/3a

6-[4-[Acetyl(isopropyl)amino]-3-methyl-phenyl]-N-[(2-methyl-3-pyridyl)methyl]pyridine-3-carboxamide (I-512)

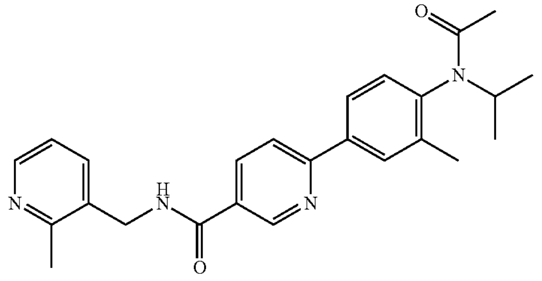 [SMILES: CC(=O)N(c1ccc(-c2ccc(C(=O)NCc3cccnc3C)cn2)cc1C)C(C)C]

Purification by flash column chromatography (silica gel, 10% MeOH/DCM) afforded 6-[4-[acetyl(isopropyl)amino]-3-methyl-phenyl]-N-[(2-methyl-3-pyridyl)methyl]pyridine-3-carboxamide as a white amorphous solid (22 mg, 59%).

LC-MS (Method 8): $R_t$=3.51 min; m/z=417.20 $(M+H)^+$.

$^1H$-NMR (300 MHz, DMSO-$d_6$): δ 0.90 (d, J=6.85 Hz, 3H), 1.18 (d, J=6.85 Hz, 3H), 1.61 (s, 3H), 2.28 (s, 3H), 4.51 (d, J=5.51 Hz, 2H), 4.68 (m, 1H), 7.20 (dd, J=7.74, 4.89 Hz, 1H), 7.28 (d, J=8.08 Hz, 1H), 7.63 (dd, J=7.74, 1.70 Hz, 1H), 8.04 (dd, J=8.18, 2.07 Hz, 1H), 8.14 (d, J=8.35 Hz, 1H), 8.28 (d, J=2.07 Hz, 1H), 8.31-8.36 (m, 2H), 9.13 (d, J=2.17 Hz, 1H), 9.21 (t, J=5.51 Hz, 1H).

Synthesis According to Scheme 6.

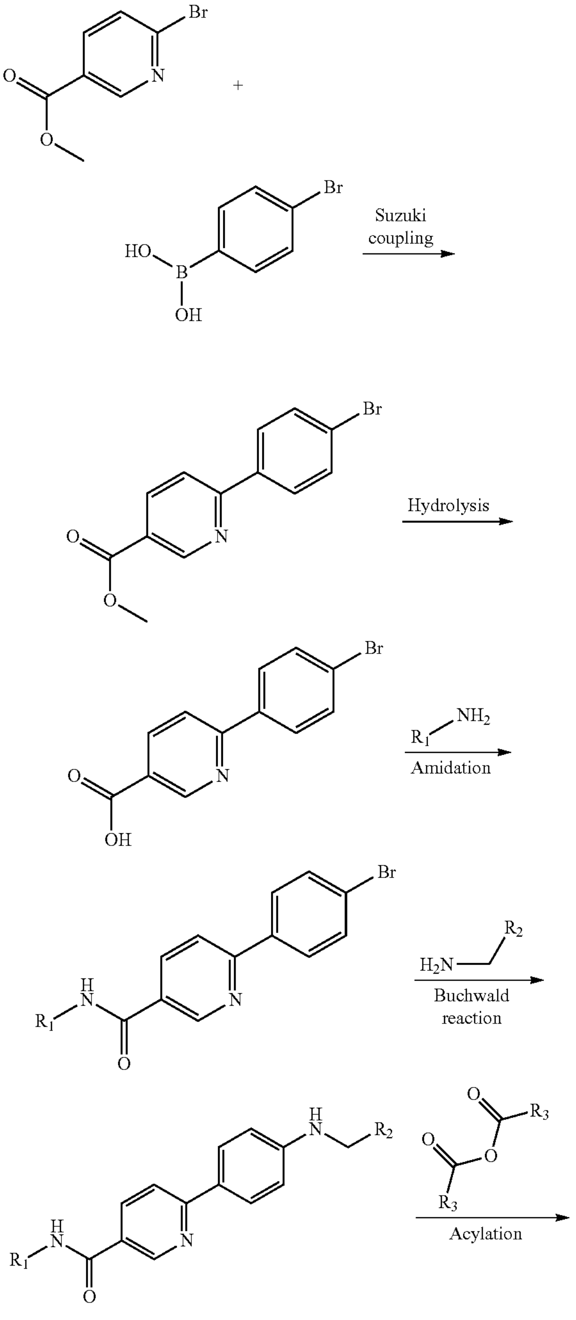

-continued

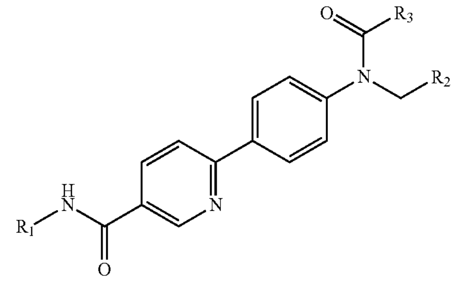

Steps 1 & 2: Suzuki coupling and hydrolysis

Methyl 6-(4-bromophenyl)pyridine-3-carboxylate and 6-(4-bromophenyl)pyridine-3-carboxylic acid and 6-(4-bromophenyl)pyridine-3-carboxylic acid

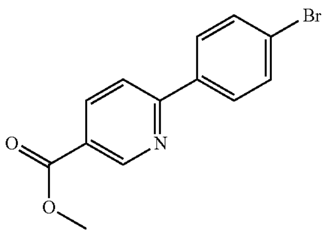

and

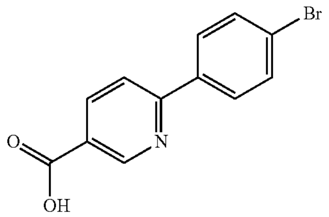

To a mixture of (4-bromophenyl)boronic acid (0.50 g, 2.49 mmol), methyl 6-bromopyridine-3-carboxylate (0.54 g, 2.49 mmol), and $Pd(PPh_3)_4$(0.057 g, 0.05 mmol), was added a degassed mixture of toluene (5.00 mL), MeOH (2.50 mL) and aq. $K_2CO_3$ (2.00 mmol/L, 2490 mL, 4.98 mmol). The RM was stirred at 90° C. overnight. After cooling to RT, the RM was diluted with water and extracted with EtOAc. The organic layers were combined, dried and concentrated in vacuo to afford methyl 6-(4-bromophenyl)pyridine-3-carboxylate (220 mg, 27%).

LC-MS (Method 2): $R_t$=1.25 min; m/z=293.90 (M−H)+. The aqueous layer was acidified by 2M HCl to pH 4 and extracted with EtOAc/iPrOH 2:1 to afford 6-(4-bromophenyl)pyridine-3-carboxylic acid (500 mg, 66%). LC-MS (Method 2): $R_t$=0.49 min; m/z=279.86 $(M-H)^+$.

Step 3. Amidation (Per Scheme 2—Step 5)

6-(4-Bromophenyl)-N-(3-pyridylmethyl)pyridine-3-carboxamide

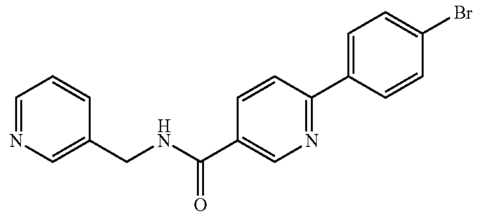 [SMILES: O=C(NCc1cccnc1)c1ccc(-c2ccc(Br)cc2)nc1]

Starting from 6-(4-bromophenyl)pyridine-3-carboxylic acid (500 mg, 1.80 mmol) and 3-pyridylmethanamine (194 mg, 1.80 mmol), trituration of the crude in DCM afforded 6-(4-bromophenyl)-N-(3-pyridylmethyl)pyridine-3-carboxamide (320 mg, 45%).

LC-MS (Method 2): $R_t$=0.98 min; m/z=368.02/370.02 $(M-H)^+$.

Step 4. Buchwald Reaction

6-[4-(3,3-Difluoropropylamino)phenyl]-N-(3-pyridylmethyl)pyridine-3-carboxamide

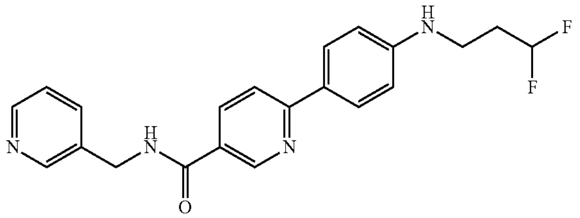 [SMILES: O=C(NCc1cccnc1)c1ccc(-c2ccc(NCCC(F)F)cc2)nc1]

To a suspension of phenol (39.4 mg, 0.42 mmol) and potassium tert-butoxide (128 mg, 1.14 mmol) in dioxane (2 mL) purged with argon, were added 6-(4-bromophenyl)-N-(3-pyridylmethyl)pyridine-3-carboxamide (140 mg, 0.38 mmol), followed by 3,3-difluoropropan-1-amine.HCl (100 mg, 0.76 mmol), $(Pd(allyl)C_1)_2$ (6.9 mg, 0.0190 mmol) and AddBippyPhosPdCl$_2$ (11.4 mg, 0.00760 mmol). The RM was purged with argon for an additional 2 minutes and heated at 100° C. for 2 h. The RM was diluted with DCM and washed with aq. $NaHCO_3$ solution and brine. The organic layers were combined, dried and concentrated in vacuo. Purification by flash column chromatography (silica gel, 10% MeOH/DCM) afforded 6-[4-(3,3-difluoropropylamino)phenyl]-N-(3-pyridylmethyl)pyridine-3-carboxamide (20 mg, 13%).

LC-MS (Method 2): $R_t$=0.90 min; m/z=383.18 $(M-H)^+$.

Step 5. Acylation

6-[4-[Acetyl(3,3-difluoropropyl)amino]phenyl]-N-(3-pyridylmethyl)pyridine-3-carboxamide (I-629)

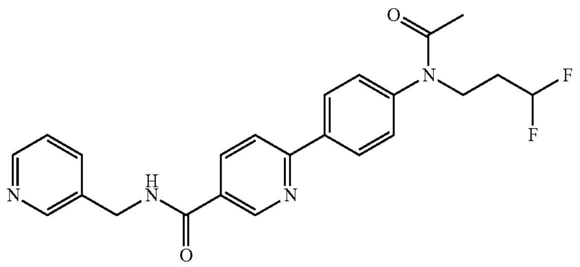 [SMILES: CC(=O)N(CCC(F)F)c1ccc(-c2ccc(C(=O)NCc3cccnc3)cn2)cc1]

A solution of 6-[4-(3,3-difluoropropylamino)phenyl]-N-(3-pyridylmethyl)pyridine-3-carboxamide (20 mg, 0.052 mmol) in acetic anhydride (1.8 mL, 17 mmol) was heated at 40° C. for 2 h, then at RT overnight. The RM was poured onto $NaHCO_3$ solution, stirred in an ice bath for 30 minutes and extracted with DCM. The organic layers were combined, washed with aq. $NaHCO_3$ solution and brine, dried and concentrated in vacuo. Purification of the crude product by flash column chromatography (silica gel, 10% MeOH in DCM) afforded 6-[4-[acetyl(3,3-difluoropropyl)amino]phenyl]-N-(3-pyridylmethyl)pyridine-3-carboxamide (18 mg, 79%).

LC-MS (Method 8): $R_t$=3.26 min; m/z=425.46 $(M+H)^+$.

$^1$H NMR (500 MHz, DMSO-$d_6$): δ 1.81 (br s, 3H), 1.96-2.08 (m, 2H), 3.82 (t, J=7.17 Hz, 2H), 4.55 (d, J=5.80 Hz, 2H), 5.99-6.27 (m, 1H), 7.33-7.40 (m, 1H), 7.51 (br d, J=8.24 Hz, 2H), 7.76 (dt, J=7.86, 1.87 Hz, 1H), 8.16 (d, J=8.24 Hz, 1H), 8.24 (d, J=8.54 Hz, 2H), 8.33 (dd, J=8.39, 2.29 Hz, 1H), 8.48 (dd, J=4.88, 1.53 Hz, 1H), 8.59 (d, J=1.83 Hz, 1H), 9.14 (d, J=1.83 Hz, 1H), 9.33 (t, J=5.80 Hz, 1H).

6-[4-[Acetyl(2,2-difluoroethyl)amino]phenyl]-N-(3-pyridylmethyl)pyridine-3-carboxamide (I-631)

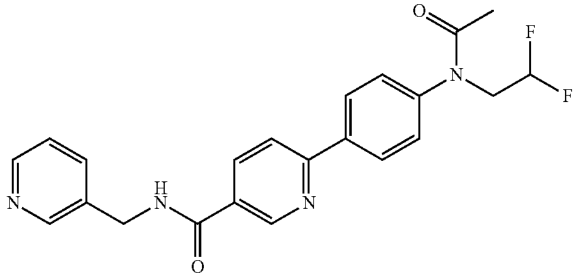 [SMILES: CC(=O)N(CC(F)F)c1ccc(-c2ccc(C(=O)NCc3cccnc3)cn2)cc1]

Purification by flash column chromatography (silica gel, 10% MeOH in DCM) afforded 6-[4-[acetyl(2,2-difluoroethyl)amino]phenyl]-N-(3-pyridylmethyl)pyridine-3-carboxamide (13 mg, 85%) as a yellow amorphous solid.

LC-MS (Method 8): $R_t$=3.21 min; m/z=411.51 $(M+H)^+$.

$^1$H NMR (500 MHz, DMSO-$d_6$): δ 1.86 (br s, 3H), 4.07 (t, J=14.69, 2H), 4.55 (d, J=5.80 Hz, 2H), 6.18 (tt, J=55.26, 4.56 Hz, 1H), 7.38 (dd, J=7.78, 4.73 Hz, 1H), 7.50 (d, J=8.24 Hz, 2H), 7.76 (d, J=7.90 Hz, 1H), 8.15 (d, J=8.24 Hz, 1H), 8.23 (d, J=8.24 Hz, 2H), 8.33 (dd, J=8.24, 2.14 Hz, 1H), 8.48 (dd, J=4.58, 1.22 Hz, 1H), 8.57-8.61 (m, 1H), 9.14 (d, J=1.83 Hz, 1H), 9.34 (t, J=5.95 Hz, 1H).

6-[4-[Acetyl(3,3-difluoropropyl)amino]-3-methyl-phenyl]-N-(3-pyridylmethyl)pyridine-3-carboxamide (I-639)

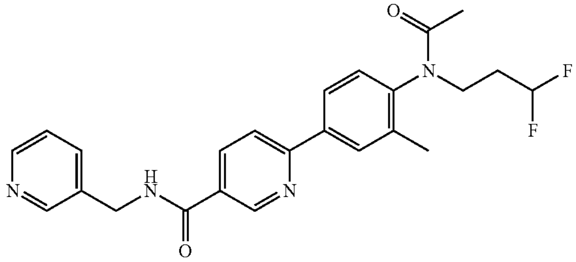 [SMILES: CC(=O)N(CCC(F)F)c1ccc(-c2ccc(C(=O)NCc3cccnc3)cn2)cc1C]

Purification by flash column chromatography (silica gel, 0-10% MeOH in DCM) afforded 6-[4-[acetyl(3,3-difluoropropyl)amino]-3-methyl-phenyl]-N-(3-pyridylmethyl)pyridine-3-carboxamide as a white amorphous solid (25 mg, 64%).

LC-MS (Method 8): $R_t$=3.39 min; m/z=439.56 $(M+H)^+$.

$^1$H NMR (300 MHz, DMSO-$d_6$): δ 1.68 (s, 3H), 1.93-2.16 (m, 2H), 2.28 (s, 3H), 3.12-3.28 (m, 1H), 4.06-4.20 (m, 1H), 4.54 (d, J=5.92 Hz, 2H), 5.90-6.38 (m, 1H), 7.37 (dd, J=7.84, 4.70 Hz, 1H), 7.42 (d, J=8.36 Hz, 1H), 7.74 (m, 1H), 8.04-8.08 (m, 1H), 8.12-8.21 (m, 2H), 8.32 (dd, J=8.19, 2.26 Hz, 1H), 8.45-8.49 (dd, J=4.83, 1.46 Hz, 1H), 8.58 (m, 1H), 9.12 (d, J=2.09 Hz, 1H), 9.29-9.37 (d, J=6.1 Hz, 1H).

Synthesis According to Scheme 7.

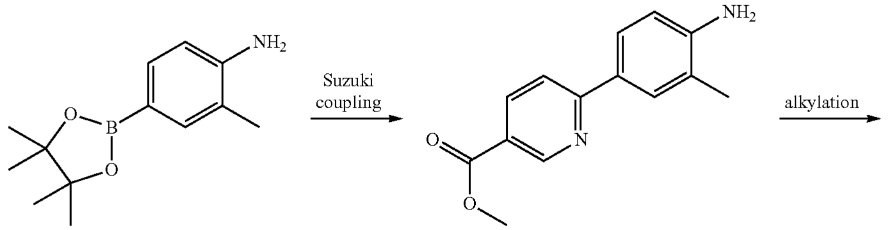

-continued

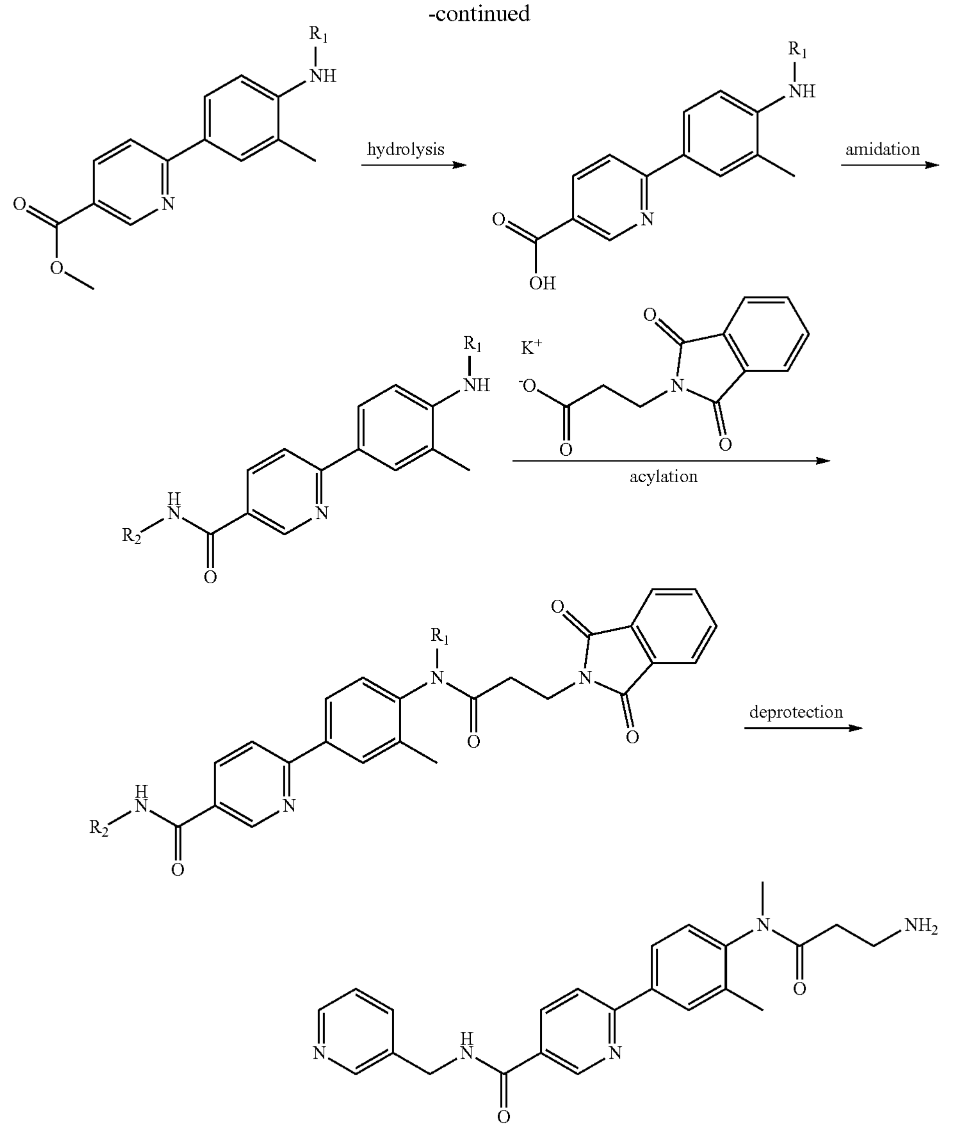

Methyl 6-(4-amino-3-methylphenyl)nicotinate (Suzuki coupling per Scheme 1—Step 1)

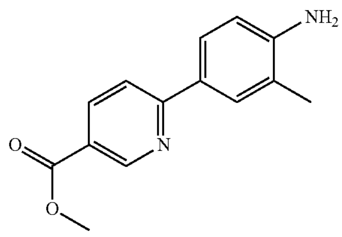 [SMILES: COC(=O)c1ccc(-c2ccc(N)c(C)c2)nc1]

Starting from 2-methyl-4-(4,4,5,5-tetramethyl-1,3,2-dioxaborolan-2-yl)aniline (200 mg, 0.858 mmol) and methyl 6-bromopyridine-3-carboxylate (271 mg, 1.25 mmol), methyl 6-(4-amino-3-methyl-phenyl)pyridine-3-carboxylate was obtained (105 mg, 45%).

LC-MS (Method 2): $R_t$=0.93 min; m/z=243.07 $(M+H)^+$.

Methyl 6-[3-methyl-4-(methylamino)phenyl]pyridine-3-carboxylate

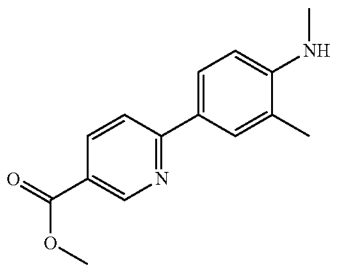 [SMILES: CNc1ccc(-c2ccc(C(=O)OC)cn2)cc1C]

To a solution of the methyl 6-(4-amino-3-methyl-phenyl) pyridine-3-carboxylate (650 mg, 2.28 mmol) in 1,1,1,3,3,3-hexafluoro-propan-2-ol (2.4 mL, 22.8 mmol) at 0° C., was added MeOTf (275 µL, 2.51 mmol) and the RM was stirred at RT for 1 h. The reaction was quenched with sat. $NaHCO_3$ and extracted with DCM. The organic layer was washed with brine, dried and concentrated in vacuo. The crude product was purified by flash column chromatography (silica gel, 0-30% EtOAc in cyclohexane) to afford methyl 6-[3-methyl-4-(methylamino)phenyl]pyridine-3-carboxylate (175 mg, 20%).

LC-MS (Method 2): $R_t$=1.11 min; m/z=257.11 $(M+H)^+$.

$^1$H NMR (400 MHz, DMSO-$d_6$): δ 2.14 (s, 3H), 2.79 (d, J=4.89 Hz, 3H), 3.86 (s, 3H), 5.60 (m, 1H), 6.56 (d, J=8.44 Hz, 1H), 7.86 (d, J=1.47 Hz, 1H), 7.91 (d, J=8.51 Hz, 2H), 8.18 (dd, J=8.56, 2.32 Hz, 1H), 9.01 (dd, J=2.32, 0.86 Hz, 1H).

6-[3-Methyl-4-(methylamino)phenyl]pyridine-3-carboxylic acid (per Scheme 1—Step 2)

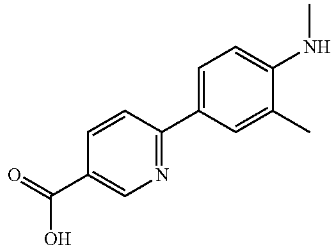 [SMILES: CNc1ccc(-c2ccc(C(=O)O)cn2)cc1C]

Hydrolysis of methyl 6-[3-methyl-4-(methylamino)phenyl]pyridine-3-carboxylate (175 mg, 0.68 mmol) afforded 6-[3-methyl-4-(methylamino)phenyl]pyridine-3-carboxylic acid (136 mg, 82%).

LC-MS (Method 2): $R_t$=0.44 min; m/z=243.08 $(M+H)^+$.

$^1$H NMR (400 MHz, DMSO-$d_6$): δ 2.14 (s, 3H), 2.79 (d, J=4.65 Hz, 3H), 5.57 (br d, J=4.65 Hz, 1H), 6.56 (d, J=8.56 Hz, 1H), 7.84-7.92 (m, 3H), 8.15 (dd, J=8.44, 2.32 Hz, 1H), 8.99 (dd, J=2.26, 0.79 Hz, 1H).

6-[3-Methyl-4-(methylamino)phenyl]-N-(3-pyridylmethyl)pyridine-3-carboxamide (per Scheme 2—Step 5)

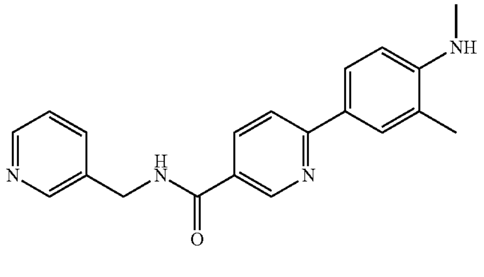 [SMILES: CNc1ccc(-c2ccc(C(=O)NCc3cccnc3)cn2)cc1C]

Starting from 6-[3-methyl-4-(methylamino)phenyl]pyridine-3-carboxylic acid (135 mg, 0.56 mmol) and 3-pyridylmethanamine (68 μl, 0.67 mmol), 6-[3-methyl-4-(methylamino)phenyl]-N-(3-pyridylmethyl)pyridine-3-carboxamide was obtained (175 mg, 94%).

LC-MS (Method 2): $R_t$=0.84 min; m/z=333.10 $(M+H)^+$.

$^1$H NMR (300 MHz, DMSO-$d_6$): δ 2.14 (s, 3H), 2.79 (d, J=4.70 Hz, 3H), 4.51 (d, J=5.75 Hz, 2H), 5.52 (br d, J=5.05 Hz, 1H), 6.55 (d, J=8.54 Hz, 1H), 7.36 (dd, J=7.66, 4.88 Hz, 1H), 7.73 (br d, J=8.01 Hz, 1H), 7.82-7.91 (m, 3H), 8.16 (dd, J=8.36, 2.26 Hz, 1H), 8.46 (dd, J=4.70, 1.57 Hz, 1H), 8.56 (d, J=1.92 Hz, 1H), 8.98 (d, J=1.92 Hz, 1H), 9.17 (t, J=5.84 Hz, 1H).

6-[4-[3-(1,3-Dioxoisoindolin-2-yl)propanoyl-methyl-amino]-3-methyl-phenyl]-N-(3-pyridylmethyl)pyridine-3-carboxamide

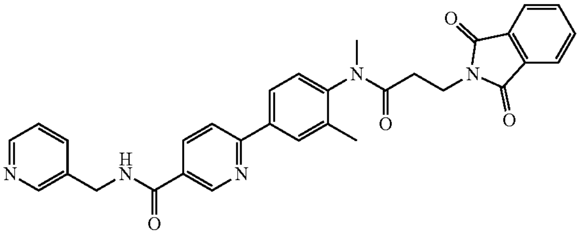 [SMILES: Cc1cc(-c2ccc(C(=O)NCc3cccnc3)cn2)ccc1N(C)C(=O)CCN1C(=O)c2ccccc2C1=O]

To a suspension of potassium-3-(1,3-dioxoisoindolin-2-yl)propanoate (140 mg, 0.54 mmol) in DCM (2.6 ml) and DMF (26 μl), was added thionylchloride (60 μl, 0.82 mmol) and the RM was heated at reflux for 2 h. The solvent was evaporated in vacuo and the remaining solid was carefully added to a solution of 6-[3-methyl-4-(methylamino)phenyl]-N-(3-pyridylmethyl)pyridine-3-carboxamide (181 mg, 0.54 mmol) dissolved in a 1:1 mixture of THF/DMF (6 mL) and pyridine (88 μl, 1.1 mmol). The RM was stirred at RT for 1 h, then concentrated in vacuo. The crude product was purified by flash column chromatography (silica gel, 0-10% MeOH in DCM) to afford 6-[4-[3-(1,3-dioxoisoindolin-2-yl)propanoyl-methyl-amino]-3-methyl-phenyl]-N-(3-pyridylmethyl)pyridine-3-carboxamide (170 mg, 59%).

LC-MS (Method 2): $R_t$=0.89 min; m/z=537.07 $(M+H)^+$.

$^1$H NMR (300 MHz, DMSO-$d_6$): δ 2.20-2.43 (m, 5H), 3.07 (s, 3H), 3.74 (t, J=7.49 Hz, 2H), 4.68 (br d, J=5.57 Hz, 2H), 7.39 (d, J=8.19 Hz, 1H), 7.79 (s, 3H), 7.94-8.05 (m, 3H), 8.09-8.18 (m, 2H), 8.35 (dd, J=8.36, 2.26 Hz, 1H), 8.45-8.51 (m, 1H), 8.79 (d, J=5.40 Hz, 1H), 8.89-8.92 (m, 1H), 9.14 (d, J=1.92 Hz, 1H), 9.58 (t, J=5.75 Hz, 1H).

6-[4-[3-aminopropanoyl(methyl)amino]-3-methyl-phenyl]-N-(3-pyridylmethyl)pyridine-3-carboxamide (I-593)

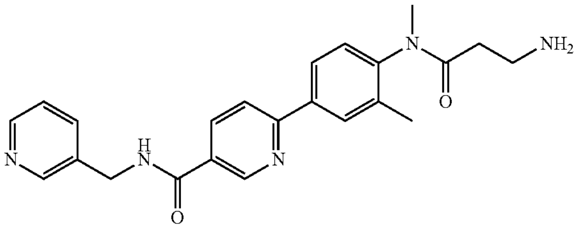 [SMILES: Cc1cc(-c2ccc(C(=O)NCc3cccnc3)cn2)ccc1N(C)C(=O)CCN]

To a suspension of 6-[4-[3-(1,3-dioxoisoindolin-2-yl)propanoyl-methyl-amino]-3-methyl-phenyl]-N-(3-pyridylmethyl)pyridine-3-carboxamide (170 mg, 0.32 mmol) in EtOH (5 mL) heated at reflux, was added hydrazine 35% in water (58 μl, 0.64 mmol). The RM was stirred at reflux for 10 h and at RT overnight. A white precipitate was formed and removed by filtration. The filtrate was evaporated and the crude product was suspended in DCM (5 mL). DCM was decanted and the residue was dissolved in sat. aq. $NaHCO_3$ (10 mL) and extracted with DCM (3×10 mL). The organic layers were combined and evaporated to afford 6-[4-[3-aminopropanoyl(methyl)amino]-3-methyl-phenyl]-N-(3-pyridylmethyl)pyridine-3-carboxamide (25 mg, 19%) as a light yellow solid.

LC-MS (Method 8): $R_t$=3.30 min; m/z=404.1 $(M+H)^+$.

$^1$H NMR (400 MHz, 80° C., DMSO-$d_6$): δ 1.93-2.01 (m, 2H), 2.08-2.17 (m, 2H), 2.28 (s, 3H), 2.71-2.78 (m, 2H), 3.11 (s, 3H), 4.55 (d, J=5.6 Hz, 2H), 7.31-7.37 (m, 2H), 7.76 (d, J=7.8 Hz, 1H), 7.99-8.08 (m, 1H), 8.12 (bs, 2H), 8.31 (d, J=7.8 Hz, 1H), 8.46 (d, J=4.6 Hz, 1H), 8.59 (bs, 1H), 9.12 (m, 1H), 9.35 (m, 1H).

6-[4-[(2-cyanoacetyl)-methyl-amino]-3-methyl-phenyl]-N-[(2-methyl-3-pyridyl)methyl]pyridine-3-carboxamide (I-492)

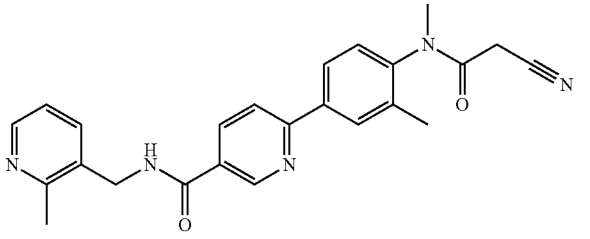 [SMILES: Cc1cc(-c2ccc(C(=O)NCc3cccnc3C)cn2)ccc1N(C)C(=O)CC#N]

Purification by flash column chromatography (silica gel, 10% MeOH in DCM) afforded 6-[4-[(2-cyanoacetyl)-methyl-amino]-3-methyl-phenyl]-N-[(2-methyl-3-pyridyl)methyl]pyridine-3-carboxamide (380 mg, 80%).

LC-MS (Method 8): $R_t$=3.31 min; m/z=414.17 $(M+H)^+$.

$^1$H NMR (500 MHz, DMSO-$d_6$): δ 2.21 and 2.30 (s, 3H), 2.54 (s, 3H), 3.13 and 3.23 (s, 3H, 3.43 (d, J=18.82 Hz, 1H), 3.60 (d, J=18.82 Hz, 1H), 4.52 (d, J=5.61 Hz, 2H), 7.21 (dd, J=7.74, 4.89 Hz, 1H), 7.29 and 7.46 (d, J=8.24 Hz, 1H), 7.63 (d, J=7.68 Hz, 1H), 8.01 and 8.07 (dd, J=8.17, 2.02 Hz, 1H), 8.10 and 8.15 (d, J=8.25 Hz, 1H), 8.18 (d, J=1.54 Hz, 1H), 8.30-8.37 (m, 2H), 9.13 and 9.14 (d, J=2.12 Hz, 1H), 9.22 (t, J=5.61 Hz, 1H).

I-492 was then taken forward into the following steps:

Ethyl N-[3-[N,2-dimethyl-4-[5-[(2-methyl-3-pyridyl)methylcarbamoyl]-2-pyridyl]anilino]-3-oxo-propyl]carbamate (I-491)

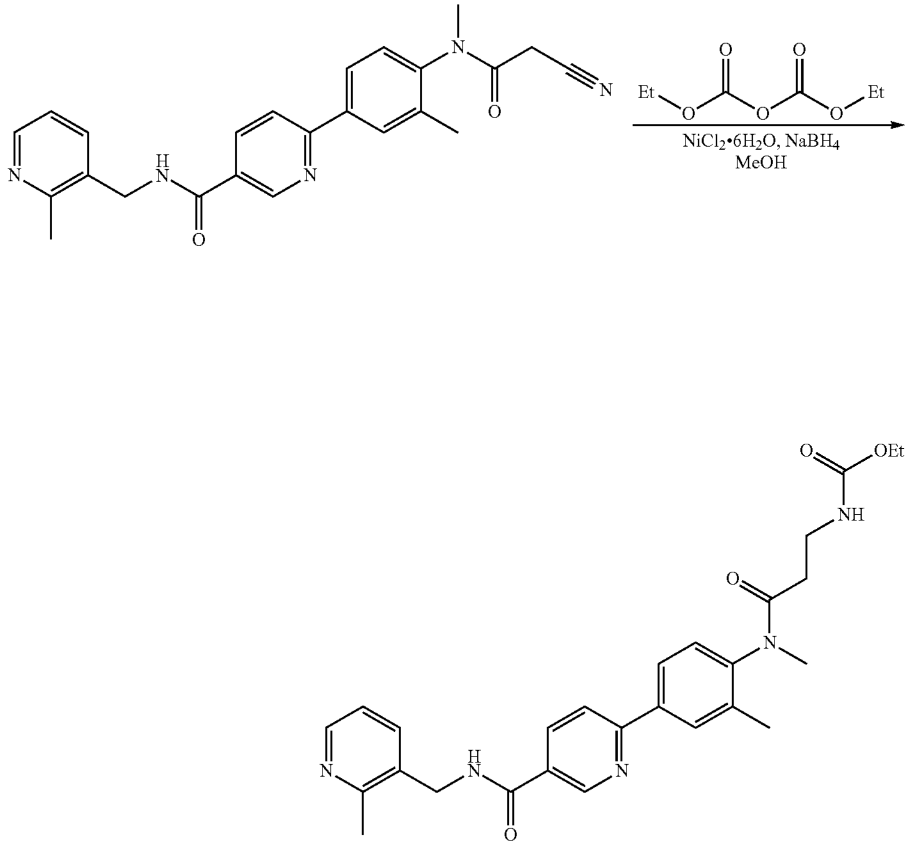

To a solution of 6-[4-[(2-cyanoacetyl)-methyl-amino]-3-methyl-phenyl]-N-[(2-methyl-3-pyridyl)methyl]pyridine-3-carboxamide (50.0 mg, 0.121 mmol) and $NiCl_2.6H_2O$ (0.0287 g, 0.121 mmol) in methanol (0.5 mL), was added $NaBH_4$ (0.0183 g, 0.484 mmol), followed by diethyl dicarbonate (0.0534 mL, 0.363 mmol). The mixture was stirred at RT for 4 h, then quenched with water. The aqueous layer was extracted with DCM. The organic layers were collected, dried and concentrated in vacuo. Purification by flash chromatography (silica gel, 0-10% MeOH in DCM) afforded ethyl N-[3-[N,2-dimethyl-4-[5-[(2-methyl-3-pyridyl)methylcarbamoyl]-2-pyridyl]anilino]-3-oxo-propyl]carbamate (14 mg, 24%).

LC-MS (Method 8): $R_t$=3.33 min; m/z=490.2 $(M+H)^+$.

$^1$H-NMR (400 MHz, DMSO-$d_6$): δ 1.08 (t, J=6.99 Hz, 2H), 2.00 (m, 1H), 2.12 (m, 1H), 2.24 (s, 3H), 2.53 (s, 3H), 3.08 (s, 3H), 3.13 (q, J=6.99 Hz, 2H), 3.88 (q, J=7.56 Hz, 2H), 4.50 (d, J=5.62 Hz, 2H), 6.95 (t, J=5.34 Hz, 1H), 7.20 (dd, J=7.69, 4.92 Hz, 1H), 7.37 (d, J=8.20 Hz, 1H), 7.63 (dd, J=7.64, 1.53 Hz, 1H), 8.04 (dd, J=8.16, 2.04 Hz, 1H), 8.13 (dd, J=8.40, 0.72 Hz, 1H), 8.16 (d, J=1.81 Hz, 1H), 8.31-8.35 (m, 2H), 9.13 (dd, J=2.38, 0.72 Hz, 1H), 9.21 (t, J=5.62 Hz, 1H).

6-[4-[3-aminopropanoyl(methyl)amino]-3-methyl-phenyl]-N-[(2-methyl-3-pyridyl)methyl]pyridine-3-carboxamide

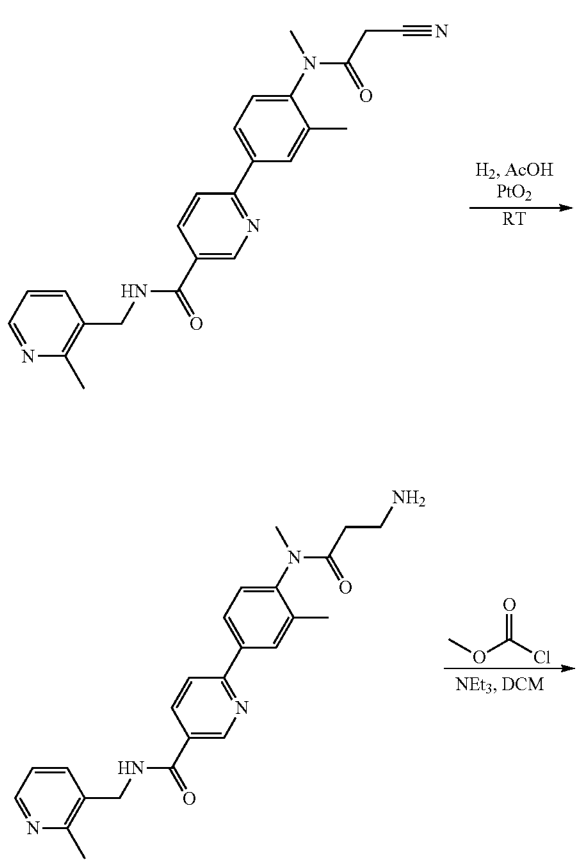

-continued

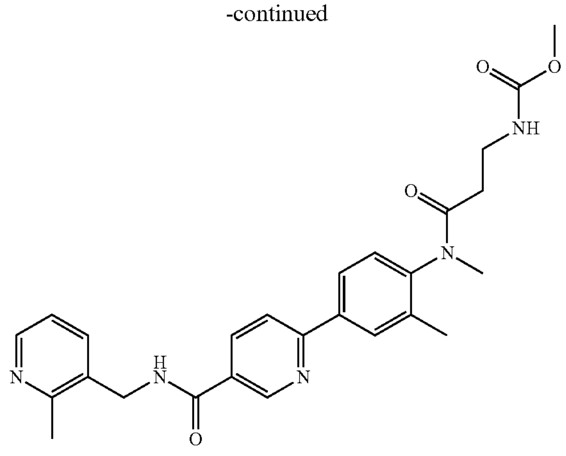

To a solution of 6-[4-[(2-cyanoacetyl)-methyl-amino]-3-methyl-phenyl]-N-[(2-methyl-3-pyridyl)methyl]pyridine-3-carboxamide (94.0 mg, 0.227 mmol) in AcOH (1.5 mL), was added $PtO_2$ (0.00774 g, 0.0341 mmol). The RM was stirred under $H_2$ atmosphere (balloon) for 4 h and then another 3 h. It was filtered over diatomaceous earth, and concentrated. DCM was added and it was washed with sat. $NaHCO_3$. The organic layer was dried and concentrated to give 6-[4-[3-aminopropanoyl(methyl)amino]-3-methyl-phenyl]-N-[(2-methyl-3-pyridyl)methyl]pyridine-3-carboxamide which was used as such in the next step.

LC-MS (Method 2): $R_t$=3.31 min; m/z=418.19 $(M+H)^+$.

Methyl N-[3-[N,2-dimethyl-4-[5-[(2-methyl-3-pyridyl)methylcarbamoyl]-2-pyridyl]anilino]-3-oxo-propyl]carbamate (I-501)

Per Scheme 3—Step 2, starting from 6-[4-[3-aminopropanoyl(methyl)amino]-3-methyl-phenyl]-N-[(2-methyl-3-pyridyl)methyl]pyridine-3-carboxamide (95.0 mg, 0.228 mmol) and methyl chloroformate (0.0215 g, 0.228 mmol), purification by flash column chromatography (silica gel, 0-10% MeOH in DCM) afforded N-[3-[N,2-dimethyl-4-[5-[(2-methyl-3-pyridyl)methylcarbamoyl]-2-pyridyl]anilino]-3-oxo-propyl]carbamate (8 mg, 7%).

LC-MS (Method 8): $R_t$=3.11 min; m/z=476.15 $(M+H)^+$.

$^1$H-NMR (500 MHz, DMSO-$d_6$): δ 2.02 (m, 1H), 2.14 (m, 1H), 2.26 (s, 3H), 2.54 (s, 3H), 3.09 (s, 3H), 3.12 (d, J=7.07 Hz, 1H), 3.16 (d, J=7.07 Hz, 1H), 3.44 (s, 3H), 4.52 (d, J=5.51 Hz, 2H), 7.02 (t, J=5.69 Hz, 1H), 7.21 (dd, J=7.74, 4.90 Hz, 1H), 7.38 (d, J=8.19 Hz, 1H), 7.63 (dd, J=7.74, 1.27 Hz, 1), 8.05 (dd, J=8.35, 1.83 Hz, 1H), 8.14 (d, J=8.21 Hz, 1H), 8.17 (d, J=1.70 Hz, 1H), 8.34 (m, 2H), 9.14 (d, J=2.15 Hz, 1H), 9.22 (t, J=5.51 Hz, 1H).

Synthesis according to Scheme 8.

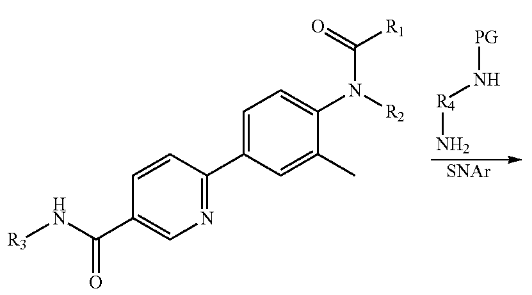

-continued

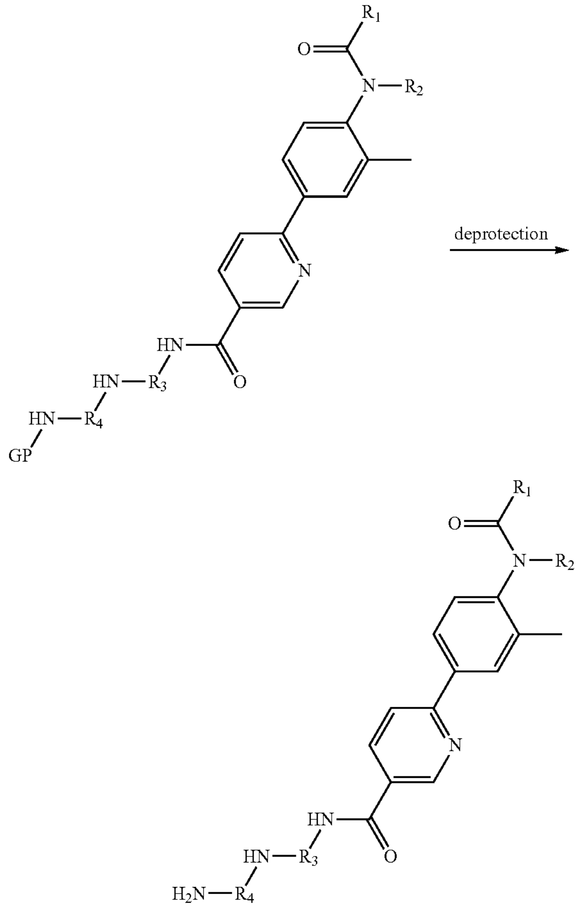

Tert-butyl (2-((5-((6-(3-methyl-4-(N-methylpropionamido)phenyl)nicotinamido)methyl)pyridin-2-yl)amino)ethyl)carbamate

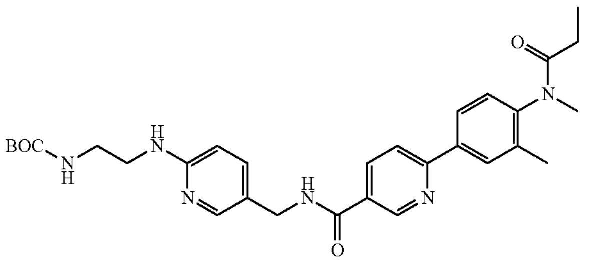 [SMILES: CCC(=O)N(C)c1ccc(-c2ccc(C(=O)NCc3ccc(NCCNC(=O)OC(C)(C)C)nc3)cn2)cc1C]

N-[(6-fluoro-3-pyridyl)methyl]-6-[3-methyl-4-[methyl(propanoyl)amino]phenyl]pyridine-3-carboxamide (725 mg, 1.30 mmol) (prepared according to Scheme 4) and tert-butyl N-(2-aminoethyl)carbamate (7.3 mL, 42 mmol) were stirred at 120° C. for 24 h and 2 days at RT. The RM was diluted with DCM, the organic layer washed with water, dried over $Na_2SO_4$ and evaporated. The sample was purified by flash column chromatography (silica gel, 0-7% MeOH in DCM) to afford tert-butyl (2-((5-((6-(3-methyl-4-(N-methylpropionamido)phenyl)nicotinamido)methyl)pyridin-2-yl)amino)ethyl)carbamate (0.33 g, 46%).

LC-MS (Method 2): $R_t$=0.96 min; m/z=547.2 $(M+H)^+$.

N-((6-((2-aminoethyl)amino)pyridin-3-yl)methyl)-6-(3-methyl-4-(N-methylpropionamido)phenyl)nicotinamide (I-527)

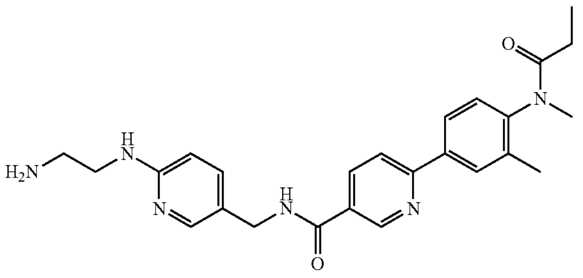 [SMILES: CCC(=O)N(C)c1ccc(-c2ccc(C(=O)NCc3ccc(NCCN)nc3)cn2)cc1C]

To a solution of tert-butyl N-[2-[[5-[[[6-[3-methyl-4-[methyl(propanoyl)amino]phenyl]pyridine-3-carbonyl]amino]methyl]-2-pyridyl]amino]ethyl]carbamate (110 mg, 0.201 mmol) in THF (3 mL) previously cooled down to 0° C., was added HCl in dioxane (4M, 1.26 mL, 5.03 mmol) and the RM was stirred at RT. The obtained solid was washed with THF and dried to afford N-[[6-(2-aminoethylamino)-3-pyridyl]methyl]-6-[3-methyl-4-[methyl(propanoyl)amino]phenyl]pyridine-3-carboxamide hydrochloride salt as a white solid (28 mg, 28%).

LC-MS (Method 4): $R_t$=1.29 min, m/z=447.19 $(M+H)^+$.

$^1H$ NMR (300 MHz, DMSO-$d_6$): δ 0.91 (t, J=7.49 Hz, 3H), 1.71-1.78 (m, 2H), 1.81-1.89 (m, 1H), 1.91-1.98 (m, 1H), 2.25 (s, 3H), 3.06 (s, 3H), 3.52-3.70 (m, 2H), 4.41 (br d, J=5.40 Hz, 2H), 7.08 (m, 1H), 7.38 (d, J=8.36 Hz, 1H), 7.94 (m, 2H), 8.00-8.12 (m, 5H), 8.13 (br d, J=9.06 Hz, 1H), 8.29-8.34 (m, 1H), 9.11 (d, J=1.74 Hz, 1H), 9.39 (m, 1H).

N-[[6-(2-aminoethylamino)-3-pyridyl]methyl]-6-[3-methyl-4-[methyl(propanoyl)amino]phenyl]pyridine-3-carboxamide hydrochloride (16.7 mg, 0.0345 mmol) was dissolved in water (5 mL) and basified to pH 8 with 1M NaOH. The RM was stirred at RT for 30 min, then extracted with DCM. The organic layers were combined, dried and evaporated to afford N-[[6-(2-aminoethylamino)-3-pyridyl]methyl]-6-[3-methyl-4-[methyl(propanoyl)amino]phenyl]pyridine-3-carboxamide (14.4 mg, 77%).

LC-MS (Method 8): $R_t$=3.09 min, m/z=447.63 $(M+H)^+$.

$^1H$ NMR (300 MHz, DMSO-$d_6$): δ 0.90 (t, J=7.32 Hz, 3H), 1.73-1.86 (m, 1H), 1.87-2.03 (m, 1H), 2.25 (s, 3H), 2.62-2.69 (m, 2H), 2.71 (m, 2H), 3.08 (s, 3H), 3.16-3.22 (m, 2H), 4.31 (br d, J=5.23 Hz, 2H), 6.44 (br d, J=8.19 Hz, 2H), 7.37 (d, J=8.19 Hz, 2H), 7.94 (m, 1H), 8.03 (br d, J=7.49 Hz, 1H), 8.07-8.16 (m, 2H), 8.25-8.31 (m, 1H), 9.08 (m, 2H).

Synthesis According to Scheme 9.

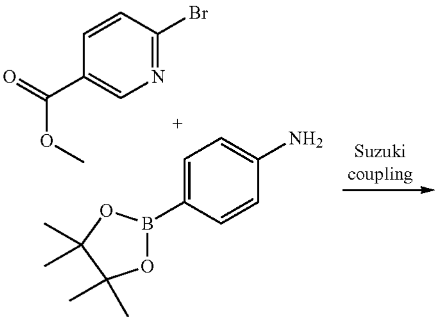

-continued

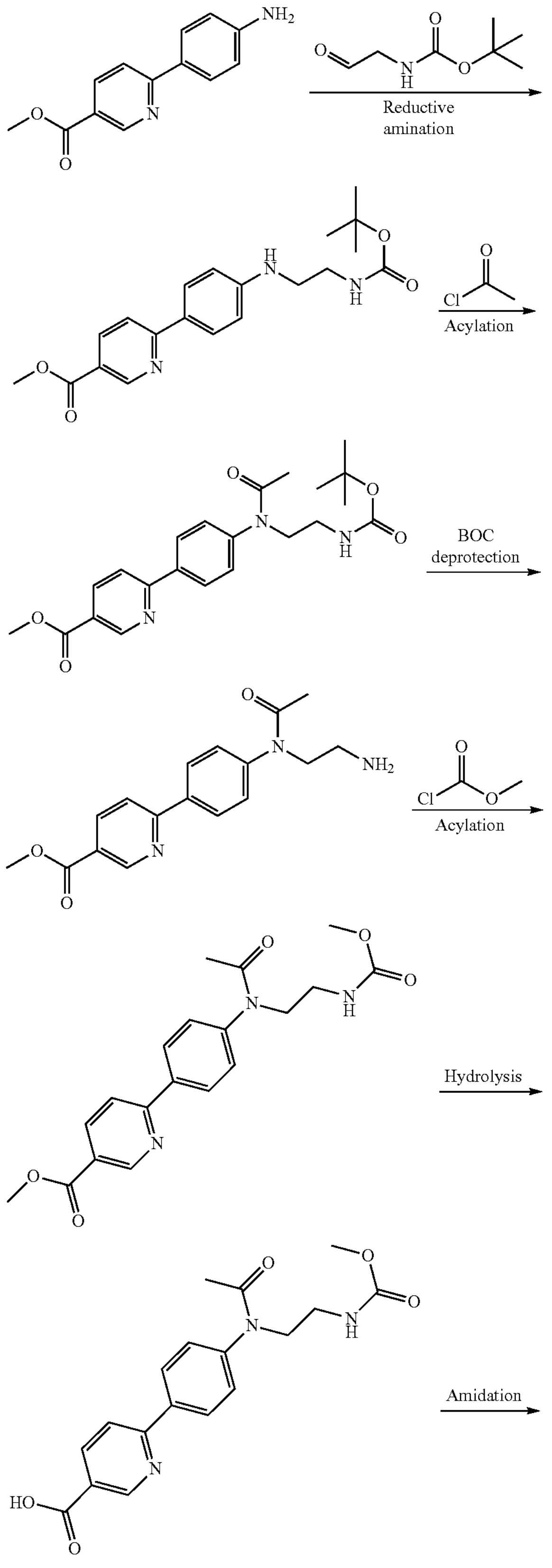

-continued

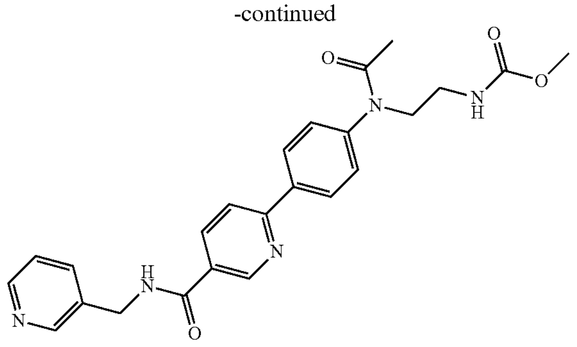

Methyl 6-(4-aminophenyl)pyridine-3-carboxylate

As described in Scheme 5—Step 1

Methyl 6-[4-[2-(tert-butoxycarbonylamino)ethyl-amino]phenyl]pyridine-3-carboxylate

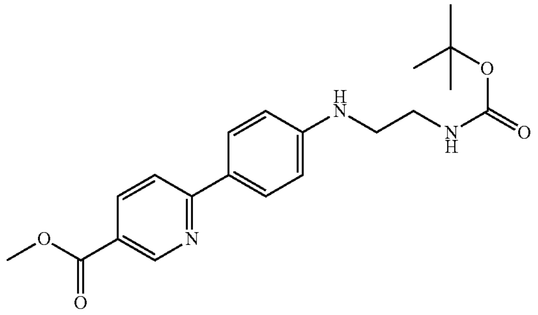 [SMILES: COC(=O)c1ccc(-c2ccc(NCCNC(=O)OC(C)(C)C)cc2)nc1]

Per Scheme 1—Step 4, using methyl 6-(4-aminophenyl) pyridine-3-carboxylate (200 mg, 0.74 mmol) and tert-butyl N-(2-oxoethyl)carbamate (129 mg, 0.81 mmol) and tetramethylammonium triacetoxyborohydride (484 mg, 1.84 mmol). Trituration of the crude product with ACN afforded methyl 6-[4-[2-(tert-butoxycarbonylamino)ethylamino]phenyl]pyridine-3-carboxylate (251 mg, 55%).

LC-MS (Method 2): $R_t$=1.14 min; m/z=372.13 $(M+H)^+$.

Methyl 6-[4-[acetyl-[2-(tert-butoxycarbonylamino) ethyl]amino]phenyl]pyridine-3-carboxylate

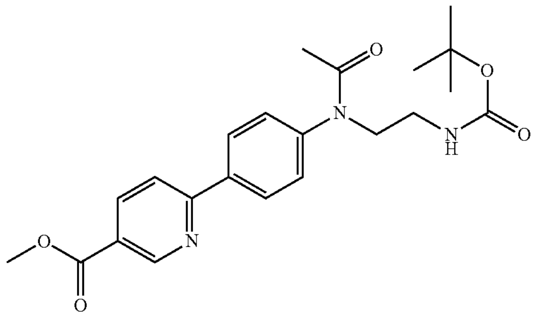 [SMILES: COC(=O)c1ccc(-c2ccc(N(CCNC(=O)OC(C)(C)C)C(C)=O)cc2)nc1]

Per Scheme 1—Step 5, using methyl 6-[4-[2-(tert-butoxy-carbonylamino)ethylamino]phenyl]pyridine-3-carboxylate (53 mg, 0.09 mmol) and acetyl chloride (86.9 μL, 0.09 mmol). Purification by flash column chromatography (silica gel, 0-5% MeOH in DCM) and additional trituration with DCM afforded methyl 6-[4-[acetyl-[2-(tert-butoxycarbonylamino)ethyl]amino]phenyl]pyridine-3-carboxylate (124 mg, 32%).

LC-MS (Method 2): $R_t$=1.04 min; m/z=358.06 $[M+H-56]^+$.

Methyl 6-[4-[acetyl(2-aminoethyl)amino]phenyl] pyridine-3-carboxylate

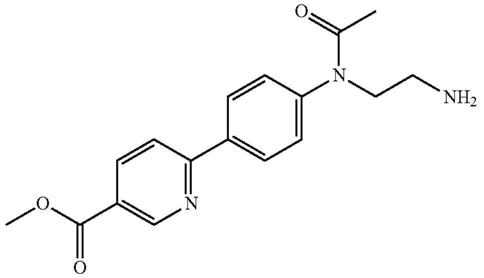 [SMILES: COC(=O)c1ccc(-c2ccc(N(CCN)C(C)=O)cc2)nc1]

The Boc deprotection was carried out similarly to described above for I-486. Starting from methyl 6-[4-[acetyl-[2-(tert-butoxycarbonylamino)ethyl]amino]phenyl] pyridine-3-carboxylate (124 mg, 0.30 mmol), methyl 6-[4-[acetyl(2-aminoethyl)amino]phenyl]pyridine-3-carboxylate (80 mg, 48%) was obtained and used as such in the next step.

LC-MS (Method 2): $R_t$=0.76 min; m/z=314.06 $(M+H)^+$.

Methyl 6-[4-[acetyl-[2-(methoxycarbonylamino) ethyl]amino]phenyl]pyridine-3-carboxylate

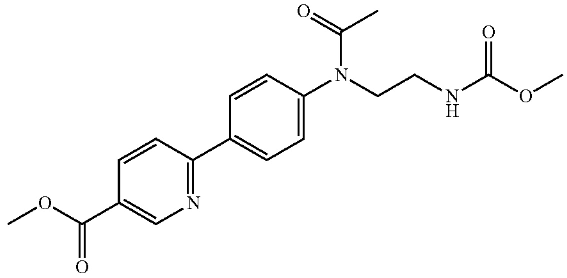

Per Scheme 1—Step 5 using methyl 6-[4-[acetyl(2-aminoethyl)amino]phenyl]pyridine-3-carboxylate (80 mg, 0.26 mmol) and methyl chloroformate (20 μL, 0.26 mmol), methyl 6-[4-[acetyl-[2-(methoxycarbonylamino)ethyl] amino]phenyl]pyridine-3-carboxylate (80 mg, 46%) was obtained and used as such in the next step.

LC-MS (Method 2): $R_t$=0.85 min; m/z=372.11 $(M+H)^+$.

6-[4-[Acetyl-[2-(methoxycarbonylamino)ethyl] amino]phenyl]pyridine-3-carboxylic acid

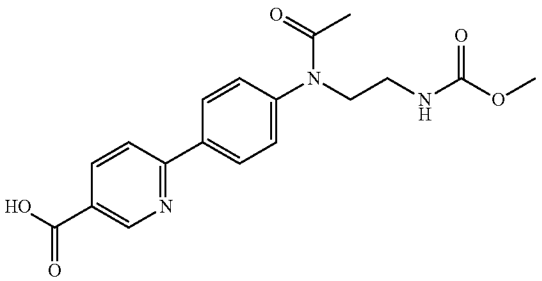 [SMILES: COC(=O)NCCN(C(C)=O)c1ccc(-c2ccc(C(=O)O)cn2)cc1]

Per Scheme 1—Step 2, hydrolysis of methyl 6-[4-[acetyl-[2-(methoxycarbonylamino)ethyl]amino]phenyl]pyridine-3-carboxylate (40 mg, 0.11 mmol) afforded 6-[4-[acetyl-[2-(methoxycarbonyl amino)ethyl]amino]phenyl]pyridine-3-carboxylic acid (15 mg, 37%).

LC-MS (Method 1): $R_t$=0.38 min; m/z=358.12 $(M+H)^+$.

Methyl N-[2-[N-acetyl-4-[5-(3-pyridylmethylcarbamoyl)-2-pyridyl]anilino]ethyl]carbamate (I-466)

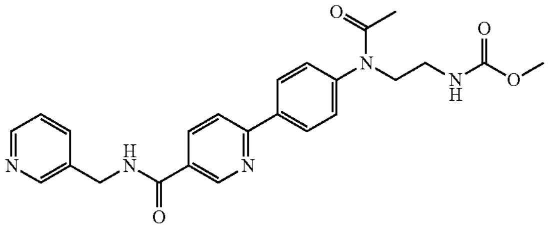 [SMILES: COC(=O)NCCN(C(C)=O)c1ccc(-c2ccc(C(=O)NCc3cccnc3)cn2)cc1]

Per Scheme 2—Step 5, starting from 6-[4-[acetyl-[2-(methoxycarbonylamino)ethyl]amino]phenyl]pyridine-3-carboxylic acid (15 mg, 0.04 mmol) and 3-pyridylmethanamine (5.1 μL, 0.05 mmol), purification by flash column chromatography (silica gel, 10% MeOH in DCM) and trituration with diethyl ether afforded methyl N-[2-[N-acetyl-4-[5-(3-pyridylmethylcarbamoyl)-2-pyridyl]anilino] ethyl]carbamate as a white solid (11 mg, 56%).

LC-MS (Method 8): $R_t$=2.82 min; m/z=448.10 $(M+H)^+$.

$^1$H NMR (400 MHz, DMSO-$d_6$): δ 1.79 (bs, 1H), 3.12 (q, J=6.26 Hz, 2H), 3.47 (s, 3H), 3.69 (t, J=6.26 Hz, 2H), 4.54 (d, J=5.76 Hz, 2H), 7.19 (bs, 1H), 7.37 (dd, J=7.89, 4.86 Hz, 1H), 7.48 (d, J=7.89 Hz, 1H), 7.76 (d, J=8.02 Hz, 1H), 8.15 (d, J=8.44 Hz, 1H), 8.21 (d, J=8.26 Hz, 2H), 8.33 (dd, J=8.26, 2.20 Hz, 1H), 8.48 (d, J=4.43 Hz, 1H), 8.59 (s, 1H), 9.13 (d, J=1.89 Hz, 1H), 9.32 (t, J=5.76 Hz, 1H).

Synthesis According to Scheme 10.

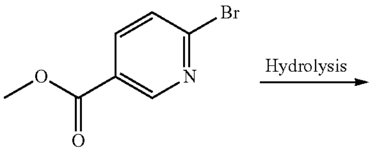

-continued

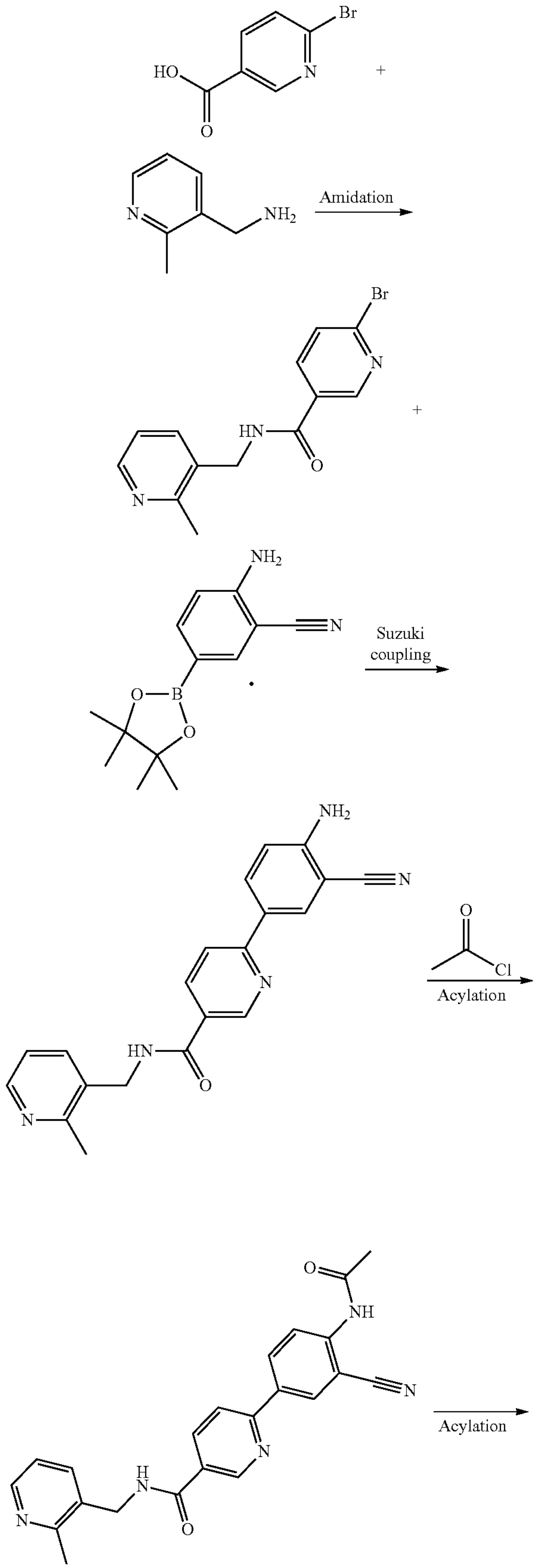

-continued

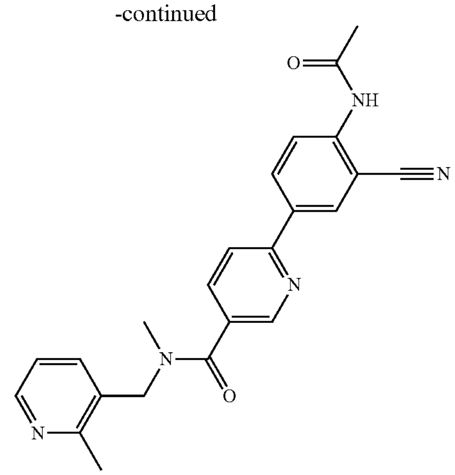

* 2-Amino-5-(4,4,5,5-tetramethyl-1,3,2-dioxaborolan-2-yl)benzonitrile for Step 2

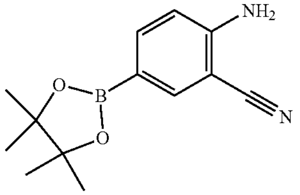 [SMILES: CC1(C)OB(c2ccc(N)c(C#N)c2)OC1(C)C]

Per Scheme 1—Step 1, starting from 4,4,5,5-tetramethyl-2-(4,4,5,5-tetramethyl-1,3,2-dioxaborolan-2-yl)-1,3,2-dioxaborolane (967 mg, 3.81 mmol) and 2-amino-5-bromobenzonitrile, purification by flash column chromatography (silica gel, 0-50% EtOAc in cyclohexane) afforded 2-amino-5-(4,4,5,5-tetramethyl-1,3,2-dioxaborolan-2-yl)benzonitrile as a white solid (387 mg, 56%).

LC-MS (Method 1): $R_t$=1.11 min; m/z=245.14 $(M+H)^+$.

6-Bromopyridine-3-carboxylic acid

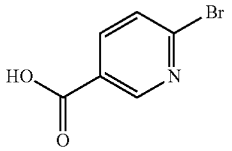

Per Scheme 1—Step 2, hydrolysis of methyl 6-bromopyridine-3-carboxylate (300 mg, 1.40 mmol) afforded 6-bromopyridine-3-carboxylic acid as a white solid (238 mg, 84%).

LC-MS (Method 1): $R_t$=0.65 min; m/z=203.93 $(M+H)^+$.

6-Bromo-N-[(2-methyl-3-pyridyl)methyl]pyridine-3-carboxamide

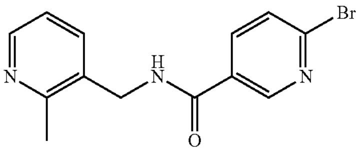 [SMILES: Cc1ncccc1CNC(=O)c1ccc(Br)nc1]

Per Scheme 2—Step 5, using 6-bromopyridine-3-carboxylic acid (238 mg, 1.17 mmol) and (2-methyl-3-pyridyl) methanamine (171 mg, 1.40 mmol), 6-bromo-N-[(2-methyl-3-pyridyl)methyl]pyridine-3-carboxamide (399 mg, 93%) was obtained as a light brown solid which was used as such in the next step.

LC-MS (Method 1): $R_t$=0.49 min; m/z=307.96 $(M+H)^+$.

6-(4-Amino-3-cyano-phenyl)-N-[(2-methyl-3-pyridyl)methyl]pyridine-3-carboxamide

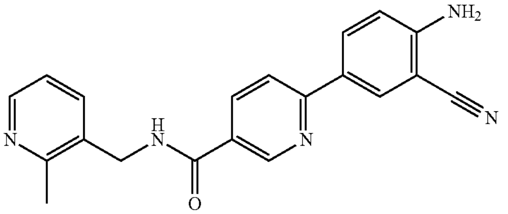 [SMILES: Cc1ncccc1CNC(=O)c1ccc(-c2ccc(N)c(C#N)c2)nc1]

Per Scheme 1—Step 1, using 2-amino-5-(4,4,5,5-tetramethyl-1,3,2-dioxaborolan-2-yl)benzonitrile (271 mg, 1.0 mmol) and 6-bromo-N-[(2-methyl-3-pyridyl)methyl]pyridine-3-carboxamide (240 mg, 0.66 mmol). Triturated with hexane/EtOAc afforded 6-(4-amino-3-cyano-phenyl)-N-[(2-methyl-3-pyridyl)methyl]pyridine-3-carboxamide (156 mg, 64%).

LC-MS (Method 1): $R_t$=0.54 min; m/z=344.06 $(M+H)^+$.

6-(4-Acetamido-3-cyano-phenyl)-N-[(2-methyl-3-pyridyl)methyl]pyridine-3-carboxamide

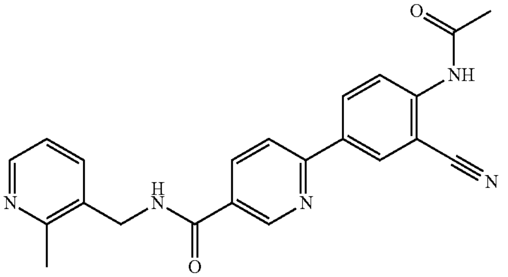 [SMILES: CC(=O)Nc1ccc(-c2ccc(C(=O)NCc3cccnc3C)cn2)cc1C#N]

Following Scheme 1—Step 5 using 6-(4-amino-3-cyano-phenyl)-N-[(2-methyl-3-pyridyl)methyl]pyridine-3-carboxamide (70 mg, 0.190 mmol) and acetyl chloride (27 µL, 0.38 mmol) afforded 6-(4-acetamido-3-cyano-phenyl)-N-[(2-methyl-3-pyridyl)methyl]pyridine-3-carboxamide (40 mg, 31%) which was used as such in the next step.

LC-MS (Method 1): $R_t$=0.51 min; m/z=386.11 $(M+H)^+$.

6-(4-Acetamido-3-cyano-phenyl)-N-methyl-N-[(2-methyl-3-pyridyl)methyl]pyridine-3-carboxamide (I-483)

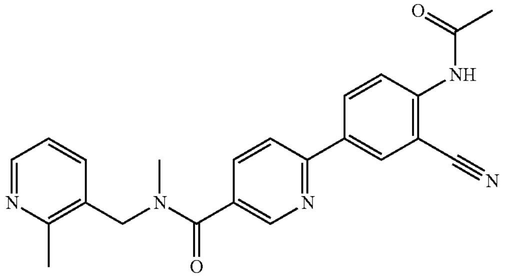 [SMILES: CC(=O)Nc1ccc(-c2ccc(C(=O)N(C)Cc3cccnc3C)cn2)cc1C#N]

Per Scheme 3—Step 3, starting from 6-(4-acetamido-3-cyano-phenyl)-N-[(2-methyl-3-pyridyl)methyl]pyridine-3-carboxamide (40.0 mg, 0.06 mmol), purification of the crude product by prep HPLC (Method 9) afforded 6-(4-acetamido-3-cyano-phenyl)-N-methyl-N-[(2-methyl-3-pyridyl)methyl]pyridine-3-carboxamide as a white solid (2.13 mg, 16%). LC-MS (Method 8): $R_t$=2.83 min; m/z=400.29 $(M+H)^+$. $^1H$ NMR (400 MHz, CDCl3): δ 2.29 (s, 3H), 2.60 (s, 3H), 2.96 (bs, 3H), 4.80 (bs, 2H), 7.19 (bs, 1H), 7.53 (d, J=7.0 Hz, 1H), 7.70 (s, 1H), 7.75 (bs, 1H), 7.90 (bs, 1H), 8.19 (bs, 1H), 8.31 (bs, 1H), 8.46 (dd, J=4.9, 1.6 Hz, 1H), 8.56 (d, J=8.8 Hz, 1H), 8.78 (bs, 1H).

Synthesis According to Scheme 11

Preparation of I-662 and I-663

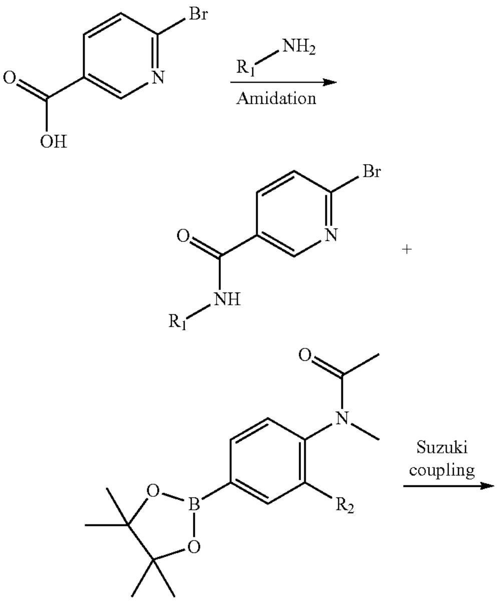

B

-continued

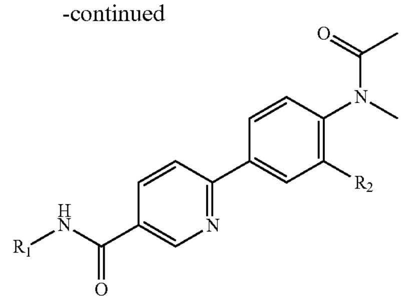

Note: Intermediate B is prepared in 2 steps according to the following scheme:

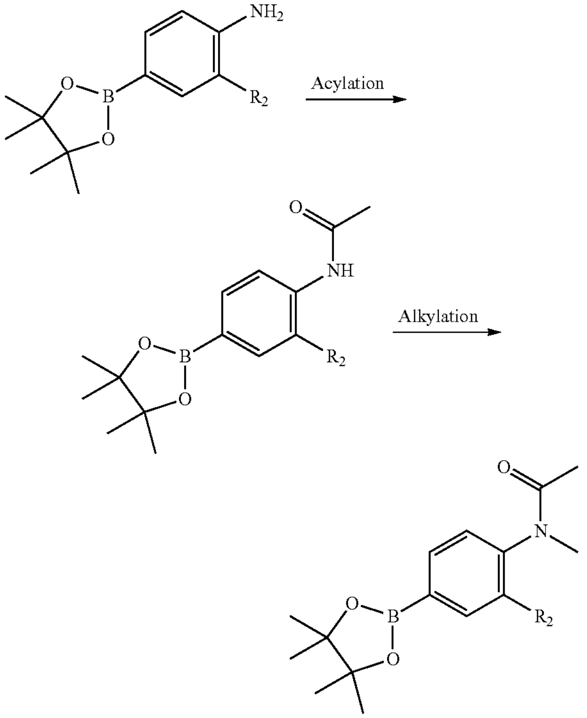

$R_2$ = COOMe or CN

Methyl 2-acetamido-5-(4,4,5,5-tetramethyl-1,3,2-dioxaborolan-2-yl)benzoate

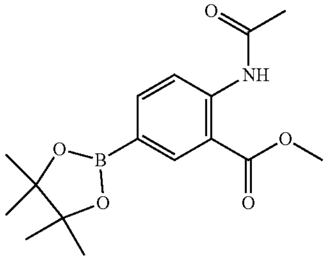

Acylation per Scheme 1—Step 5, starting from methyl 2-amino-5-(4,4,5,5-tetramethyl-1,3,2-dioxaborolan-2-yl) benzoate (150 mg, 0.54 mmol) and acetyl chloride (116 μL, 1.62 mmol), afforded methyl 2-acetamido-5-(4,4,5,5-tetramethyl-1,3,2-dioxaborolan-2-yl)benzoate (160 mg) which was used as such in the next step.

LC-MS (Method 4): $R_t$=1.40 min; m/z=320.12 $(M+H)^+$.

Methyl 2-[acetyl(methyl)amino]-5-(4,4,5,5-tetramethyl-1,3,2-dioxaborolan-2-yl)benzoate

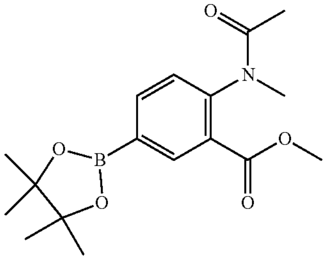

Alkylation per Scheme 3—Step 3 (using THF as solvent), starting from methyl 2-acetamido-5-(4,4,5,5-tetramethyl-1,3,2-dioxaborolan-2-yl)benzoate (160 mg, 0.500 mmol) afforded methyl 2-[acetyl(methyl)amino]-5-(4,4,5,5-tetramethyl-1,3,2-dioxaborolan-2-yl)benzoate (180 mg, 54%) which was used as such in the next step.

LC-MS (Method 4): $R_t$=1.09 min; m/z=334.14 $(M+H)^+$.

6-bromo-N-(3-pyridylmethyl)pyridine-3-carboxamide

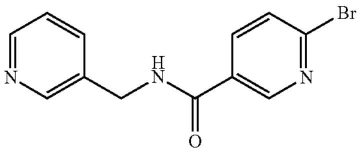 [SMILES: O=C(NCc1cccnc1)c1ccc(Br)nc1]

Per Scheme 1—Step 3, starting from 6-bromopyridine-3-carboxylic acid (870 mg, 4.3 mmol) and 3-pyridylmethanamine (0.53 mL, 5.2 mmol), purification by flash column chromatography (silica gel, 0-10% MeOH in DCM) afforded 6-bromo-N-(3-pyridylmethyl)pyridine-3-carboxamide (250 mg, 10%) as a light brown solid.

LC-MS (Method 2): $R_t$=0.68 min.; m/z=291.93/293.94 $(M+H)^+$.

Methyl 2-[acetyl(methyl)amino]-5-[5-(3-pyridylmethylcarbamoyl)-2-pyridyl]benzoate (I-662)

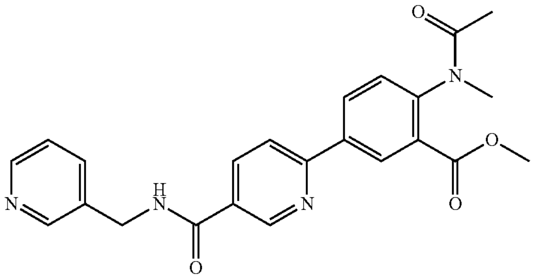 [SMILES: COC(=O)c1cc(-c2ccc(C(=O)NCc3cccnc3)cn2)ccc1N(C)C(C)=O]

Following Scheme 1—Step 1, purification by flash column chromatography (silica gel, 0-10% MeOH in DCM) afforded methyl 2-[acetyl(methyl)amino]-5-[5-(3-pyridylmethylcarbamoyl)-2-pyridyl]benzoate (34 mg, 15%).

LC-MS (Method 8): $R_t$=2.92 min, m/z=419.63 $(M+H)^+$.

$^1$H NMR (400 MHz, DMSO-$d_6$) mixture of rotamers: δ 1.67 (s, 3H), 3.07 (s, 3H), 3.86 (s, 3H), 4.54 (d, J=5.8 Hz, 2H), 7.34-7.39 (m 1H), 7.62 (d, J=8.25 Hz, 1H), 7.73-7.77 (m, 1H), 8.20-8.24 (m, 1H), 8.33-8.38 (m, 1H), 8.42-8.48 (m, 2H), 8.56-8.59 (m, 1H), 8.70 (d, J=2.14 Hz, 1H), 9.15 (d, J=2.2 Hz, 1H), 9.35 (t, J=5.85 Hz, 1H).

N-[2-cyano-4-(4,4,5,5-tetramethyl-1,3,2-dioxaborolan-2-yl)phenyl]-N-methyl-acetamide

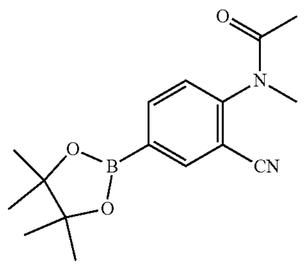 [SMILES: CC(=O)N(C)c1ccc(B2OC(C)(C)C(C)(C)O2)cc1C#N]

Similarly, N-[2-cyano-4-(4,4,5,5-tetramethyl-1,3,2-dioxaborolan-2-yl)phenyl]-N-methyl-acetamide (142 mg, 54%) was prepared and used as such in the next step.

LC-MS (Method 4): $R_t$=0.94 min; m/z=301.13 $(M+H)^+$.

6-[4-[Acetyl(methyl)amino]-3-cyano-phenyl]-N-(3-pyridylmethyl)pyridine-3-carboxamide (I-663)

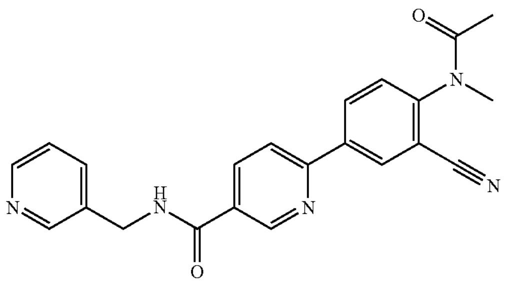 [SMILES: CC(=O)N(C)c1ccc(-c2ccc(C(=O)NCc3cccnc3)cn2)cc1C#N]

Following Scheme 1—Step 1, purification by flash column chromatography (silica gel, 0-10% MeOH in DCM) afforded 6-[4-[acetyl(methyl)amino]-3-cyano-phenyl]-N-(3-pyridylmethyl)pyridine-3-carboxamide as a light brown solid (34 mg, 38%).

LC-MS (Method 8): $R_t$=2.87 min; m/z=386.59 $(M+H)^+$.

$^1$H NMR (300 MHz, $CDCl_3$) δ: 1.90 (s, 3H), 3.32 (s, 3H), 4.71 (d, J=5.7 Hz, 2H), 6.91 (m, 1H), 7.35 (dd, J=7.8, 4.8 Hz, 1H), 7.44 (d, J=8.3 Hz, 1H), 7.79 (d, J=7.9 Hz, 1H), 7.83 (d, J=8.2 Hz, 1H), 8.24-8.35 (m, 2H), 8.44 (s, 1H), 8.61 (s, 1H), 8.71 (s, 1H), 9.10 (m, 1H).

Example 2. Cell Viability in RS4; 11 Cells and MV-4-11 Cells

Approximately 10,000 MV-4-11 cells per well of a 96-well plate were treated with DMSO (no drug control) or each compound in Tables E1 and E2 in an 8-point dose response for 4 days, Cell viability was measured using CellTiter Glo2. The $ICs_e$ of each compound was determined using CDD Vault. Exemplary results are shown in Tables E1 and E2.

Example 3. NAMPT Activity Assay

The NAMPT Activity Assay (Abcam #ab221819) was performed following manufacturers two-step reaction protocol. Briefly, compounds were added to a clear 96-well plate using the HP D300e Digital Dispenser. Purified NAMPT was added to all wells except the No NAMPT controls. Reaction Mix #1 was added to each well and the plate was incubated at 30*C for 1 hr followed by the addition of Reaction Mix #2. Absorbance was measured at OD450 nm using a multimode plate reader. Readings were recorded for 5 minutes and percent inhibition was calculated using: (1-(OD450 nm compound/OD450 nm no drug))*100. Exemplary results are shown in Table E3.

TABLE E1

| Structure | Compound Number | MV-4-11 $IC_{50}$ (μM) |
|---|---|---|
| 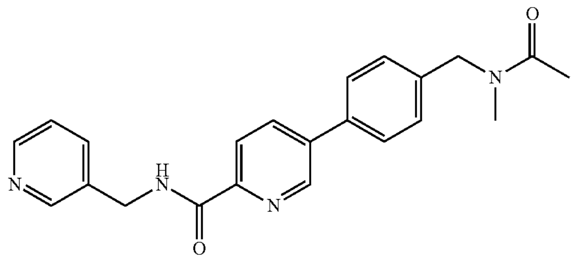 [SMILES: CC(=O)N(C)Cc1ccc(-c2ccc(C(=O)NCc3cccnc3)nc2)cc1] | I-319 | 10 |

TABLE E1-continued
| Structure | Compound Number | MV-4-11 $IC_{50}$ (μM) |
|---|---|---|
| 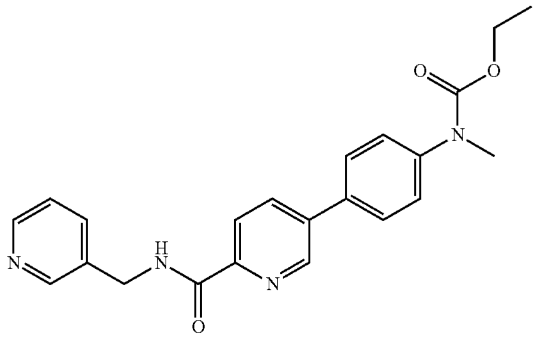 [SMILES: CCOC(=O)N(C)c1ccc(-c2ccc(C(=O)NCc3cccnc3)nc2)cc1] | I-330 | 6.08 |
| 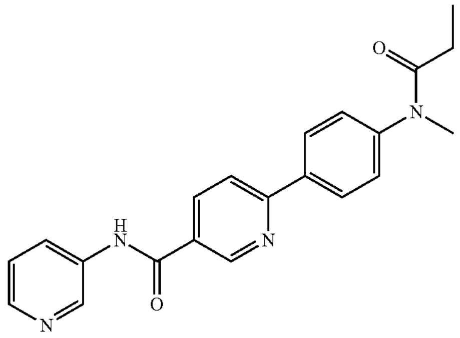 [SMILES: CCC(=O)N(C)c1ccc(-c2ccc(C(=O)Nc3cccnc3)cn2)cc1] | I-353 | 0.941 |
| 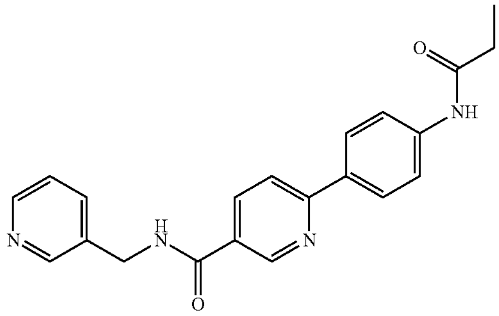 [SMILES: CCC(=O)Nc1ccc(-c2ccc(C(=O)NCc3cccnc3)cn2)cc1] | I-354 | >30.0 |
| 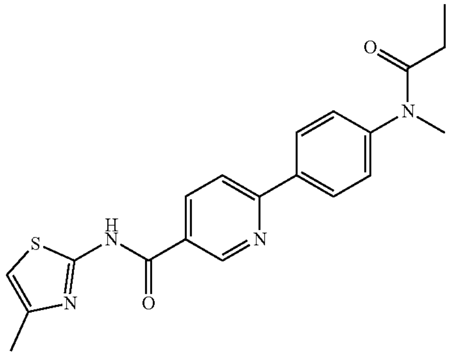 [SMILES: CCC(=O)N(C)c1ccc(-c2ccc(C(=O)Nc3nc(C)cs3)cn2)cc1] | I-355 | 2.91 |

TABLE E1-continued
| Structure | Compound Number | MV-4-11 $IC_{50}$ (μM) |
|---|---|---|
| 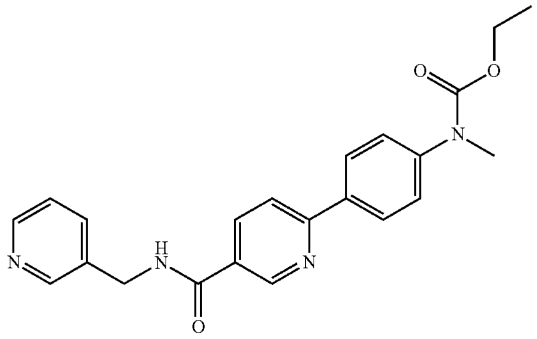 [SMILES: CCOC(=O)N(C)c1ccc(-c2ccc(C(=O)NCc3cccnc3)cn2)cc1] | I-389 | 3.17 |
| 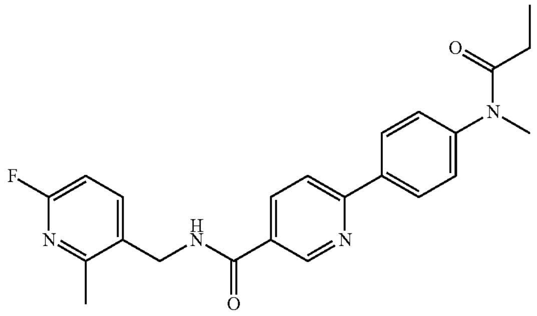 [SMILES: CCC(=O)N(C)c1ccc(-c2ccc(C(=O)NCc3ccc(F)nc3C)cn2)cc1] | I-390 | 4.26 |
| 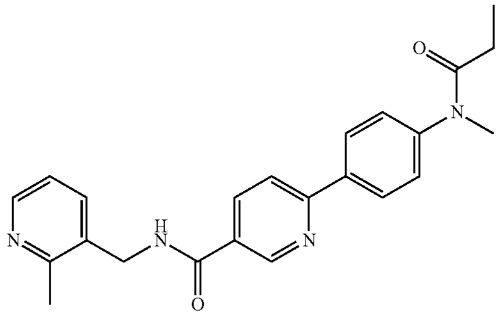 [SMILES: CCC(=O)N(C)c1ccc(-c2ccc(C(=O)NCc3cccnc3C)cn2)cc1] | I-392 | 6.23 |
| 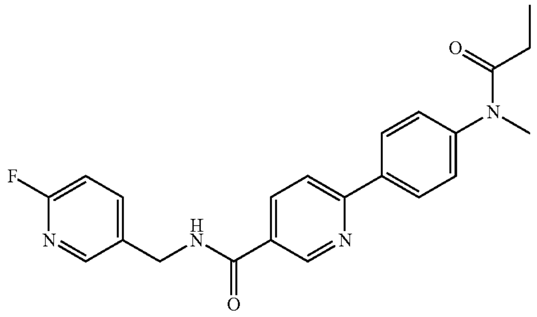 [SMILES: CCC(=O)N(C)c1ccc(-c2ccc(C(=O)NCc3ccc(F)nc3)cn2)cc1] | I-393 | >30.0 |

TABLE E1-continued
| Structure | Compound Number | MV-4-11 $IC_{50}$ (μM) |
|---|---|---|
| 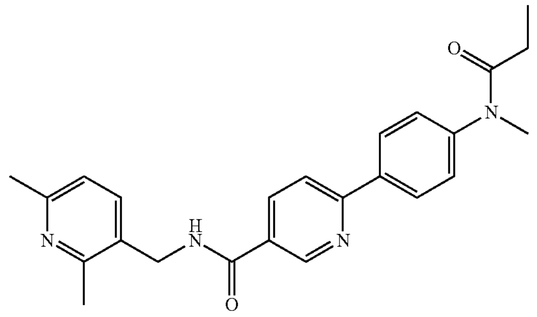 [SMILES: CCC(=O)N(C)c1ccc(-c2ccc(C(=O)NCc3ccc(C)nc3C)cn2)cc1] | I-394 | 3.52 |
| 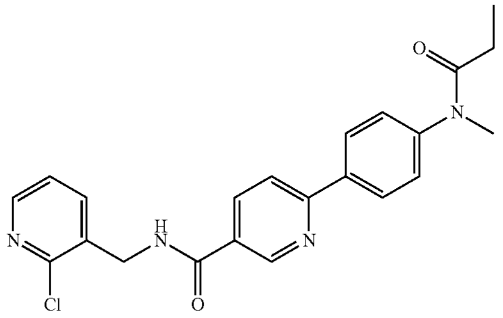 [SMILES: CCC(=O)N(C)c1ccc(-c2ccc(C(=O)NCc3cccnc3Cl)cn2)cc1] | I-395 | 6.11 |
| 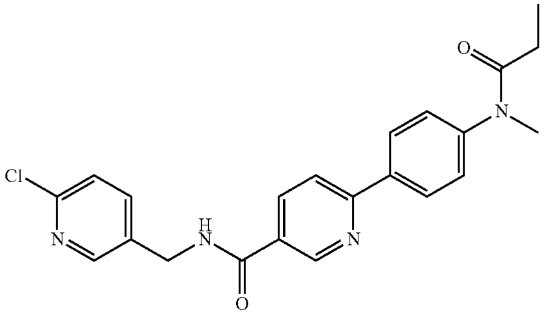 [SMILES: CCC(=O)N(C)c1ccc(-c2ccc(C(=O)NCc3ccc(Cl)nc3)cn2)cc1] | I-396 | 6.56 |
| 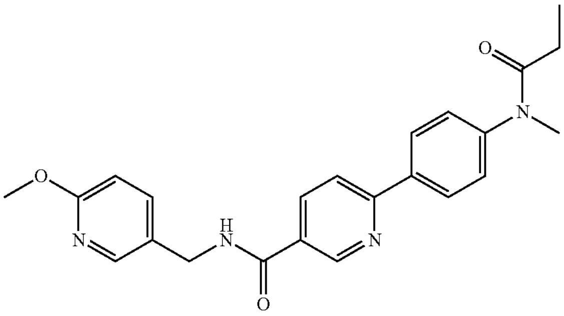 [SMILES: CCC(=O)N(C)c1ccc(-c2ccc(C(=O)NCc3ccc(OC)nc3)cn2)cc1] | I-397 | 13.8 |
| 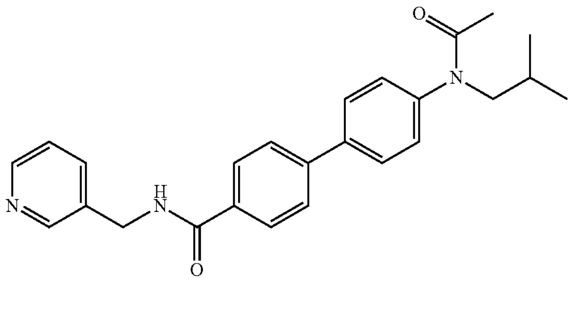 [SMILES: CC(=O)N(CC(C)C)c1ccc(-c2ccc(C(=O)NCc3cccnc3)cc2)cc1] | I-402 | 0.0587 |

TABLE E1-continued
| Structure | Compound Number | MV-4-11 $IC_{50}$ (μM) |
|---|---|---|
| 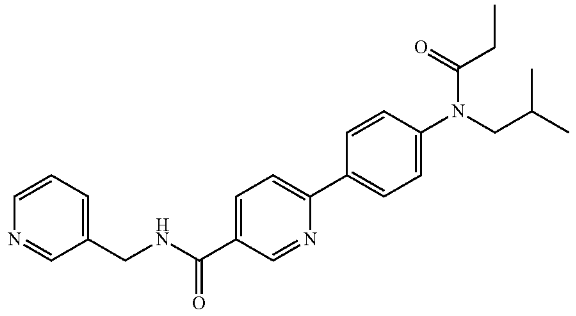 [SMILES: CCC(=O)N(CC(C)C)c1ccc(-c2ccc(C(=O)NCc3cccnc3)cn2)cc1] | I-403 | <0.0117 |
| 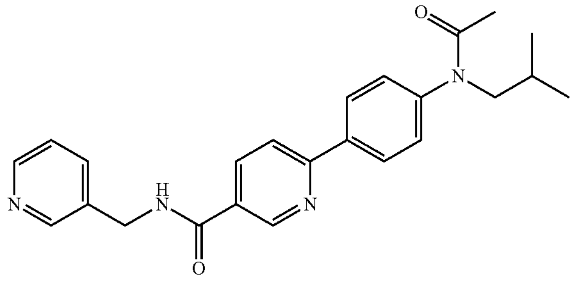 [SMILES: CC(=O)N(CC(C)C)c1ccc(-c2ccc(C(=O)NCc3cccnc3)cn2)cc1] | I-404 | 0.032 |
| 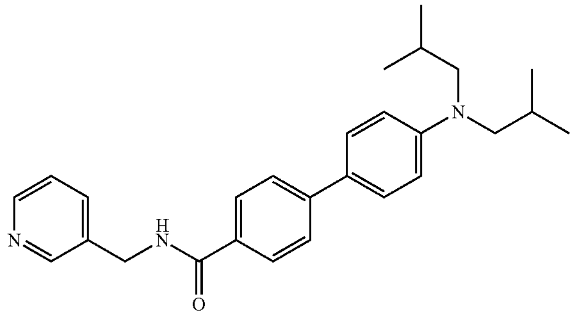 [SMILES: CC(C)CN(CC(C)C)c1ccc(-c2ccc(C(=O)NCc3cccnc3)cc2)cc1] | I-406 | 0.817 |
| 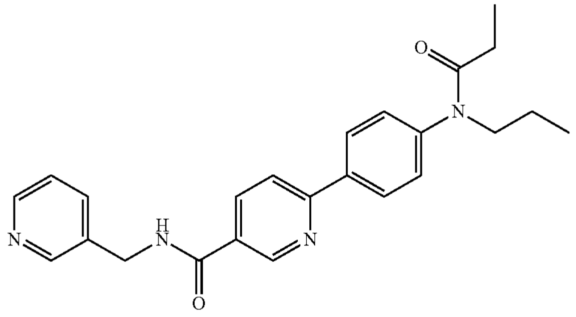 [SMILES: CCCN(C(=O)CC)c1ccc(-c2ccc(C(=O)NCc3cccnc3)cn2)cc1] | I-410 | 0.119 |
| 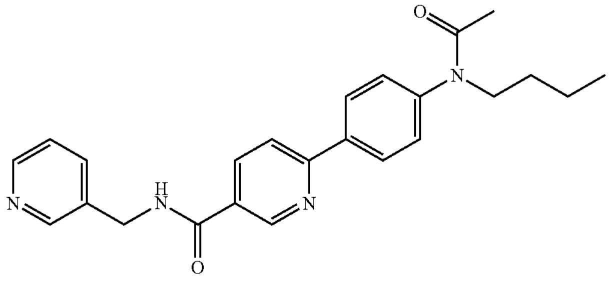 [SMILES: CCCCN(C(C)=O)c1ccc(-c2ccc(C(=O)NCc3cccnc3)cn2)cc1] | I-411 | 0.125 |

TABLE E1-continued
| Structure | Compound Number | MV-4-11 $IC_{50}$ (μM) |
|---|---|---|
| 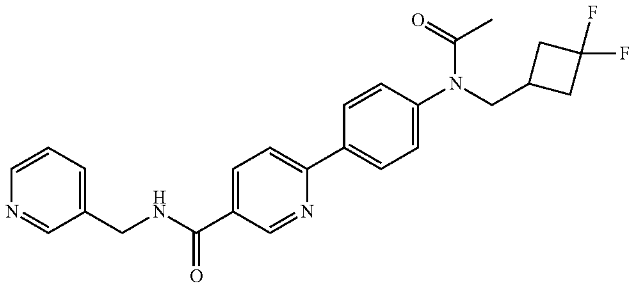 [SMILES: CC(=O)N(CC1CC(F)(F)C1)c1ccc(-c2ccc(C(=O)NCc3cccnc3)cn2)cc1] | I-412 | 0.0825 |
| 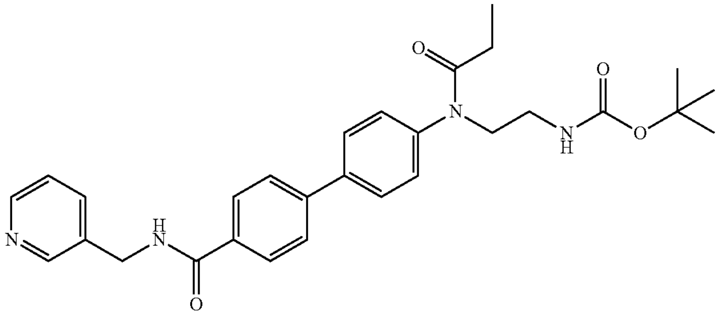 [SMILES: CCC(=O)N(CCNC(=O)OC(C)(C)C)c1ccc(-c2ccc(C(=O)NCc3cccnc3)cc2)cc1] | I-417 | 0.105 |
| 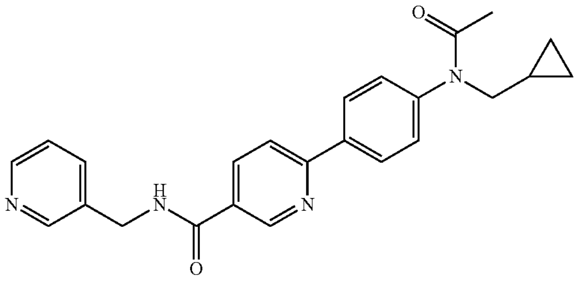 [SMILES: CC(=O)N(CC1CC1)c1ccc(-c2ccc(C(=O)NCc3cccnc3)cn2)cc1] | I-421 | 0.117 |
| 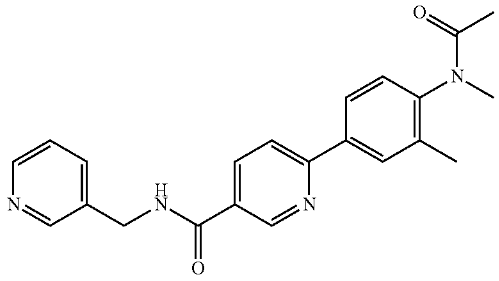 [SMILES: CC(=O)N(C)c1ccc(-c2ccc(C(=O)NCc3cccnc3)cn2)cc1C] | I-425 | 1.67 |
| 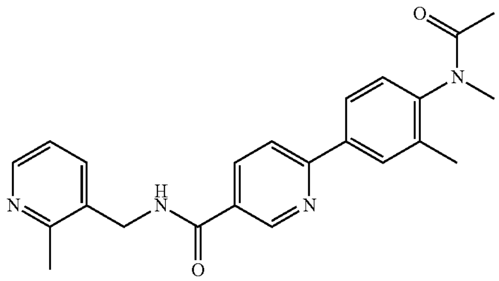 [SMILES: CC(=O)N(C)c1ccc(-c2ccc(C(=O)NCc3cccnc3C)cn2)cc1C] | I-428 | 3.46 |

TABLE E1-continued
| Structure | Compound Number | MV-4-11 $IC_{50}$ (μM) |
| --- | --- | --- |
| 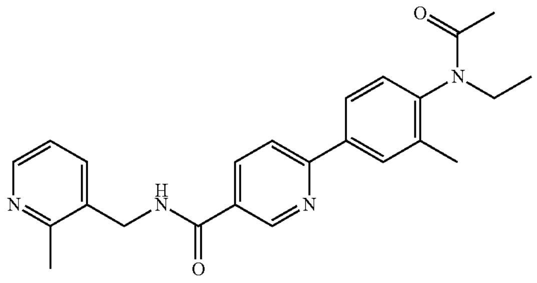 [SMILES: CCN(C(C)=O)c1ccc(-c2ccc(C(=O)NCc3cccnc3C)cn2)cc1C] | I-429 | 4.03 |
| 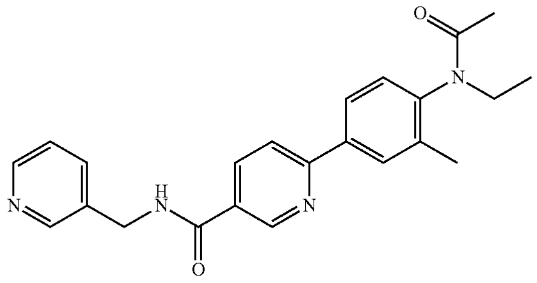 [SMILES: CCN(C(C)=O)c1ccc(-c2ccc(C(=O)NCc3cccnc3)cn2)cc1C] | I-430 | 0.267 |
| 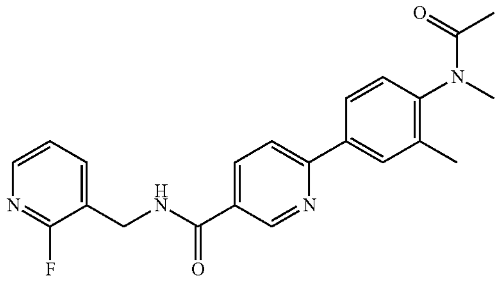 | I-436 | 13.8 |
| 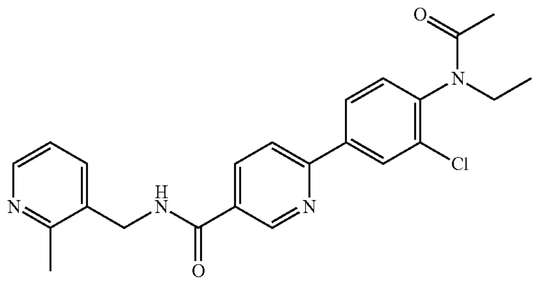 [SMILES: CCN(C(C)=O)c1ccc(-c2ccc(C(=O)NCc3cccnc3C)cn2)cc1Cl] | I-444 | 1.82 |
| 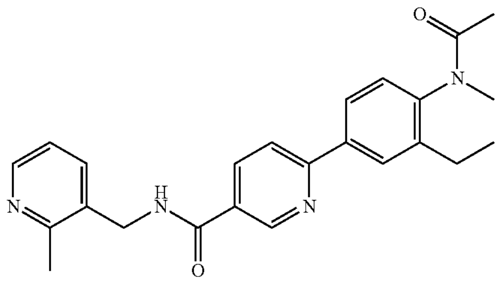 [SMILES: CCc1cc(-c2ccc(C(=O)NCc3cccnc3C)cn2)ccc1N(C)C(C)=O] | I-445 | 3.69 |

TABLE E1-continued
| Structure | Compound Number | MV-4-11 $IC_{50}$ (μM) |
|---|---|---|
| 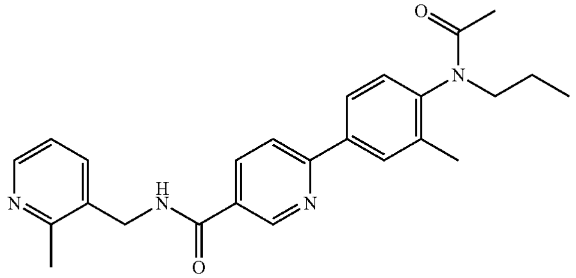 [SMILES: CCCN(C(C)=O)c1ccc(-c2ccc(C(=O)NCc3cccnc3C)cn2)cc1C] | I-446 | 2.17 |
| 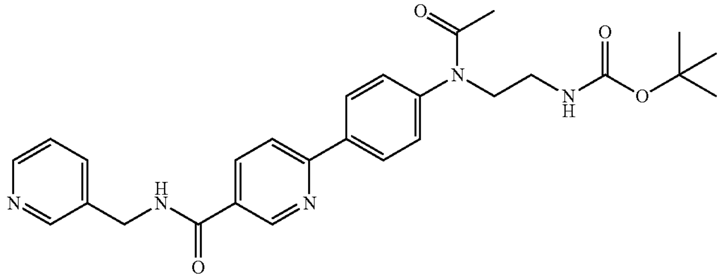 [SMILES: CC(=O)N(CCNC(=O)OC(C)(C)C)c1ccc(-c2ccc(C(=O)NCc3cccnc3)cn2)cc1] | I-448 | 0.691 |
TABLE E2
MV-4-11 Cell Viability
| Compound Number | MV-4-11 $IC_{50}$ (μM) |
|---|---|
| I-331 | 0.436 |
| I-447 | 0.493 |
| I-449 | 5.18 |
| I-450 | 7.63 |
| I-451 | 5.37 |
| I-452 | 1.82 |
| I-453 | 0.038 |
| I-454 | 2.14 |
| I-455 | 3.47 |
| I-456 | >30.0 |
| I-457 | 9.85 |
| I-458 | 1.71 |
| I-459 | 1.51 |
| I-460 | >0.694 |
| I-466 | 0.871 |
| I-467 | 4.34 |
| I-468 | 0.0333 |
| I-481 | 0.104 |
| I-482 | 0.226 |
| I-483 | >30.0 |
| I-484 | 2.66 |
| I-485 | 1.34 |
| I-486 | 2.7 |
| I-487 | 4.35 |
| I-488 | 2.82 |
| I-489 | 2.22 |
| I-490 | 4.76 |
| I-491 | 1.83 |
| I-492 | 6.77 |
| I-495 | 0.0107 |
| I-496 | >15.8 |
| I-497 | 5.72 |
| I-499 | 3.99 |
| I-500 | 2.28 |
| I-501 | 1.83 |
| I-502 | 0.224 |
| I-510 | 5.91 |
| I-511 | 7.07 |
| I-512 | 4.38 |
TABLE E2-continued
MV-4-11 Cell Viability
| Compound Number | MV-4-11 $IC_{50}$ (μM) |
|---|---|
| I-513 | 0.282 |
| I-517 | 2.44 |
| I-527 | 0.787 |
| I-593 | 1.47 |
| I-594 | <0.00664 |
| I-595 | 0.00453 |
| I-596 | 0.00239 |
| I-597 | 0.0216 |
| I-599 | 0.00328 |
| I-600 | 0.0206 |
| I-601 | 0.0627 |
| I-602 | 0.00556 |
| I-603 | <0.00589 |
| I-604 | 0.033 |
| I-605 | 0.351 |
| I-606 | 0.0211 |
| I-608 | 0.22 |
| I-609 | 0.0135 |
| I-610 | 0.037 |
| I-611 | 0.00301 |
| I-619 | 0.0672 |
| I-620 | 0.00811 |
| I-624 | 0.04 |
| I-626 | 0.0237 |
| I-629 | 0.358 |
| I-630 | 0.137 |
| I-631 | 1.58 |
| I-639 | 0.133 |
| I-652 | 0.0924 |
| I-658 | 0.15 |
| I-662 | 0.036 |
| I-663 | 1.7 |
| I-674 | 0.35 |
| I-676 | >0.997 |
| I-677 | 0.00291 |
| I-679 | 0.000566 |
| I-681 | 0.00131 |
| I-683 | >0.997 |
| I-684 | 0.341 |

TABLE E2-continued

| MV-4-11 Cell Viability | |
|---|---|
| Compound Number | MV-4-11 $IC_{50}$ (μM) |
| I-685 | 0.34 |
| I-687 | 0.261 |
| I-689 | 0.0328 |
| I-690 | 0.336 |

TABLE E3

| NAMPT Inhibition | |
|---|---|
| Compound Number | Code* |
| I-330 | A |
| I-331 | A |
| I-353 | C |
| I-354 | A |
| I-355 | A |
| I-389 | A |
| I-390 | A |
| I-392 | A |
| I-393 | A |
| I-394 | A |
| I-395 | A |
| I-396 | C |
| I-397 | B |
| I-402 | C |
| I-403 | C |
| I-404 | B |
| I-406 | B |
| I-410 | B |
| I-411 | B |
| I-412 | B |
| I-417 | A |
| I-421 | B |
| I-425 | A |
| I-430 | B |
| I-444 | A |
| I-445 | A |
| I-446 | A |
| I-447 | A |
| I-448 | A |
| I-449 | A |
| I-450 | B |
| I-451 | B |
| I-452 | A |
| I-453 | C |
| I-454 | A |
| I-455 | A |
| I-456 | A |
| I-457 | A |
| I-458 | A |
| I-459 | A |
| I-460 | A |
| I-466 | A |
| I-467 | A |
| I-468 | B |
| I-481 | A |
| I-482 | B |
| I-483 | A |
| I-484 | A |
| I-485 | A |
| I-486 | A |
| I-487 | A |
| I-488 | A |
| I-489 | A |
| I-490 | A |
| I-491 | A |
| I-492 | A |
| I-495 | C |
| I-496 | A |
| I-497 | A |
| I-499 | A |

TABLE E3-continued

| NAMPT Inhibition | |
|---|---|
| Compound Number | Code* |
| I-500 | A |
| I-501 | A |
| I-502 | A |
| I-510 | A |
| I-511 | A |
| I-512 | A |
| I-513 | B |
| I-517 | A |
| I-527 | A |
| I-593 | A |
| I-594 | C |
| I-595 | C |
| I-596 | C |
| I-597 | C |
| I-599 | C |
| I-600 | B |
| I-601 | B |
| I-602 | C |
| I-603 | C |
| I-604 | B |
| I-605 | B |
| I-606 | C |
| I-608 | B |
| I-609 | C |
| I-610 | B |
| I-611 | C |
| I-619 | C |
| I-620 | C |
| I-624 | B |
| I-626 | C |
| I-629 | B |
| I-630 | C |
| I-631 | B |
| I-639 | B |
| I-652 | C |
| I-658 | B |
| I-662 | C |
| I-663 | B |
| I-674 | B |
| I-676 | A |
| I-677 | C |
| I-679 | C |
| I-681 | C |
| I-683 | C |
| I-684 | A |
| I-685 | C |
| I-687 | A |
| I-689 | C |
| I-690 | C |
| I-693 | B |
| I-696 | C |
| I-697 | C |
| I-698 | A |

*A = <33% inhibition
B = ≥33 to <66% inhibition
C = ≥66% inhibition

REFERENCES

1. American Cancer Society. 2017. Cancer Facts & Figures, 2017. Atlanta: American Cancer Society.
2. Stewart B W, Wild C P, editors. World cancer report 2014 Lyon: International Agency for Research on Cancer; 2014.
3. Taniguchi H, Moriya C, Igarashi H, Saitoh A, Yamamoto H, Adachi Y, Imai K. 2016. Cancer stem cells in human gastrointestinal cancer. Cancer Sci 107: 1556-1562.

4. Seyfried T and Huysentruyt L C. 2013. On the Origin of Cancer Metastasis. Crit Rev Oncog.
18(1-2): 43-73.
5. Bonnet D and Dick J E. 1997. Human acute myeloid leukemia is organized as a hierarchy that originates from a primitive hematopoietic cell. Nat Med. 3(7):730-7.
6. O'Brien C A, Pollett A, Gallinger S, Dick J E. 2007. A human colon cancer cell capable of initiating tumour growth in immunodeficient mice. Nature. 445(7123):106-10.
7. Saunders L R, Bankovich A J, Anderson W C, et al. 2015. A DLL3-targeted antibody-drug conjugate eradicates high-grade pulmonary neuroendocrine tumor-initiating cells in vivo.
Science translational medicine. 7(302):302ra136.
8. Chen J, Li Y, Yu T-S, et al. 2012. A restricted cell population propagates glioblastoma growth after chemotherapy. Nature. 488: 522-26.
9. Ben-Porath I, Thomson M W, Carey V J, Ge R, Bell G W, Regev A, Weinberg R A. 2008. An embryonic stem cell-like gene expression signature in poorly differentiated aggressive human. Nat Genet 40: 499-507.
10. Hadjimichael et al., World J. Stem Cells, 2015, 7(9): 1150-1184.
11. Guinney J, et al. 2015. The consensus molecular subtypes of colorectal cancer. Nature Medicine. 21:1350-1356.
12. The Cancer Genome Atlas Research Network. 2014. Comprehensive molecular characterization of gastric adenocarcinoma. Nature 513: 202-209.
13. Asciutti S, et al. 2011. Diverse Mechanisms of Wnt Activation and Effects of Pathway Inhibition on Proliferation of Human Gastric Carcinoma Cells. Oncogene. 24; 30(8): 956-966.
14. Laranjeira et al., Expert Opin Drug Discov., 2016, 11, 1071-1080.
15. Audrito S, et al. Front. Oncol. 2020, 10, 358.
16. Galli, U, et al. Font. Pharmacol. 2020, 11, 656.
17. See also: (i) WO 97/48696 for involvement of NAMPT in the treatment of cancer, (ii) WO 97/48397 for involvement of NAMPT in immunosuppression, (iii) WO 2003/80054 for involvement of NAMPT for the treatment of diseases involving angiogenesis, (iv) WO 2008/025857 for involvement of NAMPT for the treatment of rheumatoid arthritis and septic shock, and (v) WO 2009/109610 for involvement of NAMPT for the prophylaxis and treatment of ischemia.
18. Moschen, A, et al. J Immunol. 2007, 178, 1748.
19. Zhang, Y, et al. Mol Med Rep. 2019, 19, 400.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (0):

(0)

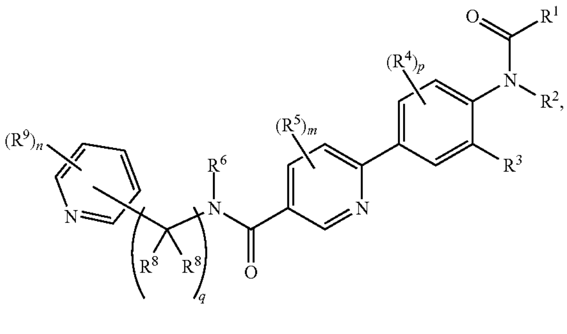

or a pharmaceutically acceptable salt, solvate, hydrate, polymorph, co-crystal, tautomer, stereoisomer, isotopically labeled derivative, or prodrug thereof, wherein:

$R^1$ is substituted or unsubstituted, $C_{1-12}$ alkyl or substituted or unsubstituted, $C_{1-12}$ heteroalkyl;

$R^2$ is hydrogen, substituted or unsubstituted, $C_{1-12}$ alkyl, substituted or unsubstituted, $C_{1-12}$ heteroalkyl, substituted or unsubstituted, 3- to 13-membered heterocyclyl-$C_{1-12}$-alkyl, substituted or unsubstituted, 3- to 13-membered carbocyclyl-$C_{1-12}$-alkyl, or a nitrogen protecting group;

when $R^2$ is unsubstituted methyl, $R^1$ is not unsubstituted ethyl;

$R^3$ is hydrogen, halogen, substituted or unsubstituted, $C_{1-6}$ alkyl, -$OR^a$, -$COOR^a$, -$COR^a$, —$N(R^a)_2$, -CN, or -(C═O)$N((R^a)_2$;

each instance of $R^a$ is independently hydrogen, substituted or unsubstituted, $C_{1-6}$ alkyl, an oxygen protecting group when attached to an oxygen atom, or a nitrogen protecting group when attached to a nitrogen atom;

each instance of $R^4$ is independently hydrogen, halogen, substituted or unsubstituted, $C_{1-6}$ alkyl, -$OR^a$, -$COOR^a$, -$COR^a$, -$N((R^a)_2$, -CN, or -(C═O)$N((R^a)$ 2;

each instance of $R^5$ is independently hydrogen, halogen, substituted or unsubstituted, $C_{1-6}$ alkyl, -$OR^a$, -$COOR^a$, -$COR^a$, -$N((R^a)_2$, -CN, or -(C═O) $N((R^a)_2$;

$R^6$ is hydrogen, substituted or unsubstituted, $C_{1-6}$ alkyl, or a nitrogen protecting group;

each instance of $R^8$ is independently hydrogen, halogen, or substituted or unsubstituted, $C_{1-6}$ alkyl;

each instance of $R^9$ is independently hydrogen, halogen, substituted or unsubstituted, $C_{1-6}$ alkyl, -$OR^a$, -$COOR^a$, -$COR^a$, -$N((R^a)_2$, -CN, or -(C═O) $N((R^a)_2$, or two instances of $R^9$ are joined to form a 3- to 13-membered heterocyclyl, 3- to 13-membered heterocyclyl, 6- to 12-membered aryl ring, or 5- to 14-membered heteroaryl ring;

n is an integer from 0 to 4, inclusive;

m is 0;

p is an integer from 0 to 3, inclusive; and q is an integer selected from 0 and 1; provided that the compound is not of the formula:

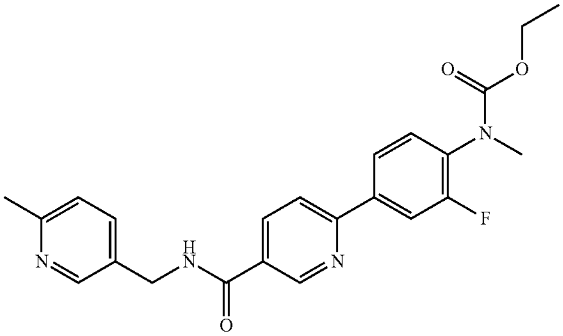

,

-continued

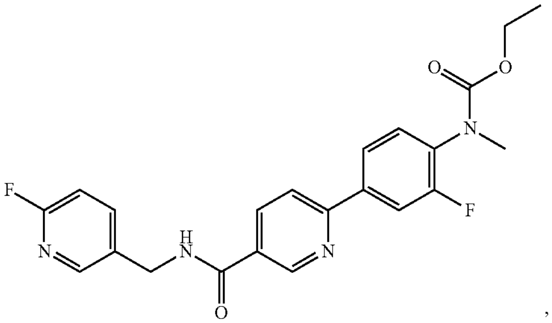

,

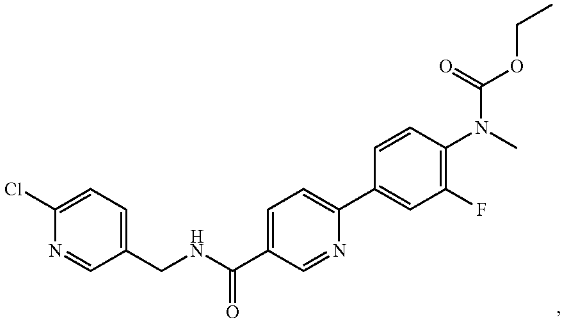

,

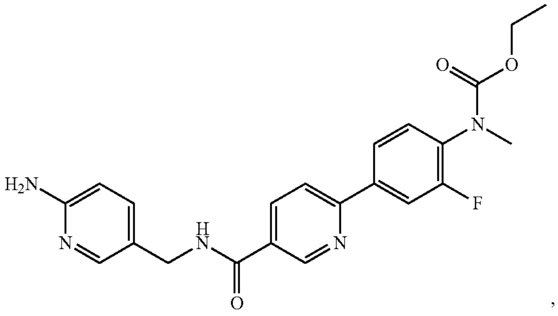

,

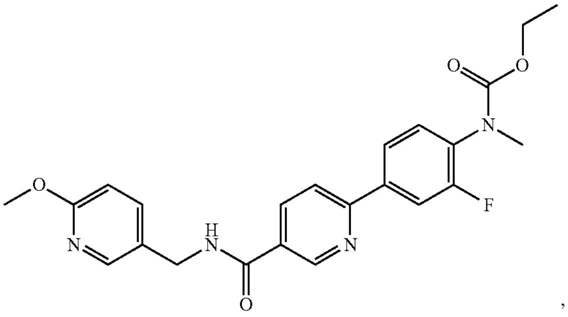

,

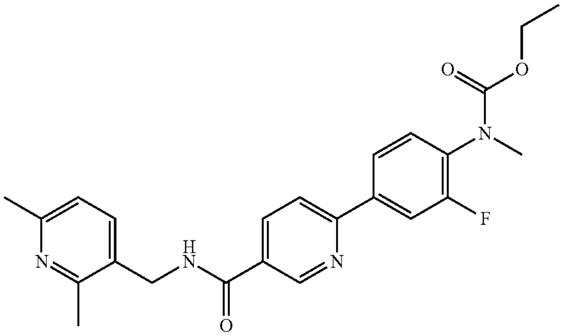

,

-continued
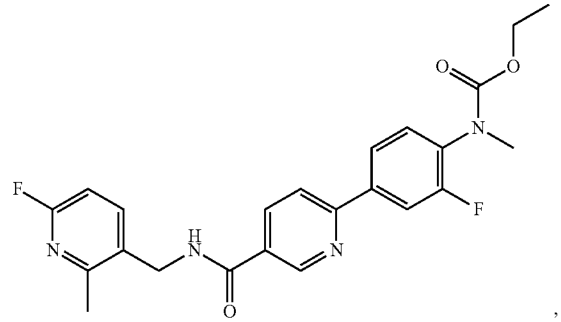
,
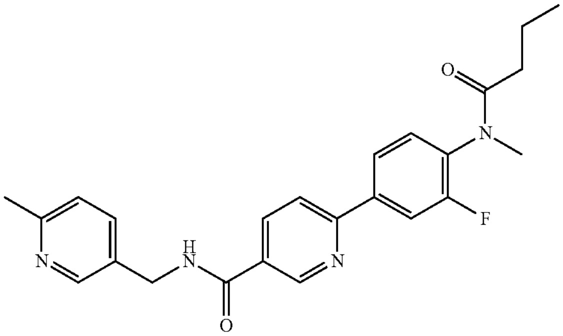
,
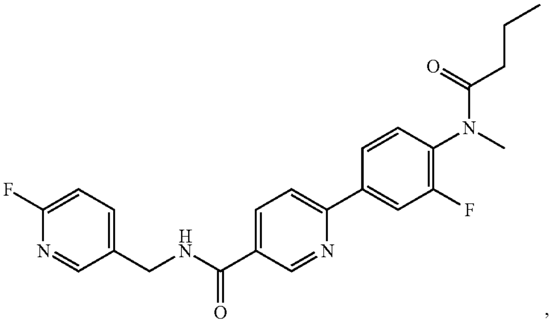
,
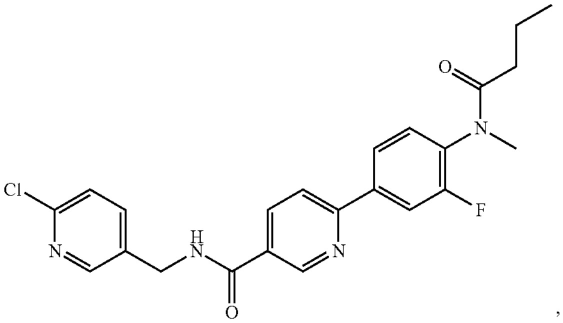
,
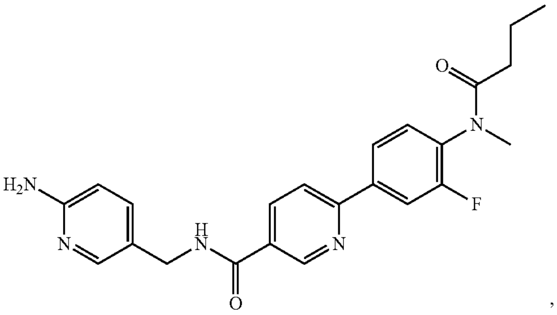
,
-continued
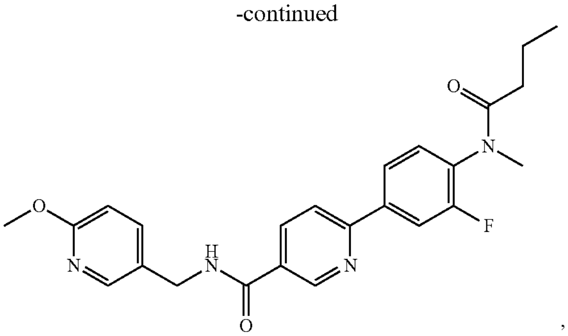
,
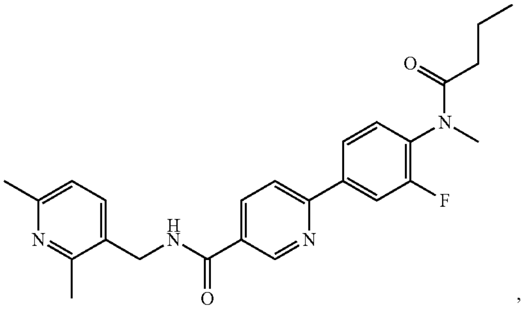
, or
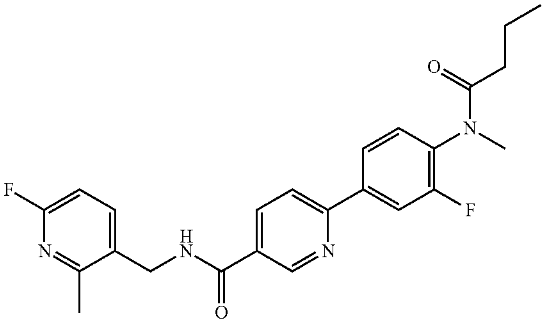
.
2. The compound of claim 1, wherein the compound is a compound of:
(a) Formula (0a):
(0a)
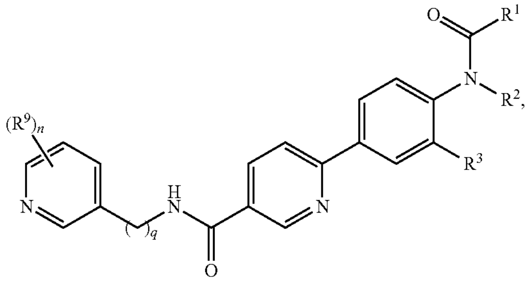
or a pharmaceutically acceptable salt, solvate, hydrate, polymorph, co-crystal, tautomer, stereoisomer, isotopically labeled derivative, or prodrug thereof;

(b) Formula (0b):

(0b)

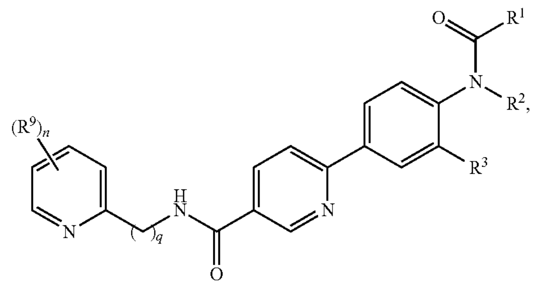

or a pharmaceutically acceptable salt, solvate, hydrate, polymorph, co-crystal, tautomer, stereoisomer, isotopically labeled derivative, or prodrug thereof; or (c) Formula (0c):

(0c)

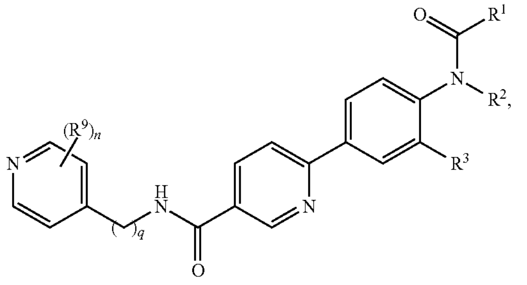

or a pharmaceutically acceptable salt, solvate, hydrate, polymorph, co-crystal, tautomer, stereoisomer, isotopically labeled derivative, or prodrug thereof.

3. The compound of claim 1, wherein the compound is of:

(a) Formula (I):

(I)

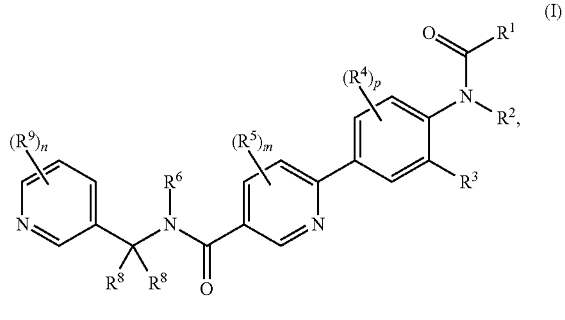

or a pharmaceutically acceptable salt, solvate, hydrate, polymorph, co-crystal, tautomer, stereoisomer, isotopically labeled derivative, or prodrug thereof;

(b) Formula (Iz):

(Iz)

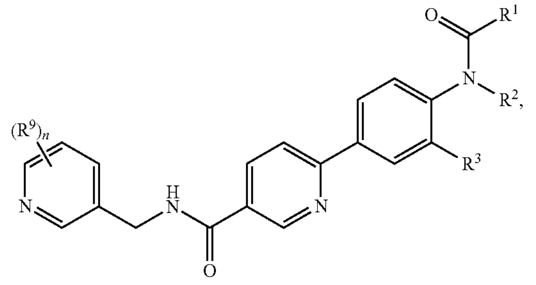

or a pharmaceutically acceptable salt, solvate, hydrate, polymorph, co-crystal, tautomer, stereoisomer, isotopically labeled derivative, or prodrug thereof;

(c) Formula (Ia):

(Ia)

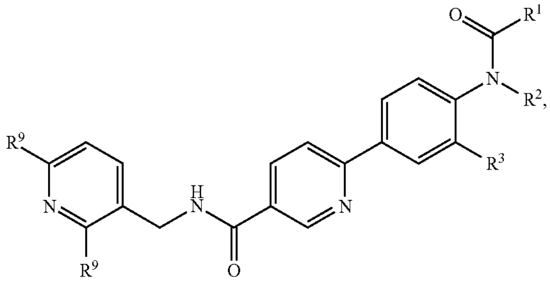

or a pharmaceutically acceptable salt, solvate, hydrate, polymorph, co-crystal, tautomer, stereoisomer, isotopically labeled derivative, or prodrug thereof;

(d) Formula (Ib):

(Ib)

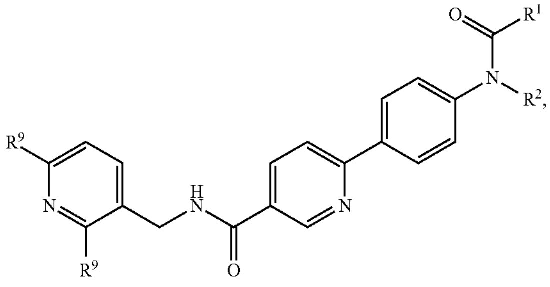

or a pharmaceutically acceptable salt, solvate, hydrate, polymorph, co-crystal, tautomer, stereoisomer, isotopically labeled derivative, or prodrug thereof; or (e) Formula (Ic):

(Ic)

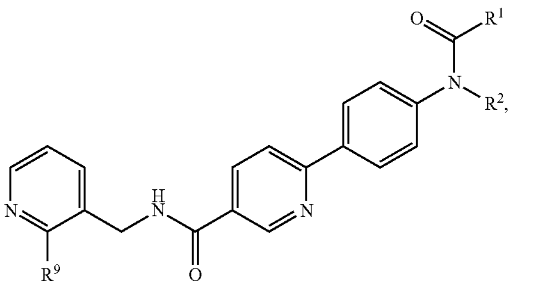

or a pharmaceutically acceptable salt, solvate, hydrate, polymorph, co-crystal, tautomer, stereoisomer, isotopically labeled derivative, or prodrug thereof.

4. The compound of claim 1, wherein each $R^9$ is independently substituted or unsubstituted methyl, chloro, fluoro, methoxy, or $-NH_2$.

5. The compound of claim 1, wherein $R^3$ is hydrogen, substituted or unsubstituted methyl, fluoro, chloro, -CN, or $-COOR^a$.

6. The compound of claim 1, wherein $R^1$ is methyl or ethyl.

7. The compound of claim 1, wherein $R^2$ is substituted or unsubstituted, $C_{1-6}$ alkyl, substituted or unsubstituted, $C_{1-6}$ heteroalkyl, substituted or unsubstituted, 3- to 6-membered heterocyclyl-$C_{1-6}$-alkyl, or substituted or unsubstituted, 3- to 6-membered carbocyclyl-$C_{1-6}$-alkyl.

8. The compound of claim 1, wherein $R^2$ is unsubstituted, 3- to 6-membered carbocyclyl-$C_{1-2}$-alkyl or substituted $C_{1-6}$ alkyl.

9. The compound of claim 1, wherein the compound is:

(a) selected from the group consisting of:

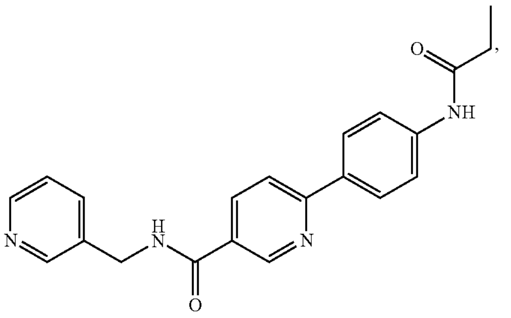

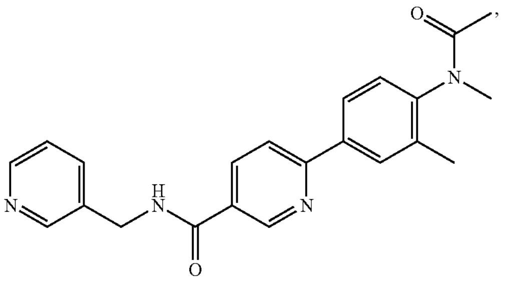

-continued

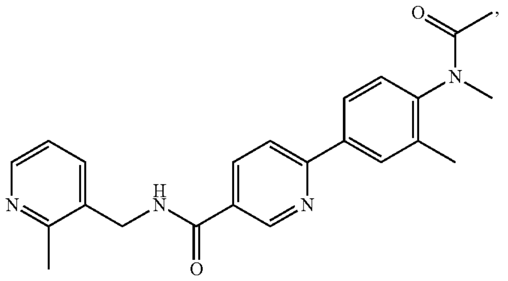

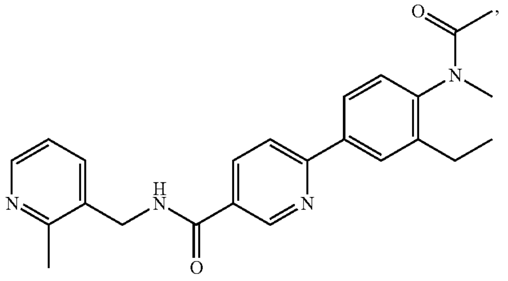

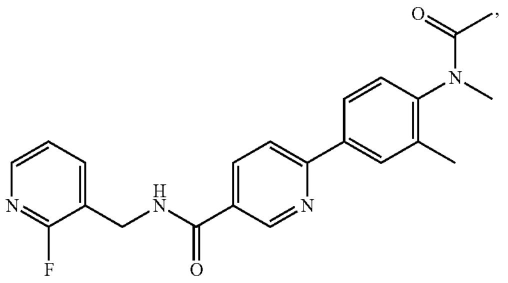

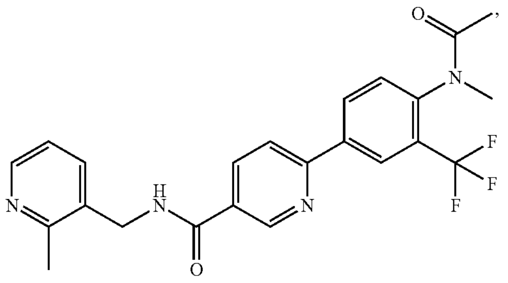

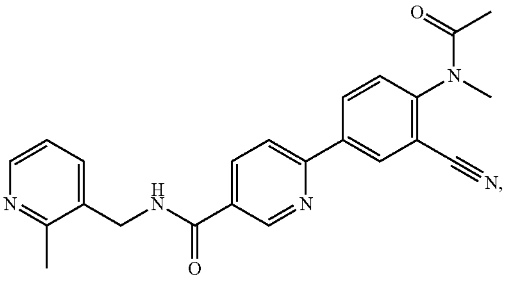

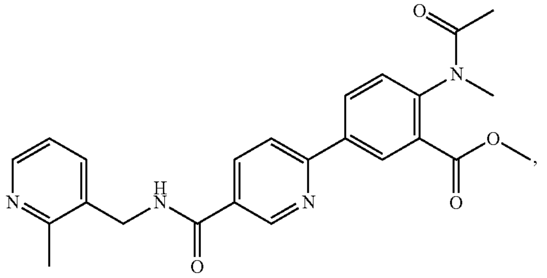

-continued
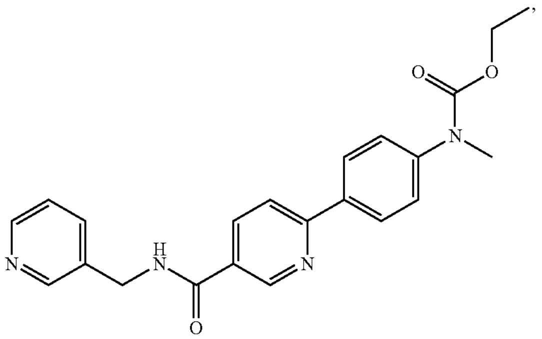
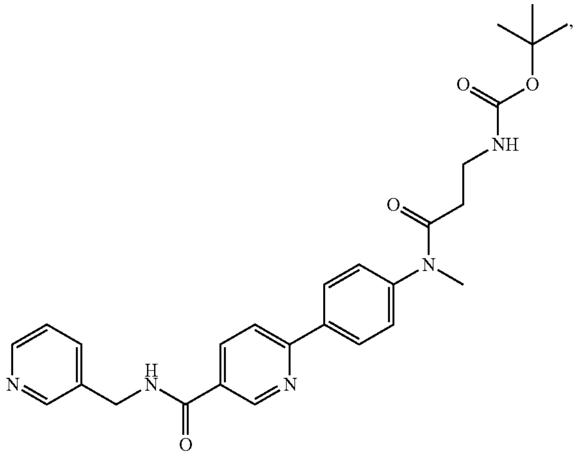
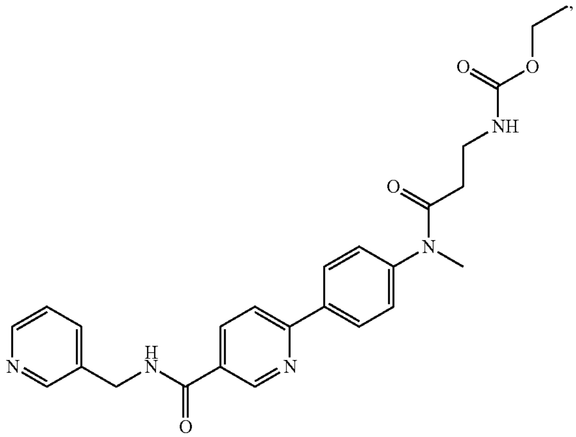
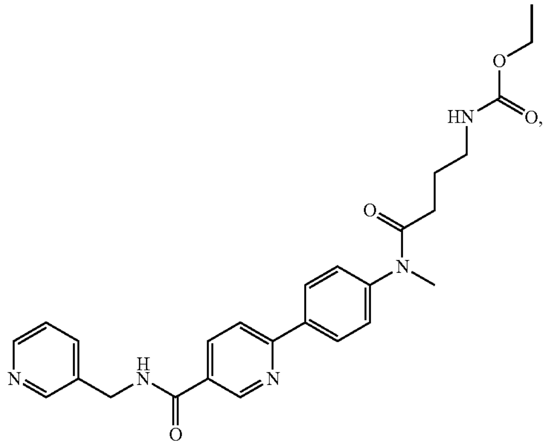
-continued
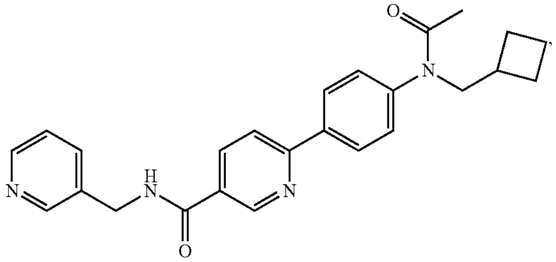
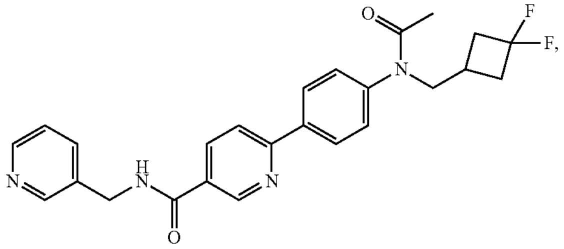
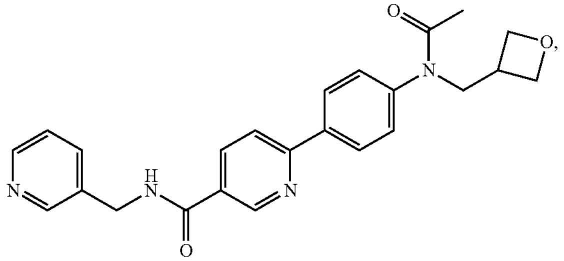
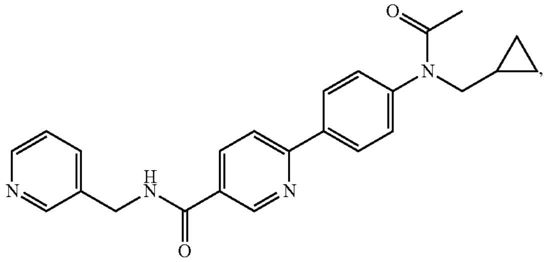
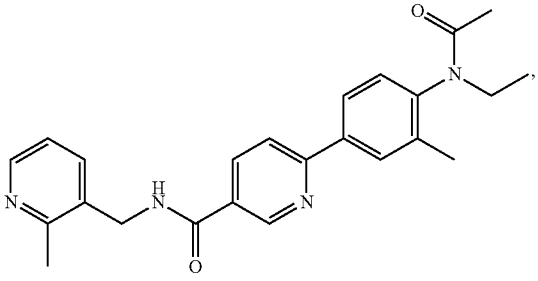
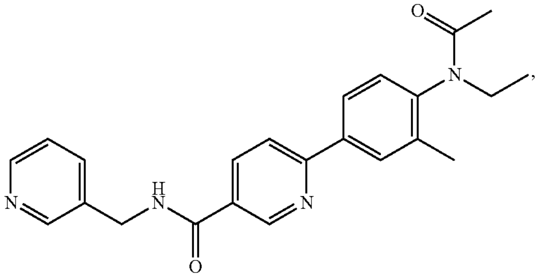

-continued
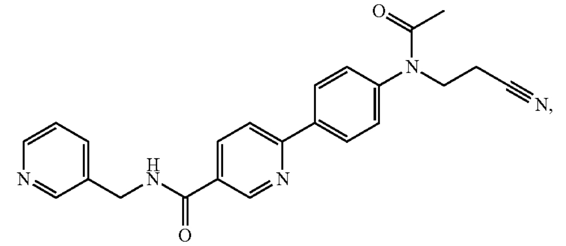
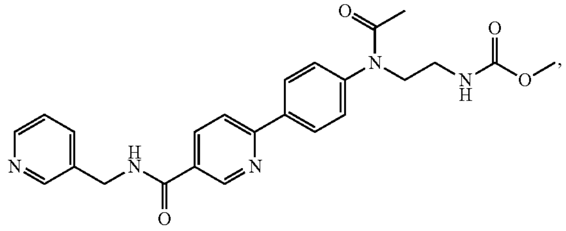
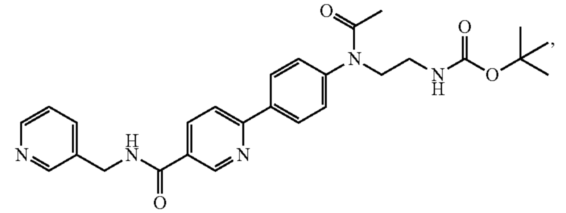
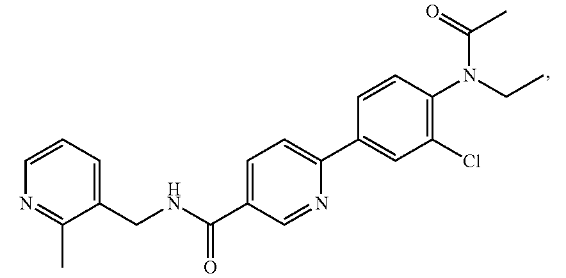
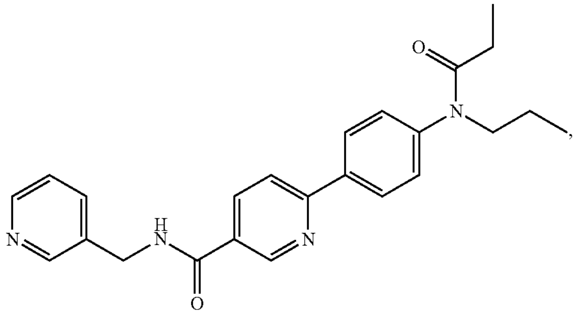
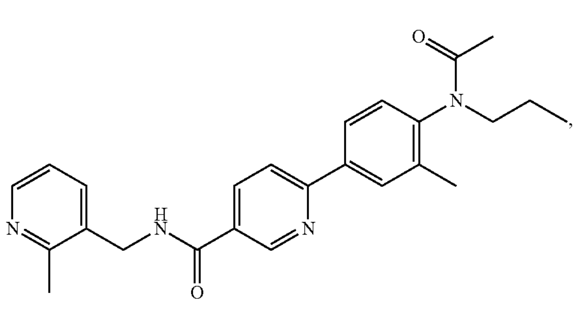
-continued
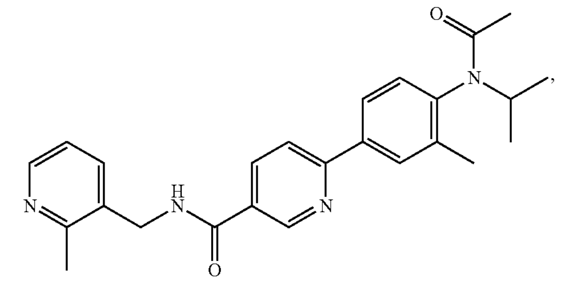
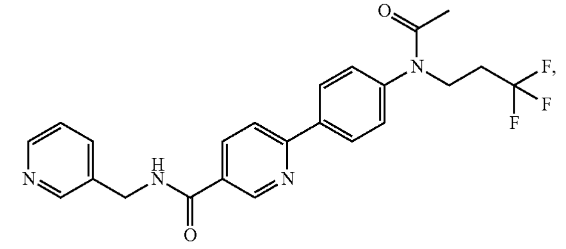
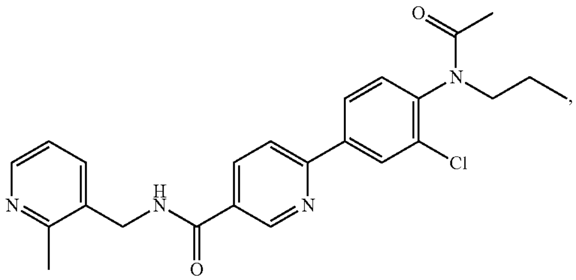
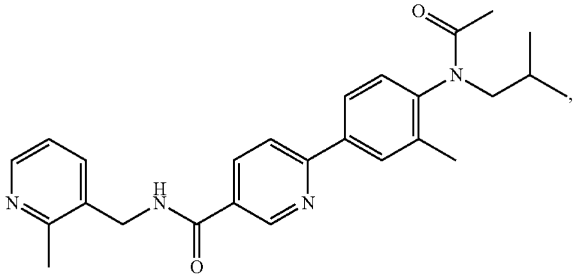
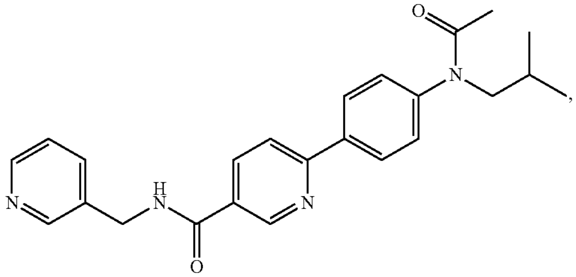
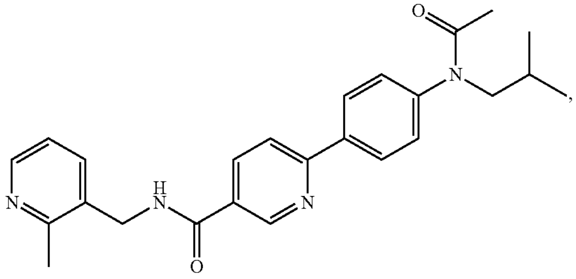

-continued
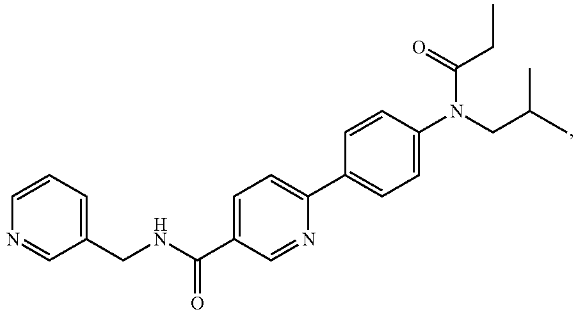
,
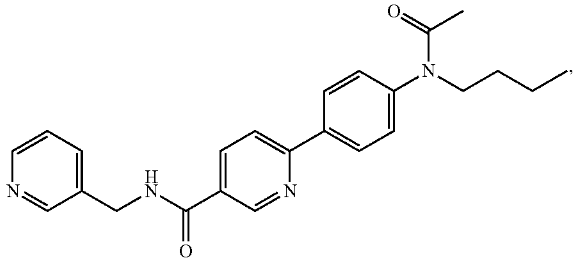
,
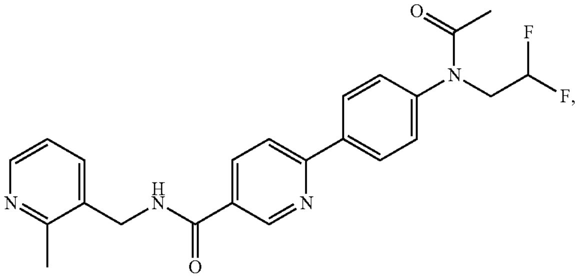
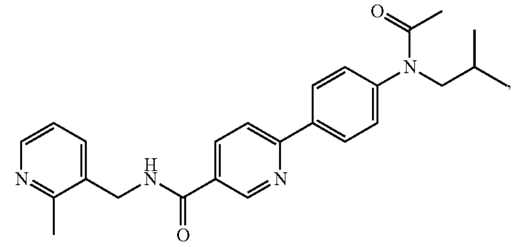
and
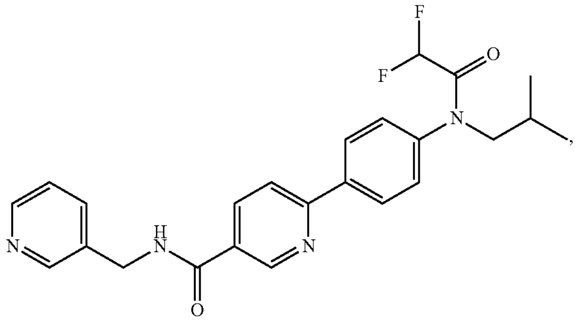
,
or a pharmaceutically acceptable salt, hydrate, polymorph, co-crystal, tautomer, stereoisomer, isotopically labeled derivative, or prodrug thereof;
(b) selected from the group consisting of:
I-466
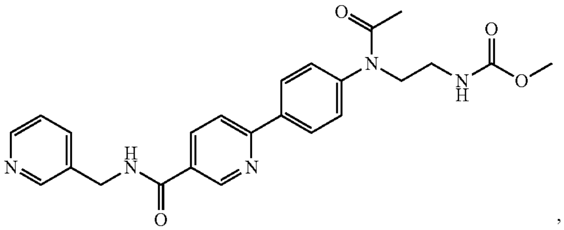
,
I-467
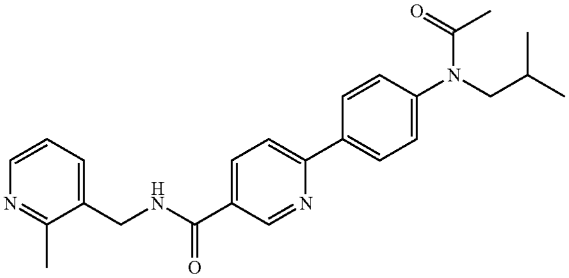
,
I-468
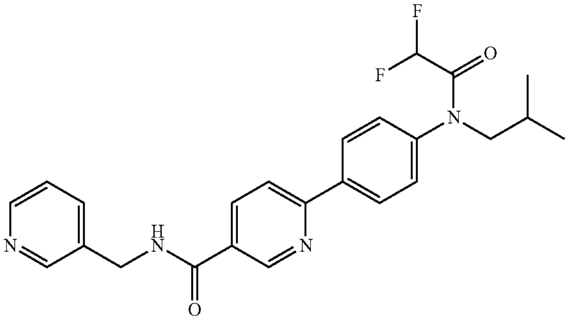
,
I-482
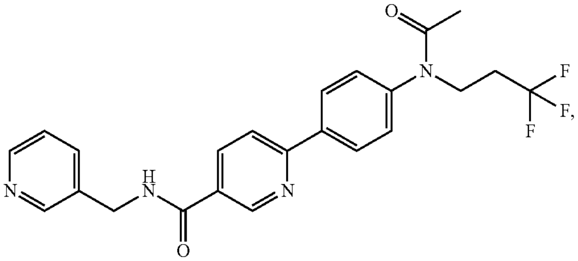
I-483
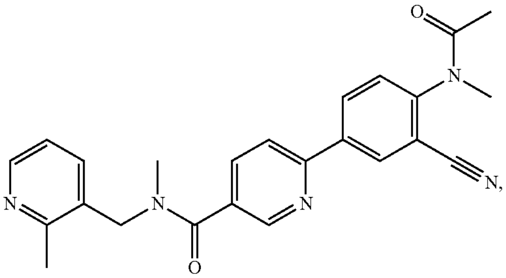

-continued
I-484
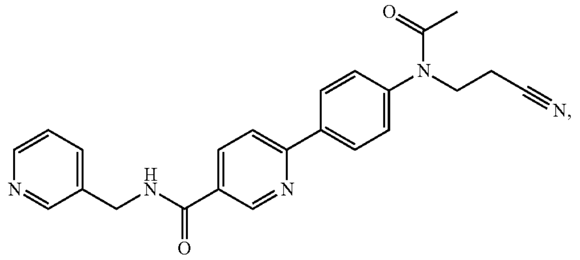
I-485
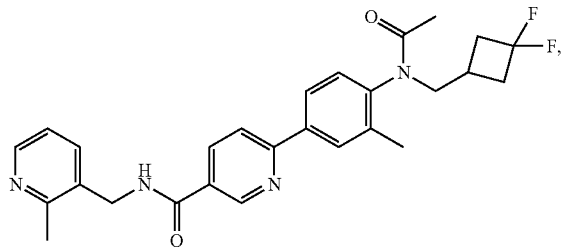
I-486
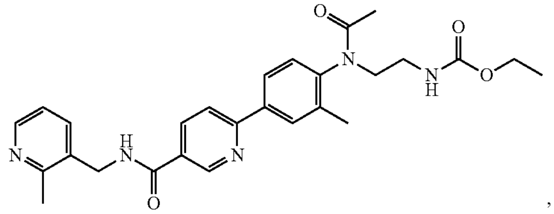
,
I-487
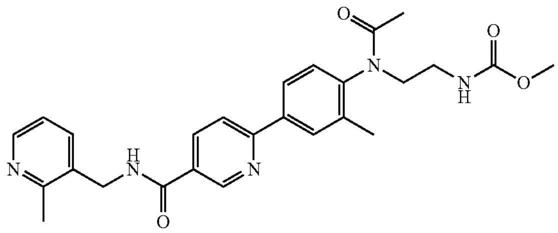
,
I-488
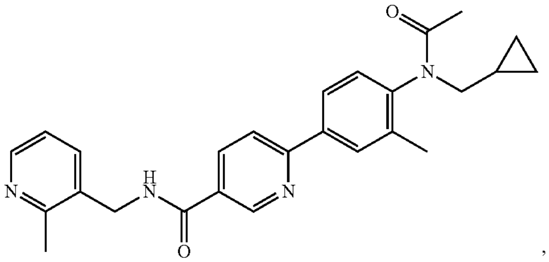
,
I-489
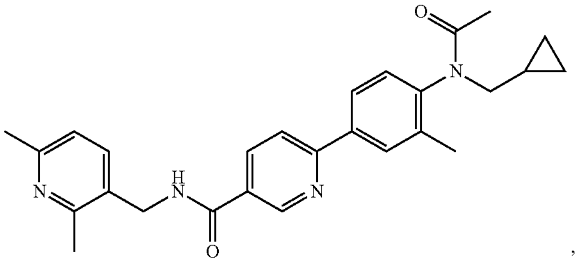
,
-continued
I-491
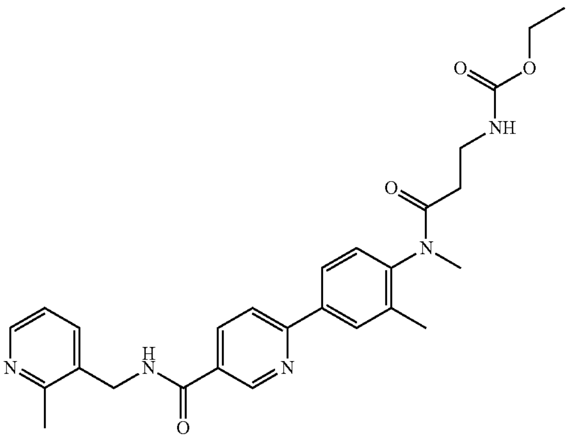
,
I-492
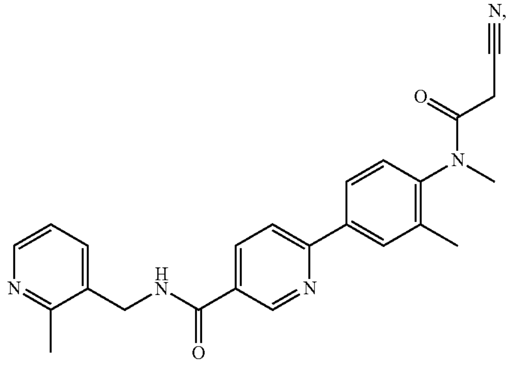
I-495
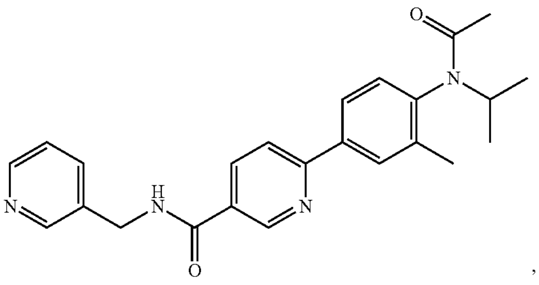
,
I-497
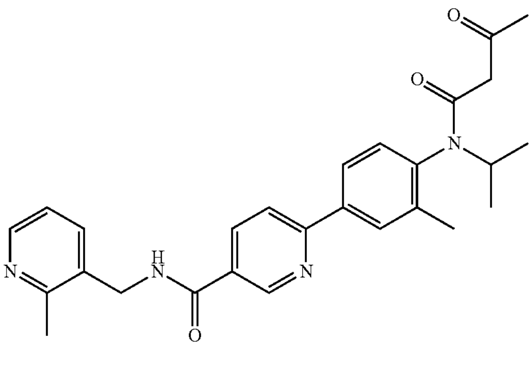
, -continued
I-499
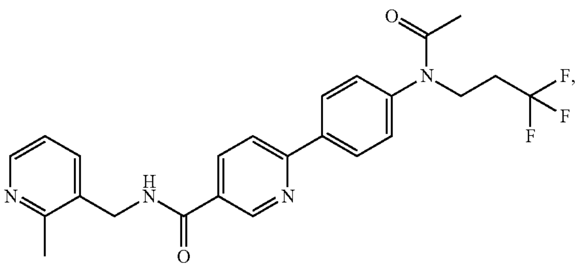
I-500
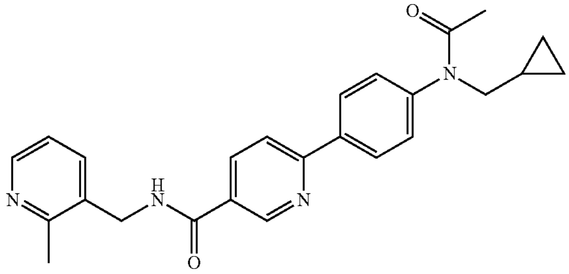
,
I-501
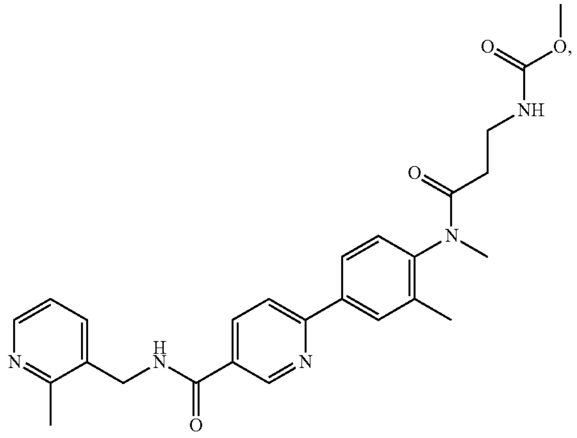
I-502
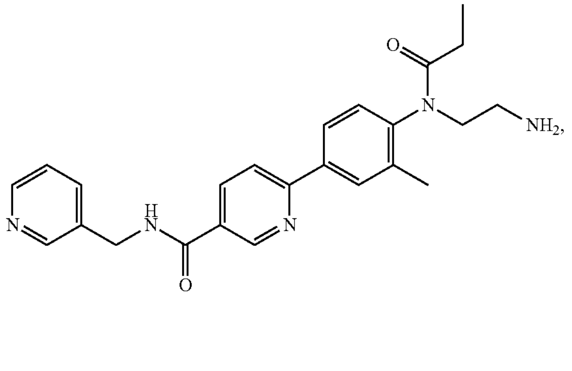
-continued
I-503
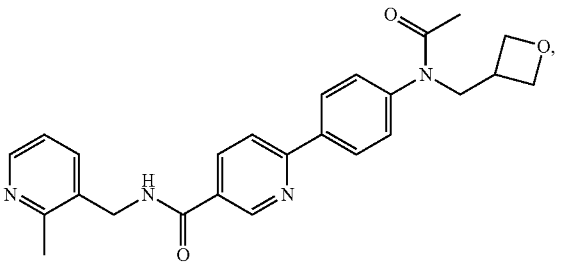
I-510
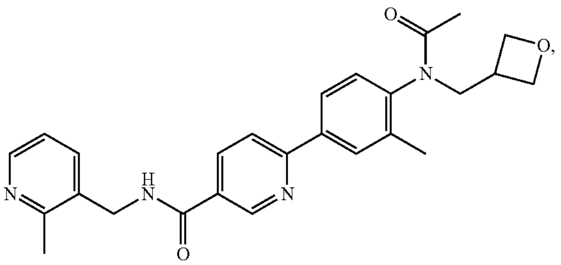
I-512
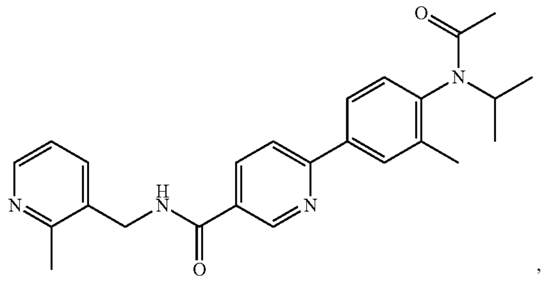
,
I-517
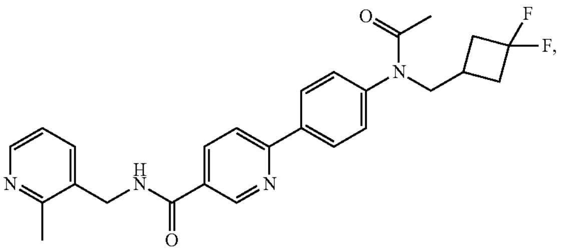
I-593
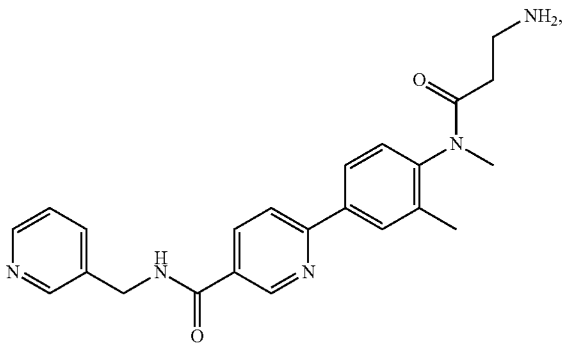

-continued
I-594
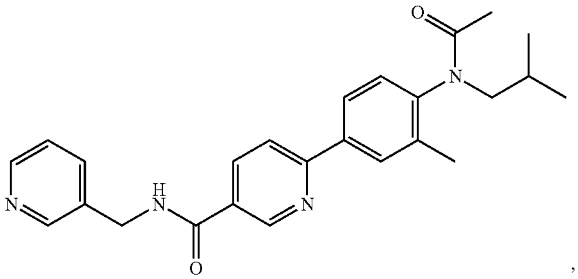
,
I-595
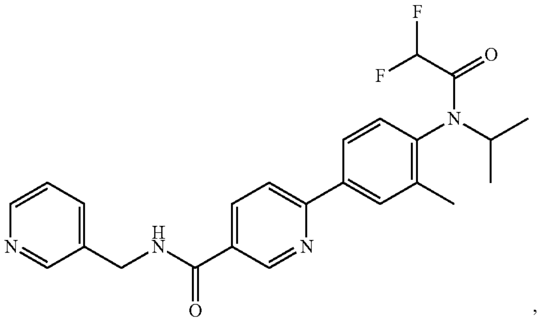
,
I-596
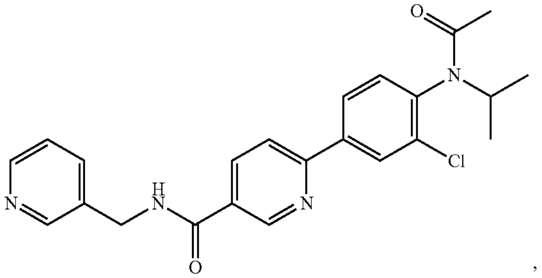
,
I-599
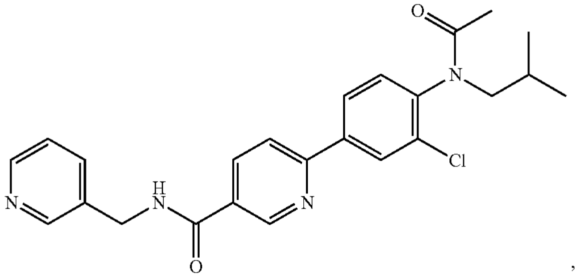
,
I-600
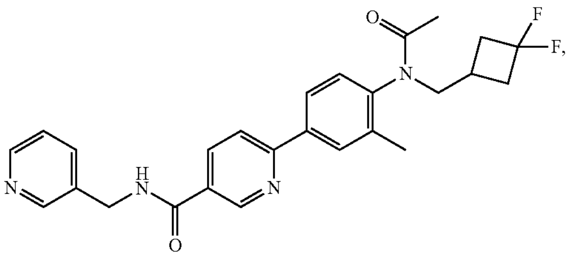
-continued
I-601
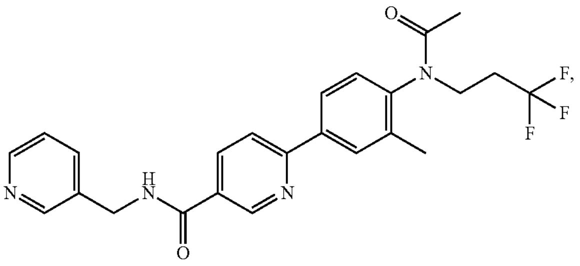
I-602
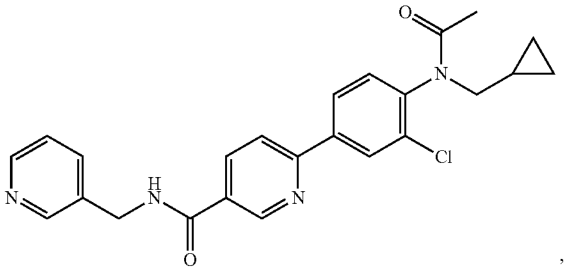
,
I-603
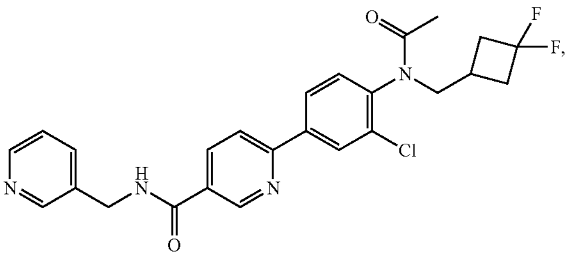
I-604
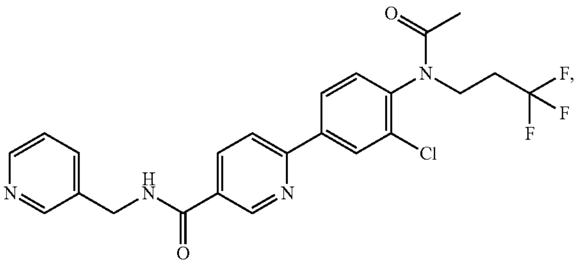
I-605
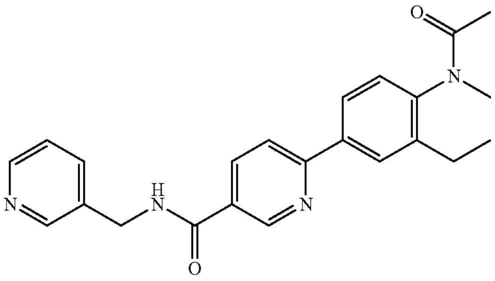
, -continued
I-606
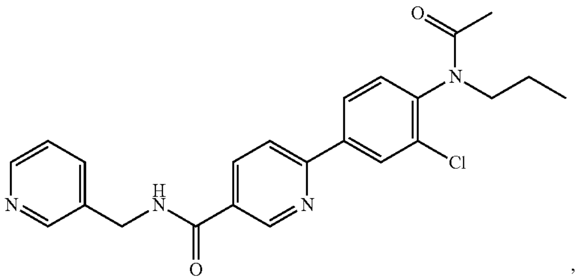
,
I-608
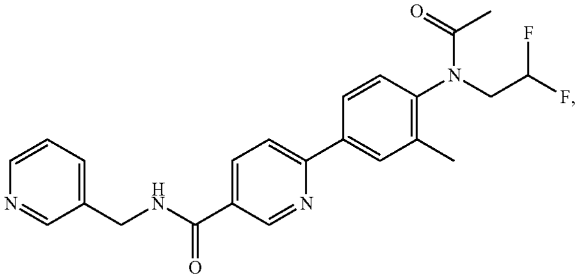
I-609
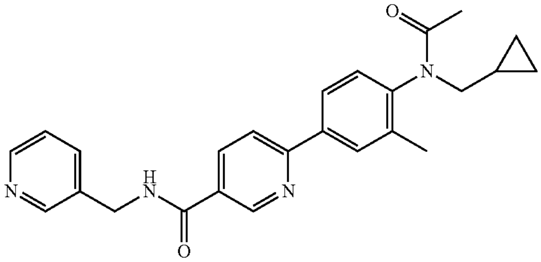
,
I-610
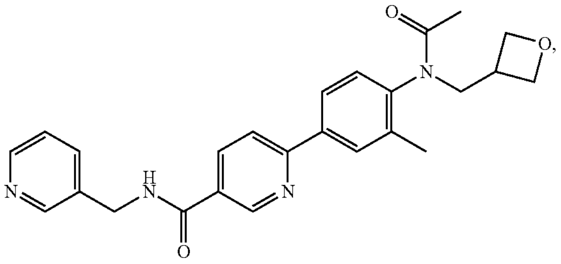
I-611
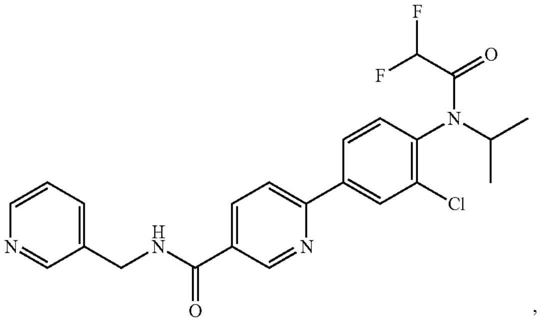
,
-continued
I-619
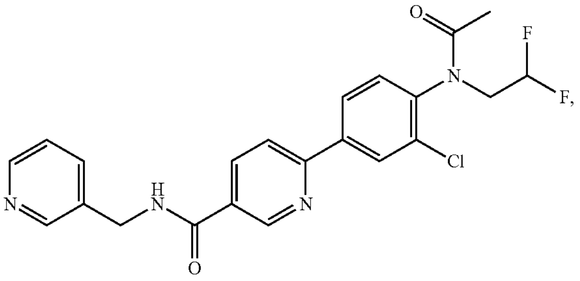
I-620
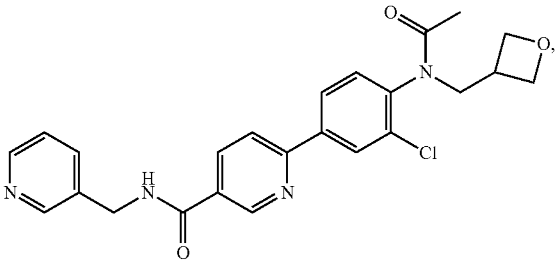
I-626
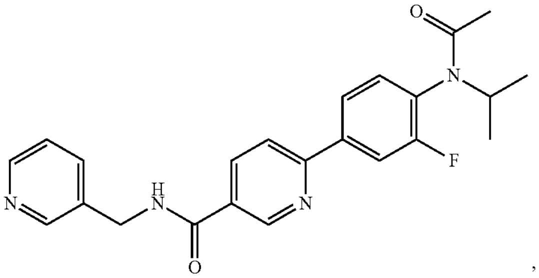
,
I-629
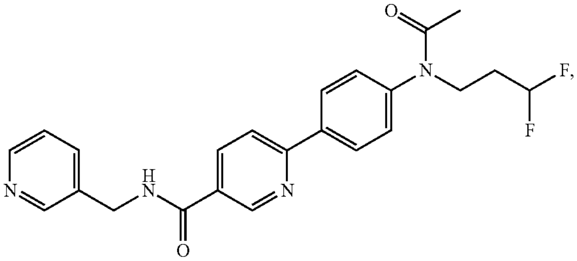
I-631
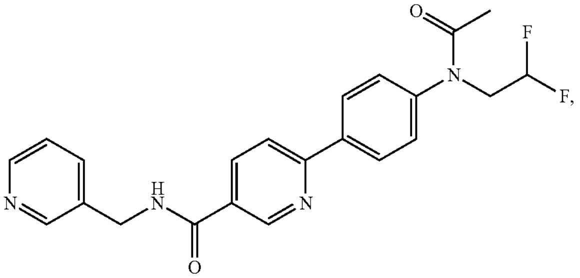

-continued
I-639
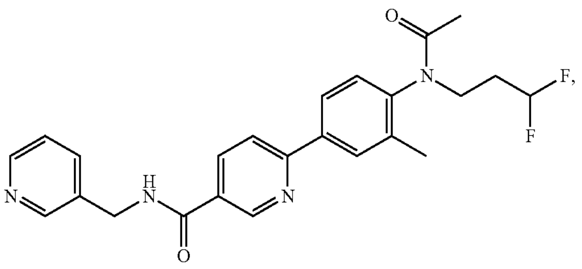
I-652
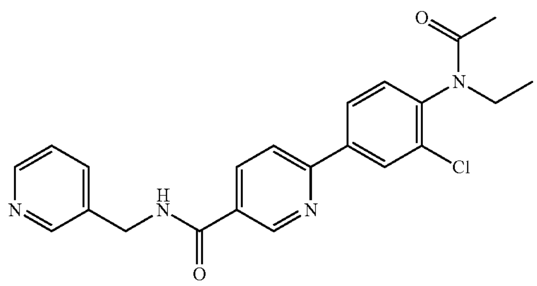
,
I-658
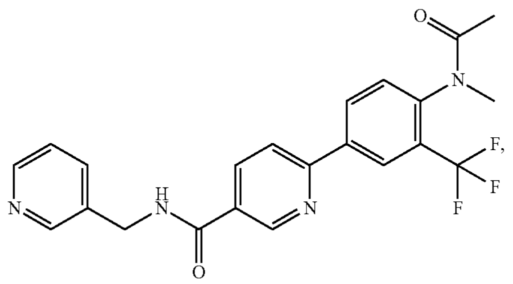
I-662
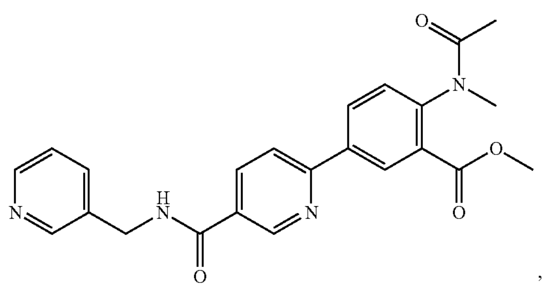
,
I-663
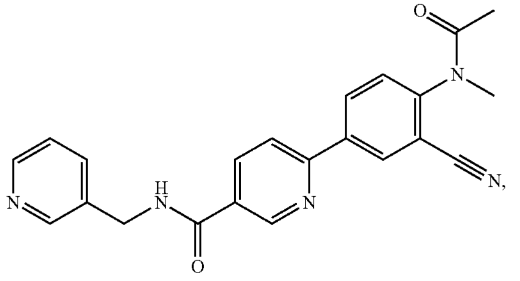
-continued
I-677
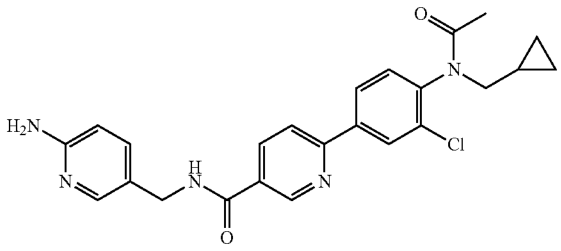
,
I-685
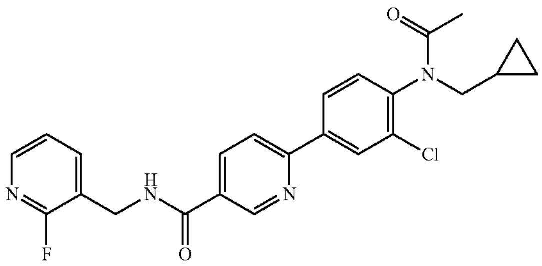
,
I-689
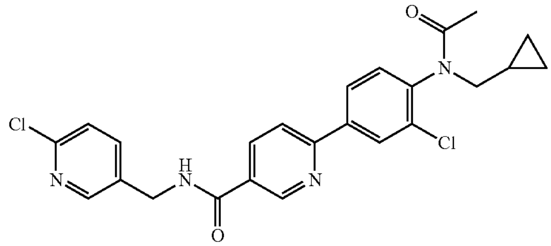
,
I-690
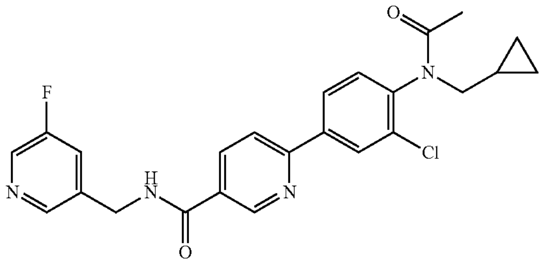
,
I-T2106
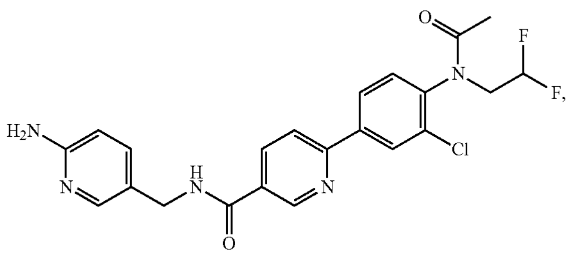

-continued
I-T2107
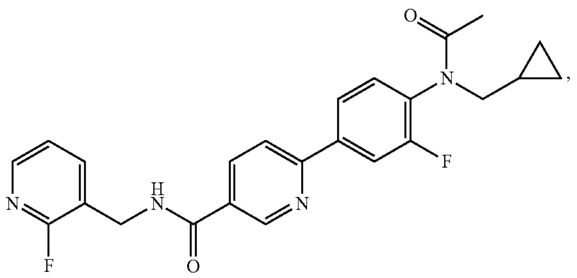
I-T2120
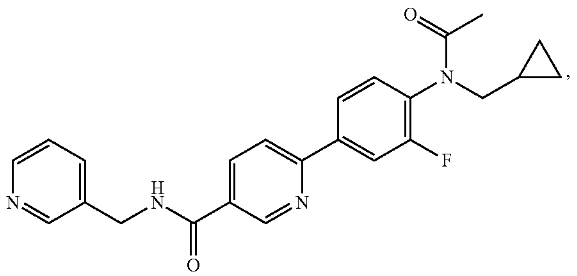
I-696
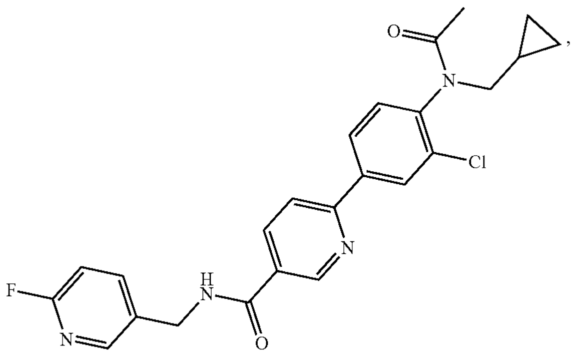
I-T2162
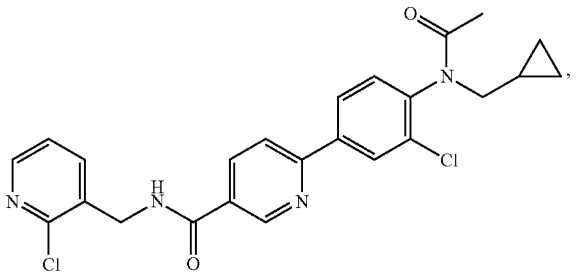
I-T2163
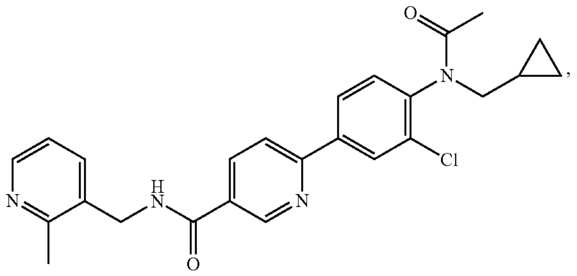
-continued
I-697
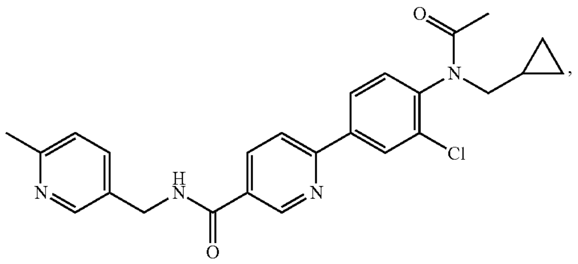
I-T2165
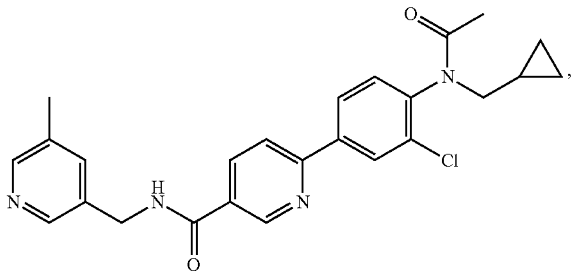
I-T2166
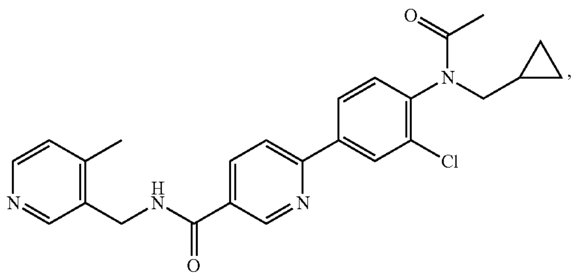
I-T2167
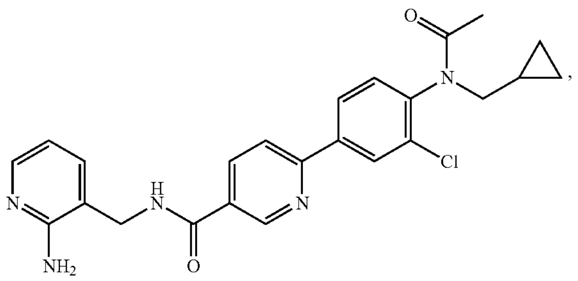
I-T2168
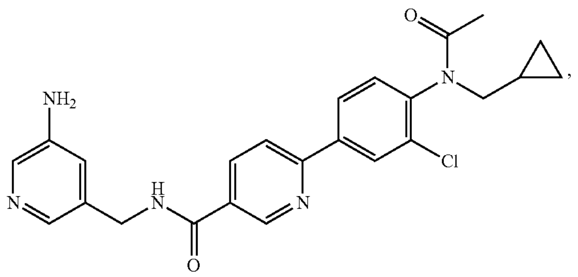

-continued
I-T2169
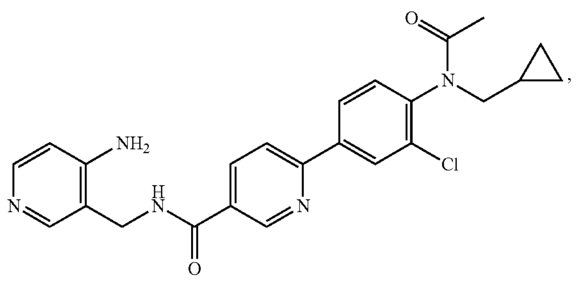
I-T2170
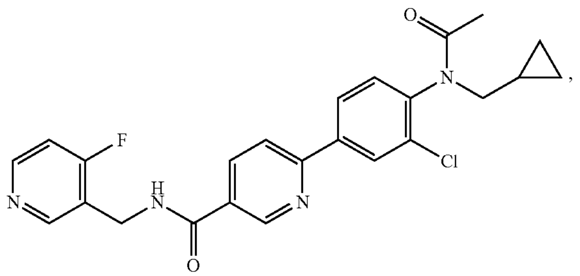
I-T2171
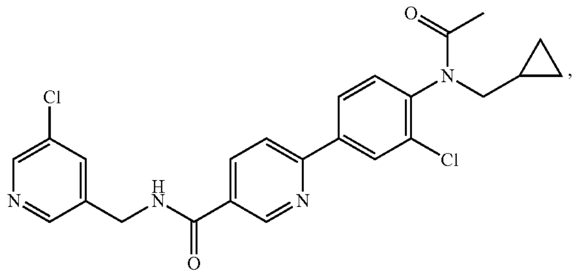
I-T2172
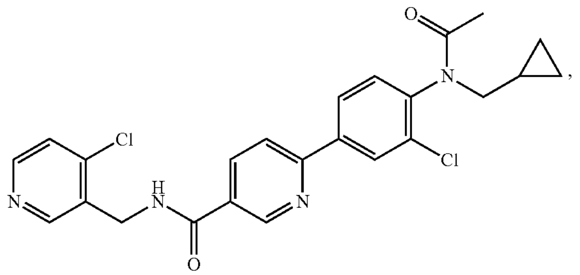
I-T2174
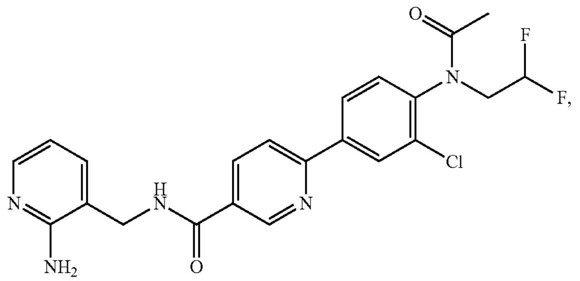
-continued
I-T2175
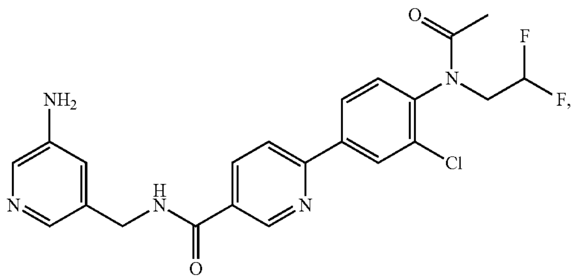
I-T2176
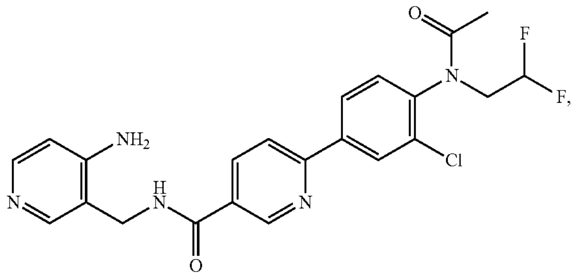
I-T2177
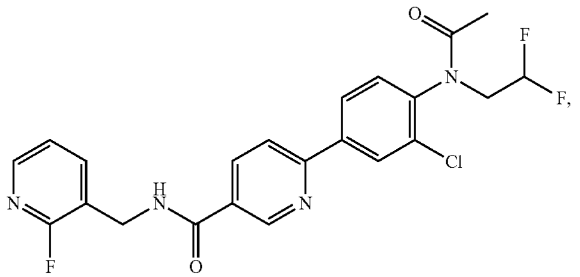
I-T2178
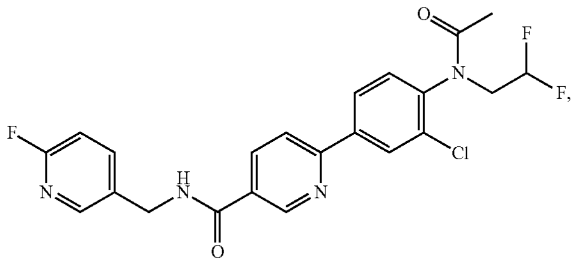
I-T2179
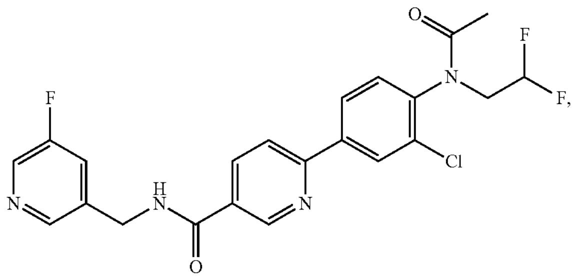

-continued
I-T2180
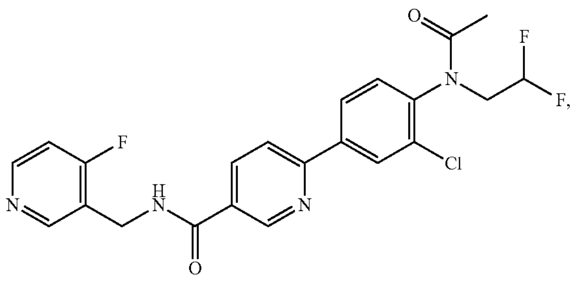
I-T2181
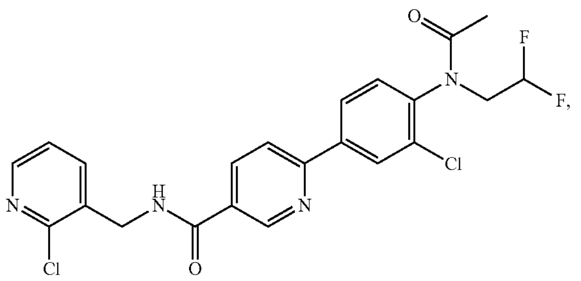
I-T2182
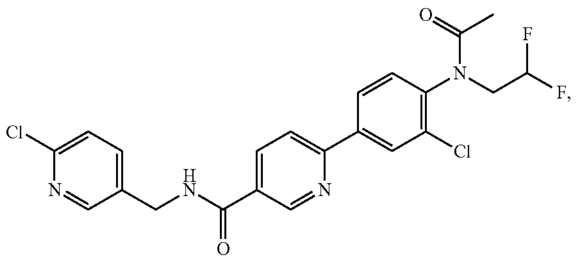
I-T2183
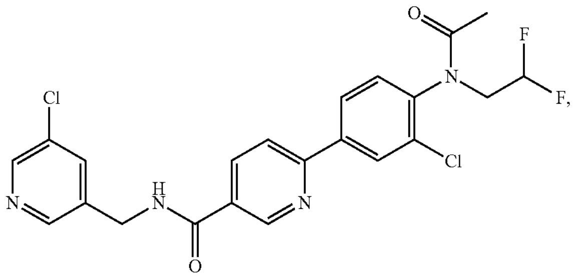
I-T2184
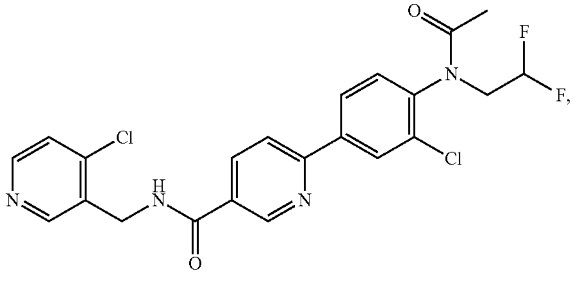
-continued
I-T2185
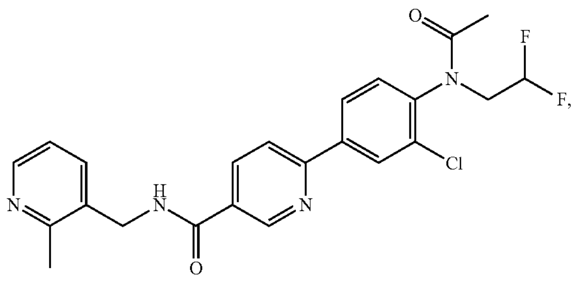
I-T2186
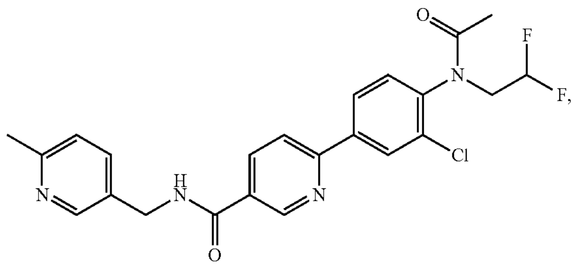
I-T2187
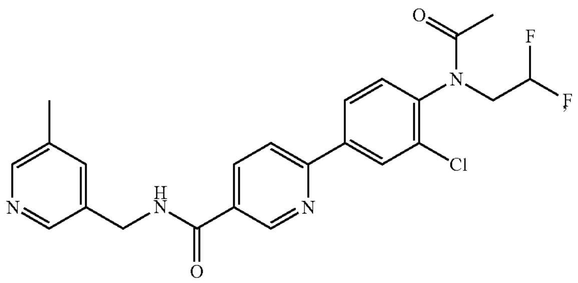
I-T2188
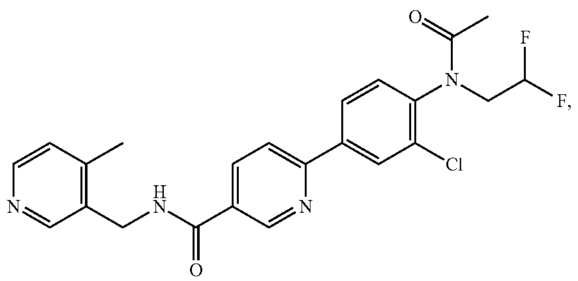
I-T2206
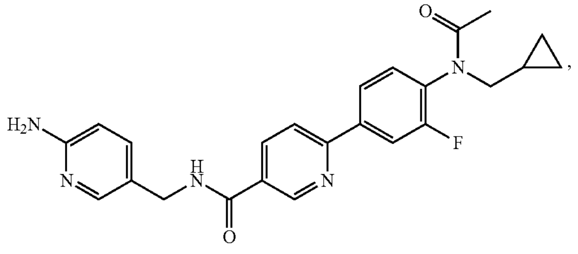

-continued
I-T2211
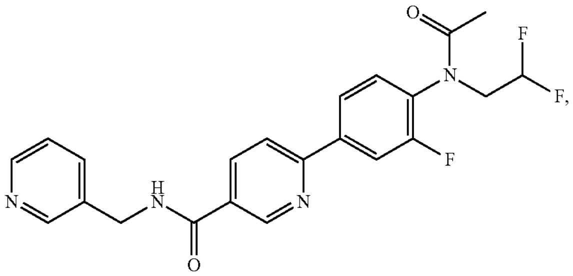
I-T2212
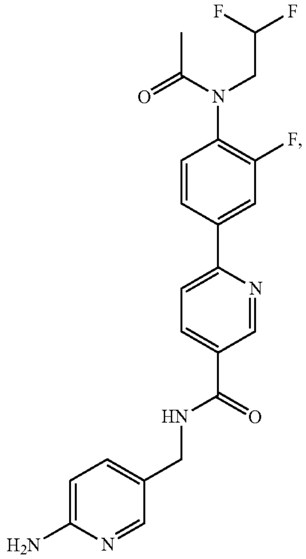
I-T2213
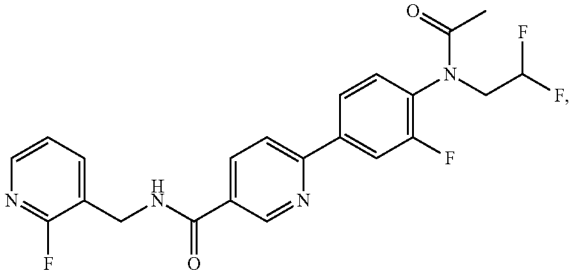
I-T2217
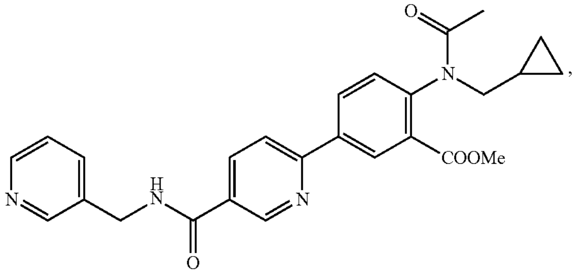
-continued
I-T2218
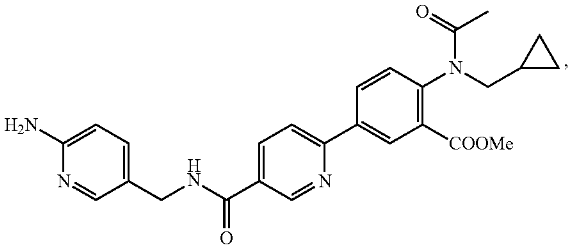
I-T2219
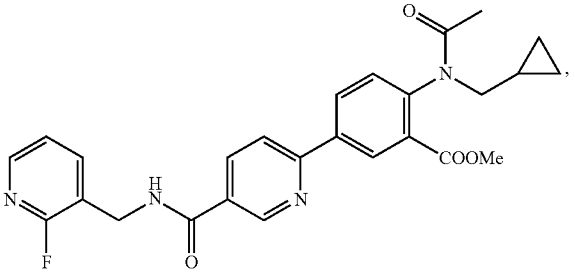
I-T2223
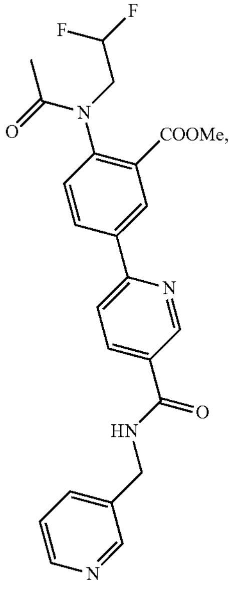
I-T2224
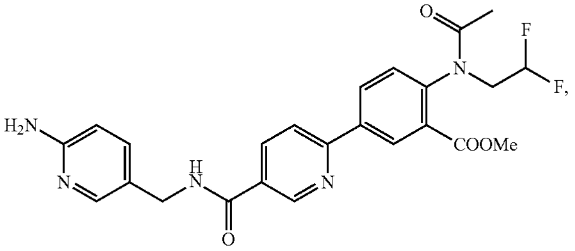

-continued
I-T2225
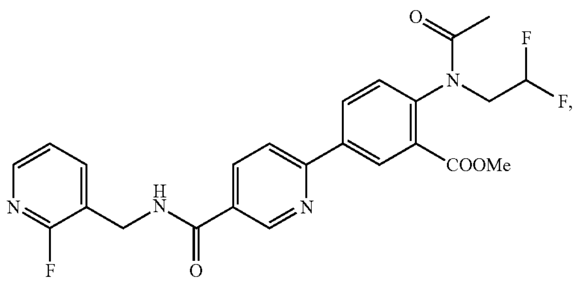
I-T2241
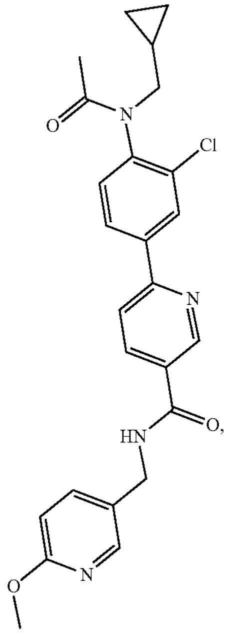
I-T2242
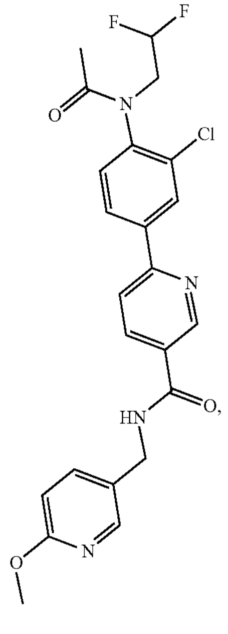
-continued
I-T2243
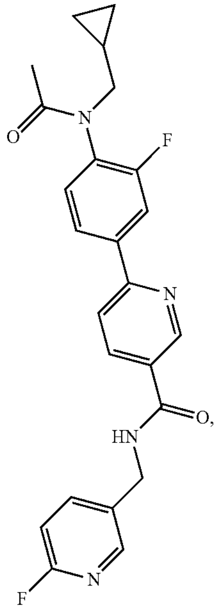
I-T2244
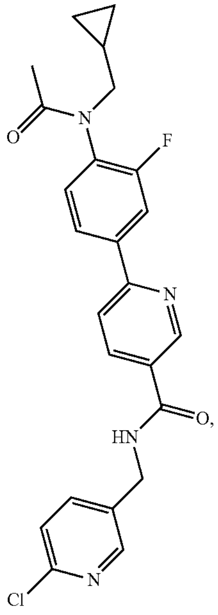

-continued
I-T2245
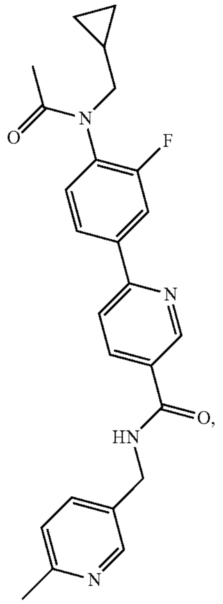
I-T2246
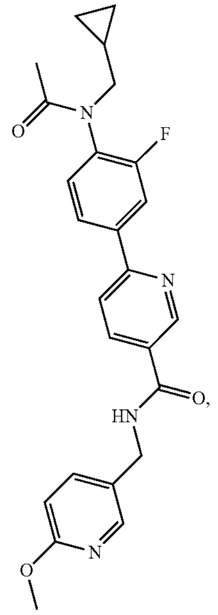
-continued
I-T2247
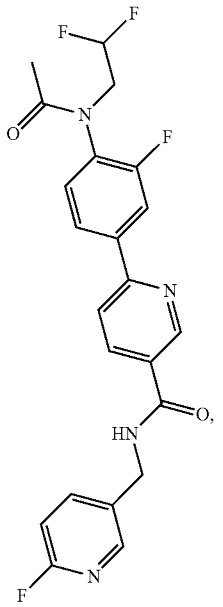
I-T2248
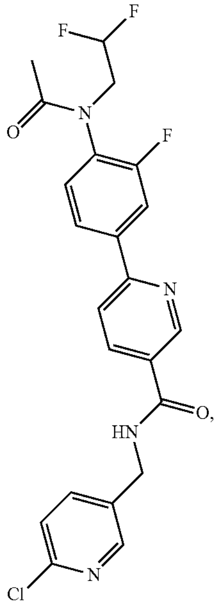

-continued
I-T2249
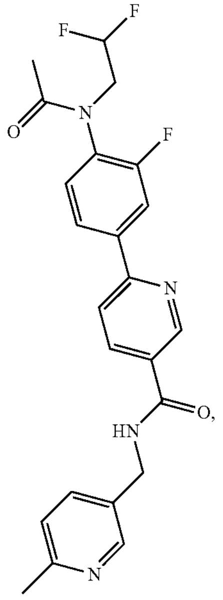
I-T2250
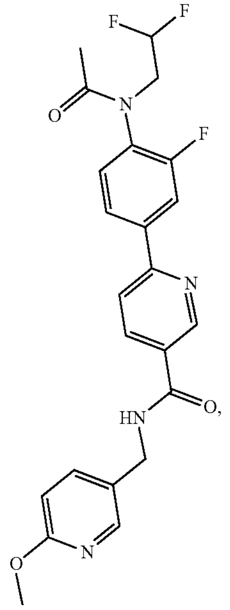
-continued
I-T2251
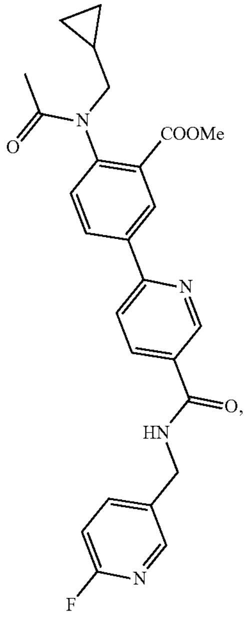
I-T2252
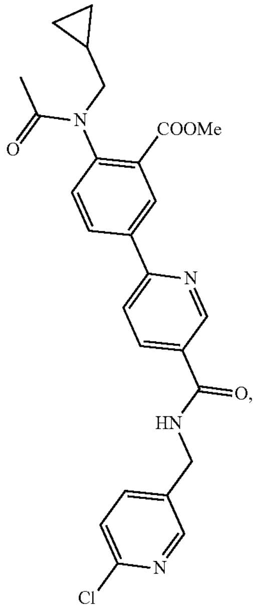

-continued
I-T2253
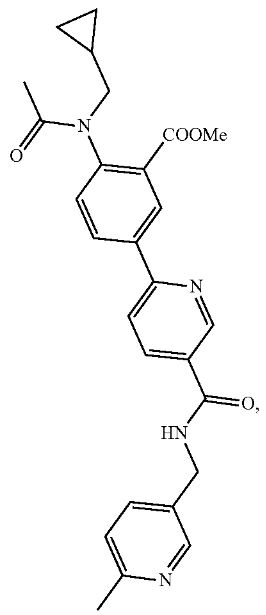
I-T2254
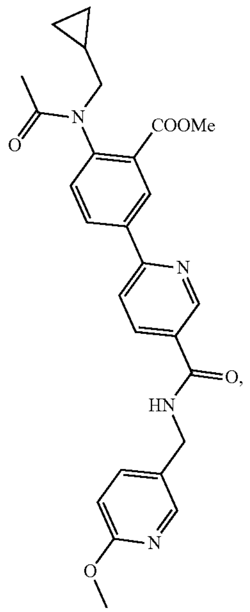
-continued
I-T2255
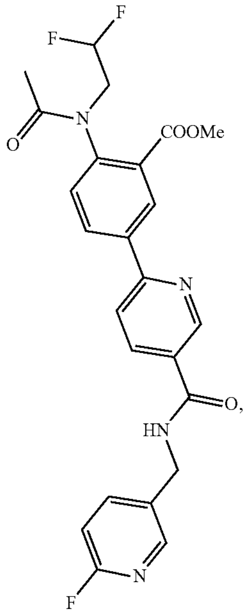
I-T2256
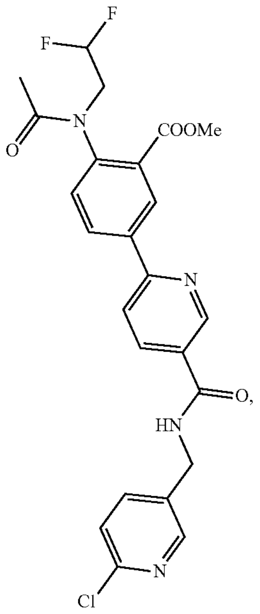

-continued
I-T2257
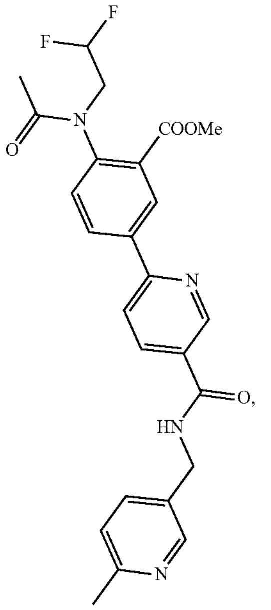
and
I-T2258
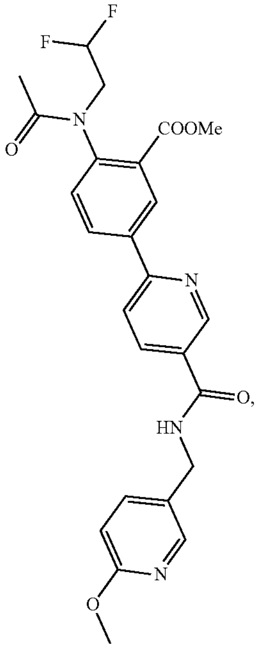
or a pharmaceutically acceptable salt, hydrate, polymorph, co-crystal, tautomer, stereoisomer, isotopically labeled derivative, or prodrug thereof;
(c) selected from the group consisting of:
I-647
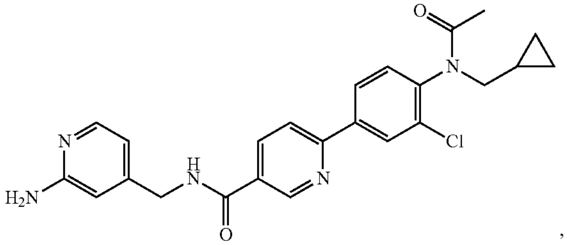
,
I-676
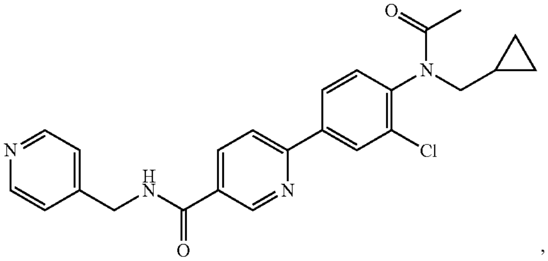
,
I-679
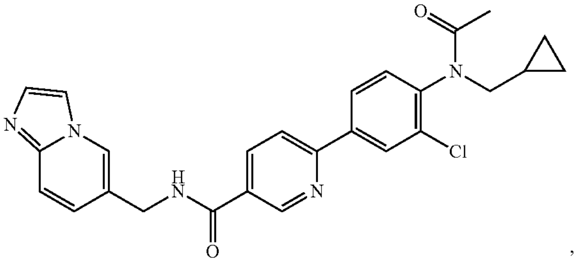
,
I-681
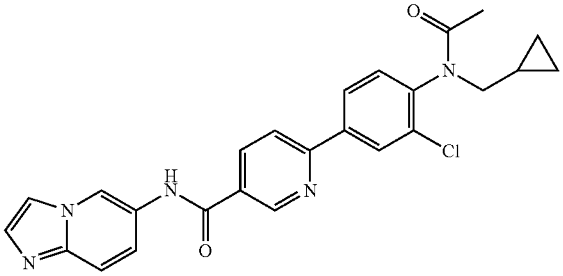
,
I-683
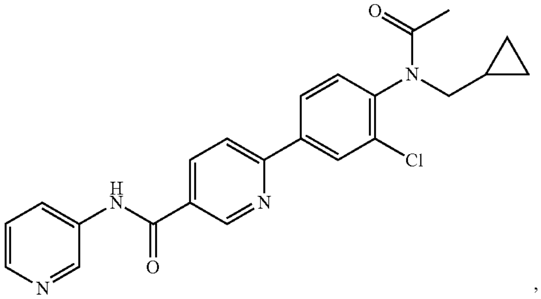
, -continued
I-684
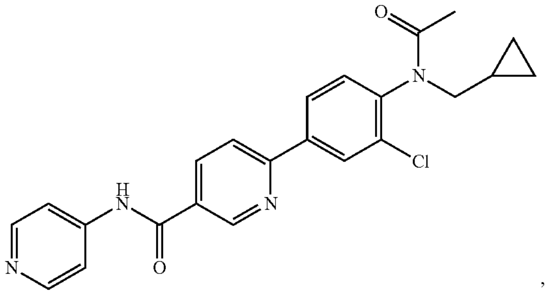
,
I-687
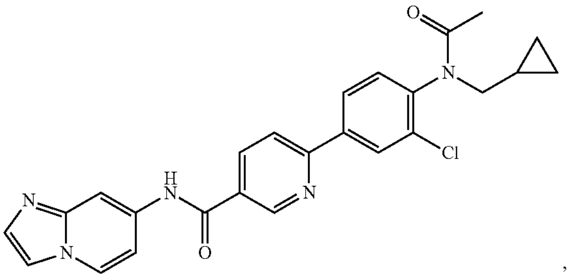
,
I-T2101
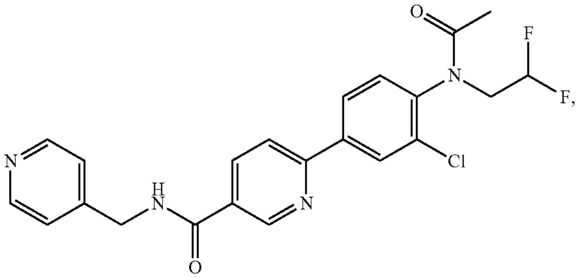
I-T2102
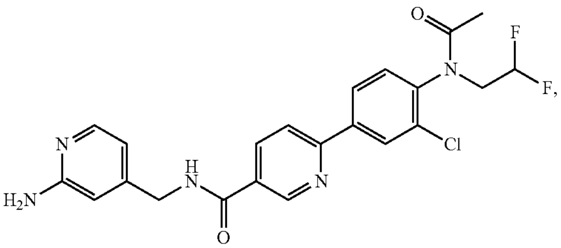
I-T2109
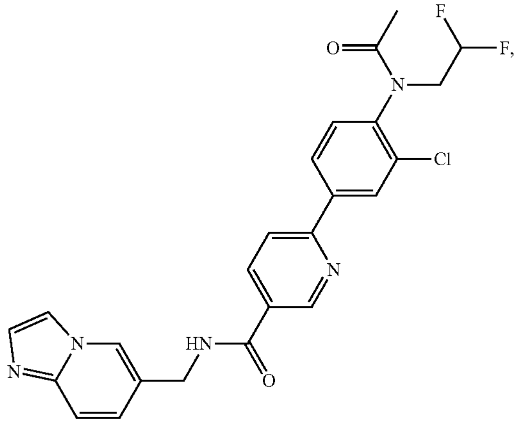
-continued
I-T2135
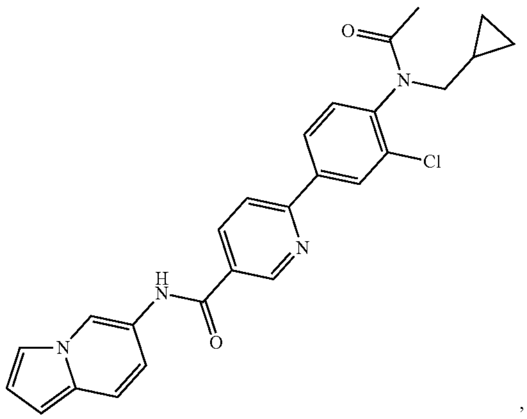
,
I-T2136
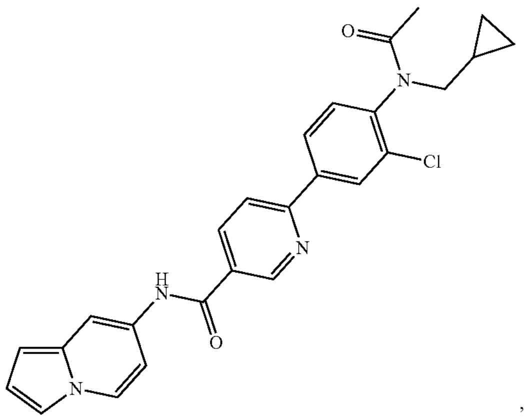
,
I-693
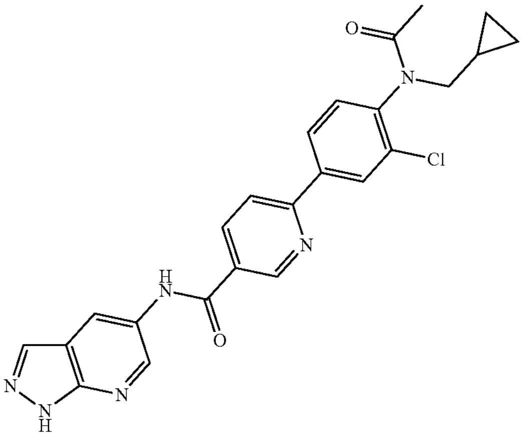
, -continued
I-T2157
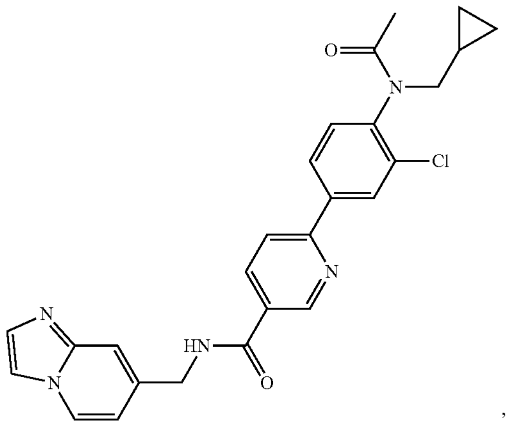
,
I-T2158
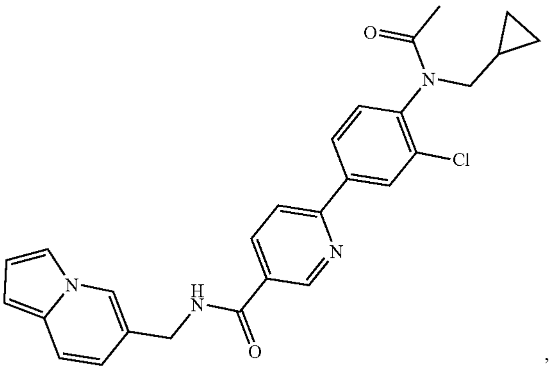
,
I-T2159
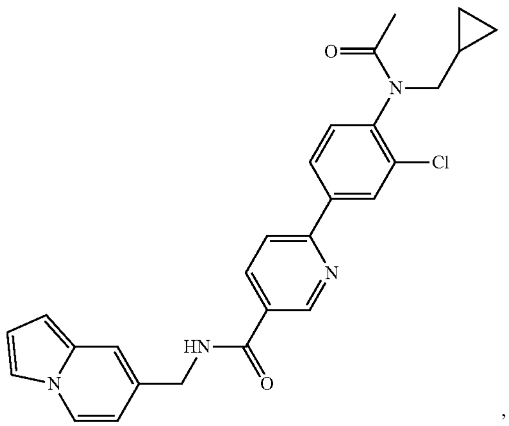
,
-continued
I-T2160
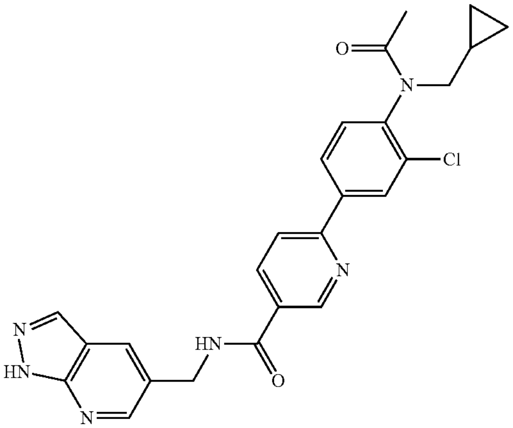
,
I-T2173
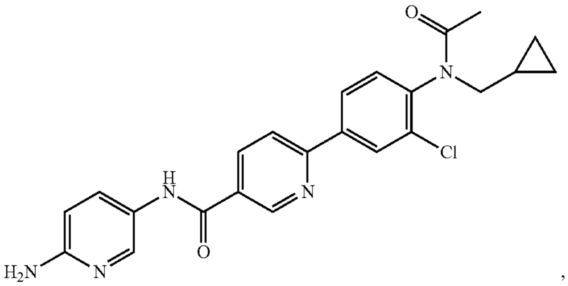
,
I-T2189
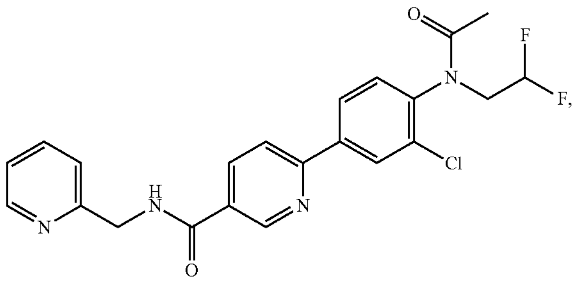
I-T2190
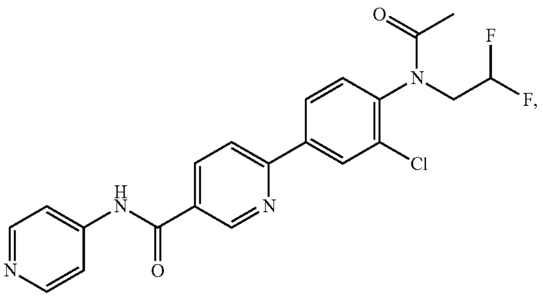

-continued
I-T2191
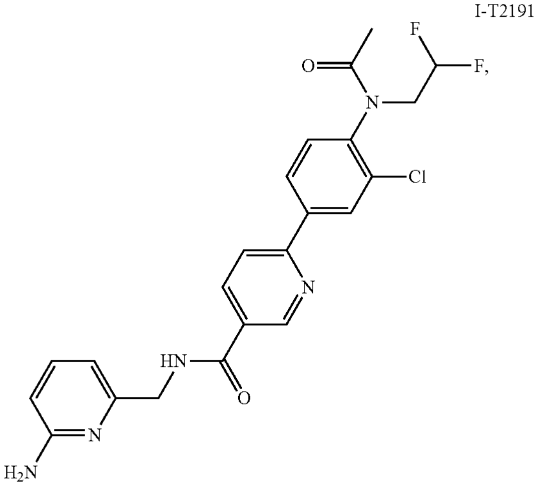
I-T2192
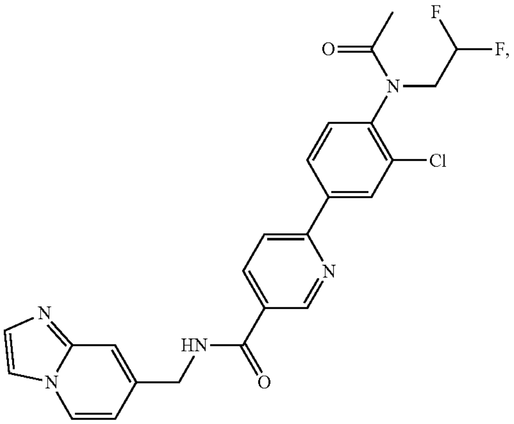
I-T2193
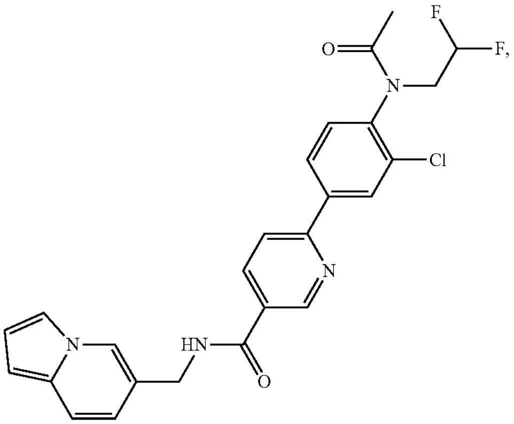
-continued
I-T2194
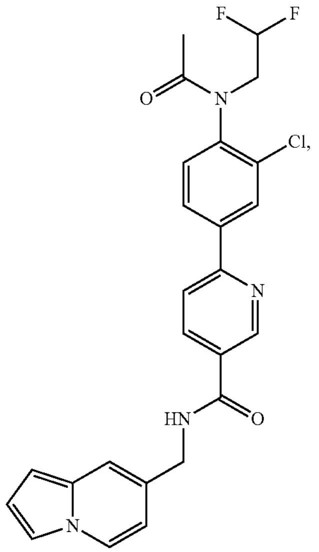
I-T2195
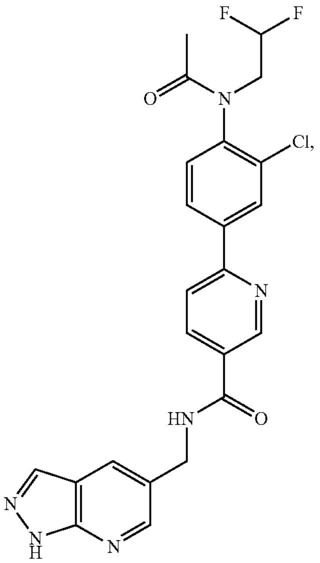

I-T2196
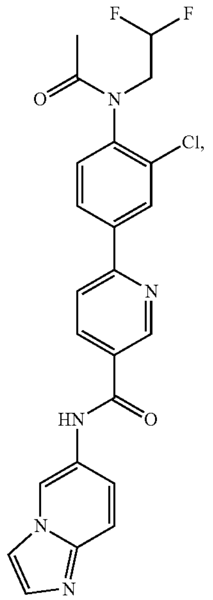
I-T2197
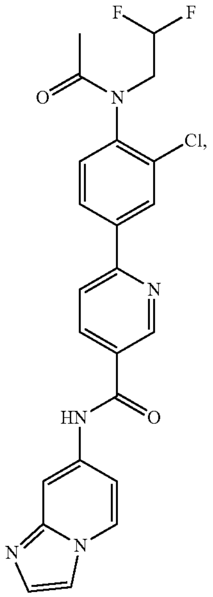
I-T2198
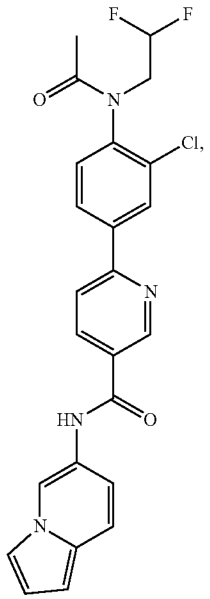
I-T2199
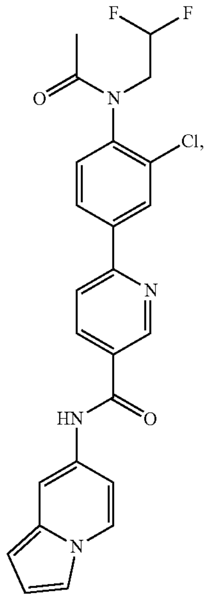

-continued
I-T2200
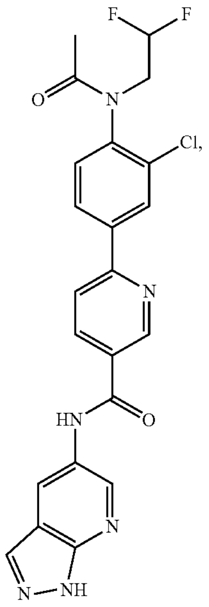
I-T2208
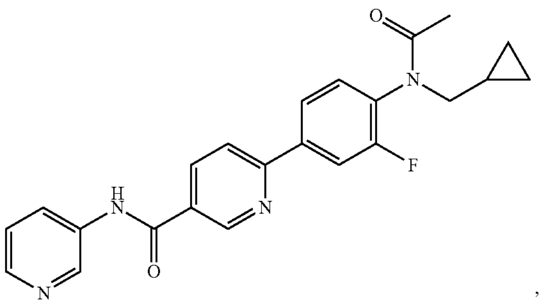
,
I-T2209
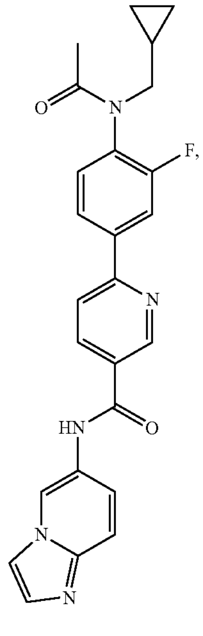
-continued
I-T2210
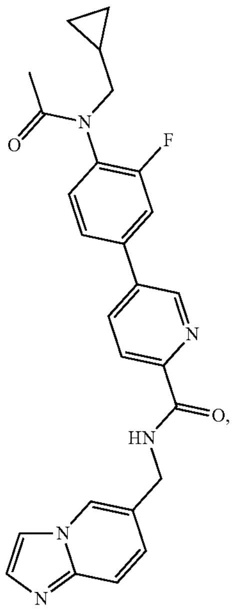
I-T2214
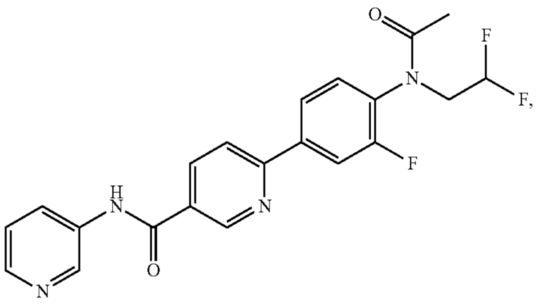
I-T2215
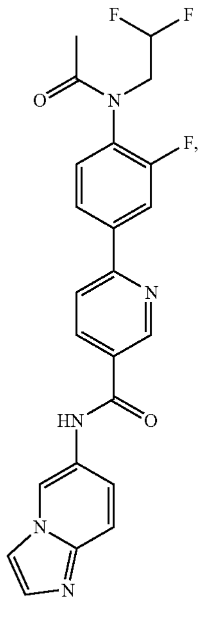

-continued
I-T2216
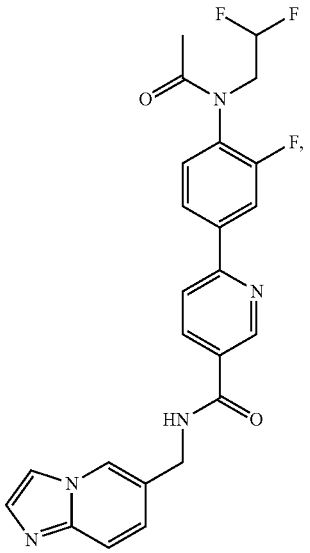
I-T2220
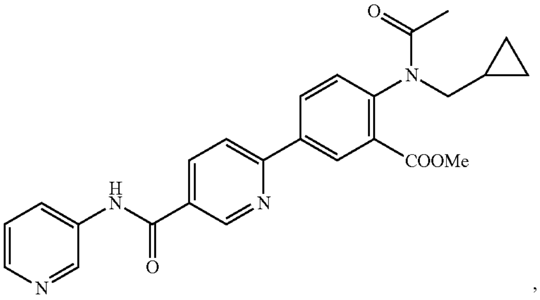
,
I-T2221
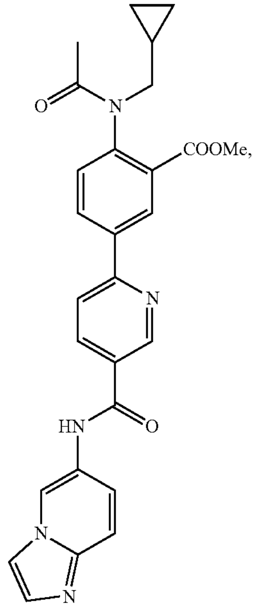
-continued
I-T2222
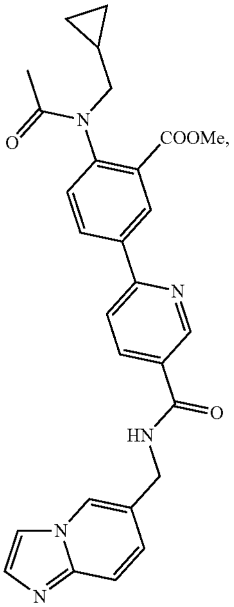
I-T2226
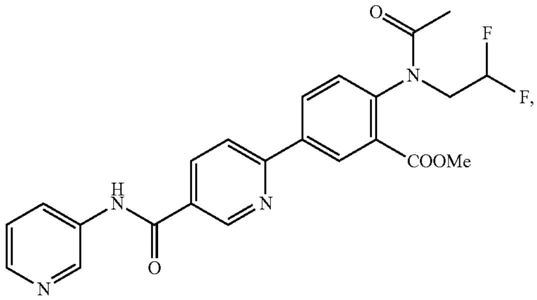
I-T2227
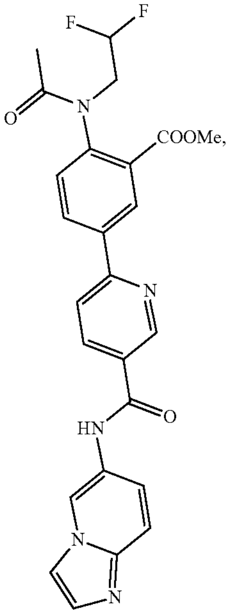

-continued
I-T2228
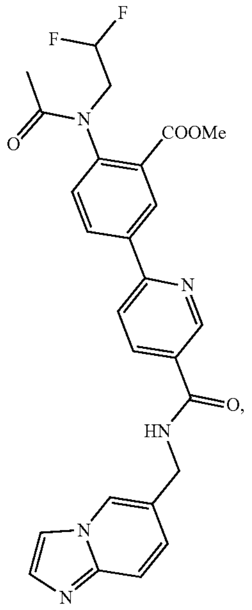
I-698
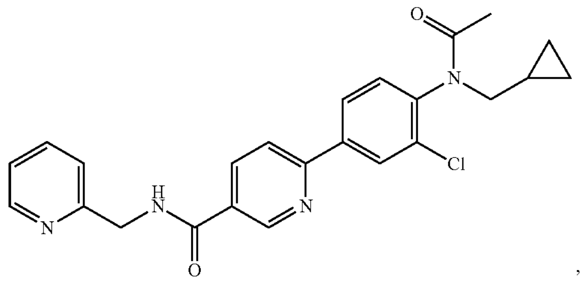
,
I-T2230
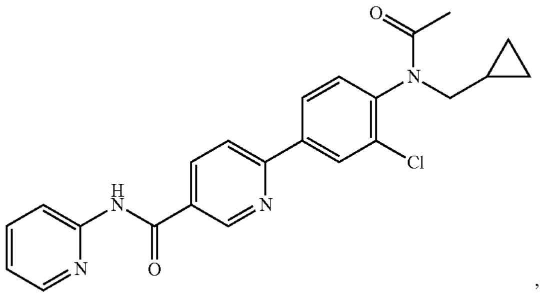
,
I-T2231
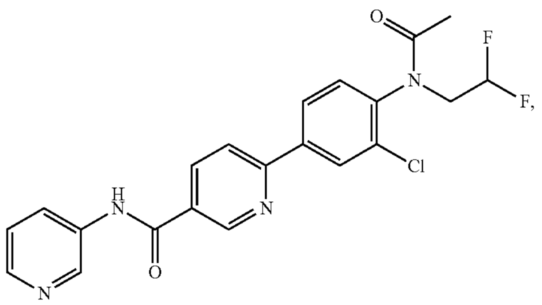
-continued
I-T2232
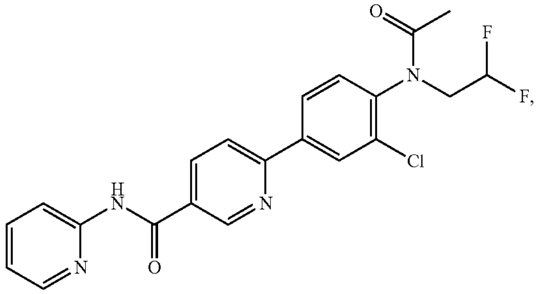
I-T2233
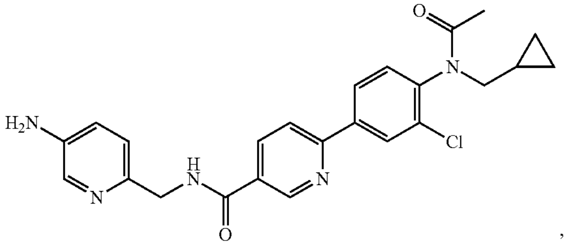
,
I-T2234
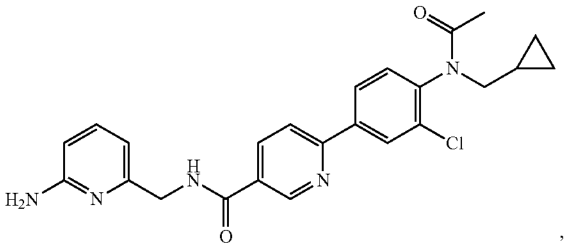
,
I-T2235
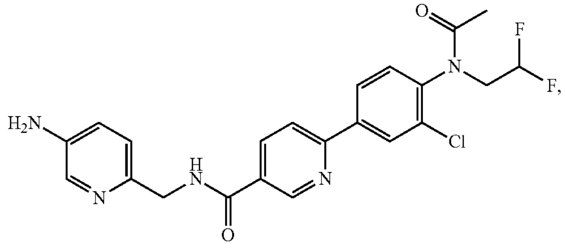
I-T2236
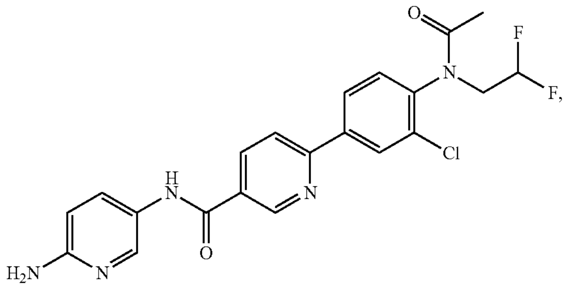

-continued
I-T2237
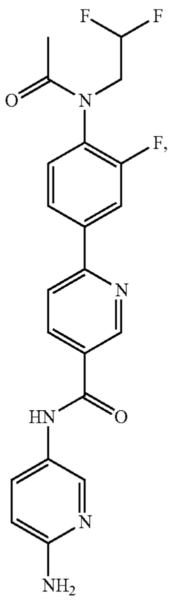
I-T2238
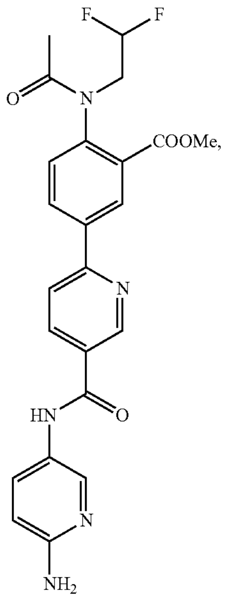
I-T2239
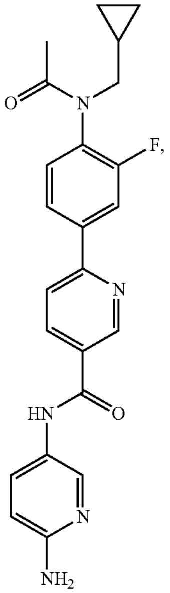
and
I-T2240
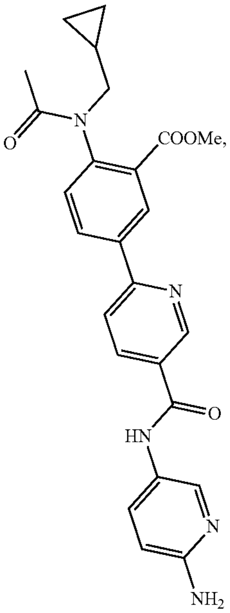
or a pharmaceutically acceptable salt, hydrate, polymorph, co-crystal, tautomer, stereoisomer, isotopically labeled derivative, or prodrug thereof; or (d) selected from the group consisting of:
I-403
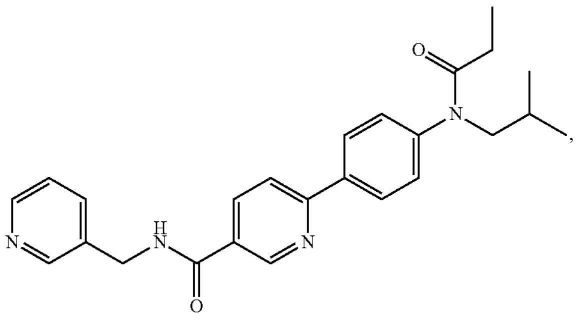
I-404
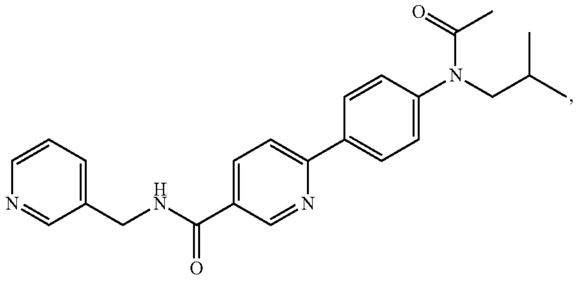
I-412
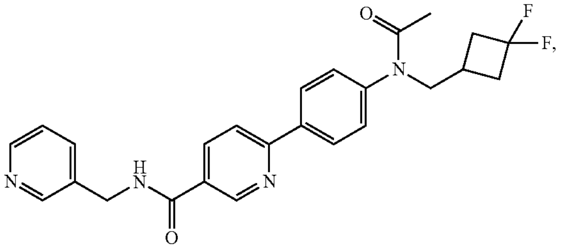
I-453
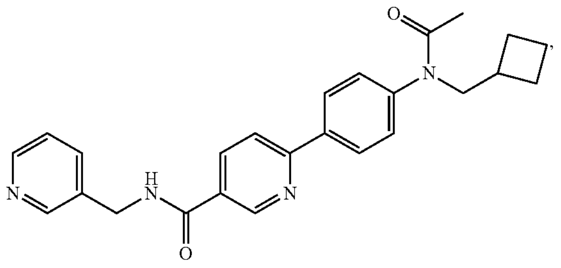
I-468
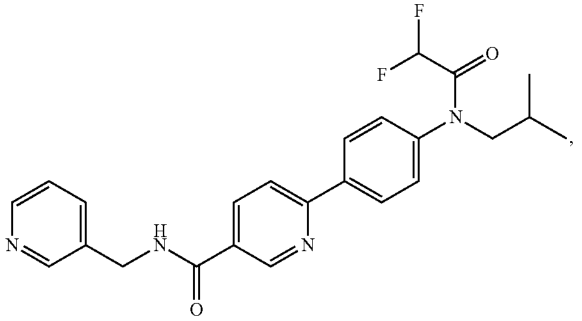
-continued
I-495
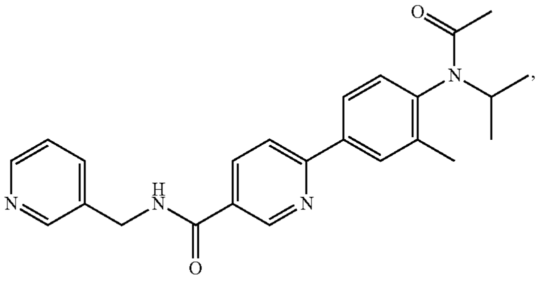
I-594
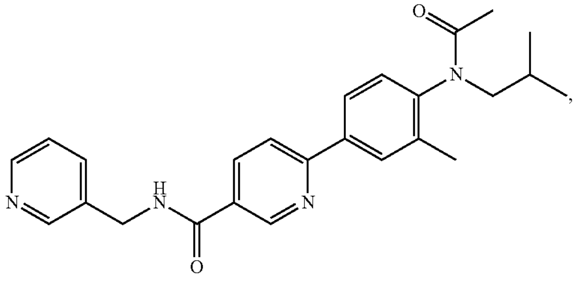
I-595
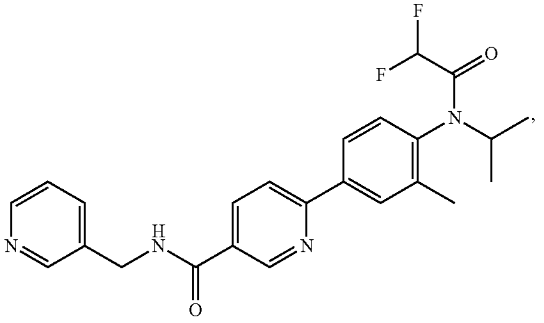
I-596
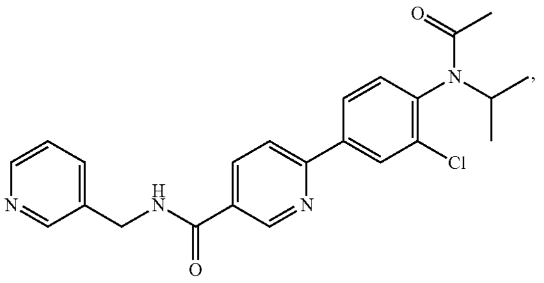
I-599
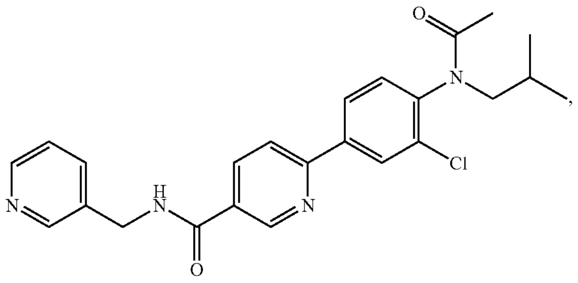

-continued
I-600
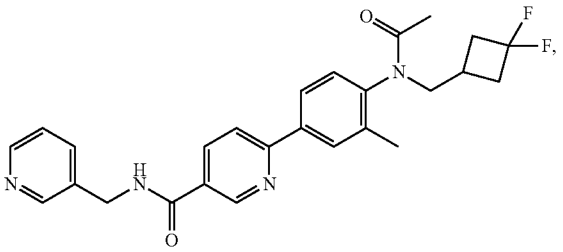
I-601
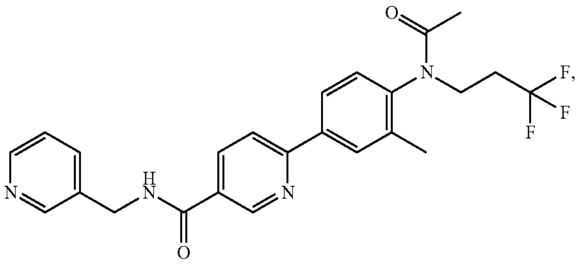
I-602
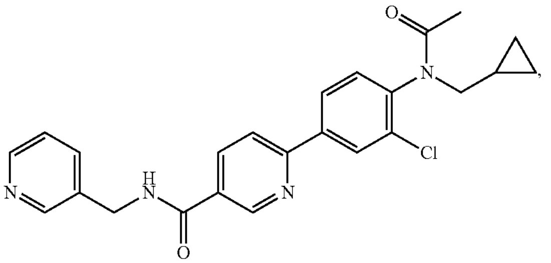
I-603
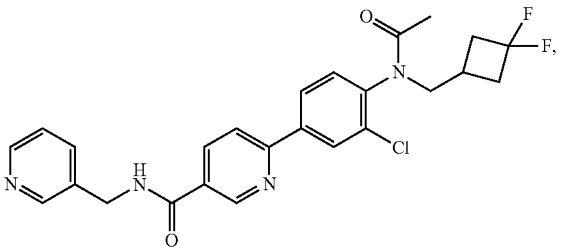
I-604
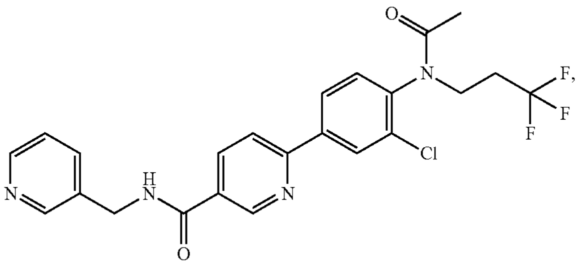
-continued
I-606
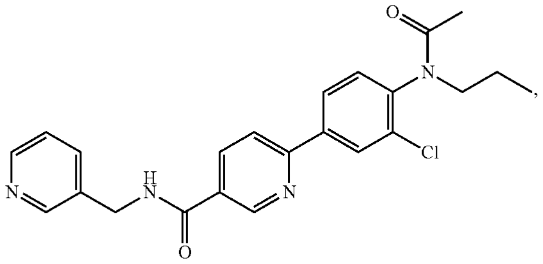
I-609
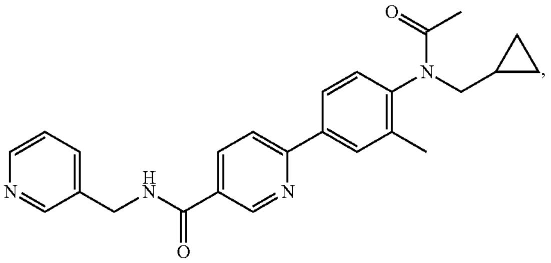
I-610
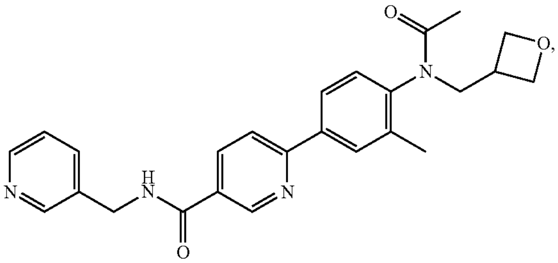
I-611
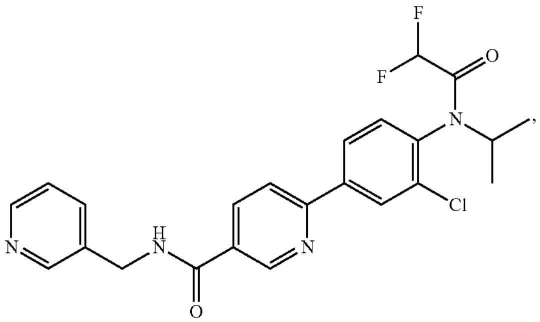
I-619
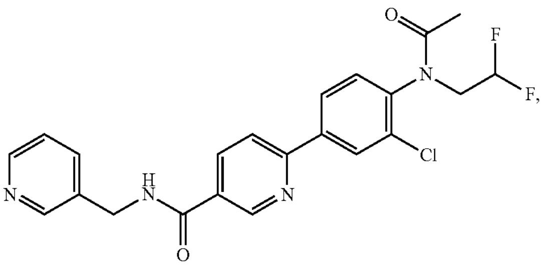

-continued
I-620
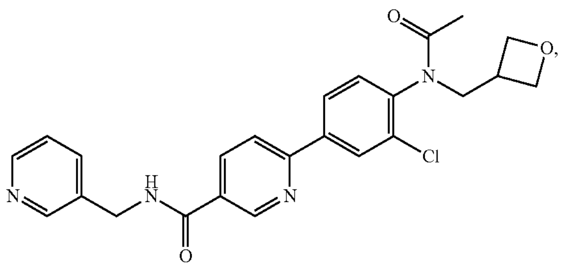
I-626
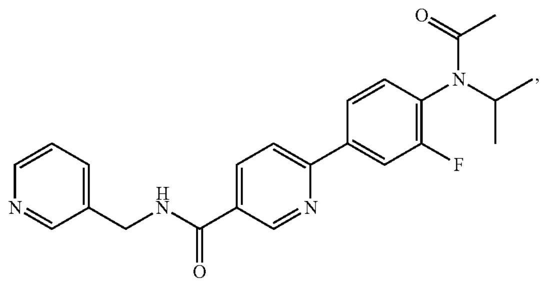
I-652
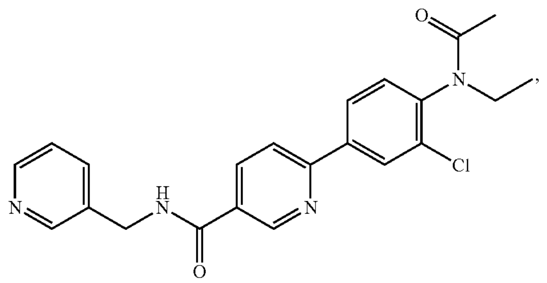
I-662
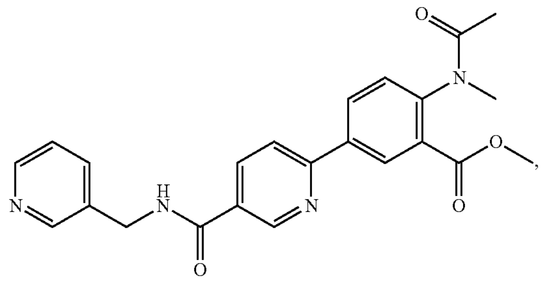
I-677
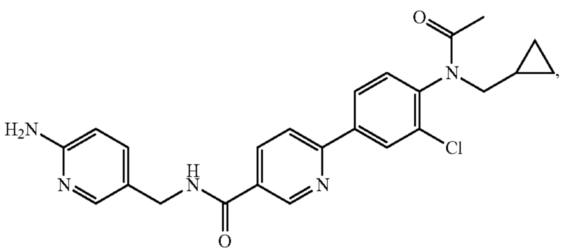
-continued
I-679
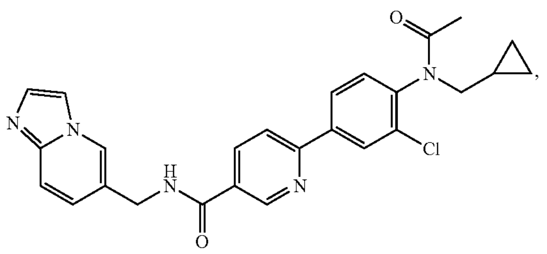
I-681
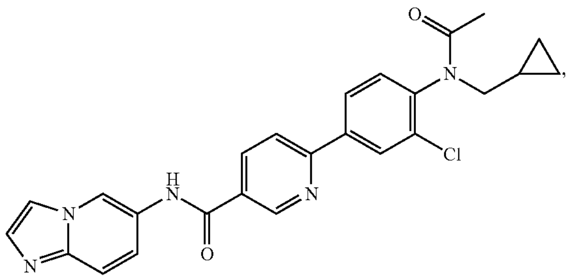
I-683
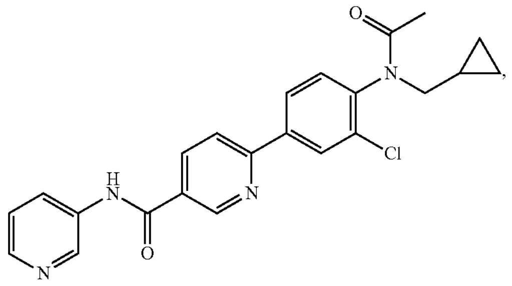
I-685
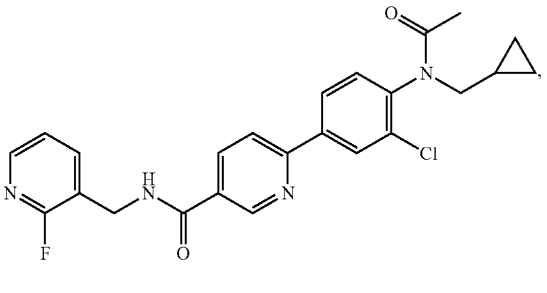
I-689
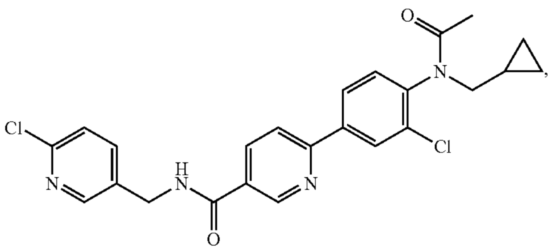

-continued

I-690

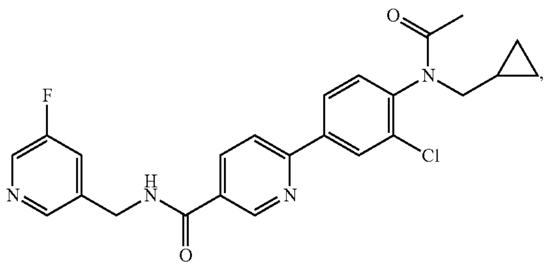

I-696

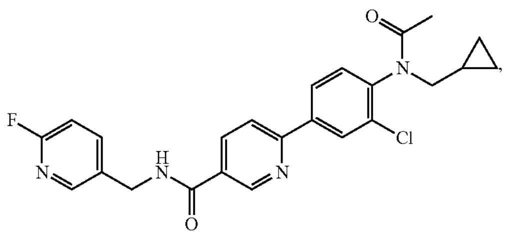

and

I-697

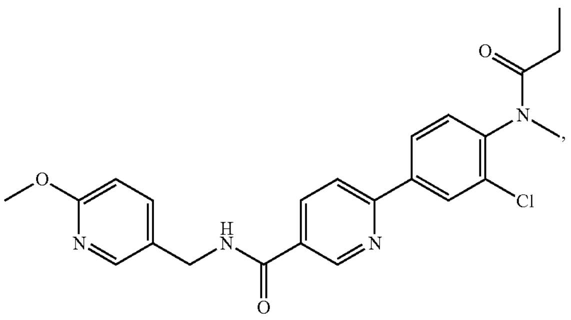

or a pharmaceutically acceptable salt, hydrate, polymorph, co-crystal, tautomer, stereoisomer, isotopically labeled derivative, or prodrug thereof.

10. A pharmaceutical composition comprising a compound of claim 1, or a pharmaceutically acceptable salt, solvate, hydrate, polymorph, co-crystal, tautomer, stereoisomer, isotopically labeled derivative, or prodrug thereof; and optionally, a pharmaceutically acceptable excipient.

11. A method of inhibiting NAMPT in a subject, the method comprising administering to the subject a compound of claim 1, or a pharmaceutically acceptable salt, solvate, hydrate, polymorph, co-crystal, tautomer, stereoisomer, isotopically labeled derivative, or prodrug thereof.

12. A method of treating a disease or disorder in a subject comprising administering to the subject a therapeutically effective amount of a compound of claim 1, or a pharmaceutically acceptable salt, solvate, hydrate, polymorph, co-crystal, tautomer, stereoisomer, isotopically labeled derivative, wherein the disease or disorder is a proliferative disease, benign neoplasm, or cancer.

13. A method of treating cancer in a subject in need thereof comprising administering to the subject a therapeutically effective amount of a compound of claim 1, or a pharmaceutically acceptable salt, solvate, hydrate, polymorph, co-crystal, tautomer, stereoisomer, isotopically labeled derivative.

14. The method of claim 13, wherein the cancer is:

(a) leukemia;

(b) acute myeloid leukemia;

(c) undifferentiated acute myeloblastic leukemia (M0);

(d) acute myeloblastic leukemia with minimal maturation (M1);

(e) acute myeloblastic leukemia with maturation (M2);

(f) acute promyelocytic leukemia (APL)(M3);

(g) acute myelomonocytic leukemia (M4);

(h) acute myelomonocytic leukemia with eosinophilia (M4 eos);

(i) acute monocytic leukemia (M5);

(j) acute erythroid leukemia (M6);

(k) acute megakaryoblastic leukemia (M7);

(l) acute monocytic leukemia;

(m) acute lymphocytic leukemia; or (n) B-cell acute lymphocytic leukemia.

15. A method of inhibiting production of nicotinamide adenine dinucleotide or nicotinamide mononucleotide in a subject, the method comprising administering to the subject a compound of claim 1, or a pharmaceutically acceptable salt, solvate, hydrate, polymorph, co-crystal, tautomer, stereoisomer, isotopically labeled derivative, or prodrug thereof.

16. A method of reducing cell proliferation in a subject, the method comprising administering to the subject a compound of claim 1, or a pharmaceutically acceptable salt, solvate, hydrate, polymorph, co-crystal, tautomer, stereoisomer, isotopically labeled derivative, or prodrug thereof.

17. A method of decreasing inflammatory activity in a subject, the method comprising administering to the subject a compound of claim 1, or a pharmaceutically acceptable salt, solvate, hydrate, polymorph, co-crystal, tautomer, stereoisomer, isotopically labeled derivative, or prodrug thereof.

18. A kit comprising:

a compound of claim 1, or a pharmaceutically acceptable salt, solvate, hydrate, polymorph, co-crystal, tautomer, stereoisomer, isotopically labeled derivative, or prodrug thereof; or a pharmaceutical composition thereof; and instructions for using the compound, pharmaceutically acceptable salt, solvate, hydrate, polymorph, co-crystal, tautomer, stereoisomer, isotopically labeled derivative, prodrug, or pharmaceutical composition.

19. The method of claim 13, wherein the cancer is acute myeloid leukemia.

20. The method of claim 13, wherein the cancer is acute lymphocytic leukemia.

21. The method of claim 13, wherein the cancer is myelodysplastic syndrome.

* * * * *